United States Patent
Sasmal et al.

(10) Patent No.: US 12,371,426 B2
(45) Date of Patent: *Jul. 29, 2025

(54) PYRIDAZINE DERIVATIVES AS SMARCA2/4 DEGRADERS

(71) Applicant: Aurigene Discovery Technologies Limited, Bangalore (IN)

(72) Inventors: Sanjita Sasmal, Hyderabad (IN); Susanta Samajdar, Bangalore (IN); Subhendu Mukherjee, Hooghly (IN); Chandrasekhar Abbineni, Hyderabad (IN)

(*) Notice: Subject to any disclaimer, the term of this patent is extended or adjusted under 35 U.S.C. 154(b) by 614 days.

This patent is subject to a terminal disclaimer.

(21) Appl. No.: 17/050,792

(22) PCT Filed: Apr. 26, 2019

(86) PCT No.: PCT/IB2019/053443
§ 371 (c)(1),
(2) Date: Oct. 26, 2020

(87) PCT Pub. No.: WO2019/207538
PCT Pub. Date: Oct. 31, 2019

(65) Prior Publication Data
US 2021/0253564 A1    Aug. 19, 2021

(30) Foreign Application Priority Data
Apr. 26, 2018    (IN) .............................. 201841015818

(51) Int. Cl.
*C07D 401/14* (2006.01)
*C07D 413/14* (2006.01)
*C07D 417/14* (2006.01)
*C07D 487/08* (2006.01)

(52) U.S. Cl.
CPC ......... *C07D 413/14* (2013.01); *C07D 401/14* (2013.01); *C07D 487/08* (2013.01)

(58) Field of Classification Search
CPC .......................... C07D 401/14; C07D 4177/14
See application file for complete search history.

(56) References Cited

FOREIGN PATENT DOCUMENTS

WO    WO-2021048799 A1 *    3/2021    ........... A61K 31/501

* cited by examiner

Primary Examiner — Samira J Jean-Louis
(74) Attorney, Agent, or Firm — Benjamin Aaron Adler

(57) ABSTRACT

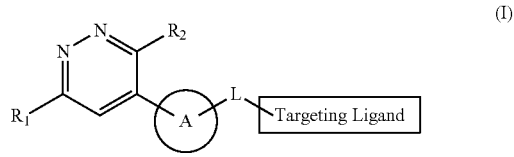

The present invention provides pyridazine derivatives of formula (I), which are therapeutically useful as SMARCA2/4 degraders. These compounds are useful in the treatment and/or prevention of diseases or disorders dependent upon SMARCA2/4 in a mammal. The present invention also provides preparation of the compounds and pharmaceutical compositions comprising at least one of the pyridazine derivatives of formula (I) or a pharmaceutically acceptable salt, or a stereoisomer thereof.

15 Claims, No Drawings

PYRIDAZINE DERIVATIVES AS SMARCA2/4 DEGRADERS

This application is a national stage under 35 U.S.C § 371 of pending international application PCT/IB2019/053443, filed 26 Apr. 2019, which claims the benefit of Indian provisional application number 201841015818, filed on 26 Apr. 2018, now abandoned; the specifications of which are hereby incorporated by reference in their entirety.

FIELD OF THE INVENTION

The present invention relates to therapeutically active pyridazine derivatives and pharmaceutically acceptable salt or stereoisomer thereof which are useful as SMARCA2/4 degraders and for the treatment of diseases or disorders dependent on SMARCA2/4, and to pharmaceutical compositions containing such compounds.

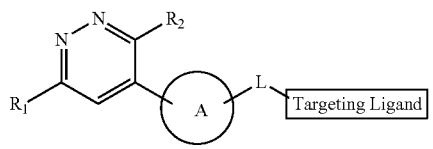
(I)

BACKGROUND OF THE INVENTION

One of the most significant findings from the cancer genome profiling is the discovery of frequent mutations in various subunits of the mammalian SWI/SNF (SWItch/Sucrose Non-Fermentable) chromatin remodeling complex. Approximately 20% of human cancers are associated with somatic mutations in subunits of the SWI/SNF complex, a chromatin remodeling complex that influences gene regulation by disrupting histone-DNA contacts (*PNAS* Feb. 25, 2014. 111 (8) 3128-3133).

SWI/SNF complexes contain either of two closely related and evolutionarily conserved catalytic ATPase subunits: Brahma (BRM/SMARCA2) or Brahma-related gene 1 (BRG1/SMARCA4). They share approximately 75% identity at the protein level. Although BRG1- and BRM-containing complexes show some redundancy, they may function distinctively. In human cancer, BRG1 seems to be one of the most frequently mutated subunit genes, whereas the BRM gene is rarely mutated. BRG1/SMARCA4 mutations occurring in ~10-15% of lung adenocarcinomas. BRM/SMARCA2, is essential for the growth of tumor cells that harbor loss of function mutations in BRG1/SMARCA4. Depletion of BRM in BRG1-deficient cancer cells leads to a cell cycle arrest, induction of senescence, and increased levels of global H3K9me31 (*PNAS* Feb. 25, 2014. 111 (8) 3128-3133).

In some tumor types, mutations within the SWI/SNF complex lead to context specific vulnerabilities such as the requirement of SMARCA2 for survival of tumour cells lacking SMARCA4. This finding of SMARCA2/4 synthetic lethal relationship translates in vivo which emphasizes SMARCA2 as a promising therapeutic target for the treatment SMARCA4-deficient cancers. Moreover, the SMARCA4-deficient patient population generally lacks targetable oncogenes (such as mutant EGFR or ALK translocations), which further emphasizes the potential of developing SMARCA2 inhibitors. Characterization of SMARCA4 function in tumors with high SMARCA4 levels, shows effects on signaling pathways that result in increased proliferation and survival. SMARCA4 knockdown in tumors that show elevated levels known to inhibit proliferation and other cancer cell properties. Studies have also shown that SMARCA4 knock down/modulation increases sensitivity to known chemotherapeutic agents, thereby indicating that SMARCA4 targeting could also be an adjuvant therapy to existing chemotherapeutic approaches (*PNAS* Feb. 25, 2014. 111 (8) 3128-3133; *J Pathol.* 2016 February; 238(3): 389-400).

Contrary to genetic silencing of SMARCA2 leading to potent anti-proliferative activity in SMARCA4-deficient cancer cell lines, PFI-3, a selective cell permeable SMARCA2/4 bromodomain inhibitor capable of binding to SMARCA2 and SMARCA4 bromodomain, pharmacological studies fails to display an antiproliferative phenotype indicating that bromodomain function of SMARCA2/4 is dispensable for tumor cell proliferation, while the catalytic ATPase activity is essential (*Cancer Res.* 2015 Sep. 15; 75(18): 3865-3878). Therefore, in order to mimic the phenotype achieved by genetic slilencing, approaches that lead to reduction or complete elimation of SMARCA2/4 may be needed.

The ubiquitin-proteasome system (UPS) is a major pathway that regulates the levels of intracellular proteins and provides a fine balance between protein synthesis and degradation required for normal maintenance of cellular function, including proliferation, differentiation, and cell death. Ubiquitination is a post-translational modification, where a small protein, ubiquitin, is covalently attached to lysine residues on a substrate protein carried out sequentially by a cascade of enzymatic reactions involving an intimate collaboration between E1 activating, E2 conjugating and E3 ligating enzymes and subsequent degradation of the tagged proteins (*J. Biosci.* 31(1), March 2006, 137-155; *Expert Opin Ther Targets.* 2013 September; 17(9): 1091-1108 and *Cell Research* (2016) 26:484-498).

Proteolysis targeting chimeras are the heterobifunctional molecules contain a ligand for a target protein of interest connected via a linker to a ligand for an E3 ubiquitin ligase. Upon such bi-functional molecule-mediated heterodimerization of the two bound proteins, the target protein is ubiquitinated and degraded by the proteasome in cells. Many such bi-functional molecules have been developed to recruit E3 ubiquitin ligases to a variety of substrates using high-affinity ligands for the protein of interest. Proteins effectively degraded using these apporahes include RIPK2 and ERRα, BRD4, BRD9, BCR/Abl and Abl and Erα. (*Cell Chemical Biology* 25, 1-10, Jan. 18, 2018). The publication by Bai et al. (*Cancer Res.* 2017 May 1; 77(9):2476-2487) "titled Targeted Degradation of BET Proteins in Triple-Negative Breast Cancer". E3 ubiquitin ligases (of which over 600 are known in humans) confer substrate specificity for ubiquitination and are more attractive therapeutic targets than general proteasome inhibitors due to their specificity for certain protein substrates.

The present invention describes the development of first in class SMARCA2/4 degrader to mimic the genetic silencing phenotype effect. In particular, the present invention is directed to compounds, which contain on one end an E3 ligase ligand targeting E3 ligase and on the other end a moiety which binds the target protein/polypeptide optionally connected with a linker moiety such that target protein is placed in proximity to the ubiquitin ligase to effect degradation of the target protein/polypeptide.

SUMMARY OF THE INVENTION

Provided herein pyridazine derivatives and pharmaceutical compositions thereof which are useful as SMARCA2/4 degraders and for the treatment of diseases or disorders dependent on SMARCA2/4.

In one aspect, the present invention provides compounds of formula (I):

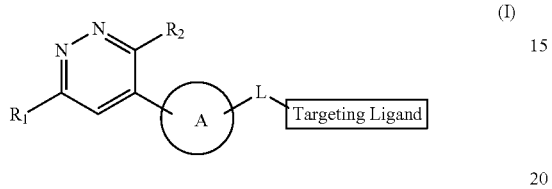

or a pharmaceutically acceptable salt thereof or a stereoisomer thereof;

wherein, $R_1$ is hydrogen, halo, alkyl, alkenyl, alkoxy, hydroxy, hydroxyalkyl, —COOR$_a$, —CON(R$_a$)$_2$ or aryl; wherein, the aryl is optionally substituted with one or more groups independently selected from hydroxy, alkoxy, halo, alkyl, amino, —O—Na, —COOR$_a$ and —OCOR$_a$; wherein R$_a$ at each occurrence is selected from hydrogen and alkyl;

$R_2$ is —NR$_3$R$_4$ or —OR$_3$; wherein, R$_3$ and R$_4$ are independently selected from hydrogen and alkyl;

Ring A is heterocyclic ring optionally substituted with one or more groups independently selected from hydroxy, halo and alkyl;

L is a linker, selected from the group consisting of:

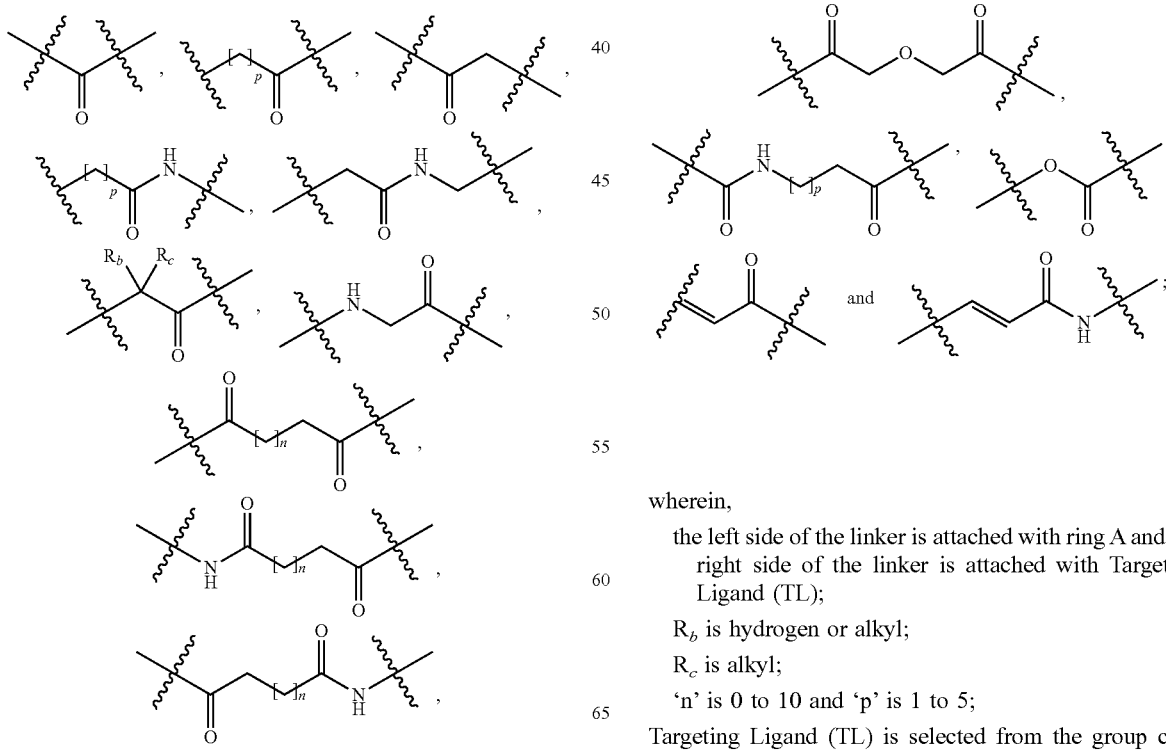

wherein, the left side of the linker is attached with ring A and the right side of the linker is attached with Targeting Ligand (TL);

R$_b$ is hydrogen or alkyl;

R$_c$ is alkyl;

'n' is 0 to 10 and 'p' is 1 to 5;

Targeting Ligand (TL) is selected from the group consisting of:

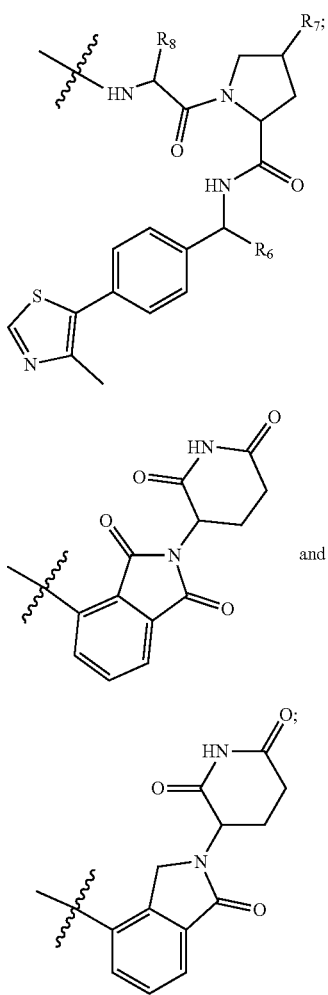

wherein,
R₆ is selected from hydrogen, alkyl, acyl and haloalkyl;
R₇ is selected from —O—R₅ and halo; wherein R₅ is selected from hydrogen, alkyl, acyl and Na; and
R₈ is selected from hydrogen and alkyl.

In yet another aspect, the present invention provides a pharmaceutical composition comprising a compound of formula (I) or a pharmaceutically acceptable salt thereof and at least one pharmaceutically acceptable excipient (such as a pharmaceutically acceptable carrier or diluent).

In yet another aspect, the present invention relates to the preparation of compounds of formula (I).

In another aspect, the present invention provides a composition comprising a compound of the disclosure and an excipient and/or pharmaceutically acceptable carrier for treating diseases or conditions or disorders that are dependent upon SMARCA2/4.

In another aspect, the present invention provides a composition comprising a compound of the disclosure and an excipient and/or pharmaceutically acceptable carrier for treating diseases or conditions that have altered SMARCA2/4 including mutations and overexpression.

In another aspect, the present invention provides a composition comprising a compound of the disclosure and an excipient and/or pharmaceutically acceptable carrier for treating diseases or conditions wherein degradation of SMARCA2/4 proteins provides a benefit, e.g., cancer.

In another aspect, the present invention provides methods of treating a condition or disease by administering a therapeutically effective amount of a compound of the disclosure to an individual, e.g., a human, in need thereof. The disease or condition of interest is treatable by degradation of SMARCA2/4, for example, a cancer, a chronic autoimmune disorder, an inflammatory condition, a proliferative disorder, sepsis, or a viral infection. Also provided are methods of preventing the proliferation of unwanted proliferating cells, such as in cancer, in a subject comprising administering a therapeutically effective amount of a compound of the disclosure to a subject at risk of developing a condition characterized by unwanted proliferating cells. In some embodiments, the compounds of the disclosure reduce the proliferation of unwanted cells by inducing apoptosis in those cells.

In another aspect, the present invention provides a composition comprising a compound of the disclosure and an excipient and/or pharmaceutically acceptable carrier for treating diseases or conditions that are dependent upon altered activity of SWI/SNF complex with or without chromatic remodeling activities.

In another aspect, the present invention provides a use of a compound of the disclosure for the manufacture of a medicament for treating a disease or condition of interest, e.g., cancer.

It is to be understood that both the foregoing summary and the following detailed description are exemplary and explanatory only, and are not restrictive of the invention as claimed.

DETAILED DESCRIPTION OF THE INVENTION

The present invention provides pyridazine derivatives, referred as a compound of formula (I), which are useful as SMARCA2/4 degraders and for the treatment of conditions dependent on SMARCA2/4. The present invention further provides pharmaceutical compositions comprising the said compounds and their derivatives as therapeutic agents.

Each embodiment is provided by way of explanation of the invention and not by way of limitation of the invention. In fact, it will be apparent to those skilled in the art that various modifications and variations can be made to the compounds, compositions and methods described herein without departing from the scope or spirit of the invention. For instance, features illustrated or described as part of one embodiment can be applied to another embodiment to yield a still further embodiment. Thus, it is intended that the present invention includes such modifications and variations and their equivalents. Other objects, features and aspects of the present invention are disclosed in or are obvious from, the following detailed description. It is to be understood by one of ordinary skill in the art that the present discussion is a description of exemplary embodiments only and is not to be construed as limiting the broader aspects of the present invention.

In first embodiment, the present invention provides compounds of formula (I),

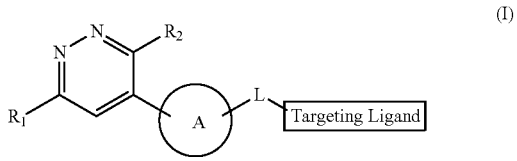

or a pharmaceutically acceptable salt thereof or a stereoisomer thereof;

wherein,

R₁ is hydrogen, halo, alkyl, alkenyl, alkoxy, hydroxy, hydroxyalkyl, —COORₐ, —CON(Rₐ)₂ or aryl; wherein, the aryl is optionally substituted with one or more groups independently selected from hydroxy, alkoxy, halo, alkyl, amino, —O—Na, —COORₐ and —OCORₐ; wherein Rₐ at each occurance is selected from hydrogen and alkyl;

R₂ is —NR₃R₄ or —OR₃; wherein, R₃ and R₄ are independently selected from hydrogen and alkyl;

Ring A is heterocyclic ring optionally substituted with one or more groups independently selected from hydroxy, halo and alkyl;

L is a linker, selected from the group consisting of:

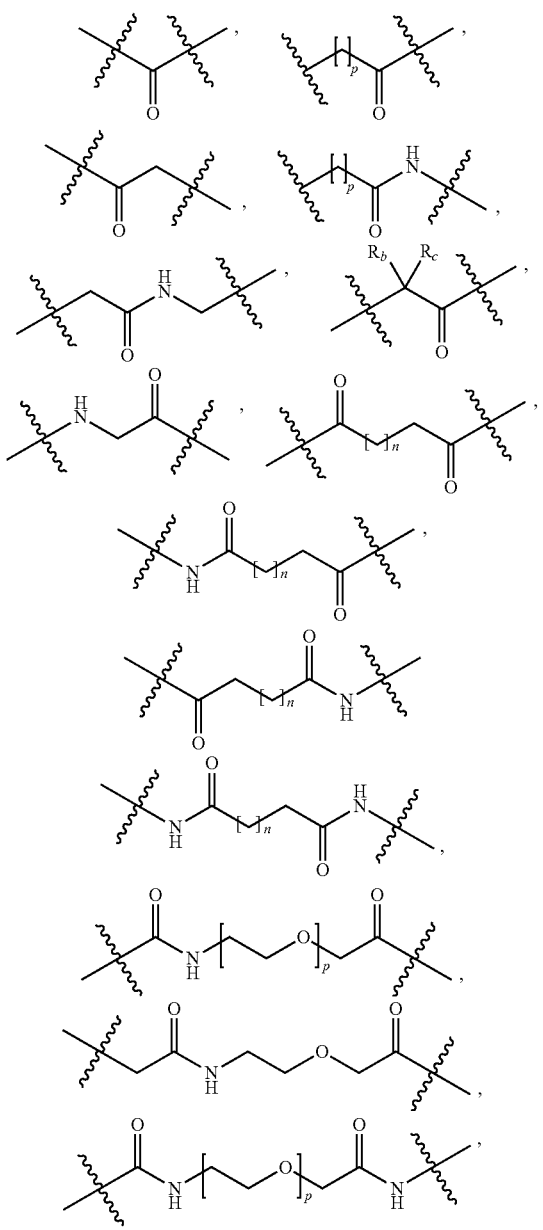

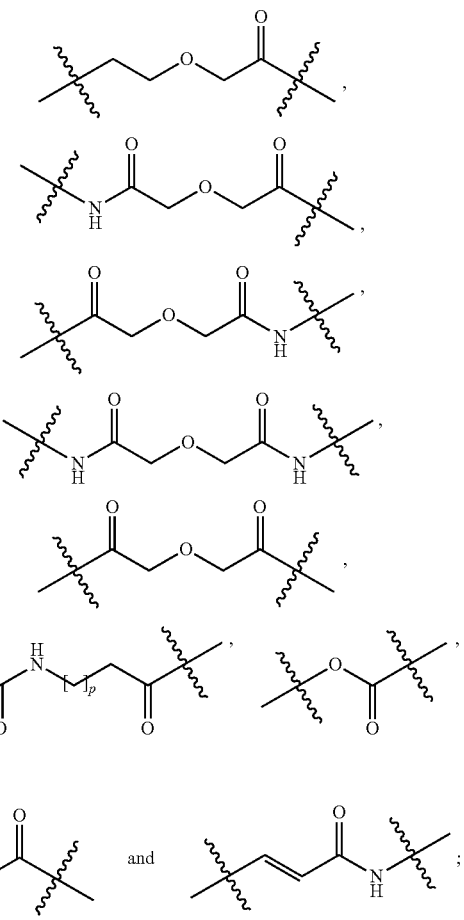

wherein
the left side of the linker is attached with ring A and the right side of the linker is attached with Targeting Ligand (TL);

R_b is hydrogen or alkyl;

R_c is alkyl;

'n' is 0 to 10 and 'p' is 1 to 5;

Targeting Ligand (TL) is selected from the group consisting of:

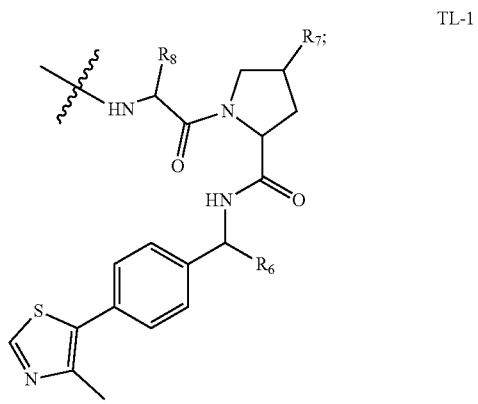

TL-1

-continued

TL-2

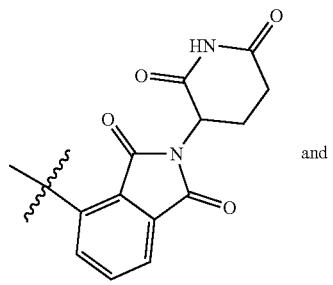

and

TL-3

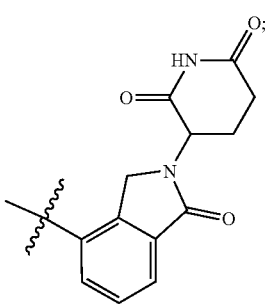

wherein,
R$_6$ is selected from hydrogen, alkyl, acyl and haloalkyl;
R$_7$ is selected from —O—R$_5$ and halo; wherein R$_5$ is selected from hydrogen, alkyl, acyl and Na; and
R$_8$ is selected from hydrogen and alkyl.

In another embodiment of the present invention, it provides compounds of formula (I),
wherein,
R$_1$ is hydrogen, halo, alkyl, alkenyl, alkoxy or aryl; wherein, the aryl is optionally substituted with one or more groups independently selected from hydroxy, alkoxy and halo;
R$_2$ is —NR$_3$R$_4$ or —OR$_3$; wherein, R$_3$ and R$_4$ are independently selected from hydrogen and alkyl;
Ring A is heterocyclic ring;
L is a linker, selected from the group consisting of:

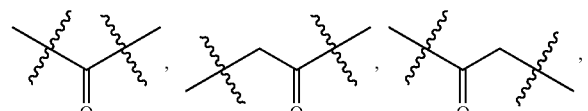

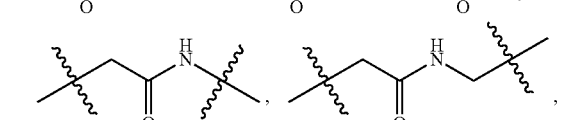

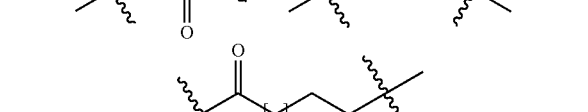

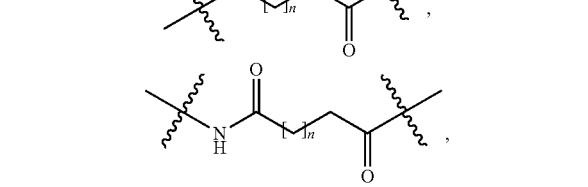

-continued

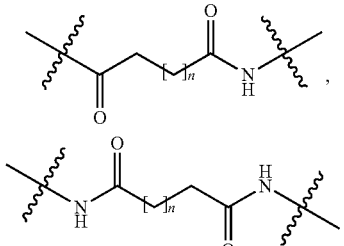

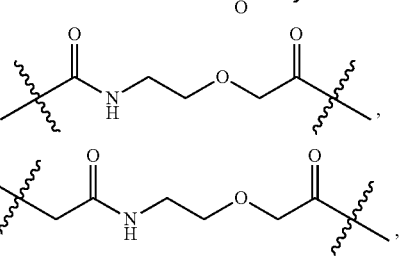

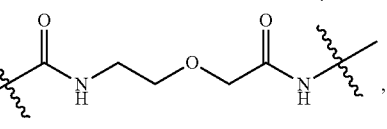

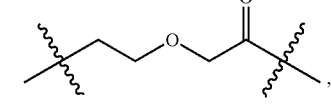

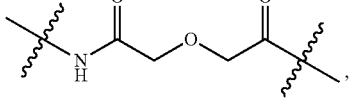

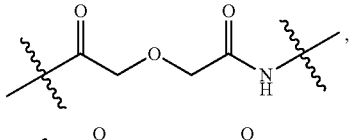

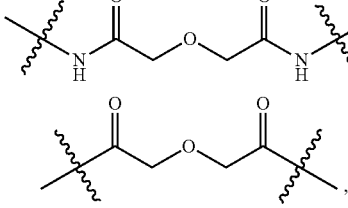

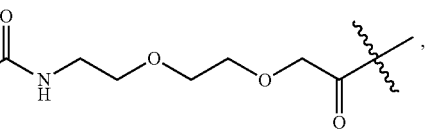

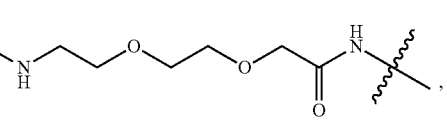

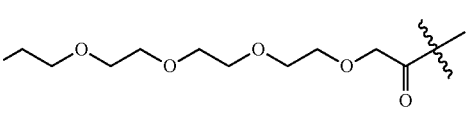

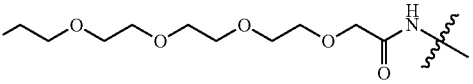

-continued

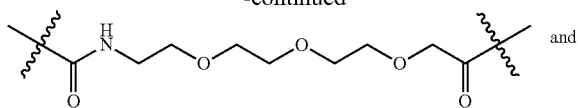 and

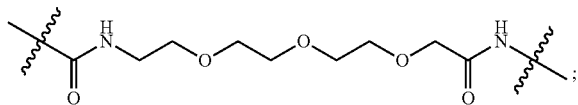;

wherein, the left side of the linker is attached with ring A and the right side of the linker is attached with Targeting Ligand (TL); and 'n' is 0 to 8;

Targeting Ligand (TL) is selected from the group consisting of:

TL-1A

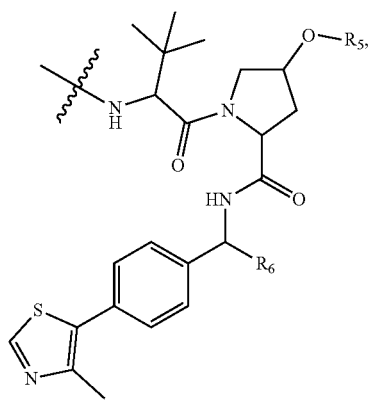

TL-2

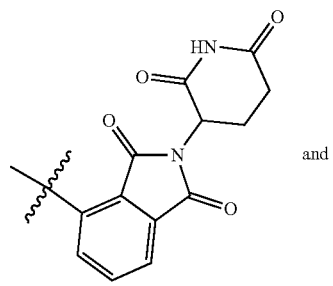 and

TL-3

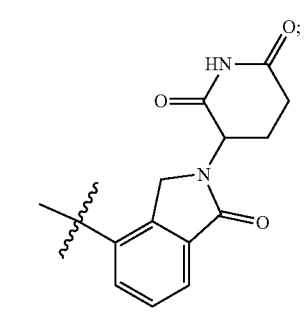;

wherein, $R_5$ and $R_6$ are independently hydrogen, alkyl or acyl.

In yet another embodiment of the present invention, it provides compounds of formula (IA),

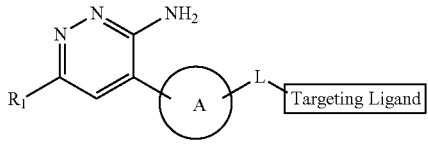
(IA)

or a pharmaceutically acceptable salt thereof or a stereoisomer thereof;

wherein, $R_1$, ring A, L and Targeting Ligand are same as defined in formula (I).

In yet another embodiment of the present invention, it provides compounds of formula (IB),

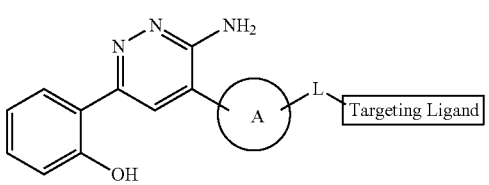
(IB)

or a pharmaceutically acceptable salt thereof or a stereoisomer thereof;

wherein, ring A, L and Targeting Ligand are same as defined in formula (I).

In yet another embodiment of the present invention, it provides compounds of formula (IC),

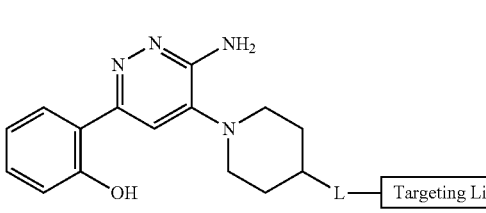
(IC)

or a pharmaceutically acceptable salt thereof or a stereoisomer thereof;

wherein, L and Targeting Ligand are same as defined in formula (I).

In yet another embodiment of the present invention, it provides compounds of formula (ID),

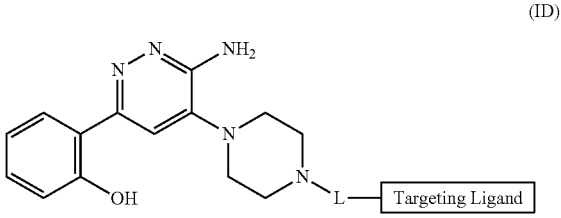
(ID)

or a pharmaceutically acceptable salt thereof or a stereoisomer thereof;

wherein, L and Targeting Ligand are same as defined in formula (I).

In yet another embodiment of the present invention, it provides compounds of formula (IE), (IE)

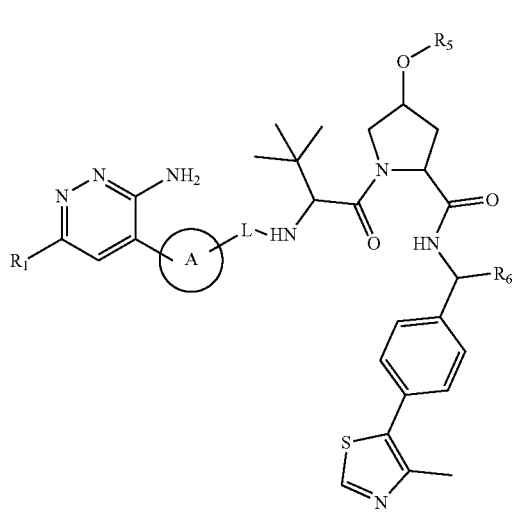

or a pharmaceutically acceptable salt thereof or a stereoisomer thereof;

wherein, $R_1$, $R_5$, $R_6$, ring A and L are same as defined in formula (I).

In certain embodiments, the present invention provides compounds of formula (IE), wherein, $R_1$ is hydrogen, halo, hydroxyalkyl, —COOR$_a$, —CON$(R_a)_2$ or an optionally substituted aryl; wherein, the aryl is optionally substituted with one or more groups independently selected from hydroxy, alkoxy, halo, alkyl, amino, —O—Na, —COOR$_a$ and —OCOR$_a$; wherein R$_a$ is selected from hydrogen and alkyl;

ring A is an optionally substituted 4-10 membered monocyclic or bicyclic heterocyclic ring; wherein the said ring is hetero aryl and heterocycloalkyl;

L is selected from,

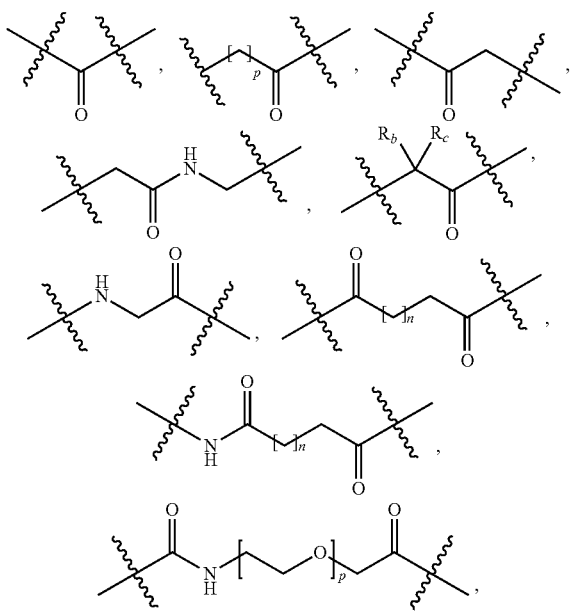

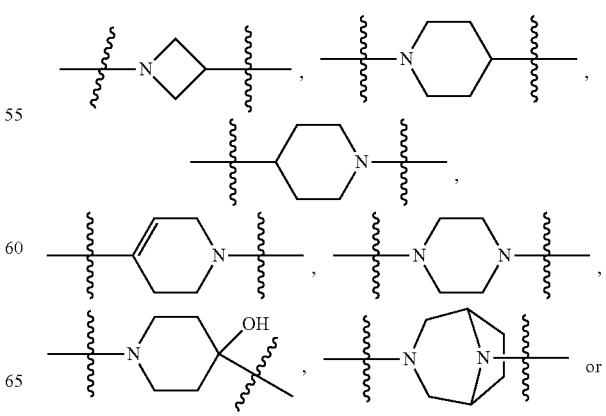

wherein, the left side of the linker is attached with ring A and the right side of the linker is attached with Targeting Ligand (TL);

$R_b$ is hydrogen or alkyl;

$R_c$ is alkyl;

'n' is 0 to 10 and 'p' is 1 to 5;

$R_5$ is selected from hydrogen, alkyl, acyl and —Na; and $R_6$ is selected from hydrogen, alkyl and haloalkyl.

In certain embodiments, the present invention provides compounds of formula (IE), wherein, $R_1$ is hydrogen, chloro, —CH$_2$OH, —COOH, —COOCH$_3$, —CONH$_2$, —CONHCH$_3$ or optionally substituted monocyclic aryl ring; the said aryl is phenyl;

ring A is

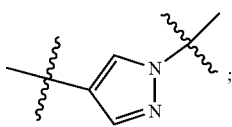
L is selected from
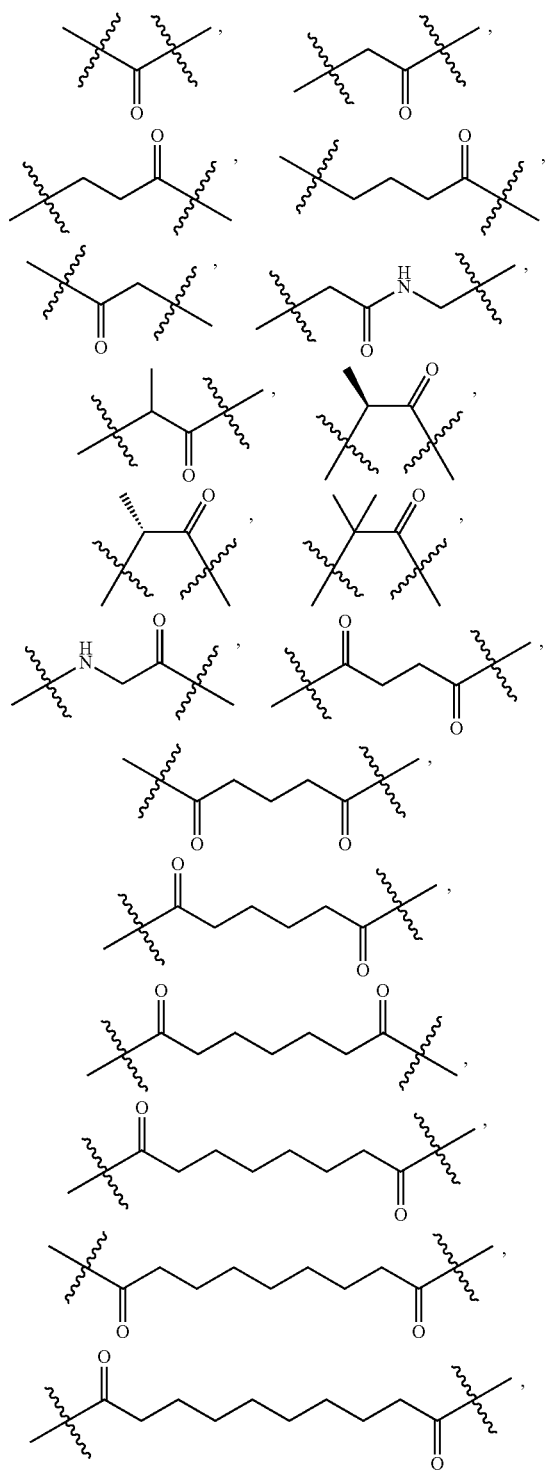
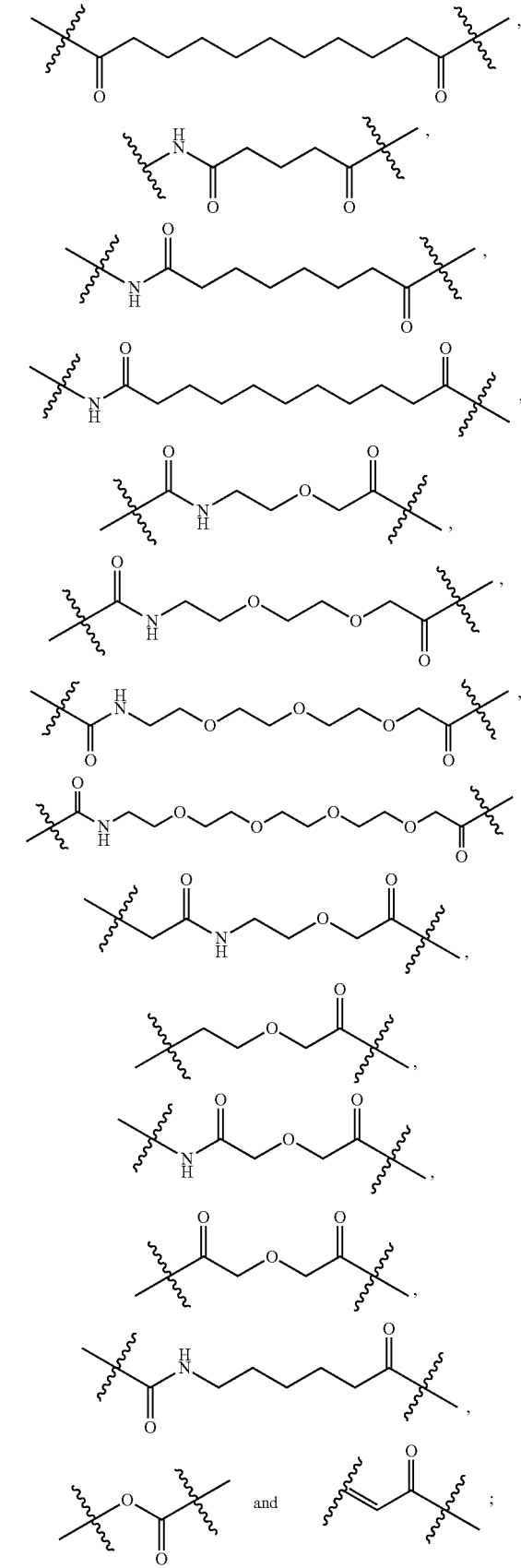

wherein,
the left side of the linker is attached with ring A and the right side of the linker is attached with Targeting Ligand (TL);
$R_5$ is selected from hydrogen, alkyl, acyl and —Na; and
$R_6$ is selected from hydrogen, alkyl and haloalkyl.

In certain embodiments, the present invention provides compounds of formula (IE), wherein,
$R_1$ is hydrogen, chloro, —CH$_2$OH, —COOH, —COOCH$_3$, —CONH$_2$— CONHCH$_3$ or optionally substituted monocyclic aryl ring; the said aryl is phenyl;

ring A is

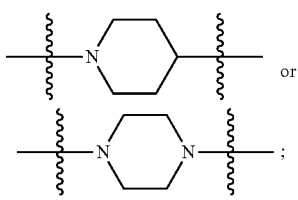

or

L is selected from

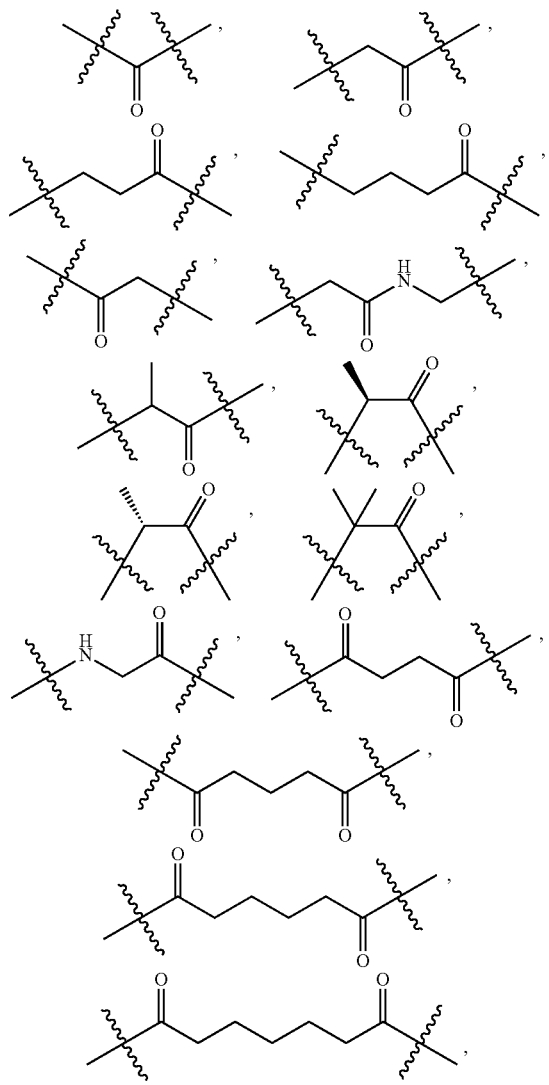

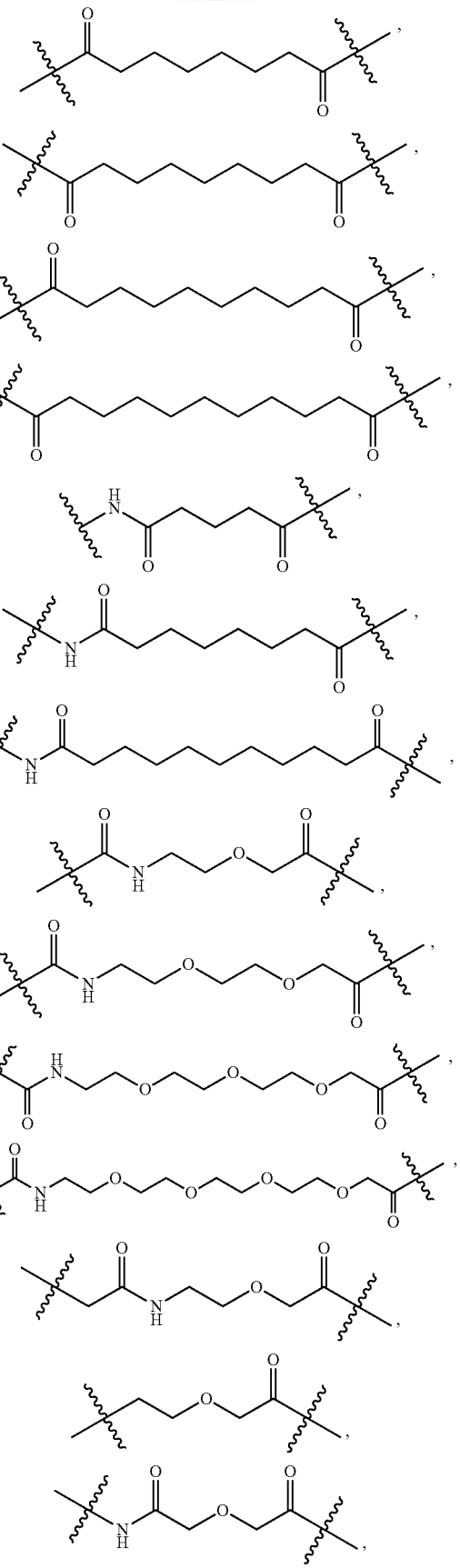

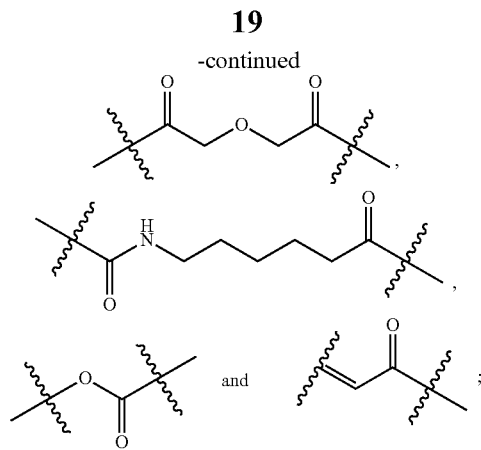
wherein,
the left side of the linker is attached with ring A and the right side of the linker is attached with Targeting Ligand (TL);
R₅ is selected from hydrogen, alkyl, acyl and —Na; and
R₆ is selected from hydrogen, alkyl and haloalkyl.
In certain embodiments, the present invention provides compounds of formula (IE), wherein,
ring A is
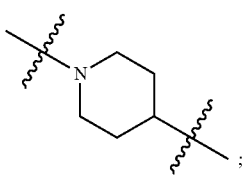 [SMILES: *C1CCN(*)CC1]
L is selected from
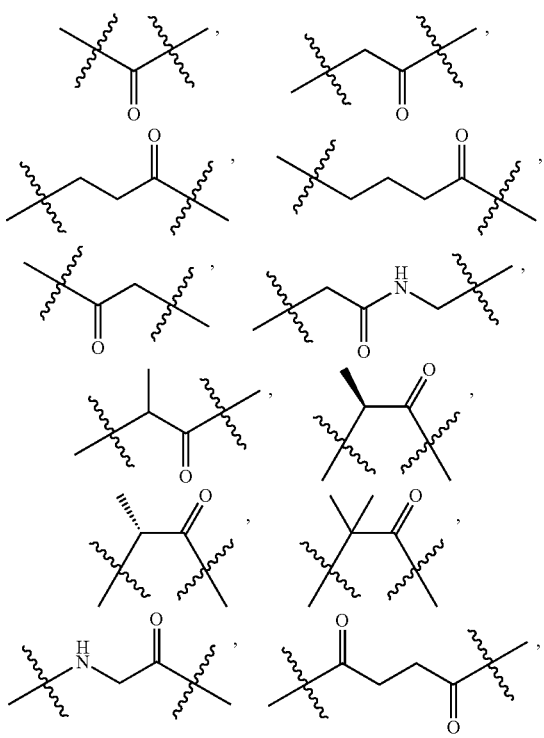
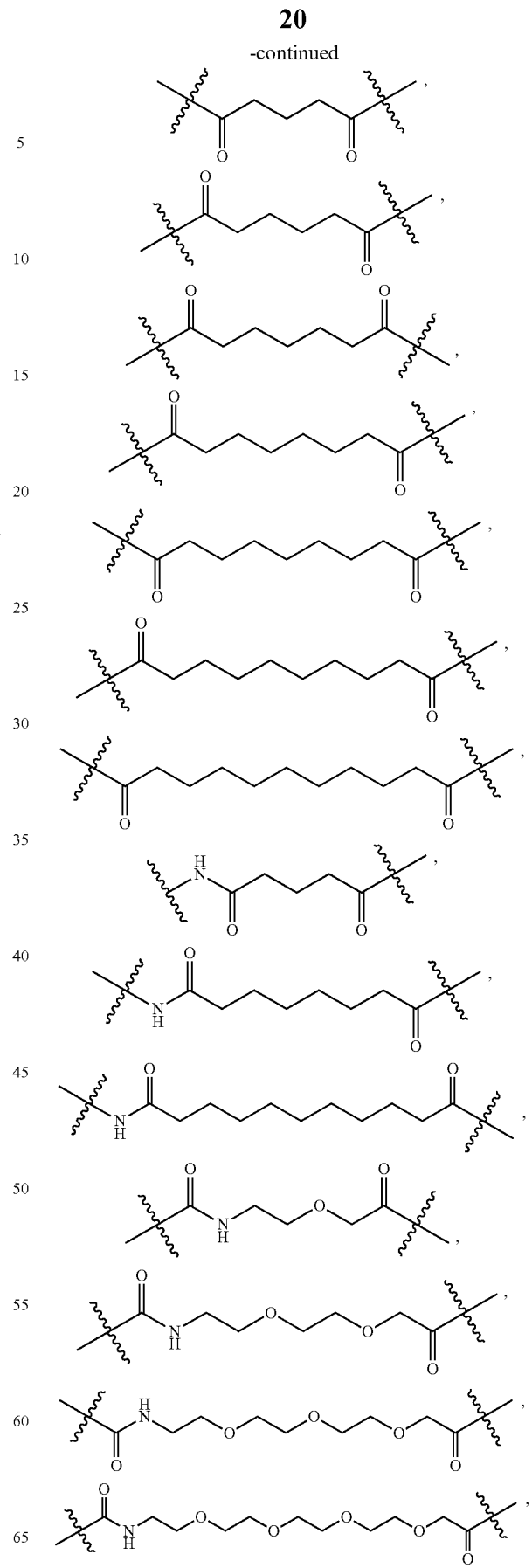

-continued

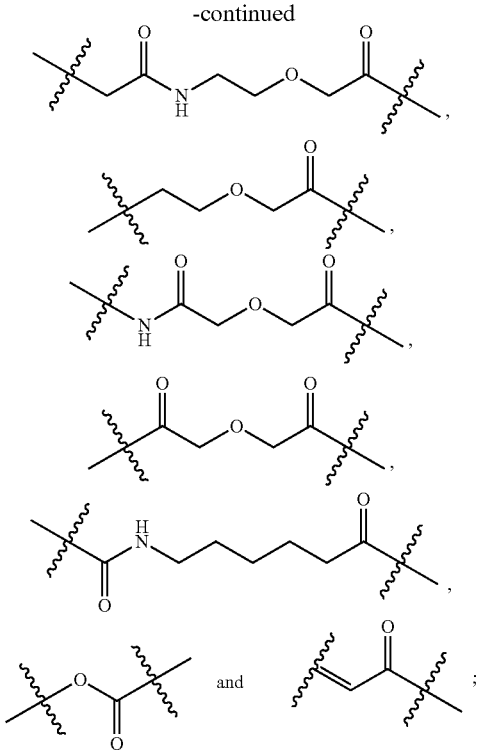

wherein,
the left side of the linker is attached with ring A and the right side of the linker is attached with Targeting Ligand (TL);
R$_1$ is chloro, —CH$_2$OH, —COOH, —COOCH$_3$, —CONH$_2$—CONHCH$_3$ or phenyl; wherein the phenyl is optionally substituted with fluoro, chloro, hydroxyl, —NH$_2$, —OCH$_3$, —ONa, —OCOCH$_3$, —COOH or methyl;
R$_5$ is hydrogen; and R$_6$ is hydrogen, methyl or —CF$_3$.

In certain embodiments, the present invention provides compounds of formula (IE), wherein,
ring A is

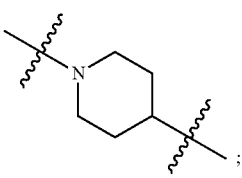 [SMILES: *C1CCN(*)CC1]

L is selected from

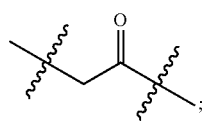

wherein,
the left side of the linker is attached with ring A and the right side of the linker is attached with Targeting Ligand (TL);

R$_1$ is phenyl substituted with hydroxyl or fluoro;
R$_5$ is hydrogen; and R$_6$ is hydrogen or methyl.

In certain embodiments, the present invention provides compounds of formula (IE), wherein,
ring A is

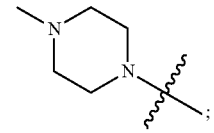 [SMILES: *N1CCN(C)CC1]

L is selected from

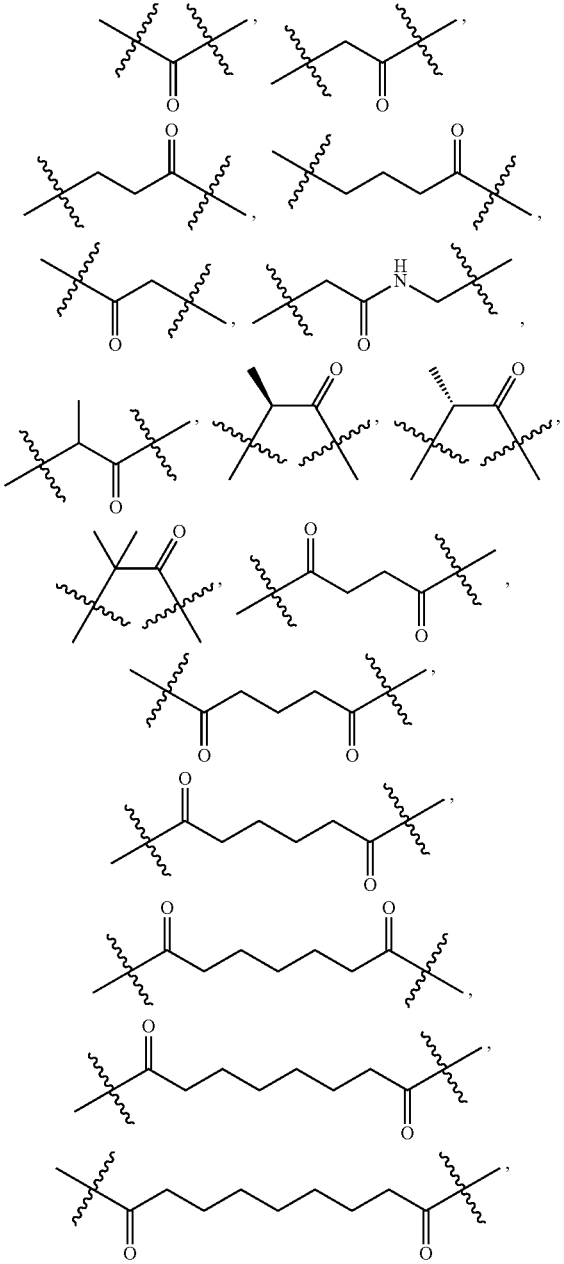

23

-continued

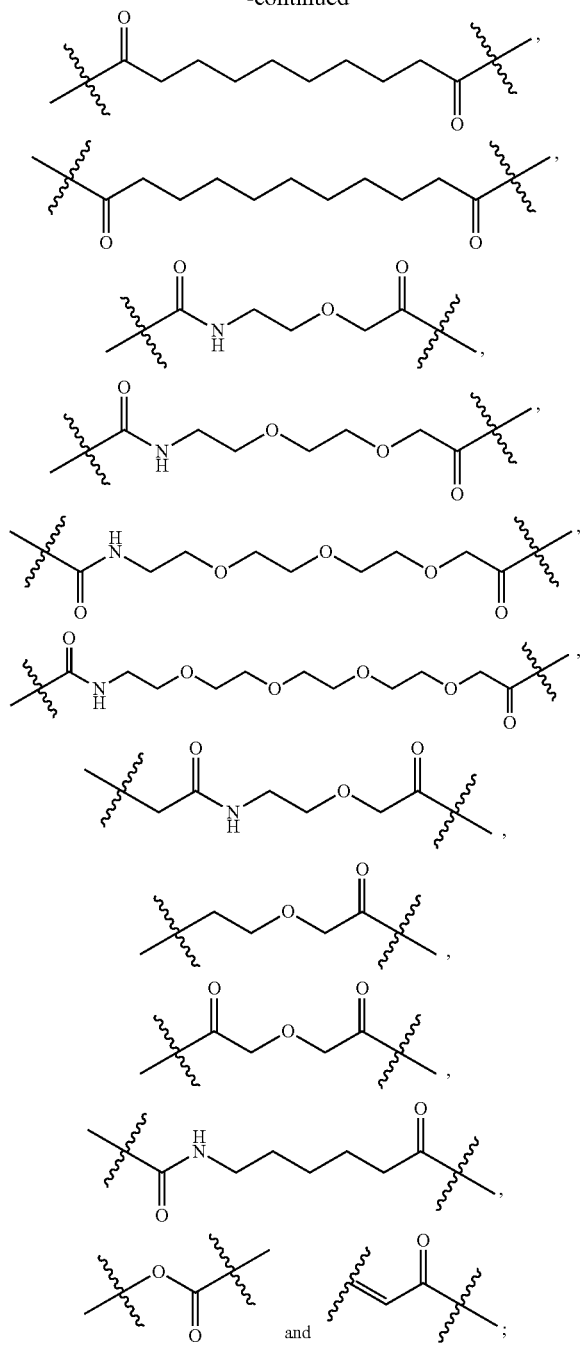

wherein,
the left side of the linker is attached with ring A and the right side of the linker is attached with Targeting Ligand (TL);
$R_1$ is chloro, —CH$_2$OH, —COOH, —COOCH$_3$, —CONH$_2$—CONHCH$_3$ or phenyl; wherein the phenyl is optionally substituted with fluoro, chloro, hydroxyl, —NH$_2$, —OCH$_3$, —ONa, —OCOCH$_3$, —COOH or methyl;
$R_5$ is hydrogen; and $R_6$ is hydrogen, methyl or —CF$_3$.

In certain embodiments, the present invention provides compounds of formula (IE), wherein,

24 ring A is;

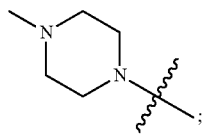 [SMILES: *N1CCN(C)CC1]

L is selected from

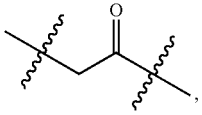

wherein,
the left side of the linker is attached with ring A and the right side of the linker is attached with Targeting Ligand (TL);
$R_1$ is phenyl substituted with hydroxyl;
$R_5$ is hydrogen; and $R_6$ is hydrogen or methyl.

In certain embodiments, the present invention provides compounds of formula (IE), wherein,
ring A is

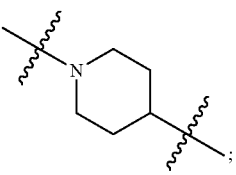 [SMILES: *C1CCN(*)CC1]

L is selected from

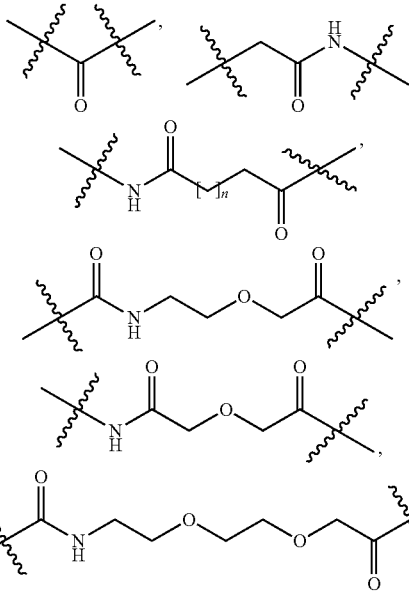

-continued

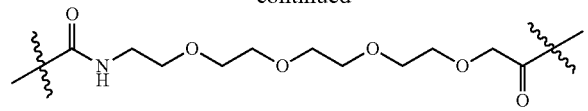

and

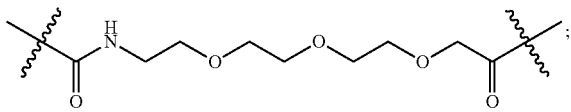

wherein,
   the left side of the linker is attached with ring A and the right side of the linker is attached with Targeting Ligand (TL);
   n is 2, 5 or 8;
   $R_1$ is phenyl substituted with hydroxy;
   $R_5$ is hydrogen; and $R_6$ is hydrogen or methyl.

In certain embodiments, the present invention provides compounds of formula (IE), wherein,
   ring A is

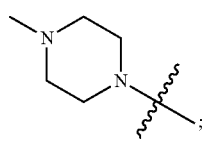 [SMILES: *N1CCN(C)CC1]

L is selected from

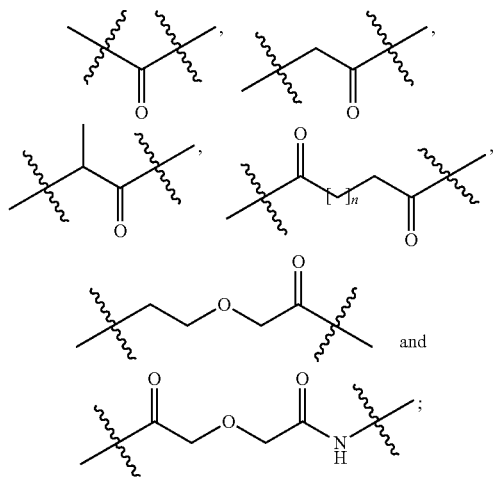

wherein,
   the left side of the linker is attached with ring A and the right side of the linker is attached with Targeting Ligand (TL);
   n is 1, 2, 5, or 8;
   $R_1$ is chloro or phenyl; wherein the phenyl is optionally substituted with fluoro, hydroxyl or alkoxy;
   $R_5$ is hydrogen or acyl; and $R_6$ is hydrogen or methyl.

In yet another embodiment of the present invention, it provides compounds of formula (IF),

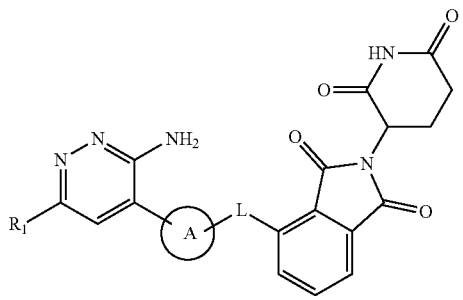

or a pharmaceutically acceptable salt thereof or a stereoisomer thereof;
   wherein, $R_1$, ring A and L are same as defined in formula (I).

In certain embodiments, the present invention provides compounds of formula (IF), wherein,
   ring A is

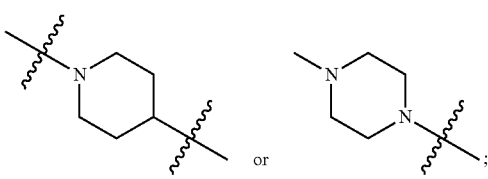

L is selected from the group consisting of:

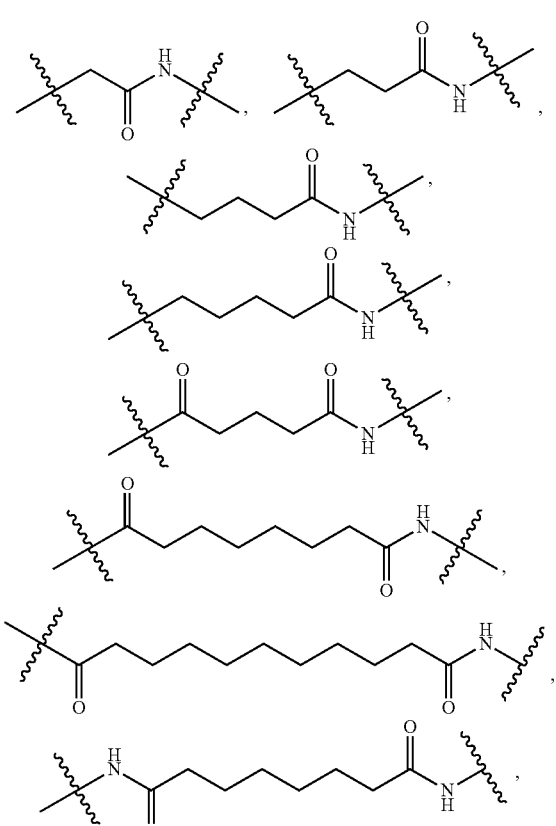

-continued

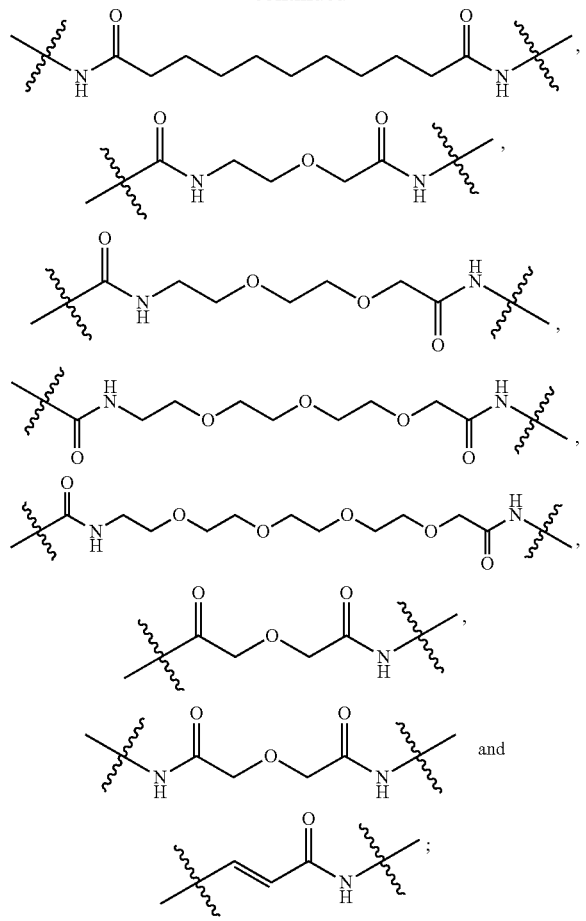

and wherein,
the left side of the linker is attached with ring A and the right side of the linker is attached with Targeting Ligand (TL); and
$R_1$ is phenyl optionally substituted with fluoro, chloro, hydroxyl, —NH$_2$, —OCH$_3$, —ONa, —OCOCH$_3$, —COOH or methyl.

In certain embodiments, the present invention provides compounds of formula (IF), wherein,
ring A is

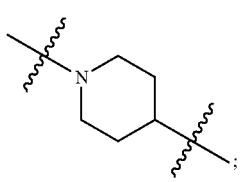 [SMILES: *C1CCN(*)CC1]

L is selected from the group consisting of:

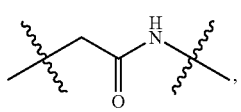

-continued

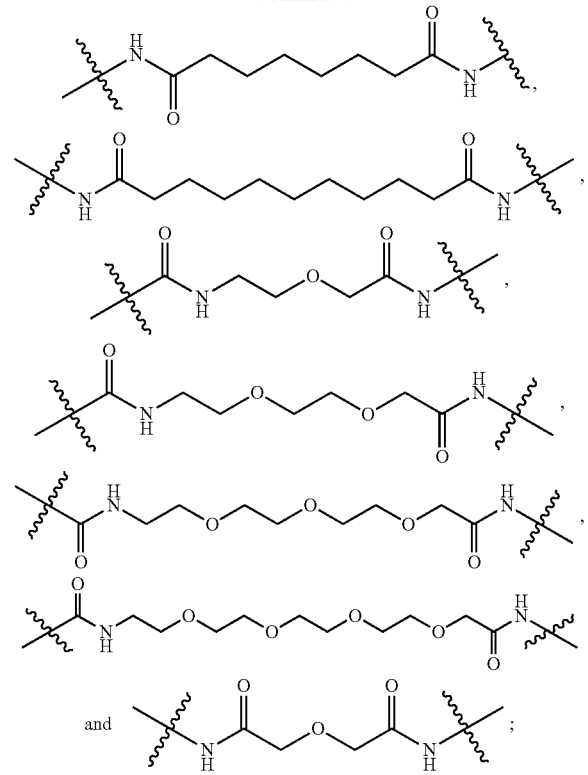

and 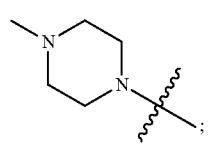;

wherein,
the left side of the linker is attached with ring A and the right side of the linker is attached with Targeting Ligand (TL); and
$R_1$ is phenyl substituted with hydroxyl.

In certain embodiments, the present invention provides compounds of formula (IF), wherein,
ring A is L is selected from the group consisting of:

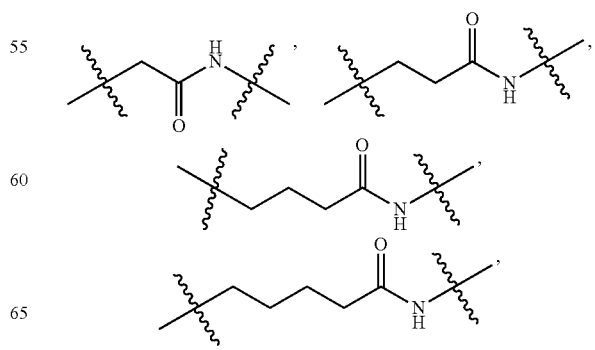

-continued

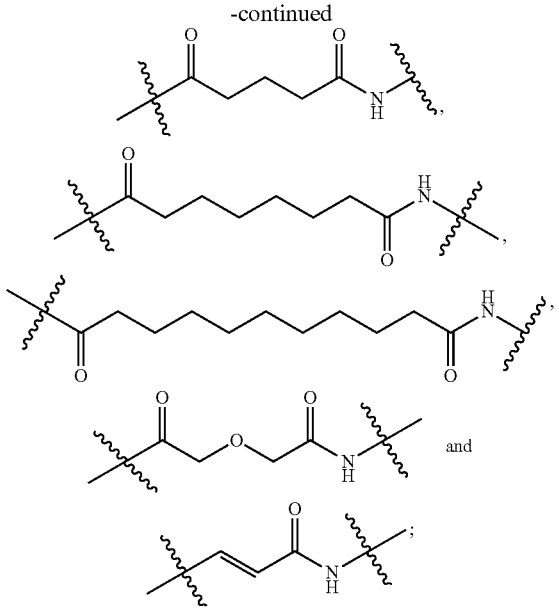

wherein,
the left side of the linker is attached with ring A and the right side of the linker is attached with Targeting Ligand (TL); and R₁ is phenyl substituted with hydroxyl.

In certain embodiments, the present invention provides compounds of formula (IF), wherein,
ring A is

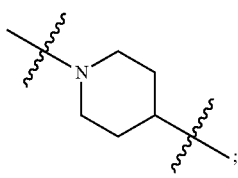 [SMILES: *C1CCN(*)CC1]

L is selected from the group consisting of:

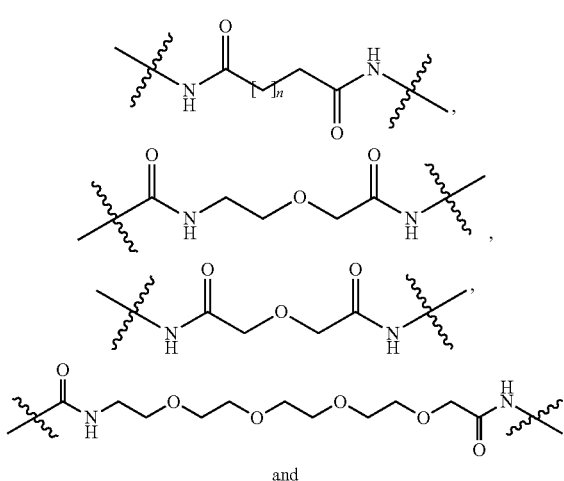

and

-continued

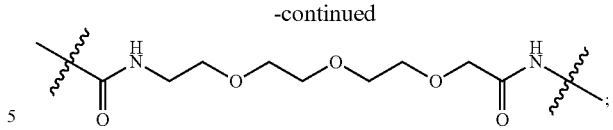

wherein
the left side of the linker is attached with ring A and the right side of the linker is attached with Targeting Ligand (TL);
n is 5; and
R₁ is phenyl substituted with hydroxyl.

In certain embodiments, the present invention provides compounds of formula (IF), wherein,
A is

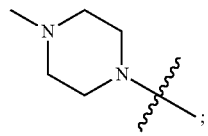 [SMILES: *N1CCN(C)CC1]

L is selected from the group consisting of:

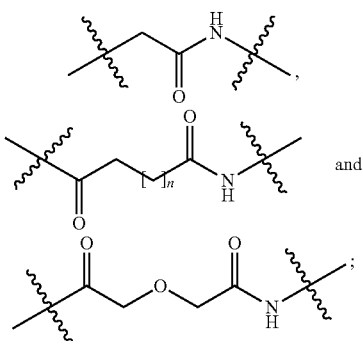

wherein,
the left side of the linker is attached with ring A and the right side of the linker is attached with Targeting Ligand (TL);
n is 5; and
R₁ is phenyl substituted with hydroxyl.

In yet another embodiment of the present invention, it provides compounds of formula (IG),

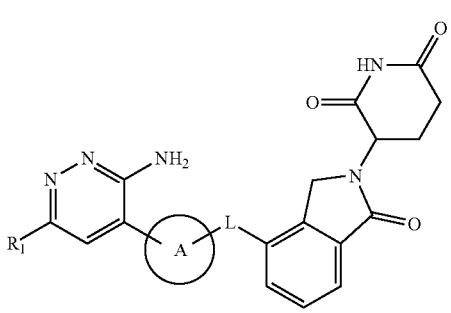

(IG)

or a pharmaceutically acceptable salt thereof or a stereoisomer thereof;

wherein, $R_1$, ring A and L are same as defined in formula (I).

In certain embodiments, the present invention provides compounds of formula (IG),
wherein,
ring A is

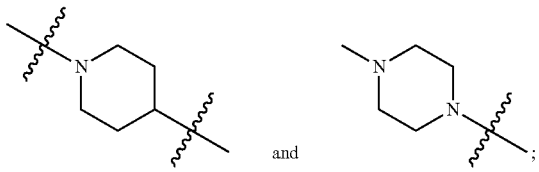

and

L is selected from the group consisting of:

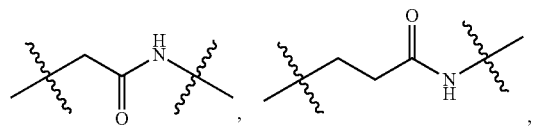

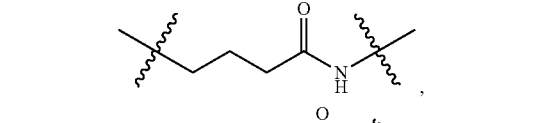

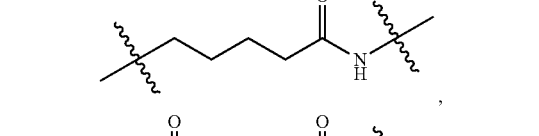

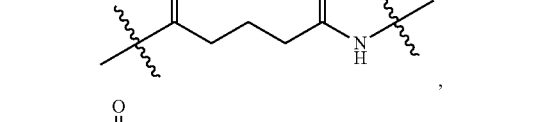

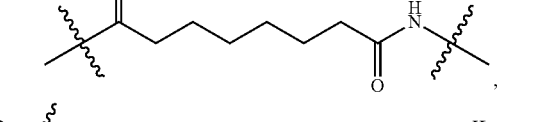

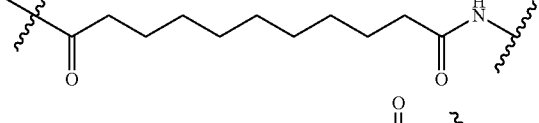

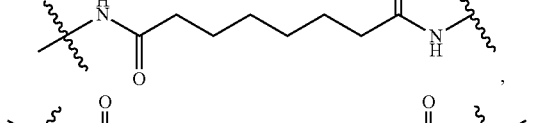

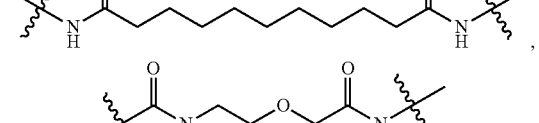

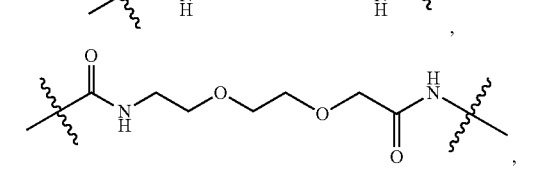

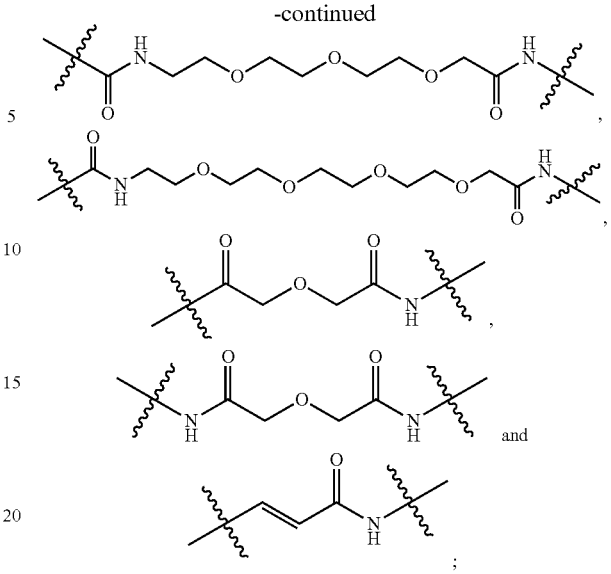

wherein,
the left side of the linker is attached with ring A and the right side of the linker is attached with Targeting Ligand (TL); and
$R_1$ is phenyl optionally substituted with fluoro, chloro, hydroxyl, —$NH_2$, —$OCH_3$, —ONa, —$OCOCH_3$, —COOH or methyl.

In certain embodiments, the present invention provides compounds of formula (IG), wherein,
ring A is

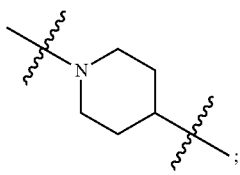 [SMILES: *C1CCN(*)CC1]

L is selected from the group consisting of:

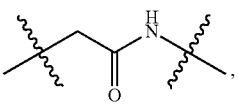

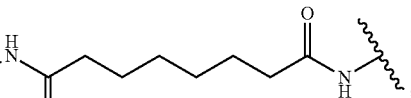

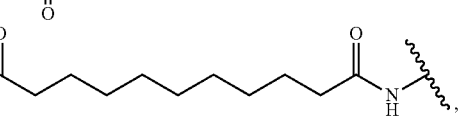

-continued

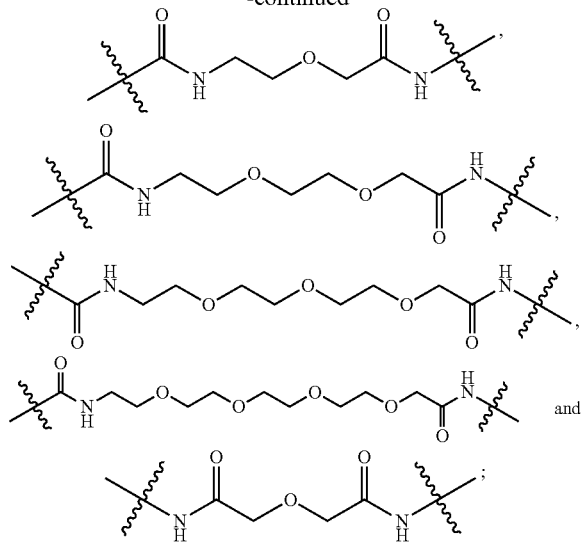

wherein,
the left side of the linker is attached with ring A and the right side of the linker is attached with Targeting Ligand (TL); and
$R_1$ is phenyl substituted with hydroxyl.

In certain embodiments, the present invention provides compounds of formula (IG), wherein,
ring A is

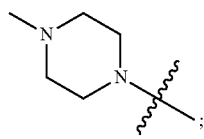 [SMILES: *N1CCN(C)CC1]

L is selected from the group consisting of:

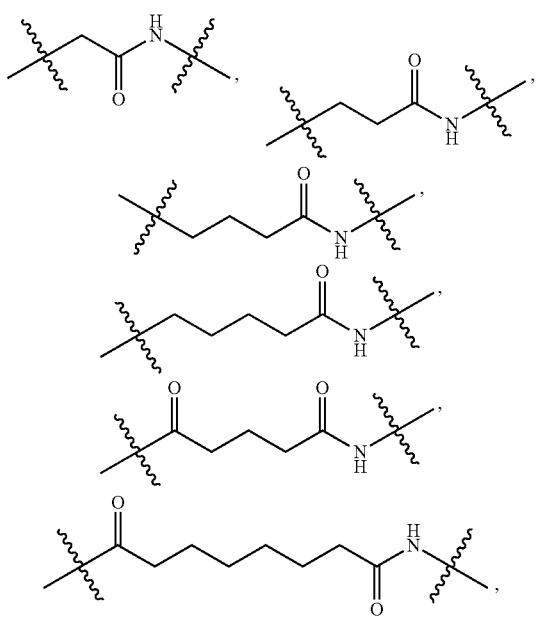

-continued

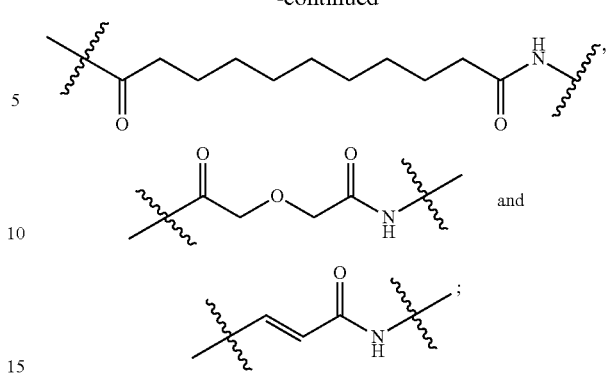

wherein,
the left side of the linker is attached with ring A and the right side of the linker is attached with Targeting Ligand (TL); and
$R_1$ is phenyl substituted with hydroxyl.

In certain embodiments, the present invention provides compounds of formula (IG), wherein,
ring A is

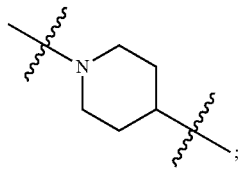 [SMILES: *C1CCN(*)CC1]

L is selected from the group consisting of:

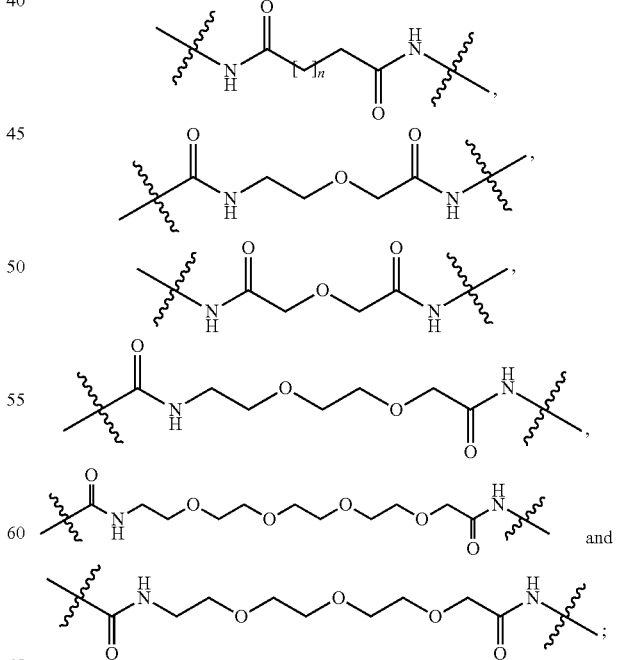

wherein,
the left side of the linker is attached with ring A and the right side of the linker is attached with Targeting Ligand (TL);
n is 5 or 8; and
$R_1$ is phenyl substituted with hydroxyl.

In certain embodiments, the present invention provides compounds of formula (IG), wherein,
ring A is

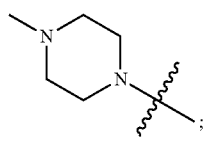 [SMILES: *N1CCN(C)CC1]

L is selected from the group consisting of:

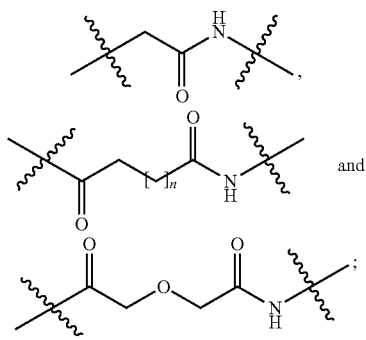

wherein
the left side of the linker is attached with ring A and the right side of the linker is attached with Targeting Ligand (TL);
n is 2, 5, or 8; and
$R_1$ is phenyl substituted with hydroxyl.

In certain embodiment, specifically provided are compounds of formula (I), wherein Targeting Ligand (TL) is,

TL-1

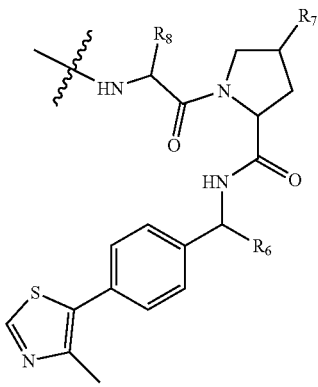

wherein,
$R_6$ is selected from hydrogen, alkyl and haloalkyl;
$R_7$ is selected from —O—$R_5$ and halo; wherein $R_5$ is selected from hydrogen, alkyl, acyl and Na; and
$R_8$ is selected from hydrogen and alkyl.

In certain further embodiment, specifically provided are compounds of formula (I), wherein
$R_6$ is selected from hydrogen, methyl and —$CF_3$;
$R_7$ is selected from hydroxy, —$OCH_3$, —$OCOCH_3$, —ONa and fluoro; and
$R_8$ is selected from hydrogen, methyl, isopropyl and tert-butyl.

In certain embodiments, the present invention provides compounds of formula (IE), wherein,
A is

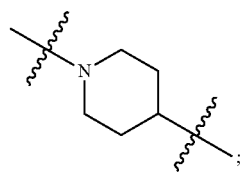 [SMILES: *C1CCN(*)CC1]

L is selected from

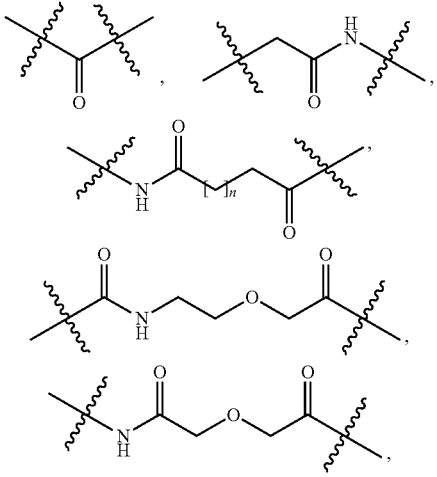

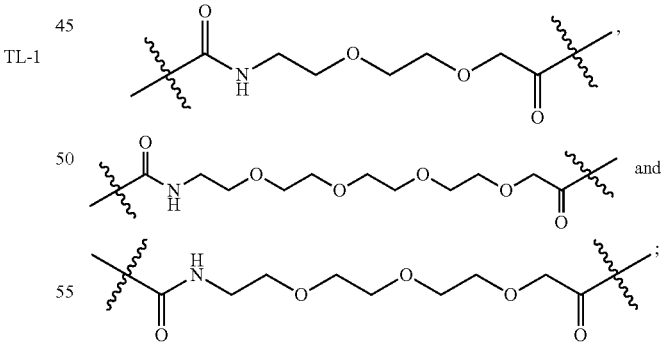

wherein,
the left side of the linker is attached with ring A and the right side of the linker is attached with Targeting Ligand (TL);
n is 2, 5 or 8;
$R_1$ is phenyl substituted with hydroxy;
$R_5$ is hydrogen; and $R_6$ is hydrogen or methyl.

In certain embodiments, the present invention provides compounds of formula (IE), wherein, A is

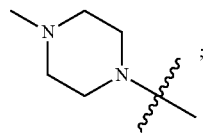

L is selected from

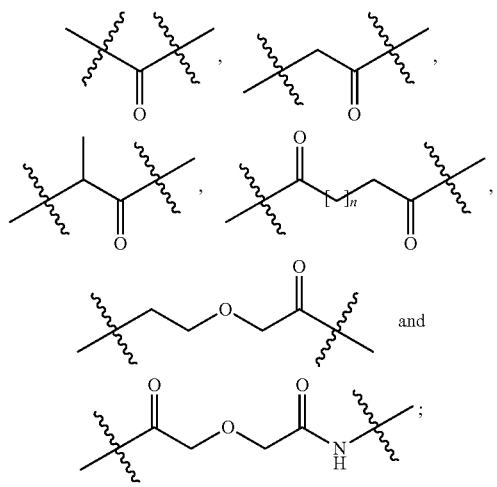

wherein,
the left side of the linker is attached with ring A and the right side of the linker is attached with Targeting Ligand (TL);
n is 1, 2, 5, or 8;
$R_1$ is chloro or phenyl; wherein the phenyl is optionally substituted with fluoro, hydroxyl or alkoxy;
$R_5$ is hydrogen or acyl; and $R_6$ is hydrogen and methyl.

In certain embodiment, specifically provided are compounds of formula (I), wherein Targeting Ligand-1A (TL-1A) is,

TL-1

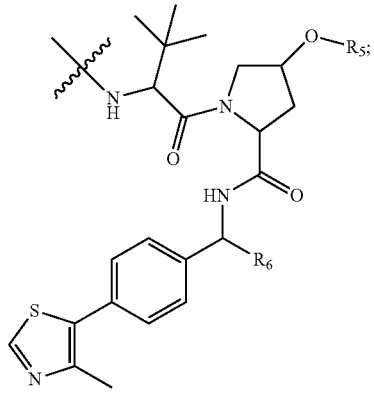

TL-4

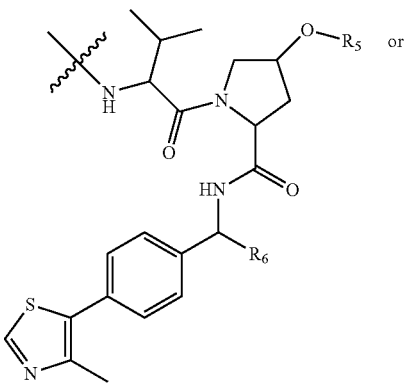

or

TL-5

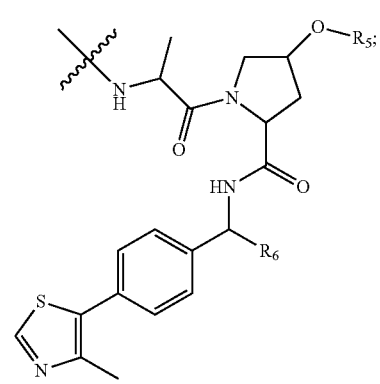

wherein,
$R_5$ is selected from hydrogen, alkyl, acyl and —Na; and
$R_6$ is selected from hydrogen, alkyl and haloalkyl.

In certain embodiment, specifically provided are compounds of formula (I), wherein Targeting Ligand (TL) is,

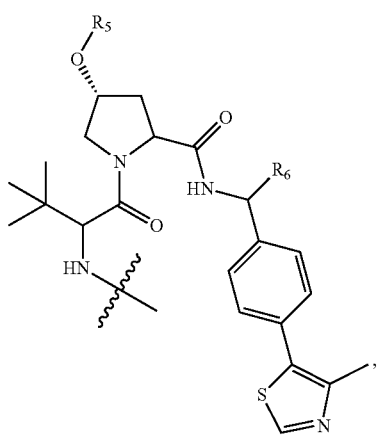

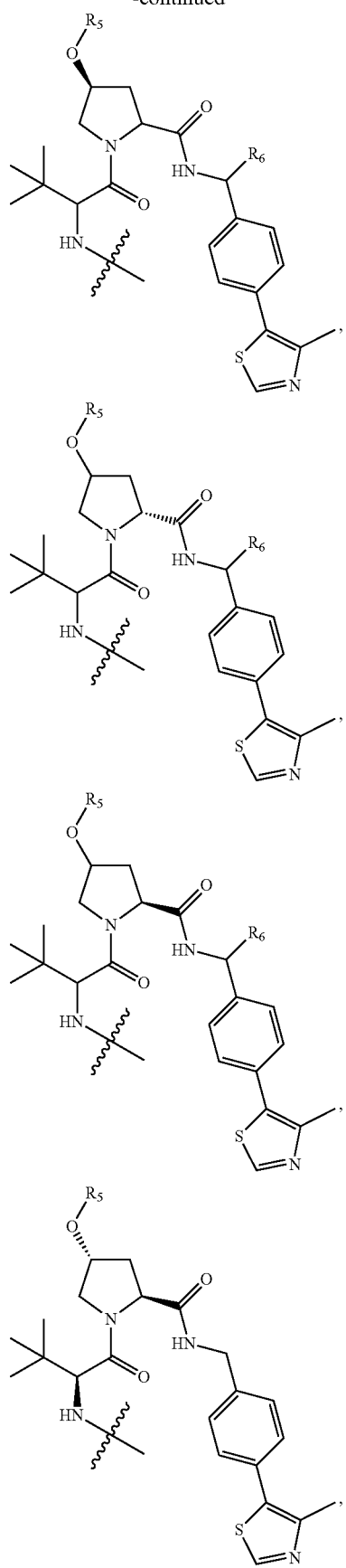
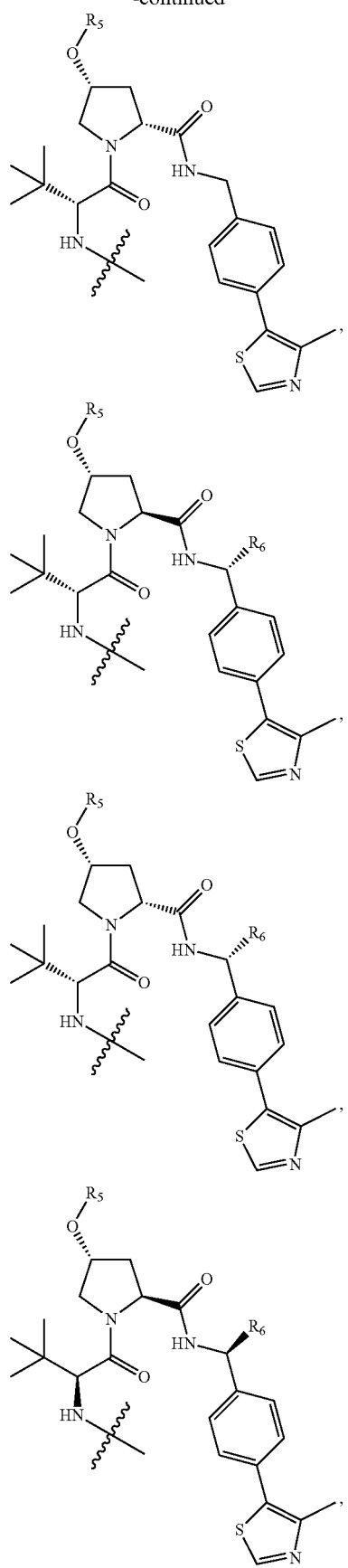

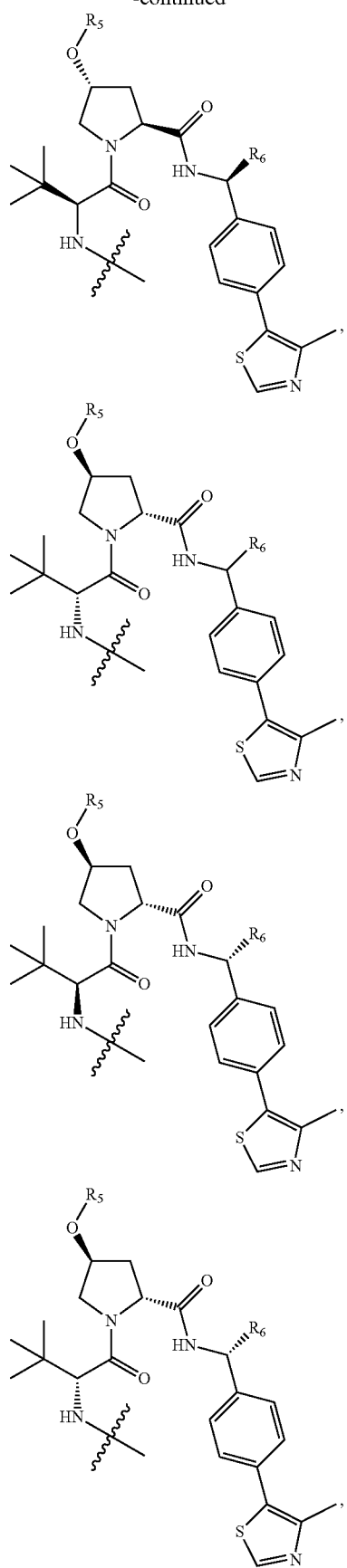
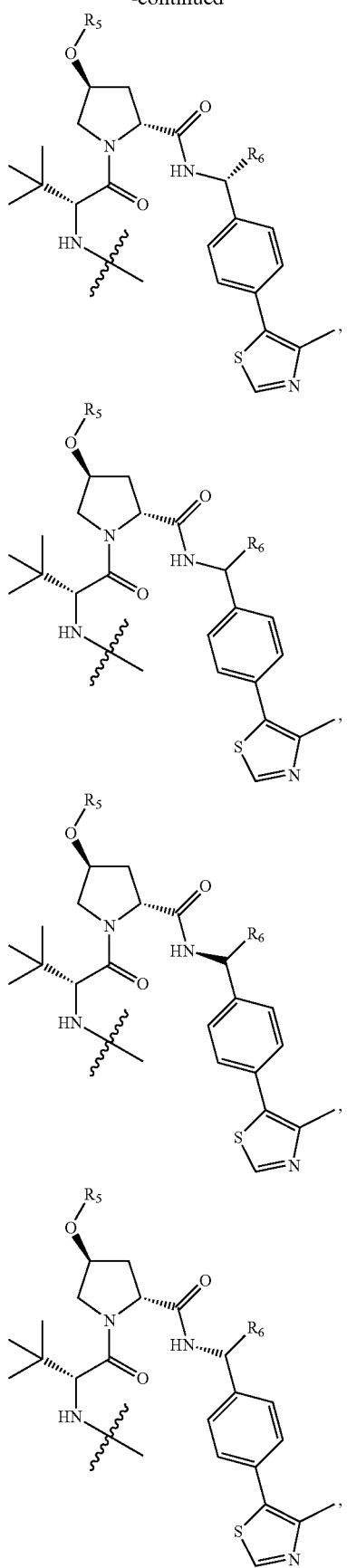

-continued
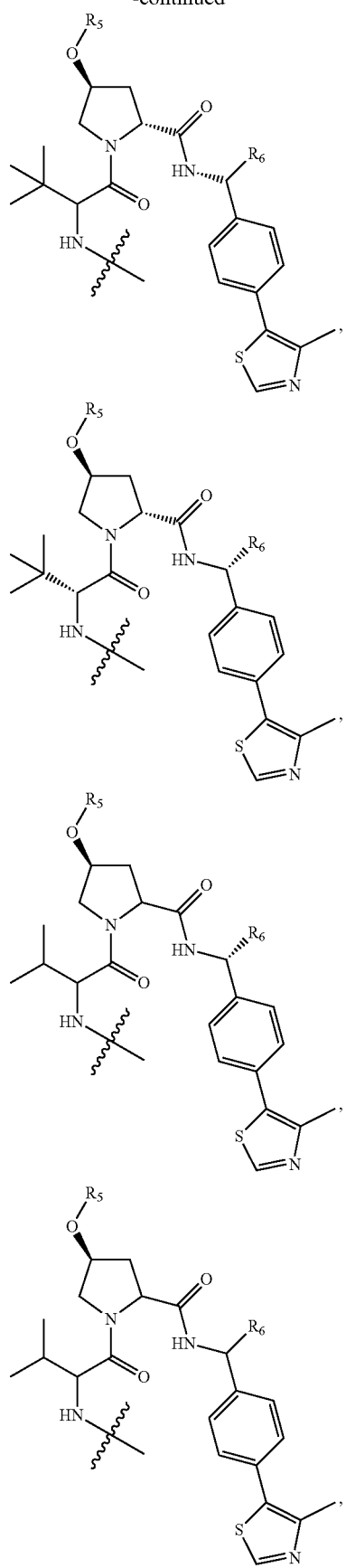
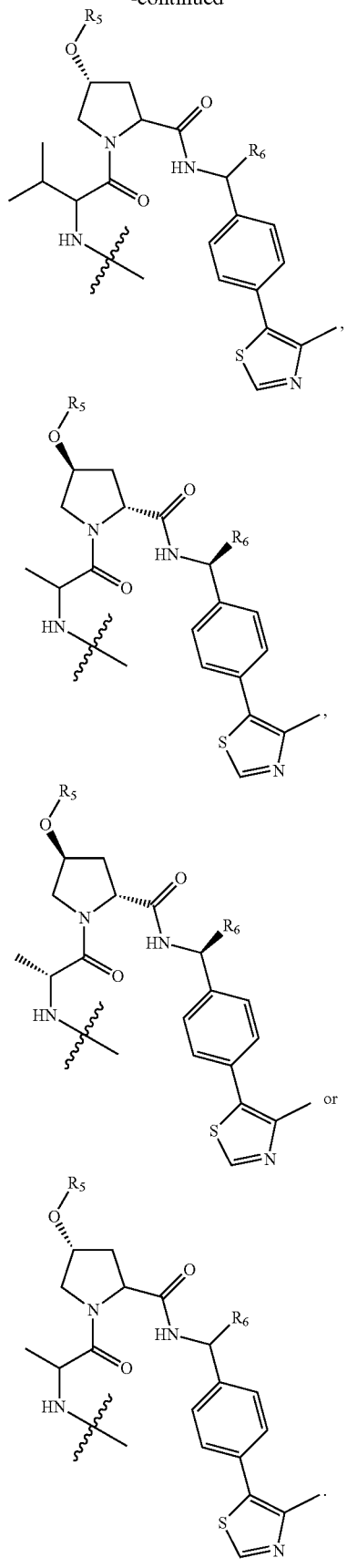
or wherein,

R₅ is selected from hydrogen, alkyl, acyl and —Na; and

R₆ is selected from hydrogen, alkyl and haloalkyl.

In certain embodiment, specifically provided are compounds of formula (I), wherein Targeting Ligand (TL) is,

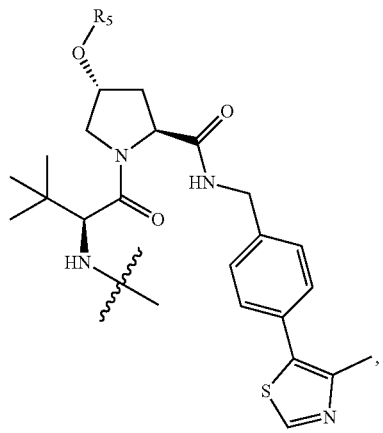

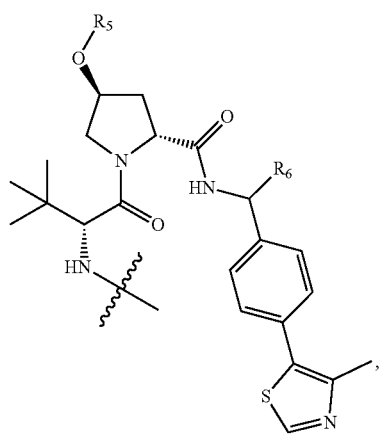

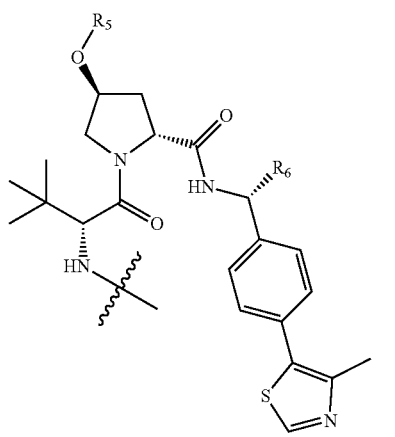

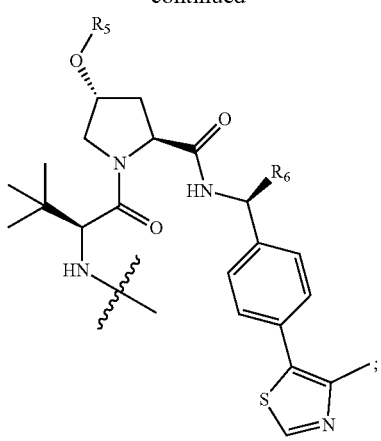

wherein, R₅ and R₆ are same as defined in formula (I).

In certain embodiment, specifically provided are compounds of formula (I), wherein Targeting Ligand-1 (TL-1) is,

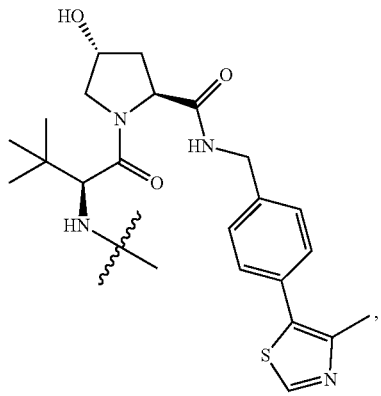

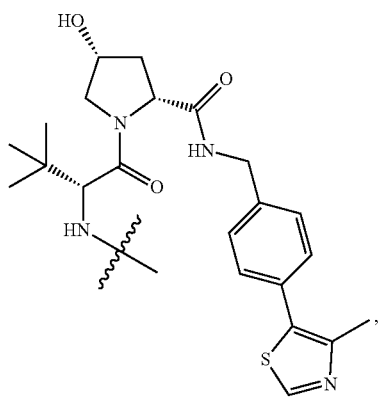

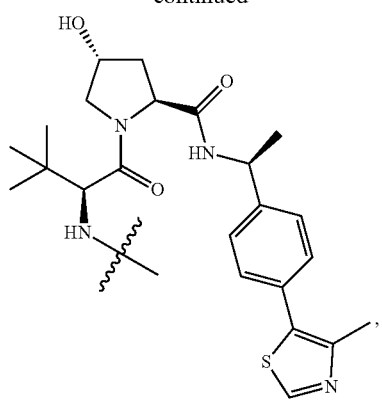
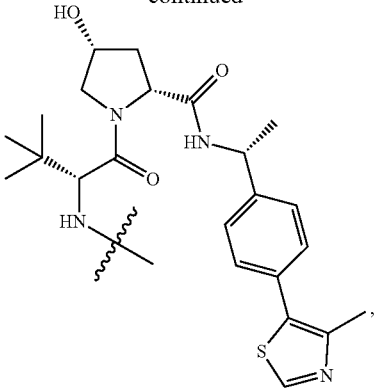
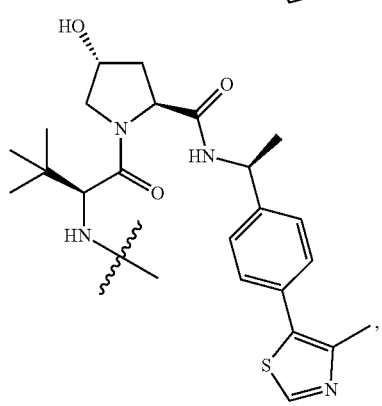
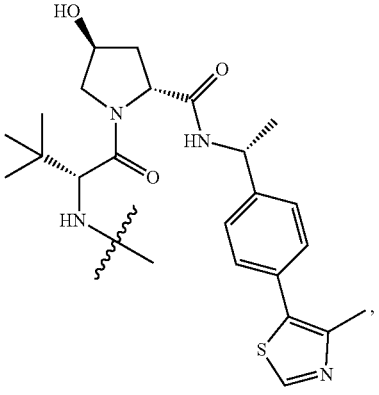
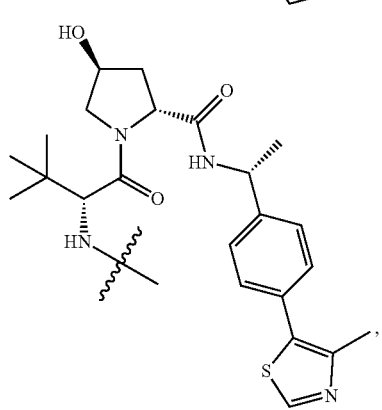
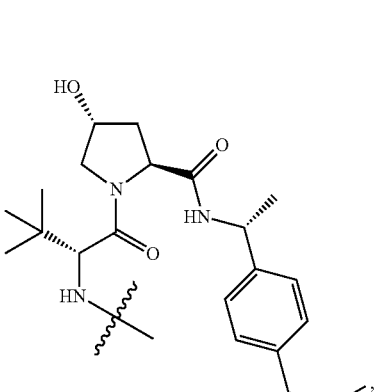
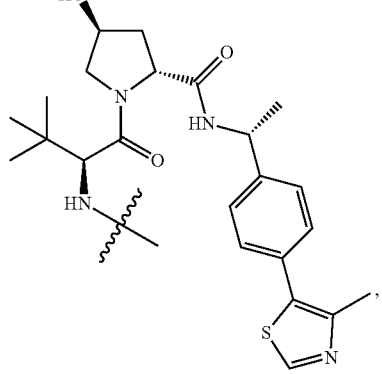
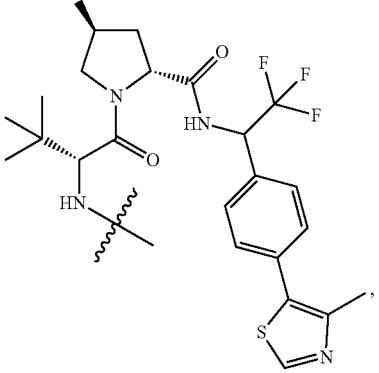

49
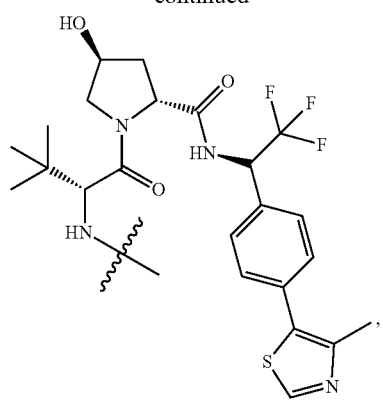
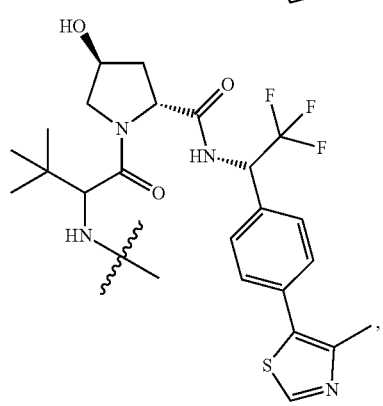
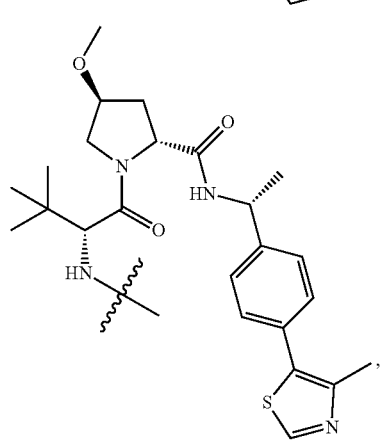
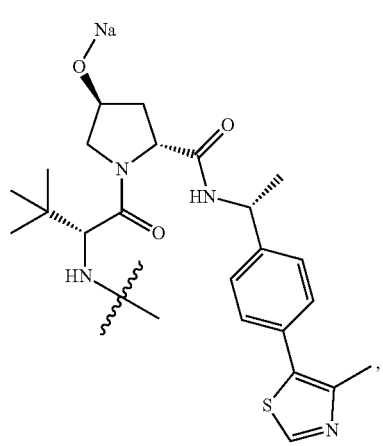
50
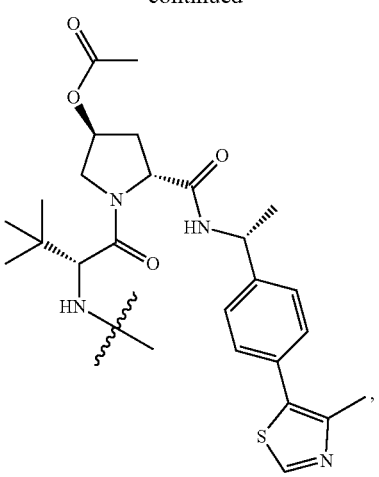
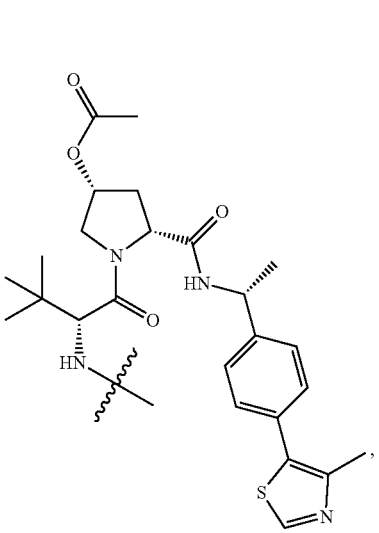
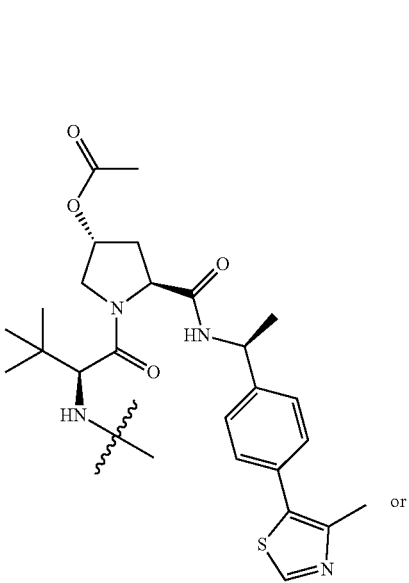
or

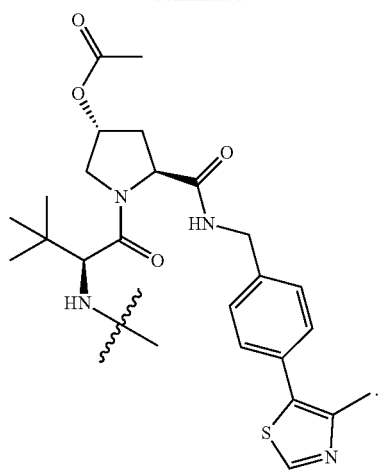
In certain embodiment, specifically provided are compounds of formula (I), wherein Targeting Ligand (TL) is,
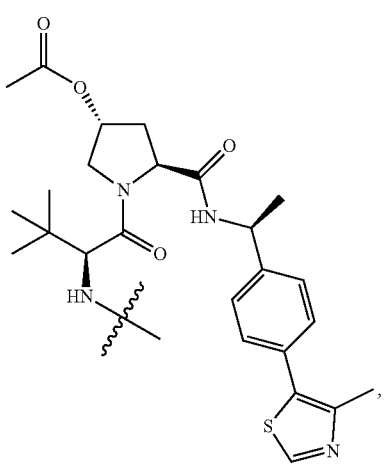
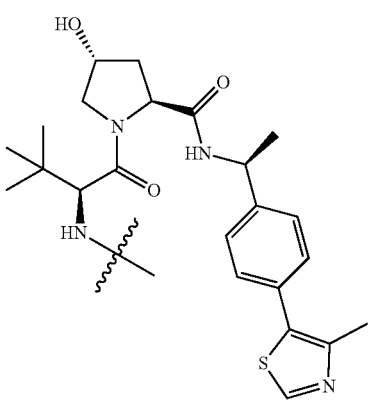
or
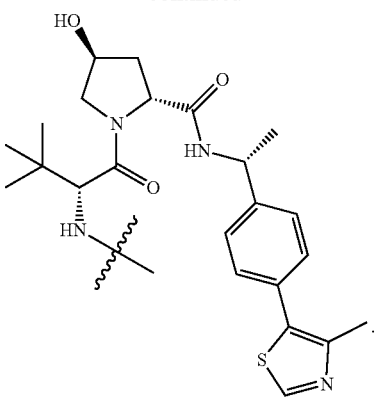
In certain embodiment, specifically provided are compounds of formula (I), wherein Targeting Ligand (TL) is,
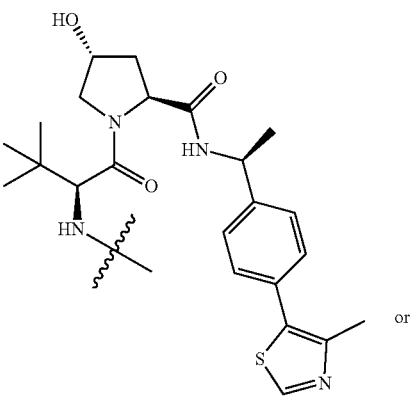
or
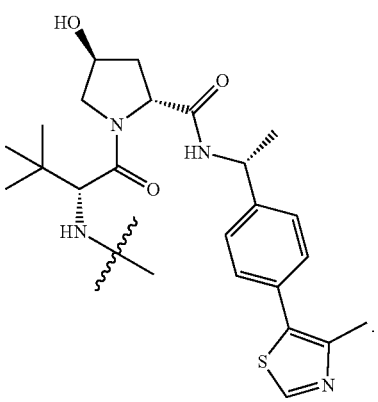
In certain embodiment, specifically provided are compounds of formula (I), wherein Targeting Ligand (TL) is, In yet another embodiment, specifically provided are compounds of formula (I), wherein L is selected from the group consisting of:

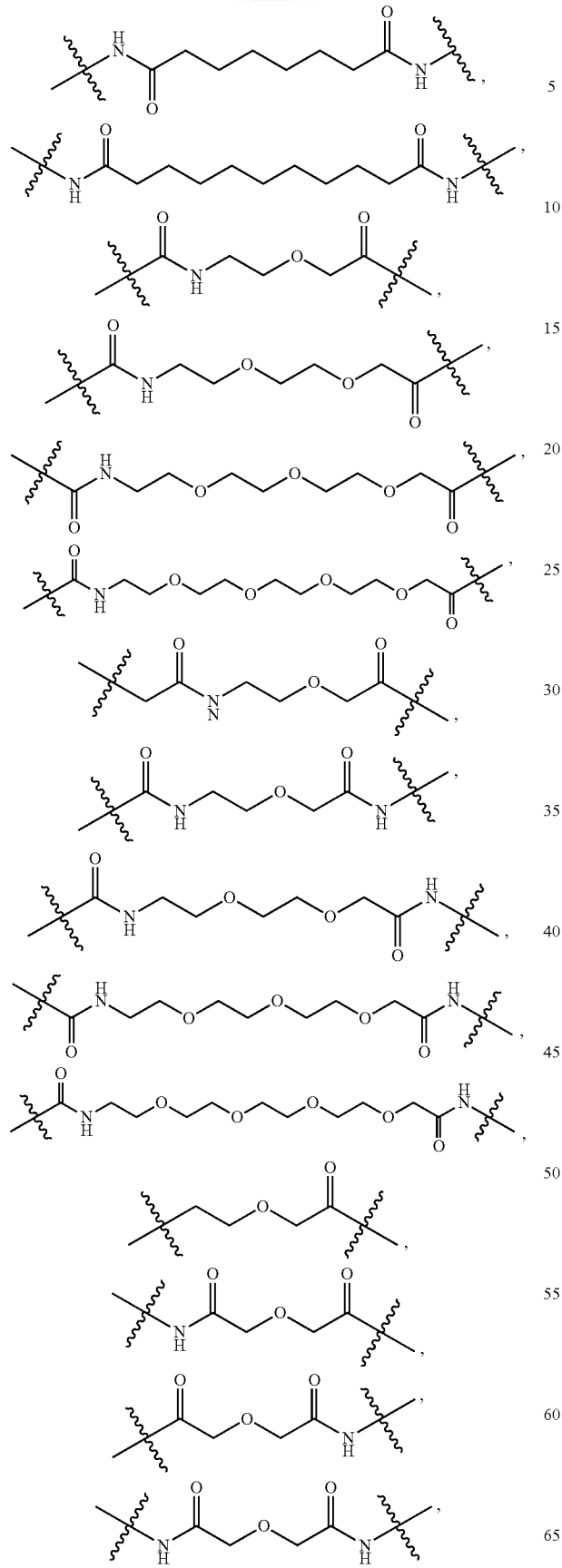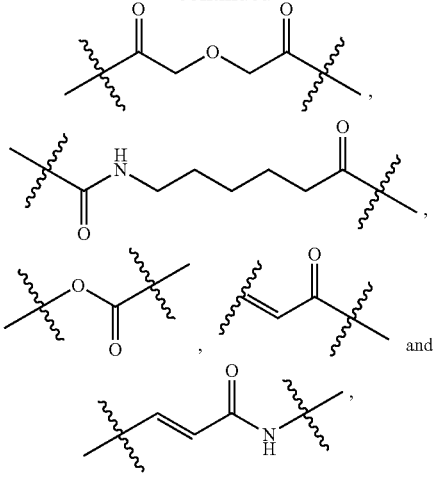
wherein, the left side of the linker is attached with ring A and the right side of the linker is attached with Targeting Ligand.
In certain embodiment, specifically provided are compounds of formula (I), wherein L is selected from the group consisting of:
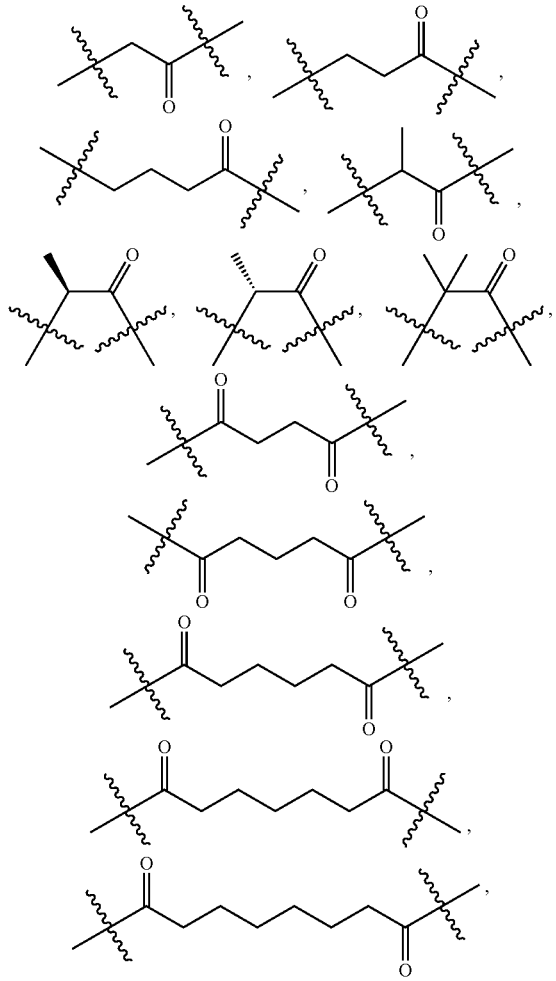

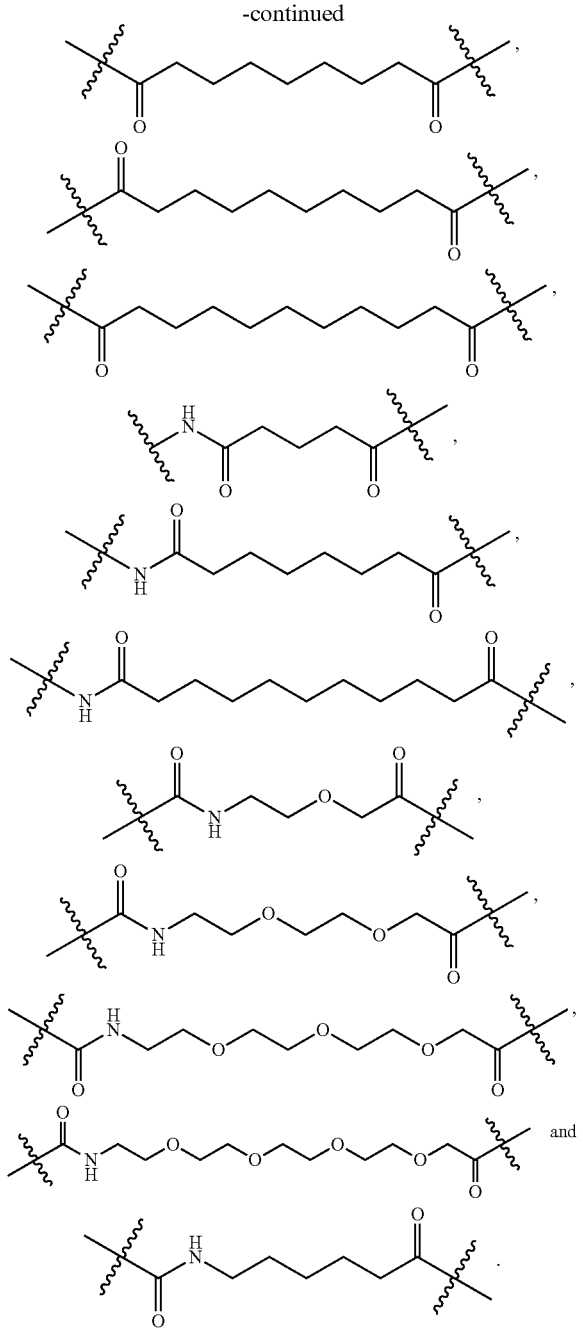

In certain embodiment, specifically provided are compounds of formula (I), wherein L is selected from the group consisting of:

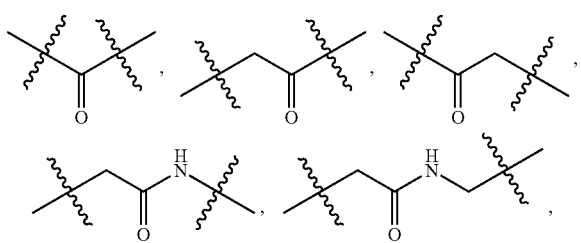

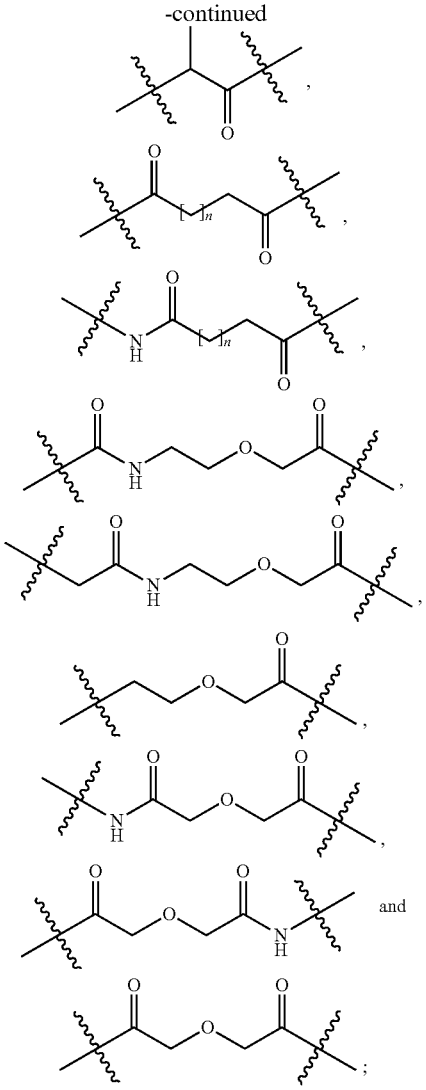

wherein,
the left side of the linker is attached with ring A and the right side of the linker is attached with Targeting Ligand (TL); and
'n' is 0 to 8.

In yet another embodiment, $R_1$ is hydrogen, halo, hydroxyalkyl, —COOR$_a$—CON(R$_a$)$_2$ or an optionally substituted aryl.

In certain embodiment, $R_1$ is hydrogen, chloro, —CH$_2$OH, —COOH, —COOCH$_3$, —CONH$_2$ or —CONHCH$_3$.

In certain embodiment, $R_1$ is an optionally substituted monocyclic aryl ring; the said aryl is phenyl.

According to yet another embodiment, specifically provided are compounds of formula (I), wherein, $R_1$ is phenyl that is optionally substituted with flouro or methoxy.

In certain embodiment, phenyl is optionally substituted with one or more groups independently selected from hydroxy, alkoxy, halo, alkyl, amino, —O—Na, —COOR$_a$ and —OCOR$_a$; wherein R$_a$ is selected from hydrogen and alkyl.

In certain embodiment, the optionally substituted phenyl is

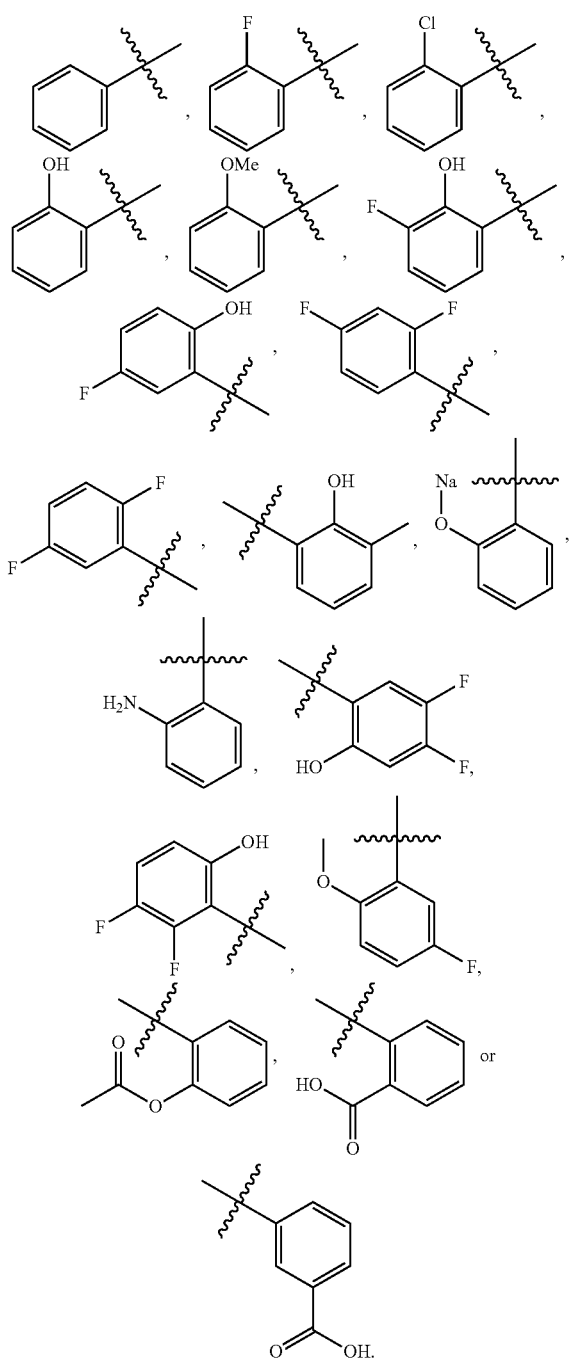

In yet another embodiment, R₂ is —NR₃R₄; wherein, R₃ and R₄ are independently selected from hydrogen and alkyl.

In certain embodiment, specifically provided are compounds of formula (I), wherein, R₂ is NH₂

In yet another embodiment, R₂ is —OR₃; wherein, R₃ is selected from hydrogen and alkyl.

In certain embodiment, specifically provided are compounds of formula (I), wherein, R₂ is OH.

According to yet another embodiment, specifically provided are compounds of formula (I), wherein, ring A is an optionally substituted 4-10 membered monocyclic or bicyclic heterocyclic ring.

In yet another embodiment, ring A is heterocyclic ring containing 1 to 3 heteroatoms independently selected from N, O or S.

In certain embodiment, wherein the said heterocyclic ring is hetero aryl or heterocycloalkyl.

In certain embodiment, ring A is 5- or 6-membered heterocyclic ring containing 1 to 3 heteroatoms independently selected from N, O or S.

In certain embodiment, ring A is 6-membered heterocyclic ring containing 1 to 2 N atoms.

In certain embodiment, specifically provided are compounds of formula (I), wherein, wherein the said heterocycloalkyl is optionally substituted with hydoxy.

In certain embodiment, specifically provided are compounds of formula (I), wherein, ring A is

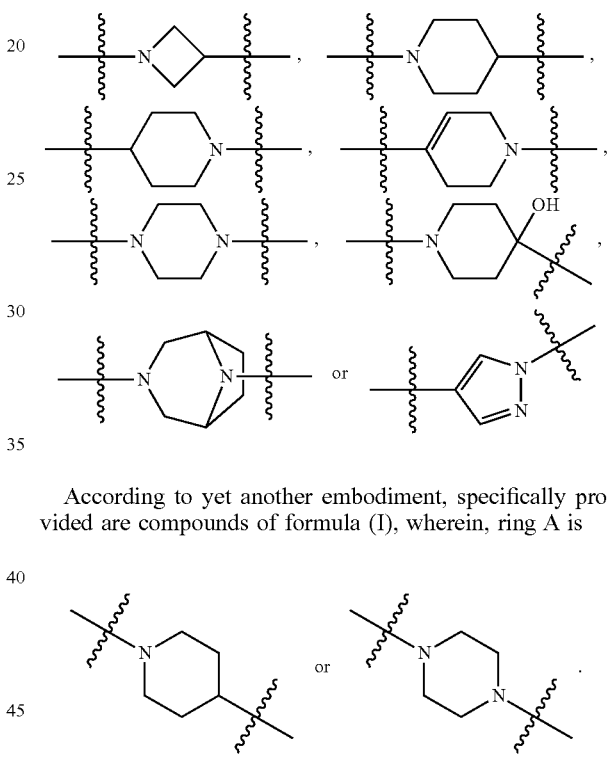

According to yet another embodiment, specifically provided are compounds of formula (I), wherein, ring A is

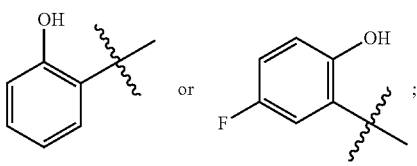 [SMILES: *c1ccccc1O ; *c1cc(F)ccc1O]

In certain embodiments, n is 1, 2, 5, or 8.
In certain embodiments, n is 2, 5, or 8.
In certain embodiments, R₅ is hydrogen or acyl.
In certain embodiments, R₆ is hydrogen or alkyl.
According to yet another embodiment, specifically provided are compounds of formula (I), wherein,
R₁ is an optionally substituted phenyl; the said phenyl is R₂ is —NH₂;

Ring A is

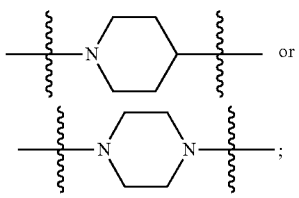

Targeting Ligand (TL) is

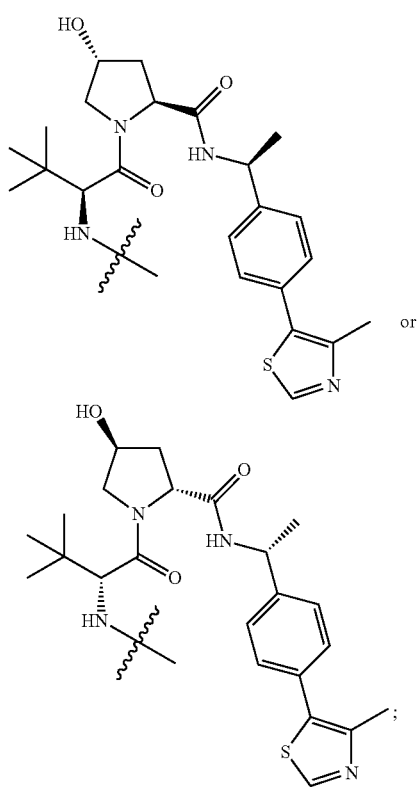

L is

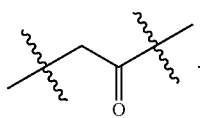 [SMILES: *CC(*)=O]

In yet another embodiment, the present invention provides a compound of formula (I),

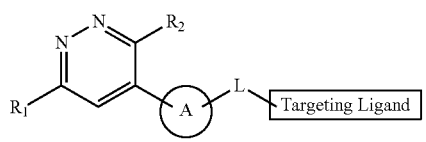

or a pharmaceutically acceptable salt thereof or a stereoisomer thereof; for use in the treatment of cancer, wherein,
- $R_1$ is hydrogen, halo, alkyl, alkenyl, alkoxy, hydroxy, hydroxyalkyl, —COOR$_a$, —CON(R$_a$)$_2$ or aryl; wherein, the aryl is optionally substituted with one or more groups independently selected from hydroxy, alkoxy, halo, alkyl, amino, —O—Na, —COOR$_a$ and —OCOR$_a$; wherein R$_a$ at each occurance is selected from hydrogen and alkyl;
- $R_2$ is —NR$_3$R$_4$ or —OR$_3$; wherein, R$_3$ and R$_4$ are independently selected from hydrogen and alkyl;
- Ring A is heterocyclic ring optionally substituted with one or more groups independently selected from hydroxy, halo and alkyl;
- L is a linker, selected from the group consisting of:

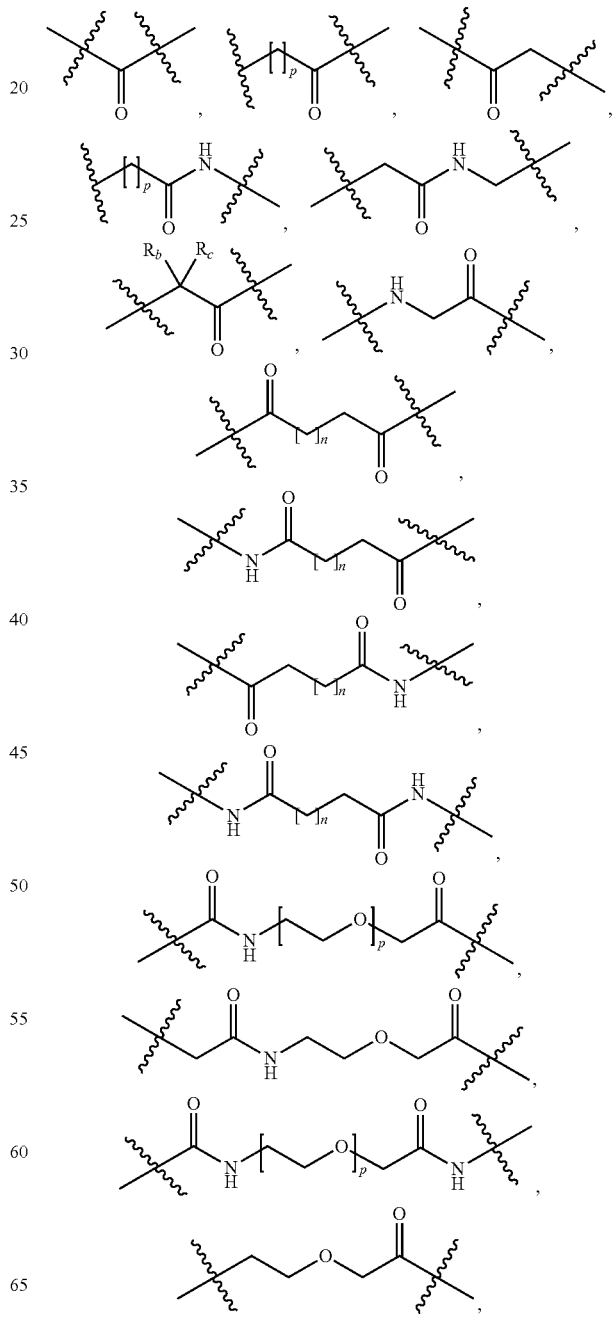

-continued

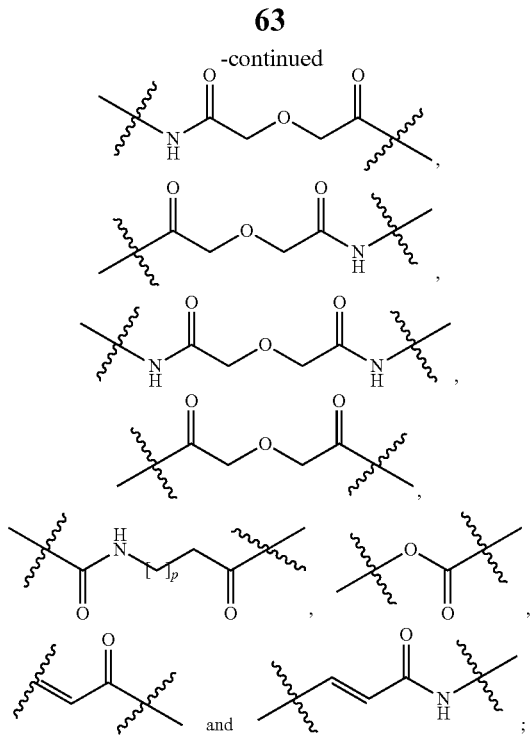

wherein,
the left side of the linker is attached with ring A and the right side of the linker is attached with Targeting Ligand (TL);
$R_b$ is hydrogen or alkyl;
$R_c$ is alkyl;
'n' is 0 to 10 and 'p' is 1 to 5;
Targeting Ligand (TL) is selected from the group consisting of:

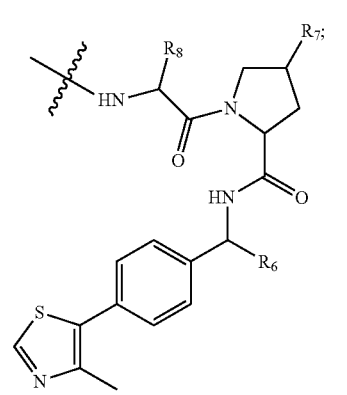

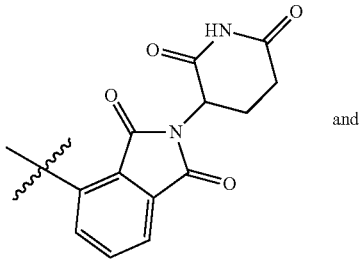

-continued

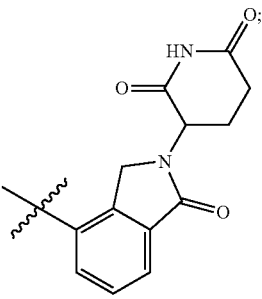

wherein,
$R_6$ is selected from hydrogen, alkyl, acyl and haloalkyl;
$R_7$ is selected from —O—$R_5$ and halo; wherein $R_5$ is selected from hydrogen, alkyl, acyl and Na; and
$R_8$ is selected from hydrogen and alkyl.

In certain embodiment, the present invention provides a pharmaceutical composition comprising a compound of formula (I), or a pharmaceutically acceptable salt thereof or a stereoisomer thereof as described herein and at least one pharmaceutically acceptable excipient (such as a pharmaceutically acceptable carrier or diluent). Preferably, the pharmaceutical composition comprises a therapeutically effective amount of at least one compound described herein. The compounds described in the present invention may be associated with a pharmaceutically acceptable excipient (such as a carrier or a diluent) or be diluted by a carrier or enclosed within a carrier which can be in the form of a capsule, sachet, paper or other container.

In certain embodiment, the present invention provides a pharmaceutical composition comprising a compound of formula (I), for use in degrading a target protein in a cell comprising contacting the cell with an effective amount of the compound, wherein the compound effectuates the degradation of the target protein.

In certain embodiment, A method of degrading a target protein comprising administering to a cell therapeutically effective amount of a compound of formula (I) or a pharmaceutically acceptable salt or a stereoisomer thereof, wherein the compound is effective for degrading the target protein.

In certain embodiment, wherein the target protein is SMARCA2/4.

In certain embodiment, the present invention provides a pharmaceutically acceptable salt or a stereoisomer thereof, for use as a medicament.

In certain embodiment, the present invention provides a pharmaceutical composition comprising a compound of formula (I), for use in the manufacture of a medicament for treating or preventing a disease or disorder in which SMARCA2/4 plays a role.

In certain embodiment, the present invention provides a pharmaceutical composition comprising a compound of formula (I), for use in treating or preventing of a disease or disorder in which SMARCA2/4 plays a role.

In certain embodiment, the present invention provides a method for treating a diseases or disorders dependent on SMARCA2/4, in a subject comprising administering a compound of formula (I), or a pharmaceutically acceptable salt thereof or a compound disclosed herein or a pharmaceutically acceptable salt thereof to the subject.

In certain embodiments, the diseases or disorders dependent on SMARCA2/4, include cancer.

In certain further embodiment, diseases or disorders dependent on SMARCA2/4, are cancers, including, but not limited to hematologic cancers, lung cancer (lung cancer is NSCLC i.e. nonsmall cell lung cancer), acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, liver cancer, lymphagioendotheliosarcoma, lymphangiosarcoma, lymphoblastic leukemia, lymphoma (Hodgkin's and non-Hodgkin's; Burkitt's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, malignant rhabdoid tumor (MRT), rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In certain further embodiment, the cancer is a SMARCA2/4-dependent cancer.

In certain embodiment, the present invention provides a pharmaceutical composition comprising a compound of formula (I), for use in the manufacture of medicament for the treatment of diseases or disorders dependent upon SMARCA2/4.

In certain embodiment, the present invention provides a pharmaceutical composition comprising a compound of formula (I), for use in the diseases or disorders dependent upon SMARCA2/4 is cancer.

In certain embodiment, use of compound of formula (I), in the manufacture of medicament for the treatment of diseases or disorders dependent upon SMARCA2/4.

In certain embodiment, diseases or disorders dependent upon SMARCA2/4 is cancer.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous, or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, including but not limited to tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required.

Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this application, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Administration of the disclosed compounds and pharmaceutical compositions can be accomplished via any mode of administration for therapeutic agents. These modes include systemic or local administration such as oral, nasal, parenteral, intravenous, transdermal, subcutaneous, vaginal, buccal, rectal or topical administration modes.

Depending on the intended mode of administration, the disclosed compounds or pharmaceutical compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising one or more compounds of the present disclosure and a pharmaceutically acceptable carrier, such as, but not limited to, a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, one or more disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

One or more disclosed compounds or compositions can be delivered by parental administration. The parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present invention.

The singular forms "a", "an" and "the" encompass plural references unless the context clearly indicates otherwise.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as the event or circumstance where the alkyl is not substituted.

The term "substituted" refers to moieties having substituents replacing hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an oxo, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heteroaryl, a heterocycloalkyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

As used herein, the term "alkyl" refers to saturated aliphatic groups, including but not limited to $C_1$-$C_{10}$ straight-chain alkyl groups or $C_3$-$C_{10}$ branched-chain alkyl groups. Preferably, the "alkyl" group refers to $C_1$-$C_6$ straight-chain alkyl groups or $C_3$-$C_6$ branched-chain alkyl groups. Most preferably, the "alkyl" group refers to $C_1$-$C_4$ straight-chain alkyl groups or $C_3$-$C_8$ branched-chain alkyl groups. Examples of "alkyl" include, but are not limited to, methyl, ethyl, 1-propyl, 2-propyl, isopropyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl and 4-octyl. The "alkyl" group may be optionally substituted.

As used herein, the term "haloalkyl" refers to alkyl substituted with one or more halogen atoms, wherein the halo and alkyl groups are as defined above. Examples of "haloalkyl" include but are not limited to fluoromethyl, difluoromethyl, chloromethyl, trifluoromethyl and 2,2,2-trifluoroethyl.

As used herein, the term "hydroxylalkyl" or "hydroxyalkyl" refers to an alkyl group, as defined above, wherein one or more of the alkyl group's hydrogen atoms have been replaced with hydroxyl group. Examples of hydroxylalkyl moieties include but are not limited to —$CH_2OH$, —$CH_2CH_2OH$, —$CH_2CH_2CH_2OH$, —$CH_2CH(OH)$ $CH_2OH$, —$CH_2CH(OH)$ $CH_3$, —$CH(CH_3)CH_2OH$.

As used herein, the term "heterocycloalkyl" refers to a non-aromatic, saturated or partially saturated, bridged bicyclic, spirocyclic, monocyclic or polycyclic ring system of 3 to 15 member having at least one heteroatom or heterogroup selected from O, N, S, S(O), S(O)$_2$, NH or C(O) with the remaining ring atoms being independently selected from the group consisting of carbon, oxygen, nitrogen, and sulfur. The term "heterocycloalkyl" also refers to the bridged bicyclic ring system having at least one heteroatom or hetero group selected from O, N, S, S(O), S(O)$_2$, NH or C(O). Examples of "heterocycloalkyl" include, but are not limited to azetidinyl, oxetanyl, imidazolidinyl, pyrrolidinyl, oxazolidinyl, thiazolidinyl, pyrazolidinyl, tetrahydrofuranyl, piperidinyl, dihydropyridinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, isoindolinyl, oxoisoindolinyl, dioxoisoindolinyl, aza-bicyclooctanyl, diazabicyclooctanyl, azocinyl, chromanyl, isochromanyl xanthenyl, 2-oxa-6-azaspiro[3.3]heptanyl, thereof. Attachment of a heterocycloalkyl substituent can occur via either a carbon atom or a heteroatom. A heterocycloalkyl group can be optionally substituted with one or more suitable groups by one or more aforesaid groups. Preferably "heterocycloalkyl" refers to 5- to 6-membered ring selected from the group consisting of azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, and thiomorpholinyl thereof. All heterocycloalkyl are optionally substituted by one or more aforesaid groups.

As used herein, the term "heteroaryl" alone or in combination with other term(s) means a completely unsaturated ring system containing a total of 5 to 14 ring atoms. At least one of the ring atoms is a heteroatom (i.e., oxygen, nitrogen, or sulfur), with the remaining ring atoms/groups being independently selected from carbon, oxygen, nitrogen or sulfur. A heteroaryl may be a single-ring (monocyclic) or multiple rings (bicyclic, tricyclic or polycyclic) fused together or linked covalently. Preferably, "heteroaryl" is a 5- to 6-membered ring. The rings may contain from 1 to 4 additional heteroatoms selected from N, O and S, wherein the N atom is optionally quarternized. Any suitable ring position of the heteroaryl moiety may be covalently linked to the defined chemical structure. Examples of "heteroaryl" include but are not limited to furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, 3-fluoropyridyl, pyrimidinyl, pyrazinyl, pyridazinyl, benzoxazolyl, benzisoxazolyl; benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, α-carbolinyl, indolizinyl, benzoisothiazolyl, benzoxazolyl, pyrrolopyridyl, furopyridinyl, purinyl, benzothiadiazolyl, benzooxadiazolyl, benzotriazolyl, benzotriadiazolyl, carbazolyl, dibenzothienyl, acridinyl and the like. Heteroaryl group may be optionally further substituted.

As used herein, the term "heterocyclyl" or "heterocyclic" alone or in combination with other term(s) includes both "heterocycloalkyl" and "heteroaryl" groups which are as defined above. Heterocyclic group may be optionally further substituted.

As used herein, the term "alkenyl" refers to a carbon chain which contains at least one carbon-carbon double bond, and which may be linear or branched or combinations thereof. Examples of "alkenyl" include, but not limited to, vinyl, allyl, isopropenyl, pentenyl, hexenyl, heptenyl, 1-propenyl, 2-butenyl and 2-methyl-2-butenyl.

As used herein, the term "amino" refers to an —$NH_2$ group.

As used herein, the term "halo" or "halogen" alone or in combination with other term(s) means fluorine, chlorine, bromine or iodine.

As used herein, the term "hydroxy" or "hydroxyl" alone or in combination with other term(s) means —OH.

As used herein, the term "oxo" refers to =O group.

As used herein, the term "alkoxy" refers to the group —O-alkyl, where alkyl groups are as defined above. Exemplary $C_1$-$C_{10}$ alkoxy group include but are not limited to methoxy, ethoxy, n-propoxy, n-butoxy or t-butoxy. An alkoxy group can be optionally substituted with one or more suitable groups.

As used herein, the term "aryl" is optionally substituted monocyclic, bicyclic or polycyclic aromatic hydrocarbon ring system of about 6 to 14 carbon atoms. Examples of a $C_6$-$C_{14}$ aryl group include, but are not limited to phenyl, naphthyl, biphenyl, anthryl, fluorenyl, indanyl, biphenylenyl and acenaphthyl. Aryl group can be unsubstituted or substituted with one or more suitable groups.

The term "acyl" refers to a group R—CO— or —CO—R wherein R is an optionally substituted alkyl group defined above. Examples of 'acyl' groups are, but not limited to, $CH_3CO$—, $CH_3CH_2CO$—, $CH_3CH_2CH_2CO$— or $(CH_3)_2CHCO$—. The term "—O-acyl" refers to —O—CO—R wherein R is an alkyl as defined above.

The term "heteroatom" as used herein designates a sulfur, nitrogen or oxygen atom.

As used herein, the term 'compound(s)' comprises the compounds disclosed in the present invention.

The term "salt/salts" refers to the salts derived from appropriate bases include alkali metal (e.g., sodium and potassium), alkaline earth metal (e.g., magnesium), ammonium and $N^+(C_{1-4} alkyl)_4$ salts.

As used herein, the term "comprise" or "comprising" is generally used in the sense of include, that is to say permitting the presence of one or more features or components.

As used herein, the term "or" means "and/or" unless stated otherwise.

As used herein, the term "including" as well as other forms, such as "include", "includes" and "included" is not limiting.

As used herein, the term "composition" is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

As used herein, the term "pharmaceutical composition" refers to a composition(s) containing a therapeutically effective amount of at least one compound of formula (I) or a pharmaceutically acceptable salt thereof; and a pharmaceutically acceptable carrier.

The pharmaceutical composition(s) usually contain(s) about 1% to 99%, for example, about 5% to 75%, or from about 10% to about 30% by weight of the compound of formula (I) or (II) or pharmaceutically acceptable salts thereof. The amount of the compound of formula (I) or pharmaceutically acceptable salts thereof in the pharmaceutical composition(s) can range from about 1 mg to about 1000 mg or from about 2.5 mg to about 500 mg or from about 5 mg to about 250 mg or in any range falling within the broader range of 1 mg to 1000 mg or higher or lower than the aforementioned range.

As used herein, "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier that has been approved by the United States Food and Drug Administration as being acceptable for use in humans or domestic animals.

The term "administer," "administering," or "administration" as used in this disclosure refers to either directly administering one or more disclosed compounds or a pharmaceutically acceptable salt of one or more disclosed compounds or a composition comprising one or more disclosed compounds to a subject, or administering a prodrug derivative or analog of the compound or a pharmaceutically acceptable salt of the compound or composition to the subject, which can form an equivalent amount of active compound within the subject's body.

The term "carrier" as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

As used herein, the term "treat", "treating" and "treatment" refer to a method of alleviating or abrogating a disease and/or its attendant symptoms.

As used herein, the term "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

As used herein, the term "subject" that may be interchangeable with 'patient', refers to an animal, preferably a mammal, and most preferably a human.

As used herein, the term, "therapeutically effective amount" refers to an amount of a compound of formula (I) or a pharmaceutically acceptable salt or a stereoisomer thereof; or a composition comprising the compound of formula (I) or a pharmaceutically acceptable salt or a stereoisomer thereof, effective in producing the desired therapeutic response in a particular patient suffering from a diseases or disorder, in particular their use in diseases or disorder associated with cancer. Particularly, the term "therapeutically effective amount" includes the amount of the compound of formula (I) or a pharmaceutically acceptable salt or a stereoisomer thereof, when administered, that induces a positive modification in the disease or disorder to be treated or is sufficient to prevent development of, or alleviate to some extent, one or more of the symptoms of the disease or disorder being treated in a subject. In respect of the therapeutic amount of the compound, the amount of the compound used for the treatment of a subject is low enough to avoid undue or severe side effects, within the scope of sound medical judgment can also be considered. The therapeutically effective amount of the compound or composition will be varied with the particular condition being treated, the severity of the condition being treated or prevented, the duration of the treatment, the nature of concurrent therapy, the age and physical condition of the end user, the specific compound or composition employed the particular pharmaceutically acceptable carrier utilized.

The term "pharmaceutically acceptable salt" refers to a product obtained by reaction of the compound of the present invention with a suitable acid or a base. Pharmaceutically acceptable salts of the compounds of this invention include those derived from suitable inorganic bases such as Li, Na, K, Ca, Mg, Fe, Cu, Al, Zn and Mn salts; Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention (compound of formula (I)) can form pharmaceutically acceptable salts with various organic bases such as lysine, arginine, guanidine, diethanolamine or metformin. Suitable base salts include, but are not limited to, aluminum, calcium, lithium, magnesium, potassium, sodium or zinc salts.

"Pharmaceutically acceptable" means that, which is useful in preparing a pharmaceutical composition that is generally safe, non-toxic and neither biologically nor otherwise undesirable and includes that which is acceptable for veterinary as well as human pharmaceutical use.

The present invention also provides methods for formulating the disclosed compounds as for pharmaceutical administration.

In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, hematologic cancers and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

The term "stereoisomers" refers to any enantiomers, diastereoisomers or geometrical isomers of the compounds of formula (I), wherever they are chiral or when they bear one or more double bonds. When the compounds of the formula (I) and related formulae are chiral, they can exist in racemic or in optically active form. It should be understood that the invention encompasses all stereochemical isomeric forms, including diastereomeric, enantiomeric and epimeric forms, as well as d-Isomers and l-Isomers and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric Isomers. The present invention includes all cis, trans, syn, anti, entgegen (E) and zusammen (Z) Isomers as well as the appropriate mixtures thereof.

The term "enantiomers" refers to a pair of stereoisomers which are non-superimposable mirror images of one another. The term "enantiomer" refers to a single member of this pair of stereoisomers. The term "racemic" refers to a 1:1 mixture of a pair of enantiomers. The disclosure includes enantiomers of the compounds described herein. Each compound herein disclosed includes all the enantiomers that conform to the general structure of the compound. The compounds may be in a racemic or enantiomerically pure form, or any other form in terms of stereochemistry. In some embodiments the compounds are the (S)-enantiomer.

The term "diastereomers" refers to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diastereomers. The term "diastereomer" refers to any member of this set of compounds. In some examples presented, the synthetic route may produce a single diastereomer or a mixture of diastereomers. The disclosure includes diastereomers of the compounds described herein.

The compounds of the present invention may be used as single drug or as a pharmaceutical composition in which the compound is mixed with various pharmacologically acceptable materials.

The compounds of the invention are typically administered in the form of a pharmaceutical composition. Such compositions can be prepared using procedures well known in the pharmaceutical art and comprise at least one compound of the invention. The pharmaceutical composition of the present patent application comprises one or more compounds described herein and one or more pharmaceutically acceptable excipients. Typically, the pharmaceutically acceptable excipients are approved by regulatory authorities or are generally regarded as safe for human or animal use. The pharmaceutically acceptable excipients include, but are not limited to, carriers, diluents, glidants and lubricants, preservatives, buffering agents, chelating agents, polymers, gelling agents, viscosifying agents and solvents.

The pharmaceutical composition can be administered by oral, parenteral or inhalation routes. Examples of the parenteral administration include administration by injection, percutaneous, transmucosal, transnasal and transpulmonary administrations.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters and polyoxyethylene.

The pharmaceutical composition may also include one or more pharmaceutically acceptable auxiliary agents, wetting agents, suspending agents, preserving agents, buffers, sweetening agents, flavouring agents, colorants or any combination of the foregoing.

The pharmaceutical compositions may be in conventional forms, for example, tablets, capsules, solutions, suspensions, injectables or products for topical application. Further, the pharmaceutical composition of the present invention may be formulated so as to provide desired release profile.

Administration of the compounds of the invention, in pure form or in an appropriate pharmaceutical composition, can be carried out using any of the accepted routes of administration of pharmaceutical compositions. The route of administration may be any route which effectively transports the active compound of the patent application to the appropriate or desired site of action. Suitable routes of administration include, but are not limited to, oral, nasal, buccal, dermal, intradermal, transdermal, parenteral, rectal, subcutaneous, intravenous, intraurethral, intramuscular or topical.

Solid oral formulations include, but are not limited to, tablets, capsules (soft or hard gelatin), dragees (containing the active ingredient in powder or pellet form), troches and lozenges.

Liquid formulations include, but are not limited to, syrups, emulsions, and sterile injectable liquids, such as suspensions or solutions.

Topical dosage forms of the compounds include ointments, pastes, creams, lotions, powders, solutions, eye or ear drops, impregnated dressings, and may contain appropriate conventional additives such as preservatives, solvents to assist drug penetration.

The pharmaceutical compositions of the present patent application may be prepared by conventional techniques known in literature.

Suitable doses of the compounds for use in treating the diseases or disorders described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects. Mode of administration, dosage forms, and suitable pharmaceutical excipients can also be well used and adjusted by those skilled in the art. All changes and modifications are envisioned within the scope of the present patent application.

According to one embodiment, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorous, sulfur, fluorine, chlorine and iodine, such as $^2H$ ("D"), $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically labeled compounds of the present inventions can generally be prepared by following procedures analogous to those disclosed in the schemes and/or in the examples herein below, by substituting an isotopically labeled reagent for a non-isotopically labeled reagent.

Experimental Section

The abbreviations used in the entire specification summarized herein below with their particular meaning:
DCM—Dichloromethane; DIPEA—N,N-Diisopropylethylamine; DMF—N, N-Dimethylformamide; DMSO—Dimethylsulfoxide; NMP: N-Methyl-2-pyrrolidone;—1-(3-Dimethylaminopropyl)-3-ethylcarbodiimide hydrochloride; EtOAc—Ethyl acetate; $H_2O$—Water; HCl—Hydrochloric acid; $K_2CO_3$—Potassium carbonate; KOH—Potassium hydroxide; $NaN_3$—Sodium azide; BnBr—Benzyl bromide; LiOH. $H_2O$—Lithium hydroxide monohydrate; NaI—Sodium iodide; NaH—Sodium hydride; KOAc—potassium acetate; AcOH—Acetic acid; $(COCl)_2$—Oxalyl chloride; $Et_3N$—Triethyl amine; $(Boc)_2O$—Boc anhydride; TsCl—tosyl chloride; NBS—N-bromo succinimide; AlBN—Azobisisobutyronitrile; $CCl_4$—carbon tetra bromide; DMA—dimethyl acetamide; TEA—triethyl amine; $H_2SO_4$—Sulfuric acid; $Pd(OAc)_2$—Palladium acetate; HATU-(1-[Bis (dimethylamino)methylene]-1H-1,2,3-triazolo[4,5-b] pyridinium3-oxid hexafluorophosphate; DMAP—4-Dimethylaminopyridine; $PtO_2$—Platium oxide; $SOCl_2$—Thionyl chloride; $Pd(PPh_3)_4$—Tetrakis(triphenylphosphine) palladium(0); m—Multiplet; $Br_2$—Bromine; $NaHCO_3$—Sodium bi carbonate; $Pd(dppf)Cl_2$—1,1'-Bisdiphenylphosphino #ferrocene]palladium(II) dichloride; NaH—Sodium hydride; Pd/C—Palladium on Carbon; MeOH—Methanol; THF—Tetrahydrofuran; ACN—acetonitrile; KI—Potassium iodide, BBr3—Boron tribromide, DAST—(Diethylamino)sulfur trifluoride, LAH—Lithium aluminum hydride, LDA—Lithium diisopropylamide, CO—Carbon monoxide. DMSO-$d_6$—Deuterated dimethylsulfoxide; $D_2O$—Deuterated water; mg—Milligrams; min—Minutes; MHz—Mega HeRtz (frequency); MW—microwave; pis—Pascal; mL—Milliters; mM—Millimolar; mmol—Millimoles; MS—Mass spectroscopy; m/z—Mass to charge ratio N—Normality; g—Gram; h—Hour; $^1H$—Proton; $H_2$—Hydrogen; $^1HNMR$—Proton nuclear magnetic resonance; %—Percentage; pH—potential of Hydrogen; M+—Molecular ion psi—Pounds per square inch; q—QuaRtet; s—Singlet; t—Triplet; anh.—Anhydrous; Hz—HeRtz; J—Coupling constant; bs—Broad singlet; Conc.—Concentrated; RT—Room temperature; ° C.—degree Celsius; d—Doublet; δ—Delta; TLC—Thin layer chomatography; LC—Liquid chomatography.

General Modes of Preparation

Following general guidelines apply to all experimental procedures described here. Until otherwise stated, experiments are performed under positive pressure of nitrogen, temperature describes are the external temperature (i.e. oil bath temperature). Reagents and solvents received from vendors are used as such without any further drying or purification. Molarities mentioned here for reagents in solutions are approximate as it was not verified by a prior titration with a standard. All reactions are stirred under magnetic stir bar. Cooling to minus temperature was done by acetone/dry ice or wet ice/salts. Magnesium sulfate and sodium sulfate were used as solvent drying agent after reaction work up and are interchangeable. Removing of solvents under reduced pressure or in vacuo or concentration of the reaction mixture means distilling of solvents in rotary evaporator.

Compounds of this invention may be made by synthetic chemical processes, examples of which are shown herein. It is meant to be understood that the order of the steps in the processes may be varied, that reagents, solvents and reaction conditions may be substituted for those specifically mentioned and that vulnerable moieties may be protected and deprotected, as necessary.

The specifics of the process for preparing compounds of the present invention are detailed in the experimental section.

The present invention shall be illustrated by means of some examples, which are not construed to be viewed as limiting the scope of the invention.

Unless otherwise stated, work-up includes distribution of the reaction mixture between the organic and aqueous phases, separation of layers and drying the organic layer over anhydrous sodium sulphate, filtration and evaporation of the solvent. Purification, unless otherwise mentioned, includes purification by silica gel chomatographic techniques, generally using ethyl acetate/petroleum ether mixture of a suitable polarity as the mobile phase.

Analysis of the compounds of the present invention unless mentioned, was conducted in the general methods well known to the person skilled in the art. Having described the invention with reference to certain preferred embodiments, other embodiments will become apparent to one skilled in the art from consideration of the specification. The invention is further defined by reference to the following examples, describing in detail the analysis of the compounds of the invention.

It will be apparent to those skilled in the art that many modifications, both to materials and methods, may be practiced without departing from the scope of the invention. Some of the intermediates were taken to next step based on TLC results, without further characterization, unless otherwise specified.

Each embodiment is provided by way of explanation of the invention, and not by way of limitation of the invention. In fact, it will be apparent to those skilled in the art that various modifications and variations can be made to the compounds, compositions and methods described herein without departing from the scope or spirit of the invention. For instance, feature illustrated or described as part of one embodiment can be applied to another embodiment to yield a still further embodiment. Thus, it is intended that the present invention includes such modifications and variations and their equivalents. Other objects, features, and aspects of the present invention are disclosed in, or are obvious from the following detailed description. It is to be understood by one of ordinary skill in the art that present discussion is a description of exemplary embodiments only, and is not to be constructed as limiting the broader aspects of the present invention.

The MS (Mass Spectral) data provided in the examples were obtained using the equipment(s)-API 2000 LC/MS/MS/Triplequad; Agilent Technologies/LC/MS/DVL/Singlequad; Shimadzu LCMS-2020/Singlequad.

The NMR data provided in the examples were obtained using the equipment(s)—1H-NMR: Varian 400 MHz and Varian 300 MHz.

The HPLC performed for the provided examples using the equipements-AgilentTechnologies 1200 Series; Agilent Technologies 1100 Series; Shimadzu (UFLC) Prominance; Shimadzu Nexera-UHPLC.

Compound purifications were performed on Combi-Flash® unless otherwise mentioned.

SYNTHESIS OF INTERMEDIATES

Intermediates—1a to 1f

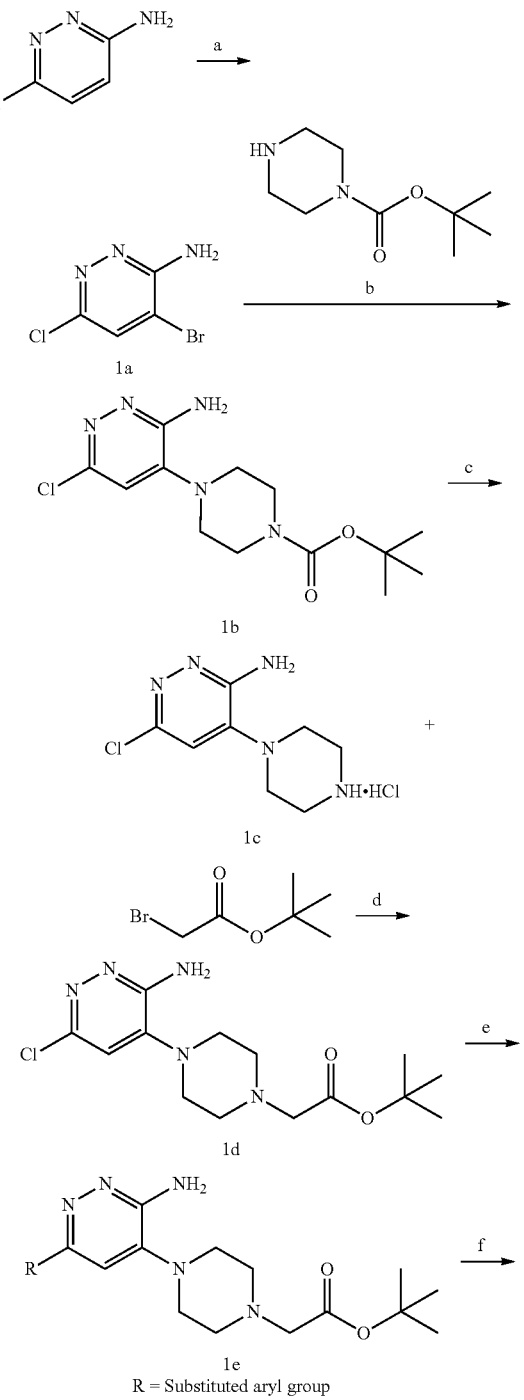

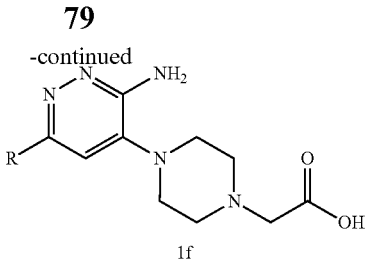

1f

Conditions: a) Br₂, NaHCO₃, MeOH, 0° C.-RT, 16 h; b) DMF, 90° C., 16 h; c) 4M HCl in 1,4-dioxane, DCM, 0° C.-RT, 16 h; d) DIPEA, DMF, 60° C., 16 h; e) Substituted aryl boronic acid, Pd(dppf)Cl₂: DCM (1:1), K₂CO₃, Dioxane:water (5:2), sealed tube, 120° C., 1 h; f) 4M HCl in Dioxane, DCM, 0° C.-RT, 16 h.

Step-a: Synthesis of 4-bromo-6-chloropyridazin-3-amine (1a)

To a stirred solution of 6-chloropyridazin-3-amine (20.0 g, 155.02 mmol) in MeOH (100 mL) was added NaHCO₃ (19.53 g, 232.00 mmol) at RT and stirred for 15 min and then bromine (8.74 mL, 170.52 mmol) was added drop wise to the reaction mixture over period of 1 h at 0° C. and stirred for 16 h at RT. After completion of the reaction (monitored by TLC), reaction mixture was quenched with water (100 mL). Dark brown colored solid was precipitated which was filtered and washed with water (50 mL) and dried under vacuum to afford crude title compound. The solid was washed with 20% EtOAc in hexane and diethyl ether to afford pure title compound (15.0 g, 46%). $^1$H NMR (400 MHz, DMSO-$d_6$): δ 7.99 (s, 1H), 6.97 (bs, 2H); LC-MS: m/z 208.0 (M+1)⁺.

Step-b: Synthesis of tert-butyl 4-(3-amino-6-chloro-pyridazin-4-yl) piperazine-1-carboxylate (1 b)

Method-A: To a stirred solution of 4-bromo-6-chloro-pyridazin-3-amine (1a, 20.0 g, 96.66 mmol) in DMF (400 mL) was added tert-butyl piperazine-1-carboxylate (53.92 g, 289.9 mmol) at RT and stirred for 16 h at 90° C. under nitrogen atmosphere. Then the reaction mixture was quenched with cold water (200 mL) and the obtained brown solid was filtered under vacuum and washed with diethyl ether, the same procedure was repeated four times to afford pure title compound (1 b, 15.0 g, 49.57%). $^1$H NMR (400 MHz, DMSO-$d_6$): δ 6.91 (s, 1H), 6.21 (s, 2H), 3.49 (t, J=4.4 Hz, 4H), 2.92 (t, J=4.8 Hz, 4H), 1.41 (m, 9H); LC-MS: m/z 314.2 (M+1)⁺.

Method-B:

To a stirred solution of 4-bromo-6-chloropyridazin-3-amine (1.0 eq) in ACN (10 vol) or DMF were added tert-butyl piperazine-1-carboxylate (1.50 eq.) and (DIPEA or TEA (1.5 eq.) at RT and stirred for 16 h at 90° C. under nitrogen atmosphere. Then the reaction mixture was quenched with cold water (5 vol) and obtained brown solid was filtered off and which was purified by CombiFlash® or washed with Diethyl ether to afford pure title compound.

Step-c: Synthesis of 6-chloro-4-(piperazin-1-yl)pyridazin-3-amine hydrochloride (1c)

To a stirred solution of tert-butyl 4-(3-amino-6-chloro-pyridazin-4-yl)piperazine-1-carboxylate (1b, 15.0 g, 47.92 mmol) in DCM (100 mL) was added 4 M HCl in Dioxane (75 mL) at 0° C. under nitrogen atmosphere and stirred for 16 h at RT. The reaction mixture was concentrated under reduced pressure to get crude brown solid compound. The brown solid was washed with diethyl ether (2×50 mL), filtered and dried under vacuum to afford the title compound (11.98 g, 100%). $^1$H NMR (400 MHz, DMSO-$d_6$): δ 9.44 (bs, 2H), 7.75 (bs, 2H), 7.32 (s, 1H), 3.30-3.25 (m, 8H); LC-MS: m/z 214.1 (M+1)⁺.

Step-d: Synthesis of tert-butyl 2-(4-(3-amino-6-chloropyridazin-4-yl)piperazin-1-yl)acetate (1d)

To a stirred solution of 6-chloro-4-(piperazin-1-yl)pyridazin-3-amine hydrochloride (1c, 12.0 g, 48.18 mmol) in DMF (100 mL) in a sealed tube were added DIPEA (25.70 mL, 144.54 mmol) and tert-butyl 2-bromoacetate (10.53 mL, 72.27 mmol) at RT and stirred for 16 h at 60° C. The reaction mixture was quenched with water (100 mL) and extracted with EtOAc (2×150 mL). The combined organic layer was washed with water (100 mL), brine (100 mL), dried over anhydrous sodium sulphate and concentrated under reduced pressure to give the crude product which was purified by CombiFlash® using 60% ethyl acetate in hexane as eluent to afford the title compound (10.0 g, 63.7%). $^1$H NMR (400 MHz, DMSO-$d_6$): δ 6.89 (s, 1H), 6.07 (s, 2H), 3.165 (s, 2H), 3.05-2.95 (m, 4H) 2.70-2.65 (m, 4H), 1.45 (s, 9H); LC-MS: m/z 328.2 (M+1)⁺.

Step-e: General procedure of Suzuki coupling with tert-butyl 2-(4-(3-amino-6-chloropyridazin-4-yl)piperazin-1-yl)acetate (1e₁-1e₁₂)

Method-A: A mixture of 1,4-dioxane:water (5:2) were taken in microwave vial and degassed with nitrogen for 5 min. To this, tert-butyl 2-(4-(3-amino-6-chloropyridazin-4-yl)piperazin-1-yl)acetate (1d, 1.0 eq.), substituted aryl boronic acid (R) (2.0 eq.) were added followed by the addition of K₂CO₃ (3.0 eq.) and Pd(dppf)Cl₂:DCM (1:1) (10% mol). The reaction mixture was heated for 45 m to 1 h at 120° C. in microwave. Once the reaction was completed (monitored by TLC), the reaction mixture was diluted with EtOAc. The combined organic layer was washed with water, brine, dried over anhydrous sodium sulphate and concentrated under vacuum to give the residue which was purified by Combi-Flash® column chomatography using 50-60% ethyl acetate in hexane as eluent to afford the title compounds (1e₁-1e₁₂).

The compounds listed in below Table-1 were prepared by procedure similar to the one described in Step-e of Intermediate-1e with appropriate variations in reactants. The characterization data of the compounds are summarized herein the below table.

TABLE 1

| R | Structure | Characterization data<br>¹H NMR (400 MHz, DMSO-d$_6$) |
|---|---|---|
| 2-hydroxyphenylboronic acid | 1e$_1$ | δ 14.15 (s, 1H), 7.94 (dd, J$_1$ = 1.6, J$_2$ = 8.4 Hz, 1H), 7.26-7.21 (m, 2H), 6.90-6.87 (m, 2H), 6.22 (s, 2H), 3.18-3.16 (m, 2H), 3.11-3.09 (m, 4H), 2.67-2.66 (m, 4H), 1.43 (s, 9H); LC-MS: m/z 386.1 (M + 1)$^+$. |
| phenylboronic acid | 1e$_2$ | δ 7.99-7.97 (m, 2H), 7.45 (t, J = 6.8Hz, 2H), 7.39, (d, J = 7.3, 1H), 7.28 (s, 1H), 5.93, (s, 2H), 3.18 (s, 2H), 3.10-3.05 (m, 4H), 2.75-2.70 (m, 4H), 1.43 (s, 9H); LC-MS: m/z 370.2 (M + 1)$^+$. |
| 2-fluorophenylboronic acid | 1e$_3$ | δ 7.81 (t, J = 7.2 Hz, 1H), 7.46-7.44 (m, 1H), 7.30 (t, J = 8.8 Hz, 2H), 7.12 (s, 1H), 6.03 (bs, 2H), 3.17 (s, 2H), 3.05-2.95 (m, 4H), 2.78-2.70 (m, 4H), 1.44 (s, 9H); LC-MS: m/z 388.2 (M + 1)$^+$. |
| 2-methoxyphenylboronic acid | 1e$_4$ | δ 7.61 (dd, J$_1$ = 1.6, J$_2$ = 7.2 Hz, 1H), 7.39-7.35 (m, 1H), 7.11 (d, J = 8.0 Hz, 1H), 7.16 (s, 1H), 7.03 (t, J = 8.0 Hz, 1H), 5.84 (s, 2H), 3.81 (s, 3H), 3.16 (s, 2H), 2.98-2.95 (m, 4H), 2.71-2.70 (m, 4H), 1.45 (s, 9H); LC-MS: m/z 400.1 (M + 1)$^+$. |
| 2-chlorophenylboronic acid | 1e$_5$ | ¹H NMR (400 MHz, DMSO-d$_6$): δ 7.58-7.53 (m, 2H), 7.45-7.44 (m, 2H), 7.05 (s, 1H), 6.06 (s, 2H), 3.17 (s, 2H), 3.06-3.00 (m, 4H), 2.71-2.66 (m, 4H), 1.42 (s, 9H); LC-MS: m/z 404.1 (M + 1)$^+$. (Yield: 33%). |
| 3-fluoro-2-hydroxyphenylboronic acid | 1e$_6$ | ¹H NMR (400 MHz, DMSO-d$_6$): δ 14.98 (s, 1H), 7.77 (d, J = 8.4 Hz, 1H), 7.53 (s, 1H), 7.21 (dd, J = 1.6 Hz, J = 8.4 Hz, 1H), 6.88-6.82 (m, 1H), 6.34 (s, 2H), 3.18 (s, 2H), 3.16-3.12 (m, 4H), 2.73-2.66 (m, 4H), 1.43 (s, 9H); LC-MS: m/z 404.2 (M + 1)$^+$. (Yield: 13%). |
| 2-hydroxy-3-methylphenylboronic acid | 1e$_7$ | ¹H NMR (400 MHz, DMSO-d$_6$): δ 14.64 (s, 1H), 7.77 (d, J = 8.0 Hz, 1H), 7.50 (s, 1H), 7.13 (d, J = 7.2 Hz, 1H), 6.79 (t, J = 8.0 Hz, 1H), 6.25 (s, 2H), 3.18 (s, 2H), 3.10-3.00 (m, 4H), 2.73-2.70 (m, 4H), 2.19 (s, 3H), 1.46-1.43 (m, 9H); LC-MS: m/z 400.2 (M + 1)$^+$. (Yield: 51.1%). |

TABLE 1-continued

| R | Structure | Characterization data<br>¹H NMR (400 MHz, DMSO-d₆) |
|---|---|---|
| (1e₈) | (1e₈) | ¹H NMR (400 MHz, DMSO-d₆): δ 8.64-8.61 (m, 1H), 8.28-8.24 (m, 1H), 8.05-7.96 (m, 1H), 7.67-7.62 (m, 1H), 7.36 (s, 1H), 6.07 (s, 2H), 3.90 (s, 3H), 3.35 (s, 2H merged with DMSO peak), 3.18-3.07 (m, 4H), 2.72-2.70 (m, 4H), 1.50 (s, 9H); LC-MS: m/z 428.3 (M + 1)⁺ (Yield: 33.2%). |
| (1e₉) | (1e₉) | ¹H NMR (400 MHz, DMSO-d₆): δ 7.46 (dd, J = 1.2 Hz, J = 7.6 Hz, 1H), 7.12 (s, 1H), 7.06-7.02 (m, 1H), 6.74 (dd, J = 0.8 Hz, J = 8.0 Hz, 1H), 6.62-6.58 (m, 1H), 6.44 (s, 2H), 5.87 (s, 2H), 3.17 (s, 2H), 3.09-3.01 (m, 4H), 2.72-2.67 (m, 4H), 1.43 (s, 9H); LC-MS: m/z 385.2 (M + 1)⁺; (Yield : 68%). |
| (1e₁₀) | (1e₁₀) | ¹H NMR (400 MHz, DMSO-d₆): δ 7.68 (dd, J = 9.6 Hz, J = 12.0 Hz, 1H), 7.30 (dd, J = 6.8 Hz, J = 12.8 Hz, 1H), 7.20 (s, 1H), 5.98 (s, 2H), 3.82 (s, 3H), 3.17 (s, 2H), 2.97-2.94 (m, 4H), 2.71-2.07 (m, 4H), 1.40 (s, 9H); LC-MS: m/z 436.2 (M + 1)⁺; (Yield : 90%). |
| (1e₁₁) | (1e₁₁) | LC-MS: m/z 428.2 (M + 1)⁺ (Yield: 36.8%). |
| (1e₁₂) | (1e₁₂) | ¹H NMR (400 MHz, DMSO-d₆): δ 7.47-7.44 (m, 1H), 6.94-6.92 (m, 1H), 6.88 (s, 1H), 6.01 (s, 2H), 3.73 (s, 3H), 3.13 (s, 2H), 2.96-2.94 (m, 4H), 2.70-2.68 (m, 4H), 1.42 (s, 9H); LC-MS: m/z 436.3 (M + 1)⁺; (Yield: 34%). |

Step-f: Method-A: General Procedure of Hydrolysis of Substituted Tert-Butyls (1f₁-1f₉ and 1f₁₁)

To a stirred solution of compound (1e₁-1e₉ and 1e₁₁. 1.0 eq.) in DCM (10 vol) was added 4 M HCl in 1,4-Dioxane (5 vol) at 0° C. under nitrogen atmosphere and stirred for 16 h at RT. After completion of the reaction (monitored by TLC), reaction mixture was concentrated under reduced pressure. The residue was washed with diethyl ether, filtered and dried under vacuum to afford compound 1f₁-1f₉ and 1f₁₁, 80-95%).

Method-B: Typical Procedure for Hydrolysis of (1f₁₀ to 1f₁₂1)

To a stirred solution of compound (1e₁₀ and 1e₁₂. 1.0 eq.) in DCM (10 vol.) was added 1M BBr₃ in DCM (3.0 eq) was added at 0° C. under nitrogen atmosphere and stirred for 16 h at RT. After completion of the reaction (monitored by TLC), reaction mixture was concentrated under reduced pressure. The residue was washed with diethyl ether, filtered and dried under vacuum to afford compound (1 f₁₀ and 1f₁₂, 50-90%).

The compounds listed in below Table-2 were prepared by procedure similar to the one described in Step-f of Intermediate-1f with appropriate variations in reactants. The characterization data of the compounds are summarized herein the below table.

TABLE 2
| Structure | Characterization data | Structure | Characterization data |
|---|---|---|---|
| 1f₁ | LC-MS: m/z 330.1 (M + 1)⁺. | 1f₂ | LC-MS: m/z 314.2 (M + 1)⁺ |
| 1f₃ | LC/MS: m/z 332.1 (M + 1)⁺. | 1f₄ | LC/MS: m/z 344.1 (M + 1)⁺. |
| 1f₅ | LC-MS: m/z 348.0 (M + 1)⁺ Yield: 98%. | 1f₆ | LC-MS: m/z 348.05 (M + 1)⁺. Yield : 80%). |
| 1f₇ | LC-MS: m/z 344.2 (M + 1)⁺. Yield: 90%. | 1f₈ | LC-MS: m/z 372.2 (M + 1)⁺. (Yield : 90%). |
| 1f₉ | LC-MS: m/z 329.1 (M + 1)⁺. Yield : 84%. | 1f₁₀ | LC-MS: m/z 364.05 (M − 1) Yield : 90%. |
| 1f₁₁ | LC-MS: m/z 372.2 (M + 1)⁺. Yield: 90%. | 1f₁₂ | LC-MS: m/z 366.1 (M + 1)⁺. Yield : 50%. |
Intermediate-1Be
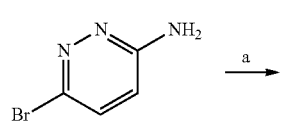
-continued
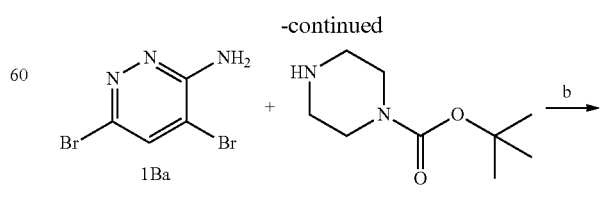

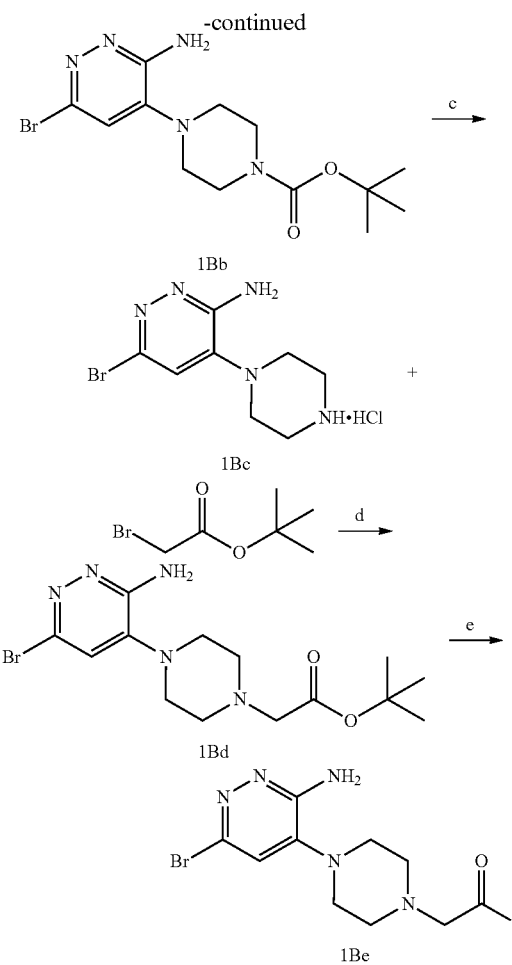

carboxylate (Yield: 90%) $^1$H NMR (400 MHz, DMSO-$d_6$): δ 9.59 (bs, 2H), 8.21 (bs, 2H), 7.44 (s, 1H), 3.37-3.28 (m, 8H); LC-MS: m/z 258.0 (M+1)$^+$.

Step-d: Synthesis of tert-butyl 2-(4-(3-amino-6-bromopyridazin-4-yl)piperazin-1-yl)acetate (1 Bd)

The title compound was synthesized by using the same procedure which was followed for Intermediate-1d using tert-butyl 2-bromoacetate (Yield: 41.6%). $^1$H NMR (400 MHz, DMSO-$d_6$): δ 6.96 (s, 1H), 6.10 (bs, 2H), 3.15 (s, 2H), 3.01-2.93 (m, 4H), 2.68-2.65 (m, 4H), 1.43 (s, 9H); LC-MS: m/z 374.27 (M+2)$^+$.

Step-e: Synthesis of 2-(4-(3-amino-6-chloro-pyridazin-4-yl)piperazin-1-yl)acetic acid (1 Be)

The title compound was synthesized by using the same procedure which was followed for Intermediate-1f using tert-butyl 2-(4-(3-amino-6-bromopyridazin-4-yl)piperazin-1-yl)acetate to afford title compound (Yield: 98%). $^1$H NMR (400 MHz, DMSO-$d_6$): δ 11.20 (bs, 1H), 8.27 (bs, 2H), 7.50 (s, 1H), 4.21 (s, 2H), 3.60-3.39 (m, 8H); LC-MS: m/z 318.1 (M+2)$^+$.

Intermediate-2b:

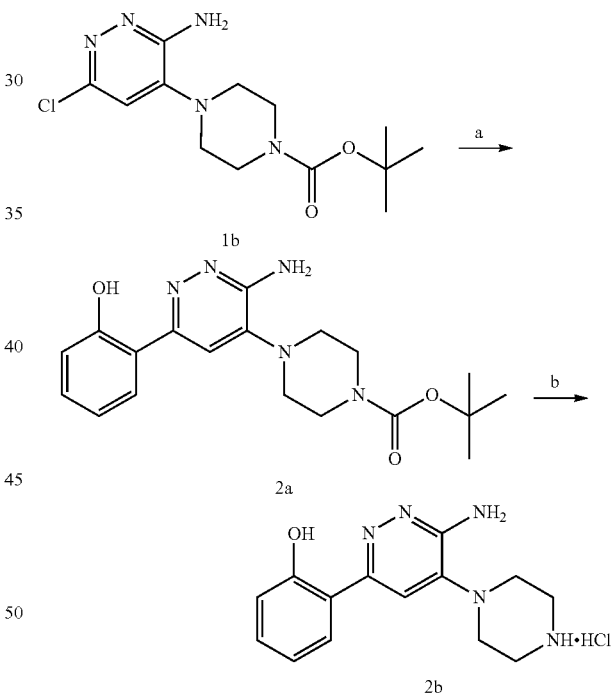

Conditions: a) (2-hydroxyphenyl)boronic acid, Pd(dppf)Cl$_2$: DCM (1:1), K$_2$CO$_3$, 1,4-Dioxane:water (5:2), sealed tube, 120° C., 1 h; b) 4M HCl in Dioxane, DCM, 0° C.-RT, 16 h;

Conditions: a) Br$_2$, NaHCO$_3$, MeOH, 0° C.-RT, 16 h; b) K$_2$CO$_3$, DMF, 90° C., 16 h; c) 4M HCl in 1,4-dioxane, DCM, 0° C.-RT, 16 h; d) DIPEA, DMF, 60° C., 16 h; e) 4M HCl in Dioxane, DCM, 0° C.-RT, 16 h.

Step-a: Synthesis of 4,6-dibromopyridazin-3-amine (1 Ba)

The title compound was synthesized by using the same procedure which was followed for Intermediate-1a using 6-bromopyridazin-3-amine (Yield: 40%) $^1$H NMR (400 MHz, DMSO-$d_6$): δ 8.07 (s, 1H), 6.99 (bs, 2H); LC-MS: m/z 253.8 (M+1)$^+$.

Step-b: Synthesis of tert-butyl 4-(3-amino-6-bromopyridazin-4-yl)piperazine-1-carboxylate (1 Bb)

The title compound was synthesized by using the same procedure which was followed for Intermediate-1b using tert-butyl piperazine-1-carboxylate (Yield: 84%) $^1$H NMR (400 MHz, DMSO-$d_6$): δ 6.98 (s, 1H), 8.30 (bs, 2H), 3.50 (t, J=4.4 Hz, 4H), 2.93 (t, J=5.1 Hz, 4H), 1.43 (s, 9H); LC-MS: m/z 358.1 (M+1)$^+$.

Step-c: Synthesis 6-bromo-4-(piperazin-1-yl)pyridazin-3-amine hydrochloride (1Bc)

The title compound was synthesized by using the same procedure which was followed for Intermediate-1c using tert-butyl 4-(3-amino-6-bromopyridazin-4-yl)piperazine-1-

Step-a: Synthesis of tert-butyl 4-(3-amino-6-(2-hydroxyphenyl)pyridazin-4-yl)piperazine-1-carboxylate (2a)

The title compound was synthesized using the same procedure which was followed for Intermediate 1e$_1$-1e$_{12}$ using tert-butyl 4-(3-amino-6-chloropyridazin-4-yl) piperazine-1-carboxylate and (2-hydroxyphenyl)boronic acid as starting material. Yield: 92% $^1$H NMR (400 MHz, DMSO-d$_6$): δ 14.16 (s, 1H), 7.92 (d, J=7.2 Hz, 1H), 7.54 (s, 1H), 7.23 (d, J=7.2 Hz, 1H), 6.88 (t, J=4.4 Hz, 2H), 6.36 (bs, 2H), 3.55 (s, 4H), 3.03 (bs, 4H), 1.43 (s, 9H); LC-MS: m/z 372.1 (M+1)$^+$.

Step-b: Synthesis of 2-(6-amino-5-(piperazin-1-yl) pyridazin-3-yl)phenol hydrochloride (2b)

The title compound was synthesized using the same procedure which was followed for 1f$_1$-1f$_{12}$ using tert-butyl 4-(3-amino-6-(2-hydroxyphenyl)pyridazin-4-yl) piperazine-1-carboxylate as staring material. Yield: 97% $^1$H NMR (400 MHz, CD$_3$OD): δ 7.71 (bs, 1H), 7.62 (d, J=7.8 Hz, 1H), 7.43 (t, J=7.8 Hz, 1H), 7.07-7.03 (m, 2H), 3.63-3.58 (m, 4H), 3.52 (t, J=4.8 Hz, 4H); LC-MS: m/z 272.1 (M+1)$^+$.
Intermediate-3d:

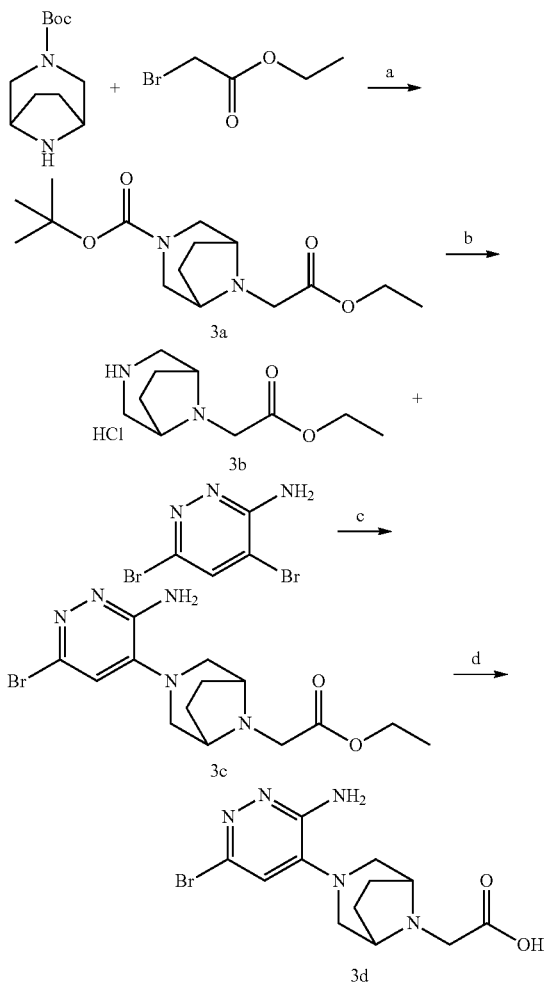

Conditions: a) K$_2$CO$_3$, ACN, 25-30° C., 16 h; b) 4M HCl in 1,4-dioxane, DCM, 0° C.-25-30° C., 16 h; c) DIPEA, DMF, 90° C., 16 h; d) LiOH·H$_2$O, THF:MeOH:H$_2$O, RT-16 h.

Step-a: Synthesis of tert-butyl 8-(2-ethoxy-2-oxo-ethyl)-3,8-diazabicyclo[3.2.1]octane-3-carboxylate (3a)

To a stirred solution of tert-butyl (1R,5S)-3,8-diazabicyclo[3.2.1]octane-3-carboxylate (1c, 0.40 g, 1.88 mmol) in ACN (10 mL) in a two neck RB were added K$_2$CO$_3$ (0.78 g, 5.65 mmol) and Ethyl 2-bromoacetate (0.41 mL, 3.76 mmol) at 25-30° C. and stirred for 16 h at 25-30° C. The reaction mixture was quenched with water (50 mL) and extracted with EtOAc (2×50 mL). The combined organic layer was washed with water (50 mL), brine (50 mL), dried over anhydrous sodium sulphate and concentrated under reduced pressure to give the crude product which was purified by combi flash using 60% ethyl acetate in hexane as eluent to afford the title compound (0.60 g (crude). $^1$H NMR (400 MHz, DMSO-d$_6$): δ 4.10-4.06 (m, 2H), 3.20 (s, 4H), 3.13 (s, 2H), 3.00-2.97 (m, 1H), 2.87-2.84 (m, 1H), 1.82-1.80 (m, 2H), 1.46-1.40 (m, 11H), 1.22-1.16 (m, 3H); LC-MS: m/z 299.2 (M+1)$^+$.

Step-b: ethyl 2-(3,8-diazabicyclo[3.2.1]octan-8-yl) acetate hydrochloride (3b)

The title compound was synthesized by using the general procedure of Step-f of Method-A hydrolysis of substituted tert-butyls Intermediate 1f$_1$-1f$_{12}$ (Yield: 90%) LC-MS: m/z 199.11 (M+1)$^+$.

Step-c: Synthesis of ethyl 2-(3-(3-amino-6-bromopyridazin-4-yl)-3,8-diazabicyclo[3.2.1]octan-8-yl)acetate (3c)

To a stirred solution of 4-bromo-6-bromopyridazin-3-amine (3a), (0.20 g, 0.79 mmol) in DMF (5 mL) were ethyl 2-(3,8-diazabicyclo[3.2.1]octan-8-yl)acetate hydrochloride (0.278 g, 1.11 mmol) and DIPEA (0.7 mL, 3.95 mmol) at RT and stirred for 16 h at 90° C. under nitrogen atmosphere. Then the reaction mixture was quenched with cold water (20 mL) and the brown solid obtained was washed with diethyl ether, filtered and dried under vacuum. The same procedure was repeated four times to afford pure title compound (0.155 g, Yield: 55%). $^1$H NMR (400 MHz, DMSO-d$_6$): δ 6.96 (s, 1H), 5.76 (s, 2H), 4.15-4.03 (m, 2H), 3.37-3.29 (m, 2H), 3.19 (s, 2H), 3.16-3.14 (m, 2H), 2.83-2.80 (m, 2H), 1.85 (s, 4H), 1.23-1.13 (m, 3H); LC-MS: m/z 371.1 (M+1)$^+$.

Step-d: Synthesis of 2-(3-(3-amino-6-bromopyridazin-4-yl)-3,8-diazabicyclo[3.2.1]octan-8-yl)acetic. (3d)

To a stirred solution of ethyl 2-(3-(3-amino-6-bromopyridazin-4-yl)-3,8-diazabicyclo[3.2.1]octan-8-yl)acetate (3c) (0.15 g, 0.41 mmol) in a mixture of solvent (THF:MeOH:H$_2$O) (2:2:1) (5 mL) was added LiOH·H$_2$O (0.052 g, 1.18 mmol) at 25-30° C. and stirred for 16 h at RT. The reaction mixture was concentrated under reduced pressure and the residue was diluted with water and neutralized with 1N HCl. The precipitated solid was filtered and dried under vacuum to afford the title compound (0.15 g, Crude) $^1$H NMR (400 MHz, DMSO-d$_6$): δ 6.98 (s, 1H), 5.79 (s, 2H), 3.46 (s, 2H), 3.21-3.19 (m, 4H), 2.93-2.90 (m, 2H), 1.91 (s, 4H); LC-MS: m/z 342.0 (M+1)$^+$.
Intermediate-4b:

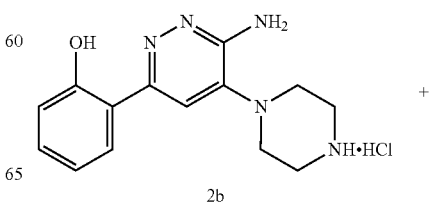

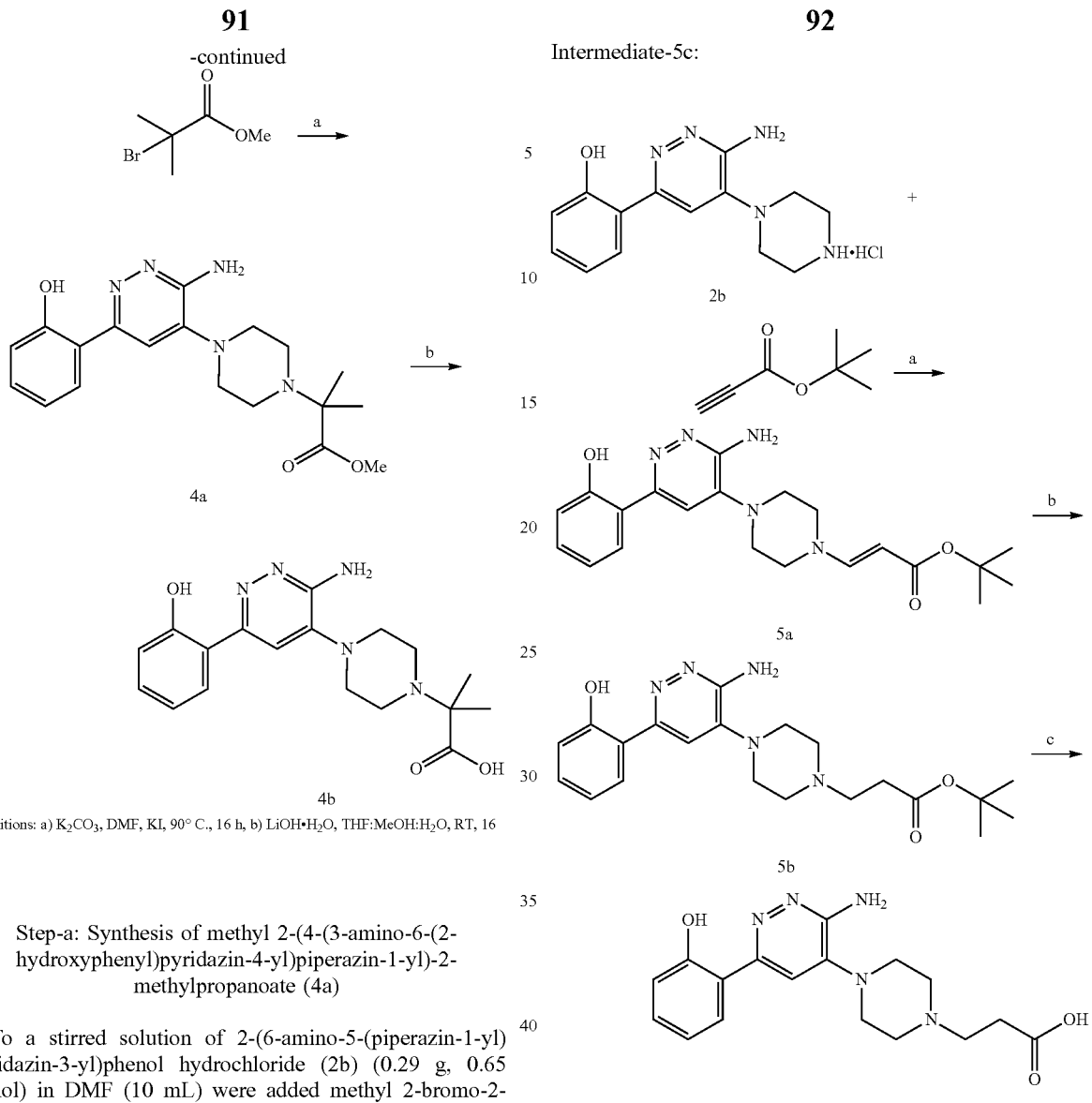

Conditions: a) K₂CO₃, DMF, KI, 90° C., 16 h, b) LiOH•H₂O, THF:MeOH:H₂O, RT, 16 h.

Step-a: Synthesis of methyl 2-(4-(3-amino-6-(2-hydroxyphenyl)pyridazin-4-yl)piperazin-1-yl)-2-methylpropanoate (4a)

To a stirred solution of 2-(6-amino-5-(piperazin-1-yl) pyridazin-3-yl)phenol hydrochloride (2b) (0.29 g, 0.65 mmol) in DMF (10 mL) were added methyl 2-bromo-2-methylpropanoate (0.17 g, 0.65 mmol), KI (0.018 g, 0.065 mmol) and K₂CO₃ (0.26 g, 19.5 mmol) at RT and stirred for 16 h at 90° C. under nitrogen atmosphere. Then the reaction mixture was quenched with cold water (20 mL) and the brown solid obtained was washed with diethyl ether, filtered and dried under vacuum. The same procedure was repeated four times to afford pure title compound (Yield: 98%). ¹H NMR (400 MHz, DMSO-d₆): δ 14.20 (s, 1H), 7.91 (d, J=7.2 Hz, 1H), 7.48 (s, 1H), 7.23 (t, J=7.6 Hz, 1H), 6.89-6.86 (m, 2H), 6.24 (s, 2H), 3.65 (s, 3H), 3.08-306 (m, 4H), 2.67-2.65 (m, 4H), 1.29 (s, 6H); LC-MS: m/z 372.1 (M+1)⁺.

Step-b: Synthesis of 2-(4-(3-amino-6-(2-hydroxyphenyl)pyridazin-4-yl)piperazin-1-yl)-2-methylpropanoic acid (4b)

The title compound was synthesized by using the same procedure which was followed for Intermediate-3d using methyl 2-(4-(3-amino-6-(2-hydroxyphenyl)pyridazin-4-yl) piperazin-1-yl)-2-methylpropanoate (Yield: 84%) ¹H NMR (400 MHz, DMSO-d₆): δ 7.82-7.80 (m, 1H), 7.54 (s, 1H), 7.31 (t, J=7.6 Hz, 1H), 6.92-6.91 (m, 2H), 6.83 (bs, 2H), 2.67-2.66 (m, 4H), 2.33-2.32 (m, 4H), 1.47 (s, 6H); LC-MS: m/z 358.0 (M+1)⁺.

Intermediate-5c:

Conditions: a) DIPEA, DMF, 25-30° C.-16 h; b) Pd/C, H₂ gas, MeOH, 25-30° C.-RT, 16 h; c) 4M HCl in 1,4-dioxane, DCM, 0° C.-RT, 16 h.

Step-a Synthesis of tert-butyl (E)-3-(4-(3-amino-6-(2-hydroxyphenyl)pyridazin-4-yl)piperazin-1-yl) acrylate (5a)

To a stirred solution 2-(6-amino-5-(piperazin-1-yl) pyridazin-3-yl)phenol hydrochloride (0.20 g, 0.64 mmol) in DMF (5 mL) were added tert-butyl propiolate (0.18 g, 1.29 mmol) and DIPEA (0.3 mL, 1.90 mmol) at RT and stirred for 16 h at 25-30° C. under nitrogen atmosphere. Then the reaction mixture was quenched with cold water (20 mL) extracted with EtOAc (2×50 mL). The combined organic layer was washed with water, brine, dried over anhydrous sodium sulphate and concentrated under vacuum to give the residue which was purified by combi flash column chomatography using 50-60% ethyl acetate in hexane as eluent to afford the title compounds, yield: 46% LC-MS: m/z 398.2 (M+1)⁺.

Step-b: Synthesis of tert-butyl 3-(4-(3-amino-6-(2-hydroxyphenyl)pyridazin-4-yl)piperazin-1-yl)propanoate (5b)

To a stirred solution of tert-butyl (E)-3-(4-(3-amino-6-(2-hydroxyphenyl)pyridazin-4-yl)piperazin-1-yl)acrylate (0.10 g, 0.27 mmol) in methanol (6 mL) was added 10% Pd/C (80 mg). The reaction was performed under hydrogen atmosphere (60 psi) at RT for 16 h. After completion of the reaction (monitored by TLC) the reaction mixture was filtered though celite. The filtrate was concentrated to afford title compound (60 mg, 63%) which was used in the next step without further purification. $^1$H NMR (400 MHz, DMSO-$d_6$): δ 14.24 (s, 1H), 7.92 (dd, J=1.6 Hz, J=8.4 Hz, 1H), 7.50 (s, 1H), 7.25-7.21 (m, 1H), 6.90-6.86 (m, 2H), 6.24 (s, 2H), 3.08 (s, 4H), 2.66-2.59 (m, 6H), 2.39 (t, J=7.2 Hz, 2H), 1.39 (s, 9H); LC-MS: m/z 400.2 (M+1)$^+$.

Step-c: Synthesis of 3-(4-(3-amino-6-(2-hydroxyphenyl)pyridazin-4-yl)piperazin-1-yl)propanoic acid (5c)

The title compound was synthesized by using the same procedure which was followed for 1f$_1$-1f$_{12}$ using tert-butyl 3-(4-(3-amino-6-(2-hydroxyphenyl)pyridazin-4-yl) piperazin-1-yl)propanoate (Yield: 90%) LC-MS: m/z 344.2 (M+1)$^+$.

Intermediate-6c:

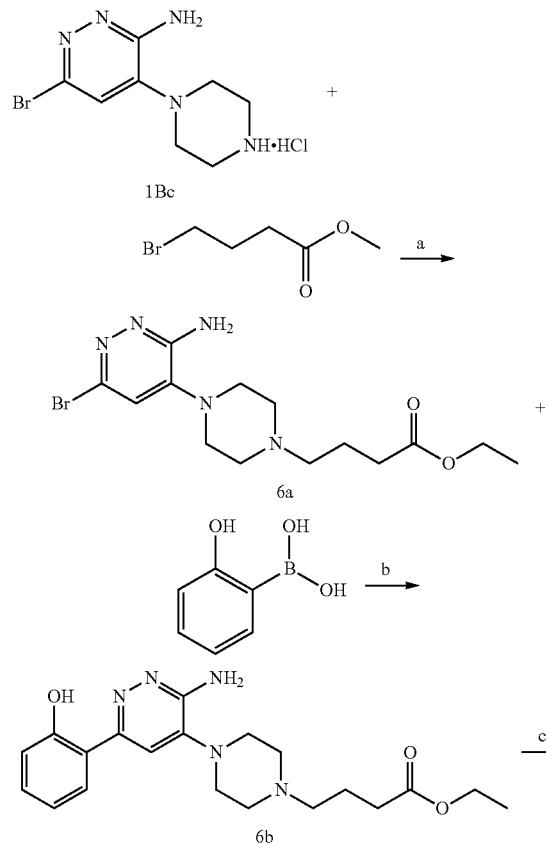

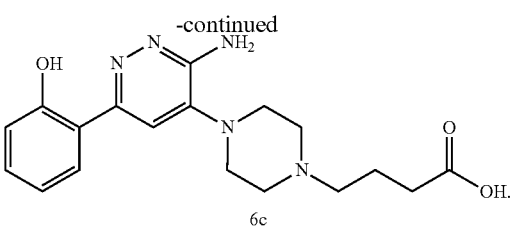

Conditions: a) DIPEA, ACN, 25-30° C.-16 h; b) Pd(dppf)Cl$_2$:DCM (1:1) 2M K$_2$CO$_3$, Dioxane-H$_2$O, 120° C.-1 h, MW c) LiOH•H$_2$O, THF:MeOH:H$_2$O, RT-16 h.

Step-a: Synthesis of methyl 4-(4-(3-amino-6-bromopyridazin-4-yl)piperazin-1-yl)butanoate (6a)

To a stirred solution of 6-bromo-4-(piperazin-1-yl) pyridazin-3-amine hydrochloride (0.39 g, 1.32 mmol) in ACN (5 mL) were added DIPEA (1.2 mL, 3.96 mmol) followed by methyl 4-bromobutanoate (0.40 mL, 2.64 mmol) at RT and stirred for 16 h at 25-30° C. under nitrogen atmosphere. Then the reaction mixture was quenched with cold water (20 mL) extracted with EtOAc (2×50 mL). The combined organic layer was washed with water, brine, dried over anhydrous sodium sulphate and concentrated under vacuum to give the residue which was purified by combi flash column chomatography using 50-60% ethyl acetate in hexane as eluent to afford the title compounds. (0.25 g, 53%) $^1$H NMR (400 MHz, DMSO-$d_6$): δ 6.91 (s, 1H), 6.04 (s, 2H), 4.04-4.02 (m, 2H), 2.94 (s, 4H), 2.40-2.25 (m, 6H), 1.72-1.62 (m, 2H), 1.15 (t, J=6.8 Hz, 3H); LC-MS: m/z 374.1 (M+1)$^+$.

Step-b: methyl 4-(4-(3-amino-6-(2-hydroxyphenyl) pyridazin-4-yl)piperazin-1-yl)butanoate (6b)

The title compound was synthesized by using Step-e of Intermediate-1e$_1$-1e$_{12}$ the General procedure of Suzuki coupling which was followed for (1e$_1$-1e$_{12}$) using methyl 4-(4-(3-amino-6-bromopyridazin-4-yl) piperazin-1-yl) butanoate (Yield: 75%); LC-MS: m/z 387.2 (M+1)$^+$.

Step-c: Synthesis of 4-(4-(3-amino-6-(2-hydroxyphenyl)pyridazin-4-yl)piperazin-1-yl)butanoic acid (6c)

The title compound was synthesized by using the general procedure of hydrolysis of methyl or ethyl esters which was followed for Intermediate-3d using with methyl 4-(4-(3-amino-6-(2-hydroxyphenyl)pyridazin-4-yl)piperazin-1-yl) butanoate (Yield: 90%); LC-MS: m/z 358.2 (M+1)$^+$.

Intermediate-7a-7c:

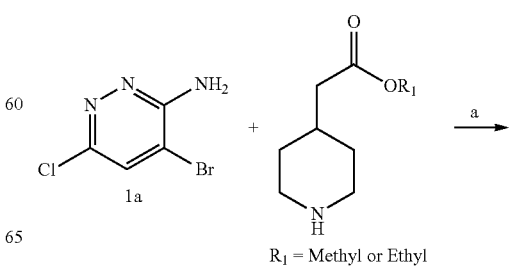

R$_1$ = Methyl or Ethyl

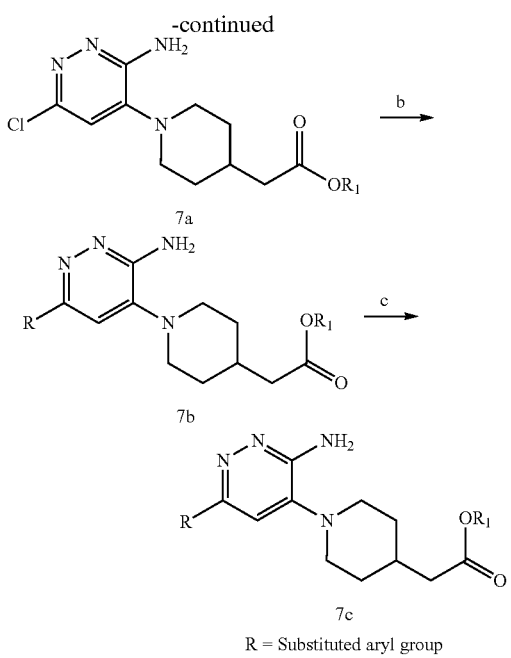

R = Substituted aryl group

Conditions: a) DIPEA, DMF, 100° C. 16 h; b) Substituted aryl boronic acid, Pd(dppf)Cl₂:DCM (1:1), 2M K₂CO₃, Dioxane:water (1:3), sealed tube, 120° C.-16 h; c) LiOH•H₂O, THF:MeOH:H₂O, RT-16 h.

Step-a: Synthesis of methyl 2-(1-(3-amino-6-chloro-pyridazin-4-yl)piperidin-4-yl)acetate (7a)

To a stirred solution of 4-bromo-6-chloropyridazin-3-amine (15.0 g, 72.57 mmol) in DMF (150 mL) was added DIPEA (28.0 g, 217.71 mmol) followed by methyl 2-(piperidin-4-yl)acetate (17.09 g, 108.85 mmol) at RT. The reaction mixture was stirred for 16 h at 100° C. in sealed tube. Then the reaction mixture was poured into ice cold water and extracted with ethyl acetate (2×200 mL). The combined organic layer was washed with water (100 mL), brine (100 mL), dried over anhydrous sodium sulphate and concentrated under vacuum to give the residue which was purified by combi flash column chomatography using 85% ethyl acetate in hexane as eluent to afford the title compound (8.0 g, 37%). $^1$H NMR (400 MHz, DMSO-$d_6$): δ 6.86 (s, 1H), 6.03 (s, 2H), 3.61 (s, 3H), 3.38-3.34 (m, 2H), 2.60-2.54 (m, 2H), 2.31-2.29 (m, 2H), 1.91-1.80 (m, 1H), 1.74-1.71 (m, 2H), 1.46- 1.42 (m, 2H); LC-MS: m/z 285.1 (M+1)$^+$.

Step-b: General procedure of Suzuki coupling with ethyl or methyl 2-(1-(3-amino-6-chloropyridazin-4-yl)piperidin-4-yl)acetate To a stirred solution of ethyl 2-(1-(3-amino-6-chloropyridazin-4-yl)piperidin-4-yl)acetate in 1,4-dioxane in a sealed tube were added substituted Aryl boronic acids or Aryl boronic esters (R) (2.0 eq.), Pd(dppf)Cl₂·DCM (10% mol) and followed by aq. 2M K₂CO₃ solution (3.0 eq.) and The reaction mixture was evacuated with vacuum and purged with N₂ gas, them reaction mixture was stirred for 16 h at 120° C. The reaction was monitored by TLC, after completion of reaction was diluted with EtOAc, filtered off though celite pad and filtrate washed with water, brine, dried over anhydrous sodium sulphate and concentrated under vacuum to give the residue which was purified by combi flash column chomatography using 50-60% ethyl acetate in hexane as eluent to afford the title compounds (7b₁-7b₈). Yield: 30-90%.

TABLE 3

| R | Structure | Characterization data |
|---|---|---|
| ![2-fluorophenylboronic acid] | ![7b₁ structure] 7b₁ | $^1$H NMR (400 MHz, DMSO-$d_6$): δ 7.81 (t, J = 8.0 Hz, 1H), 7.46-7.44 (m, 1H), 7.30 (t, J = 8.8 Hz, 2H), 7.10 (bs, 1H), 6.01 (s, 2H), 3.61 (s, 3H), 3.37 (d, J = 7.6 Hz, 2H), 2.61-2.56 (m, 2H), 2.31 (d, J = 6.8 Hz, 2H), 1.86-1.84 (m, 1H), 1.76-1.73 (m, 2H), 1.51-1.46 (m, 2H); LC-MS: m/z 345.2 (M + 1)$^+$; Yield : 83%. |
| ![3-fluoro-2-hydroxyphenylboronic acid] | ![7b₂ structure] 7b₂ | $^1$H NMR (400 MHz, DMSO-$d_6$): δ 15.06 (s, 1H), 7.76 (d, J = 8.0 Hz, 1H), 7.52 (s, 1H), 7.23-7.17 (m, 1H), 6.87-6.82 (m, 1H), 6.33 (s, 2H), 4.08 (q, J = 7.2 Hz, 2H), 3.48-3.45 (m, 2H), 2.72-2.69 (m, 2H), 2.32-2.29 (m, 2H), 1.89-1.88 (m, 1H), 1.79-1.75 (m, 2H), 1.52-1.48 (m, 2H), 1.20 (t, J = 6.8 Hz, 3H); LC-MS: m/z 375.10 (M + 1)$^+$ ; (Yield : 33%). |
| ![5-fluoro-2-hydroxyphenylboronic acid] | ![7b₃ structure] 7b₃ | $^1$H NMR (400 MHz, DMSO-$d_6$): δ 14.08 (bs, 1H), 7.80 (d, J = 13.6 Hz, 1H), 7.52 (s, 1H), 7.10-7.05 (m, 1H), 6.90-6.86 (m, 1H), 6.27 (s, 1H), 4.18 (dd, J = 14.2 Hz, J = 7.1 Hz, 2H), 3.47 (d, J = 12.4 Hz, 2H), 2.73 (t, J = 11.6 Hz, 2H), 2.31 (d, J = 6.8 Hz, 2H), 1.99-1.86 (m, 3H), 1.54-1.46 (m, 2H), 1.26-1.06 (m, 4H); LC-MS: m/z 375.07 (M + 1)$^+$. |

TABLE 3-continued

| R | Structure | Characterization data |
|---|---|---|
| 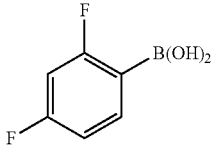 | 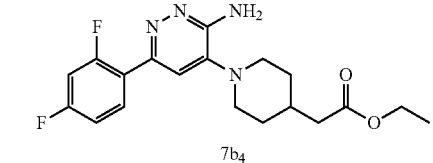 [SMILES: CCOC(=O)CC1CCN(c2cc(-c3ccc(F)cc3F)nnc2N)CC1]<br>7b$_4$ | $^1$H NMR (400 MHz, DMSO-d$_6$): δ 7.89-7.83 (m, 1H), 7.39-7.33 (m, 1H), 7.22-7.19 (m, 1H), 7.08 (d, J = 2.0 Hz, 1H), 6.03 (s, 2H), 4.14-4.03 (m, 2H), 3.37 (s, 2H), 2.67-2.55 (m, 2H), 2.28 (d, J = 6.8 Hz, 2H), 1.86-1.84 (m, 1H), 1.76-1.73 (m, 2H), 1.48-1.45 (m, 2H), 1.21-1.17 (m, 3H); LC-MS: m/z 377.2 (M + 1)$^+$; (Yield: 68%). |
| 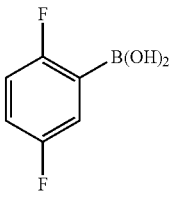 | 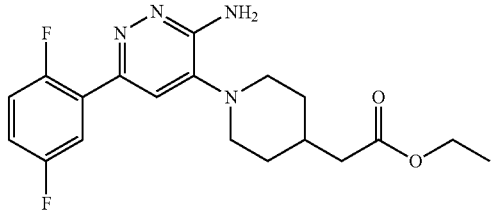<br>7b$_5$ | $^1$H NMR (400 MHz, DMSO-d$_6$): δ 7.65-7.62 (m, 1H), 7.38-7.29 (m, 2H), 7.14-7.08 (m, 1H), 6.12 (s, 2H), 4.26-4.06 (m, 2H), 3.41-3.40 (m, 2H), 2.50-2.49 (m, 2H), 2.33-2.27 (m, 2H), 1.86-1.85 (m, 1H), 1.67-1.63 (m, 2H), 1.49-1.48 (m, 2H), 1.19-1.16 (m, 3H); LC-MS: m/z 377.1 (M + 1)$^+$. |
| 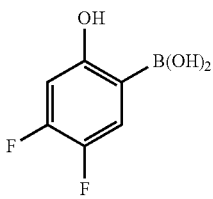 | 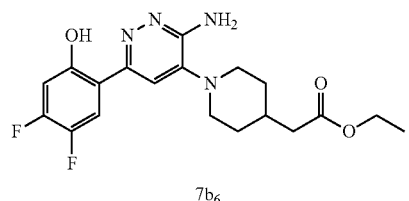<br>7b$_6$ | LC-MS: m/z 393.2 (M + 1)$^+$. |
| 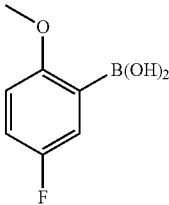 | 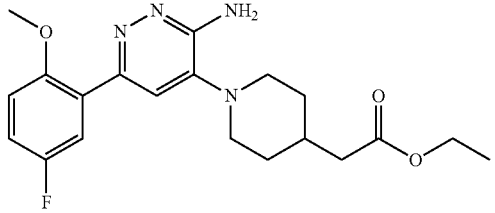<br>7b$_7$ | LC-MS: m/z 389.2 (M + 1)$^+$.<br>(Yield: 88%). |
| 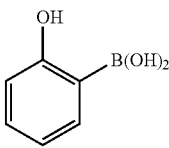 | 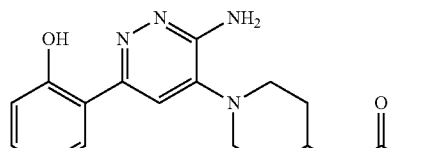<br>7b$_8$ | $^1$H NMR (400 MHz, DMSO-d$_6$): δ 14.20 (bs, 1H), 7.89 (d, J = 6.9 Hz, 1H), 7.49 (s, 1H), 7.26-7.21 (m, 1H), 6.90-6.87 (m, 2H), 6.21 (s, 2H), 3.62 (s, 3H), 3.48-3.45 (m, 2H), 2.73-2.67 (m, 2H), 2.32 (d, J = 6.9 Hz, 2H), 1.92-1.86 (m, 1H), 1.78-1.76 (m, 2H), 1.54-1.48 (m, 2H); LC-MS: m/z 343.2 (M + 1)$^+$. |

Step-c: General procedure of hydrolysis of substituted Metyl or Ethyl-(7c$_1$-7c$_8$)

The title compound was synthesized by using the general procedure of hydrolysis of methyl or ethyl esters which was followed for Intermediate-3d using with substituted Methyl or Ethyl (Yield: 60-90%%).

The compounds listed in below Table-4 were prepared by procedure similar to the one described in Intermediate-3d with appropriate variations in reactants. The characterization data of the compounds are summarized herein the below table.

TABLE 4

| Structure | Characterization data |
|---|---|
| 7c₁ | ¹H NMR (400 MHz, DMSO-d₆): δ 7.81 (t, J = 6.8 Hz, 1H), 7.47-7.26 (m, 1H), 7.30 (t, J = 8.4 Hz, 2H), 7.10 (bs, 1H), 5.99 (s, 2H), 3.32 (s, 2H), 2.61-2.50 (m, 2H), 2.19 (d, J = 6.8 Hz, 2H), 1.79-1.75 (m, 3H), 1.49-1.41 (m, 2H); LC-MS: m/z 331.2 (M + 1)⁺ ; (Yield : 89% |
| 7c₂ | ¹H NMR (400 MHz, DMSO-d₆): δ 7.75 (d, J = 8.0 Hz, 1H), 7.51 (s, 1H), 7.21-7.17 (m, 1H), 6.85-6.24 (m, 1H), 6.32 (s, 2H), 3.48-3.45 (m, 2H), 2.73-2.67 (m, 2H), 2.32-2.31 (m, 2H), 1.87-1.77 (m, 3H), 1.53-1.47 (m, 2H); (Yield : 72%). |
| 7c₃ | ¹H NMR (400 MHz, DMSO-d₆): δ 13.01 (bs, 1H), 7.85 (d, J = 10.4 Hz, 1H), 7.51 (s, 1H), 7.09-7.04 (m, 1H), 6.89-6.86 (m, 1H), 6.26 (s, 2H), 3.47 (d, J = 11.6 Hz, 2H), 2.72 (t, J = 11.2 Hz, 2H), 2.23 (d, J = 6.8 Hz, 2H), 1.86-1.77 (m, 3H), 1.52-1.44 (m, 3H); LC-MS: m/z 347.2 (M + 1)⁺. |
| 7c₄ | ¹H NMR (400 MHz, DMSO-d₆): δ 12.0 (s, 1H), 7.88-7.82 (m, 1H), 7.40-7.35 (m, 1H), 7.24-7.20 (m, 1H), 7.14 (s, 1H), 6.32 (s, 2H), 3.42-3.39 (m, 2H), 2.66-2.61 (m, 2H), 2.20 (d, J = 6.0 Hz, 2H), 1.85-1.75 (m, 3H), 1.50-1.42 (m, 2H); LC-MS: m/z 349.2 (M + 1)⁺; (Yield: 43%). |
| 7c₅ | LC-MS: m/z 349.2 (M + 1)⁺ ; (Yield: 77%). |
| 7c₆ | ¹H NMR (400 MHz, DMSO-d₆): δ 8.15-8.09 (m, 1H), 7.50 (s, 1H), 6.96-6.93 (m, 2H), 6.35 (s, 2H), 3.48-3.46 (m, 2H), 2.52-2.51 (m, 2H), 2.23-2.21 (m, 2H), 1.91-1.77 (m, 3H), 1.33-1.22 (m, 2H); LC-MS: m/z 363.1 (M − 1). |

| Structure | Characterization data |
|---|---|
| 7c7 | LC-MS: m/z 361.2 (M + 1)+; (Yield: 77%). |
| 7c8 | ¹H NMR (400 MHz, DMSO-d₆): δ 7.91-7.89 (m, 2H), 7.49 (s, 1H), 7.25-7.23 (m, 1H), 6.90-6.86 (m, 2H), 6.18 (s, 2H), 3.47-3.44 (m, 2H), 2.72-2.66 (m, 2H), 2.22 (d, J = 6.8 Hz, 2H), 1.91-1.78 (m, 3H), 1.54-1.48 (m, 2H); LC-MS: m/z 329.2 (M + 1)+. |

Intermediate-8c:

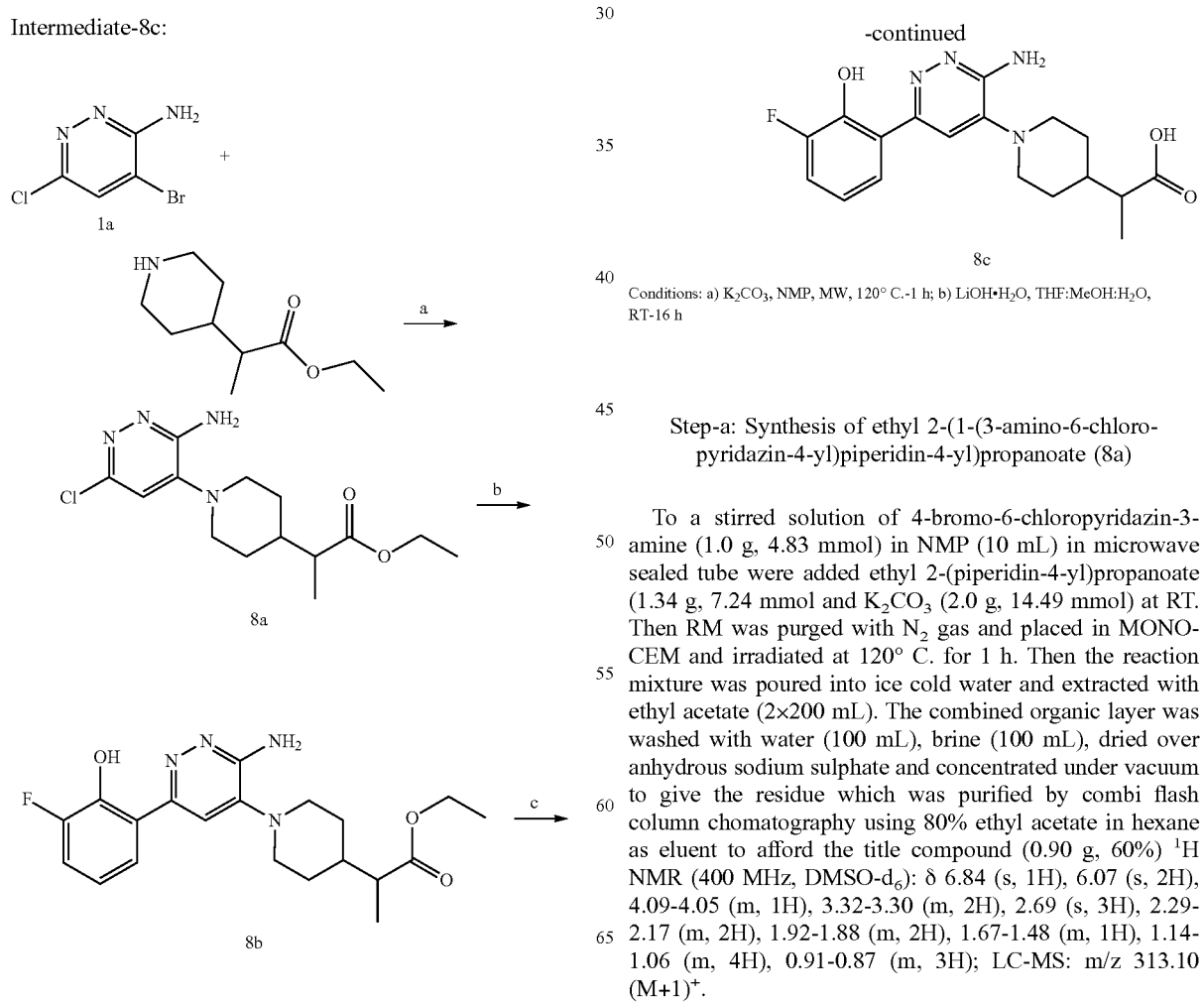

Conditions: a) K₂CO₃, NMP, MW, 120° C.-1 h; b) LiOH·H₂O, THF:MeOH:H₂O, RT-16 h

Step-a: Synthesis of ethyl 2-(1-(3-amino-6-chloro-pyridazin-4-yl)piperidin-4-yl)propanoate (8a)

To a stirred solution of 4-bromo-6-chloropyridazin-3-amine (1.0 g, 4.83 mmol) in NMP (10 mL) in microwave sealed tube were added ethyl 2-(piperidin-4-yl)propanoate (1.34 g, 7.24 mmol and K₂CO₃ (2.0 g, 14.49 mmol) at RT. Then RM was purged with N₂ gas and placed in MONO-CEM and irradiated at 120° C. for 1 h. Then the reaction mixture was poured into ice cold water and extracted with ethyl acetate (2×200 mL). The combined organic layer was washed with water (100 mL), brine (100 mL), dried over anhydrous sodium sulphate and concentrated under vacuum to give the residue which was purified by combi flash column chomatography using 80% ethyl acetate in hexane as eluent to afford the title compound (0.90 g, 60%) ¹H NMR (400 MHz, DMSO-d₆): δ 6.84 (s, 1H), 6.07 (s, 2H), 4.09-4.05 (m, 1H), 3.32-3.30 (m, 2H), 2.69 (s, 3H), 2.29-2.17 (m, 2H), 1.92-1.88 (m, 2H), 1.67-1.48 (m, 1H), 1.14-1.06 (m, 4H), 0.91-0.87 (m, 3H); LC-MS: m/z 313.10 (M+1)+.

Step-b: Synthesis of ethyl 2-(1-(3-amino-6-(3-fluoro-2-hydroxyphenyl)pyridazin-4-yl)piperidin-4-yl)propanoate (8b)

The title compound was synthesized by using the general procedure suzuki copling which was followed for (1e₁-1e₁₂) using with ethyl 2-(1-(3-amino-6-chloropyridazin-4-yl) piperidin-4-yl) propanoate (8a) (Yield: 50%) ¹H NMR (400 MHz, DMSO-d₆): δ 15.05 (s, 1H), 7.75 (d, J=8.0 Hz, 1H), 7.50 (s, 1H), 7.22-7.17 (m, 1H), 6.87-6.82 (m, 1H), 6.35 (s, 2H), 4.12-4.06 (m, 1H), 3.52-3.41 (m, 2H), 2.69-2.61 (m, 2H), 1.72-1.53 (m, 6H), 1.23-1.18 (m, 4H), 1.10 (d, J=7.2 Hz, 3H); LC-MS: m/z 389.15 (M+1)⁺.

Step-c: Synthesis of 2-(1-(3-amino-6-(3-fluoro-2-hydroxyphenyl)pyridazin-4-yl)piperidin-4-yl)propanoic acid (8c)

The title compound was synthesized by using the general procedure of hydrolysis of methyl or ethyl esters which was followed for 3d using with ethyl 2-(1-(3-amino-6-(3-fluoro-2-hydroxyphenyl)pyridazin-4-yl) piperidin-4-yl) propanoate (Yield: 80%) ¹H NMR (400 MHz, DMSO-d₆): δ 15.05 (s, 1H), 7.75 (d, J=8.0 Hz, 1H), 7.50 (s, 1H), 7.20-7.15 (m, 1H), 6.86-6.81 (m, 1H), 6.32 (s, 2H), 2.61-2.50 (m, 3H), 1.99-1.98 (m, 1H), 1.88-1.66 (m, 2H), 1.58-1.42 (m, 4H), 0.98 (d, J=7.2 Hz, 3H); LC-MS: m/z 361.05 (M+1)⁺.

Intermediate-9e:

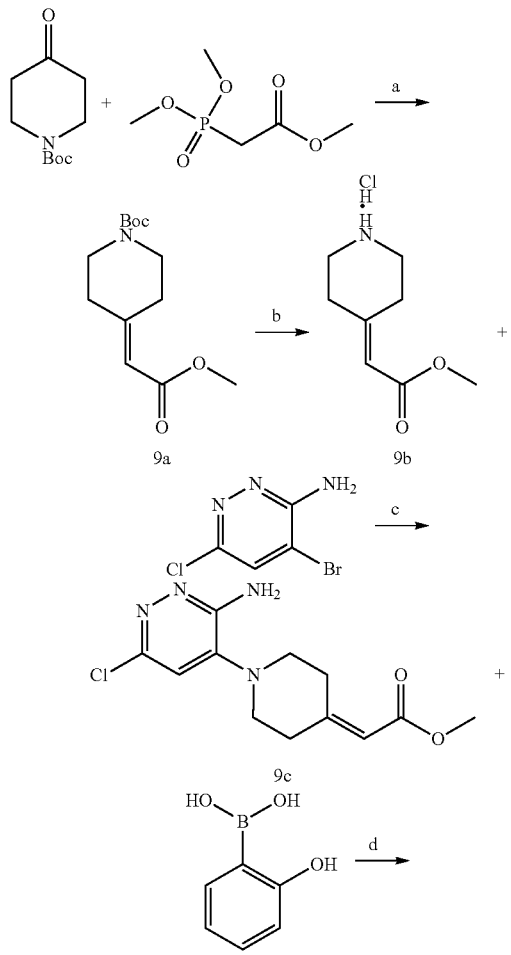

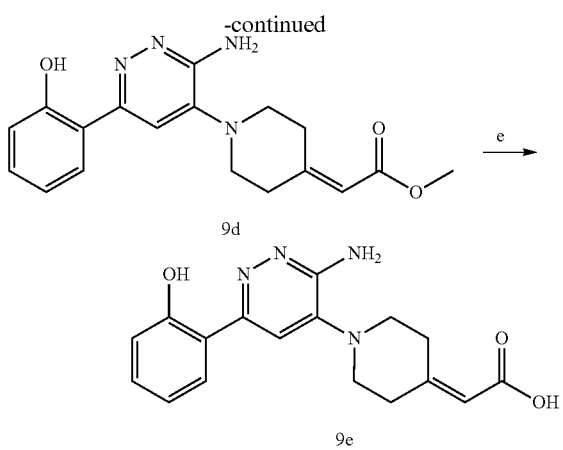

Conditions: a) NaH (56-60%), DMF, 0° C.-RT-16 h; b) 4M HCl in Dioxane, DCM, 0° C.-RT, 16 h; c) DIPEA, DMF, 120° C.-1 h, MW; d) (2-Hydroxy) Phenylboronic acid, Pd(dppf)Cl₂:DCM (1:1), 2M K₂CO₃, Dioxane, MW, 120° C., -1 h, Method-B; e) LiOH•H₂O, THF:MeOH:H₂O, RT-16 h.

Step-a: Synthesis of tert-butyl 4-(2-methoxy-2-oxo-ethylidene)piperidine-1-carboxylate (9a)

To a stirred solution of tert-butyl 4-oxopiperidine-1-carboxylate (3.0 g, 15 mmol) in DMF (30 mL) in two neck RB was wadded NaH (56-60%) (0.54 g, 22.5 mmol) portion wise at 0° C. and stirred for 30 mins at RT then methyl 2-(dimethoxyphosphoryl)acetate (3.29 g, 18 mmol) was added and stirred for 16 h at RT. The reaction mixture was quenched with cold water and extracted with ethyl acetate (2×100 mL). The combined organic layer was washed with water (100 mL), brine (100 mL), dried over anhydrous sodium sulphate and concentrated under vacuum to give the residue which was purified by combi flash column chomatography using 80% ethyl acetate in hexane as eluent to afford the title compound (3.0 g, 78.1%) ¹H NMR (400 MHz, DMSO-d₆): δ 5.77 (s, 1H), 3.61 (s, 3H), 3.41-3.33 (m, 4H), 2.82 (t, J=6.0 Hz, 2H), 2.26 (t, J=5.6 Hz, 2H), 1.44 (s, 9H). LC-MS: m/z 255.1 (M+1)⁺.

Step-b: Synthesis of methyl 2-(piperidin-4-ylidene)acetate hydrochloride (9b)

The title compound was synthesized by using the same procedure which was followed for step e-c of Intermediate-3b using tert-butyl 4-(2-methoxy-2-oxoethylidene)piperidine-1-carboxylate (Yield: 90%) ¹H NMR (400 MHz, DMSO-d₆): δ 9.37 (bs, 2H), 5.85 (s, 1H), 3.64 (s, 3H), 3.14-3.10 (m, 6H), 2.55-2.44 (m, 2H); LC-MS: m/z 155.07 (M+1)⁺.

Step-c: Synthesis of methyl 2-(1-(3-amino-6-chloro-pyridazin-4-yl)piperidin-4-ylidene)acetate (9c)

To a stirred solution of 4-bromo-6-chloropyridazin-3-amine (2.38 g, 11.5 mmol) in DMF (20 mL) in microwave sealed tube were added methyl 2-(piperidin-4-ylidene)acetate hydrochloride (2.2 g, 11.5 mmol) and DIPEA (6.16 mL, 34.5 mmol) at RT. Then RM was purged with N₂ gas and placed in MONOCEM and irradiated at 120° C. for 1 h. Then the reaction mixture was poured into ice cold water and extracted with ethyl acetate (2×200 mL). The combined organic layer was washed with water (100 mL), brine (100 mL), dried over anhydrous sodium sulphate and concentrated under vacuum to give the residue which was purified by combi flash column chomatography using 80% ethyl acetate in hexane as eluent to afford the title compound (1.60 g, 49.3%). $^1$H NMR (400 MHz, DMSO-$d_6$): δ 6.81 (s, 1H), 6.01 (s, 2H), 5.61 (s, 1H), 3.58-3.55 (m, 5H), 3.52-3.50 (m, 2H), 3.14-3.04 (m, 4H); LC-MS: m/z 283.1 (M+1)$^+$.

Step-d: Synthesis of methyl 2-(1-(3-amino-6-(2-hydroxyphenyl)pyridazin-4-yl)piperidin-4-ylidene) acetate (9d)

The title compound was synthesized by using the Genereal procedure of Suzuki coupling which was followed for (1e$_1$-1e$_{12}$) using methyl 2-(1-(3-amino-6-chloropyridazin-4-yl)piperidin-4-ylidene)acetate (Yield: 28%); LC-MS: m/z 341.2 (M+1)$^+$.

Step-e: Synthesis of 2-(1-(3-amino-6-(2-hydroxyphenyl)pyridazin-4-yl) piperidin-4-ylidene) acetic acid (9e)

The title compound was synthesized by using the general procedure of hydrolysis of methyl or ethyl esters which was followed for 3d using with methyl 2-(1-(3-amino-6-(2-hydroxyphenyl)pyridazin-4-yl)piperidin-4-ylidene)acetate (Yield: 65.2%); LC-MS: m/z 327.2 (M+1)$^+$.

Intermediate-10c:

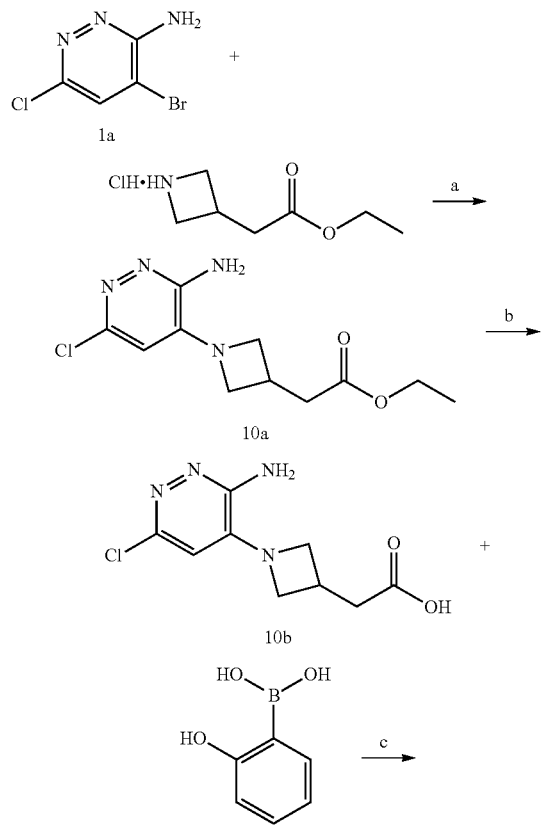

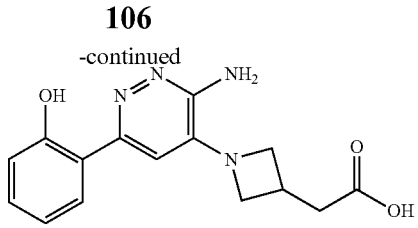

Conditions: a) DIPEA, ACN, 90° C.-16 h; b) LiOH•H$_2$O, THF:MeOH:H$_2$O, RT-16 h; c) (2-Hydroxy) Phenyl boronic acid, Pd(dppf)Cl$_2$:DCM (1:1), 2M K$_2$CO$_3$, Dioxane:water (1:3), MW, 120° C.-1 h;

Step-a: Synthesis of ethyl 2-(1-(3-amino-6-chloropyridazin-4-yl)azetidin-3-yl)acetate (10a)

The title compound was synthesized by using the same procedure which was followed for Intermediate-1 b of Method-B using 4-bromo-6-chloropyridazin-3-amine (Yield: 45%) $^1$H NMR (400 MHz, DMSO-$d_6$): δ 6.28 (s, 1H), 5.68 (s, 2H), 4.20 (t, J=8.0 Hz, 2H), 4.05 (q, J=6.8 Hz, 2H), 3.72 (q, J=6.0 Hz, 2H), 2.93-2.86 (m, 1H), 2.73-2.67 (m, 2H), 1.20 (t, J=7.2 Hz, 3H); LC-MS: m/z 271.0 (M+1)$^+$.

Step-b: Synthesis of 2-(1-(3-amino-6-chloropyridazin-4-yl)azetidin-3-yl)acetic acid (10b)

The title compound was synthesized by using the general procedure of hydrolysis of methyl or ethyl esters which was followed for Intermediate-3d using with ethyl 2-(1-(3-amino-6-chloropyridazin-4-yl)azetidin-3-yl)acetate (Yield: 39%). $^1$H NMR (400 MHz, DMSO-$d_6$): δ 12.20 (s, 1H), 6.28 (s, 1H), 5.69 (s, 2H), 4.20 (t, J=8.0 Hz, 2H), 3.72 (t, J=6.0 Hz, 2H), 2.90-2.80 (m, 1H), 2.61 (d, J=7.6 Hz, 2H); LC-MS: m/z 243.0 (M+1)$^+$.

Step-c: Synthesis of 2-(1-(3-amino-6-(2-hydroxyphenyl)pyridazin-4-yl)azetidin-3-yl)acetic acid (10c)

The title compound was synthesized by using the General procedure of Suzuki coupling which was followed for (1e$_1$-1e$_{12}$) using 2-(1-(3-amino-6-chloropyridazin-4-yl) azetidin-3-yl) acetic acid (crude 40%). LC-MS: m/z 301.0 (M+1)$^+$.

Intermediate-11c:

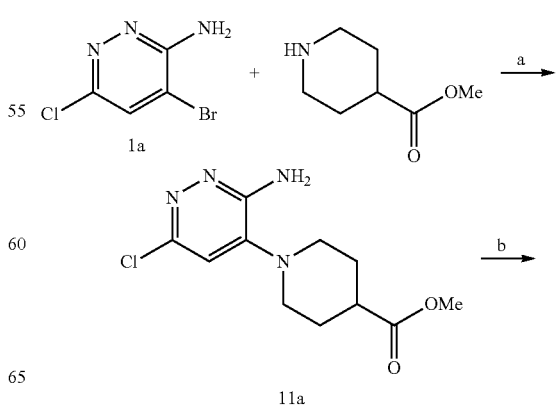

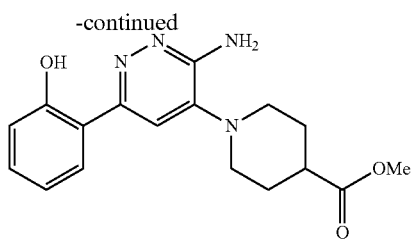

11b

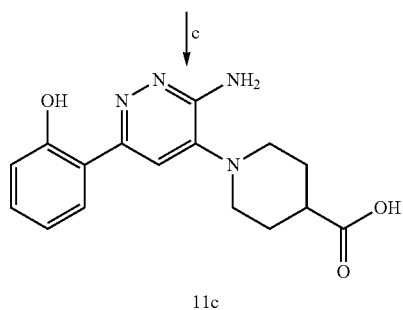

11c

Conditions: a) ACN, 90° C.-16 h; b) (2-hydroxyphenyl)boronic acid, Pd(dppf)Cl₂:DCM (1:1), K₂CO₃, Dioxane:water (5:2), M.W, 120° C., 1 h; c) LiOH·H₂O, MeOH:THF:H₂O (2:2:1), 0° C.-RT, 16 h.

Step-a: Synthesis of methyl 1-(3-amino-6-chloro-pyridazin-4-yl)piperidine-4-carboxylate (11a)

To a stirred solution of 4-bromo-6-chloropyridazin-3-amine (0.38 g, 1.84 mmol) in acetonitrile (7 mL) was added methyl piperidine-4-carboxylate (1.31 g, 9.22 mmol) at RT and stirred for 16 h at 90° C. under nitrogen atmosphere. Then the reaction mixture was quenched with cold water (50 mL) and extracted with EtOAc (2×50 mL). The combined organic layer was washed with water (50 mL), brine (50 mL), dried over anhydrous sodium sulphate and concentrated under vacuum to give the residue which was purified by combi flash using 60% ethyl acetate in hexane as eluent to afford title compound (0.36 g, 72.2%) $^1$H NMR (400 MHz, DMSO-d₆): δ 6.86 (s, 1H), 6.09 (s, 2H), 3.63 (s, 3H), 3.68-3.51 (m, 3H), 2.68-2.61 (m, 2H), 1.93-1.81 (m, 4H); LC-MS: m/z 271.0 (M+1)⁺.

Step-b: Synthesis of methyl 1-(3-amino-6-chloro-pyridazin-4-yl)piperidine-4-carboxylate (11b)

A mixture of 1,4-dioxane:water (5:2) (6 mL) were taken in microwave vial and degassed under nitrogen atmosphere for 5 min. To this methyl 1-(3-amino-6-chloropyridazin-4-yl)piperidine-4-carboxylate (0.25 g, 0.92 mmol) and (2-hydroxyphenyl)boronic acid (0.25 g, 1.84 mmol) were added followed the addition of K₂CO₃ (0.25 g, 1.84 mmol) and Pd(dppf)Cl₂·DCM (0.075 g, 0.151 mmol). The reaction mixture was heated for 1 h at 120° C. in Microwave. Once the reaction was completed (monitored by TLC), the reaction mixture was diluted with EtOAc (2×100 mL). The combined organic layer was washed with water (100 mL), brine (100 mL), dried over anhydrous sodium sulphate and concentrated under reduced pressure to give the residue which was purified by combi flash column chomatography using 70% ethyl acetate in hexane as eluent to afford the title compound (0.06 g, 20%), LC-MS: m/z 329.1 (M+1)⁺.

Step-c: Synthesis of 1-(3-amino-6-(2-hydroxyphenyl)pyridazin-4-yl)piperidine-4-carboxylic acid (11c)

To a stirred solution of methyl 1-(3-amino-6-chloro-pyridazin-4-yl)piperidine-4-carboxylate (0.18 g, 0.54 mmol) in a mixture of solvent (THF:MeOH:H₂O) (2:2:1) (10 mL) was added LiOH·H₂O (0.069 g, 1.64 mmol) at 0° C. and stirred for 16 h at RT. The reaction mixture was concentrated under reduced pressure and the residue was diluted with water and neutralized with 1N HCl. The precipitated solid was filtered and dried under vacuum to afford the title compound (0.14 g, 82%), $^1$H NMR (400 MHz, DMSO-d₆): δ 13.20 (bs, 1H), 7.92-7.90 (m, 1H), 7.50 (s, 1H), 7.25-7.21 (m, 1H), 6.89-6.86 (m, 2H), 6.23 (s, 2H), 3.44-3.41 (m, 2H), 2.78-2.73 (m, 2H), 2.46-2.41 (m, 1H), 1.97-1.85 (m, 4H). Intermediate-12c:

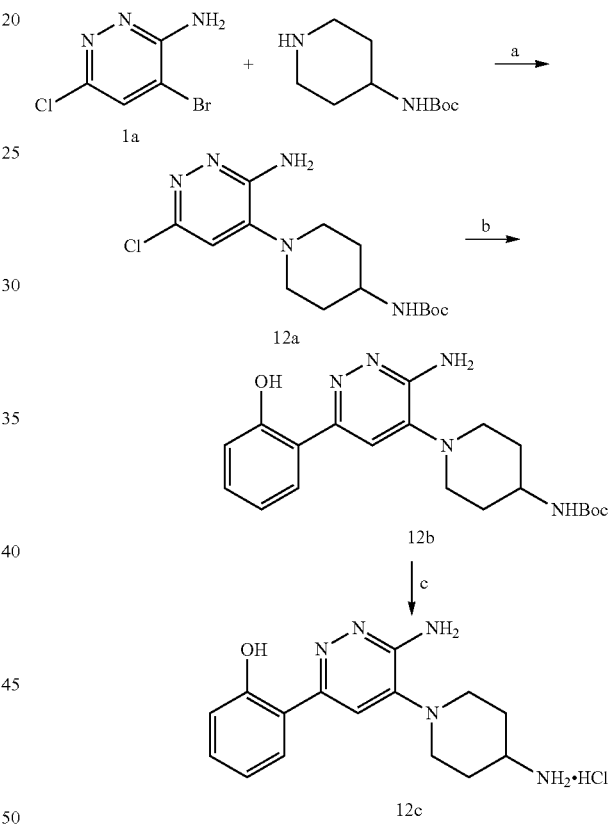

Conditions: a) ACN, 90° C., 16 h; b) (2-hydroxyphenyl)boronic acid, Pd(dppf)Cl₂, DCM, K₂CO₃, 1,4-dioxane:water (5:2), MW, 120° C.-1 h; c) 4M HCl in 1,4-Dioxane, 1,4-Dioxane, 0° C.-RT.

Step-a: Synthesis of tert-butyl (1-(3-amino-6-chloropyridazin-4-yl)piperidin-4-yl)carbamate (12a)

To a stirred solution of 4-bromo-6-chloropyridazin-3-amine (1a, 0.4 g, 1.94 mmol) in ACN (7 mL) was added tert-butyl piperidin-4-ylcarbamate (1.94 g, 9.70 mmol) at RT and stirred for 16 h at 90° C. under nitrogen atmosphere. The reaction mixture was quenched with cold water (50 mL) and extracted with EtOAc (2×50 mL). The combined organic layer was washed with water (50 mL), brine (50 mL), dried over anhydrous sodium sulphate and concentrated under reduced pressure to give the crude product which was purified by combi flash using 60% ethyl acetate in hexane as eluent to afford the title compound (0.4 g, 63.7%). ¹H NMR (400 MHz, DMSO-d₆): δ 6.91 (d, J=6.8 Hz, 1H), 6.86 (s, 1H), 6.04 (s, 2H), 3.40-3.31 (m, 3H), 3.64 (t, J=10.8 Hz, 2H), 1.81 (d, J=10.4 Hz, 2H), 1.63-1.53 (m, 2H), 1.39 (m, 9H); LC-MS: m/z 328.2 (M+1)⁺.

Step-b: Synthesis of tert-butyl (1-(3-amino-6-(2-hydroxyphenyl)pyridazin-4-yl)piperidin-4-yl)carbamate (12b)

To a mixture of 1,4-dioxane:water (5:2) (6 mL) were taken in microwave vial and degassed with nitrogen for 5 min. To this methyl tert-butyl (1-(3-amino-6-chloropyridazin-4-yl) piperidin-4-yl) carbamate (0.2 g, 0.61 mmol) and (2-hydroxyphenyl) boronic acid (0.17 g, 1.22 mmol) were added followed the addition of K₂CO₃ (0.17 g, 1.22 mmol) and Pd(dppf)Cl₂·DCM (0.049 g, 0.061 mmol). The reaction mixture was heated for 1 h at 120° C. in microwave. Then the reaction mixture was extracted with EtOAc (2×100 mL). The combined organic layer was washed with water (100 mL), brine (100 mL), dried over anhydrous sodium sulphate and concentrated under vacuum to give the crude product which was purified by combi flash column chomatography using 70% ethyl acetate in hexane as eluent to afford the title compound (0.06 g, 26%). ¹H NMR (400 MHz, DMSO-d₆): δ 14.13 (s, 1H), 7.90 (dd, J₁=1.2, J₂=8.4 Hz, 1H), 7.50 (s, 1H), 7.25-7.21 (m, 1H), 6.95-6.98 (m, 3H), 6.20 (s, 2H), 3.40-3.31 (m, 3H), 2.79-2.73 (m, 2H), 1.90-1.85 (m, 2H), 1.69-1.63 (m, 2H), 1.40 (s, 9H); LC-MS: m/z 386.1 (M+1)⁺.

Step-c: 2-(6-amino-5-(4-aminopiperidin-1-yl) pyridazin-3-yl)phenol hydrochloride (12c)

To a stirred solution of tert-butyl (1-(3-amino-6-(2-hydroxyphenyl)piperidin-4-yl)carbamate (0.6 g, 1.56 mmol) in DCM (10.0 mL) was added 4 M HCl in 1,4-dioxane (6.0 mL) at 0° C. under nitrogen atmosphere. The reaction mixture was stirred for 16 h and then the solvent was evaporated under reduced pressure to get the crude product as brown solid. The solid was washed with diethyl ether (2×50 mL), filtered and dried under vacuum to afford the title compound (0.5 g, 100%). ¹H NMR (400 MHz, DMSO-d₆): δ 8.20 (bs, 3H), 7.51 (d, J=7.3 Hz, 1H), 7.47 (bs, 1H), 7.39 (t, J=7.3 Hz, 1H), 7.09-7.07 (m, 1H), 7.00-6.96 (m, 1H), 5.75 (s, 2H), 3.75-3.70 (m, 2H), 3.01-2.98 (m, 2H), 2.67-2.60 (m, 1H), 2.03-2.01 (m, 2H), 1.82-1.79 (m, 2H), LC-MS: m/z 286.1 (M+1)⁺.

Intermediate-13d:

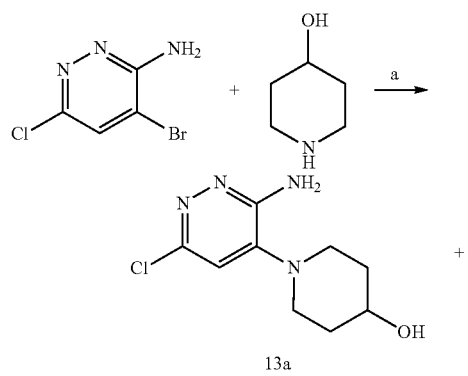

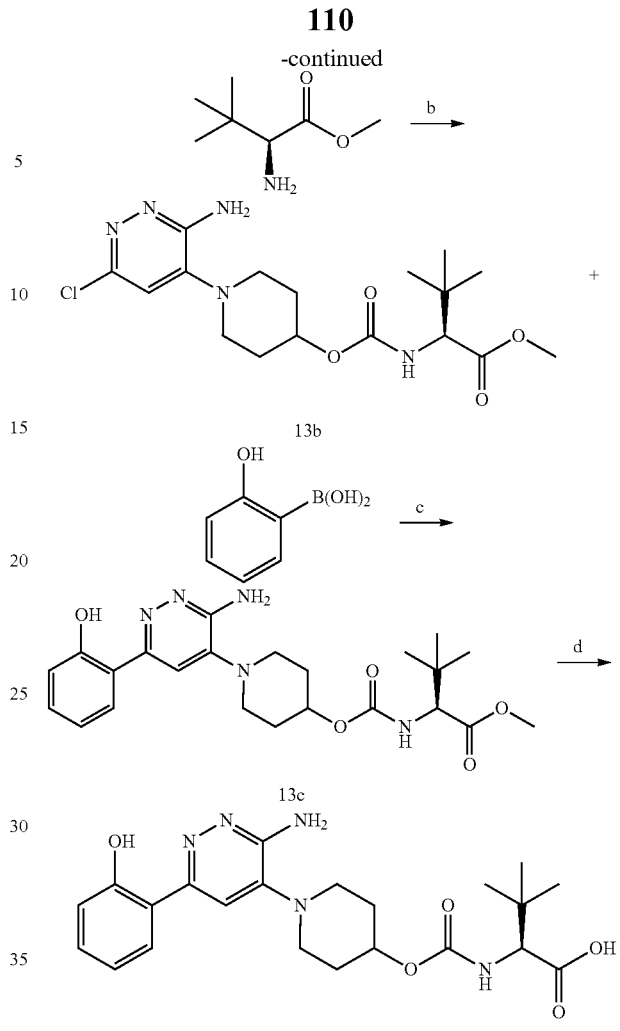

Conditions: a) ACN, 90° C.-16 h; b) triphosgene, Pyridine, DCM, 0° C.-RT-3 h; c) (2-hydroxyphenyl) boronic acid, Pd(dppf)Cl₂:DCM (1:1), K₂CO₃, Dioxane:water (5:2), M.W, 120° C.-1 h; d) LiOH·H₂O, MeOH:THF:H₂O (2:2:1), 0° C.-RT, 16 h.

Step-a: Synthesis of 1-(3-amino-6-chloropyridazin-4-yl)piperidin-4-ol (13a)

The title compound was synthesized by using the same procedure which was followed for (11a) using 4-bromo-6-chloropyridazin-3-amine (Yield: 45%). ¹H NMR (400 MHz, DMSO-d₆): δ 6.85 (s, 1H), 6.03 (s, 2H), 4.72 (d, J=4.0 Hz, 1H), 3.66-3.63 (m, 1H), 3.31-3.20 (m, 2H), 2.75-2.72 (m, 2H), 1.86-1.82 (m, 2H), 1.62-1.55 (m, 2H); LC-MS: m/z 229.1 (M+1)⁺.

Step-b: Synthesis of methyl (S)-2-((((1-(3-amino-6-chloropyridazin-4-yl)piperidin-4-yl)oxy) carbonyl) amino)-3,3-dimethylbutanoate (13b)

To a stirred solution of methyl (S)-2-amino-3,3-dimethylbutanoate (015 g, 0.87 mmol) in DCM (10 mL) in two neck RB were wadded Pyridine (0.2 mL, 2.63 mmol) followed by triphosgene (0.12 g, 0.43 mmol) portionwise at 0° C., then 13a (0.2 g, 0.87 mmol) and stirred for 3 h at RT. The reaction mixture was quenched with cold water and extracted with DCM (2×50 mL). The combined organic layer was washed with water (50 mL), brine (50 mL), dried over anhydrous sodium sulphate and concentrated under vacuum to give the residue which was purified by combi flash column chomatography using 80% ethyl acetate in hexane as eluent to afford the title compound (0.15 g, 43%). $^1$H NMR (400 MHz, DMSO-$d_6$): δ 7.48 (d, J=8.8 Hz, 1H), 6.89 (s, 1H), 6.13 (s, 2H), 4.67-4.66 (m, 1H), 3.90 (d, J=8.0 Hz, 1H), 3.60 (s, 3H), 3.26-3.23 (m, 2H), 2.89-2.82 (m, 2H), 1.99-1.90 (m, 2H), 1.78-1.76 (m, 2H), 0.94 (s, 9H); LC-MS: m/z 400.1 (M+1)$^+$.

Step-c: Synthesis of methyl (S)-2-((((1-(3-amino-6-(2-hydroxyphenyl)pyridazin-4-yl)piperidin-4-yl)oxy) carbonyl)amino)-3,3-dimethylbutanoate (13c)

The title compound was synthesized by using the Genereal procedure of Suzuki coupling which was followed for Intermediate-1e$_1$-1e$_{12}$ using methyl (S)-2-((((1-(3-amino-6-chloropyridazin-4-yl)piperidin-4-yl)oxy)carbonyl)amino)-3,3-dimethylbutanoate (Yield: 58%).
$^1$H NMR (400 MHz, DMSO-$d_6$): δ 14.23 (s, 1H), 7.91 (d, J=7.6 Hz, 1H), 7.52-7.48 (m, 2H), 7.26-7.21 (m, 1H), 6.90-6.87 (m, 2H), 6.29 (s, 2H), 4.72-4.71 (m, 1H), 3.92 (s, 1H), 3.72 (s, 3H), 3.37-3.34 (m, 2H), 2.96-2.91 (m, 2H), 2.33-2.32 (m, 2H), 1.90-1.82 (m, 2H), 0.95 (s, 9H); LC-MS: m/z 458.1 (M+1)$^+$.

Step-d: Synthesis of (S)-2-((((1-(3-amino-6-(2-hydroxyphenyl)pyridazin-4-yl)piperidin-4-yl)oxy)carbonyl)amino)-3,3-dimethylbutanoic acid (13d)

The title compound was synthesized by using the general procedure of hydrolysis of methyl or ethyl esters which was followed for Intermediate-3d using with methyl (S)-2-((((1-(3-amino-6-(2-hydroxyphenyl)pyridazin-4-yl) piperidin-4-yl)oxy) carbonyl)amino)-3,3-dimethylbutanoate (Yield: 58%) LC-MS: m/z 444.3 (M+1)$^+$.

Intermediate-14e:

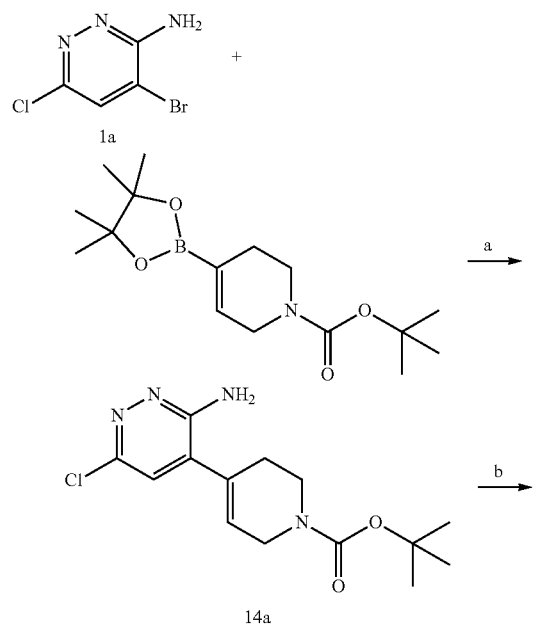

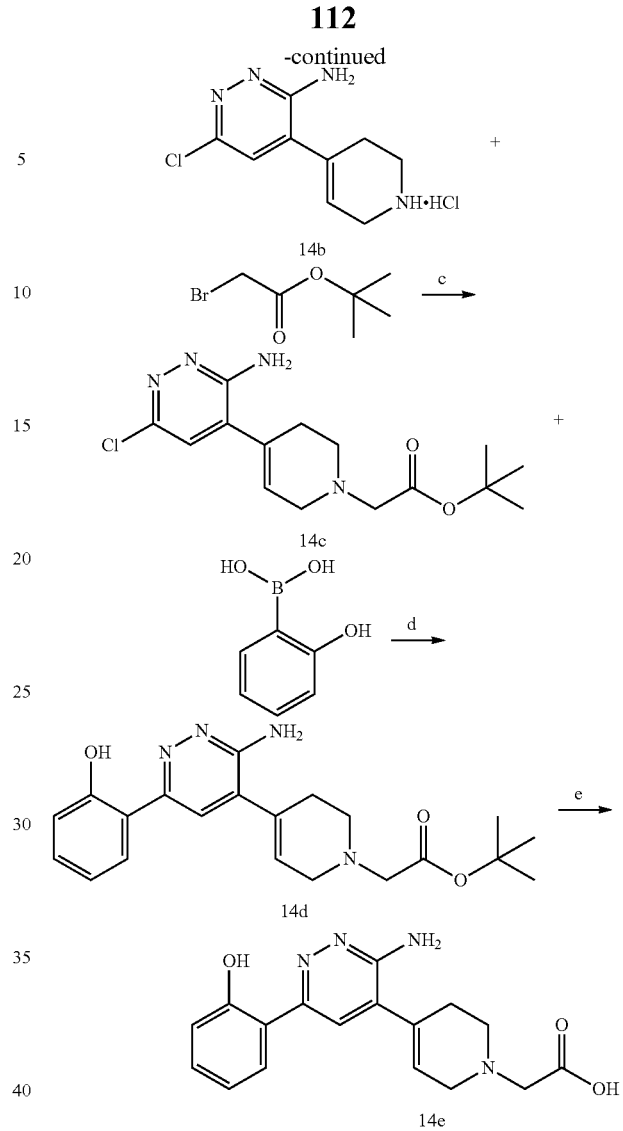

Conditions: a) Pd(dppf)Cl$_2$:DCM (1:1), K$_2$CO$_3$, Dioxane:water (5:2), 120° C.-1 h, MW; b) 4M HCl in 1,4-dioxane, DCM, 0° C.-RT-16 h; c) DIPEA, DMF, 60° C.-16 h; d) Pd(dppf)Cl$_2$:DCM (1:1), K$_2$CO$_3$, Dioxane:water (5:2), 120° C.-1 h, MW; e) 4M HCl in Dioxane, DCM, 0° C.-RT, 16 h.

Step-a: Synthesis of tert-butyl 4-(3-amino-6-chloro-pyridazin-4-yl)-3,6-dihydropyridine-1(2H)-carboxylate (14a)

The title compound was synthesized by using the Genereal procedure of Suzuki coupling which was followed for Intermediate-1e$_1$-1e$_{12}$ using methyl (S)-2-((((1-(3-amino-6-chloropyridazin-4-yl)piperidin-4-yl)oxy)carbonyl)amino)-3,3-dimethylbutanoate (Yield: 67%). $^1$H NMR (400 MHz, DMSO-$d_6$): δ 7.28 (s, 1H), 6.45 (s, 2H), 5.98 (s, 1H), 3.96-3.90 (m, 2H), 3.56-3.51 (m, 2H), 2.32-2.29 (m, 2H), 1.44 (s, 9H); LC-MS: m/z 311.2 (M+1)$^+$.

Step-b: Synthesis of 6-chloro-4-(1,2,3,6-tetrahydro-pyridin-4-yl)pyridazin-3-amine hydrochloride (14b)

The title compound was synthesized by using the same procedure which was followed for 1f$_1$-1f$_{12}$ using tert-butyl 4-(3-amino-6-chloropyridazin-4-yl)-3,6-dihydropyridine-1

(2H)-carboxylate (Yield: 90%) $^1$H NMR (400 MHz, DMSO-$d_6$): δ 9.43 (bs, 4H), 7.56 (s, 1H), 6.01 (s, 1H), 3.68-3.60 (m, 2H), 3.56-3.52 (m, 2H), 2.52-2.50 (m, 2H merged in DMSO); LC-MS: m/z 211.1 (M+1)$^+$.

Step-c: Synthesis of tert-butyl 2-(4-(3-amino-6-chloropyridazin-4-yl)-3,6-dihydropyridin-1(2H)-yl)acetate (14c)

The title compound was synthesized by using same procedure which was followed for 1d using with 6-chloro-4-(1,2,3,6-tetrahydropyridin-4-yl)pyridazin-3-amine hydrochloride (Yield: 45%) NMR (400 MHz, DMSO-$d_6$): δ 7.29 (s, 1H), 6.48 (s, 2H), 6.01-5.99 (m, 1H), 3.29 (s, 2H), 3.24-3.21 (m, 2H), 2.78-2.73 (m, 2H), 2.38-2.33 (m, 2H), 1.46 (s, 9H); LC-MS: m/z 325.2 (M+1)$^+$.

Step-d: Synthesis of t tert-butyl 2-(4-(3-amino-6-(2-hydroxyphenyl)pyridazin-4-yl)-3,6-dihydropyridin-1(2H)-yl)acetate (14d)

The title compound was synthesized by using the Genereal procedure of Suzuki coupling which was followed for (1e$_1$-1e$_{12}$) using tert-butyl 2-(4-(3-amino-6-chloropyridazin-4-yl)-3,6-dihydropyridin-1(2H)-yl)acetate (Yield: 68%) $^1$H NMR (400 MHz, DMSO-$d_6$): δ 13.71 (s, 1H), 7.92 (d, J=1.6 Hz, 1H), 7.91 (s, 1H), 7.26-7.21 (m, 1H), 6.91-6.86 (m, 2H), 6.45 (s, 2H), 6.04-5.99 (m, 1H), 3.34-3.23 (m, 4H), 2.82 (t, J=5.6 Hz, 2H), 2.49-2.44 (m, 2H), 1.42 (s, 9H); LC-MS: m/z 383.2 (M+1)$^+$.

Step-e: Synthesis of 6-chloro-4-(1,2,3,6-tetrahydropyridin-4-yl)pyridazin-3-amine hydrochloride (14e)

The title compound was synthesized by using the same procedure which was followed for Intermediate 1f$_1$-1f$_{12}$ using tert-butyl 2-(4-(3-amino-6-(2-hydroxyphenyl)pyridazin-4-yl)-3,6-dihydropyridin-1(2H)-yl)acetate (Yield: 73%). $^1$H NMR (400 MHz, DMSO-$d_6$): δ 10.20 (s, 1H), 8.06 (s, 1H), 7.69 (d, J=7.2 Hz, 1H), 7.34-7.30 (m, 1H), 7.01-6.93 (m, 2H), 6.02 (s, 1H), 4.27 (s, 2H), 3.96-3.90 (m, 2H), 3.56-3.50 (m, 7H).

Intermediate-15b:

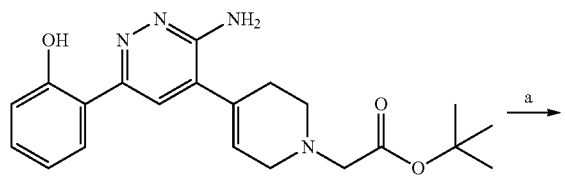

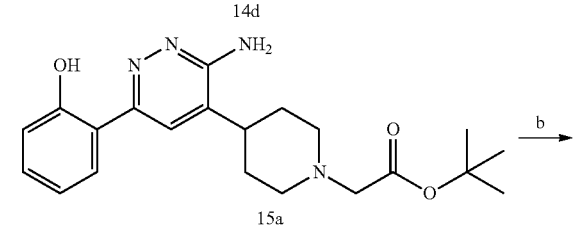

Conditions: a) Pd/C, H$_2$ gas, MeOH, 25-30° C. - RT, 16 h; b) 4M HCl in 1,4-dioxane, DCM, 0° C. - RT, 16 h;

Step-a: Synthesis of tert-butyl 2-(4-(3-amino-6-(2-hydroxyphenyl)pyridazin-4-yl)piperidin-1-yl)acetate (15a)

The title compound was synthesized by using the same procedure which was followed for Intermediate-5b using with tert-butyl 2-(4-(3-amino-6-(2-hydroxyphenyl)pyridazin-4-yl)piperidin-1-yl)acetate (Yield: 73%) $^1$H NMR (400 MHz, DMSO-$d_6$): δ 13.88 (s, 1H), 7.99-7.97 (m, 1H), 7.91 (s, 1H), 7.25-7.21 (m, 1H), 6.90-6.86 (m, 2H), 6.66 (s, 2H), 3.16 (s, 2H), 2.95-2.92 (m, 2H), 2.67-2.66 (m, 1H), 2.42-2.39 (m, 2H), 1.77-1.71 (m, 4H), 1.42 (s, 9H); LC-MS: m/z 385.2 (M+1)$^+$.

Step-b: Synthesis of 2-(4-(3-amino-6-(2-hydroxyphenyl)pyridazin-4-yl)-3,6-dihydropyridin-1(2H)-yl)acetic acid (15b)

The title compound was synthesized by using the same procedure which was followed for Intermediate-1f$_1$-1f$_{12}$ using tert-butyl 2-(4-(3-amino-6-(2-hydroxyphenyl)pyridazin-4-yl)piperidin-1-yl)acetate (Yield: 90%) $^1$H NMR (400 MHz, DMSO-$d_6$): δ 10.22 (s, 1H), 8.27 (bs, 3H), 8.05 (s, 1H), 7.63 (d, J=7.6 Hz, 1H), 7.37-7.33 (m, 1H), 7.06 (d, J=8.4 Hz, 1H), 6.98-6.94 (m, 1H), 4.22 (s, 2H), 3.39-3.37 (m, 2H), 3.23-3.16 (m, 2H), 3.10-3.08 (m, 1H), 2.15-2.01 (m, 4H); LC-MS: m/z 329.10 (M+1)$^+$.

Intermediate-16b:

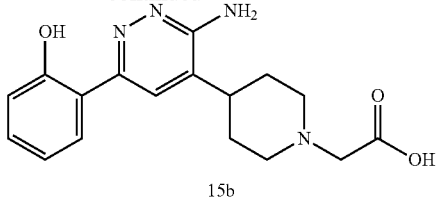

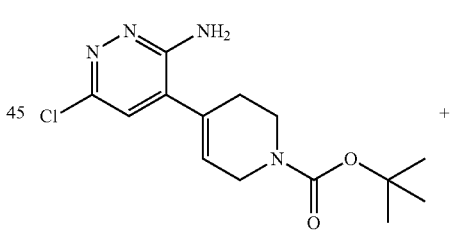

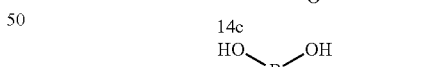

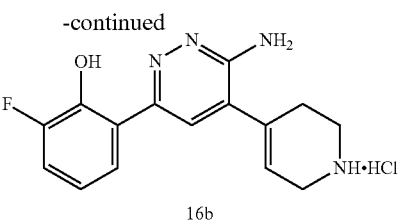

16b

Conditions: a) Pd(dppf)Cl₂:DCM (1:1), K₂CO₃, Dioxane:water, MW, 120° C. - 1 h, Method-B; b) 4M HCl in Dioxane, DCM, 0° C. - RT, 16 h.

Step-a: Synthesis of tert-butyl 4-(3-amino-6-(3-fluoro-2-hydroxyphenyl)pyridazin-4-yl)-3,6-dihydropyridine-1(2H)-carboxylate (16a)

The title compound was synthesized by using the Genereal procedure of Suzuki coupling which was followed for Intermediate $1e_1$-$1e_{12}$ Method B using tert-butyl 4-(3-amino-6-chloropyridazin-4-yl)-3,6-dihydropyridine-1(2H)-carboxylate (Yield: 56%). ¹H NMR (400 MHz, DMSO-$d_6$): δ 14.33 (s, 1H), 7.96 (s, 1H), 7.75 (d, J=8.0 Hz, 1H), 7.22-7.17 (m, 1H), 6.88-6.82 (m, 1H), 6.67 (s, 2H), 6.03 (s, 1H), 4.02 (d, J=7.6 Hz, 2H), 3.59 (t, J=5.6 Hz, 2H), 2.40-2.38 (m, 2H), 1.44 (s, 9H); LC-MS: m/z 387.1 (M+1)⁺.

Step-b: Synthesis of 2-(6-amino-5-(1,2,3,6-tetrahydropyridin-4-ylpyridazin-3-yl)-6-fluorophenol hydrochloride (16b)

The title compound was synthesized by using the same procedure which was followed for Intermediate $1f_1$-$1f_{12}$ using with tert-butyl 4-(3-amino-6-(3-fluoro-2-hydroxyphenyl)pyridazin-4-yl)-3,6-dihydropyridine-1(2H)-carboxylate (Yield: 67%) H NMR (400 MHz, DMSO-$d_6$): δ 9.43 (bs, 2H), 8.20 (bs, 1H), 8.01 (s, 1H), 7.48 (d, J=8.0 Hz, 1H), 7.36-7.31 (m, 1H), 6.98-6.93 (m, 1H), 6.08 (s, 1H), 3.72 (s, 2H), 3.39-3.35 (m, 2H), 2.59-2.58 (m, 2H); LC-MS: m/z 287.0 (M+1)⁺.

Intermediate-17g:

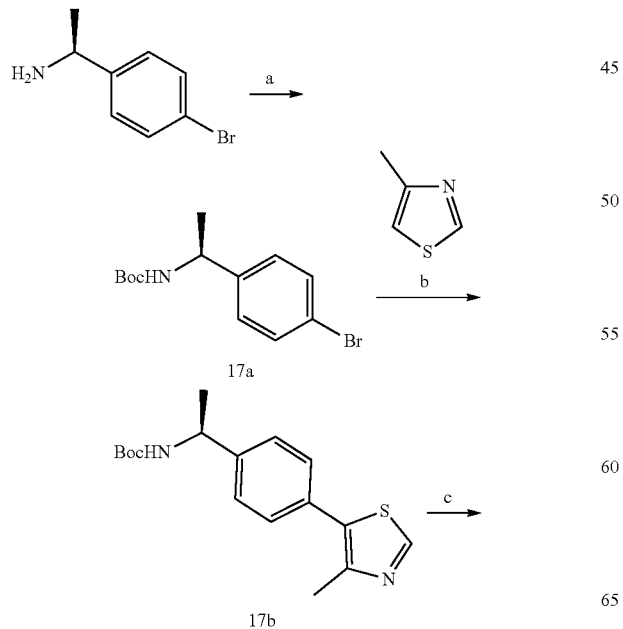

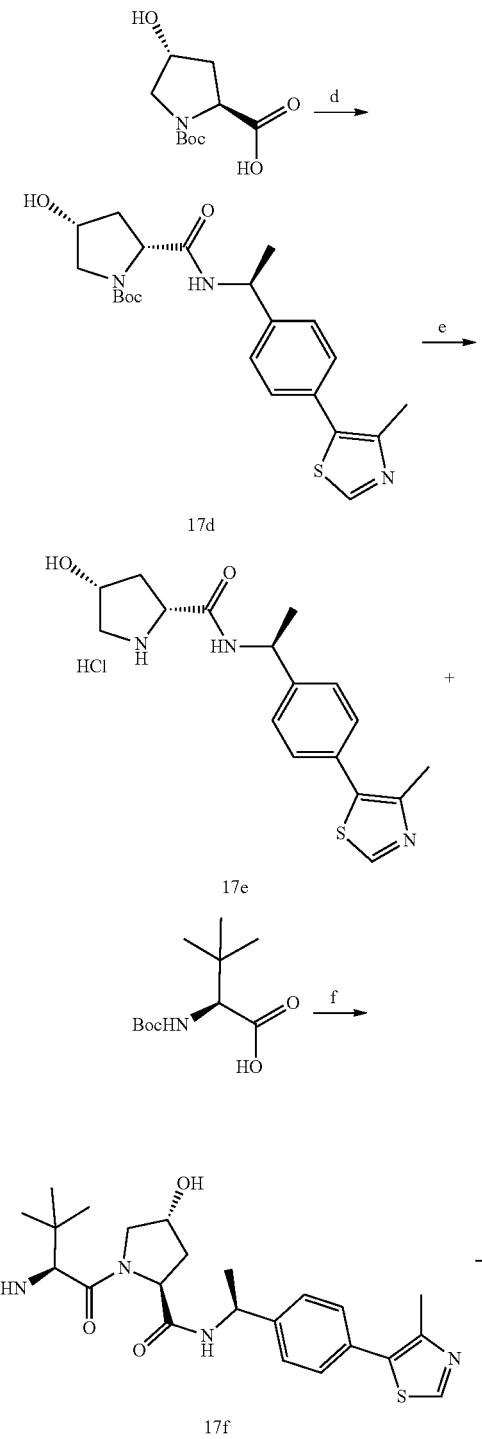

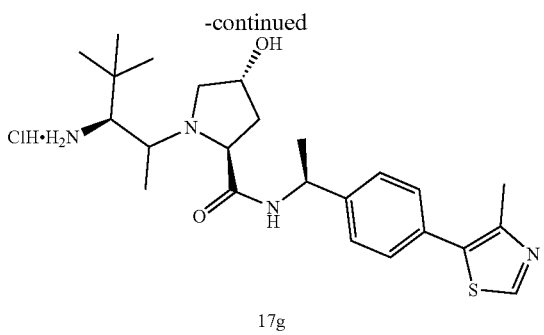

17g

Conditions: a) Boc anhydride, Et₃N, DCM, 0° C. - RT, 16 h; b) Pd(OAc)₂, KOAc, DMF, 120° C., 16 h; c) 4M HCl in 1,4-Dioxane, 1,4-Dioxane, 0° C. - RT, 16 h; d) HATU, DIPEA, DCM, 0° C. - RT, 18 h; e) 4M HCl in 1,4-Dioxane, 1,4-Dioxane, 0° C. - RT; f) HATU, DIPEA, DCM, 0° C. - RT, 18 h; g) 4M HCl in 1,4-Dioxane, 1,4-Dioxane, 0° C. - RT.

Step-a: Synthesis of tert-butyl (S)-(1-(4-bromophenyl)ethyl)carbamate (17a)

To a solution of (S)-1-(4-bromophenyl)ethan-1-amine (20.0 g, 100.0 mmol) in DCM (200 mL) at 0° C. was added triethyl amine (21.6 mL, 120 mmol) followed by the addition of Boc-anhydride (27.5 mL, 150.0 mmol) and the reaction mixture was stirred for 6 h at RT. Then it was quenched with water (200 mL) and extracted with DCM (2×500 mL). The combined organic layer was washed with water (200 mL), brine (200 mL), dried over anhydrous sodium sulphate and concentrated under reduced pressure to afford the title compound (23.0 g, 66%). $^1$H NMR (400 MHz, DMSO-d₆): δ 7.51 (d, J=8.8 Hz, 2H), 7.40 (d, J=7.4 Hz, 1H), 7.41 (d, J=7.2 Hz, 2H), 4.60-4.55 (m, 1H), 1.35 (s, 8H), 1.28 (d, J=6.8 Hz, 4H).

Step-b: Synthesis of tert-butyl (S)-(1-(4-(4-methylthiazol-5-yl)phenyl)ethyl)carbamate (17b)

To a stirred solution of tert-butyl (S)-(1-(4-bromophenyl)ethyl)carbamate (20.0 g, 66.66 mmol) and 4-methylthiazole (13.11 g, 133.32 mmol) in DMF (250 mL) was added KOAc (19.66 g, 99.98 mmol) and Pd(OAC)₂ (0.75 g, 33.33 mmol). The reaction mixture was heated at 120° C. for 16 h. After completion of the reaction (monitored by TLC) the reaction mixture was allowed to cool to RT and poured into ice cold water. The resulting mixture was extracted with ethyl acetate (2×500 mL). The combined organic layer was washed with water (200 mL), brine (200 mL), dried over anhydrous sodium sulphate and concentrated under vacuum to give the residue which was purified by combi flash column chomatography using 15% ethyl acetate in hexane as eluent to afford the title compound (14.0 g, 66%). $^1$H NMR (400 MHz, DMSO-d₆): δ 8.97 (s, 1H), 7.44 (d, J=7.6 Hz, 2H), 7.38-7.35 (m, 3H), 4.63 (d, J=6.8 Hz, 1H), 2.45 (s, 3H), 1.35 (s, 9H), 1.25 (d, J=7.3 Hz, 3H), LC-MS: m/z 319.1 (M+1)⁺.

Step-c: Synthesis of (S)-1-(4-(4-methylthiazol-5-yl)phenyl)ethan-1-amine hydrochloride (17c)

To a stirred solution of tert-butyl (S)-(1-(4-(4-methylthiazol-5-yl)phenyl)ethyl)carbamate (17b, 14.0 g, 44.02 mmol) in 1,4-dioxane (70 mL) at 0° C. was added 4M HCl in 1,4-dioxane (70 mL). The reaction mixture was stirred at room temperature for 16 h. After completion of the reaction (monitored by TLC) the reaction mixture was concentrated under reduced pressure and washed with diethyl ether to afford the title compound (11.0 g, 98.3%). $^1$H NMR (400 MHz, DMSO-d₆): δ 9.08 (s, 1H), 8.65 (bs, 2H), 7.64 (d, J=8.4 Hz, 2H), 7.56-7.50 (m, 3H), 4.46-4.43 (m, 1H), 2.47 (s, 3H), 1.55 (d, J=8.4 Hz, 3H), LC-MS: m/z 219.0 (M+1)⁺.

Step-d: Synthesis of tert-butyl (2S,4R)-4-hydroxy-2-(((S)-1-(4-(4-methylthiazol-5-yl)phenyl) ethyl) carbamoyl)pyrrolidine-1-carboxylate (17d)

To a solution of (S)-1-(4-(4-methylthiazol-5-yl)phenyl) ethan-1-amine hydrochloride (11.0 g, 43.30 mmol) and (2S,4R)-1-(tert-butoxycarbonyl)-4-hydroxypyrrolidine-2-carboxylic acid (9.97 g, 43.30 mmol) in DCM (150 mL) at 0° C. was added HATU (19.6 g, 51.96 mmol) followed by dropwise addition of DIPEA (39.78 mL, 216.5 mmol) and stirred for 16 h at RT. After completion of the reaction (monitored by TLC) the reaction mixture poured into ice cold water. The resulting mixture was extracted with DCM (2×500 mL). The combined organic layer was washed with water (200 mL), brine (200 mL), dried over anhydrous sodium sulphate and concentrated under vacuum to give the crude product which was purified by combi flash column chomatography using 6% MeOH in DCM as eluent to afford the title compound (10.0 g, 53%). $^1$H NMR (400 MHz, DMSO-d₆): δ 8.98 (s, 1H), 8.38-8.80 (m, 1H), 7.45-7.36 (m, 4H), 4.99-4.18 (m, 2H), 4.21-4.18 (m, 2H), 3.39-3.35 (m, 1H), 3.26- 3.16 (m, 1H), 2.45 (s, 3H), 2.06-2.03 (m, 1H), 1.80-1.17 (m, 1H), 1.40-1.37 (m, 6H), 1.33 (s, 6H); LC-MS: m/z 432.2 (M+1)⁺.

Step-e: Synthesis of (2S,4R)-4-hydroxy-N—((S)-1-(4-(4-methylthiazol-5-yl)phenyl)ethyl) pyrrolidine-2-carboxamide hydrochloride (17e)

To a stirred solution of tert-butyl (2S,4R)-4-hydroxy-2-(((S)-1-(4-(4-methylthiazol-5-yl)phenyl)ethyl)carbamoyl) pyrrolidine-1-carboxylate (10.0 g, 23.20 mmol) in 1,4-dioxane (50 mL) at 0° C. was added 4M HCl in 1,4-dioxane (50 mL). The reaction mixture was stirred at room temperature for 16 h. The solvents were evaporated under reduced pressure and the residue was washed with diethyl ether to afford the title compound (8.5 g, 100%) which was used in the next step without further purification. $^1$H NMR (400 MHz, DMSO-d₆): δ 10.20 (bs, 1H), 9.22-9.30 (m, 1H), 9.15 (s, 1H), 8.67 (bs, 1H), 7.46-7.42 (m, 3H), 5.01-4.95 (m, 1H), 4.50-4.40 (m, 2H), 3.30-3.20 (m, 1H), 3.20-3.00 (m, 1H), 2.50 (s, 3H), 2.40-2.35 (m, 2H), 1.80-1.70 (m, 1H), 1.43 (d, J=8.4 Hz, 3H), LC-MS: m/z 332.1 (M+1)⁺.

Step-f: Synthesis of tert-butyl ((S)-1-((2S,4R)-4-hydroxy-2-(((S)-1-(4-(4-methylthiazol-5-yl)phenyl) ethyl)carbamoyl)pyrrolidin-1-yl)-3,3-dimethyl-1-oxobutan-2-yl)carbamate (17f)

To a solution of (2S,4R)-4-hydroxy-N—((S)-1-(4-(4-methylthiazol-5-yl)phenyl)ethyl) pyrrolidine-2-carboxamide hydrochloride (10.0 g, 27.24 mmol) and (S)-2-((tert-butoxycarbonyl)amino)-3,3-dimethylbutanoic acid (6.29 g, 27.24 mmol) in DCM (150 mL) at 0° C. was added HATU (12.4 g, 32.69 mmol) followed by dropwise addition of DIPEA (25.0 mL, 136.2 mmol) and stirred for 16 h at RT. Then the reaction mixture was poured into ice cold water and the resulting mixture was extracted with DCM (2×500 mL). The combined organic layer was washed with water (200 mL), saturated sodium bicarbonate solution (100 mL), brine (200 mL), dried over anhydrous sodium sulphate and concentrated under vacuum to give the crude product which was washed with chilled acetone and filtered to afford the title compound (9.8 g, 67.5%) which was used in the next step without further purification. ¹H NMR (400 MHz, DMSO-d₆): δ 8.97 (s, 1H), 8.38 (d, J=6.4 Hz, 1H), 7.44-7.31 (m, 4H), 6.38 (d, J=8.4 Hz, 1H), 5.10 (s, 1H), 4.91-4.88 (m, 1H), 4.28 (bs, 1H), 4.14 (d, J=8.8 Hz, 1H), 3.62-3.58 (m, 2H), 2.45 (s, 3H), 2.08-2.00 (m, 2H), 1.78-1.76 (m, 1H), 1.48 (s, 9H), 1.44 (d, J=6.9 Hz, 3H), 0.93 (s, 9H); LC-MS: m/z 545.3 (M+1)⁺.

Step-g: Synthesis of (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (17g)

To a stirred solution of tert-butyl ((S)-1-((2S,4R)-4-hydroxy-2-(((S)-1-(4-(4-ethylthiazol-5-yl)phenyl)ethyl)carbamoyl)pyrrolidin-1-yl)-3,3-dimethyl-1-oxobutan-2-yl)carbamate (5.0 g, 9.19 mmol) in 1,4-dioxane (25 mL) at 0° C. was added 4M HCl in 1,4-dioxane (25 mL). The reaction mixture was stirred at RT for 16 h. Solvents from the reaction mixture was evaporated under reduced pressure and the residue was washed with diethyl ether to afford the title compound (4.5 g, 97%). ¹H NMR (400 MHz, DMSO-d₆): δ 9.60 (s, 1H), 8.58 (d, J=7.2 Hz, 1H), 8.12 (s, 3H), 7.44 (d, J=8.4 Hz, 2H), 7.38 (d, J=8.4 Hz, 2H), 4.92 (d, J=7.0 Hz, 1H), 4.54 (t, J=8.4 Hz, 1H), 4.30 (s, 1H), 3.89-3.88 (m, 1H), 3.75-3.72 (m, 1H), 3.51-3.48 (m, 2H), 2.46 (s, 3H), 2.12-2.08 (m, 1H), 1.80-1.75 (m, 1H), 1.38 (d, J=6.8 Hz, 3H), 1.05 (s, 9H); LC-MS: m/z 445.3 (M+1)⁺.

Intermediate-18d:

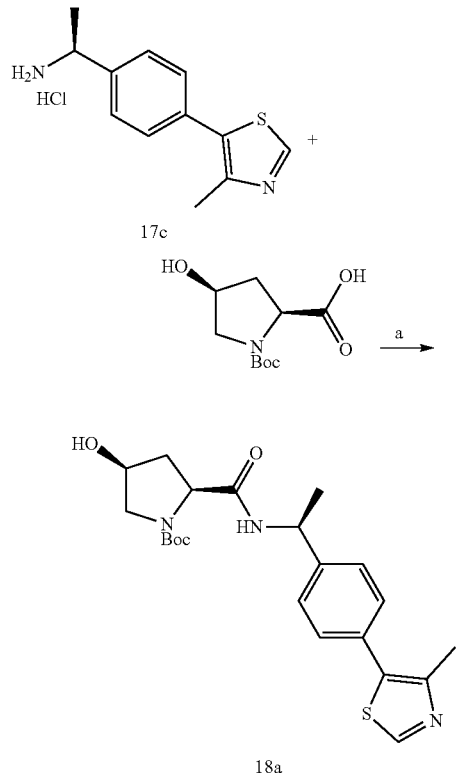

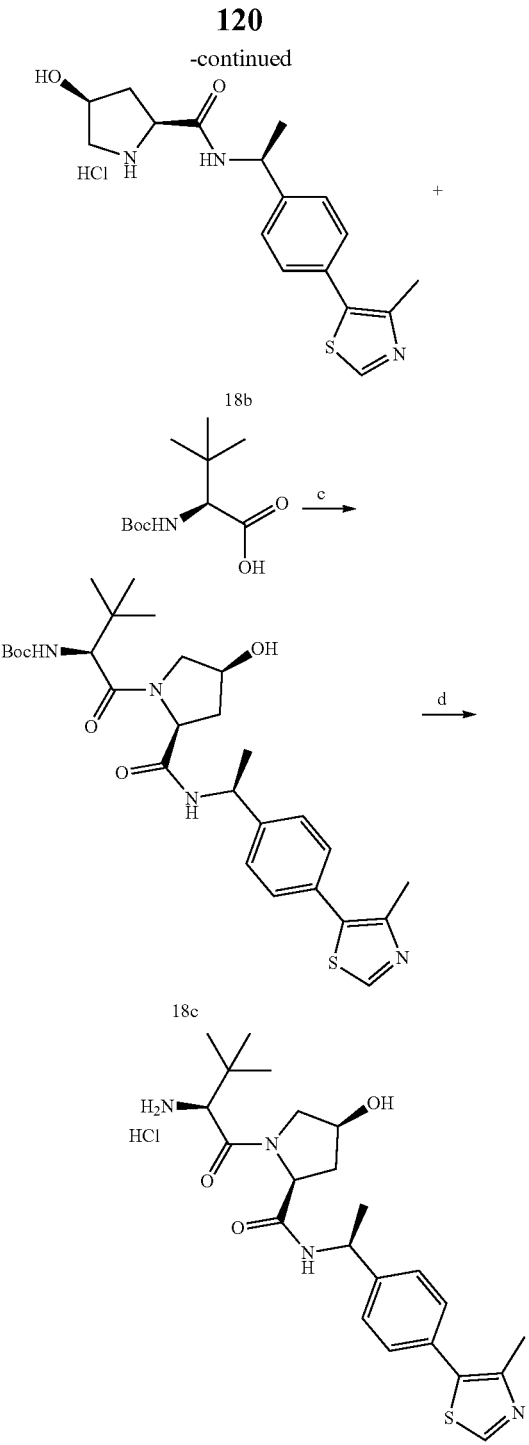

Conditions: a) HATU, DIPEA, DCM, 0° C. - RT, 16 h; b) 4M HCl in 1,4-Dioxane, 1,4-Dioxane, 0° C. - RT - 16 h; d) HATU, DIPEA, DCM, 0° C. - RT - 16 h; d) 4M HCl in 1,4-Dioxane, 1,4-Dioxane, 0° C. - RT - 16 h.

Step-a: Synthesis of tert-butyl (2S,4S)-4-hydroxy-2-(((S)-1-(4-(4-methylthiazol-5-yl)phenyl) ethyl)carbamoyl)pyrrolidine-1-carboxylate (18a)

The title compound was synthesized by using the same procedure which was used for Intermediate-17d using 6-chloro-4-(1-(4-methoxybenzyl)-1H-pyrazol-4-yl) pyridazin-3-amine (Yield: 89%); ¹H NMR (400 MHz, DMSO-d$_6$): δ 8.98 (s, 1H), 8.39 (d, J=8.0 Hz, 1H), 7.46-7.41 (m, 4H), 5.17-5.16 (m, 1H), 5.00-4.97 (m, 1H), 4.20-4.10 (m, 2H), 3.66-3.60 (m, 1H), 3.50-3.46 (m, 1H), 2.45 (s, 3H), 2.37-2.32 (m, 1H), 1.69-1.64 (m, 1H), 1.41 (s, 3H), 1.32 (s, 9H).

Step-b: Synthesis of (2S,4S)-4-hydroxy-N—((S)-1-(4-(4-methylthiazol-5-yl)phenyl)ethyl) pyrrolidine-2-carboxamide hydrochloride (18b)

The title compound was synthesized by using the same procedure which was followed for Intermediate-17e using tert-butyl (2S,4S)-4-hydroxy-2-(((S)-1-(4-(4-methylthiazol-5-yl)phenyl)ethyl)carbamoyl)pyrrolidine-1-carboxylate (Yield: 80%); LC-MS: m/z 332.2 (M+1)$^+$ Step-c: Synthesis of tert-butyl ((S)-1-((2S,4S)-4-hydroxy-2-(((S)-1-(4-(4-methylthiazol-5yl)phenyl)ethyl)carbamoyl)pyrrolidin-1-yl)-3,3-dimethyl-1-oxobutan-2-yl)carbamate (18c)

The title compound was synthesized by using the same procedure which was followed for Intermediate-17f using (2S,4S)-4-hydroxy-N—((S)-1-(4-(4-methylthiazol-5-yl)phenyl)ethyl) pyrrolidine-2-carboxamide hydrochloride (Yield: 64%) $^1$H NMR (400 MHz, DMSO-d$_6$): δ 8.98 (s, 1H), 8.36 (d, J=6.8 Hz, 1H), 7.44-7.37 (m, 4H), 6.56 (d, J=8.4 Hz, 1H), 5.31 (d, J=6.4 Hz, 1H), 4.91 (t, J=7.2 Hz, 1H), 4.36 (t, J=6.4 Hz, 1H), 4.18 (t, J=5.6 Hz, 1H), 4.09 (d, J=8.4 Hz, 1H), 3.39-3.36 (m, 1H), 3.17-3.11 (m, 1H), 2.45 (s, 3H), 2.34-2.29 (m, 1H), 1.67-1.60 (m, 1H), 1.37 (s, 9H), 1.26 (d, J=5.6 Hz, 3H), 0.94 (s, 9H).

Step-d: Synthesis of (2S,4S)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (18d)

The title compound was synthesized by using the same procedure which was followed for-Intermediate-17g using tert-butyl ((S)-1-((2S,4S)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamate (Yield: 80%) $^1$H NMR (400 MHz, DMSO-d$_6$): δ 9.06 (s, 1H), 8.54 (d, J=7.6 Hz, 1H), 8.16 (bs, 3H), 7.46-7.38 (m, 4H), 4.93 (t, J=7.2 Hz, 1H), 4.42 (t, J=8.0 Hz, 1H), 4.17 (t, J=6.4 Hz, 1H), 4.01-3.91 (m, 1H), 3.90 (d, J=4.8 Hz, 1H), 3.25-3.21 (m, 1H), 3.13-3.09 (m, 1H), 2.49 (s, 3H), 2.46-2.41 (m, 1H), 1.65-1.58 (m, 1H), 1.39 (d, J=6.8 Hz, 3H), 1.09 (s, 9H); LC-MS: m/z 445.3 (M+1)$^+$.

Intermediate-19d:

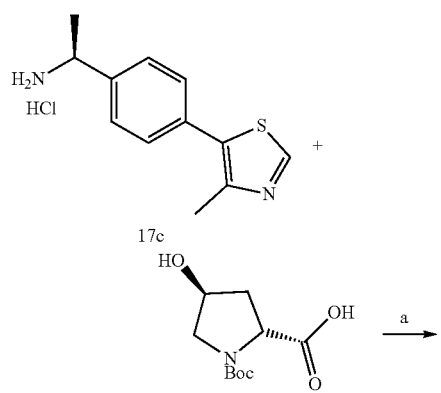

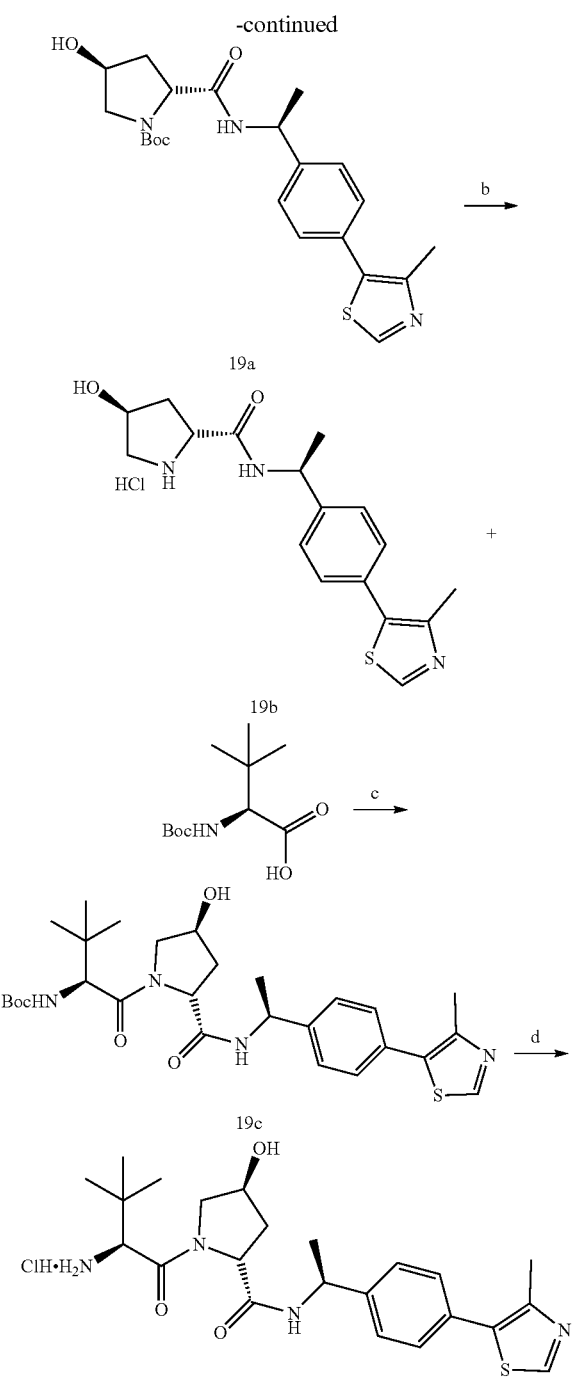

Conditions: a) HATU, DIPEA, DCM, 0° C.- RT, 16 h; b) 4M HCl in 1,4-Dioxane, 1,4-Dioxane, 0° C.- RT- 16 h; c) HATU, DIPEA, DCM, 0° C.- RT, 16 h; d) 4M HCl in 1,4-Dioxane, 1,4-Dioxane, 0° C.- RT, 16 h.

Step-a: Synthesis of tert-butyl (2R,4S)-4-hydroxy-2-(((S)-1-(4-(4-methylthiazol-5-yl)phenyl) ethyl) carbamoyl)pyrrolidine-1-carboxylate (19a)

The title compound was synthesized by using the same procedure which was used for (17d) using 6-chloro-4-(1-(4-methoxybenzyl)-1H-pyrazol-4-yl)pyridazin-3-amine (Yield: 76%) $^1$H NMR (400 MHz, DMSO-d$_6$): δ 8.98 (s, 1H), 8.38-8.34 (m, 1H), 7.48-7.38 (m, 4H), 5.00-4.95 (m, 2H), 4.24-4.22 (m, 1H), 4.20-4.13 (m, 1H), 3.70-3.60 (m, 1H), 3.20-3.10 (m, 1H), 2.43 (s, 3H), 2.10- 2.00 (m, 1H), 1.90-1.80 (m, 1H), 1.39-1.23 (m, 12H); LC-MS: m/z 432.2 (M+1)⁺.

Step-b: Synthesis of (2R,4S)-4-hydroxy-N—((S)-1-(4-(4-methylthiazol-5-yl)phenyl)ethyl) pyrrolidine-2-carboxamide hydrochloride (19b)

The title compound was synthesized by using the same procedure which was followed for Intermediate-17e using tert-butyl (2R,4S)-4-hydroxy-2-(((S)-1-(4-(4-methylthiazol-5-yl)phenyl)ethyl) carbamoyl)pyrrolidine-1-carboxylate (Yield: 90%) ¹H NMR (400 MHz, DMSO-d₆): δ 9.90 (s, 1H), 9.21 (d, J=7.6 Hz, 1H), 9.05 (s, 1H), 8.62 (s, 1H), 7.47 (s, 5H), 5.01-4.96 (m, 1H), 4.45 (s, 1H), 4.36-4.32 (m, 1H), 3.32-3.31 (m, 1H), 3.10-3.09 (m, 1H), 2.42 (s, 3H), 2.37-2.32 (m, 1H), 1.96-1.90 (m, 1H), 1.41 (d, J=7.2 Hz, 3H); LC-MS: m/z 332.2 (M+1)⁺.

Step-c: Synthesis of tert-butyl ((S)-1-((2R,4S)-4-hydroxy-2-(((S)-1-(4-(4-methylthiazol-5yl)phenyl) ethyl)carbamoyl)pyrrolidin-1-yl)-3,3-dimethyl-1-oxobutan-2-yl)carbamate (19c)

The title compound was synthesized by using the same procedure which was followed for Intermediate-17f using (2R,4S)-4-hydroxy-N—((S)-1-(4-(4-methylthiazol-5-yl) phenyl)ethyl) pyrrolidine-2-carboxamide hydrochloride (Yield: 66%) ¹H NMR (400 MHz, DMSO-d₆): δ 8.98 (s, 1H), 8.22 (d, J=8.0 Hz, 1H), 7.47-7.40 (m, 4H), 6.56 (d, J=9.2 Hz, 1H), 5.11 (d, J=4.0 Hz, 1H), 4.92-4.88 (m, 1H), 4.41-4.35 (m, 2H), 4.13 (d, J=9.2 Hz, 1H), 3.65-3.59 (m, 1H), 3.20-3.10 (m, 1H), 2.45 (s, 3H), 1.99-1.94 (m, 2H), 1.39-1.31 (m, 12H), 0.90 (s, 9H).

Step-d: Synthesis of (2R,4S)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (19d)

The title compound was synthesized by using the same procedure which was followed for Intermediate-17g using tert-butyl ((S)-1-((2R,4S)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamate (Yield: 90%) ¹H NMR (400 MHz, DMSO-d₆): δ 9.02 (s, 1H), 8.53 (d, J=8.0 Hz, 1H), 8.38 (bs, 3H), 7.49-7.42 (m, 4H), 5.00-4.96 (m, 1H), 4.37-4.30 (m, 2H), 3.98-3.95 (m, 1H), 3.87-3.86 (m, 2H), 3.13-3.10 (m, 1H), 2.46 (s, 3H), 2.10-2.00 (m, 1H), 1.91-1.88 (m, 1H), 1.42 (d, J=6.8 Hz, 3H), 0.99 (s, 9H); LC-MS: m/z 445.2 (M+1)⁺.

Intermediate-20e:

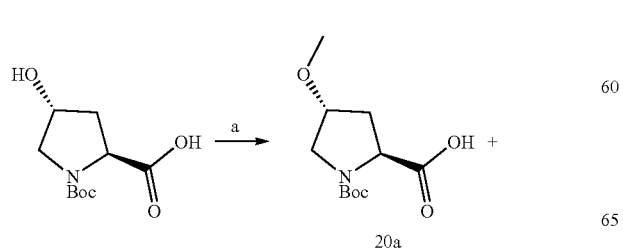

20a

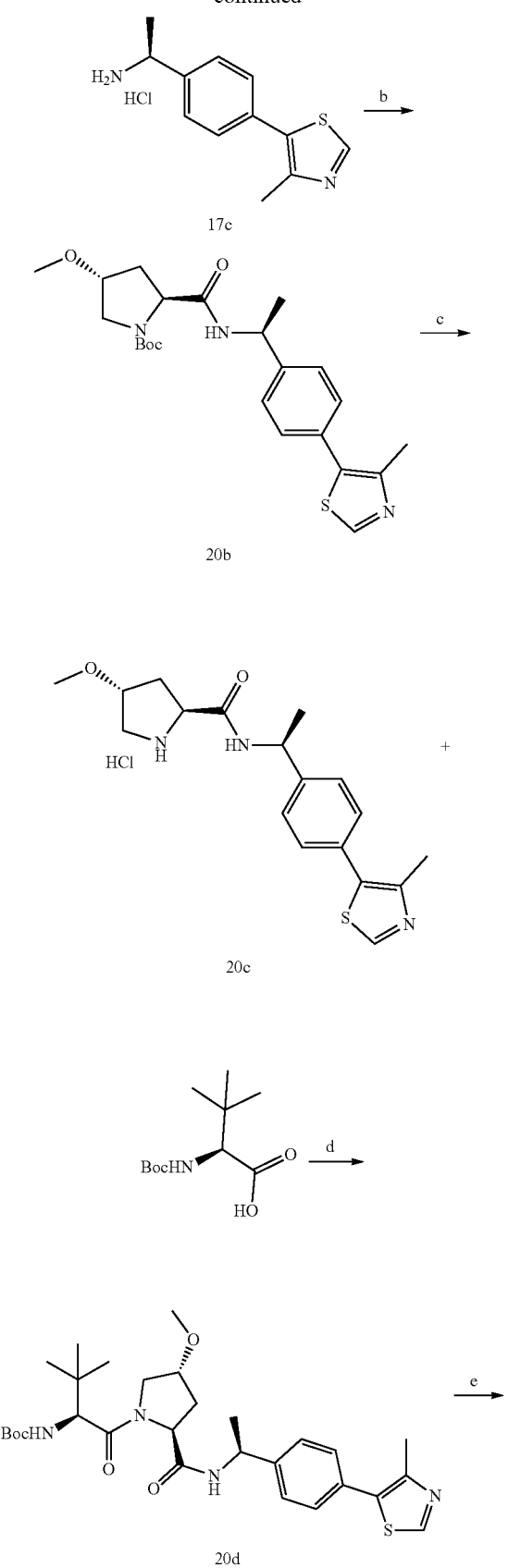

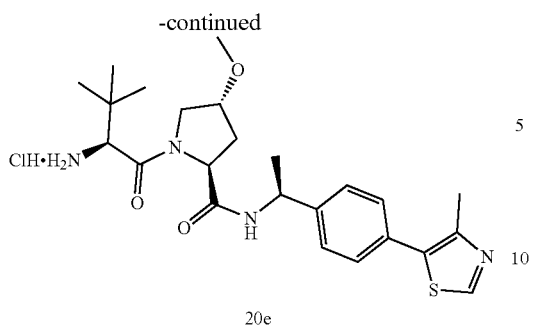

20e

Conditions: a) NaH (56-60%), THF, 0° C. - RT - 4 h; b) HATU, DIEPA, DCM, 0° C. - RT, 16 h; c) 4M HCl in 1,4-Dioxane, 1,4-Dioxane, 0° C. -RT, 16 h; d) HATU, DIPEA, DCM, 0° C. - RT - 16 h; e) 4M HCl in 1,4-Dioxane, 1,4-Dioxane, 0° C. - RT, 16 h.

Step-a: Synthesis of (2S,4R)-1-(tert-butoxycarbonyl)-4-methoxypyrrolidine-2-carboxylic acid (20a)

To a stirred solution of (2S,4R)-1-(tert-butoxycarbonyl)-4-hydroxypyrrolidine-2-carboxylic acid (2.0 g, 8.64 mmol) in THF (20 mL) in two neck RB was wadded NaH (56-60%) (1.0 g, 25.9 mmol) portion wise at 0° C. and stirred for 30 min at RT then methyl iodide (0.59 mL, 9.51 mmol) was added and stirred for 4 h at RT. The reaction mixture was quenched with cold water and extracted with ethyl acetate (2×100 mL). The combined organic layer was washed with water (50 mL), brine (50 mL), dried over anhydrous sodium sulphate and concentrated under vacuum to give the residue which was purified by combi flash column chomatography using 80% ethyl acetate in hexane as eluent to afford the title compound (1.0 g, 47%). $^1$H NMR (400 MHz, DMSO-$d_6$): δ 12.20 (bs, 1H), 4.07-4.03 (m, 1H), 3.93 (s, 1H), 3.39-3.34 (m, 2H), 3.16 (s, 3H), 2.29-2.26 (m, 1H), 1.98-1.91 (m, 1H), 1.34 (s, 9H).

Step-b: Synthesis of tert-butyl (2S,4R)-4-methoxy-2-(((S)-1-(4-(4-methylthiazol-5-yl)phenyl) ethyl)carbamoyl)pyrrolidine-1-carboxylate (20b)

The title compound was synthesized by using the same procedure which was followed for Intermediate-17d using (S)-1-(4-(4-methylthiazol-5-yl)phenyl)ethan-1-amine hydrochloride (Yield: 88%) $^1$H NMR (400 MHz, DMSO-$d_6$): δ 8.98 (s, 1H), 8.41-8.36 (m, 1H), 7.45-7.38 (m, 4H), 4.99-4.95 (m, 1H), 4.16-4.12 (m, 1H), 3.89 (s, 1H), 3.45-3.38 (m, 2H), 3.20 (s, 3H), 2.45 (s, 3H), 2.27-2.22 (m, 1H), 1.81-1.76 (m, 1H), 1.38 (s, 12H); LC-MS: m/z 446.6 (M+1)$^+$ Step-c: Synthesis of (2S,4R)-4-methoxy-N—((S)-1-(4-(4-methylthiazol-5-yl)phenyl)ethyl) pyrrolidine-2-carboxamide hydrochloride (20c)

The title compound was synthesized by using the same procedure which was followed for Intermediate-17e using tert-butyl (2R,4R)-4-methoxy-2-(((S)-1-(4-(4-methylthiazol-5-yl)phenyl)ethyl)carbamoyl)pyrrolidine-1-carboxylate (Yield: 87%) $^1$H NMR (400 MHz, DMSO-$d_6$): δ 9.82 (s, 1H), 9.11 (d, J=7.6 Hz, 1H), 9.01 (s, 1H), 8.67 (s, 1H), 7.48-7.40 (m, 4H), 5.01-4.96 (m, 1H), 4.28-4.22 (m, 2H), 3.62-3.56 (m, 2H), 3.26 (s, 3H), 2.61-2.56 (m, 1H), 2.46 (s, 3H), 1.82-1.75 (m, 1H), 1.43 (d, J=7.6 Hz, 3H).

Step-d: Synthesis of tert-butyl ((S)-1-((2S,4R)-4-methoxy-2-(((S)-1-(4-(4-methylthiazol-5-yl)phenyl)ethyl)carbamoyl)pyrrolidin-1-yl)-3,3-dimethyl-1-oxobutan-2-yl)carbamate (20d)

The title compound was synthesized by using the same procedure which was followed for (17f) using (S)-2-((tert-butoxycarbonyl)amino)-3,3-dimethylbutanoic acid (Yield: 85%), $^1$H NMR (400 MHz, DMSO-$d_6$): δ 8.98 (s, 1H), 8.37 (d, J=7.6 Hz, 1H), 7.44-7.36 (m, 4H), 6.52 (d, J=9.2 Hz, 1H), 4.92-4.88 (m, 1H), 4.38 (d, J=8.4 Hz, 1H), 4.20-4.10 (m, 1H), 4.00-3.90 (m, 2H), 3.70-3.60 (m, 1H), 3.19 (s, 3H), 2.49 (s, 3H), 2.22-2.19 (m, 1H), 1.82-1.76 (m, 1H), 1.40 (s, 12H), 0.90 (s, 9H); LC-MS: m/z 559.3 (M+1)$^+$.

Step-e: Synthesis of (2S,4R)-1-((S)-2-amino-3,3-dimethylbutanoyl)-4-methoxy-N—((S)-1-(4-(4-methylthiazol-5-yl)phenyl)ethyl)pyrrolidine-2-carboxamide hydrochloride (20e)

The title compound was synthesized by using the same procedure which was followed for (17g) using tert-butyl ((S)-1-((2S,4R)-4-methoxy-2-(((S)-1-(4-(4-methylthiazol-5-yl)phenyl) ethyl)carbamoyl)pyrrolidin-1-yl)-3,3-dimethyl-1-oxobutan-2-yl)carbamate (Yield: 90%), $^1$H NMR (400 MHz, DMSO-$d_6$): δ 9.07 (s, 1H), 8.60 (d, J=7.6 Hz, 1H), 8.08 (s, 3H), 7.46-7.38 (m, 4H), 4.94-4.90 (m, 1H), 4.48 (t, J=8.8 Hz, 1H), 4.00 (s, 2H), 3.61-3.58 (m, 4H), 3.47-3.44 (m, 1H), 2.46 (s, 3H), 2.33-2.30 (m, 1H), 1.80-1.60 (m, 1H), 1.38 (d, J=7.6 Hz, 3H), 1.03 (s, 9H); LC-MS: m/z 459.1 (M+1)$^+$.

Intermediate-21:

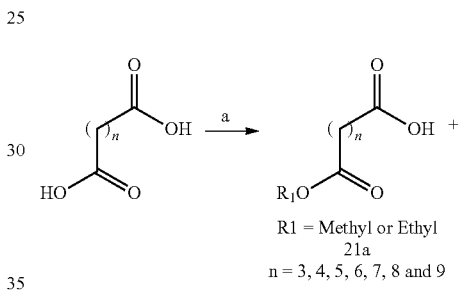

R1 = Methyl or Ethyl
21a
n = 3, 4, 5, 6, 7, 8 and 9

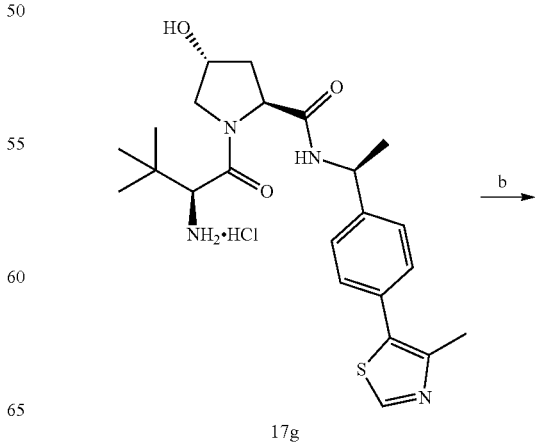

17g

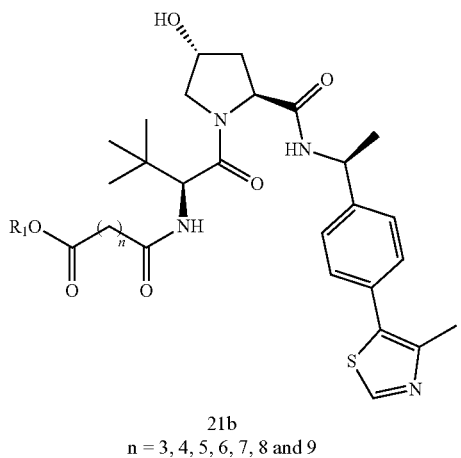

21b
n = 3, 4, 5, 6, 7, 8 and 9

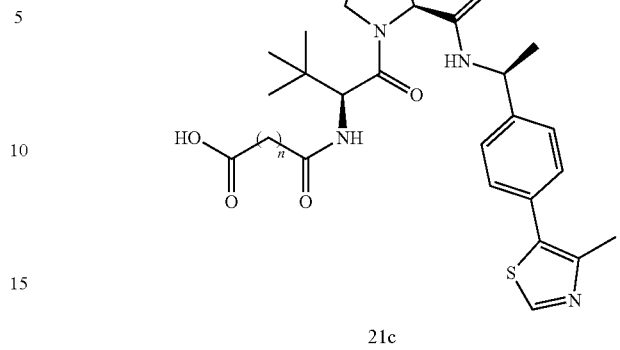

21c
n = 3, 4, 5, 6, 7, 8 and 9

Conditions: a) Ethanol, Conc•H$_2$SO$_4$, 80° C., 16 h; b) HATU, DIPEA, DCM, 0° C. - RT, 18 h; c) LiOH•H$_2$O, THF:H$_2$O, 0° C. - RT, 16 h.

Step-a: General Procedure for Synthesis of Compound (21a$_1$-21a$_7$)

To a stirred solution of dicarboxylic acid (1.0 eq.) in ethanol (10 vol.) was added Conc. H$_2$SO$_4$ (1 vol.) at 0° C. The reaction mixture allowed to come to RT and then refluxed for 16 h. After completion of the reaction (monitored by TLC) solvents were removed under reduced pressure and the residue was neutralised with saturated aq. NaHCO$_3$ solution. The resulting mixture was extracted with ethyl acetate. Further aqueous layer was acidified with Conc. HCl and extracted with ethyl acetate (2 times). The combined organic layer was washed with water, brine, dried over anhydrous sodium sulphate and concentrated under reduced pressure to give the residue which was purified by combi flash column chomatography using 2-3% methanol in DCM as eluent to afford the title compound (21a$_1$-21a$_7$, yield: 4-63%).

TABLE 5

| Structure | Characterization Data $^1$H NMR (400 MHz, DMSO-d$_6$) |
|---|---|
| 21a$_1$ (n = 3) | $^1$H NMR (400 MHz, DMSO-d$_6$): δ 12.06 (s, 1H), 3.58 (s, 3H), 2.33 (t, J = 7.6 Hz, 2H), 2.26-2.22 (m, 2H), 1.76-1.68 (m, 2H); LC-MS: m/z 147.1 (M + 1)$^+$. |
| 21a$_2$ (n = 4) | LC-MS; commercial available |
| 21a$_3$ (n = 5) | $^1$H NMR (400 MHz, DMSO-d$_6$): δ 11.95 (bs, 1H), 3.57 (s, 3H), 2.30 (t, J = 7.4 Hz, 2H), 2.18 (t, J = 7.4 Hz, 2H), 1.53-1.48 (m, 4H), 1.28-1.26 (m, 2H). |

TABLE 5-continued

| Structure | Characterization Data $^1$H NMR (400 MHz, DMSO-$d_6$) |
|---|---|
| 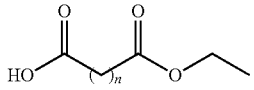 21a$_4$ (n = 6) | LC-MS: m/z 203.0 (M + 1)$^+$ |
| 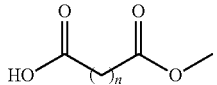 21a$_5$ (n = 7) | LC-MS; commercial available |
| 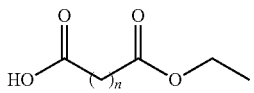 21a$_6$ (n = 8) | $^1$H NMR (400 MHz, DMSO-$d_6$): δ 11.94 (s, 1H), 4.04 (q, J = 7.2 Hz, 2H), 2.25 (t, J = 7.6 Hz, 2H), 2.18 (t, J = 7.6 Hz, 2H), 1.50-1.48 (m, 4H), 1.24 (s, 8H), 1.17 (t, J = 6.8 Hz, 3H); Yield: 63% |
| 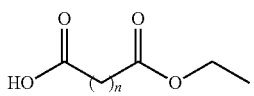 21a$_7$ (n = 9) | LC-MS; commercial available |

Step-b: General Procedure for Synthesis of Compound (21 b$_1$-21 b$_7$)

To a solution of (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (Intermediate-17g) (1.0 eq) and compound (21a$_1$-21a$_7$, 1.0 eq.) in DMF (5 vol.) at 0° C. was added HATU (1.2 eq.) followed by the dropwise addition of DIPEA (5.0 eq.) and the reaction mixture was stirred for 16 h at RT. Then the reaction mixture was poured into ice cold water and extracted with ethyl acetate. The combined organic layer was washed with water, brine, dried over anhydrous sodium sulphate and concentrated under vacuum to give the crude product which was purified by combi flash column chomatography using 3-5% methanol in DCM as eluent to afford the title compound (21b$_1$-21 b$_7$, 40-68%).

TABLE 6

| Structure | Characterization Data |
|---|---|
| 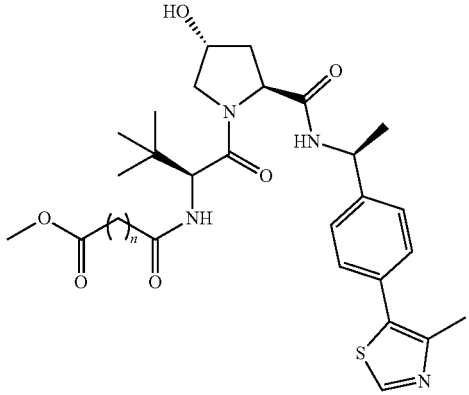 21b$_1$ (n = 3) | $^1$H NMR (400 MHz, DMSO-$d_6$): δ 8.97 (s, 1H), 8.36 (d, J = 8.0 Hz, 1H), 7.83 (d, J = 9.2 Hz, 1H), 7.44-7.36 (m, 4H), 5.09-5.08 (m, 1H), 4.91-4.88 (m, 1H), 4.50 (d, J = 9.2 Hz, 1H), 4.43-4.24 (m, 1H), 4.27 (bs, 1H), 3.60 (s, 3H), 2.50 (s, 3H), 2.32-2.22 (m, 5H), 2.13-1.98 (m, 1H), 1.81-1.71 (m, 4H), 1.37 (d, J = 7.2 Hz, 3H), 1.47 (s, 9H); LC-MS: m/z 573.8 (M + 1)$^+$. |

TABLE 6-continued
| Structure | Characterization Data |
|---|---|
| 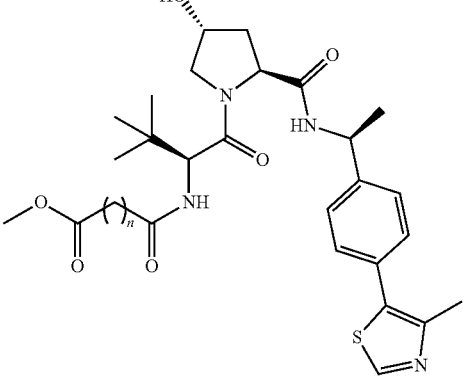<br>21b$_2$ (n = 4) | $^1$H NMR (400 MHz, DMSO-d$_6$): δ 8.98 (s, 1H), 8.36 (d, J = 7.8 Hz, 1H), 7.76 (d, J = 9.2 Hz, 1H), 7.42 (d, J = 7.9 Hz, 2H), 7.38 (d, J = 8.2 Hz, 2H), 5.08 (d, J = 3.4 Hz, 1H), 4.95-4.86 (m, 1H), 4.52 (d, J = 9.2 Hz, 1H), 4.43-4.40 (m, 1H), 4.26 (bs, 1H), 3.63-3.60 (m, 2H), 3.57 (s, 3H), 2.45 (s, 3H), 2.43-2.12 (m, 3H), 2.09-1.98 (m, 1H), 1.82-1.76 (m, 1H), 1.52-1.46 (m, 4H), 1.38-1.36 (m, 4H), 0.93 (s, 9H); LC-MS: m/z 587.25 (M + 1)$^+$; (Yield : 49%). |
| 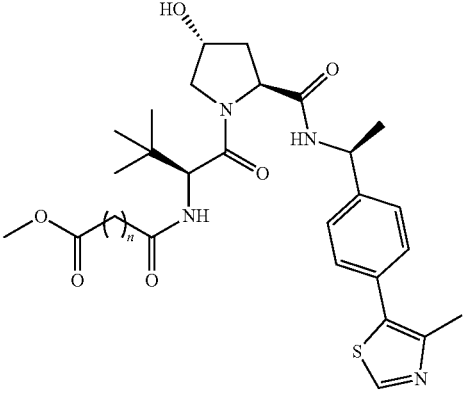<br>21b$_3$ (n = 5) | $^1$H NMR (400 MHz, DMSO-d$_6$): δ 8.98 (s, 1H), 8.36 (d, J = 7.8 Hz, 1H), 7.76 (d, J = 9.1 Hz, 1H), 7.42 (d, J = 7.8 Hz, 2H), 7.39 (d, J = 8.2 Hz, 2H), 5.08 (d, J = 3.5 Hz, 1H), 4.96-4.88 (m, 1H), 4.52 (d, J = 9.2 Hz, 1H), 4.40 (t, J = 8.2 Hz, 1H), 4.26 (bs, 1H), 3.63-3.60 (m, 2H), 3.57 (s, 3H), 2.30-1.90 (m, 4H), 1.82-1.76 (m, 1H), 1.52-1.46 (m, 4H), 1.38 (d, J = 6.8 Hz, 3H), 1.27-1.20 (m, 6H), 0.93 (s, 9H); LC-MS: m/z 601.1 (M + 1)$^+$; (Yield : 56%). |
| 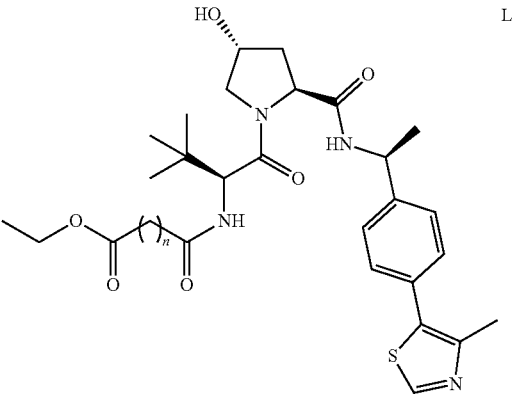<br>21b$_4$ (n = 6) | LC-MS: m/z 629.35 (M + 1)$^+$ |

| Structure | Characterization Data |
|---|---|
| 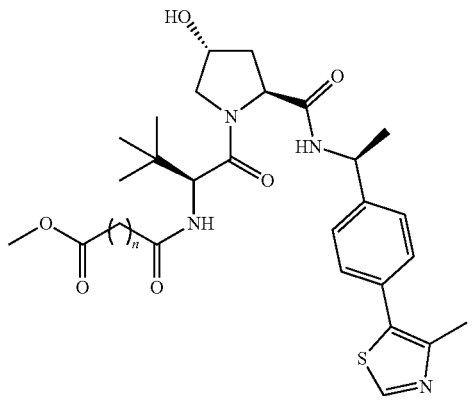<br>21b₅ (n = 7) | ¹H NMR (400 MHz, DMSO-d₆): δ 8.98 (s, 1H), 8.36 (d, J = 7.9 Hz, 1H), 7.75 (d, J = 9.3 Hz, 1H), 7.45 (d, J = 7.8 Hz, 2H), 7.38 (d, J = 8.3 Hz, 2H), 5.08 (d, J = 3.9 Hz, 1H), 4.93 (d, J = 7.3 Hz, 1H), 4.52 (d, J = 9.3 Hz, 1H), 4.43-4.40 (m, 1H), 4.28-4.27 (m, 1H), 3.62-3.56 (m, 5H), 2.66 (s, 3H), 2.45-2.30 (m, 3H), 2.25-2.01 (m, 2H), 1.80-1.75 (m, 1H), 1.48-1.45 (m, 4H), 1.38 (d, J = 6.3 Hz, 3H), 1.24-1.20 (m, 6H), 0.93 (s, 9H); LC-MS: m/z 629.35 (M + 1)⁺; (Yield: 46%). |
| 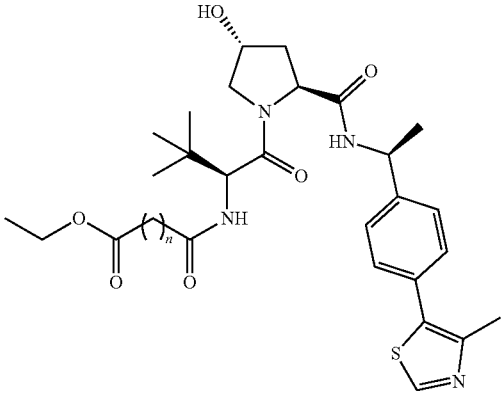<br>21b₆ (n = 8) | ¹H NMR (400 MHz, DMSO-d₆): δ 8.98 (s, 1H), 8.35 (d, J = 8.0 Hz, 1H), 7.76 (d, J = 9.2 Hz, 1H), 7.44-7.36 (m, 4H), 5.07 (d, J = 3.2 Hz, 1H), 4.93-4.89 (m, 1H), 4.51 (d, J = 9.2 Hz, 1H), 4.42 (t, J = 7.6 Hz, 1H), 4.27 (s, 1H), 4.06-4.00 (m, 2H), 3.61-3.60 (m, 2H), 2.45 (s, 3H), 2.27-2.22 (m, 4H), 2.11-2.08 (m, 1H), 1.85-1.72 (m, 1H), 1.50-1.43 (m, 4H), 1.37 (d, J = 6.8 Hz, 3H), 1.23 (s, 8H), 1.20-1.10 (m, 3H), 0.93 (s, 9H); LC-MS: m/z 657.2 (M + 1)⁺; (Yield: 68%). |
| 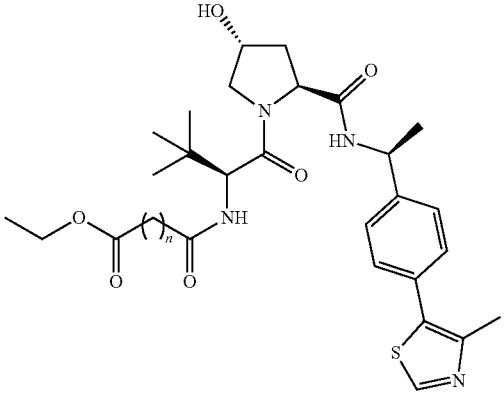<br>21b₇ (n = 9) | LC-MS: m/z 671.4 (M + 1)⁺ |

Step-c: General procedure for synthesis of compound (21c₁-21c₇)

To a stirred solution of compound (21 b₁-21 b₇, 1.0 eq.) in THF H₂O (2:1,20 vol.) was added LiOH·H₂O (2.0 eq.) at 0° C. The reaction mixture was stirred for 16 h at RT. Then the reaction mixture was evaporated under reduced pressure and the resultant residue was diluted with water and neutralized with aqueous 1 M HCl solution. The obtained solid was filtered and dried under vacuum to afford the title compound (21c₁-21c₇, 55-74%).

TABLE 7

| Structure | Characterization Data |
|---|---|
| 21c₁ (n = 3) | ¹H NMR (400 MHz, DMSO-d₆): δ 8.98 (s, 1H), 8.36 (d, J = 7.6 Hz, 1H), 7.82 (d, J = 9.6 Hz, 1H), 7.43 (d, J = 8.0 Hz, 2H), 7.37 (d, J = 8.4 Hz, 2H), 4.93-4.89 (m, 1H), 4.50 (d, J = 9.2 Hz, 1H), 4.43 (t, J = 8.0 Hz, 1H), 4.27 (s, 1H), 3.60 (s, 2H), 2.45 (s, 3H), 2.25-2.16 (m, 5H), 2.14-2.08 (m, 1H), 1.82-1.75 (m, 1H), 1.71-1.68 (m, 2H), 1.37 (d, J = 6.8 Hz, 3H), 0.93 (s, 9H). LC-MS: m/z 559.2 (M + 1)⁺. |
| 21c₂ (n = 4) | ¹H NMR (400 MHz, DMSO-d₆): δ 8.98 (s, 1H), 8.36 (d, J = 7.9 Hz, 1H), 7.76 (d, J = 9.3 Hz, 1H), 7.42 (d, J = 7.8 Hz, 2H), 7.36 (d, J = 8.3 Hz, 2H), 4.95-4.88 (m, 1H), 4.52 (d, J = 9.2 Hz, 1H), 4.43-4.40 (m, 1H), 4.20 (bs, 1H), 3.63-3.57 (m, 3H), 2.45 (s, 3H), 2.43-2.12 (m, 4H), 2.09-1.98 (m, 1H), 1.82-1.76 (m, 1H), 1.51-1.47 (m, 4H), 1.38-1.36 (m, 4H), 0.93 (s, 9H); LC-MS: m/z 573.25 (M + 1)⁺ ; Yield : 68%. |
| 21c₃ (n = 5) | ¹H NMR (400 MHz, DMSO-d₆): δ 11.94 (bs, 1H), 8.98 (s, 1H), 8.36 (d, J = 7.9 Hz, 1H), 7.70 (d, J = 9.2 Hz, 1H), 7.42 (d, J = 7.8 Hz, 2H), 7.38 (d, J = 8.3 Hz, 2H), 5.08 (d, J = 3.0 Hz, 1H), 4.99-4.97 (m, 1H), 4.53 (d, J = 9.2 Hz, 1H), 4.43 (t, J = 8.0 Hz, 1H), 4.20 (bs, 1H), 3.68-3.60 (m, 2H), 2.50 (s, 3H), 2.30-2.00 (m, 5H), 1.72-1.65 (m, 1H), 1.54-1.52 (m, 6H), 1.37-1.36 (m, 3H), 0.93 (s, 9H); LC-MS: m/z 587.1 (M + 1)⁺. |

TABLE 7-continued

| Structure | Characterization Data |
|---|---|
| 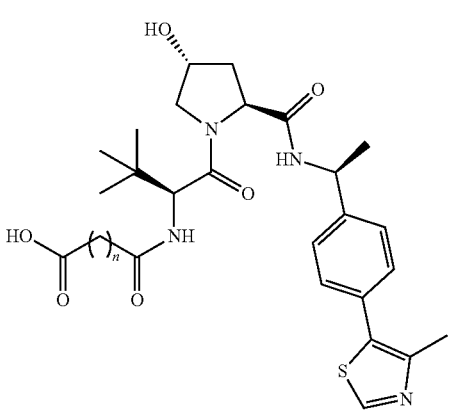<br>21c₄ (*n* = 6) | ¹H NMR (400 MHz, DMSO-ds): δ 11.93 (s, 1H), 8.98 (s, 1H), 8.36 (d, J = 8.0 Hz, 1H), 7.78 (d, J = 9.2 Hz, 1H), 7.44-7.36 (m, 4H), 5.08 (d, J = 4.0 Hz, 1H), 4.93 -4.89 (m, 1H), 4.52 (d, J = 9.2 Hz, 1H), 4.44 (t, J = 8.2 Hz, 1H), 4.27 (s, 1H), 3.61-3.60 (m, 2H), 2.45 (s, 3H), 2.24-2.00 (m, 5H), 1.75-1.84 (m, 1H), 1.47-1.45 (m, 4H), 1.38 (d, J = 7.2 Hz, 3H), 1.25-1.23 (m, 4H), 0.93 (s, 9H).<br>LC-MS: m/z 601.3 (M + 1)⁺. |
| 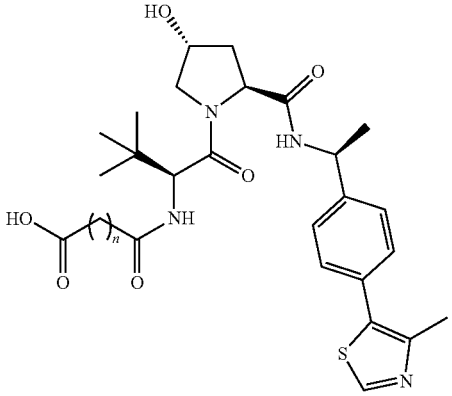<br>21c₅ (*n* = 7) | ¹H NMR (400 MHz, DMSO-d₆): δ 11.93 (bs, 1H), 8.99 (s, 1H), 8.36 (d, J = 7.8 Hz, 1H), 7.78 (d, J = 9.3 Hz, 1H), 7.44-7.35 (m, 4H), 4.93 (t, J = 7.1 Hz, 1H), 4.53 (d, J = 9.3 Hz, 1H), 4.42 (t, J = 8.0 Hz, 1H), 4.21 (s, 1H), 3.60 (t, J = 12.2 Hz, 2H), 2.50 (s, 3H), 2.26-2.03 (m, 6H), 1.93-1.70 (m, 1H), 1.47-1.45 (m, 4H), 1.38 (d, J = 6.3 Hz, 3H), 1.25-1.20 (m, 6H), 0.93 (s, 9H); LC-MS: m/z 613.1 (M − 1); Yield: 98% |
| 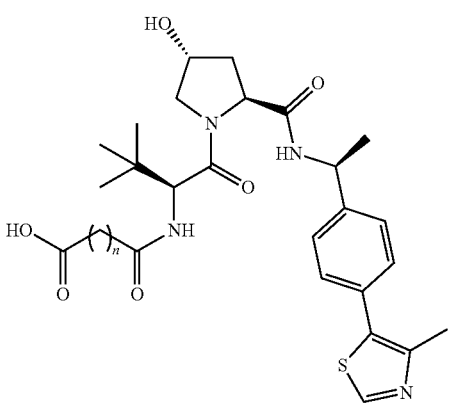<br>21c₆ (*n* = 8) | ¹H NMR (400 MHz, DMSO-d₆): δ 9.01 (s, 1H), 8.36 (d, J = 8.0 Hz, 1H), 7.76 (d, J = 9.6 Hz, 1H), 7.44-7.37 (m, 4H), 4.93-4.89 (m, 1H), 4.51 (d, J = 9.2 Hz, 1H), 4.46-4.40 (m, 1H), 4.27 (s, 1H), 3.61-3.60 (m, 2H), 2.45 (s, 3H), 2.24-2.17 (m, 4H), 2.16-2.00 (m, 2H), 1.82-1.78 (m, 1H), 1.49-1.46 (m, 4H), 1.37 (d, J = 6.8 Hz, 3H), 1.24 (s, 8H), 0.93 (s, 9H); LC-MS: m/z 629.3 (M + 1)⁺; Yield: 74%. |

TABLE 7-continued

| Structure | Characterization Data |
|---|---|
| 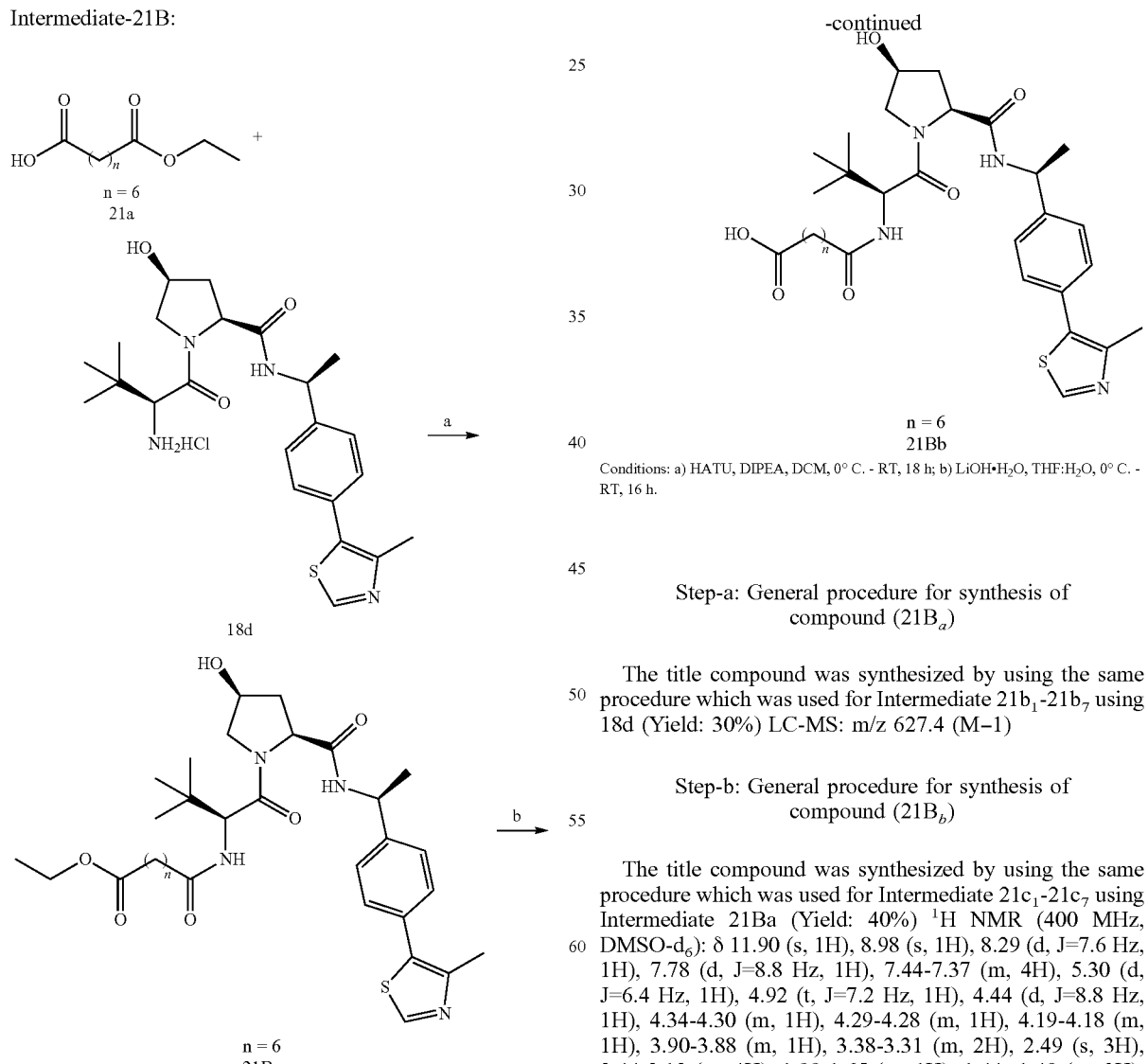<br>21c₇ (n = 9) | ¹H NMR (400 MHz, DMSO-d₆): δ 12.20(s, 1H), 8.98 (s, 1H), 8.36 (d, J = 8.0 Hz, 1H), 7.78 (d, J = 8.8 Hz, 1H), 7.44-7.32 (m, 4H) 4.93-4.89 (m, 1H),4.52 (d, J = 3.6 Hz,1H), 4.46-4.40 (m, 1H), 4.27-4.23 (m, 1H), 3.68-3.57 (m, 3H), 2.45 (m, 3H), 2.81-2.20 (m, 3H), 2.18-1.98 (m, 2H), 1.82-1.76 (m, 1H), 1.54-1.40 (m, 4H) 1.38 (d, J = 7.2 Hz, 3H), 1.30-1.20 (m, 10H), 0.99-0.90 (m, 9H).LC-MS: m/z 641.4 (M − 1). |

Intermediate-21B:

Conditions: a) HATU, DIPEA, DCM, 0° C. - RT, 18 h; b) LiOH•H₂O, THF:H₂O, 0° C. - RT, 16 h.

Step-a: General procedure for synthesis of compound (21B$_a$)

The title compound was synthesized by using the same procedure which was used for Intermediate 21b₁-21b₇ using 18d (Yield: 30%) LC-MS: m/z 627.4 (M−1)

Step-b: General procedure for synthesis of compound (21B$_b$)

The title compound was synthesized by using the same procedure which was used for Intermediate 21c₁-21c₇ using Intermediate 21Ba (Yield: 40%) ¹H NMR (400 MHz, DMSO-d₆): δ 11.90 (s, 1H), 8.98 (s, 1H), 8.29 (d, J=7.6 Hz, 1H), 7.78 (d, J=8.8 Hz, 1H), 7.44-7.37 (m, 4H), 5.30 (d, J=6.4 Hz, 1H), 4.92 (t, J=7.2 Hz, 1H), 4.44 (d, J=8.8 Hz, 1H), 4.34-4.30 (m, 1H), 4.29-4.28 (m, 1H), 4.19-4.18 (m, 1H), 3.90-3.88 (m, 1H), 3.38-3.31 (m, 2H), 2.49 (s, 3H), 2.44-2.12 (m, 4H), 1.99-1.65 (m, 1H), 1.44- 1.40 (m, 3H), 1.38 (d, J=7.2 Hz, 3H), 1.25-1.24 (m, 4H), 0.94 (s, 9H); LC-MS: m/z 599.3 (M−1).

Intermediate-22c:

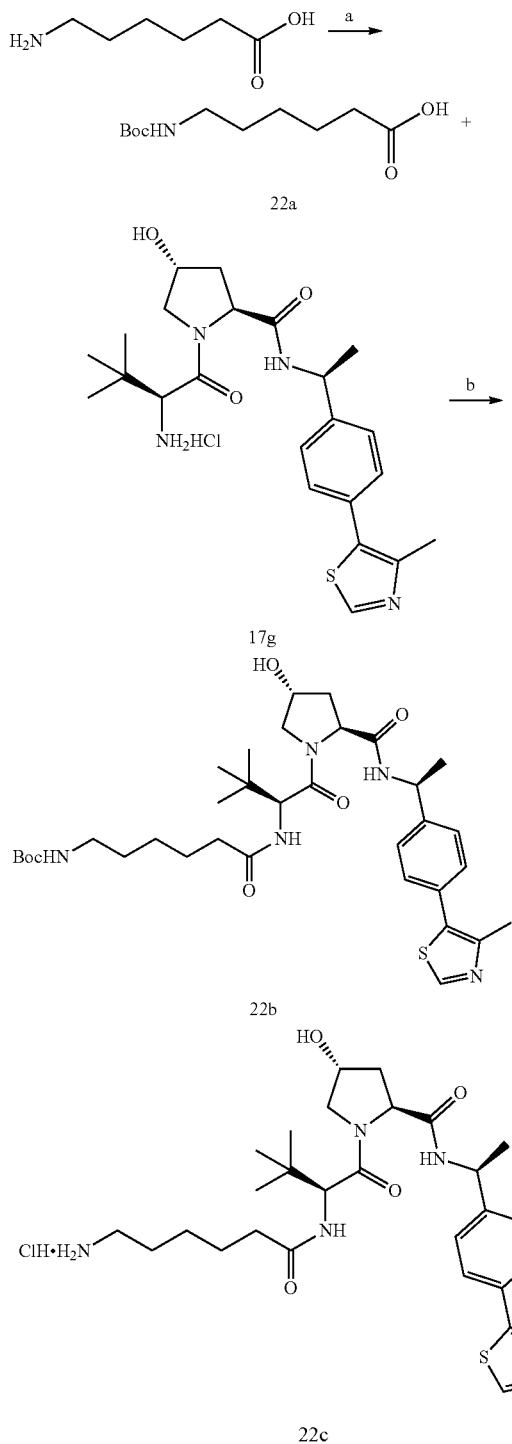

Conditions: a) Boc anhydride, Et₃N, DCM, 0° C. - RT - 16 h; b) HATU, DIPEA, DCM, 0° C - RT, 18 h; c) 4M HCl in 1,4-Dioxane, 1,4-Dioxane, 0° C. - RT.

Step-a: Synthesis of 6-((tert-butoxycarbonyl)amino) hexanoic acid (22a)

The title compound was synthesized by using the same procedure which was used for Intermediate 17a using 6-aminohexanoic acid (Yield: 30%), $^1$H NMR (400 MHz, DMSO-$d_6$): δ 11.95 (bs, 1H), 6.74 (s, 1H), 2.88 (q, J=6.4 Hz, 2H), 2.17 (t, J=7.6 Hz, 2H), 1.51-1.43 (m, 2H), 1.36 (s, 11H), 1.26-1.19 (m, 2H).

Step-b: Synthesis of tert-butyl (6-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-6-oxohexyl)carbamate (22b)

The title compound was synthesized by using the same procedure which was followed for Intermediate 21b₁-21b₇ using (2S,4R)-1-((S)-2-amino-3,3-dimethylbutanoyl)-4-hydroxy-N—((S)-1-(4-(4-methylthiazol-5-yl)phenyl)ethyl) pyrrolidine-2-carboxamide hydrochloride (Yield: 70%), $^1$H NMR (400 MHz, DMSO-$d_6$): δ 8.98 (s, 1H), 8.35 (d, J=8.0 Hz, 1H), 7.76 (d, J=9.6 Hz, 1H), 7.44-7.36 (m, 4H), 6.72 (s, 1H), 5.07 (d, J=3.6 Hz, 1H), 4.93-4.91 (m, 1H), 4.50 (d, J=9.6 Hz, 1H), 4.42 (t, J=8.4 Hz, 1H), 4.28 (s, 1H), 3.61-3.60 (m, 2H), 2.88 (q, J=7.2 Hz, 2H), 2.49 (s, 3H), 2.29-2.20 (m, 1H), 2.15-2.09 (m, 1H), 2.05-2.00 (m, 1H), 1.85-1.75 (m, 1H), 1.47-1.43 (m, 2H), 1.38 (s, 14H), 1.25-1.17 (m, 2H), 0.93 (s, 9H); LC-MS: m/z 658.1 (M+1)⁺.

Step-c: Synthesis of (2S,4R)-1-((S)-2-(6-aminohexanamido)-3,3-dimethylbutanoyl)-4-hydroxy-N—((S)-1-(4-(4-methylthiazol-5-yl)phenyl)ethyl)pyrrolidine-2-carboxamide hydrochloride (22c)

The title compound was synthesized by using the same procedure which was followed for Intermediate-17e using tert-butyl (6-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-6-oxohexyl)carbamate (Yield: 90%), $^1$H NMR (400 MHz, MeOH-$d_4$): δ 9.95 (s, 1H), 7.56-7.48 (m, 4H), 5.01 (q, J=6.8 Hz, 1H), 4.61 (s, 1H), 4.56 (t, J=8.0 Hz, 1H), 4.42 (s, 1H), 3.86 (d, J=11.6 Hz, 1H), 3.75-3.70 (m, 1H), 2.91 (t, J=6.8 Hz, 2H), 2.60 (s, 3H), 2.33-2.17 (m, 4H), 1.96-1.90 (m, 1H), 1.70-1.59 (m, 4H), 1.50 (d, J=6.8 Hz, 3H), 1.44-1.28 (m, 2H), 1.03 (s, 9H); LC-MS: m/z 558.2 (M+1)⁺.

Intermediate-23b:

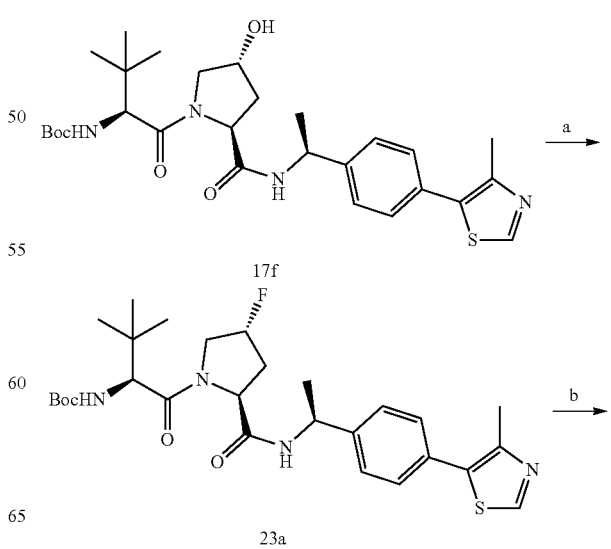

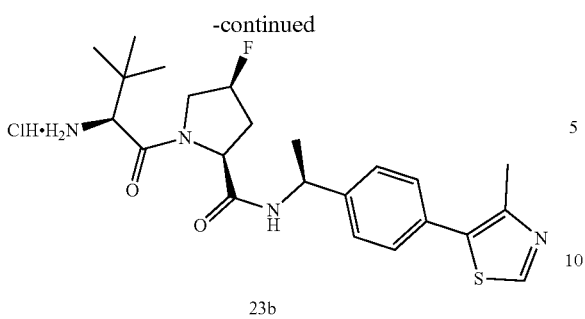

23b

Conditions: a) DAST, DCM, -78° C., RT - 16 h; b) 4M HCl in Dioxane, DCM, 0° C., RT, 16 h.

Step-a: Synthesis of tert-butyl ((S)-1-((2S,4S)-4-fluoro-2-(((S)-1-(4-(4-methylthiazol-5-yl)phenyl)ethyl)carbamoyl)pyrrolidin-1-yl)-3,3-dimethyl-1-oxobutan-2-yl)carbamate (23a)

To a solution of tert-butyl ((S)-1-((2S,4S)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamate (0.8 g 1.47 mmol) in DCM (10 mL) at −78° C. was added DAST (0.35 g, 2.20 mmol) and the reaction mixture was stirred for 16 h at RT. Then it was quenched with saturated aq. $NH_4Cl$ solution, extracted with DCM (2×50 mL). The combined organic layers were washed with water (20 mL), brine (20 mL), dried over anhydrous sodium sulphate and concentrated under reduced pressure to get residue which was purified by Combi flash using 5% MeOH in DCM as eluent to afford the title compound (0.8 g, crude). LC-MS: m/z 547.30 $(M+1)^+$.

Step-b: Synthesis of ((2S,4S)-1-((S)-2-amino-3,3-dimethylbutanoyl)-4-fluoro-N—((S)-1-(4-(4-methylthiazol-5-yl)phenyl)ethyl)pyrrolidine-2-carboxamide hydrochloride (23b)

The title compound was synthesized by using the same procedure which was followed for $1f_1$-$1f_{12}$ using tert-butyl ((S)-1-((2S,4S)-4-fluoro-2-(((S)-1-(4-(4-methylthiazol-5-yl)phenyl) ethyl)carbamoyl)pyrrolidin-1-yl)-3,3-dimethyl-1-oxobutan-2-yl) carbamate (Yield: 40%) $^1$H NMR (400 MHz, DMSO-$d_6$): δ 9.04 (s, 1H), 8.54 (d, J=8.0 Hz, 1H), 8.14-8.10 (m, 3H), 7.46-7.38 (m, 4H), 4.95-4.91 (m, 1H), 4.59-4.57 (m, 1H), 4.42 (t, J=8.0 Hz, 1H), 4.21-4.17 (m, 1H), 4.01-3.97 (m, 1H), 3.91-3.90 (m, 1H), 2.42 (s, 3H), 2.05-1.98 (m, 1H), 1.63-1.60 (m, 1H), 1.38 (d, J=4.4 Hz, 3H), 1.02 (s, 9H); LC-MS: m/z 445.0 $(M+1)^+$.

Intermediate-24:

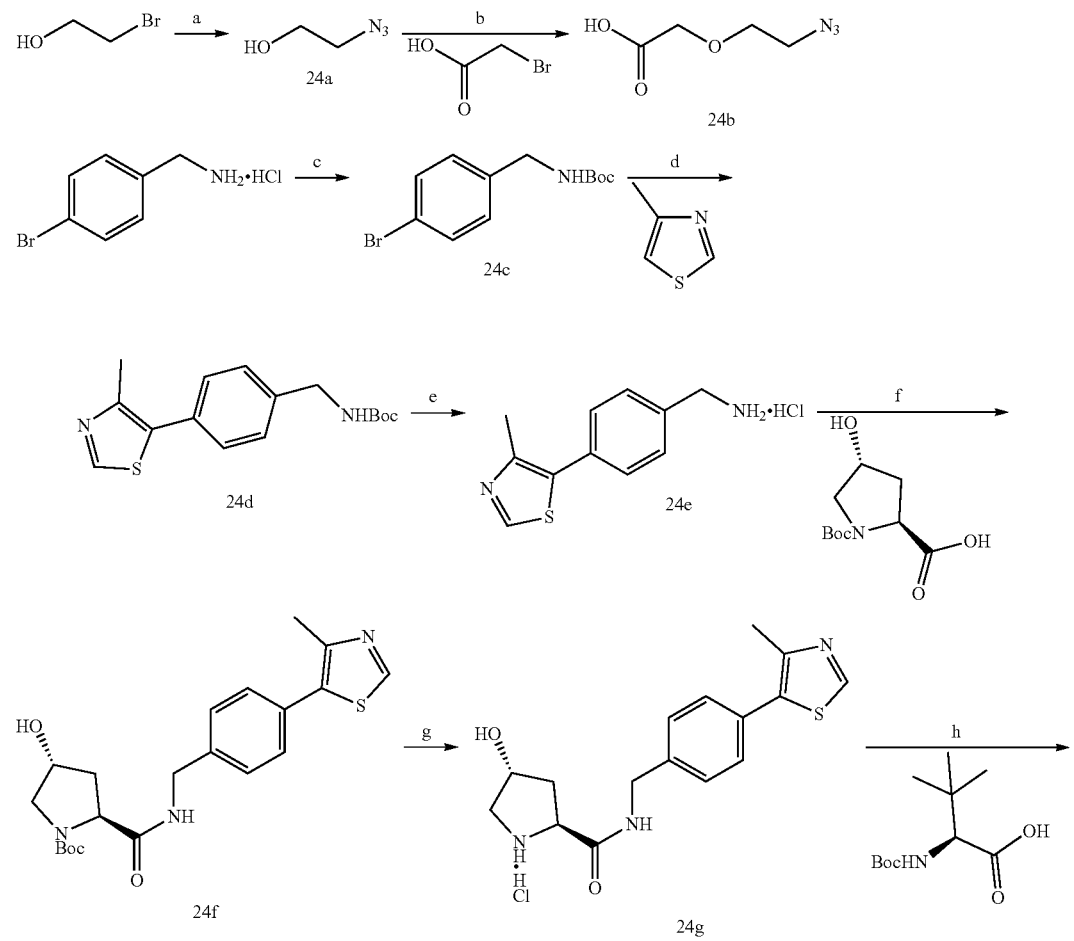

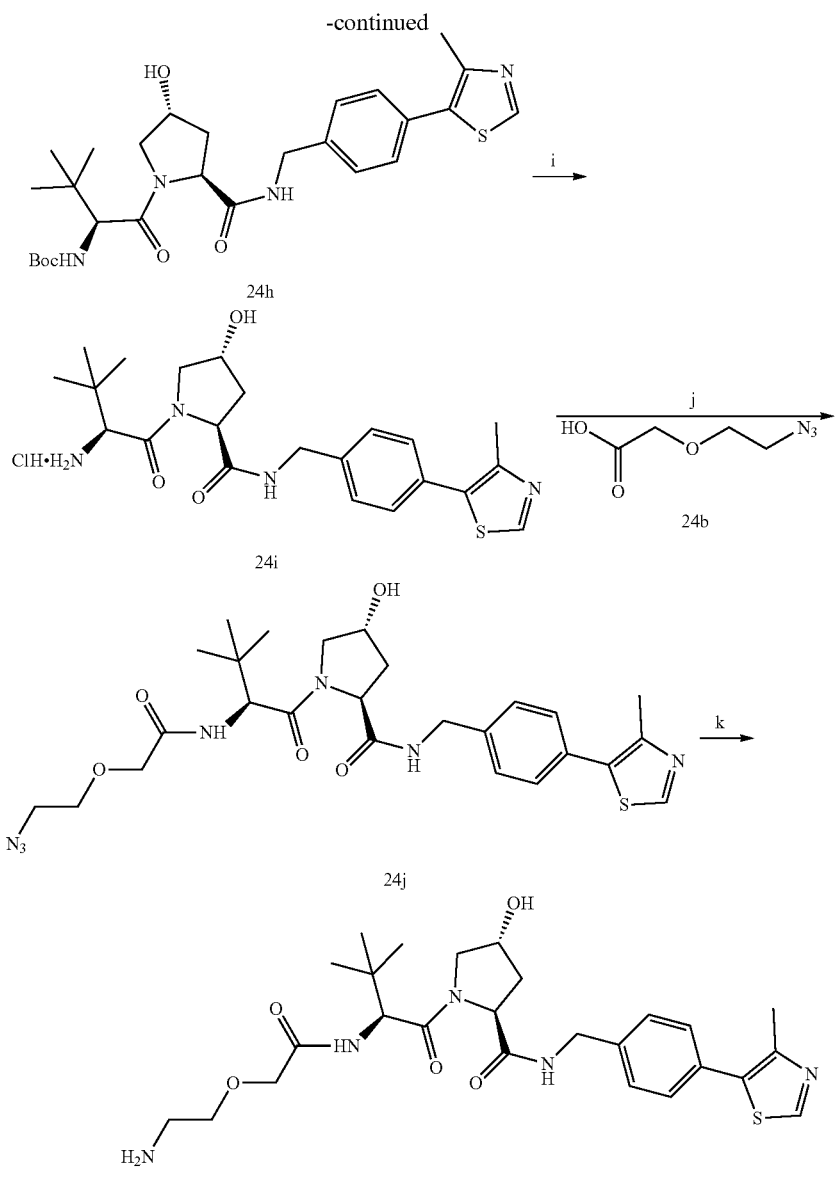

Conditions: a) NaN₃, H₂O, 104° C., 16 h; b) NaI, NaH, THF, 0° C., 3 h; c) Boc anhydride, Et₃N, DCM, 0° C. - RT, 16 h; d) Pd(OAc)₂, KOAc, DMF, 100° C., 16 h; e) 4M HCl in 1,4-Dioxane, 1,4-Dioxane, 0° C. - RT, 16 h; f) HATU, DIPEA, DCM, 0° C. - RT, 18 h; g) 4M HCl in 1,4-Dioxane, 1,4-Dioxane, 0° C. - RT; h) HATU, DIPEA, DCM, 0° C. - RT, 18 h; i) 4M HCl in 1,4-Dioxane, 1,4-Dioxane, 0° C. - RT - 16 h; j) HATU, DIPEA, DMF, 0° C. - RT, 2 h; k) 10% Pd/C, H₂ atm (50 psi), EtOAc, RT, 16 h.

Step-a: Synthesis of 2-azidoethan-1-ol (24a)

To a stirred solution of 2-bromoethan-1-ol (30.0 mL, 422.0 mmol) in H₂O (500 mL) was added sodium azide (41.96 g, 633.0 mmol) at RT and stirred for 16 h at 104° C. under nitrogen atmosphere. After completion of the reaction (monitored by TLC), sodium chloride was added to the reaction mixture to saturate the solution. Then it was extracted with diethyl ether (5×300 mL). The combined organic layer was washed with water (500 mL), brine (500 mL), dried over anhydrous sodium sulphate and concentrated under reduced pressure to afford the title compound (31.0 g, 63.7%). ¹H NMR (400 MHz, CDCl₃): δ 3.78 (q, J=5.2 Hz, 2H), 3.45 (t, J=4.8 Hz, 2H), 1.99-1.89 (m, 1H).

Step-b: Synthesis of 2-(2-azidoethoxy)acetic acid (24b)

To a stirred solution of 2-azidoethan-1-ol (24a, 12.00 g, 137.93 mmol), 2-bromoacetic acid (22.99 g, 165.51 mmol) and NaI (0.2 g, 1.37 mmol) in THF (500 mL) was added NaH (55-60%, 17.93 g, 411.9 mmol) at 0° C. under nitrogen atmosphere over 1.5 h. Reaction mixture was stirred at same temperature for 2 h and then poured into crushed ice. The resulting mixture was acidified with 1 N HCl to pH-3 and extracted with ethyl acetate (5×300 mL). The combined organic layer was washed with water (500 mL), brine (500 mL), dried over anhydrous sodium sulphate and concentrated under reduced pressure to afford title compound (18.5 g, 93%). ¹H NMR (400 MHz, CDCl₃): δ 9.19 (bs, 1H), 4.21 (s, 2H), 3.76 (t, J=4.8 Hz, 2H), 3.45 (t, J=5.2 Hz, 2H).

Step-c: Synthesis of tert-butyl (4-bromobenzyl)carbamate 24c

The title compound was synthesized using the same procedure which was followed for Intermediate-17a using (4-bromophenyl) methanamine hydrochloride as starting material. Yield: 99% $^1$H NMR (400 MHz, DMSO-$d_6$): δ 7.50 (d, J=8.4 Hz, 2H), 7.40 (t, J=5.4 Hz, 1H), 7.18 (d, J=8.4 Hz, 2H), 4.08 (d, J=5.9 Hz, 2H), 1.38 (s, 9H). LC-MS: m/z 186.0 (M-Boc)$^+$1)$^+$.

Step-d: Synthesis of tert-butyl (4-(4-methylthiazol-5-yl)benzyl)carbamate (24d)

The title compound was synthesized using the same procedure which was followed for-Intermediate-17b using tert-butyl (4-bromobenzyl) carbamate and 4-methylthiazole. Yield: 60% $^1$H NMR (400 MHz, DMSO-$d_6$): δ 8.98 (s, 1H), 7.44 (d, J=7.8 Hz, 3H), 7.33 (d, J=8.3 Hz, 2H), 4.16 (d, J=6.4 Hz, 2H), 2.45 (s, 3H), 1.40 (s, 9H), LC-MS: m/z 305.3 (M+1)$^+$.

Step-e: Synthesis of (4-(4-methylthiazol-5-yl)phenyl)methanamine hydrochloride (24e)

The title compound was synthesized using the same procedure which was followed for Intermediate-17c using tert-butyl (4-(4-methylthiazol-5-yl)benzyl)carbamate. (Yield: 98%). $^1$H NMR (400 MHz, DMSO-$d_6$): δ 9.10 (s, 1H), 8.59 (bs, 2H), 7.62 (d, J=8.4 Hz, 2H), 7.55 (d, J=8.3 Hz, 2H), 5.70 (bs, 1H), 4.06 (q, J=5.8 Hz, 2H), 2.47 (s, 3H); LC-MS: m/z 205.1 (M+1)$^+$.

Step-f: Synthesis of tert-butyl (2S,4R)-4-hydroxy-2-((4-(4-methylthiazol-5-yl)benzyl) carbamoyl)pyrrolidine-1-carboxylate (24f)

The title compound was synthesized using the same procedure which was followed for Intermediate-17d using (4-(4-methylthiazol-5-yl)phenyl)methanamine hydrochloride and (2S,4R)-1-(tert-butoxycarbonyl)-4-hydroxypyrrolidine-2-carboxylic acid as starting materials. (Yield: 74%) $^1$H NMR (400 MHz, DMSO-$d_6$): δ 8.98 (s, 1H), 8.49-8.45 (m, 1H), 7.44-7.36 (m, 4H), 5.00-4.98 (m, 1H), 4.39-4.33 (m, 1H), 4.28-4.15 (m, 3H), 3.47-3.43 (m, 1H), 2.69 (s, 2H), 2.48 (s, 3H), 1.89-1.83 (m, 1H), 1.26 (s, 9H). LC-MS: m/z 418.3 (M+1)$^+$.

Step-g: Synthesis of (2S,4R)-4-hydroxy-N-(4-(4-methylthiazol-5-yl)benzyl)pyrrolidine-2-carboxamide hydrochloride (24g)

The title compound was synthesized using the same procedure which was followed for Intermediate-17e using tert-butyl (2S,4R)-4-hydroxy-2-((4-(4-methylthiazol-5-yl)benzyl) carbamoyl) pyrrolidine-1-carboxylate as starting materials. (Yield: 98%) $^1$H NMR (400 MHz, DMSO-$d_6$): δ 10.23 (bs, 1H), 9.35 (t, J=5.8 Hz, 1H), 9.13 (s, 1H), 8.65 (bs, 1H), 7.66-7.59 (m, 3H), 7.45 (d, J=8.3 Hz, 2H), 4.43-4.37 (m, 4H), 3.38-3.34 (m, 1H), 3.11-3.08 (m, 1H), 2.46 (s, 3H), 1.95-1.88 (m, 1H), 1.32- 1.26 (m, 1H); LC-MS: m/z 318.0 (M+1)$^+$.

Step-h: Synthesis of tert-butyl ((S)-1-((2S,4R)-4-hydroxy-2-((4-(4-methylthiazol-5-yl)benzyl) carbamoyl)pyrrolidin-1-yl)-3,3-dimethyl-1-oxobutan-2-yl)carbamate (24h)

The title compound was synthesized using the same procedure which was followed for Intermediate-17f using (2S,4R)-4-hydroxy-N-(4-(4-methylthiazol-5-yl)benzyl)pyrrolidine-2-carboxamide hydrochloride and (S)-2-((tert-butoxycarbonyl)amino)-3,3-dimethylbutanoic acid as starting materials. (Yield: 35%) $^1$H NMR (400 MHz, DMSO-$d_6$): δ 8.96 (s, 1H), 8.56 (t, J=5.8 Hz, 1H), 8.25 (bs, 1H), 7.46-7.37 (m, 4H), 5.12 (d, J=3.6 Hz, 1H), 4.47-4.24 (m, 4H), 3.67-3.61 (m, 1H), 3.13 (bs, 1H), 2.91 (bs, 1H), 2.44 (s, 3H), 2.06-2.02 (m, 1H), 1.93-1.88 (m, 1H), 1.38 (s, 9H), 0.93 (s, 9H); LC-MS: m/z 531.3 (M+1)$^+$.

Step-i: Synthesis of (2S,4R)-1-((S)-2-amino-3,3-dimethylbutanoyl)-4-hydroxy-N-(4-(4-methylthiazol-5-yl)benzyl)pyrrolidine-2-carboxamide hydrochloride (24i)

The title compound was synthesized using the same procedure which was followed for Intermediate-17g using tert-butyl ((S)-1-((2S,4R)-4-hydroxy-2-((4-(4-methylthiazol-5-yl)benzyl) carbamoyl) pyrrolidin-1-yl)-3,3-dimethyl-1-oxobutan-2-yl)carbamate as starting material. (Yield: 95%) $^1$H NMR (400 MHz, DMSO-$d_6$): δ 9.08 (s, 1H), 8.74 (t, J=6.0 Hz, 1H), 8.17 (bs, 3H), 7.40 (s, 4H), 4.57-4.53 (m, 1H), 4.45-4.40 (m, 2H), 4.37-4.22 (m, 2H), 3.90-3.85 (m, 1H), 3.80-3.77 (m, 1H), 3.41- 3.35 (m, 1H), 2.45 (s, 3H), 2.13-2.10 (m, 1H), 1.92-1.87 (m, 1H), 1.03 (s, 9H). LC-MS: m/z 431.2 (M+1)$^+$.

Step-j: Synthesis of (2S,4R)-1-((S)-2-(2-(2-azidoethoxy)acetamido)-3,3-dimethylbutanoyl)-4-hydroxy-N-(4-(4-methylthiazol-5-yl)benzyl)pyrrolidine-2-carboxamide (24j)

The title compound was synthesized using the same procedure which was followed for Intermediate-21 $b_1$-21 $b_7$ using (2S,4R)-1-((S)-2-amino-3,3-dimethylbutanoyl)-4-hydroxy-N-(4-(4-methylthiazol-5-yl)benzyl)pyrrolidine-2-carboxamide hydrochloride and 2-(2-azidoethoxy)acetic acid as starting materials. (Yield: 33%) $^1$H NMR (400 MHz, DMSO-$d_6$): δ 8.98 (s, 1H), 8.59 (m, 1H), 7.44-7.37 (m, 5H), 5.13 (d, J=3.9 Hz, 1H), 4.57 (d, J=9.8 Hz, 1H), 4.46-4.35 (m, 3H), 4.38-4.24 (m, 2H), 4.02 (d, J=3.4 Hz, 2H), 3.69-3.66 (m, 4H), 3.49-3.47 (m, 2H), 2.44 (s, 3H), 1.92-1.87 (m, 1H), 0.92 (s, 9H); LC-MS: m/z 558.2 (M+1)$^+$.

Step-k: Synthesis of (2S,4R)-1-((S)-2-(2-(2-aminoethoxy)acetamido)-3,3-dimethylbutanoyl)-4-hydroxy-N-(4-(4-methylthiazol-5-yl)benzyl)pyrrolidine-2-carboxamide (24k)

To a stirred solution of (2S,4R)-1-((S)-2-(2-(2-azidoethoxy)acetamido)-3,3-dimethylbutanoyl)-4-hydroxy-N-(4-(4-methylthiazol-5-yl)benzyl)pyrrolidine-2-carboxamide (24j), 2.3 g, 33.00 mmol) in ethyl acetate (30 mL) was added 10% Pd/C (2.0 g). Reaction was performed under hydrogen atmosphere (50 psi) at RT for 16 h. After completion of the reaction (monitored by TLC) the reaction mixture was filtered though celite and the filtrate was concentrated to afford title compound (1.20 g, 52%). $^1$H NMR (400 MHz, DMSO-$d_6$): δ 8.98 (s, 1H), 8.57 (t, J=5.9 Hz, 1H), 7.72 (d, J=9.3 Hz, 1H), 7.40 (s, 4H), 5.25 (bs, 1H), 4.59 (d, J=9.3 Hz, 1H), 4.45-4.35 (m, 3H), 4.27-4.22 (m, 1H), 4.02-3.92 (m, 2H), 3.68-3.59 (m, 3H), 3.49-3.46 (m, 3H), 2.78 (t, J=5.4 Hz, 1H), 2.44 (s, 3H), 3.08-3.03 (m, 1H), 1.93-1.87 (m, 2H), 0.95 (s, 9H), LC-MS: m/z 532.2 (M+1)$^+$.

Intermediate-25:

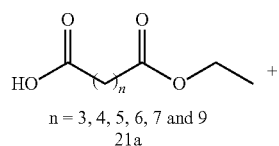

n = 3, 4, 5, 6, 7 and 9
21a

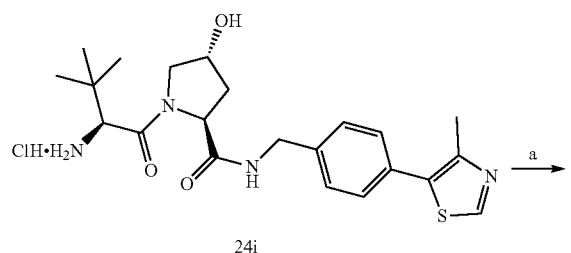

24i

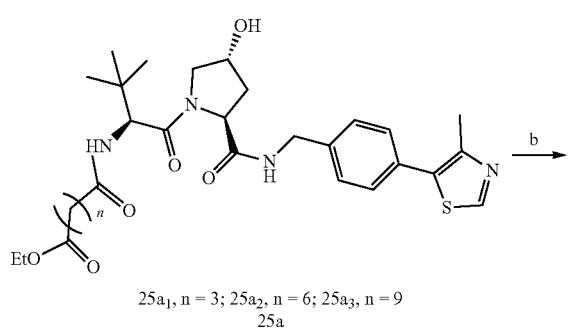

25a₁, n = 3; 25a₂, n = 6; 25a₃, n = 9
25a

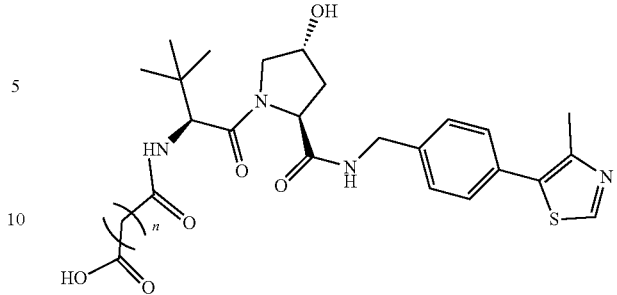

25b₁, n = 3; 25b₂, n = 6; 25b₃, n = 9
25b

Conditions: a) HATU, DIPEA, DMF, 0° C. - RT, 16 h; b) LiOH·H₂O, THF:H₂O, 0° C. - RT, 16 h.

Step-a: Synthesis of Compound (25a₁-25a₃)

The title compounds were synthesized using the same procedure which was followed for Intermediate-21b₁-21b₇ using compounds 21a 1-21a 7 and (2S,4R)-1-((S)-2-amino-3,3-dimethylbutanoyl)-4-hydroxy-N-(4-(4-methylthiazol-5-yl)benzyl)pyrrolidine-2-carboxamide hydrochloride as starting materials. (Yield: 30-40%).

TABLE 8

| Structure | Characterization Data |
|---|---|
| 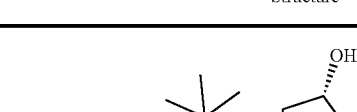<br>25a₁ | LC-MS: m/z 573.3 (M + 1)⁺ |

US 12,371,426 B2
151	152
TABLE 8-continued
| Structure | Characterization Data |
|---|---|
| 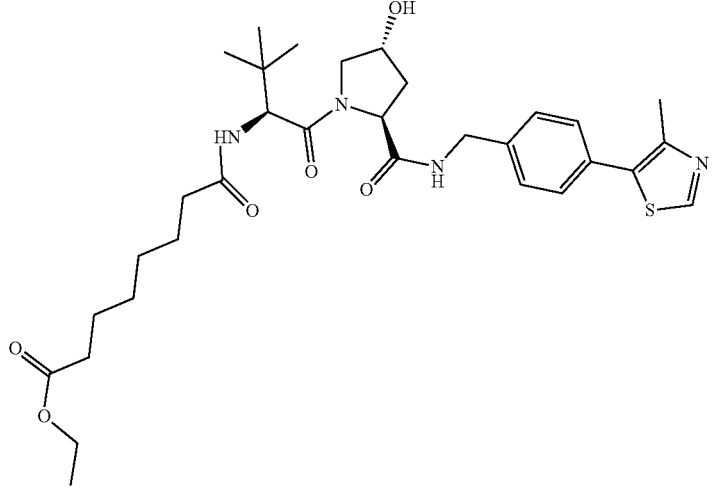 25a₂ | LC-MS: m/z 615.3 (M + 1)⁺ |
| 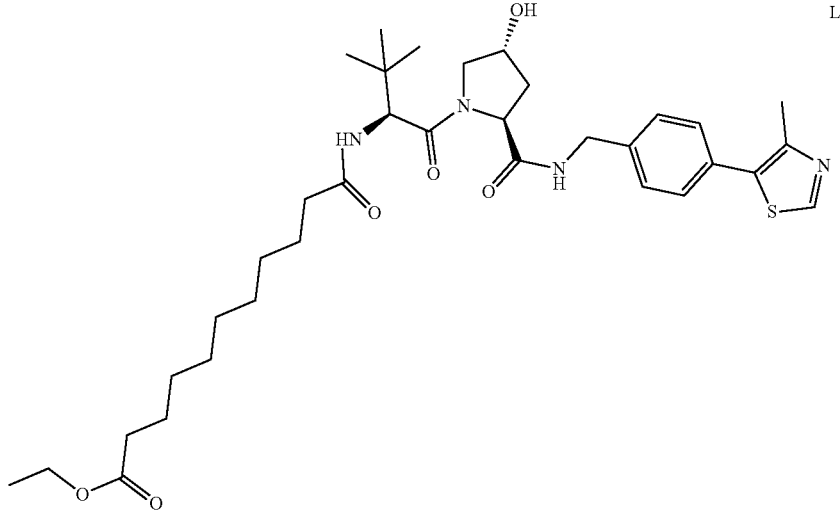 25a₃ | LC-MS: m/z 657.4 (M + 1)⁺ |

Step-b: Synthesis of Compound (25b$_1$-25b$_3$1

The title compound was synthesized using the same procedure which was followed for 21c$_1$-21c$_7$ using compound (25a$_1$-25a$_3$) as starting material. (Yield: 90-95%).

TABLE 9

| Structure | Characterization Data<br>$^1$H NMR (400 MHz, DMSO-d$_6$) |
| --- | --- |
| 25b$_1$ | δ 8.9 (s, 1H), 8.56 (d, J = 5.3 Hz, 1H), 7.95-7.88 (m, 1H), 7.40 (q, J = 8.3 Hz, 4H), 4.51 (bs, 1H), 4.92-4.41 (m, 2H), 4.38 (bs, 1H), 4.25-4.21 (m, 1H), 3.65 (d, J = 2.3 Hz, 2H), 3.42-3.30 (m, 1H), 3.27-3.25 (m, 1H), 2.44 (s, 3H), 2.19-2.10 (m, 2H), 2.05-1.86 (m, 4H), 1.67-1.63 (m, 2H), 0.93 (s, 9H); LC-MS: m/z 545.2 (M + 1)$^+$. |
| 25b$_2$ | δ 12.0 (bs, 1H), 8.98 (s, 1H), 8.56 (t, J = 5.3 Hz, 1H), 7.83 (d, J = 9.3 Hz, 1H), 7.40 (q, J = 8.3 Hz, 4H), 4.54 (d, J = 9.3 Hz, 1H), 4.45-4.40 (m, 2H), 4.35 (bs, 1H), 4.25-4.19 (m, 1H), 3.69-3.62 (m, 2H), 2.44 (s, 6H), 2.44-2.20 (m, 3H), 1.93-1.90 (m, 1H), 1.47 (t, J = 6.3 Hz, 4H), 1.25-1.23 (m, 4H), 0.93 (s, 9H). LC-MS: m/z 585.3 (M − 1). |
| 25b$_3$ | δ 8.99 (s, 1H), 8.54 (t, J = 6.0 Hz, 1H), 7.82 (d, J = 9.2 Hz, 1H), 7.40 (q, J = 8.3 Hz, 4H), 4.54 (d, J = 9.2 Hz, 1H), 4.46-4.40 (m, 2H), 4.35 (s, 1H), 4.24-4.19 (m, 1H), 3.66-3.65 (m, 2H), 2.45 (s, 3H), 2.27-2.22 (m, 1H), 2.18-2.13 (m, 2H), 2.12-2.03 (m, 2H), 1.95-1.89 (m, 1H), 1.5-1.45 (m, 4H), 1.30-1.20 (m, 12H), 0.91 (s, 9H). LC-MS: m/z 627.4 (M − 1). |

Intermediate-26:

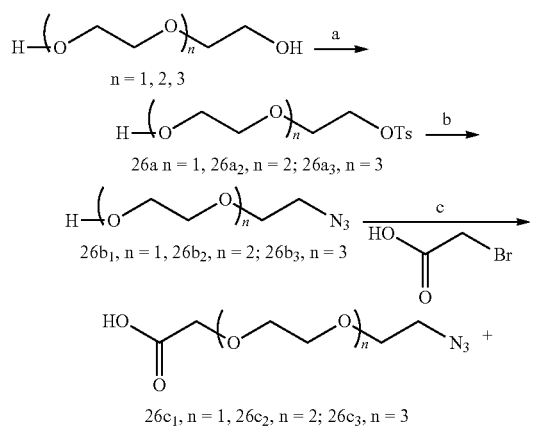

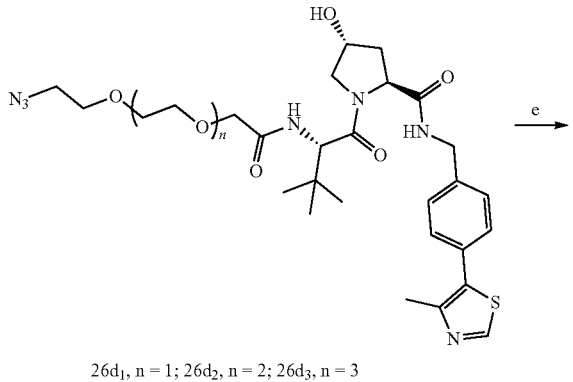

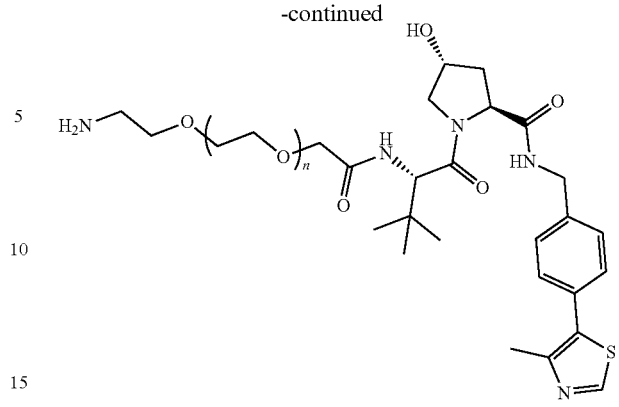

26e₁, n = 1; 26e₂, n = 2; 26e₃, n = 3

Conditions: a) TsCl, Et₃N, DCM, 0° C. - RT, 20 h; b) NaN₃, DMF, 60° C., 5 h; c) NaI, NaH, THF, 0° C., 4 h; d) HATU, DIPEA, DMF, 0° C. - RT, 2 h; e) 10% Pd/C, H₂ atm (50 psi), EtOAc, RT - 16 h.

Step-a: General Procedure for Tosylation of Alcohols (26a₁-26a₃)

To a stirred solution of substituted ethylene glycol (1.0 eq.) and triethylamine (0.1 eq.) in DCM (500 mL) was added tosyl chloride (0.1 eq.) in DCM (10 vol.) dropwise at 0° C. for 2 h under nitrogen atmosphere. Stirring was continued at RT for 20 h and then the reaction mixture was washed with saturated NH₄Cl solution, water, brine dried over anhydrous sodium sulphate and concentrated under vacuum to give the residue which was purified by combi flash using 10-15% ethyl acetate in n-hexane as eluent to afford title compounds (26a₁-26a₃, yield: 45-50%).

TABLE 10

| Structure | Characterization Data |
| --- | --- |
| 26a₁ HO~O~OTs | LC-MS: m/z 261.2 (M + 1)⁺ |
| 26a₂ HO~O~O~OTs | LC-MS: m/z 305.0 (M + 1)⁺ |
| 26a₃ HO~O~O~O~OTs | $^1$H NMR (400 MHz, DMSO-$d_6$): δ 7.78 (d, J = 8.3 Hz, 2H), 7.48 (d, J = 8.3 Hz, 2H), 4.55 (t, J = 5.4 Hz 1H), 4.11 (t, J = 3.9 Hz, 2H), 3.59 (t, J = 3.9 Hz, 2H), 3.51-3.39 (m, 12H), 2.41 (s, 3H). |

Step-b: General Procedure for Azide Formation $26b_1$-$26b_3$1

To a stirred solution of compound ($26a_1$-$26a_3$, 1.0 eq.) in DMF (5 vol.) was added sodium azide (1.5 eq.) at RT. Stirring was continued at 60° C. for 5 h. After completion of the reaction (monitored by TLC), the reaction mixture was poured into water and extracted with ethyl acetate. Organic layer was washed water, brine, dried over anhydrous sodium sulphate and concentrated under vacuum to afford title compound ($26b_1$-$26b_3$, yield: 40-50%).

TABLE 11

| Structure | Characterization Data |
|---|---|
| 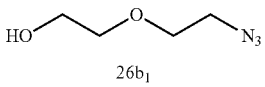 $26b_1$ | $^1$H NMR (400 MHz, DMSO-$d_6$): δ 4.60 (t, J = 4.9 Hz, 2H), 3.6 (t, J = 4.9 Hz, 2H), 3.60 (t, J = 4.9 Hz 1H), 3.47-3.40 (m, 2H), 3.39 (t, J = 5.4 Hz, 2H). |
| 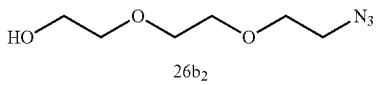 [SMILES: [N-]=[N+]=NCCOCCOCCO] $26b_2$ | $^1$H NMR (400 MHz, DMSO-$d_6$): δ 4.55 (t, J = 2.5 Hz, 1H), 3.72-3.68 (m, 2H), 3.67-3.52 (m, 4H), 3.51 (t, J = 1.5 Hz, 2H), 3.49-3.44 (m, 4H). |
| 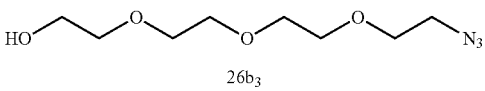 [SMILES: [N-]=[N+]=NCCOCCOCCOCCO] $26b_3$ | LC-MS: m/z 220.0 (M + 1)$^+$. |

Step-c: General Procedure for Synthesis of Compound ($26c_1$-$26c_3$)

The title compounds were synthesized using the same procedure which was followed for Intermediate-24b using compound ($26b_1$-$26b_3$) and 2-bromoacetic acid (Yield: 65-75%).

TABLE-12

| Structure | Characterization Data |
|---|---|
| 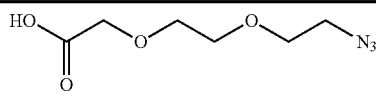 $26c_1$ | LC-MS: m/z 188.1 (M − 1) |
| 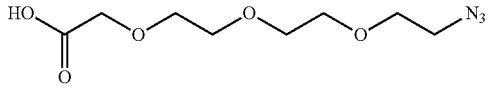 $26c_2$ | LC-MS: m/z 232.2 (M − 1) |
| 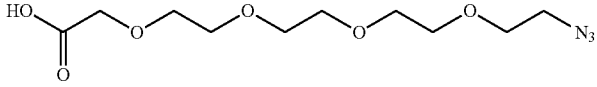 $26c_3$ | LC-MS: m/z 276.1 (M − 1) |

Step-d: Synthesis of Compound ($26d_1$-$26d_3$)

The title compounds were synthesized using the same procedure which was followed for Intermediate-24j using (2S,4R)-1-((S)-2-amino-3,3-dimethylbutanoyl)-4-hydroxy-N-(4-(4-methylthiazol-5-yl)benzyl)pyrrolidine-2-carboxamide hydrochloride and compound ($26c_1$-$26C_3$) as starting materials. (Yield: 30-40%)

TABLE-13
| Structure | Characterization Data |
|---|---|
| 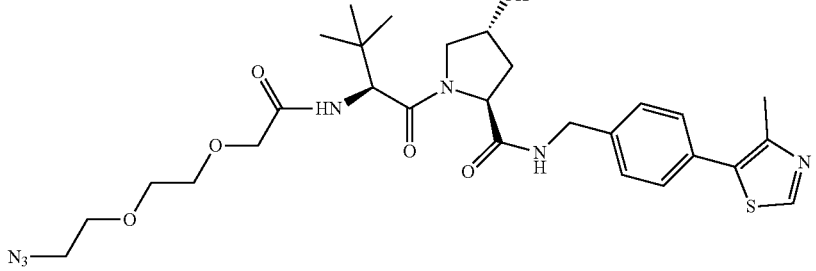<br>26d$_1$ | LC-MS: m/z 602.2 (M + 1)$^+$. |
| 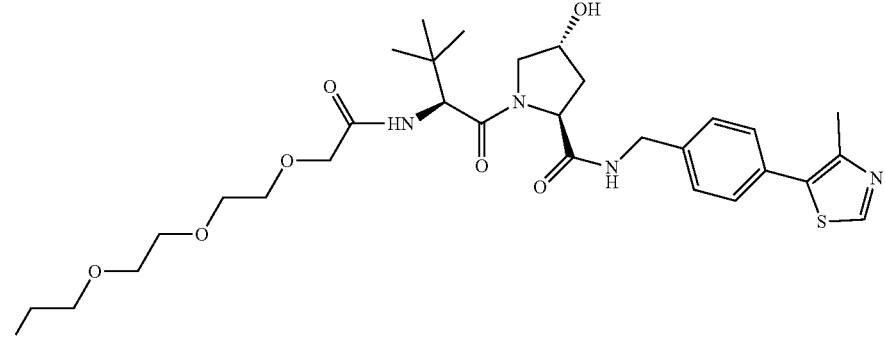<br>26d$_2$ | LC-MS: m/z 646.3 (M + 1)$^+$. |
| 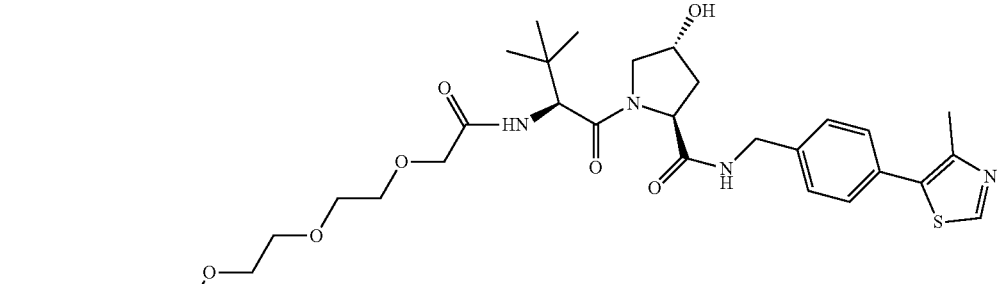<br>26d$_3$ | LC-MS: m/z 690.3 (M + 1)$^+$. |
Step-e: Synthesis of Compound (26e$_1$-26e$_3$)
The title compounds were synthesized using the same procedure which was followed for Intermediate-24k using compound (26d$_1$-26d$_3$) as starting materials. (Yield: 60-65%).

TABLE-14

| Structure | Characterization Data<br>¹H NMR (400 MHz, DMSO-d₆) |
|---|---|
| 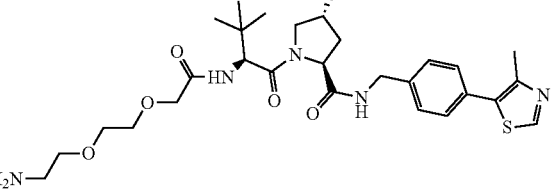<br>26e₁ | δ 8.98 (s, 1H), 8.62-8.50 (m, 1H), 7.43-7.40 (m, 5H), 4.57 (d, J = 9.8 Hz, 1H), 4.46-4.35 (m, 3H), 4.27-4.22 (m, 1H), 3.97-3.92 (m, 2H), 3.68-3.57 (m, 6H), 3.45-3.39 (m, 6H), 2.69-2.64 (m, 2H), 2.45 (s, 3H), 2.08-2.03 (m, 1H), 1.93-1.81 (m, 1H), 0.9 (s, 9H). |
| 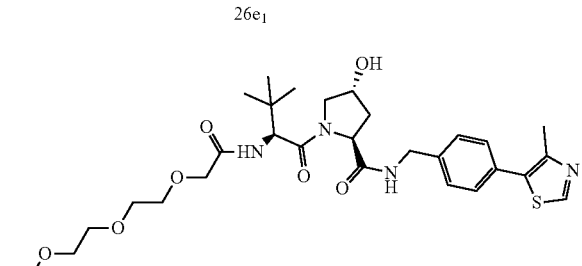<br>26e₂ | δ 8.98 (s, 1H), 8.62-8.59 (m, 1H), 7.43-7.37 (m, 5H), 4.55 (d, J = 9.2 Hz, 1H), 4.46-4.38 (m, 1H), 4.37-4.35 (m, 1H), 4.27-4.22 (m, 1H), 3.96 (s, 2H), 3.70-3.65 (m, 1H), 3.66-3.53 (m, 9H), 3.37-3.33 (m, 6H), 3.31-3.16 (m, 1H), 2.66-2.60 (m, 2H), 2.45 (s, 3H), 2.08-1.98 (m, 1H), 1.93-1.89 (m, 1H), 0.92 (s, 9H).<br>LC-MS: m/z 620.3 (M + 1)⁺. |
| 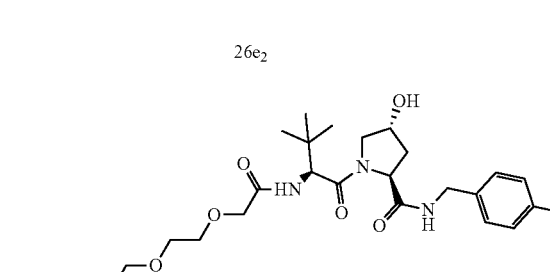<br>26e₃ | ¹H NMR (400 MHz, MeOH-d₄) δ 9.53 (s, 1H), 7.52-7.43 (m, 4H), 4.65-4.63 (m, 1H), 4.57-4.50 (m, 4H), 4.42-4.38 (m, 1H), 4.10 (s, 2H), 3.92-3.84 (m, 1H), 3.81-3.80 (m, 1H), 3.73-3.61 (m, 13H), 3.20 (t, J = 4.8 Hz, 2H), 2.54 (s, 3H), 2.29-2.20 (m, 1H), 2.13-2.06 (m, 1H), 1.09 (s, 9H).<br>LC-MS: m/z 664.3 (M + 1)⁺. |

Intermediate-27:

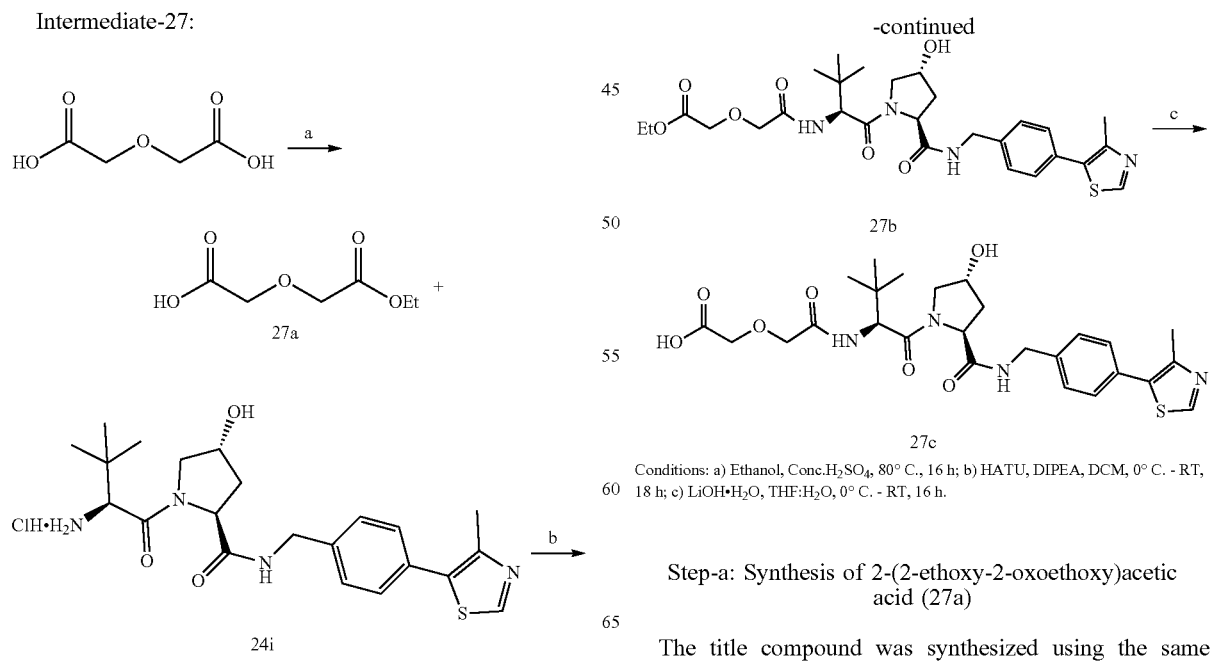

Conditions: a) Ethanol, Conc.H₂SO₄, 80° C., 16 h; b) HATU, DIPEA, DCM, 0° C. - RT, 18 h; c) LiOH•H₂O, THF:H₂O, 0° C. - RT, 16 h.

Step-a: Synthesis of 2-(2-ethoxy-2-oxoethoxy)acetic acid (27a)

The title compound was synthesized using the same procedure which was followed for Intermediate-21a₁-21a₇ using 2,2'-oxydiacetic acid as starting material. (Yield: 30%) ¹H NMR (400 MHz, DMSO-d₆): δ 4.16 (s, 2H), 4.12-4.10 (m, 2H), 3.92 (s, 2H), 1.19 (t, J=8.4 Hz, 3H).

Step-b: Synthesis of ethyl 2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetate (27b)

The title compound was synthesized using the same procedure which was followed for 24f using 2-(2-ethoxy-2-oxoethoxy)acetic acid and (2S,4R)-1-((S)-2-amino-3,3-dimethyl butanoyl)-4-hydroxy-N-(4-(4-methylthiazol-5-yl)benzyl)pyrrolidine-2-carboxamide hydrochloride as starting materials. (Yield: 66%) ¹H NMR (400 MHz, DMSO-d₆): δ 8.98 (s, 1H), 8.58 (t, J=6 Hz, 1H), 7.54 (d, J=9.6 Hz, 1H) 7.46-7.35 (m, 4H), 5.12 (d, J=3.6 Hz, 1H), 4.58-4.53 (m, 1H), 4.56-4.35 (m, 3H), 4.29-4.19 (m, 3H), 4.16-4.09 (m, 2H), 4.04-4.00 (m, 2H), 3.68-3.59 (m, 2H), 2.39 (s, 3H), 2.11-2.03 (m, 1H), 1.93-1.88 (m, 1H), 1.33-1.14 (m, 3H), 0.93-0.83 (m, 9H); LC-MS: 575.3 (M+1)⁺.

Step-c: Synthesis of 2-(2-(((S)-1-((2S,4R)-4-hydroxy-2-((4-(4-methylthiazol-5-yl)benzyl) carbamoyl)pyrrolidin-1-yl)-3,3-dimethyl-1-oxobutan-2-yl)amino)-2-oxoethoxy)acetic acid (27c)

The title compound was synthesized using the same procedure which was followed for 3d using ethyl 2-(2-(((S)-1-((2S,4R)-4-hydroxy-2-((4-(4-methylthiazol-5-yl)benzyl)carbamoyl) pyrrolidin-1-yl)-3,3-dimethyl-1-oxobutan-2-yl)amino)-2-oxoethoxy)acetate using as starting material. (Yield: 49.3%) ¹H NMR (400 MHz, DMSO-d₆): δ 8.97 (s, 1H), 8.92 (d, J=9.3 Hz, 1H), 8.54 (t, J=7.3 Hz, 1H), 7.45-7.40 (m, 4H), 4.48-4.40 (m, 2H), 4.38-4.35 (m, 2H), 4.28-4.23 (m, 1H), 4.09 (bs, 1H), 3.91 (s, 2H), 3.68-3.64 (m, 4H), 2.44 (s, 3H), 2.08-2.01 (m, 1H), 1.93-1.87 (m, 1H), 0.96 (s, 9H). LC-MS: m/z 547.2 (M+1)⁺.

Intermediate-28:

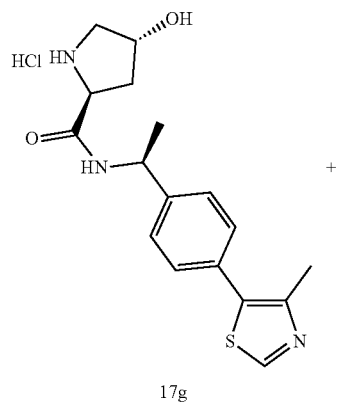

17g

+

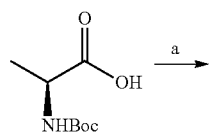

a →

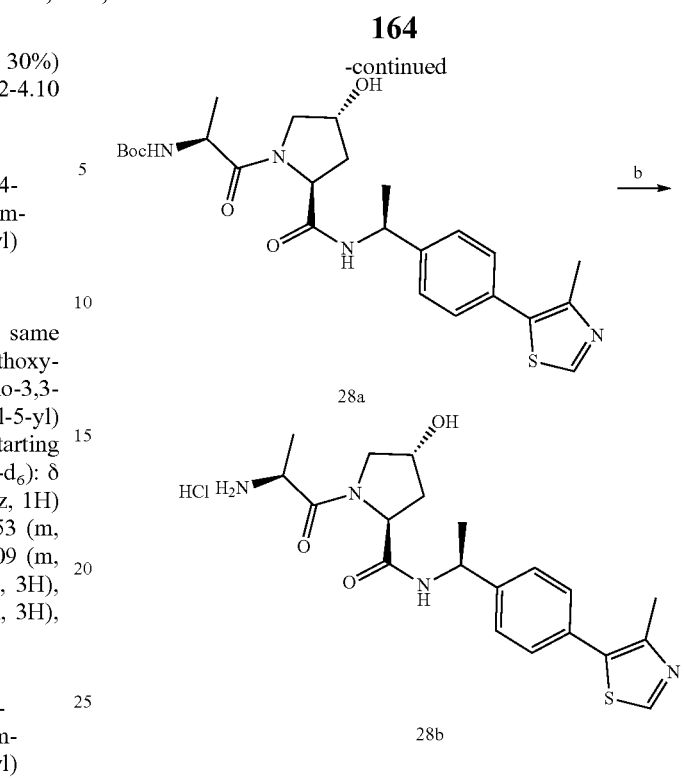

Conditions: a) HATU, DIPEA, DMF, RT - 16 h; b) 4M HCl in Dioxane, DCM, 0° C. - RT - 16 h.

Step-a: Synthesis of tert-butyl ((S)-1-((2S,4R)-4-hydroxy-2-(((S)-1-(4-(4-methylthiazol-5-yl)phenyl)ethyl)carbamoyl)pyrrolidin-1-yl)-1-oxopropan-2-yl)carbamate (28a)

The title compound was synthesized by using the same procedure which was followed for 21 b₁-21 b₇ using (2S,4R)-4-hydroxy-N—((S)-1-(4-(4-methylthiazol-5-yl)phenyl)ethyl) pyrrolidine-2-carboxamide (Yield: 51.2%) ¹H NMR (400 MHz, DMSO-d₆): δ 8.98 (s, 1H), 8.27 (d, J=8.0 Hz, 1H), 7.43 (d, J=8.4 Hz, 2H), 7.36 (d, J=8.0 Hz, 2H), 6.92 (d, J=7.2 Hz, 1H), 5.20-5.09 (m, 1H), 4.99-4.90 (m, 1H), 4.41-4.38 (m, 1H), 4.31 (bs, 1H), 4.23-4.21 (m, 1H), 4.19-4.15 (M, 1H) 3.75-3.49 (m, 2H), 3.17 (d, J=4.8 Hz, 2H), 1.80-1.76 (m, 1H), 1.45 (s, 12H), 1.37-1.36 (m, 1H), 1.14 (d, J=6.8 Hz, 3H); LC-MS: m/z 503.2 (M+1)⁺.

Step-b: Synthesis of ((2S,4R)-1-(L-alanyl)-4-hydroxy-N—((S)-1-(4-(4-methylthiazol-5-yl)phenyl)ethyl)pyrrolidine-2-carboxamide hydrochloride (28b)

The title compound was synthesized by using the same procedure which was followed for 17g using tert-butyl ((S)-1-((2S,4R)-4-hydroxy-2-(((S)-1-(4-(4-methylthiazol-5-yl)phenyl)ethyl)carbamoyl)pyrrolidin-1-yl)-1-oxopropan-2-yl)carbamate. (Yield: 90%) ¹H NMR (400 MHz, CD₃OD): δ 10.01 (s, 1H), 7.57-7.50 (m, 4H), 5.03-4.98 (m, 1H), 4.63 (t, J=8.4 Hz, 1H), 4.48 (bs, 1H), 4.29-4.25 (m, 1H), 3.64 (s, 3H), 2.61 (s, 3H), 2.30-2.25 (m, 1H), 1.93-1.88 (m, 1H), 1.56 (s, 3H), 1.51-1.50 (m, 2H); LC-MS: m/z 403.2 (M+1)⁺.

Intermediate-29:

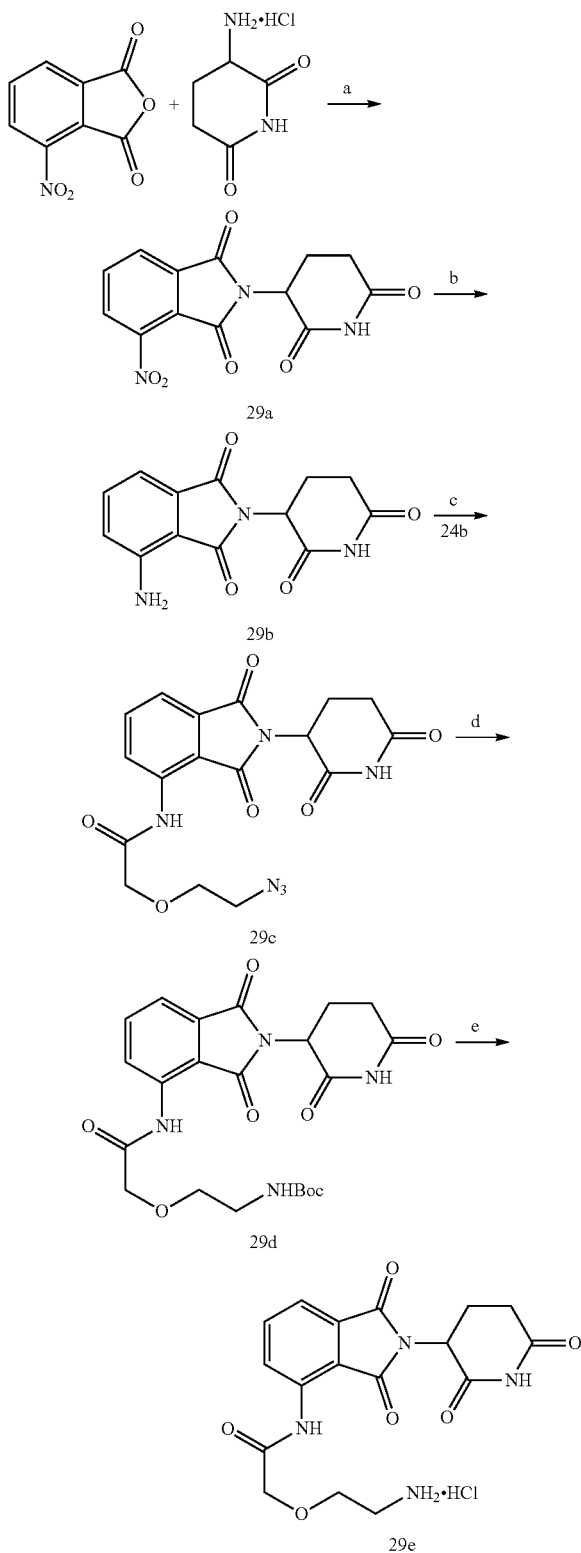

Conditions: a) KOAc, AcOH, 90° C., 16 h; b) 10% Pd/C, DMF:H₂O (9:1), H₂ (60 psi), RT, 18 h; c) i) (COCl)₂, DMF, DCM, 0° C. - RT, 3 h, ii) DIPEA, THF, 90° C., 16 h; d) 20% Pd(OH)₂, Et₃N, (Boc)₂O, 1,4-dioxane, H₂ (50 psi), RT, 16 h; e) 4M HCl in 1,4-Dioxane, 1,4-Dioxane, 0° C. - RT, 3 h.

Step-a: Synthesis of 2-(2,6-dioxopiperidin-3-yl)-4-nitroisoindoline-1,3-dione (29a)

To a stirred solution of 4-nitroisobenzofuran-1,3-dione (50.0 g, 259.0 mmol) and 3-aminopiperidine-2,6-dione hydrochloride (46.7 g, 284.09 mmol) in AcOH (400 mL) was added KOAc (78.60 g, 802.9 mmol) at RT and stirred for 16 h at 90° C. under nitrogen atmosphere. After completion of the reaction (monitored by TLC) acetic acid was removed under reduced pressure and the residue was washed with methanol to afford the title compound (78.0 g, 99.5%) which was utilized in the next step without further purification. $^1$H NMR (400 MHz, DMSO-$d_6$): δ 11.13 (bs, 1H), 8.35 (d, J=8.0 Hz, 1H), 8.24 (d, J=6.8 Hz, 1H), 8.12 (t, J=8.0 Hz, 1H), 5.23 (dd, $J_1$=6.0, $J_2$=12.8 Hz, 1H), 2.93-2.84 (m, 1H), 2.66-2.58 (m, 2H), 2.09-2.07 (m, 1H).

Step-b: Synthesis of 4-amino-2-(2,6-dioxopiperidin-3-yl)isoindoline-1,3-dione (29b)

To a stirred solution of 2-(2,6-dioxopiperidin-3-yl)-4-nitroisoindoline-1,3-dione (29a, 10.0 g, 33.00 mmol) in DMF:H₂O (9:1, 75 mL) was added 10% Pd/C (2.0 g). The reaction was performed in par shaker at 60 psi under hydrogen atmosphere at RT for 18 h. After completion of the reaction (monitored by TLC) the reaction mixture was filtered though celite. Then cold water was added to the filtrate to get the solid which was filtered off and dried under vacuum to afford the title compound (5.50 g, 61.1%) which was used in the next step without further purification. $^1$H NMR (400 MHz, DMSO-$d_6$): δ 11.07 (bs, 1H), 7.46 (t, J=6.8 Hz, 1H), 7.00 (t, J=8.0 Hz, 2H), 6.51 (bs, 2H), 5.06-5.01 (m, 1H), 2.89-2.84 (m, 1H), 2.60-2.54 (m, 2H), 2.03-2.0 (m, 1H); LC-MS: m/z 274.1 (M+1)$^+$.

Step-c: Synthesis of 2-(2-azidoethoxy)-N-(2-(2,6-dioxopiperidin-3-yl)-1,3-dioxoisoindolin-4-yl) acetamide (29c)

To a stirred solution of 2-(2-azidoethoxy)acetic acid (24b, 5.50 g, 37.93 mmol) in DCM (100 mL) was added oxalyl chloride (4.33 mL, 50.5 mmol) and DMF (0.08 mL) at 0° C. and stirring was continued at RT for 3 h. The reaction mixture was concentrated under reduced pressure and the residue was added to 4-amino-2-(2,6-dioxopiperidin-3-yl) isoindoline-1,3-dione (29b, 6.89 g, 25.20 mmol) in THF (100 mL) followed by the addition of DIPEA (13.17 mL, 75.60 mmol). The reaction mixture was stirred for 16 h at 90° C. After completion of the reaction (monitored by TLC) the reaction mixture was quenched with water (100 mL) and extracted with EtOAc (2×500 mL). The combined organic layer was washed with water (200 mL), brine (200 mL), dried over anhydrous sodium sulphate and concentrated under reduced pressure to give the crude product which was purified by combi flash using 4% MeOH in DCM as eluent to afford title compound (1.20 g, 12%). $^1$H NMR (400 MHz, DMSO-$d_6$): δ 11.13 (s, 1H), 10.34 (s, 1H), 8.71 (d, J=8.4 Hz, 1H), 7.87 (t, J=8.0 Hz, 1H), 7.63 (d, J=7.2 Hz, 1H), 5.17 (d, $J_1$=4.8, $J_2$=12.8 Hz, 1H), 4.25 (s, 2H), 3.82-3.80 (m, 2H), 3.59-3.57 (m, 2H), 2.90-2.87 (m, 1H), 2.63-2.52 (m, 2H), 2.09-2.07 (m, 1H).

Step-d: Synthesis of tert-butyl (2-(2-((2-(2,6-dioxopiperidin-3-yl)-1,3-dioxoisoindolin-4-yl)amino)-2-oxoethoxy)ethyl)carbamate (29d)

To a stirred solution of -(2-azidoethoxy)-N-(2-(2,6-dioxopiperidin-3-yl)-1,3-dioxoisoindolin-4-yl)acetamide (29c, 2.30 g, 5.75 mmol) in 1,4-dioxane (20 mL) was added (Boc)$_2$O (1.88 g, 8.62 mmol), triethyl amine (1.59 mL, 11.50 mmol) and 20% Pd(OH)$_2$ (0.23 g). Reaction was performed at RT at 50 psi under hydrogen atmosphere for 18 h. The reaction mixture was filtered though celite and the celite was washed with ethyl acetate (2×50 mL). The organic layer was washed with water (100 mL), brine (100 mL), dried over anhydrous sodium sulphate and concentrated under reduced pressure to give the residue which was purified by combi flash using 0.3% MeOH in DCM as eluent to afford the title compound (1.7 g, 62.5%). $^1$H NMR (400 MHz, DMSO-d$_6$): δ 11.14 (s, 1H), 10.33 (s, 1H), 8.70 (d, J=8.0 Hz, 1H), 7.87 (t, J=7.2 Hz, 1H), 7.63 (d, J=7.6 Hz, 1H), 6.83 (t, J=7.2 Hz, 2H), 5.18 (dd, J$_1$=5.6, J$_2$=13.2 Hz, 1H), 4.17 (s, 2H), 3.61 (t, J=5.6 Hz, 2H), 3.23 (q, J$_1$=6.0, J$_2$=5.6 Hz, 1H), 2.94-2.85 (m, 1H), 2.63-2.53 (m, 2H), 2.10-2.08 (m, 1H), 1.34 (s, 9H); LC-MS: m/z 473.2 (M−1).

Step-e: Synthesis of 2-(2-aminoethoxy)-N-(2-(2,6-dioxopiperidin-3-yl)-1,3-dioxoisoindolin-4-yl) acetamide hydrochloride (29e)

To a stirred solution of tert-butyl (2-(2-((2-(2,6-dioxopiperidin-3-yl)-1,3-dioxoisoindolin-4-yl)amino)-2-oxoethoxy)ethyl)carbamate (1.7 g, 3.58 mmol) in 1,4-dioxane (15.0 mL) was added 4 M HCl in 1,4-Dioxane (15.0 mL) at 0° C. under nitrogen atmosphere. The reaction mixture was stirred for 3 h at RT and then the solvent was evaporated under reduced pressure to get crude solid product. The solid was washed with diethyl ether (2×50 mL), filtered and dried under vacuum to afford title compound (1.4 g, 95%). $^1$H NMR (400 MHz, DMSO-d$_6$): δ 11.14 (s, 1H), 10.27 (s, 1H), 8.65 (d, J=8.4 Hz, 1H), 7.99 (bs, 3H) 7.89 (t, J=7.2 Hz, 2H), 5.18 (dd, J$_1$=5.6, J$_2$=13.2 Hz, 1H), 4.24 (q, J=3.2 Hz, 1H), 3.83 (t, J=5.2 Hz, 2H), 3.12-3.11 (m, 2H), 2.91-2.86 (m, 1H), 2.65-2.55 (m, 2H), 2.10-2.05 (m, 2H); LC-MS: m/z 375.0 (M+1)$^+$.

Intermediate-30:

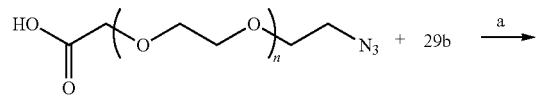 + 29b →ᵃ

26c$_1$, n = 1; 26c$_2$, n = 2; 26c$_3$, n = 3

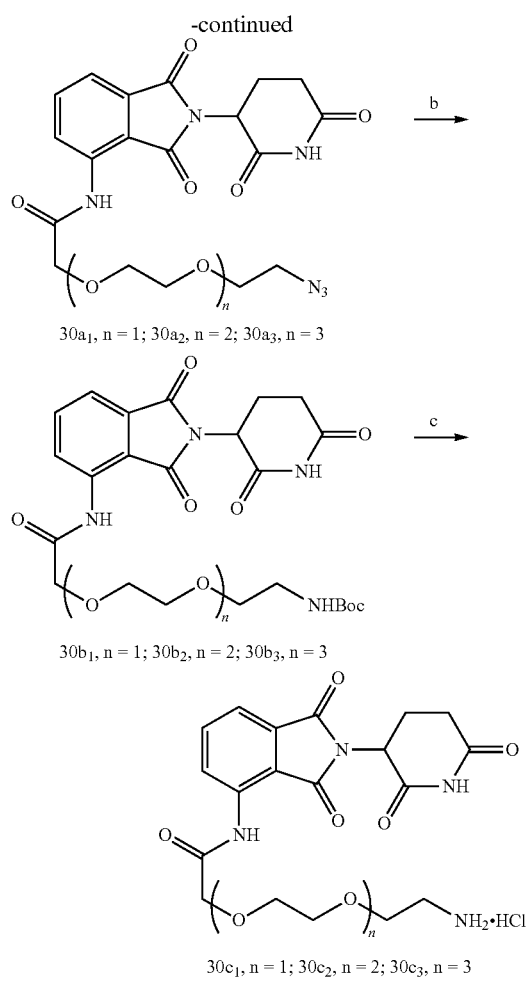

30a$_1$, n = 1; 30a$_2$, n = 2; 30a$_3$, n = 3

30b$_1$, n = 1; 30b$_2$, n = 2; 30b$_3$, n = 3

30c$_1$, n = 1; 30c$_2$, n = 2; 30c$_3$, n = 3

Conditions: a) COCl)$_2$, DMF, DCM, 0° C.-RT, 3 h
ii) DIPEA, THF 90° C., 16 h; b) 20% Pd(OH)$_2$,
Et$_3$N, (Boc)$_2$O, 1,4-dioxane, H$_2$ (50 psi), 16 h;
c) 4M HCl in 1,4-Dioxane, 1,4-Dioxane, 0° C.-RT, 1 h.

Step-a: General procedure for Synthesis of compound (30a$_1$-30a$_3$)

The title compounds were synthesized using the same procedure which was followed for Intermediate-29c using Intermediate-26c$_1$-26c$_3$ and 4-amino-2-(2,6-dioxopiperidin-3-yl)isoindoline-1,3-dione. (Yield: 90-95%).

TABLE-15

| Structure | Characterization Data |
|---|---|
| 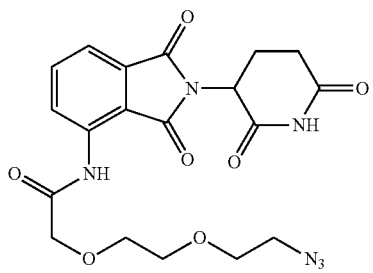<br>30a$_1$ | LC-MS: m/z 445.1 (M + 1)$^+$ |

TABLE-15-continued

| Structure | Characterization Data |
|---|---|
| 30a₂ | LC-MS: m/z 489.1 (M + 1)⁺ |
| 30a₃ | LC-MS: m/z 533.2 (M + 1)⁺ |

Step-e: General procedure for Synthesis of compound (30b₁-30b₃)

The title compounds were synthesized using the same procedure which was followed for Intermediate-29d using 30a₁-30a₃. (Yield: 65-70%).

TABLE-16

| Structure | Characterization Data |
|---|---|
| 30b₁ | LC-MS: m/z 517.3 (M − 1) |
| 30b₂ | LC-MS: m/z 561.3 (M − 1) |

TABLE-16-continued

| Structure | Characterization Data |
|---|---|
| 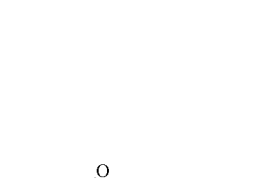 30b₃ | LC-MS: m/z 605.3 (M − 1) |

Step-f: General Procedure for Synthesis of Compound (30c₁-30c₃)h

The title compounds were synthesized using the same procedure which was followed for Intermediate-29e using 30b₁-30b₃. (Yield: 85-90%).

TABLE-17

| Structure | Characterization Data |
|---|---|
|  30c₁ | $^1$H NMR (400 MHz, DMSO-$d_6$): δ 11.15 (s, 1H), 10.34 (s, 1H), 8.73 (d, J = 8.4 Hz 1H), 7.95 (bs, 3H), 7.87 (t, J = 8.0 Hz 1H), 7.64 (d, J = 7.6 Hz 1H), 5.18-5.14 (dd, $J_1$ = 5.6 Hz, $J_2$ = 12.8 Hz 1H), 3.81-3.78 (m, 2H), 3.72-3.70 (m, 2H), 3.66-3.64 (t, J = 4.8 Hz, 2H), 3.44 (s, 1H), 2.98-2.91 (m, 3H), 2.67-2.53 (m, 2H), 2.10-2.06 (m, 2H); LC-MS: m/z 419.3 (M + 1)$^+$. |

TABLE-17-continued
| Structure | Characterization Data |
|---|---|
| 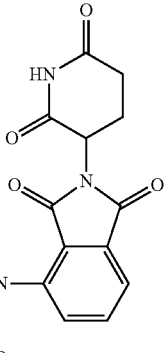 30c₂ | ¹H NMR (400 MHz, DMSO-d₆) δ 11.14 (S, 1H), 10.34 (S, 1H), 8.73-.71 (d, J = 8.8 Hz 1H), 7.89-7.85 (m, 1H), 7.79 (bs, 3H), 7.65-7.63 (d, J = 7.2 Hz, 1H), 5.15 (dd, J₁ = 5.2 Hz, J₂ = 12.4 Hz, 1H), 4.21 (s, 2H), 3.78-3.76 (m, 2H), 3.69-3.66 (m, 2H), 3.58-3.56 (m, 6H), 2.96-2.85 (m, 3H), 2.67-2.6 (m, 2H), 2.10-1.23 (m, 1H); LC-MS: 463.1 m/z (M + 1)⁺. |
| 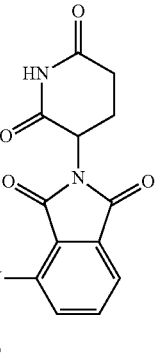 30c₃ | ¹H NMR (400 MHz, DMSO-d₆) δ 11.14 (s, 1H), 10.35 (s, 1H), 8.73-8.71 (d, J = 8.4 Hz 1H), 7.89-7.85 (m, 3H), 7.64 (d, J = 7.2 Hz, 2H), 5.15 (dd, J₁ = 5.6 Hz, J₂ = 13.2 Hz, 1H), 4.21 (s, 2H), 3.77-3.75 (m, 2H), 3.68-3.65 (m, 2H), 3.59-3.50 (m, 10H), 2.95 (t, J = 5.4 Hz, 2H), 2.91-2.85 (m, 1H), 2.67-2.55 (m, 2H), 2.10-2.06 (m, 1H); LC-MS: m/z 507.2 (M + 1)⁺. |
Intermediate-31:
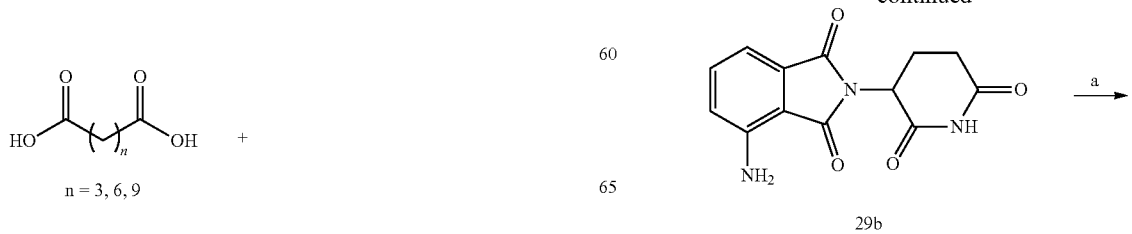

175
-continued

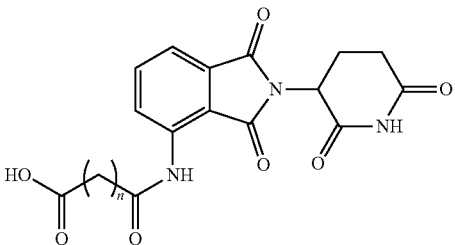

31a₁, n = 3; 31a₂, n = 6; 31a₃, n = 9

Conditions: a) i) (COCl)2, DMF, DCM, 0° C.- RT, 3 h;
ii) THF, 80° C., 2 h.

176

Step-a: General procedure for synthesis of compound ($31_{b1}$-$31_{b3}$)

To a stirred solution of dicarboxylic acids (3.0 eq.) in DCM (10 vol.) was added oxalyl chloride (6.5 eq.) and DMF (catalytic amount) at 0° C. Stirring was continued at RT for 3 h. The reaction mixture was concentrated under reduced pressure and the residue was added to 4-amino-2-(2,6-dioxopiperidin-3-yl)isoindoline-1,3-dione (5d, 1.0 eq.) in THF (5 vol.). The reaction mixture was stirred for 45 min at 80° C. After completion of the reaction (monitored by TLC) the reaction mixture was quenched with water and extracted with ethyl acetate. The combined organic layer was washed with water, brine, dried over anhydrous sodium sulphate and concentrated under vacuum to give the residue which was purified by combi flash using 7-9% MeOH in DCM as eluent to afford title compound (31a₁-31a₃, yield: 55-60%).

TABLE-18

| Structure | Characterization Data<br>¹H NMR (400 MHz, DMSO-d₆) |
|---|---|
| $31_{b1}$ | δ 12.08 (s, 1H), 11.13 (s, 1H), 9.72 (s, 1H), 8.44 (d, J = 8 Hz, 1H), 7.83 (t, J = 7.6 Hz, 1H), 7.61 (d, J = 7.6 Hz, 1H), 5.15 (dd, J₁ = 5.2 Hz, J₂ = 12.4 Hz, 1H), 2.89-2.85 (m, 1H), 2.63-2.50 (m, 4H), 2.31 (t, J = 7.2 Hz, 2H), 2.07-2.05 (m, 1H), 1.87-1.8 (m, 2H); LC-MS: m/z 386.4 (M − 1) |
| $31_{b2}$ | δ 11.98 (bs, 1H), 11.13 (s, 1H), 9.69 (s, 1H), 8.46 (d, J = 8.4 Hz, 1H), 7.82 (t, J = 7.6 Hz, 1H), 7.61 (d, J = 7.2 Hz, 1H), 5.14 (dd, J₁ = 5.2 Hz, J₂ = 12.4 Hz, 1H), 2.90-2.85 (m, 1H), 2.66-2.54 (m, 2H), 2.47-2.43 (m, 2H), 2.19 (t, J = 7.2 Hz, 2H), 2.08-2.05 (m, 2H), 1.63-1.58 (m, 1H), 1.49-1.48 (m, 2H), 1.35-1.25 (m, 4H). |
| $31_{b3}$ | δ 11.94 (s, 1H), 11.13 (s, 1H), 9.68 (s, 1H), 8.47 (d, J = 8 Hz, 1H), 7.8 (t, J = 7.2 Hz, 1H), 7.6 (d, J = 7.6 Hz, 1H), 5.14 (dd, J₁ = 6 Hz, J₂ = 12.8 Hz, 1H), 2.91-2.89 (m, 1H), 2.63-2.50 (m, 2H), 2.47 (t, J = 9.2 Hz, 2H), 2.18 (t, J = 7.2 Hz, 2H), 2.08-2.05 (m, 1H), 1.63-1.60 (m, 2H), 1.58-1.49 (m, 2H), 1.48-1.25 (m, 10H), LC-MS: m/z 472.2 (M + 1)⁺. |

Intermediate-32:

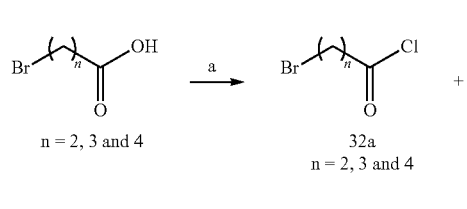

n = 2, 3 and 4      32a
                   n = 2, 3 and 4

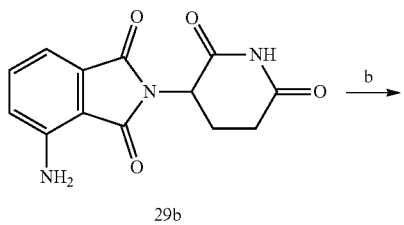

29b

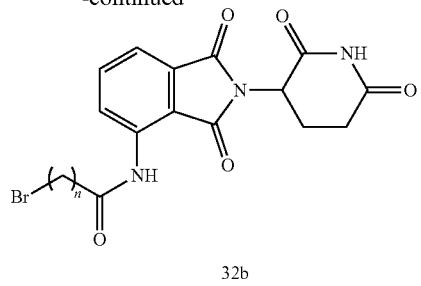

32b
n = 2, 3 and 4

Conditions: a) terminal halide mono acids, oxalyl chloride, cat.DMF, DCM, 0° C., RT, 16 h; b) 29b, THF, 65° C., 4 h.

Step-a: General Procedure for Synthesis of Compound ($32b_1$-$32b_3$)

To a stirred solution of terminal halide mono acids (1.0 eq.) in DCM (10 vol.) was added oxalyl chloride (2.0 eq.) and DMF (catalytic amount) at 0° C. Stirring was continued at RT for 16 h. The reaction mixture was concentrated under reduced pressure and the residue was added to 4-amino-2-(2,6-dioxopiperidin-3-yl)isoindoline-1,3-dione (29b, 1.0 eq.) in THF (10 vol.). The reaction mixture was stirred for 4h at 65° C. After completion of the reaction (monitored by TLC) the reaction mixture was quenched with water and extracted with ethyl acetate. The combined organic layer was washed with aq. NaHCO$_3$ solution, water, brine, dried over anhydrous sodium sulphate and concentrated under vacuum to give the residue which was purified by combi flash using 1-2% MeOH in DCM as eluent to afford title compound ($32a_1$-$32a_3$ yield: 7-89%).

TABLE-19

| Structure | Characterization Data |
|---|---|
| 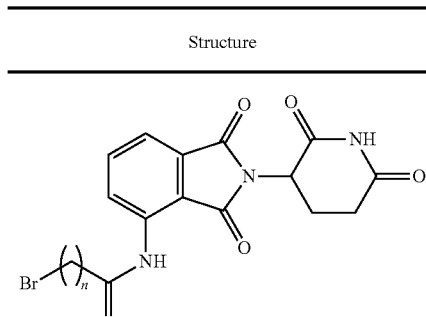<br>n = 2 | $^1$H NMR (400 MHz, DMSO-d$_6$): δ 11.14 (s, 1H), 9.88 (s, 1H), 8.43 (d, J = 8.4 Hz, 1H), 7.85 (t, J = 8.0 Hz, 1H), 7.64 (d, J = 7.2 Hz, 1H), 5.17 (dd, J = 5.6 Hz, J = 13.2 Hz, 1H), 3.73 (t, J = 6.4 Hz, 2H), 3.13 (t, J = 6.0 Hz, 2H), 2.89-2.88 (m, 1H), 2.63-2.58 (m, 1H), 2.55-2.52 (m, 1H), 2.09-2.05 (m, 1H); LC-MS: m/z 409.9 (M + 1)$^+$. (Yield: 7%) |
| 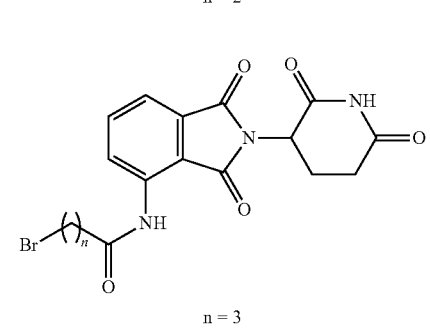<br>n = 3 | $^1$H NMR (400 MHz, DMSO-d$_6$): δ 11.63 (s, 1H), 9.82 (s, 1H), 8.39 (d, J = 8.0 Hz, 1H), 7.83 (t, J = 7.6 Hz, 1H), 7.63 (d, J = 7.2 Hz, 1H), 5.15 (dd, J = 6.2 Hz, J = 12.8 Hz, 1H), 3.66-3.54 (m, 3H), 2.94-2.89 (m, 1H), 2.70-2.60 (m, 1H), 2.45-2.44 (m, 2H), 2.16-2.01 (m, 3H); LC-MS: m/z 422.2 (M + 1)$^+$. (Yield: 13%) |

| Structure | Characterization Data |
|---|---|
| 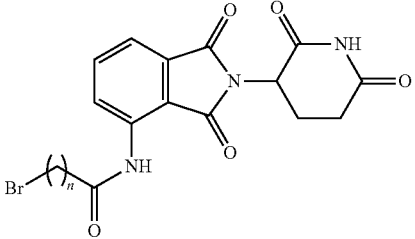 n = 4 | LC-MS: m/z 436.1 (M + 1)⁺.<br>(Yield: 89%) |

Intermediate-33:

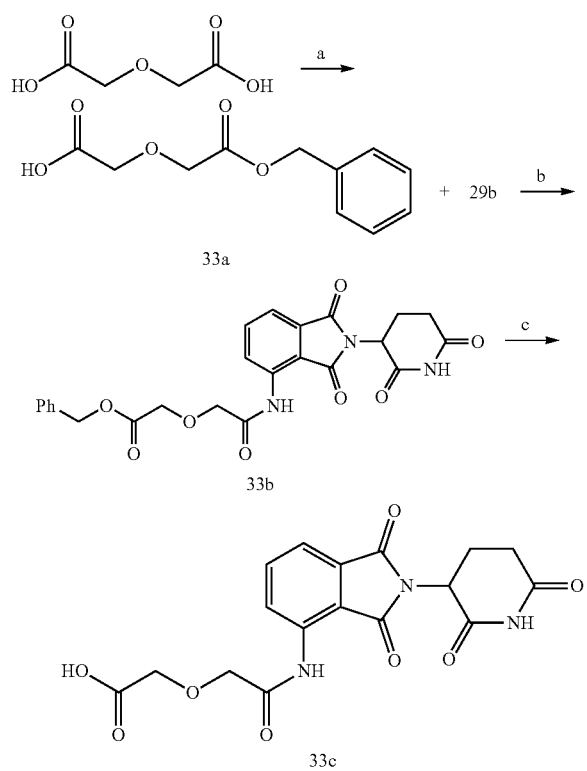

Conditions: a) BnBr, Et₃N, Acetone, RT, 16 h; b) HATU, DIPEA, DMF, 0° C.-RT, 16 h; c) 10% Pd/C, DMF, H₂ (60 psi), RT, 12 h.

Step-a: Synthesis of 2-(2-(benzyloxy)-2-oxoethoxy) acetic acid (33a)

To a stirred solution of 2,2'-oxydiacetic acid (1.0 eq.) and bezyl bromide (1.0 eq.) in acetone (5 vol.) was added triethyl amine (1.3 eq.). Stirring was continued at RT for 16 h. After completion of the reaction (monitored by TLC), the reaction mixture was filtered off and the filtrate was washed with ethyl acetate. The organic layer was concentrated under reduced pressure to get the residue which was dissolved in aqueous sodium bicarbonate solution. The resulting solution was washed with ethyl acetate. The aqueous layer was acidified to pH 2 with 1N aqueous HCl solution and extracted with DCM. The organic layer was washed with water, brine, dried over anhydrous sodium sulphate and concentrated under vacuum to give the crude product which was purified by combi flash using 6-8% ethyl acetate in n-hexane as eluent to afford title compound (39a, 50%). $^1$H NMR (400 MHz, DMSO-$d_6$): δ 7.38-7.37 (m, 5H), 5.15 (s, 2H), 4.26 (s, 2H), 4.11 (s, 2H); LC-MS: m/z 223.0 (M−1)

Step-b: Synthesis of benzyl 2-(2-((2-(2,6-dioxopiperidin-3-yl)-1,3-dioxoisoindolin-4-yl)amino)-2-oxoethoxy)acetate (33b)

The title compound was synthesized using the same procedure which was followed for 21 $b_1$ 21$b_7$ using 29b and 33a as starting material. Yield: 25% $^1$H NMR (400 MHz, DMSO-$d_6$): δ 11.14 (s, 1H), 10.34 (s, 1H), 8.68 (d, J=8.8 Hz, 1H), 7.85 (t, J=7.6 Hz, 1H), 7.63 (d, J=6.8 Hz, 1H), 7.38-7.31 (m, 5H), 5.37 (s, 2H), 5.16 (dd, $J_1$=4.4 Hz, $J_2$=10 Hz, 1H), 4.47 (s, 2H), 4.29 (s, 2H), 2.90-2.84 (m, 1H), 2.63-2.51 (m, 2H), 2.08-2.05 (m, 1H). LC-MS: m/z 480.1 (M+1)⁺.

Step-c: Synthesis of 2-(2-((2-(2,6-dioxopiperidin-3-yl)-1,3-dioxoisoindolin-4-yl)amino)-2-oxoethoxy) acetic acid (33c)

To a stirred solution of compound (33b 1.0 eq.) in DMF (5 vol.) was added 10% Pd/C (10%, w/w). The reaction was performed under hydrogen atmosphere (60 psi) at RT for 2 h. After completion of the reaction (monitored by TLC) the reaction mixture was filtered though celite pad. Cold water was added to the filtrate to obtain the solid which was filtered and dried to afford the title compound (39c, Yield: 84%). $^1$H NMR (400 MHz, DMSO-$d_6$): δ 13.48 (bs, 1H), 11.13 (s, 1H), 10.14 (s, 1H), 8.70 (d, J=8.4 Hz, 1H), 7.87 (t, J=7.6 Hz, 1H), 7.63 (d, J=7.2 Hz, 1H), 5.17 (dd, $J_1$=5.16 Hz, $J_2$=12.8 Hz, 1H), 4.26 (s, 4H), 2.89-2.84 (m, 1H), 2.63-2.54 (m, 2H), 2.19-2.05 (m, 1H). LC-MS: m/z 390.0 (M+1)⁺.

Intermediate-34:

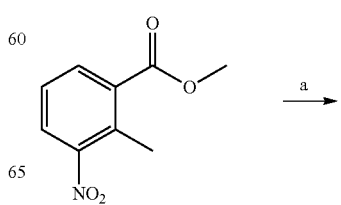

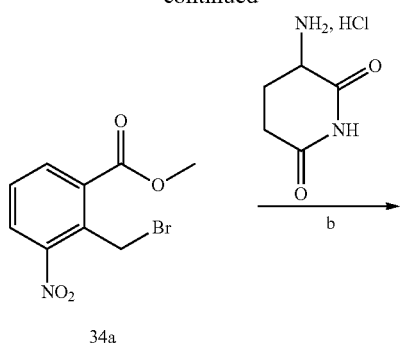

34a

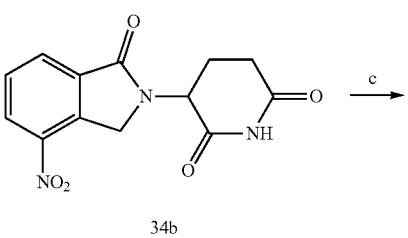

34b

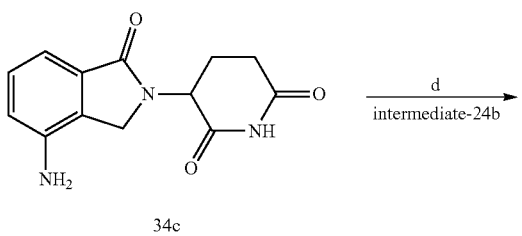

34c

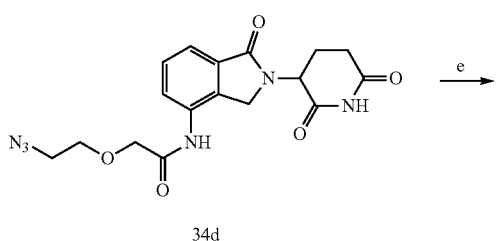

34d

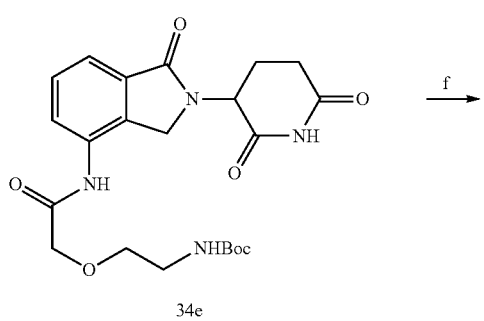

34e

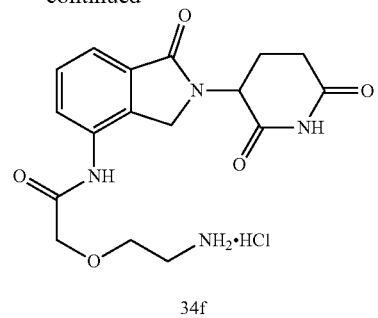

34f

Conditions: a) NBS, AIBN, CCl₄, 80° C., 16 h;
b) Et₃N, DMA, 85° C., 4 h;
c) 10% Pd/C, MeOH, H₂ atm (60 psi), RT, 26 h;
d) HATU, DIPEA, DMF, 0° C. –RT, 16 h;
e) 20% Pd(OH)₂, Et₃N, (Boc)₂O, 1,4-dioxane, H₂ (50 psi), 16 h;
f) 4M HCl in 1,4-Dioxane, 1,4-Dioxane, 0° C.-RT.

Step-a: Synthesis of methyl 2-(bromomethyl)-3-nitrobenzoate (34a)

To a stirred solution of methyl 2-methyl-3-nitrobenzoate (2.0 g, 10.25 mmol) in CCl₄ (30 mL) was added NBS (2.18 g, 12.30 mmol) and AIBN (0.168 g, 1.02 mmol) at RT. Stirring was continued at 80° C. for 16 h. Then the reaction mixture was cooled to room temperature and poured into water and extracted with DCM (2×200 mL). The organic layer was washed water (100 mL), brine (100 mL), dried over anhydrous sodium sulphate and concentrated under vacuum to give the residue which was purified by combi flash using 6% ethyl acetate in n-hexane as eluent to afford the title compound (2.1 g, 77%). $^1$H NMR (400 MHz, CDCl₃): δ 8.10 (dd, $J_1$=1.2 Hz, $J_2$=1.6 Hz, 1H), 7.95 (dd, $J_1$=1.5 Hz, $J_2$=1.0 Hz, 1H), 7.53 (t, J=7.8 Hz, 1H), 5.15 (s, 2H), 4.00 (s, 3H).

Step-b: Synthesis of 3-(4-nitro-1-oxoisoindolin-2-yl)piperidine-2,6-dione (34b)

To a stirred solution of methyl 2-(bromomethyl)-3-nitrobenzoate (1.0 g, 3.64 mmol) and 3-aminopiperidine-2,6-dione hydrochloride (0.55 g, 3.64 mmol) in DMA (30 mL) was added triethyl amine (0.92 g, 9.12 mmol) at RT. Stirring was continued at 85° C. for 4 h. After completion of the reaction (monitored by TLC) the reaction mixture was poured into crushed ice. Solid formed was filtered off and washed with ethyl acetate to afford title compound (0.59 g, 56%). $^1$H NMR (400 MHz, DMSO-d₆): δ 8.47 (d, J=7.6 Hz, 1H), 8.19 (d, J=7.2 Hz, 1H), 7.84 (t, J=7.8 Hz, 1H), 5.17 (dd, $J_1$=5.2 Hz, $J_2$=13.2 Hz, 1H), 4.93-4.77 (m, 2H), 2.92-2.90 (m, 2H), 2.62-2.58 (m, 2H), 2.05-2.00 (m, 1H); LC-MS: m/z 290.0 (M+1)⁺.

Step-c: Synthesis of 3-(4-amino-1-oxoisoindolin-2-yl)piperidine-2,6-dione (34c)

To a stirred solution of 3-(4-nitro-1-oxoisoindolin-2-yl)piperidine-2,6-dione (3.0 g, 10.37 mmol) in methanol (60 mL) was added 10% Pd/C (0.7 g). The reaction was performed under hydrogen atmosphere (40 psi) at RT for 16 h. After completion of the reaction (monitored by TLC) the reaction mixture was filtered though celite. The filtrate was concentrated to afford title compound (2.4 g, 89%) which was used in the next step without further purification. $^1$H NMR (400 MHz, DMSO-d$_6$): δ 10.98 (s, 1H), 7.18 (t, J=8 Hz, 1H), 6.91 (d, J=6.8 Hz, 1H), 6.79 (d, J=7.2 Hz, 1H), 5.40 (s, 2H), 5.10 (dd, J$_1$=4.8 Hz, J$_2$=13.2 Hz, 1H), 4.22-4.08 (m, 2H), 2.96-2.95 (m, 1H), 2.59-2.50 (m, 1H), 2.33-2.29 (m, 1H), 2.05-2.01 (m, 1H); LC-MS: m/z 260.1 (M+1)$^+$.

Step-d: Synthesis of 2-(2-azidoethoxy)-N-(2-(2,6-dioxopiperidin-3-yl)-1-oxoisoindolin-4-yl) acetamide (34d)

To a stirred solution of 3-(4-amino-1-oxoisoindolin-2-yl) piperidine-2,6-dione (6.0 g, 23.16 mmol) and 2-(2-azidoethoxy)acetic acid, 24b 4.36 g, 30.11 mmol) in DMF (40 mL) was added HATU (9.65 g, 25.47 m·mol) at 0° C. followed by dropwise addition of DIPEA (12.34 mL, 69.48 mmol). Stirring was continued at RT for 16 h. Then the reaction mixture was poured into crushed ice and the solid formed was filtered off to get the crude product which was purified by combi flash using 0.4% MeOH in DCM as eluent to afford title compound (3.0 g, 33.5%). $^1$H NMR (400 MHz, DMSO-d$_6$): δ 11.01 (s, 1H), 9.72 (s, 1H), 7.76 (dd, J$_1$=1.2 Hz, J$_2$=7.6 Hz, 1H), 7.57-7.50 (m, 2H), 5.14 (dd, J$_1$=8.0 Hz, J$_2$=13.2 Hz, 1H), 4.43-4.32 (q, J=17.2 Hz, 2H), 4.18 (s, 2H), 3.75 (t, J=4.4 Hz, 2H), 3.51 (t, J=4.8 Hz, 2H), 2.94-2.90 (m, 1H), 2.67-2.52 (m, 1H), 2.49-2.44 (m, 1H), 2.03-2.00 (m, 1H); LC-MS: m/z 387.1 (M+1)$^+$.

Step-e: Synthesis of tert-butyl (2-(2-((2-(2,6-dioxopiperidin-3-yl)-1-oxoisoindolin-4-yl)amino)-2-oxoethoxy)ethyl)carbamate (34e)

The title compound was synthesized using the same procedure which was followed for Intermediate-29d using 2-(2-azidoethoxy)-N-(2-(2,6-dioxopiperidin-3-yl)-1-oxoisoindolin-4-yl)acetamide as starting material. (Yield: 87%); $^1$H NMR (400 MHz, DMSO-d$_6$): δ 10.99 (s, 1H), 9.68 (s, 1H), 7.71 (d, J=7.2 Hz, 1H), 7.58-7.50 (m, 2H), 6.93 (m, 1H), 5.14 (dd, J$_1$=8.14 Hz, J$_2$=13.6 Hz, 1H), 4.31 (q, J=17.6 Hz, 2H), 4.13 (s, 2H), 3.54 (t, J=5.6 Hz, 2H), 3.12 (q, J=5.6 Hz, 2H), 2.96-2.87 (m, 1H), 2.66-2.57 (m, 1H), 2.49-2.40 (m, 1H), 2.03-1.99 (m, 1H), 1.35 (s, 9H); LC-MS: m/z 459.4 (M−1).

Step-f: Synthesis of 2-(2-aminoethoxy)-N-(2-(2,6-dioxopiperidin-3-yl)-1-oxoisoindolin-4-yl) acetamide hydrochloride (34f)

The title compound was synthesized using the same procedure which was followed for Intermediate-29e using tert-butyl (2-(2-((2-(2,6-dioxopiperidin-3-yl)-1-oxoisoindolin-4-yl)amino)-2-oxoethoxy)ethyl)carbamate as starting material. (Yield: 98%); $^1$H NMR (400 MHz, DMSO-d$_6$): δ 11.00 (s, 1H), 9.97 (s, 1H), 8.12 (bs, 2H), 7.72 (dd, J$_1$=0.8 Hz, J$_2$=7.6 Hz, 1H), 7.60-7.51 (m, 2H), 5.17 (dd, J$_1$=5.20 Hz, J$_2$=13.2 Hz, 1H), 4.48 (q, J=17.2 Hz, 2H), 4.19 (s, 2H), 3.74 (t, J=4.8 Hz, 2H), 3.02 (q, J=5.6 Hz, 2H), 2.95-2.87 (m, 2H), 2.62-2.58 (m, 1H), 2.49-2.33 (m, 1H), 2.03-1.60 (m, 1H); LC-MS: m/z 361.1 (M+1)$^+$.

Intermediate-35b:

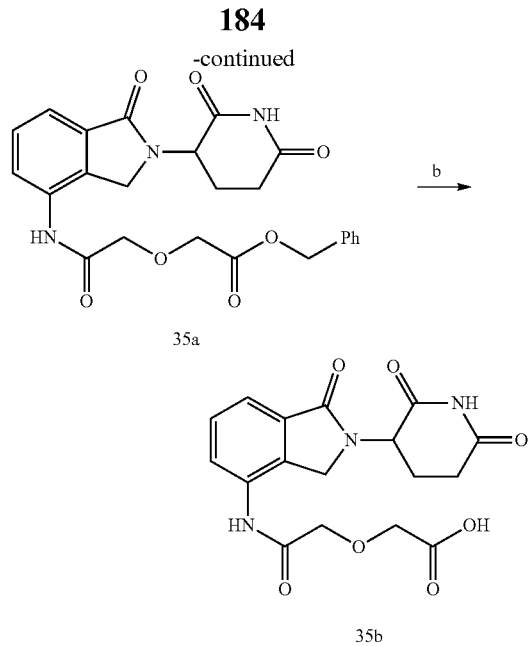

Conditions: a) HATU, DIPEA, DMF, 0° C.-RT, 16 h;
b) 10% Pd/C., DMF, H$_2$ (60 psi), RT, 12 h.

Step-a: Synthesis of benzyl 2-(2-((2-(2,6-dioxopiperidin-3-yl)-1-oxoisoindolin-4-yl)amino)-2-oxoethoxy)acetate (35a)

The title compound was synthesized using the same procedure which was followed for 21 b$_1$-21b$_7$ using 33a and 34c as starting materials. Yield: 50% $^1$H NMR (400 MHz, DMSO-d$_6$): δ 11.00 (s, 1H), 9.82 (s, 1H), 7.26 (d, J=7.3 Hz, 1H), 7.54-7.51 (m, 2H), 7.39-7.34 (m, 5H), 5.18 (s, 2H), 5.17-5.14 (m, 1H), 4.38 (s, 2H), 4.36 (s, 2H), 4.25 (s, 2H), 2.90-2.84 (m, 1H), 2.63-2.51 (m, 1H), 2.39-2.30 (m, 1H), 2.08-2.05 (m, 1H); LC-MS: m/z 466.1 (M+1)$^+$.

Step-b: Synthesis of 2-(2-((2-(2,6-dioxopiperidin-3-yl)-1-oxoisoindolin-4-yl)amino)-2-oxoethoxy)acetic acid (35b)

The title compound was synthesized using the same procedure which was followed for 33c using 2-(2-(benzyloxy)-2-oxoethoxy) acetic acid and 3-(4-amino-1-oxoisoindolin-2-yl) piperidine-2,6-dione as starting materials. (Yield: 26%) $^1$H NMR (400 MHz, DMSO-d$_6$): δ 13.48 (bs, 1H), 10.99 (s, 1H), 9.89 (s, 1H), 7.81 (dd, J$_1$=1.2 Hz, J$_2$=7.6 Hz, 1H), 7.56-7.49 (m, 2H), 5.14 (dd, J$_1$=5.6 Hz, J$_2$=14 Hz, 1H), 4.45-4.33 (m, 2H), 4.29 (s, 2H), 4.22 (s, 2H), 2.95-2.87 (m, 1H), 2.6-2.51 (m, 1H), 2.49-2.32 (m, 1H), 2.04-2.00 (m, 1H). LC-MS: m/z 376.0 (M+1)$^+$.

Intermediate-36:

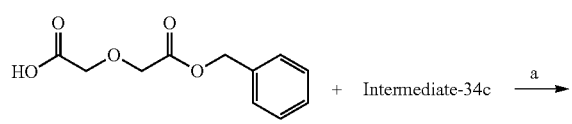

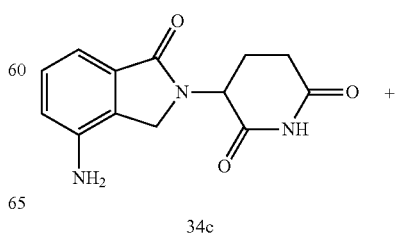

185

-continued

HO⟵O⟶(O⟵)ₙO⟵N₃  (carboxylic acid–PEG–azide)

26c₁, n = 1; 26c₂, n = 2; 26c₃, n = 3

[lenalidomide-NH–CO–CH₂–O–(CH₂CH₂O)ₙ–CH₂CH₂–N₃]

36a₁, n = 1; 36a₂, n = 2; 36a₃, n = 3

[lenalidomide-NH–CO–CH₂–O–(CH₂CH₂O)ₙ–CH₂CH₂–NHBoc]

36b₁, n = 1; 36b₂, n = 2; 36b₃, n = 3

186

-continued

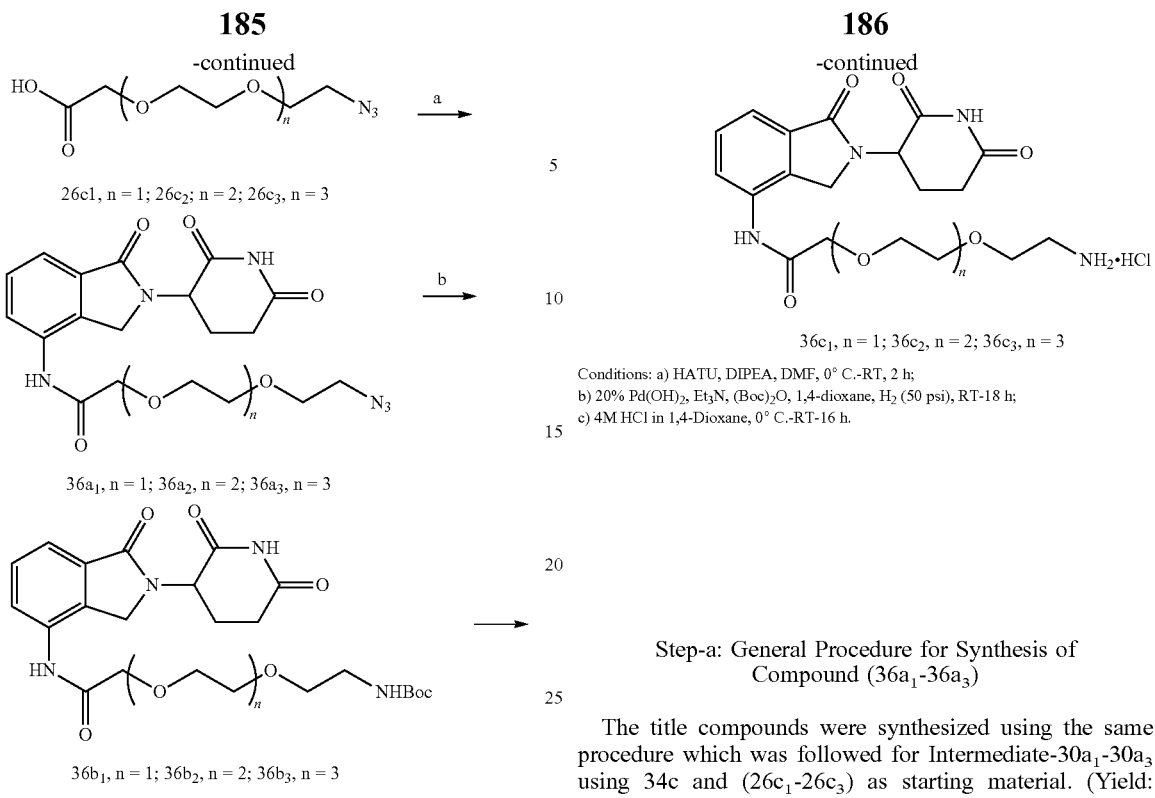

36c₁, n = 1; 36c₂, n = 2; 36c₃, n = 3

Conditions: a) HATU, DIPEA, DMF, 0° C.-RT, 2 h;
b) 20% Pd(OH)₂, Et₃N, (Boc)₂O, 1,4-dioxane, H₂ (50 psi), RT-18 h;
c) 4M HCl in 1,4-Dioxane, 0° C.-RT-16 h.

Step-a: General Procedure for Synthesis of Compound (36a₁-36a₃)

The title compounds were synthesized using the same procedure which was followed for Intermediate-30a₁-30a₃ using 34c and (26c₁-26c₃) as starting material. (Yield: 40-45%).

TABLE-20

| Structure | Characterization Data |
|---|---|
| 36a₁ | LC-MS: m/z 431.1 (M + 1)⁺. |
| 36a₂ | LC-MS: m/z 475.2 (M + 1)⁺. |

TABLE-20-continued

| Structure | Characterization Data |
|---|---|
| 36a₃ | LC-MS: m/z 519.2 (M + 1)⁺. |

Step-b: General Procedure for Synthesis of Compound (36b₁-36b₃)

The title compounds were synthesized using the same procedure which was followed for 30b₁-30b₃ using (36a₁-36a₃) as the starting materials. (Yield: 55-60%).

Step-c: General Procedure for Synthesis of Compound (36c₁-36c₃)

The title compounds were synthesized using the same procedure which was followed for 30c₁-30c₃ using 36b₁-36b₃) as the starting materials. (Yield: 90-95%)

TABLE-21

| Structure | Characterization Data |
|---|---|
| 36b₁ | LC-MS: m/z 503.2 (M − 1). |
| 36b₂ | LC-MS: m/z 547.3 (M − 1). |
| 36b₃ | LC-MS: m/z 591.3 (M − 1). |

TABLE-22
| Structure | Characterization Data<br>$^1$H NMR (400 MHz, DMSO-$d_6$) |
|---|---|
| 36c$_2$ | δ 11.00 (s, 1H), 9.77 (s, 1H), 7.82 (bs, 2H), 7.75 (d, J = 5.7 Hz, 2H), 7.56-7.52 (m, 2H), 5.18-5.12 (m, 1H), 4.39-4.36 (m, 2H), 4.17 (s, 2H), 3.71-3.62 (m, 6H), 2.99-2.98 (m, 2H), 2.68-2.61 (m, 2H), 2.39-2.31 (m, 1H), 2.07-1.95 (m, 1H); LC-MS: m/z 405.1 (M + 1)$^+$. |
| 36c$_2$ | δ 11.00 (s, 1H), 9.82 (s, 1H), 7.94 (bs, 3H), 7.75 (d, J = 8.0 Hz, 1H), 7.57-7.50 (m, 2H), 5.14 (dd, J$_1$ = 4.8 Hz, J$_2$ = 13.2 Hz, 1H), 4.38 (q, J = 17.6 Hz, 2H), 4.17 (s, 2H), 3.70-3.68 (m, 2H), 3.64-3.58 (m, 9H), 2.96-2.89 (m, 2H), 2.58-2.63 (m, 1H), 2.38-2.33 (m, 1H), 2.08-2.00 (m, 1H); LC-MS: m/z 449.2 (M + 1)$^+$. |
| 36c$_3$ | δ 11.00 (s, 1H), 9.80 (s, 1H), 7.94 (bs, 2H), 7.76 (d, J = 7.2 Hz, 2H), 7.57-7.50 (m, 2H), 5.16 (dd, J$_1$ = 5.2 Hz, J$_2$ = 13.6 Hz, 1H), 4.45-4.16 (m, 2H), 3.7 (s, 2H), 3.70-3.68 (m, 2H), 3.63-3.59 (m, 5H), 3.57-3.55 (m, 7H), 2.96-2.87 (m, 3H), 2.62-2.58 (m, 1H), 2.38-2.34 (m, 1H), 2.03-2.00 (m, 1H); LC-MS: m/z 493.2 (M + 1)$^+$. |
Intermediate-37:
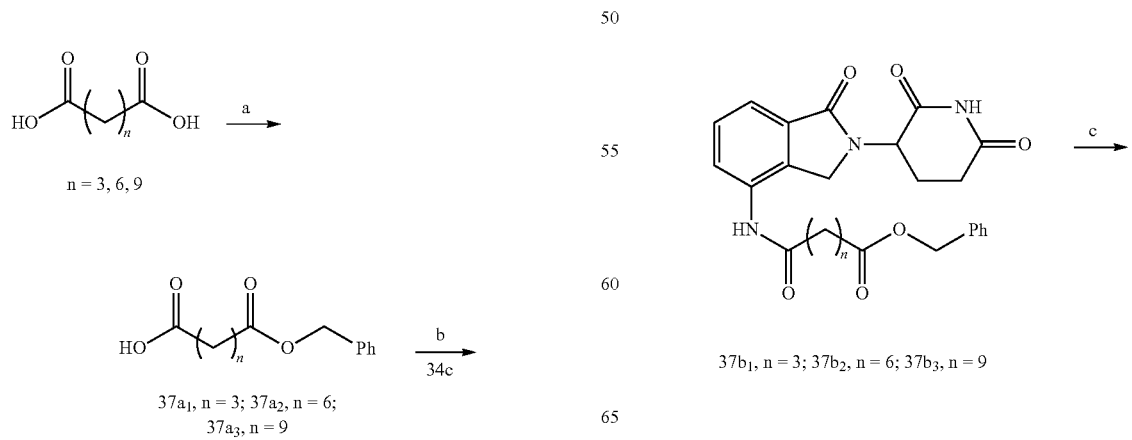
37a$_1$, n = 3; 37b$_2$, n = 6; 37b$_3$, n = 9

-continued

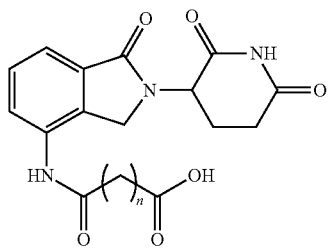

$37c_1$, n = 3; $37c_2$, n = 6; $37c_3$, n = 9

Conditions: a) Benzyl bromide, TEA, Acetone, RT, 16 h;
b) HATU, DIPEA, DMF, 0° C., RT, 16 h;
c) 10% Pd/C, DMF, $H_2$ (60 psi), RT, 2 h.

Step-a: General Procedure for Synthesis of Compound ($37a_1$-$37a_3$)

To a stirred solution of dicarboxylic acid (1.0 eq.) and bezyl bromide (1.0 eq.) in acetone (5 vol.) was added triethyl amine (1.3 eq.). Stirring was continued at RT for 16 h. After completion of the reaction (monitored by TLC), the reaction mixture was filtered off and the filtrate was washed with ethyl acetate. The organic layer was concentrated under reduced pressure to get the residue which was dissolved in aqueous sodium bicarbonate solution. The resulting solution was washed with ethyl acetate. The aqueous layer was acidified to pH 2 with 1N aqueous HCl solution and extracted with DCM. The organic layer was washed with water, brine, dried over anhydrous sodium sulphate and concentrated under vacuum to give the crude product which was purified by combi flash using 6-8% ethyl acetate in n-hexane as eluent to afford title compound ($37a_1$-$37a_3$, 15-20%).

TABLE-23

| Structure | Characterization Data |
| --- | --- |
| $37a_1$ | LC-MS: m/z 221.0 (M − 1). |
| $37a_2$ | LC-MS: m/z 263.1 (M − 1). |
| $37a_3$ | LC-MS: m/z 307.0 (M + 1)$^+$. |

Step-b: General Procedure for Synthesis of Compound ($37b_1$-$37b_3$)

The title compound was synthesized using the same procedure which was followed for Intermediate-35a using compound ($37a_1$-$37a_3$) and 3-(4-amino-1-oxoisoindolin-2-yl)piperidine-2,6-dione as starting materials. (Yield: 40-45%)

TABLE-24

| Structure | Characterization Data |
| --- | --- |
| $37b_1$ | LC-MS: m/z 464.1 (M + 1)$^+$. |

TABLE-24-continued

| Structure | Characterization Data |
|---|---|
| 37b₂ | LC-MS: m/z 506.2 (M + 1)⁺. |

Step-c: General Procedure for Synthesis of Compound (37c₁-37c₃1

To a stirred solution of compound (374b₁-37b₃, 1.0 eq.) in DMF (5 vol.) was added 10% Pd/C (10%, w/w). The reaction was performed under hydrogen atmosphere (60 psi) at RT for 2 h. After completion of the reaction (monitored by TLC) the reaction mixture was filtered though celite pad. Cold water was added to the filtrate to obtain the solid which was filtered and dried to afford the title compound (37c₁-37c₃, Yield: 60-70%).

TABLE-25

| Structure | Characterization Data $^1$H NMR (400 MHz, DMSO-d$_6$) |
|---|---|
| 37c₁ | δ 12.15 (s, 1H), 11.03 (s, 1H), 9.81 (s, 1H), 7.82-7.80 (m, 1H), 7.48 (q, J = 6.9 Hz, 2H), 5.17-5.12 (m, 1H), 4.35 (q, J = 18.0 Hz, 2H), 2.89 (t, J = 5.8 Hz, 1H), 2.62 (bs, 1H), 2.40 (t, J = 7.3 Hz, 3H), 2.29 (t, J = 6.9 Hz, 2H), 2.05-2.04 (m, 1H), 1.86-1.80 (m, 2H); LC-MS: m/z 374.0 (M + 1)⁺. |
| 37c₂ | δ 11.99 (bs, 1H), 11.0 (s, 1H), 9.75 (s, 1H), 7.80 (dd, J₁ = 2.0 Hz, J₂ = 6.8 Hz, 1H), 7.51-7.46 (m, 2H), 5.13 (dd, J₁ = 5.2 Hz, J₂ = 13.2 Hz, 1H), 4.42 (d, J = 17.6 Hz, 2H), 2.96-2.86 (m, 1H), 2.63-2.58 (m, 1H), 2.35 (t, J = 7.4 Hz, 3H), 2.20 (t, J = 7.4 Hz, 2H), 2.04-2.00 (m, 1H), 1.61-1.56 (m, 2H), 1.54-1.47 (m, 2H), 1.35-1.30 (m, 4H); LC-MS: m/z 416.1 (M + 1)⁺. |
| 37c₃ | δ 11.94 (s, 1H), 11.0 (s, 1H), 9.74 (s, 1H), 7.80 (dd, J₁ = 2.0 Hz, J₂ = 7.2 Hz, 1H), 7.51-7.46 (m, 2H), 5.13 (dd, J₁ = 4.8 Hz, J₂ = 13.2 Hz, 1H), 4.35 (q, J = 17.6 Hz, 2H), 2.91-2.88 (m, 1H), 2.67-2.58 (m, 1H), 2.36-2.32 (m, 3H), 2.20-2.16 (m, 2H), 2.04-1.98 (m, 1H), 1.61-1.58 (m, 2H), 1.49-1.46 (m, 2H), 1.29-1.09 (m, 10H); LC-MS: m/z 458.2 (M + 1)⁺. |

EXAMPLES

The present invention is further exemplified, but not limited by the following examples that illustrate the preparation of compounds according to the invention.

Example-I: Synthesis of 1-(3-amino-6-(2-hydroxyphenyl)pyridazin-4-yl)-N-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)piperidine-4-carboxamide (compound-1)

h. After completion of the reaction (monitored by TLC) the reaction mixture was poured into crushed ice. Solid formed was filtered off to get the crude product which was purified by combi flash using 0.4% MeOH in DCM as eluent to afford title compound (0.05 g, 32%) as a pale yellow solid. $^1$H NMR (400 MHz, DMSO-$d_6$): δ 14.25 (s, 1H), 8.95 (s, 1H), 8.57-8.54 (m, 1H), 8.01-7.98 (m, 1H), 7.90 (d, J=7.6 Hz, 1H), 7.47-7.37 (m, 6H), 7.23 (dd, J=7.2 Hz, 7.2 Hz, 1H), 6.89-6.85 (m, 2H), 6.20 (m, 2H), 5.15 (d, J=2.8 Hz, 1H), 4.58-4.55 (m, 1H), 4.46-4.42 (m, 1H), 4.38-4.23 (m, 3H), 4.02-3.92 (m, 2H), 3.66-3.60 (m, 2H), 3.52-3.47 (m, 4H),

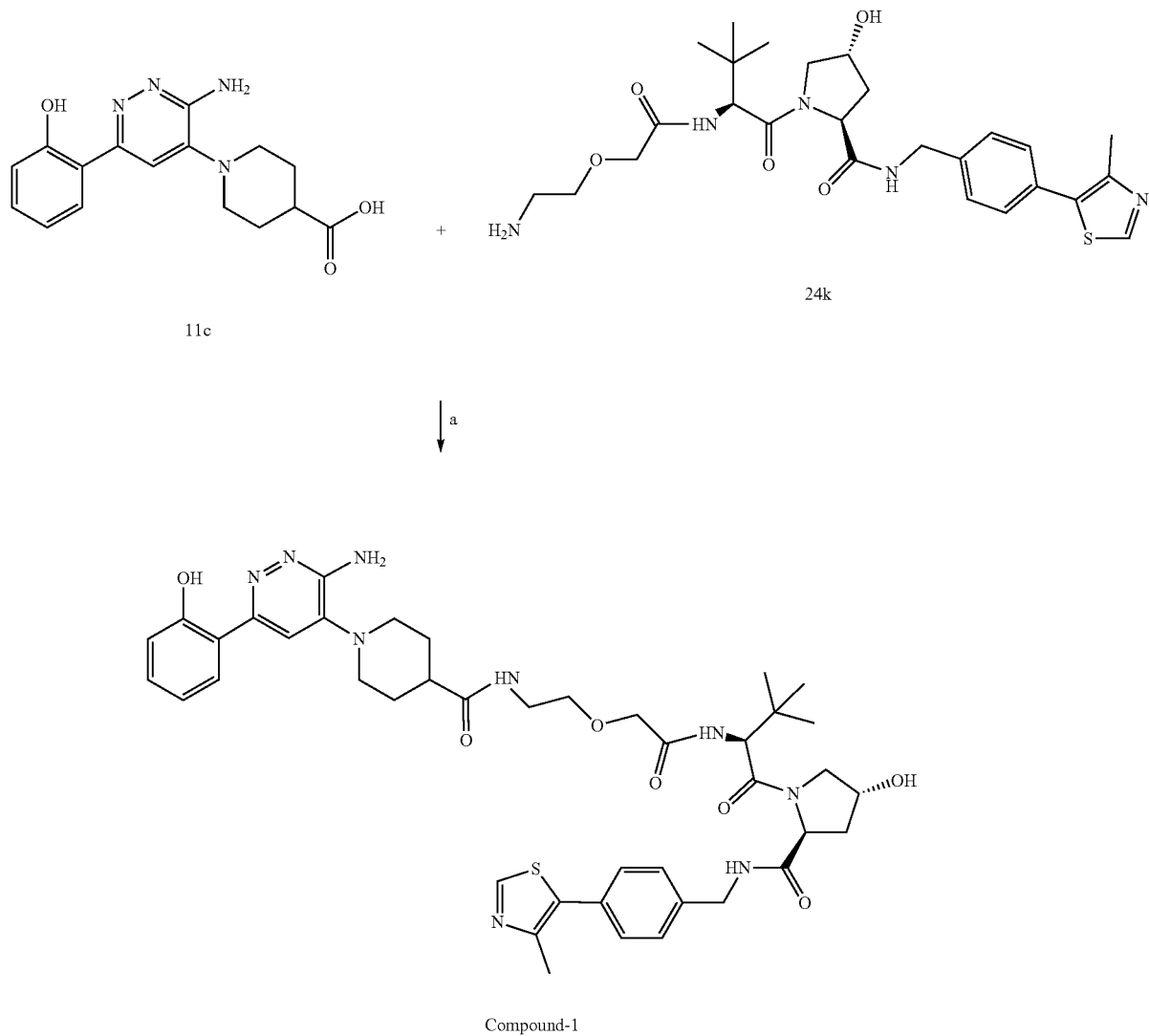

Compound-1

Conditions: a) HATU, DIPEA, DMF, 0° C.-RT, 16 h.

To a stirred solution of 1-(3-amino-6-(2-hydroxyphenyl)pyridazin-4-yl)piperidine-4-carboxylic acid (0.088 g, 0.28 mmol) and (2S,4R)-1-((S)-2-(2-(2-aminoethoxy)acetamido)-3,3-dimethylbutanoyl)-4-hydroxy-N-(4-(4-methylthiazol-5-yl)benzyl)pyrrolidine-2-carboxamide (0.1 g, 0.188 mmol) in DMF (3 mL) was added HATU (0.1 g, 0.282 mmol) at 0° C. followed by the drop wise addition of DIPEA (0.086 mL, 0.47 mmol). Stirring was continued at RT for 16

2.69-2.63 (m, 3H), 2.44-2.42 (m, 4H), 2.09-1.82 (m, 7H), 0.95 (s, 9H); LC/MS: 828.4 (M+1)$^+$.

The compounds listed in below Table-26 were prepared by procedure similar to the one described in Example-I with appropriate variations in reactants, quantities of reagents, protections and deprotections, solvents and reaction conditions. The characterization data of the compounds are summarized herein the below table.

TABLE-26

| Comp No. | Structure | Characterization Data ¹H NMR (400 MHz, DMSO-$d_6$) |
|---|---|---|
| 2 | 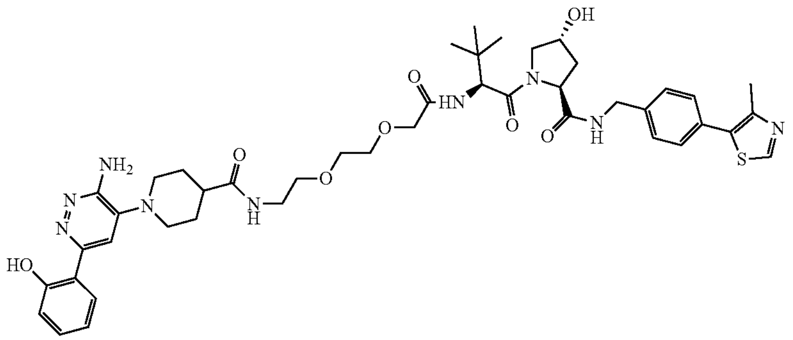 [SMILES: Cc1ncsc1-c1ccc(CNC(=O)[C@@H]2C[C@@H](O)CN2C(=O)[C@@H](NC(=O)COCCOCCNC(=O)C2CCN(c3cc(-c4ccccc4O)nnc3N)CC2)C(C)(C)C)cc1] | δ 14.24 (s, 1H), 8.97 (s, 1H), 8.58-8.55 (m, 1H), 7.92-7.88 (m, 2H), 7.50-7.48 (m, 1H), 7.45-7.40 (m, 1H), 7.39 (s, 4H), 7.25-7.21 (m, 2H), 6.89-6.86 (m, 2H), 6.20 (s, 2H), 5.15 (d, J = 3.6 Hz, 1H), 4.58 (d, J = 9.6 Hz, 1H), 4.47-4.39 (m, 1H), 4.36-4.35 (m, 2H), 4.29-4.24 (m, 1H), 3.93 (s, 2H), 3.68-3.53 (m, 4H), 3.49-3.44 (m, 5H), 3.28-3.21 (m, 2H), 2.69-2.64 (m, 2H), 2.44 (s, 3H), 2.09-2.04 (m, 1H), 1.93-1.85 (m, 4H), 1.82-1.75 (m, 2H), 0.94 (s, 9H); LC/MS: 872.4 (M + 1)⁺. |
| 3 | 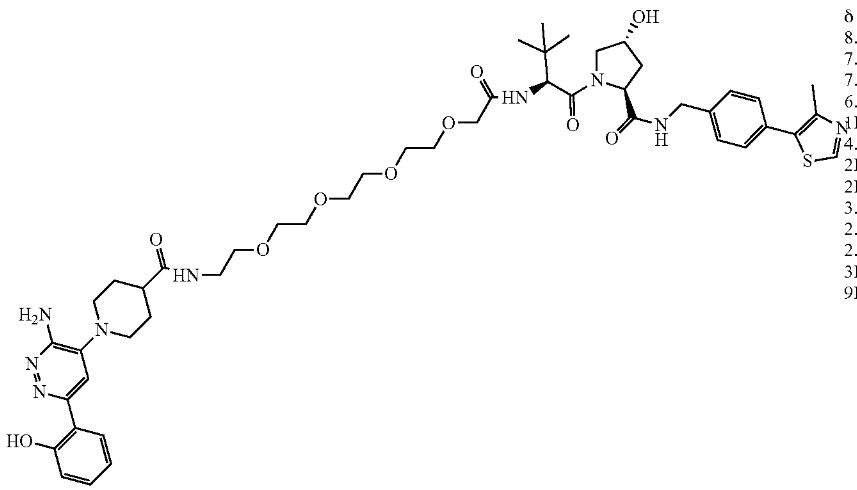 | δ 14.23 (s, 1H), 8.97 (s, 1H), 8.56-8.60 (m, 1H), 7.92-7.89 (m, 2H), 7.49 (s, 1H), 7.39 (s, 5H), 7.23-7.21 (m, 1H), 6.89-6.86 (m, 2H), 6.20 (s, 2H), 5.13 (d, J = 3.2 Hz, 1H), 4.56 (d, J = 9.6 Hz, 1H), 4.43-4.42 (m, 2H), 4.38-4.36 (m, 2H), 4.27-4.26 (m, 2H), 3.96 (s, 2H), 3.66-3.49 (m, 14H), 3.45-3.39 (m, 2H), 3.23-3.20 (m, 2H), 2.69-2.64 (m, 3H), 2.49 (s, 3H), 2.08-1.92 (m, 1H), 1.90-1.86 (m, 3H), 1.78-1.76 (m, 2H), 0.92 (s, 9H); LC/MS: 960.5 (M + 1)⁺. |
| 4 | 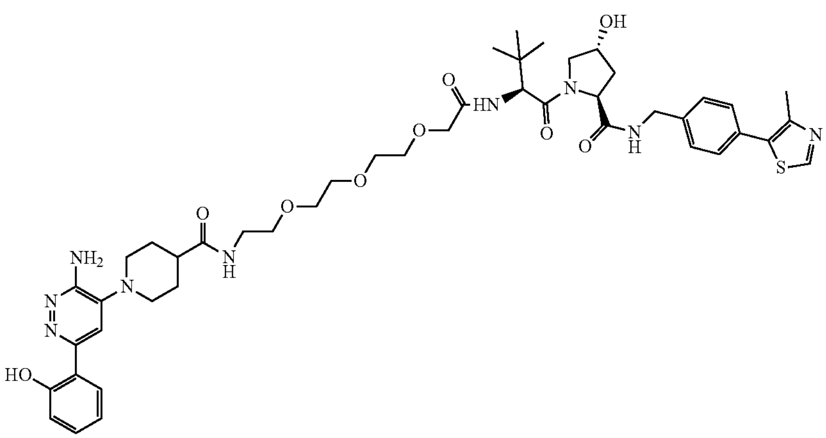 [SMILES: Cc1ncsc1-c1ccc(CNC(=O)[C@@H]2C[C@@H](O)CN2C(=O)[C@@H](NC(=O)COCCOCCOCCNC(=O)C2CCN(c3cc(-c4ccccc4O)nnc3N)CC2)C(C)(C)C)cc1] | δ 14.24 (s, 1H), 8.97 (s, 1H), 8.59-8.56 (m, 1H), 7.92-7.87 (m, 2H), 7.49 (s, 1H), 7.43-7.39 (m, 5H), 7.25-7.19 (m, 1H), 6.89-6.86 (m, 2H), 6.07 (s, 2H), 5.14 (d, J = 3.6 Hz, 1H), 4.56 (d, J = 9.6 Hz, 1H), 4.48-4.40 (m, 1H), 4.39-4.31 (m, 2H), 4.30-4.22 (m, 1H), 3.97 (s, 2H), 3.68-3.44 (m, 9H), 3.40-3.36 (m, 3H), 3.21-3.11 (m, 2H), 2.76-2.59 (m, 3H), 2.44 (s, 4H), 2.08-1.98 (m, 1H), 1.92-1.84 (m, 4H), 1.78-1.49 (m, 2H), 0.94 (s, 9H); LC/MS: 916.4 (M + 1)⁺. |
| 5 | 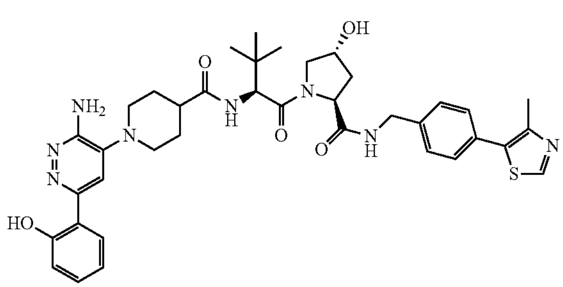 [SMILES: Cc1ncsc1-c1ccc(CNC(=O)[C@@H]2C[C@@H](O)CN2C(=O)[C@@H](NC(=O)C2CCN(c3cc(-c4ccccc4O)nnc3N)CC2)C(C)(C)C)cc1] | δ 14.26 (s, 1H), 8.98 (s, 1H), 8.56 (dd, J = 6.0 Hz, J = 5.6 Hz, 1H), 7.93-7.88 (m, 2H), 7.50 (s, 1H), 7.42 (d, J = 8.0 Hz, 2H), 7.38 (d, J = 8.0 Hz, 2H), 7.23 (dd, J = 7.6 Hz, J = 6.8 Hz, 1H), 6.89-6.87 (m, 2H), 6.20 (s, 2H), 5.13 (d, J = 3.2 Hz, 1H), 4.59-4.56 (m, 1H), 4.46-4.36 (m, 3H), 4.25-4.19 (m, 1H), 3.71-3.62 (m, 2H), 3.54-2.47 (m, 2H), 2.73-2.60 (m, 2H), 2.32 (s, 3H), 2.07-1.72 (m, 7H), 0.96 (s, 9H); LC/MS: 727.3 (M + 1)⁺. |

TABLE-26-continued

| Comp No. | Structure | Characterization Data<br>¹H NMR (400 MHz, DMSO-d₆) |
|---|---|---|
| 6 | 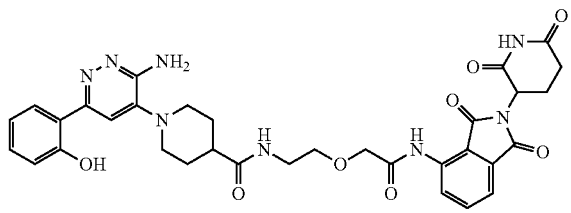 [SMILES: Nc1nnc(-c2ccccc2O)cc1N1CCC(C(=O)NCCOCC(=O)Nc2cccc3c2C(=O)N(C2CCC(=O)NC2=O)C3=O)CC1] | δ 14.24 (s, 1H), 11.14 (s, 1H), 10.35 (s, 1H), 8.72 (d, J = 8 Hz, 1H), 7.96-7.85 (m, 3H), 7.63 (d, J = 8 Hz, 1H), 7.48 (s, 1H), 7.25-7.22 (m, 1H), 6.89-6.86 (m, 2H), 6.21 (s, 2H), 5.19-5.14 (m, 1H), 4.20 (s, 2H), 3.66-3.63 (m, 2H), 3.49-3.46 (m, 2H), 3.40-3.39 (m, 2H), 2.93-2.87 (m, 1H), 2.70-2.57 (m, 4H), 2.01-1.77 (m, 6H); LC/MS: 671.2 (M + 1)⁺. |
| 7 | 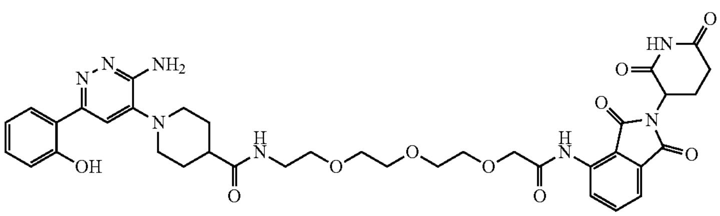 [SMILES: Nc1nnc(-c2ccccc2O)cc1N1CCC(C(=O)NCCOCCOCCOCC(=O)Nc2cccc3c2C(=O)N(C2CCC(=O)NC2=O)C3=O)CC1] | δ 14.25 (s, 1H), 11.14 (s, 1H), 10.35 (s, 1H), 8.72 (d, J = 8 Hz, 1H), 7.91-7.83 (m, 3H), 7.62 (d, J = 8 Hz, 1H), 7.48 (s, 1H), 7.25-7.21 (m, 1H), 6.89-6.86 (m, 2H), 6.19 (s, 2H), 5.18-5.14 (m, 1H), 4.21 (s, 2H), 3.77-3.75 (m, 2H), 3.68-3.67 (m, 2H), 3.56-3.46 (m, 6H), 3.41-3.38 (m, 2H), 3.22-3.17 (m, 2H), 2.95-2.85 (m, 1H), 2.73-2.85 (m, 4H), 2.09-2.06 (m, 1H), 1.98-1.75 (m, 5H); LC/MS: 759.3 (M + 1)⁺. |
| 8 | 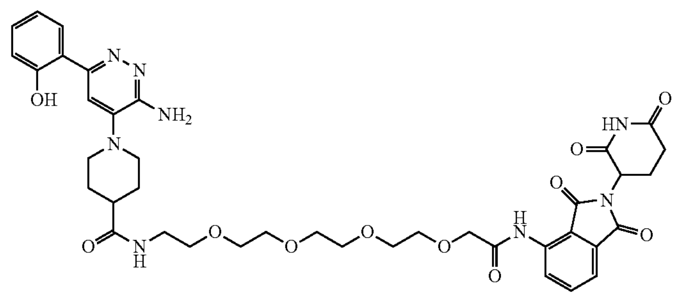 [SMILES: Nc1nnc(-c2ccccc2O)cc1N1CCC(C(=O)NCCOCCOCCOCCOCC(=O)Nc2cccc3c2C(=O)N(C2CCC(=O)NC2=O)C3=O)CC1] | δ 14.25 (s, 1H), 11.14 (s, 1H), 10.35 (s, 1H), 8.71 (d, J = 8 Hz, 1H), 7.91-7.83 (m, 3H), 7.62 (d, J = 8 Hz, 1H), 7.49 (s, 1H), 7.25-7.21 (m, 1H), 6.89-6.85 (m, 2H), 6.20 (s, 2H), 5.18-5.13 (m, 1H), 4.20 (s, 2H), 3.77-3.75 (m, 2H), 3.68-3.66 (m, 2H), 3.55-3.48 (m, 10H), 3.41-3.38 (m, 3H), 3.26-3.21 (m, 3H), 2.69-2.64 (m, 4H), 2.08-2.06 (m, 1H), 1.98-1.76 (m, 4H); LC/MS: 803.3 (M + 1)⁺. |
| 9 | 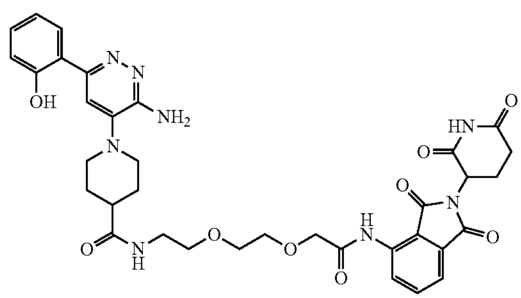 [SMILES: Nc1nnc(-c2ccccc2O)cc1N1CCC(C(=O)NCCOCCOCC(=O)Nc2cccc3c2C(=O)N(C2CCC(=O)NC2=O)C3=O)CC1] | δ 14.12 (s, 1H), 11.14 (s, 1H), 10.37 (s, 1H), 8.72 (d, J = 8.8 Hz, 1H), 7.87-7.83 (m, 2H), 7.62 (d, J = 7.2 Hz, 1H), 7.46 (s, 1H), 7.31-7.25 (m, 1H), 6.93-6.91 (m, 2H), 6.45 (bs, 2H), 5.75 (s, 1H), 5.22-5.14 (m, 1H), 4.21 (s, 2H), 3.77-3.76 (m, 2H), 3.68-3.67 (m, 2H), 3.54-3.51 (m, 2H), 3.47-3.44 (m, 2H), 3.25-3.22 (m, 2H), 3.16 (s, 2H), 2.95-2.87 (m, 1H), 2.71-2.59 (m, 3H), 2.39-2.29 (m, 2H), 2.12-2.08 (m, 1H), 1.87-1.75 (m, 2H); LC/MS: 715.3 (M + 1)⁺. |
| 10 | 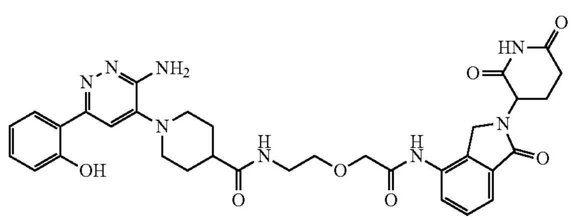 [SMILES: Nc1nnc(-c2ccccc2O)cc1N1CCC(C(=O)NCCOCC(=O)Nc2cccc3c2CN(C2CCC(=O)NC2=O)C3=O)CC1] | δ 14.25 (s, 1H), 11.00 (s, 1H), 9.71 (s, 1H), 8.00 (t, J = 5.4 Hz, 1H), 7.90 (d, J = 7.6 Hz, 1H), 7.76 (d, J = 8.0 Hz, 1H), 7.58-7.50 (m, 2H), 7.49 (s, 1H), 7.25 (t, J = 8.4 Hz, 1H), 6.90-6.87 (m, 2H), 6.21 (bs, 2H), 5.19 (m, 1H), 4.46 (m, 2H), 4.13 (s, 2H), 3.60 (s, 2H), 3.50-3.30 (m, 2H), 2.95-2.83 (m, 1H), 2.02-1.99 (m, 2H), 1.91-1.83 (m, 3H), 1.78-1.75 (m, 3H), 1.30-1.14 (m, 4H); LC/MS: 657.3 (M + 1)⁺. |

TABLE-26-continued

| Comp No. | Structure | Characterization Data<br>¹H NMR (400 MHz, DMSO-d₆) |
|---|---|---|
| 11 | 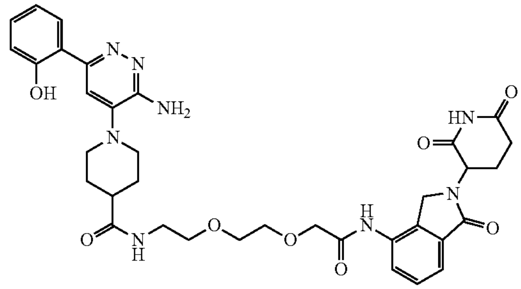 [SMILES: Nc1nnc(-c2ccccc2O)cc1N1CCC(C(=O)NCCOCCOCC(=O)Nc2cccc3c2CN(C2CCC(=O)NC2=O)C3=O)CC1] | δ 14.24 (s, 1H), 10.99 (s, 1H), 9.70 (s, 1H), 7.91-7.86 (m, 2H), 7.74 (d, J = 8 Hz, 1H), 7.56-7.47 (m, 3H), 7.25-7.22 (m, 1H), 6.90-6.87 (m, 2H), 6.22 (s, 2H), 5.16-5.11 (m, 1H), 4.44-4.33 (m, 2H), 4.15 (s, 2H), 3.70-3.69 (m, 2H), 3.63-3.62 (m, 2H), 3.50-3.45 (m, 3H), 3.26-3.21 (m, 2H), 3.17-3.16 (m, 1H), 2.94-2.86 (m, 1H), 2.67-2.57 (m, 3H), 2.43-2.27 (m, 2H), 2.02-1.99 (m, 1H), 1.90-1.82 (m, 2H), 1.76-1.73 (m, 2H); LC/MS: 701.3 (M + 1)⁺. |
| 12 | 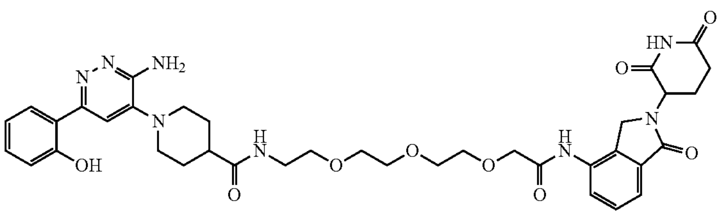 [SMILES: Nc1nnc(-c2ccccc2O)cc1N1CCC(C(=O)NCCOCCOCCOCC(=O)Nc2cccc3c2CN(C2CCC(=O)NC2=O)C3=O)CC1] | δ 14.24 (s, 1H), 10.99 (s, 1H), 9.68 (s, 1H), 7.91-7.85 (m, 2H), 7.74 (d, J = 8 Hz, 1H), 7.56-7.49 (m, 3H), 7.23 (dd, J = 8.4 Hz, J = 7.2 Hz, 1H), 6.89-6.86 (m, 2H), 6.21 (s, 2H), 5.16-5.11 (m, 1H), 4.43-4.32 (m, 2H), 4.14 (s, 1H), 4.08-4.07 (m, 1H), 3.71-3.47 (m, 8H), 3.41-3.38 (m, 2H), 3.21-3.16 (m, 2H), 2.96-2.85 (m, 1H), 2.69-2.62 (m, 4H), 2.38-2.28 (m, 1H), 2.02-1.99 (m, 1H), 1.89-1.83 (m, 2H), 1.78-1.75 (m, 2H), 1.43-1.33 (m, 2H); LC/MS: 745.4 (M + 1)⁺. |
| 13 | 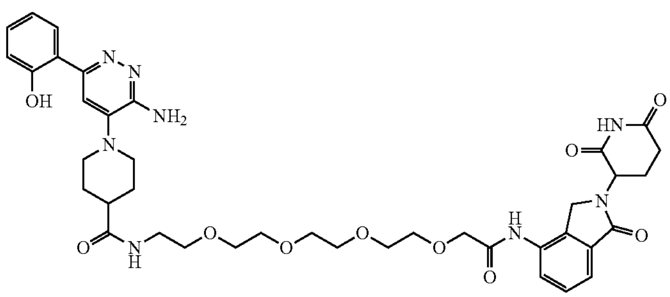 [SMILES: Nc1nnc(-c2ccccc2O)cc1N1CCC(C(=O)NCCOCCOCCOCCOCC(=O)Nc2cccc3c2CN(C2CCC(=O)NC2=O)C3=O)CC1] | δ 14.25 (s, 1H), 10.99 (s, 1H), 9.67 (s, 1H), 7.91-7.87 (m, 2H), 7.72 (d, J = 8 Hz, 1H), 7.57-7.49 (m, 3H), 7.23 (dd, J = 8.4 Hz, J = 7.2 Hz, 1H), 6.89-6.87 (m, 2H), 6.22 (s, 2H), 5.16-5.11 (m, 1H), 4.43-4.32 (m, 2H), 4.14 (s, 2H), 3.73-3.62 (m, 4H), 3.59-3.47 (m, 10H), 3.42-3.38 (m, 3H), 3.21-3.16 (m, 3H), 2.01-1.75 (m, 9H); LC/MS: 789.3 (M + 1)⁺. |
| 14 | 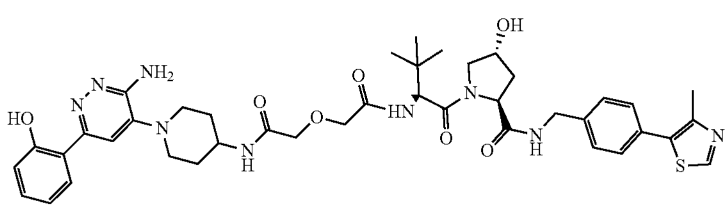 [SMILES: Cc1ncsc1-c1ccc(CNC(=O)[C@@H]2C[C@@H](O)CN2C(=O)[C@@H](NC(=O)COCC(=O)NC2CCN(c3cc(-c4ccccc4O)nnc3N)CC2)C(C)(C)C)cc1] | δ 14.23 (s, 1H), 8.96 (s, 1H), 8.54 (s, 1H), 8.58-8.55 (m, 1H), 8.13 (d, J = 7.6 Hz, 2H), 7.91-7.85 (m, 2H), 7.50 (s, 1H), 7.42-7.37 (m, 5H), 6.90-6.87 (m, 1H), 7.23 (t, J = 6.8 Hz, 2H), 6.22 (s, 2H), 5.13 (d, J = 2.8 Hz, 1H), 4.56 (d, J = 9.6 Hz, 1H), 4.45-4.34 (m, 3H), 4.26-4.24 (m, 1H), 4.08 (s, 2H), 4.06-4.00 (m, 2H), 3.85-3.80 (m, 1H), 3.64-3.62 (m, 2H), 2.82 (t, J = 10.4 Hz, 2H), 2.43 (s, 3H), 2.10-2.00 (m, 1H), 1.90-1.87 (m, 2H), 1.75-1.72 (m, 2H), 0.94 (s, 9H); LC/MS: 814.4 (M + 1)⁺. |
| 15 | 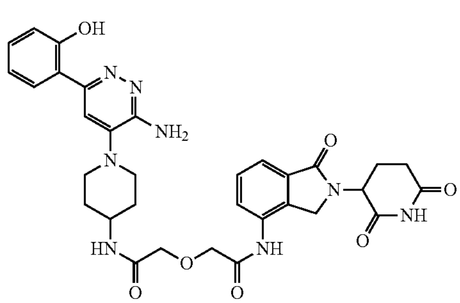 [SMILES: Nc1nnc(-c2ccccc2O)cc1N1CCC(NC(=O)COCC(=O)Nc2cccc3c2CN(C2CCC(=O)NC2=O)C3=O)CC1] | δ 14.23 (s, 1H), 11.03 (s, 1H), 10.20 (s, 1H), 8.15 (d, J = 7.2 Hz, 1H), 7.92-7.86 (m, 2H), 7.57-7.50 (m, 3H), 7.28 (t, J = 7.6 Hz, 1H), 6.91-6.86 (m, 2H), 6.24 (s, 2H), 5.19 (dd, J₁ = 5.2, J₂ = 13.2 Hz, 1H), 4.49-4.37 (m, 2H), 4.24 (s, 2H), 4.13 (s, 2H), 3.83 (m, 1H), 3.50 (d, J = 6.8 Hz, 2H), 2.97-2.94 (m, 1H), 2.90-2.78 (m, 3H), 2.67-2.59 (m, 1H), 2.09-1.99 (m, 1H), 1.92-1.89 (m, 2H), 1.87-1.71 (m, 2H); LC/MS: 643.3 (M + 1)⁺. |

TABLE-26-continued

| Comp No. | Structure | Characterization Data<br>¹H NMR (400 MHz, DMSO-d₆) |
|---|---|---|
| 16 | 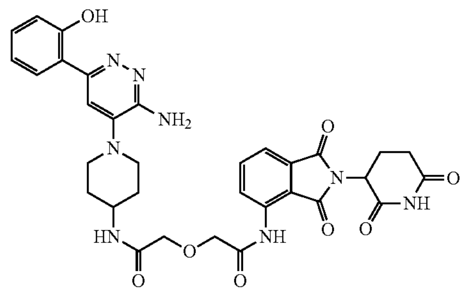 [SMILES: Nc1nnc(-c2ccccc2O)cc1N1CCC(NC(=O)COCC(=O)Nc2cccc3c2C(=O)N(C2CCC(=O)NC2=O)C3=O)CC1] | δ 14.24 (s, 1H), 11.13 (s, 1H), 10.39 (s, 1H), 7.92-7.86 (m, 2H), 7.89 (d, J = 8.0 Hz, 1H), 7.65 (d, J = 7.6 Hz, 1H), 7.50 (s, 1H), 7.23 (t, J = 6.8 Hz, 1H), 6.89 (d, J = 8.0 Hz, 2H), 6.21 (bs, 2H), 5.19-5.14 (m, 1H), 4.28 (s, 2H), 4.16 (s, 2H), 3.83 (bs, 1H), 3.50-3.44 (m, 2H), 2.85-2.76 (m, 3H), 2.59-2.55 (m, 3H), 2.09-2.06 (m, 1H), 1.92-1.90 (m, 2H), 1.81-1.76 (m, 2H); LC/MS: 657.3 (M + 1)⁺. |
| 17 | 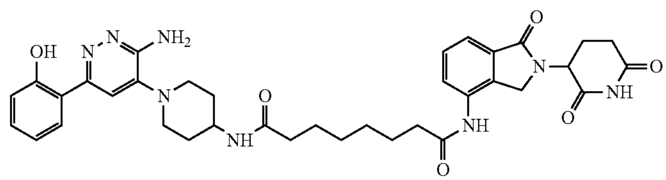 [SMILES: Nc1nnc(-c2ccccc2O)cc1N1CCC(NC(=O)CCCCCCC(=O)Nc2cccc3c2CN(C2CCC(=O)NC2=O)C3=O)CC1] | δ 14.23 (s, 1H), 11.00 (s, 1H), 9.75 (s, 1H), 7.91 (d, J = 1.2 Hz, 1H), 7.82 (d, J = 7.2 Hz, 2H), 7.51-7.45 (m, 3H), 7.26-7.21 (m, 1H), 6.90-6.87 (m, 2H), 6.23 (bs, 2H), 5.16 (dd, J₁ = 4.8, J₂ = 13.2 Hz, 1H), 4.42-4.31 (m, 2H), 4.10-4.06 (m, 1H), 3.74-3.72 (m, 2H), 3.37-3.32 (m, 2H), 2.94-2.87 (m, 1H), 2.82-2.76 (m, 2H), 2.96-2.88 (m, 1H), 2.10-2.01 (m, 4H), 1.87-1.85 (m, 2H), 1.67-1.57 (m, 4H), 1.54-1.50 (m, 2H), 1.32-1.23 (m, 4H); LC/MS: 683.3 (M + 1)⁺. |
| 18 | 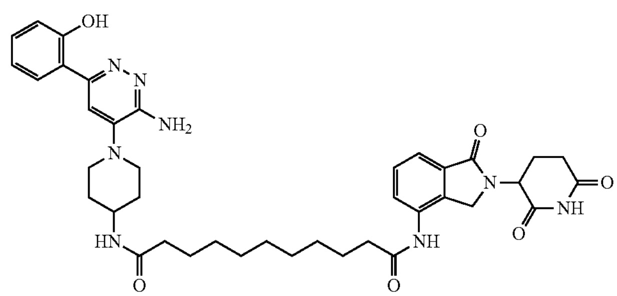 [SMILES: Nc1nnc(-c2ccccc2O)cc1N1CCC(NC(=O)CCCCCCCCCC(=O)Nc2cccc3c2CN(C2CCC(=O)NC2=O)C3=O)CC1] | δ 14.21 (s, 1H), 9.74 (s, 1H), 7.89 (d, J = 7.6 Hz, 1H), 7.80 (d, J = 7.2 Hz, 2H), 7.51-7.45 (m, 3H), 7.23 (t, J = 7.2 Hz, 1H), 6.90-6.87 (m, 2H), 6.23 (bs, 2H), 5.16-5.12 (dd, J₁ = 4.8, J₂ = 13.2 Hz, 1H), 4.35 (q, J₁ = 17.6, J₂ = 8.4 Hz, 2H), 3.64-3.59 (m, 2H), 3.44 (d, J = 12.0 Hz, 2H), 3.15-3.12 (m, 1H), 2.96-2.88 (m, 1H), 2.82-2.77 (m, 2H), 2.66-2.58 (m, 2H), 2.39-2.29 (m, 3H), 2.08-2.00 (m, 2H), 1.90-1.85 (m, 2H), 1.68-1.60 (m, 4H), 1.51-1.49 (m, 2H), 1.29-1.22 (m, 9H); LC/MS: 725.4 (M + 1)⁺. |
| 19 | 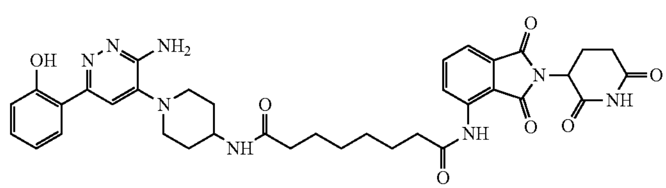 [SMILES: Nc1nnc(-c2ccccc2O)cc1N1CCC(NC(=O)CCCCCCC(=O)Nc2cccc3c2C(=O)N(C2CCC(=O)NC2=O)C3=O)CC1] | δ 14.23 (s, 1H), 11.13 (s, 1H), 9.68 (s, 1H), 8.47 (d, J = 8.4 Hz, 1H), 7.91-7.89 (m, 1H), 7.87-7.84 (m, 2H), 7.61-7.60 (m, 1H), 7.50 (s, 1H), 7.25-7.21 (m, 1H), 6.90-6.86 (m, 2H), 6.22 (bs, 2H), 5.16-5.12 (dd, J₁ = 5.2 Hz, J₂ = 12.4 Hz, 1H), 3.74-3.72 (m, 1H), 3.45-3.42 (m, 2H), 2.94-2.88 (m, 1H), 2.86-2.77 (m, 2H), 2.67-2.54 (m, 2H), 2.49-2.44 (m, 2H), 2.10-2.05 (m, 2H) 1.88-1.85 (m, 2H), 1.68-1.59 (m, 4H), 1.55-1.48 (m, 2H), 1.32-1.22 (m, 5H); LC/MS: 697.0 (M + 1)⁺. |
| 20 | 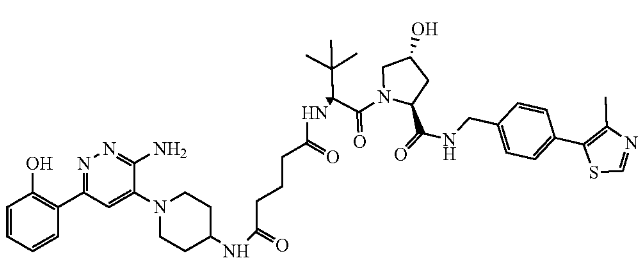 [SMILES: Cc1ncsc1-c1ccc(CNC(=O)[C@@H]2C[C@@H](O)CN2C(=O)[C@@H](NC(=O)CCCC(=O)NC2CCN(c3cc(-c4ccccc4O)nnc3N)CC2)C(C)(C)C)cc1] | δ 14.2 (s, 1H), 8.97 (s, 1H), 8.60-8.50 (m, 1H), 7.90-7.80 (m, 3H), 7.50 (s,1H), 7.43-7.37 (m, 4H), 7.28-7.20 (m, 1H), 6.90-6.88 (m, 2H), 6.24 (s, 2H),5.13 (d, J = 2.8 Hz, 1H), 4.57 (d, J = 8.0 Hz,1H), 4.42-4.40 (m, 2H), 4.35 (bs, 1H) 4.25-4.20 (m, 1H), 3.75-3.65 (m, 3H), 3.44 (d, J = 11.6 Hz, 2H), 2.81 (t, J = 12.0 Hz, 2H), 2.44 (s, 3H), 2.30-2.00 (m, 5H), 1.90-1.87 (m, 3H), 1.74-1.66 (m, 4H), 0.948 (s, 9H); LC/MS: 812.1 (M + 1)⁺. |

TABLE-26-continued

| Comp No. | Structure | Characterization Data ¹H NMR (400 MHz, DMSO-d$_6$) |
|---|---|---|
| 21 | 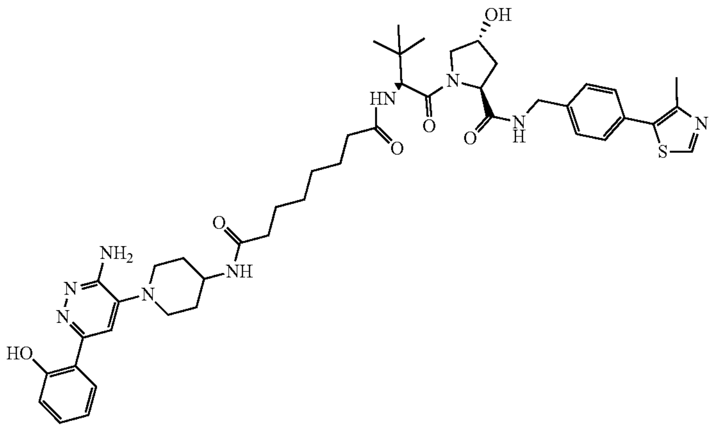 [SMILES: Cc1ncsc1-c1ccc(CNC(=O)[C@@H]2C[C@@H](O)CN2C(=O)[C@@H](NC(=O)CCCCCCC(=O)NC2CCN(c3cc(-c4ccccc4O)nnc3N)CC2)C(C)(C)C)cc1] | δ 14.21 (s, 1H), 8.97 (s, 1H), 8.55 (t, J = 5.6 Hz, 1H), 7.90 (d, J = 7.2 Hz, 1H), 7.84-7.80 (m, 2H), 7.50 (s, 1H), 7.40 (q, J$_1$ = 8.4, J$_2$ = 7.2 Hz, 4H), 7.23 (t, J = 7.2 Hz, 1H), 6.89-6.88 (m, 2H), 6.22 (s, 2H), 5.12 (d, J = 3.2 Hz, 1H), 4.54 (d, J = 9.2 Hz, 1H), 4.46-4.40 (m, 2H), 4.35 (bs, 1H), 4.24-4.20 (m, 1H), 3.74-3.66 (m, 3H), 3.44 (d, J = 11.6 Hz, 2H), 2.80 (t, J = 11.2 Hz, 2H), 2.44 (s, 3H), 2.72-2.23 (m, 1H) 2.13-2.01 (m, 2H), 1.93-1.86 (m, 3H), 1.68-1.63 (m, 2H), 1.48 (bs, 4H), 1.24 (bs, 6H), 0.94 (s, 9H); LC/MS: 854.2 (M + 1)⁺. |
| 22 | 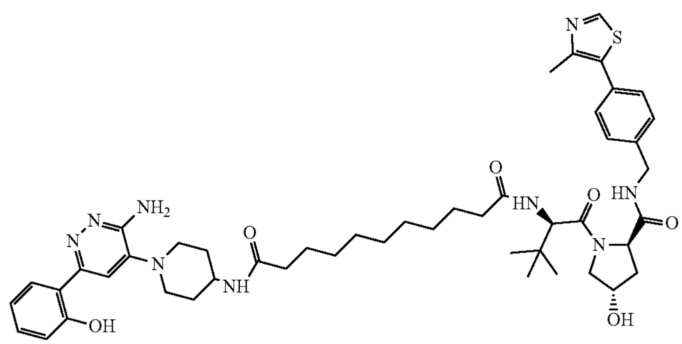 [SMILES: Cc1ncsc1-c1ccc(CNC(=O)[C@H]2C[C@H](O)CN2C(=O)[C@H](NC(=O)CCCCCCCCCC(=O)NC2CCN(c3cc(-c4ccccc4O)nnc3N)CC2)C(C)(C)C)cc1] | δ 14.22 (s, 1H), 8.97 (s, 1H), 8.56-8.53 (m, 1H), 7.91-7.89 (m, 1H), 7.83-7.80 (m, 2H), 7.50 (s, 1H), 7.43 (d, J = 7.6 Hz, 2H), 7.38 (d, J = 8.0 Hz, 2H), 7.23 (t, J = 7.2 Hz, 1H), 6.90-6.88 (m, 2H), 6.22 (s, 2H), 5.12 (d, J = 2.8 Hz, 1H), 4.56 (d, J = 7.2 Hz, 1H), 4.46 (d, J = 9.6 Hz, 1H), 4.43 (t, J = 7.2 Hz, 1H), 4.35 (s, 1H), 4.24-4.19 (m, 1H), 3.74-3.70 (m, 1H), 3.66-3.62 (m, 2H), 3.46-3.43 (m, 2H), 2.82-2.77 (m, 2H), 2.45 (s, 3H), 2.29-2.22 (m, 1H) 2.14-2.01 (m, 4H), 1.93-1.85 (m, 3H), 1.68-1.60 (m, 2H), 1.50-1.48 (m, 4H), 1.24 (s, 10H), 0.91 (s, 9H); LC/MS: 896.3 (M + 1)⁺. |
| 23 | 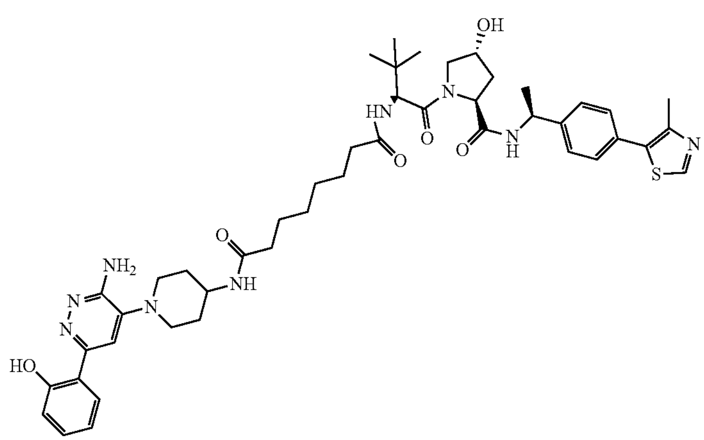 [SMILES: Cc1ncsc1-c1ccc([C@H](C)NC(=O)[C@@H]2C[C@@H](O)CN2C(=O)[C@@H](NC(=O)CCCCCCC(=O)NC2CCN(c3cc(-c4ccccc4O)nnc3N)CC2)C(C)(C)C)cc1] | δ 14.21 (s, 1H), 8.97 (s, 1H), 8.36 (d, J = 8.0 Hz, 1H), 7.90 (d, J = 7.2 Hz, 1H), 7.82-7.76 (m, 2H), 7.50 (s, 1H), 7.43 (d, J = 7.6 Hz, 2H), 7.38 (d, J = 8.0 Hz, 2H), 7.23 (t, J = 7.2 Hz, 1H), 6.90-6.88 (m, 2H), 6.22 (s, 2H), 5.09 (d, J = 2.4 Hz, 1H), 4.92 (t, J = 7.2 Hz, 1H), 4.52 (d, J = 9.6 Hz, 1H), 4.43 (t, J = 7.2 Hz, 1H), 4.28 (bs, 1H), 3.73 (bs, 1H), 3.60 (s, 2H), 3.44 (d, J = 11.6 Hz, 2H), 2.80 (t, J = 11.6 Hz, 2H), 2.45 (s, 3H), 2.24-2.22 (m, 1H), 2.13-1.98 (m, 4H), 1.66-1.63 (m, 2H), 1.48 (bs, 5H), 1.37 (d, J = 6.4 Hz, 3H), 1.24 (bs, 6H), 0.94 (s, 9H). LC/MS: 868.24 (M + 1)⁺. |

TABLE-26-continued

| Comp No. | Structure | Characterization Data <br> ¹H NMR (400 MHz, DMSO-d₆) |
|---|---|---|
| 24 | 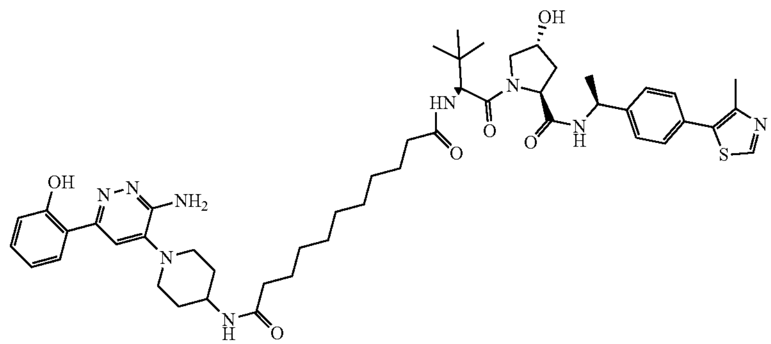 [SMILES: Cc1ncsc1-c1ccc([C@H](C)NC(=O)[C@@H]2C[C@@H](O)CN2C(=O)[C@@H](NC(=O)CCCCCCCCCC(=O)NC2CCN(c3cc(-c4ccccc4O)nnc3N)CC2)C(C)(C)C)cc1] | δ 14.30 (s, 1H), 8.97 (s, 1H), 8.35 (d, J = 8 Hz, 1H), 7.90 (d, J = 7.2 Hz, 1H), 7.81 (d, J = 7.2 Hz, 2H), 7.76 (d, J = 9.2 Hz, 1H), 7.50 (s, 1H), 7.43 (d, J = 8.4 Hz, 2H), 7.38 (d, J = 8.4 Hz, 2H), 6.90-6.87 (m, 2H), 6.22 (s, 2H), 5.08 (d, J = 3.6 Hz, 1H), 4.93-4.90 (m, 1H), 4.53-4.50 (m, 1H), 4.44-4.40 (m, 1H), 4.27 (bs, 1H), 3.76-3.69 (m, 1H), 3.62-3.55 (m, 2H), 3.46-3.43 (m, 2H), 2.82-2.77 (m, 2H), 2.45 (s, 3H), 2.26-2.21 (m, 1H), 2.12-1.98 (m, 4H), 1.91-1.77 (m, 3H), 1.68-1.60 (m, 2H), 1.52-1.45 (m, 4H), 1.37 (d, J = 6.8 Hz, 3H), 1.33-1.24 (m, 10H), 0.93 (s, 9H); LC/MS: 910.2 (M + 1)⁺. |
| 25 | 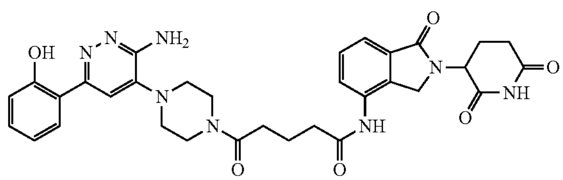 [SMILES: Nc1nnc(-c2ccccc2O)cc1N1CCN(C(=O)CCCC(=O)Nc2cccc3c2CN(C2CCC(=O)NC2=O)C3=O)CC1] | δ 14.25 (s, 1H), 11.00 (s, 1H), 9.75 (s, 1H), 7.90 (d, J = 8.0 Hz, 1H), 7.80 (d, J = 6.8 Hz, 1H), 7.52-7.47 (m, 3H), 7.24 (dd, J = 8.4 Hz, 6.8 Hz, 1H), 6.90-6.86 (m, 2H), 6.40 (m, 2H), 5.16-5.12 (m, 1H), 4.36 (q, J = 17.6 Hz, 2H), 3.68 (bs, 4H), 3.03-2.91 (m, 4H), 2.67-2.57 (m, 3H), 2.38-2.33 (m, 7H); LC/MS: 627.3 (M + 1)⁺. |
| 26 | 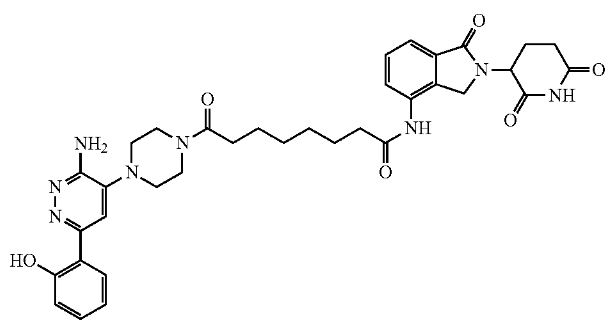 [SMILES: Nc1nnc(-c2ccccc2O)cc1N1CCN(C(=O)CCCCCCC(=O)Nc2cccc3c2CN(C2CCC(=O)NC2=O)C3=O)CC1] | δ 14.21 (s, 1H), 11.00 (s, 1H), 9.75 (s, 1H), 7.90 (d, J = 8.0 Hz, 1H), 7.80 (d, J = 6.8 Hz, 1H), 7.52-7.47 (m, 3H), 7.24 (t, J = 6.8 Hz, 1H), 6.89 (d, J = 7.6 Hz, 2H), 6.40 (bs, 2H), 5.16-5.12 (dd, J₁ = 5.2, J₂ = 8.0 Hz, 1H), 4.36 (d, J = 8.0, 2H), 3.68 (bs, 4H), 3.05 (d, J = 16.8 Hz, 4H), 2.90-2.82 (m, 2H), 2.67-2.62 (m, 2H), 2.38-2.08 (m, 7H), 2.04-2.00 (m, 1H), 1.62-1.54 (m, 4H); LC/MS: 669.3 (M + 1)⁺. |
| 27 | 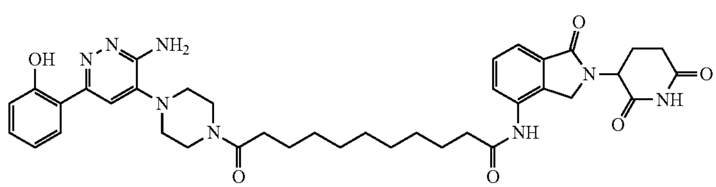 [SMILES: Nc1nnc(-c2ccccc2O)cc1N1CCN(C(=O)CCCCCCCCCC(=O)Nc2cccc3c2CN(C2CCC(=O)NC2=O)C3=O)CC1] | δ 14.15 (s, 1H), 11.01 (s, 1H), 9.74 (s, 1H), 7.92-7.89 (m, 1H), 7.81-7.79 (m, 1H), 7.53-7.45 (m, 3H), 7.26-7.21 (m, 1H), 6.90-6.86 (m, 2H), 6.40 (s, 2H), 5.16-5.12 (dd, J₁ = 5.2, J₂ = 8.0 Hz, 1H), 4.35 (q, J₁ = 17.2, J₂ = 8.4 Hz, 2H), 3.67 (bs, 4H), 3.07-3.03 (m, 4H), 2.93-2.88 (m, 1H), 2.62-2.58 (m, 2H), 2.36-2.29 (m, 4H), 2.04-2.01 (m, 2H), 1.60-1.51 (m, 4H), 1.26 (bs, 9H); LC/MS: 711.2 (M + 1)⁺. |
| 28 | 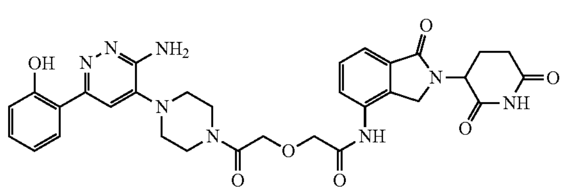 [SMILES: Nc1nnc(-c2ccccc2O)cc1N1CCN(C(=O)COCC(=O)Nc2cccc3c2CN(C2CCC(=O)NC2=O)C3=O)CC1] | δ 14.12 (s, 1H), 11.01 (s, 1H), 10.41 (s, 1H), 7.95-7.89 (m, 2H), 7.55-7.50 (m, 3H), 7.26-7.21 (m, 1H), 6.90-6.87 (m, 2H), 6.42 (s, 2H), 5.18-5.13 (dd, J₁ = 4.8, J₂ = 8.4 Hz, 1H), 4.51 (s, 2H), 4.45 (d, J = 8.4 Hz, 2H), 4.25 (s, 2H), 3.72-3.63 (m, 4H), 3.00 (bs, 4H), 2.96-2.87 (m, 1H), 2.63-2.55 (m, 1H), 2.40-2.35 (m, 1H), 2.05-2.03 (m, 1H); LC/MS: 629.3 (M + 1)⁺. |

TABLE-26-continued

| Comp No. | Structure | Characterization Data ¹H NMR (400 MHz, DMSO-d₆) |
|---|---|---|
| 29 | 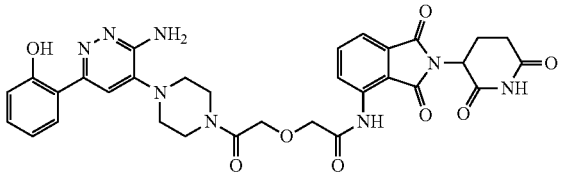 [SMILES: Nc1nnc(-c2ccccc2O)cc1N1CCN(C(=O)COCC(=O)Nc2cccc3c2C(=O)N(C2CCC(=O)NC2=O)C3=O)CC1] | δ 14.12 (s, 1H), 11.13 (s, 1H), 10.47 (s, 1H), 8.74 (d, J = 8.8 Hz, 1H), 7.90-7.88 (m, 2H), 7.64 (d, J = 7.2 Hz, 1H), 7.50 (s, 1H), 7.25-7.21 (m, 1H), 6.89-6.84 (m, 2H), 6.40 (s, 2H), 5.16-5.12 (dd, $J_1$ = 5.2 Hz, $J_2$ = 12.4 Hz, 1H), 4.54 (s, 2H), 4.25 (s, 2H), 3.70-3.61 (m, 4H), 3.09 (bs, 4H), 2.86-2.83 (m, 1H), 2.67-2.55 (m, 2H), 2.05-2.02 (m, 1H); LC/MS: 643.1 (M + 1)⁺. |
| 30 | 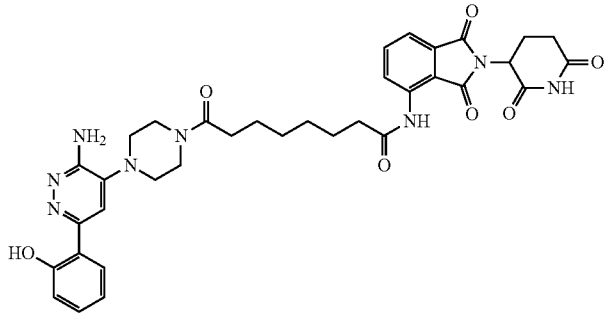 [SMILES: Nc1nnc(-c2ccccc2O)cc1N1CCN(C(=O)CCCCCCC(=O)Nc2cccc3c2C(=O)N(C2CCC(=O)NC2=O)C3=O)CC1] | ¹H NMR (400 MHz, MeOH-d₄): δ 14.15 (s, 1H), 11.13 (s, 1H), 9.68 (s, 1H), 8.46 (d, J = 8.8 Hz, 1H), 7.90 (d, J = 7.2 Hz, 1H), 7.81 (t, J = 7.8 Hz, 1H), 7.60 (d, J = 7.6 Hz, 1H), 7.52 (s, 1H), 7.25-7.21 (m, 1H), 6.89-6.86 (m, 2H), 6.39 (s, 2H), 5.16-5.11 (dd, $J_1$ = 5.6 Hz, $J_2$ = 12.8 Hz, 1H), 3.67 (s, 4H), 3.07-3.03 (m, 4H), 2.90-2.86 (m, 1H), 2.67-2.54 (m, 1H), 2.37-2.34 (m, 3H), 2.33-2.32 (m, 2H), 2.08-2.04 (m, 1H), 1.65-1.62 (m, 2H), 1.55-1.52 (m, 2H), 1.23-1.15 (m, 4H); LC/MS: 682.73 (M + 1)⁺. |
| 31 | 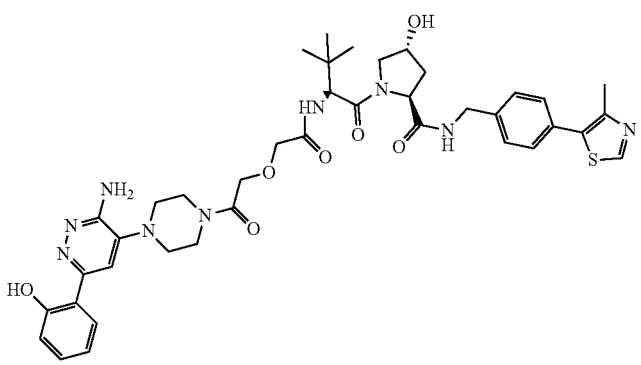 [SMILES: Cc1ncsc1-c1ccc(CNC(=O)[C@@H]2C[C@@H](O)CN2C(=O)[C@@H](NC(=O)COCC(=O)N2CCN(c3cc(-c4ccccc4O)nnc3N)CC2)C(C)(C)C)cc1] | δ 14.13 (s, 1H), 8.96 (s, 1H), 8.58-8.53 (m, 1H), 7.91-7.88 (dd, $J_1$ = 1.6 Hz, $J_2$ = 8.4 Hz, 1H), 7.79 (d, J = 9.2 Hz, 1H), 7.51 (s, 1H), 7.39 (s, 4H), 7.24-7.21 (m, 1H), 6.90-6.86 (m, 2H), 6.41 (s, 2H), 5.14 (d, J = 4.0 Hz, 1H), 4.58-4.57 (d, J = 9.6 Hz, 1H), 4.46-4.33 (m, 5H), 4.27-4.23 (m, 1H), 4.05-4.02 (m, 2H), 3.69-3.61 (m, 6H), 3.08 (s, 4H), 2.49 (s, 3H), 2.09-2.01 (m, 1H), 1.87-1.76 (m, 1H), 0.94 (s, 9H); LC/MS: 800.1 (M + 1)⁺. |
| 32 | 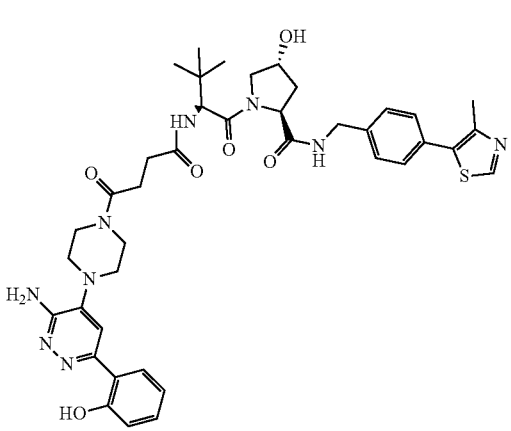 [SMILES: Cc1ncsc1-c1ccc(CNC(=O)[C@@H]2C[C@@H](O)CN2C(=O)[C@@H](NC(=O)CCC(=O)N2CCN(c3cc(-c4ccccc4O)nnc3N)CC2)C(C)(C)C)cc1] | δ 14.15 (s, 1H), 8.98 (s, 1H), 8.54 (s, 1H), 7.92 (t, J = 8.3 Hz, 2H), 7.52 (s, 1H), 7.40 (q, J = 8.3 Hz, 4H), 7.22 (t, J = 7.3 Hz, 1H), 6.88-6.85 (m, 2H), 6.40 (bs, 2H), 5.10 (d, J = 3.4 Hz, 1H), 4.53 (d, J = 9.3 Hz, 1H), 4.40 (t, J = 8.34 Hz, 2H), 4.30 (bs, 1H), 4.23 (d, J = 6.0 Hz, 1H), 3.69-3.63 (m, 6H), 3.09-3.03 (m, 4H), 2.57 (t, J = 5.4 Hz, 2H), 2.44 (s, 3H), 2.42-2.32 (m, 2H), 2.08-1.90 (m, 2H), 0.94 (s, 9H); LC/MS: 784.1 (M + 1)⁺. |

TABLE-26-continued

| Comp No. | Structure | Characterization Data ¹H NMR (400 MHz, DMSO-d$_6$) |
|---|---|---|
| 33 | 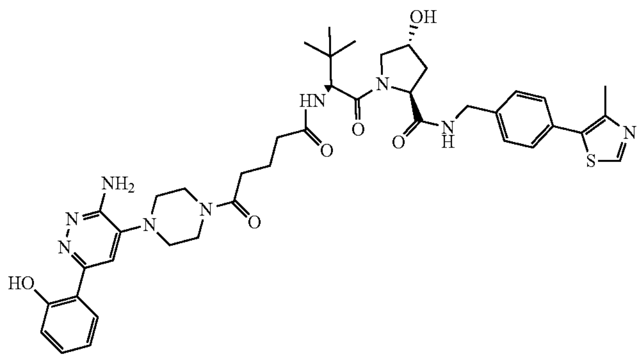 [SMILES: Cc1ncsc1-c1ccc(CNC(=O)[C@@H]2C[C@@H](O)CN2C(=O)[C@@H](NC(=O)CCCC(=O)N2CCN(c3cc(-c4ccccc4O)nnc3N)CC2)C(C)(C)C)cc1] | δ 14.15 (s, 1H), 8.97 (s, 1H), 8.53 (t, J = 5.8 Hz, 1H), 7.90 (d, J = 6.90 Hz, 2H), 7.53 (s, 1H), 7.41-7.36 (m, 4H), 7.25-7.21 (m, 1H), 6.89-6.85 (m, 2H), 6.40 (bs, 2H), 5.10 (d, J = 3.9 Hz, 1H), 4.55 (d, J = 9.3 Hz, 1H), 4.44-4.35 (m, 3H), 4.23-4.18 (m, 1H), 4.05 (q, J = 5.3 Hz, 1H), 3.67 (bs, 5H) 3.16-3.17 (m, 4H), 2.49 (s, 3H), 2.36-2.26 (m, 4H), 2.01-2.04 (m, 1H), 1.93-1.90 (m, 1H), 1.78-1.73 (m, 2H), 0.94 (s, 9H); LC/MS: 799.1 (M + 1)⁺. |
| 34 | 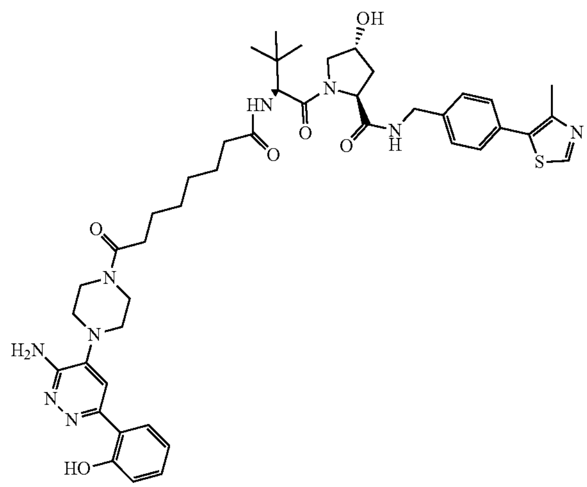 [SMILES: Cc1ncsc1-c1ccc(CNC(=O)[C@@H]2C[C@@H](O)CN2C(=O)[C@@H](NC(=O)CCCCCCC(=O)N2CCN(c3cc(-c4ccccc4O)nnc3N)CC2)C(C)(C)C)cc1] | δ 14.15 (s, 1H), 8.97 (s, 1H), 8.35 (d, J = 7.9 Hz, 1H), 7.91 (d, J = 7.8 Hz, 1H), 7.70 (d, J = 9.2 Hz, 1H), 7.53 (s,1H), 7.43 (d, J = 7.8 Hz, 2H), 7.38 (d, J = 8.3 Hz, 2H), 7.24 (t, J = 7.8 Hz, 1H), 6.85 (dd, J$_1$ = 5.3, J$_2$ = 7.9 Hz, 2H), 6.40 (s, 2H), 5.07 (d, J = 3.4 Hz, 1H), 4.91 (t, J = 7.3 Hz, 1H), 4.51 (d, J = 9.3 Hz, 1H), 4.43 (t, J = 7.9 Hz, 1H), 4.03 (d, J = 6.9 Hz, 1H), 3.00 (bs, 4H), 3.59 (bs, 2H), 3.07 (d, J = 17.2 Hz, 4H), 2.45 (s, 3H), 2.36-2.30 (m, 1H), 2.23 (dd, J$_1$ = 6.9, J$_2$ = 7.8 Hz, 1H), 2.21 (dd, J$_1$ = 6.8, J$_2$ = 6.3 Hz, 1H), 2.08-1.90 (m, 1H), 1.82-1.76 (m, 1H), 1.50 (dd, J$_1$ = 6.4, J$_2$ = 6.8 Hz, 4H), 1.37 (d, J = 6.9 Hz, 3H) 1.28-1.15 (m, 3H), 0.93 (s, 9H); LC/MS: 840.2 (M + 1)⁺. |
| 35 | 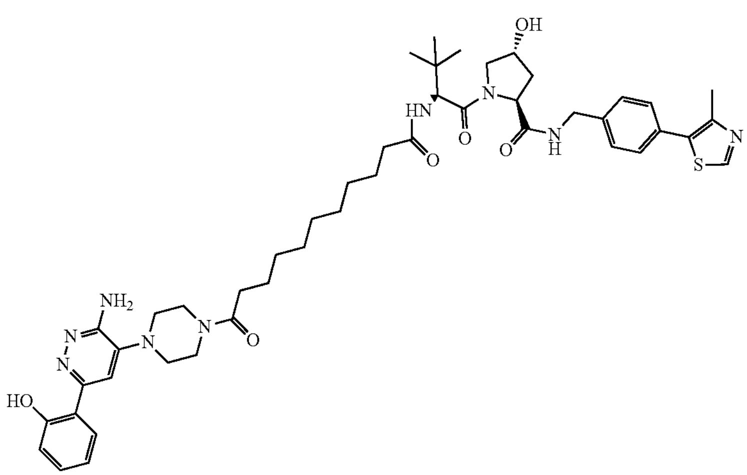 [SMILES: Cc1ncsc1-c1ccc(CNC(=O)[C@@H]2C[C@@H](O)CN2C(=O)[C@@H](NC(=O)CCCCCCCCCC(=O)N2CCN(c3cc(-c4ccccc4O)nnc3N)CC2)C(C)(C)C)cc1] | δ 8.97 (s, 1H), 8.53 (t, J = 6.15 Hz, 1H), 7.91-7.89 (m, 1H) 7.81 (d, J = 9.2 Hz, 2H), 7.52 (s, 1H), 7.44-7.36 (m, 4H), 7.25-7.21 (m, 1H), 6.90-6.86 (m, 2H), 6.39 (bs, 2H), 5.10 (d, J = 3.6 Hz, 1H), 4.53 (d, J = 9.3 Hz, 1H), 4.50-4.45 (m, 2H), 4.44-4.34 (m, 3H), 4.28-4.18 (m, 1H), 3.64-3.44 (m, 7H), 3.1-3.02 (m, 4H), 2.40 (s, 3H), 2.36 (s, 3H), 1.90-2.20 (m, 4H), 1.91-1.85 (m, 1H), 1.50-1.20 (m, 9H), 1.26 (s, 9H); LC/MS: 882.2 (M + 1)⁺. |

TABLE-26-continued

| Comp No. | Structure | Characterization Data<br>¹H NMR (400 MHz, DMSO-d₆) |
|---|---|---|
| 36 | 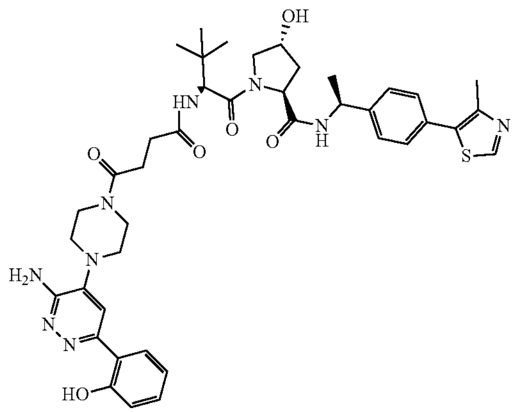 [SMILES: Cc1ncsc1-c1ccc([C@H](C)NC(=O)[C@@H]2C[C@@H](O)CN2C(=O)[C@@H](NC(=O)CCC(=O)N2CCN(c3cc(-c4ccccc4O)nnc3N)CC2)C(C)(C)C)cc1] | δ 14.15 (s, 1H), 8.98 (s, 1H), 8.35 (d, J = 7.8 Hz, 1H), 7.92-6.92 (m, 2H), 7.53 (s, 1H), 7.43 (d, J = 8.3 Hz, 2H), 7.37 (d, J = 8.3 Hz, 2H), 7.26-7.21 (m, 1H), 6.90-6.87 (m, 2H), 6.40 (bs, 2H), 5.08 (d, J = 3.9 Hz, 1H), 4.89 (d, J = 7.3 Hz, 1H), 4.51 (d, J = 8.8 Hz, 1H), 4.42 (t, J = 7.8 Hz, 1H), 4.28 (bs, 1H), 3.69 (bs, 4H), 3.61-3.59 (m, 2H), 3.09-3.03 (bs, 4H), 2.62-2.54 (m, 2H), 2.45 (s, 3H), 2.44-2.40 (m, 2H), 2.0 (d, J = 7.6 Hz, 1H), 1.79 (s, 1H), 1.37 (d, J = 6.8 Hz, 3H), 0.94 (s, 9H); LC/MS: 798.1 (M + 1)⁺. |
| 37 | 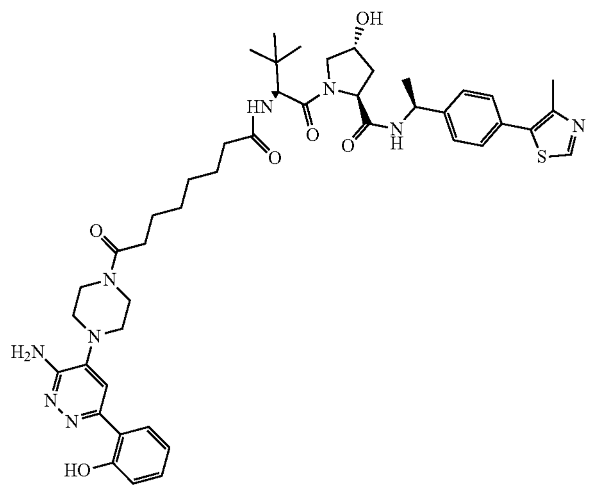 [SMILES: Cc1ncsc1-c1ccc([C@H](C)NC(=O)[C@@H]2C[C@@H](O)CN2C(=O)[C@@H](NC(=O)CCCCCCC(=O)N2CCN(c3cc(-c4ccccc4O)nnc3N)CC2)C(C)(C)C)cc1] | δ 14.18 (s, 1H), 8.97 (s, 1H), 8.35 (d, J = 7.9 Hz, 1H), 7.92 (d, J = 1.5 Hz, 1H), 7.78 (d, J = 9.2 Hz, 1H), 7.53 (s, 1H), 7.43 (d, J = 8.3 Hz, 2H), 7.37 (d, J = 8.3 Hz, 2H), 7.25-7.21 (m, 1H), 6.88-6.86 (m, 2H), 6.40 (bs, 2H), 5.06 (d, J = 4.0 Hz, 1H), 4.90 (t, J = 7.4 Hz, 1H), 4.51 (d, J = 9.3 Hz, 1H), 4.41 (t, J = 8.4 Hz, 1H), 4.27 (bs, 1H), 3.68 (bs, 4H), 3.59 (s, 2H), 3.08 (dd, J₁ = 5.4 Hz, 4H), 2.45 (s, 3H), 2.35 (t, J = 7.8 Hz, 2H), 2.28-2.21 (m, 1H), 2.15-2.02 (m, 1H), 1.99-1.90 (m, 1H), 1.82-1.76 (m, 1H), 1.50-1.42 (m, 4H), 1.37 (d, J = 7.4 Hz, 3H), 1.28-1.15 (m, 4H), 0.93 (s, 9H); LC/MS: 854.2 (M + 1)⁺. |
| 38 | 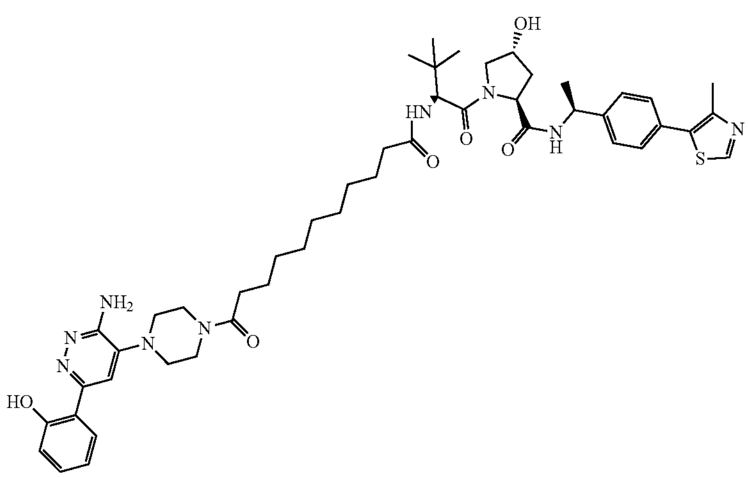 [SMILES: Cc1ncsc1-c1ccc([C@H](C)NC(=O)[C@@H]2C[C@@H](O)CN2C(=O)[C@@H](NC(=O)CCCCCCCCCC(=O)N2CCN(c3cc(-c4ccccc4O)nnc3N)CC2)C(C)(C)C)cc1] | δ 14.15 (s, 1H), 8.97 (s, 1H), 8.34 (d, J = 7.6 Hz, 1H), 7.92-7.89 (dd, J₁ = 1.6 Hz, J₂ = 8.4 Hz, 1H), 7.75 (d, J = 9.6 Hz, 1H), 7.53 (s, 1H), 7.43 (d, J = 8.4 Hz, 2H), 7.37 (d, J = 8.0 Hz, 2H), 7.25-7.21 (m, 1H), 6.90-6.86 (m, 2H), 6.39 (s, 2H), 5.07 (d, J = 3.6 Hz, 1H), 4.91 (t, J = 14.4 Hz, 1H), 4.51 (d, J = 9.2 Hz, 1H), 4.41 (t, J = 8.0 Hz, 1H), 4.27 (bs, 1H), 3.67 (bs, 4H), 3.60-3.59 (m, 2H), 3.07-3.03 (m, 4H), 2.52-2.45 (m, 4H), 2.62-2.20 (m, 2H), 2.13-2.08 (m, 1H), 2.00-1.98 (m, 1H), 1.82-1.79 (m, 1H), 1.51-1.44 (m, 4H), 1.38-1.33 (m, 4H), 1.26-1.25 (m, 9H), 0.93 (s, 9H); LC/MS: 896.2 (M + 1)⁺. |
| 39 | 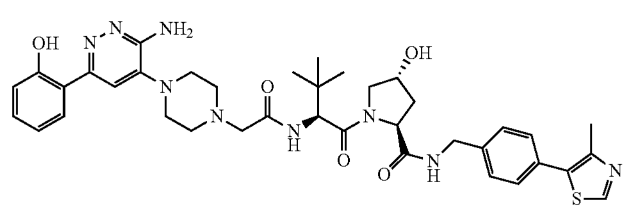 [SMILES: Cc1ncsc1-c1ccc(CNC(=O)[C@@H]2C[C@@H](O)CN2C(=O)[C@@H](NC(=O)CN2CCN(c3cc(-c4ccccc4O)nnc3N)CC2)C(C)(C)C)cc1] | δ 14.14 (s, 1H), 8.86 (s, 1H), 8.57 (s, 1H), 7.92 (d, J = 6.8 Hz, 1H), 7.80 (d, J = 9.8 Hz, 1H), 7.50 (s, 1H), 7.41-7.36 (dd, J₁ = 8.4 Hz, J₂ = 8.3 Hz, 5H), 7.23-7.21 (dd, J₁ = 6.6 Hz, J₂ = 1.5 Hz, 1H), 6.89-6.84 (m, 1H), 6.25 (bs, 2H), 5.13 (d, J = 3.4 Hz, 1H), 4.55 (d, J = 9.8 Hz, 1H), 4.45 (t, J = 7.9 Hz, 1H), 4.37-4.20 (m, 2H), 3.67- |

TABLE-26-continued

| Comp No. | Structure | Characterization Data ¹H NMR (400 MHz, DMSO-d₆) |
|---|---|---|
| | | 3.60 (m, 2H), 3.17-3.0 (m, 7H), 2.73 (bs, 4H), 2.40 (s, 3H), 2.09-2.0 (m, 1H), 1.95-1.85 (m, 1H), 0.98 (s, 9H); LC/MS: 742.3 (M + 1)⁺. |
| 40 | 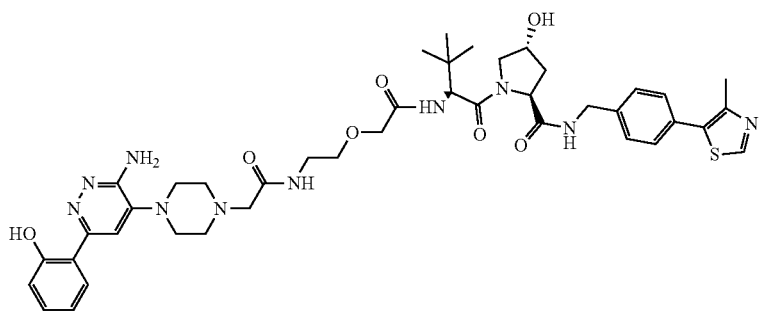 [SMILES: Cc1ncsc1-c1ccc(CNC(=O)[C@@H]2C[C@@H](O)CN2C(=O)[C@@H](NC(=O)COCCNC(=O)CN2CCN(c3cc(-c4ccccc4O)nnc3N)CC2)C(C)(C)C)cc1] | δ 14.20 (s, 1H), 8.96 (s, 1H), 8.54 (bs, 1H), 7.91-7.88 (m, 2H), 7.47 (d, J = 3.6 Hz, 2H), 7.44-7.38 (m, 5H), 7.24-7.22 (m, 1H), 6.88 (d, J = 8.4 Hz, 2H), 6.23 (s, 2H), 5.12 (d, J = 3.6 Hz, 1H), 4.55 (d, J = 9.2 Hz, 1H), 4.42-4.33 (m, 3H), 4.27-4.26 (m, 1H), 3.98-3.97 (m, 2H), 3.62-3.59 (m, 2H), 3.55-3.52 (m, 2H), 3.17-3.15 (m, 4H), 3.03 (s, 2H), 2.67-2.66 (m, 5H), 2.43 (d, J = 4.4 Hz, 3H), 2.10-2.0 (m, 1H), 1.92-1.85 (m, 1H), 0.94 (s, 9H); LC/MS: 843.1 (M + 1)⁺. |
| 41 | 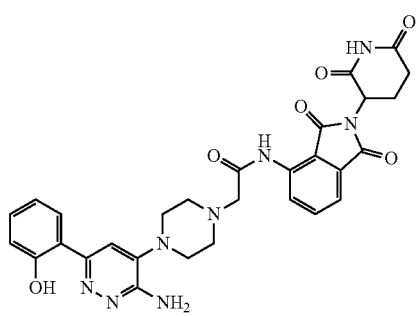 [SMILES: Nc1nnc(-c2ccccc2O)cc1N1CCN(CC(=O)Nc2cccc3c2C(=O)N(C2CCC(=O)NC2=O)C3=O)CC1] | δ 14.21 (s, 1H), 11.07 (s, 1H), 11.00 (s, 1H), 8.80 (d, J = 8.4 Hz, 1H), 7.94 (d, J = 6.8 Hz, 1H), 7.88-7.84 (m, 1H), 7.61-7.60 (d, J = 7.2 Hz, 1H), 7.52 (s, 1H), 7.27-7.22 (m, 1H), 6.90-6.87 (m, 2H), 6.28 (s, 2H), 5.13-5.08 (dd, J₁ = 5.6 Hz, J₂ = 12.8 Hz, 1H), 3.41-3.35 (m, 2H), 3.25 (s, 3H), 2.84-2.78 (m, 5H), 2.59-2.55 (m, 1H), 2.45-2.44 (m, 1H), 2.08-2.04 (m, 2H); LC/MS: 585.1 (M + 1)⁺. |
| 42 | 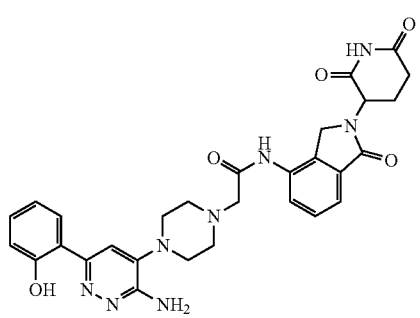 [SMILES: Nc1nnc(-c2ccccc2O)cc1N1CCN(CC(=O)Nc2cccc3c2CN(C2CCC(=O)NC2=O)C3=O)CC1] | δ 14.21 (s, 1H), 10.98 (s, 1H), 9.80 (s, 1H), 7.91 (d, J = 7.2 Hz, 1H), 7.81 (d, J = 7.6 Hz, 1H), 7.56-7.50 (m, 3H), 7.26-7.22 (m, 1H), 6.91-6.88 (m, 2H), 6.26 (s, 2H), 5.14-5.09 (dd, J₁ = 5.2 Hz, J₂ = 13.2, 1H), 4.46-4.35 (m, 2H), 3.20 (s, 4H), 2.94-2.85 (m, 1H), 2.80 (s, 4H), 2.66 (s, 2H), 2.45-2.38 (m, 1H), 2.32-1.98 (m, 2H); LC/MS: 571.1 (M + 1)⁺. |
| 43 | 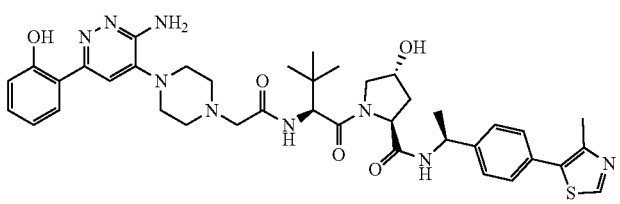 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4O)nnc3N)CC2)C(C)(C)C)cc1] | δ 14.22 (s, 1H), 8.97 (s, 1H), 8.41 (d, J = 7.8 Hz, 1H), 7.95 (d, J = 7.4 Hz, 1H), 7.77 (d, J = 9.8 Hz, 1H), 7.56 (s, 1H), 7.43 (d, J = 8.3 Hz, 2H), 7.36 (d, J = 8.3 Hz, 2H), 7.25 (t, J = 6.8 Hz, 1H), 6.88 (dd, J₁ = 5.8 Hz, J₂ = 4.4 Hz, 2H), 6.25 (s, 2H), 5.11 (d, J = 3.5 Hz, 1H), 4.89 (d, J = 7.3 Hz, 1H), 4.53 (d, J = 9.8 Hz, 1H), 4.44 (t, J = 7.8 Hz, 1H), 4.29 (bs, 1H), 3.60 (d, J = 5.9 Hz, 2H), 3.17 (bs, 4H), 3.13 (s, 1H), 3.0 (d, J = 16.0 Hz, 1H), 2.69 (dd, J₁ = 4.4 Hz, J₂ = 2.0 Hz, 4H), 2.45 (s, 3H), 2.08 (d, J = 13.2 Hz, 1H), 1.81-1.74 (m, 1H), 1.36 (d, J = 6.9 Hz, 3H), 0.96 (s, 9H); LC/MS: 756.1 (M + 1)⁺. |

TABLE-26-continued

| Comp No. | Structure | Characterization Data <br> ¹H NMR (400 MHz, DMSO-d₆) |
|---|---|---|
| 44 | 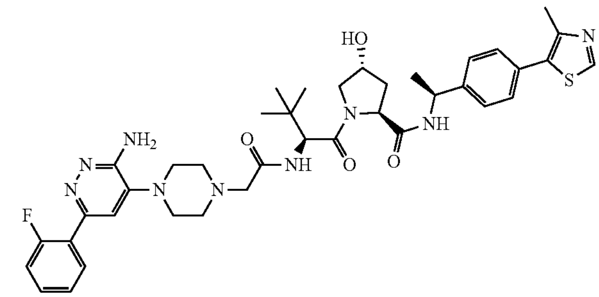 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4F)nnc3N)CC2)C(C)(C)C)cc1] | δ 8.97 (s, 1H), 8.41 (t, J = 7.3 Hz, 1H), 7.83 (t, J = 7.3 Hz, 1H), 7.77 (s, 1H), 7.48-7.27 (m, 7H), 7.16 (s, 1H), 6.09 (bs, 2H), 5.11 (d, J = 3.4 Hz, 1H), 4.88 (t, J = 6.9 Hz, 1H), 4.53 (d, J = 9.4 Hz, 1H), 4.43 (t, J = 8.3 Hz, 1H), 4.23 (bs, 1H), 3.62-3.55 (m, 2H), 3.15 (d, J = 11.3 Hz, 2H), 3.07 (bs, 4H), 2.71 (bs, 4H), 2.45 (bs, 3H), 2.08-2.02 (m, 1H), 1.79-1.73 (m, 1H), 1.36 (d, J = 6.8 Hz, 3H), 0.94 (s, 9H); LC/MS: 758.4 (M + 1)⁺. |
| 45 | 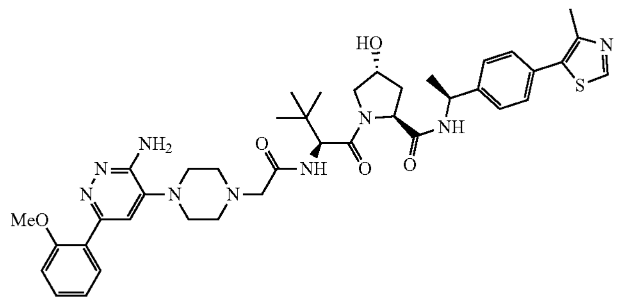 [SMILES: COc1ccccc1-c1cc(N2CCN(CC(=O)N[C@H](C(=O)N3C[C@H](O)C[C@H]3C(=O)N[C@@H](C)c3ccc(-c4scnc4C)cc3)C(C)(C)C)CC2)c(N)nn1] | δ 8.97 (s, 1H), 8.40 (d, J = 7.2 Hz, 1H), 7.60 (dd, J = 7.2 Hz, 1.2 Hz, 1H), 7.43-7.34 (m, 6H), 7.20 (s, 1H), 7.12 (d, J = 8.4 Hz, 1H), 7.04 (dd, J = 7.6 Hz, 7.2 Hz, 1H), 5.95 (s, 2H), 5.11 (d, J = 3.6 Hz, 1H), 4.92-4.87 (m, 1H), 4.52-4.50 (m, 1H), 4.45-4.41 (m, 1H), 4.28 (s, 1H), 3.81 (s, 3H), 3.63-3.56 (m, 2H), 3.25-3.05 (m, 6H), 2.70-2.60 (m, 3H), 2.45 (s, 4H), 2.08-2.04 (m, 1H), 1.80-1.71 (m, 1H), 1.36 (d, J = 6.8 Hz, 3H), 0.93 (s, 9H); LC/MS: 770.1 (M + 1)⁺. |
| 46 | 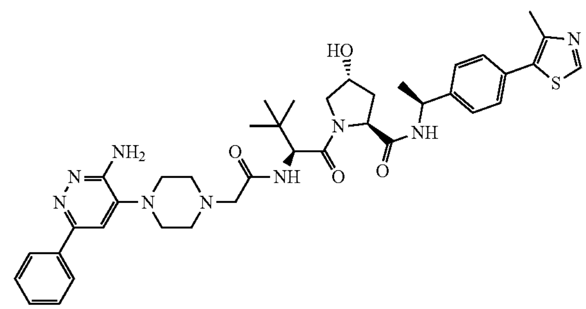 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4)nnc3N)CC2)C(C)(C)C)cc1] | δ 8.97 (s, 1H), 8.41 (d, J = 7.6 Hz, 1H), 8.00 (d, J = 7.6 Hz, 2H), 7.78 (d, J = 9.2 Hz, 1H), 7.47-7.33 (m, 9H), 6.00 (s, 2H), 5.11 (d, J = 3.6 Hz, 1H), 4.91-4.87 (m, 1H), 4.54-4.52 (m, 1H), 4.46-4.42 (m, 1H), 4.29 (s, 1H), 3.62-3.56 (m, 2H), 3.18-3.03 (m, 6H), 2.80-2.67 (m, 4H), 2.45 (s, 3H), 1.80-1.73 (m, 1H), 1.28 (d, J = 6.8 Hz, 3H), 0.96 (s, 9H); LC/MS: 740.2 (M + 1)⁺. |

Example-II: Synthesis of (3R,5S)-1-((S)-2-(2-(4-(3-amino-6-(2-hydroxy phenyl)pyridazin-4-yl) piperazin-1-yl)acetamido)-3,3-dimethylbutanoyl)-5-(((S)-1-(4-(4-methylthiazol-5-yl)phenyl) ethyl)carbamoyl) pyrrolidin-3-yl acetate (Compound-47)

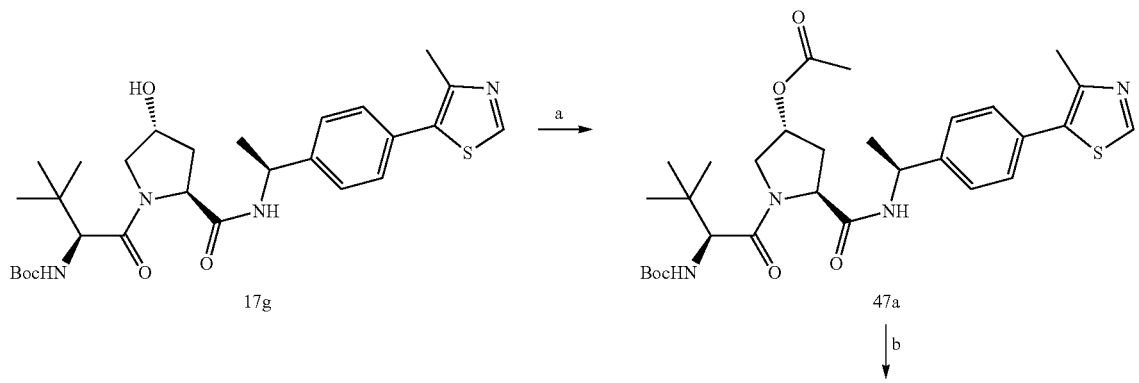

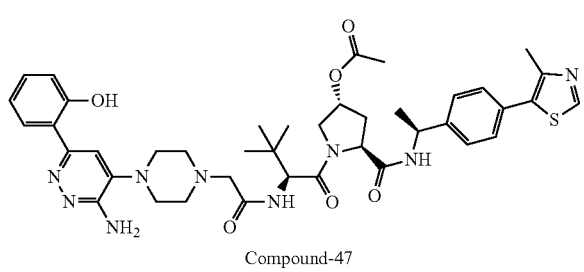

Compound-47

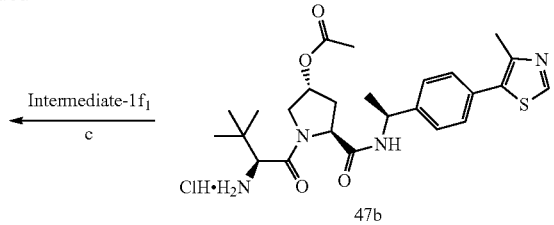

47b

Conditions: a) Acetic anhydride, DMAP, DCM, RT, 16 h; b) 4M HCl in 1,4-dioxane, DCM, RT, 5 h; c) HATU, DIPEA, DMF, 0° C.-RT, 16 h.

Step-a: Synthesis of (3R,5S)-1-((S)-2-((tert-butoxycarbonyl)amino)-3,3-dimethylbutanoyl)-5-(((S)-1-(4-(4-methylthiazol-5-yl)phenyl)ethyl)carbamoyl) pyrrolidin-3-yl acetate. (47a)

To a stirred solution of tert-butyl ((S)-1-(((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl) carbamate (1f, 0.50 g, 0.91 mmol) and acetic anhydride (0.093 g, 0.91 mmol) in DCM was added DMAP (1.60 g, 1.36 mmol) at RT and stirring was continued for 16 h at RT. After completion of the reaction (monitored by TLC) the reaction mixture was quenched with water (10 mL) and extracted with DCM (2×15 mL). The combined organic layer was washed with water (20 mL), brine (20 mL), dried over anhydrous sodium sulphate and concentrated under vacuum to give the residue which was purified by combi flash column chomatography using 5% MeOH in DCM as eluent to afford the title compound as a brown solid (0.40 g, 74.34%). $^1$H NMR (400 MHz, DMSO-$d_6$): δ 8.90 (s, 1H), 8.44 (d, J=7.2 Hz, 1H), 7.46-7.34 (m, 4H), 6.63 (d, J=7.6 Hz, 1H), 5.17 (s, 1H), 4.92-4.89 (m, 1H), 4.52-4.48 (m, 1H), 4.05-3.96 (m, 2H), 3.69-3.66 (m, 1H), 2.44 (s, 3H), 2.27-2.22 (m, 1H), 1.99-1.90 (m, 4H), 1.48-1.37 (m, 12H), 0.99 (s, 9H); LC-MS: m/z 587.1 (M+1)$^+$.

Step-b: Synthesis of (3R,5S)-1-((S)-2-amino-3,3-dimethylbutanoyl)-5-(((S)-1-(4-(4-methyl thiazol-5-yl)phenyl)ethyl)carbamoyl)pyrrolidin-3-yl acetate hydrochloride (47b)

To a stirred solution of (3R,5S)-1-((S)-2-((tert-butoxycarbonyl)amino)-3,3-dimethyl butanoyl)-5-(((S)-1-(4-(4-methylthiazol-5-yl)phenyl)ethyl)carbamoyl)pyrrolidin-3-yl acetate (0.40 g, 0.68 mmol) in DCM (4 mL) was added 4 M HCl in 1,4-dioxane (4 mL) at RT under nitrogen atmosphere and stirring was continued for 5 h at RT. After completion of the reaction (monitored by TLC) the reaction mixture was evaporated under reduced pressure to get crude brown solid compound. The obtained brown solid was washed with diethyl ether (2×50 mL), filtered and dried under vacuum to afford the title compound (0.3 g, 84.26%). $^1$H NMR (400 MHz, DMSO-$d_6$): δ 9.02 (s, 1H), 8.63 (d, J=7.4 Hz, 1H), 8.13-8.08 (m, 3H), 7.45-7.37 (m, 4H), 5.23 (bs, 1H), 4.94-4.90 (m, 1H), 4.57-4.53 (m, 1H), 3.98-3.93 (m, 2H), 3.70-3.66 (m, 1H), 3.39-3.37 (m, 1H), 2.46 (s, 3H), 2.32-2.28 (m, 1H), 2.08-1.98 (m, 2H), 1.81-1.72 (m, 1H), 1.38 (d, J=6.8 Hz, 3H), 1.02 (s, 9H); LC-MS: m/z 487.1 (M+1)$^+$.

Step-c: Synthesis of (3R,5S)-1-((S)-2-(2-(4-(3-amino-6-(2-hydroxyphenyl)pyridazin-4-yl) piperazin-1-yl)acetamido)-3,3-dimethylbutanoyl)-5-(((S)-1-(4-(4-methylthiazol-5-yl)phenyl)ethyl)carbamoyl) pyrrolidin-3-yl acetate (compound 47)

The title compound was synthesized using the same procedure which was followed for compound-1 using (3R,5S)-1-((S)-2-amino-3,3-dimethylbutanoyl)-5-(((S)-1-(4-(4-methylthiazol-5-yl)phenyl)ethyl)carbamoyl)pyrrolidin-3-yl acetate hydrochloride and 2-(4-(3-amino-6-(2-hydroxyphenyl)pyridazin-4-yl)piperazin-1-yl)acetic acid as starting materials (brown solid, yield: 14%): $^1$H NMR (400 MHz, DMSO-$d_6$): δ 14.22 (s, 1H), 8.97 (s, 1H), 8.43 (d, J=7.3 Hz, 1H), 7.95 (d, J=8.0 Hz, 1H), 7.73 (d, J=8.8 Hz, 1H), 7.50 (s, 1H), 7.43 (d, J=7.9 Hz, 2H), 7.36 (d, J=7.8 Hz, 2H), 7.25 (t, J=7.8 Hz, 1H), 6.89 (t, J=3.9 Hz, 2H), 6.26 (bs, 2H), 5.20 (bs, 1H), 4.90 (t, J=7.0 Hz, 1H), 4.49-4.39 (m, 2H), 3.92 (d, J=11.7 Hz, 1H), 3.77 (d, J=7.8 Hz, 1H), 3.17 (bs, 4H), 3.02 (d, J=5.3 Hz, 2H), 2.72 (bs, 4H), 2.45 (s, 3H), 2.32-2.24 (m, 1H), 2.01 (s, 3H), 1.97 (d, J=4.9 Hz, 1H), 1.38 (d, J=6.9 Hz, 3H), 0.98 (s, 9H); LC-MS: m/z 798.2 (M+1)$^+$.

Example-III: Synthesis of (3R,5S)-1-((S)-2-(2-(4-(3-amino-6-(2-hydroxyphenyl)pyridazin-4-yl)piperazin-1-yl)acetamido)-3,3-dimethylbutanoyl)-5-((4-(4-methylthiazol-5-yl)benzyl)carbamoyl)pyrrolidin-3-yl acetate (compound-48)

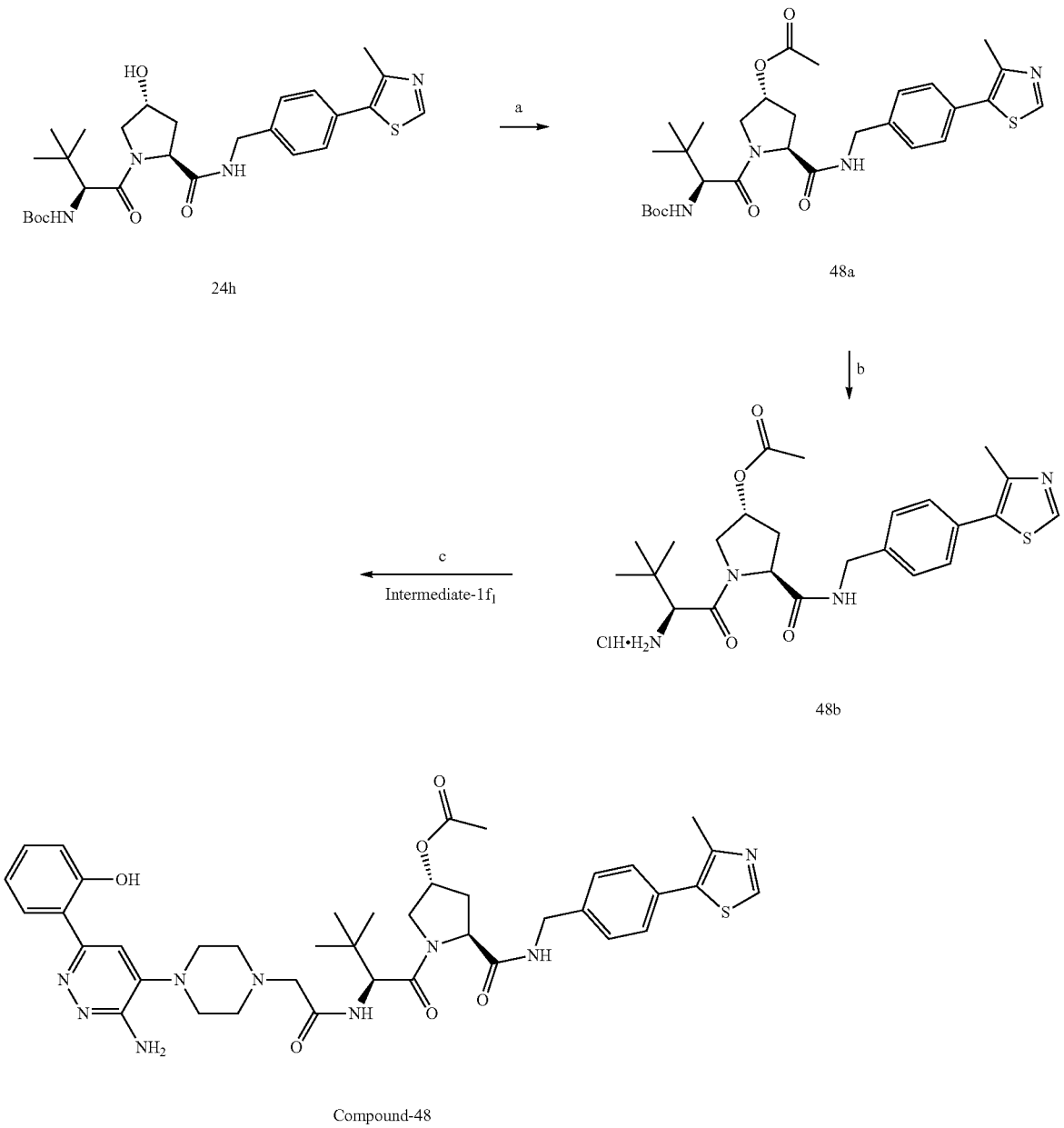

Conditions: a) Acetic anhydride, DMAP, DCM, RT, 16 h;
b) 4 M HCl in 1,4-dioxane, DCM, RT, 16 h;
c) HATU, DIPEA, DMF, 0° C.-RT, 16 h.

Step-a: Synthesis of (3R,5S)-1-((S)-2-((tert-butoxycarbonyl)amino)-3,3-dimethylbutanoyl)-5-((4-(4-methylthiazol-5-yl)benzyl)carbamoyl)pyrrolidin-3-yl acetate (48a)

The title compound was synthesized using the same procedure which was followed for Intermediate-47a using tert-butyl ((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)carbamate as starting material (Yield: 78%). $^1$H NMR (400 MHz, DMSO-$d_6$): δ 8.98 (s, 1H), 8.59 (t, J=5.9 Hz, 1H), 7.40 (t, J=8 Hz, 4H), 6.68 (d, J=8.8 Hz, 1H), 5.23 (bs, 1H), 4.50 (t, J=8.3 Hz, 1H). 4.44 (dd, $J_1$=6.9 Hz, $J_2$=6.3 Hz, 1H), 4.27-4.22 (m, 1H), 4.01 (d, J=8.8 Hz, 2H), 3.74 (d, J=9.7 Hz, 1H), 2.44 (s, 3H), 2.28-2.10 (m, 2H), 2.00 (s, 3H), 1.37 (s, 9H), 0.94 (s, 9H); LC-MS: m/z 573.1 (M+1)$^+$.

223

Step-b: Synthesis of (3R,5S)-1-((S)-2-amino-3,3-dimethylbutanoyl)-5-((4-(4-methylthiazol-5-yl)benzyl)carbamoyl)pyrrolidin-3-yl acetate hydrochloride (48b)

The title compound was synthesized using the same procedure which was followed for Intermediate-47b using (3R,5S)-1-((S)-2-((tert-butoxycarbonyl)amino)-3,3-dimethylbutanoyl)-5-((4-(4-methylthiazol-5-yl)benzyl)carbamoyl)pyrrolidin-3-yl acetate as starting material (Yield: 84.5%). $^1$H NMR (400 MHz, DMSO-d$_6$): δ 9.01 (s, 1H), 8.77 (t, J=5.9 Hz, 1H), 8.15 (bs, 3H), 7.40 (s, 4H), 5.3 (bs, 1H), 4.53 (t, J=7.8 Hz, 1H), 4.46-4.41 (m, 1H), 4.29-4.23 (m, 1H), 4.00-3.95 (m, 1H), 3.76-3.72 (m, 1H), 2.44 (s, 3H), 2.32-2.14 (m, 1H), 2.15-2.08 (m, 1H), 2.05 (s, 4H), 1.02 (s, 9H), LC-MS: m/z 473.1 (M+1)$^+$.

Step-c: Synthesis of (3R,5S)-1-((S)-2-(2-(4-(3-amino-6-(2-hydroxyphenyl)pyridazin-4-yl)piperazin-1-yl)acetamido)-3,3-dimethylbutanoyl)-5-(((S)-1-(4-(4-methylthiazol-5-yl)phenyl)ethyl)carbamoyl)pyrrolidin-3-yl acetate (Compound-48)

The title compound was synthesized using the same procedure which was followed for compound-1 using (3R,5S)-1-((S)-2-amino-3,3-dimethylbutanoyl)-5-((4-(4-methylthiazol-5-yl)benzyl)carbamoyl)pyrrolidin-3-yl acetate hydrochloride and 2-(4-(3-amino-6-(2-hydroxy phenyl)pyridazin-4-yl)piperazin-1-yl)acetic acid as starting materials (brown solid, yield: 32%). $^1$H NMR (400 MHz, DMSO-d$_6$): δ 14.22 (s, 1H), 8.90 (s, 1H), 8.58 (s, 1H), 7.93 (d, J=7.8 Hz, 1H), 7.99-7.73 (m, 1H), 7.54 (s, 1H), 7.39 (s, 4H), 7.24 (s, 1H), 6.88 (d, J=8.4 Hz, 2H), 6.25 (bs, 2H), 5.27 (bs, 1H), 4.48-4.39 (m, 4H), 3.80-3.99 (m, 2H), 3.16 (bs, 4H), 3.10 (s, 2H), 2.72 (bs, 4H), 2.43 (bs, 3H), 2.15-2.38 (m, 2H), 1.97 (s, 3H), 0.98 (s, 9H); LC/MS: 784.1 (M+1)$^+$.

Example-IV: Synthesis of (2S,4R)-1-((S)-2-((2-(4-(3-amino-6-(2-hydroxyphenyl)pyridazin-4-yl)piperazin-1-yl)-2-oxoethyl)amino)-3,3-dimethylbutanoyl)-4-hydroxy-N—((S)-1-(4-(4-methylthiazol-5-yl)phenyl)ethyl)pyrrolidine-2-carboxamide. (compound-49)

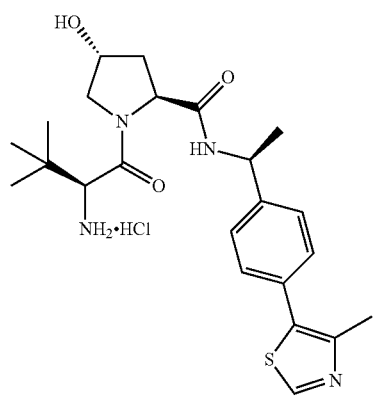

17g

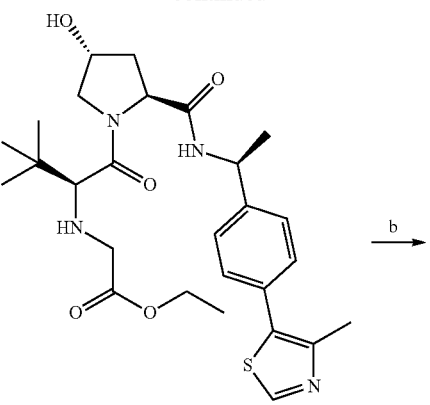

49a

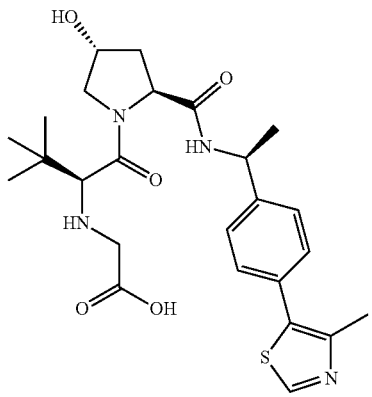

49b

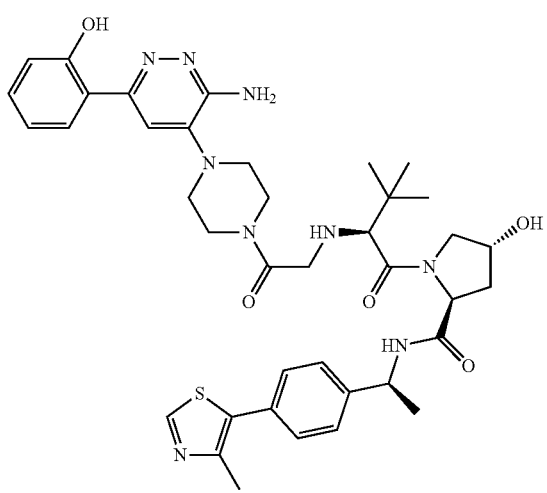

Compound-49

Conditions: a) Ethyl bromo acetate, K$_2$CO$_3$, DMF, RT, 2h;
b) LiOH.H$_2$O, MeOH: THF: H$_2$O (1:1:1), 16 h, RT;
c) HATU, DIPEA, DMF, RT, 16 h.

Step-a: Synthesis of ethyl ((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)glycinate (49a)

To a stirred solution of (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (11h, 0.30 g, 0.62 mmol) in DMF (100 mL) in a two neck round bottomed flask were added and tert-butyl 2-bromoacetate (0.10 mL, 0.93 mmol) and $K_2CO_3$ (0.25 g, 1.86 mmol). The reaction mixture was stirred for 2 h at RT. After completion of the reaction (monitored by TLC) the reaction mixture was quenched with water (10 mL) and extracted with EtOAc (2×10 mL). The combined organic layer was washed with water (20 mL), brine (20 mL), dried over anhydrous sodium sulphate and concentrated under vacuum to give the residue which was purified by combi flash column chomatography using 60% ethyl acetate in hexane as eluent to afford the title compound as a brown solid (0.15 g, 45.45%). $^1$H NMR (400 MHz, DMSO-$d_6$): δ 8.97 (s, 1H), 8.37 (d, J=7.6 Hz, 1H), 7.48-7.36 (m, 5H), 5.00 (d, J=3.6 Hz, 1H), 4.94-4.88 (m, 1H), 4.54-4.50 (m, 1H), 4.26 (s, 1H), 4.11-4.05 (m, 4H), 3.55-3.48 (m, 2H), 2.46 (s, 3H) 2.20-2.11 (m, 1H), 2.02-2.00 (m, 1H), 1.82-1.73 (m, 1H), 1.42-1.36 (m, 3H), 1.32-1.17 (m, 3H), 0.92 (s, 9H); LC/MS: m/z 531.1 (M+1)$^+$.

Step-b: Synthesis of ((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)glycine (49b)

To a stirred solution of ethyl ((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)glycinate (46a, 0.12 g, 0.22 mmol) in a mixture of solvents of MeOH:THF:H2O (1:1:1) was added LiOH·H$_2$O (0.020 g, 0.44 mmol) at RT and the reaction mixture was stirred for 16 h at same temperature. After completion of the reaction (monitored by TLC) the reaction mixture was concentrated under reduced pressure to get crude compound which was dissolved in methanol and neutralised to pH 7 with acidic resin and then filtered off. The filtrate was evaporated under reduced pressure to afford the title compound (0.10 g, 90.9%). $^1$H NMR (400 MHz, DMSO-$d_6$): δ 8.97 (s, 1H), 8.35 (d, J=8.5 Hz, 1H), 7.46-7.36 (m, 4H), 4.90 (t, J=7.2 Hz, 1H), 4.52 (t, J=8.3 Hz, 1H), 4.22 (bs, 1H), 3.50 (d, J=10.2 Hz, 1H), 3.50-3.40 (m, 3H), 3.06 (s, 1H), 2.95-2.75 (m, 2H), 2.45 (s, 3H), 2.05-1.99 (m, 1H), 1.80-1.75 (m, 1H), 1.38 (d, J=6.9 Hz, 3H), 0.91 (s, 9H) LC-MS: m/z 503.1 (M+1)$^+$.

Step-c: Synthesis of (2R,4S)-1-((R)-2-((2-(4-(3-amino-6-(2-hydroxyphenyl)pyridazin-4-yl) piperazin-1-yl)-2-oxoethyl)amino)-3,3-dimethylbutanoyl)-4-hydroxy-N—((S)-1-(4-(4-methylthiazol-5-yl)phenyl)ethyl)pyrrolidine-2-carboxamide (compound-49)

The title compound was synthesized using the same procedure which was followed for compound-1 using ((S)-1-((2S,4R)-4-hydroxy-2-(((S)-1-(4-(4-methylthiazol-5-yl)phenyl)ethyl) carbamoyl)pyrrolidin-1-yl)-3,3-dimethyl-1-oxobutan-2-yl)glycine and 2-(6-amino-5-(piperazin-1-yl)pyridazin-3-yl)phenol hydrochloride (Yield: 28%). $^1$H NMR (400 MHz, DMSO-$d_6$): δ 13.80 (bs, 1H), 8.89 (s, 1H), 7.78 (d, J=7.4 Hz, 1H), 7.82 (d, J=7.4 Hz, 1H), 7.48 (d, J=7.1 Hz, 2H), 7.40 (d, J=6.8 Hz, 2H), 7.38 (d, J=8.3 Hz, 2H), 7.22 (t, J=7.2 Hz, 1H), 6.89-6.85 (m, 2H), 6.07 (bs, 2H), 4.99-4.91 (m, 1H), 4.70 (bs, 1H), 4.61-4.57 (m, 1H), 4.31-4.26 (m, 2H), 3.66-3.55 (m, 4H), 3.54-3.52 (m, 2H), 3.41-3.37 (m, 1H), 3.27-3.23 (m, 1H), 3.10-3.09 (m, 7H), 2.09-1.94 (m, 2H), 1.43 (d, J=7.3 Hz, 3H), 0.96 (s, 9H); LC/MS: 756.1 (M+1)$^+$.

Example-V: Synthesis of (2S,4R)-1-((S)-2-(2-(4-(3-amino-6-chloropyridazin-4-yl) piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide (Compound-50)

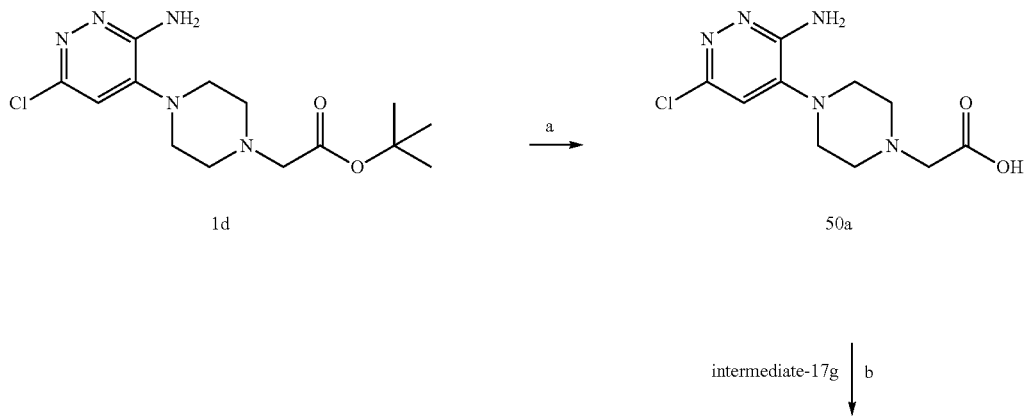

-continued

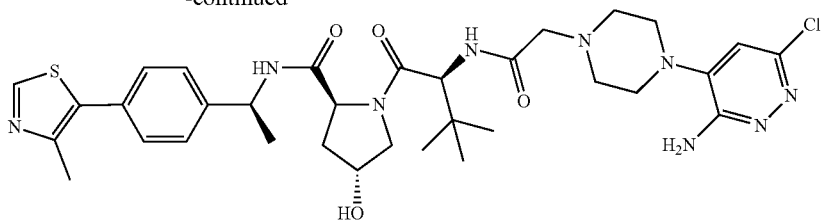

Compound-50

Conditions: a) HATU, DIPEA, DMF, 0° C.-RT, 16 h;
b) 4 M HCl in Dioxane, DCM, 0° C. - RT, 16 h.

Step-a: Synthesis of 2-(4-(3-amino-6-chloro-pyridazin-4-yl)piperazin-1-yl)acetic acid. (50a)

The title compound was synthesized using the same procedure which was followed for Intermediate-1f₁ using tert-butyl 2-(4-(3-amino-6-chloropyridazin-4-yl)piperazin-1-yl)acetate (Yield: 41.6%); LC-MS: m/z 272.1 (M+1)⁺.

Step-b: Synthesis of (2S,4R)-1-((S)-2-(2-(4-(3-amino-6-chloropyridazin-4-yl)piperazin-1-yl) acetamido)-3,3-dimethylbutanoyl)-4-hydroxy-N—((S)-1-(4-(4-methylthiazol-5-yl)phenyl)ethyl) pyrrolidine-2-carboxamide (50b)

The title compound was synthesized using the same procedure which was followed for compound-1 using 2-(4-(3-amino-6-chloropyridazin-4-yl)piperazin-1-yl)acetic acid and (2S,4R)-1-((S)-2-amino-3,3-dimethylbutanoyl)-4-hydroxy-N—((S)-1-(4-(4-methylthiazol-5-yl)phenyl)ethyl) pyrrolidine-2-carboxamide hydrochloride as starting materials (Yield: 23%). $^1$H NMR (400 MHz, DMSO-d₆): δ 8.97 (s, 1H), 8.41 (d, J=8 Hz, 1H), 7.74 (d, J=9.6 Hz, 1H), 7.43 (d, J=7.6 Hz, 2H), 7.36 (d, J=8.4 Hz, 2H), 6.95 (s, 1H), 6.10 (s, 2H), 5.10 (d, J=3.6 Hz, 1H), 4.91-4.89 (m, 1H), 4.52-4.43 (m, 2H), 4.28 (s, 1H), 3.60-3.58 (m, 2H), 3.14-2.99 (m, 6H), 2.67-2.66 (m, 4H), 2.49 (s, 3H), 2.09-2.01 (m, 1H), 1.82-1.70 (m, 1H), 1.37 (d, J=7.2 Hz, 3H), 0.95 (s, 9H); LC/MS: 698.30 (M+1)⁺.

Example-VI: Synthesis of (2S,4R)-1-((S)-2-(2-(1-(3-amino-6-(2-hydroxyphenyl)pyridazin-4-yl)piperidin-4-yl)acetamido)-3,3-dimethylbutanoyl)-4-hydroxy-N—((S)-1-(4-(4-methylthiazol-5-yl)phenyl)ethyl)pyrrolidine-2-carboxamide (Compound-51)

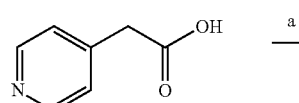

a →

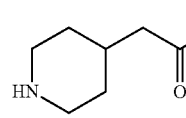

b →

51a

-continued

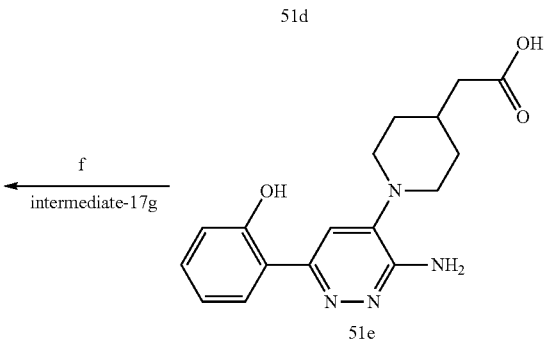

229

-continued

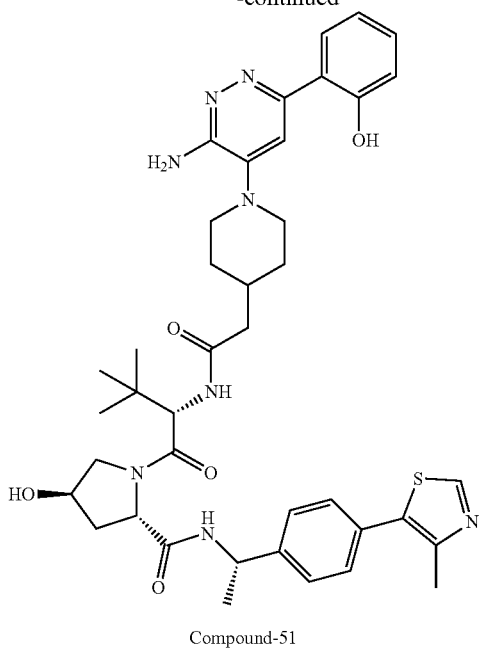

Compound-51

Conditions: a) PtO₂, H₂ (60 psi), 50% ACOH, RT, 5h;
b) MeOH, SOCl₂, 0° C.-80° C., 5h;
c) DIPEA, ACN, 100° C., 16 h;
d) (2-hydroxyphenyl)boronic acid, K₂CO₃, Pd(dppf)Cl₂: DCM (1: 1), 1,4-dioxane: water (5:2), 120° C., 1 h, MW;
e) LiOH.H₂O, THF: MeOH: H₂O, RT, 16 h;
f) HATU, DIPEA, DMF, 0° C.-RT, 18 h.

Step-a: Synthesis of 2-(piperidin-4-yl)acetic acid. (51a)

To a solution of 2-(pyridin-4-yl)acetic acid (2.20 g, 12.67 mmol) in 50% acetic acid was added PtO₂ (0.17 g, 0.76 mmol). Reaction was performed under H₂ atmosphere in parr shaker for 5 h at RT. After completion of the reaction (monitored by TLC), the reaction mixture was filtered though celite and the filtrate was concentrated under vacuum to get white solid which was further washed with acetone to afford the title compound (2.0 g, 87.33%). $^1$H NMR (400 MHz, DMSO-$d_6$): δ 10.01-9.50 (bs, 2H), 3.21-3.18 (m, 2H), 2.86-2.79 (m, 2H), 2.19-2.17 (m, 2H), 1.93-1.90 (m, 1H), 1.81-1.77 (m, 2H), 1.43-1.37 (m, 2H).

Step-b: Synthesis of methyl 2-(piperidin-4-yl)acetate (51 b)

To a solution of 2-(piperidin-4-yl)acetic acid (51a, 2.0 g, 13.98 mmol) in methanol (20 mL) was added thionyl chloride (20 mL, 279.72 mmol) for 15-20 min at 0° C. and the reaction mixture was refluxed for 5h. After completion of the reaction (monitored by TLC), excess of solvents were evaporated under vacuum and residue was co-distilled with toluene to afford the title compound (1.8 g, 72.7%). $^1$H NMR (400 MHz, DMSO-$d_6$): δ 11.58-11.50 (bs, 1H), 3.59 (s, 3H), 3.21-3.18 (m, 2H), 2.88-2.79 (m, 2H), 2.30-2.28 (m, 2H), 1.98-1.91 (m, 1H), 1.79-1.76 (m, 2H), 1.44-1.33 (m, 2H); LC-MS: m/z 158.2 (M+1)$^+$.

Step-c: Synthesis of methyl 2-(1-(3-amino-6-chloropyridazin-4-yl)piperidin-4-yl)acetate (51c)

To a stirred solution of 4-bromo-6-chloropyridazin-3-amine (1.2 g, 5.76 mmol) in ACN (30 mL) was added methyl

230

2-(piperidin-4-yl)acetate (1.8 g, 11.52 mmol) and DIPEA (3.18 mL, 17.28 mmol) at RT. The reaction mixture was stirred for 16 h at 100° C. in sealed tube. Then the reaction mixture was poured into ice cold water and extracted with ethyl acetate (2×200 mL). The combined organic layer was washed with water (100 mL), brine (100 mL), dried over anhydrous sodium sulphate and concentrated under vacuum to give the residue which was purified by combi flash column chomatography using 85% ethyl acetate in hexane as eluent to afford the title compound (0.75 g, 45.45%). $^1$H NMR (400 MHz, DMSO-$d_6$): δ 6.86 (s, 1H), 6.03 (s, 2H), 3.61 (s, 3H), 3.38-3.34 (m, 2H), 2.60-2.54 (m, 2H), 2.31-2.29 (m, 2H), 1.91-1.80 (m, 1H), 1.74-1.71 (m, 2H), 1.46-1.42 (m, 2H); LC-MS: m/z 285.1 (M+1)$^+$.

Step-d: Synthesis of methyl 2-(1-(3-amino-6-(2-hydroxyphenyl)pyridazin-4-yl)piperidin-4-yl)acetate (51d)

The title compound was synthesized using the same procedure which was followed for Intermediate-1e₁-1e₁₂ using methyl 2-(1-(3-amino-6-chloropyridazin-4-yl)piperidin-4-yl)acetate and (2-hydroxyphenyl)boronic acid as starting materials (Yield: 25%). $^1$H NMR (400 MHz, DMSO-$d_6$): δ 14.20 (brs, 1H), 7.89 (d, J=6.9 Hz, 1H), 7.49 (s, 1H), 7.26-7.21 (m, 1H), 6.90-6.87 (m, 2H), 6.21 (s, 2H), 3.62 (s, 3H), 3.48-3.45 (m, 2H), 2.73-2.67 (m, 2H), 2.32 (d, J=6.9 Hz, 2H), 1.92-1.86 (m, 1H), 1.78-1.76 (m, 2H), 1.54-1.48 (m, 2H); LC-MS: m/z 343.2 (M+1)$^+$.

Step-e: Synthesis of 2-(1-(3-amino-6-(2-hydroxyphenyl)pyridazin-4-yl)piperidin-4-yl)acetic acid (51e)

The title compound was synthesized using the same procedure which was followed for Intermediate-3d using methyl 2-(1-(3-amino-6-(2-hydroxyphenyl)pyridazin-4-yl)piperidin-4-yl)acetate (Yield: 69.9%). $^1$H NMR (400 MHz, DMSO-$d_6$): δ 7.91-7.89 (m, 2H), 7.49 (s, 1H), 7.25-7.23 (m, 1H), 6.90-6.86 (m, 2H), 6.18 (s, 2H), 3.47-3.44 (m, 2H), 2.72-2.66 (m, 2H), 2.22 (d, J=6.8 Hz, 2H), 1.91-1.78 (m, 3H), 1.54-1.48 (m, 2H); LC-MS: m/z 329.2 (M+1)$^+$.

Step-f: Synthesis of (2S,4R)-1-((S)-2-(2-(1-(3-amino-6-(2-hydroxyphenyl)pyridazin-4-yl) piperidin-4-yl)acetamido)-3,3-dimethylbutanoyl)-4-hydroxy-N—((S)-1-(4-(4-methylthiazol-5-yl)phenyl)ethyl)pyrrolidine-2-carboxamide (compound-51)

The title compound was synthesized using the same procedure which was followed for compound-1 using 2-(1-(3-amino-6-(2-hydroxyphenyl)pyridazin-4-yl)piperidin-4-yl)acetic acid and (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride as starting materials (brown solid, yield: 20%): $^1$H NMR (400 MHz, DMSO-$d_6$): δ 14.20 (s, 1H), 8.98 (s, 1H), 8.36 (d, J=7.8 Hz, 1H), 7.91-7.87 (m, 2H), 7.49 (s, 1H), 7.43 (d, J=8.3 Hz, 2H), 7.38 (d, J=8.3 Hz, 2H), 7.25-7.21 (m, 1H), 6.90-6.86 (m, 2H), 6.19 (bs, 2H), 5.0 (d, J=3.4 Hz, 1H), 4.93 (t, J=7.4 Hz, 1H), 4.55 (d, J=9.3 Hz, 1H), 4.43 (t, J=7.8 Hz, 1H), 4.29 (bs, 1H), 3.62 (d, J=1.9 Hz, 2H), 3.45-3.41 (m, 2H), 2.67-2.33 (m, 2H), 2.45 (s, 3H), 2.32-2.62 (m, 1H), 2.16-2.08 (m, 1H), 2.00-1.98 (m, 1H), 1.90-1.75 (m, 4H), 1.50-1.45 (m, 2H), 1.38 (t, J=6.7 Hz, 3H), 0.96 (s, 9H); LC/MS: 755.4 (M+1)$^+$.

Example-VII: Synthesis of 4-(3-amino-6-(2-hydroxyphenyl)pyridazin-4-yl)-N—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)piperazine-1-carboxamide (Compound-52)

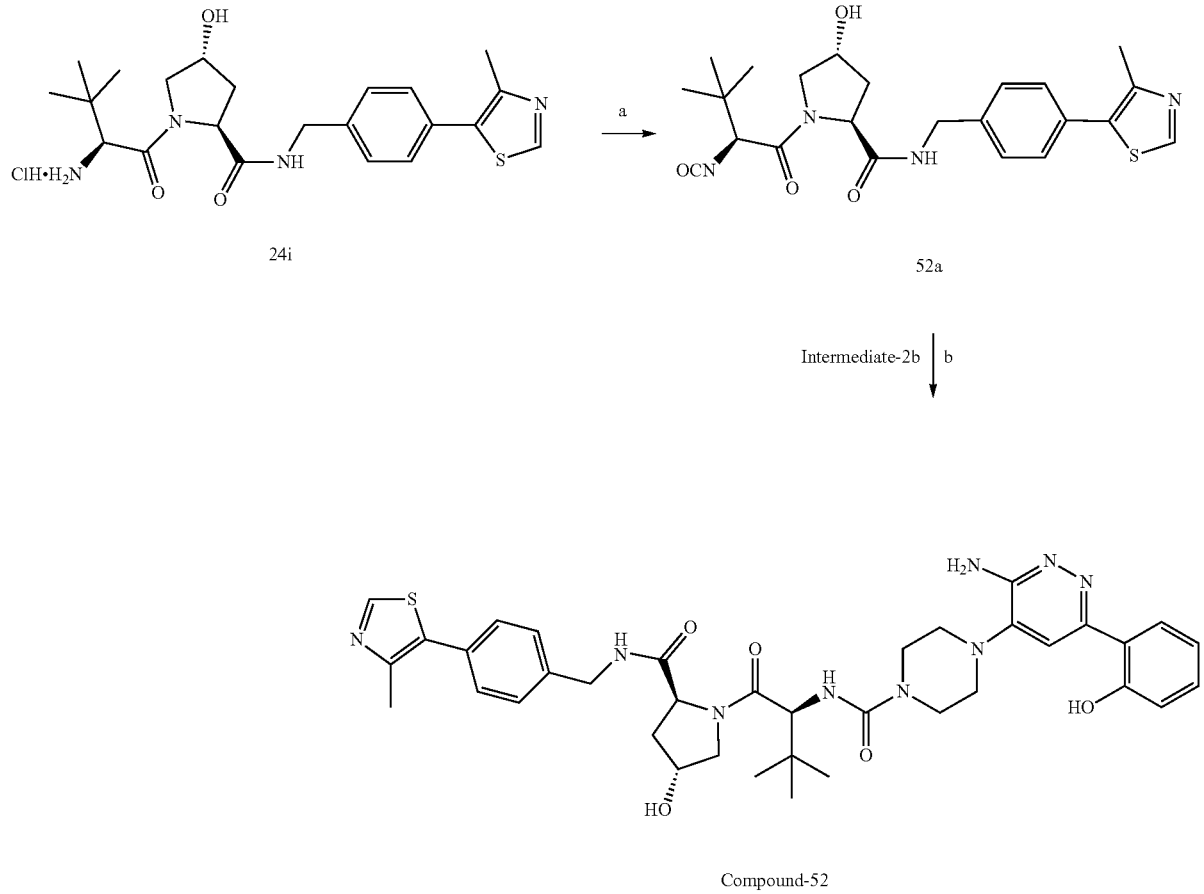

Conditions: a) Tri phosgene, Et₃N, DCM, 0° C.,-RT, 5 h; b) Et₃N, DCM, RT, 16 h.

Step-a: Synthesis of (2S,4R)-4-hydroxy-1-((S)-2-isocyanato-3,3-dimethylbutanoyl)-N-(4-(4-methylthiazol-5-yl)benzyl)pyrrolidine-2-carboxamide (52a)

To a solution of (2S,4R)-1-((S)-2-amino-3,3-dimethylbutanoyl)-4-hydroxy-N-(4-(4-methylthiazol-5-yl)benzyl)pyrrolidine-2-carboxamide hydrochloride (24i) 0.1 g, 0.21 mmol) in DCM (5 mL) was added triethyl amine (0.1 mL, 0.63 mmol) followed by the dropwise addition of triphosgene (0.063 g, 0.21 mmol) in DCM. Stirring was continued for 5 h at RT. After completion of the reaction (monitored by TLC) the reaction mixture was directly used in the next step without any workup.

Step-b: Synthesis of 4-(3-amino-6-(2-hydroxyphenyl)pyridazin-4-yl)-N—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)piperazine-1-carboxamide (compound-52)

To a solution of 2-(6-amino-5-(piperazin-1-yl)pyridazin-3-yl)phenol hydrochloride (2b, 0.05 g, 0.16 mmol) in DCM was added triethyl amine (0.13 mL, 0.96 mmol) followed by the dropwise addition of above prepared (2S,4R)-4-hydroxy-1-((S)-2-isocyanato-3,3-dimethylbutanoyl)-N-(4-(4-methylthiazol-5-yl)benzyl)pyrrolidine-2-carboxamide (0.11 g, 0.24 mmol). Stirring was continued at RT 16 h. After completion of the reaction (monitored by TLC) the reaction mixture was poured into ice cold water and extracted with DCM (2×100 mL). The combined organic layer was washed with water (25 mL), brine (25 mL), dried over anhydrous sodium sulphate and concentrated under vacuum to give the residue which was purified by combi flash column chomatography using 7% MeOH in DCM as eluent to afford the title compound (0.01g, 8%) as a brown solid. ¹H NMR (400 MHz, DMSO-d₆): δ 14.18 (s, 1H), 8.98 (s, 1H), 8.54 (s, 1H), 7.91 (d, J=7.2 Hz, 1H), 7.52 (s, 1H), 7.40 (s, 4H), 7.24-7.22 (m, 1H), 6.90-6.86 (m, 2H), 6.35 (bs, 2H), 6.05 (d, J=8.8 Hz, 1H), 5.13 (d, J=3.6 Hz, 1H), 4.47-4.25 (m, 4H), 4.26-4.25 (m, 1H), 3.72-3.68 (m, 2H), 3.58 (bs, 4H), 3.06 (bs, 4H), 2.45 (s, 3H), 2.03 (bs, 1H), 1.92 (bs, 1H), 0.96 (s, 9H); LC/MS: 728.4 (M+1)⁺.

233

Example-VIII: Synthesis of (2S,4R)-1-((S)-2-(2-(2-(4-(3-amino-6-(2-hydroxyphenyl)pyridazin-4-yl)piperazin-1-yl)ethoxy)acetamido)-3,3-dimethylbutanoyl)-4-hydroxy-N-(4-(4-methylthiazol-5-yl)benzyl)pyrrolidine-2-carboxamide (Compound-53)

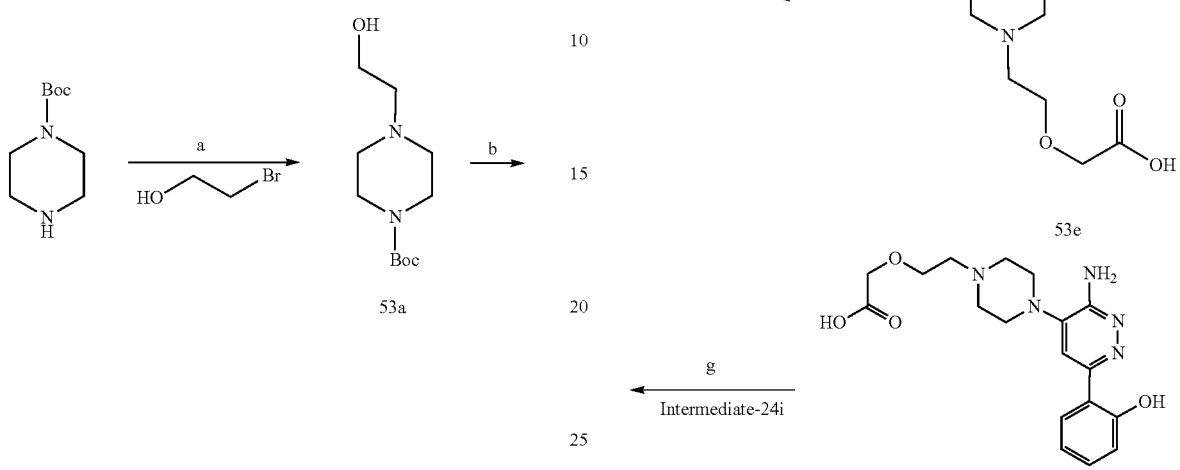

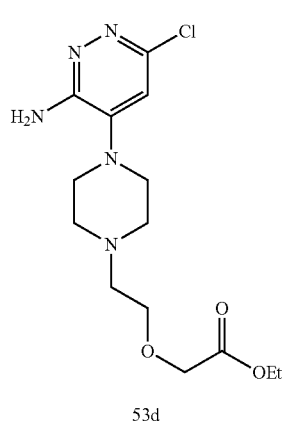

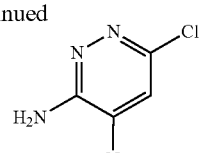

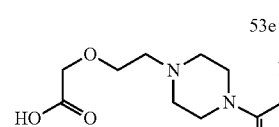

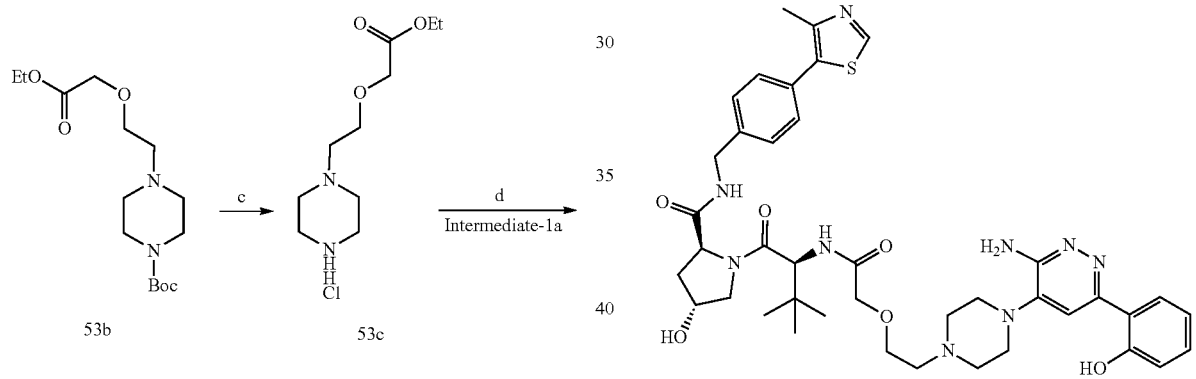

Compound-53

Conditions: a) Et₃N, ACN, 90° C., 16 h; b) Bromo ethylacetate, NaH, THF, 0° C-RT, 24 h; c) 4M HCl in 1,4-Dioxane, DCM, 0° C-RT; d) DIPEA, ACN, 90° C., 48 h; e) LiOH.H₂O, THF: MeOH: H₂O, 0° C-RT, 16 h; f) (2-hydroxyphenyl) boronic acid, Pd(dppf)Cl₂: DCM (1: 1), K₂CO₃, 1,4-Dioxane: water (5:2), M.W, 120° C., 1 h; g) HATU, DIPEA, DMF, 0° C.-RT. 18 h.

Step-a: Synthesis of tert-butyl 4-(2-hydroxyethyl)piperazine-1-carboxylate (53a)

To a stirred solution of tert-butyl piperazine-1-carboxylate (10.0 g, 55.55 mmol) and 2-bromoethan-1-ol (10.0 g, 83.33 mmol) in ACN (100 mL) was added triethyl amine (23.0 mL, 166.65 mmol) at RT. The reaction mixture was stirred for 16 h at 90° C. under nitrogen atmosphere. After completion of the reaction (monitored by TLC), the reaction mixture was extracted with ethyl acetate (2×500 mL). The combined organic layer was washed with water (500 mL), brine (500 mL), dried over anhydrous sodium sulphate and concentrated under reduced pressure to afford title compound (6.00 g, 48%), ¹H NMR (400 MHz, DMSO-d₆): δ

4.38 (t, J=5.2 Hz, 1H), 3.48 (q, J=5.6 Hz, 2H), 3.28 (t, J=4.8 Hz, 4H), 2.37-2.32 (m, 6H), 1.38 (s, 9H); LC-MS: m/z 231.1 (M+1)$^+$.

Step-b: Synthesis of tert-butyl 4-(2-(2-ethoxy-2-oxoethoxy)ethyl)piperazine-1-carboxylate. (53b)

To a stirred solution of tert-butyl 4-(2-hydroxyethyl)piperazine-1-carboxylate (4.50 g, 19.56 mmol) in THF was added NaH (55-60%, 2.51 g, 58.68 mmol) at RT. The reaction mixture was stirred for 30 min at same temperature and then to it bromoethyl acetate (6.53 mL, 58.68 mmol) was added dropwise. Stirring was continued at RT for 48 h. The reaction mixture was poured into crushed ice and extracted with ethyl acetate (5×300 mL). The combined organic layer was washed with water (500 mL), brine (500 mL), dried over anhydrous sodium sulphate and concentrated under vacuum to give the residue which was purified by Combi flash column chomatography using 50% EtOAC in n-Hexane as eluent to afford the title compound (1.5 g, 29%). $^1$H NMR (400 MHz, DMSO-d$_6$): δ 4.09-4.16 (m, 4H), 3.59-3.55 (m, 2H), 3.32 (s, 1H), 3.31-3.24 (m, 5H), 2.40-2.32 (m, 4H), 1.38 (s, 9H), 1.25-1.18 (m, 3H), LC-MS: m/z 317.1 (M+1)$^+$.

Step-c: Synthesis of ethyl 2-(2-(piperazin-1-yl)ethoxy)acetate hydrochloride (53c)

The title compound was synthesized using the same procedure which was followed for Intermediate-1f$_1$-1f$_{12}$ using tert-butyl 4-(2-(2-ethoxy-2-oxoethoxy)ethyl)piperazine-1-carboxylate as starting material (Yield: 90%). LC-MS: m/z 217.0 (M+1)$^+$.

Step-d: Synthesis of ethyl 2-(2-(4-(3-amino-6-chloropyridazin-4-yl)piperazin-1-yl)ethoxy)acetate (53d)

The title compound was synthesized using the same procedure which was followed for 51c using ethyl 2-(2-(piperazin-1-yl)ethoxy)acetate hydrochloride and 4-bromo-6-chloropyridazin-3-amine as starting material (Yield: 18%). LC-MS: m/z 344.8 (M+1)$^+$.

Step-e: Synthesis of 2-(2-(4-(3-amino-6-chloro-pyridazin-4-yl)piperazin-1-yl)ethoxy)acetic acid (53e)

The title compound was synthesized using the same procedure which was followed for 51e using ethyl 2-(2-(4-(3-amino-6-chloropyridazin-4-yl)piperazin-1-yl)ethoxy)acetate as starting material (Yield: 73%). $^1$H NMR (400 MHz, DMSO-d$_6$): δ 6.92 (s, 1H), 6.14 (s, 2H), 3.99 (s, 3H), 3.67 (t, J=5.2 Hz, 3H), 3.07 (bs, 3H), 2.83 (bs, 4H), 2.74 (bs, 2H); LC-MS: m/z 316.0 (M+1)$^+$.

Step-f: Synthesis of 2-(2-(4-(3-amino-6-(2-hydroxyphenyl)pyridazin-4-yl)piperazin-1-yl) ethoxy)acetic acid (53f)

The title compound was synthesized using the same procedure which was followed for 51d using 2-(2-(4-(3-amino-6-chloropyridazin-4-yl)piperazin-1-yl)ethoxy)acetic acid as starting material (Yield: 34%). LC-MS: m/z 373.1 (M+1)$^+$.

Step-g: (2S,4R)-1-((S)-2-(2-(2-(4-(3-amino-6-(2-hydroxyphenyl)pyridazin-4-yl)piperazin-1-yl)ethoxy)acetamido)-3,3-dimethylbutanoyl)-4-hydroxy-N-(4-(4-methylthiazol-5-yl)benzyl) pyrrolidine-2-carboxamide (Compound-53)

The title compound was synthesized using the same procedure which was followed for compound-1 using 2-(2-(4-(3-amino-6-(2-hydroxyphenyl)pyridazin-4-yl)piperazin-1-yl)ethoxy) acetic acid and (2S,4R)-1-((S)-2-amino-3,3-dimethylbutanoyl)-4-hydroxy-N-(4-(4-methyl thiazol-5-yl)benzyl)pyrrolidine-2-carboxamide hydrochloride as starting materials (Yield: 53%). $^1$H NMR (400 MHz, DMSO-d$_6$): δ 14.21 (s, 1H), 8.94 (s, 1H), 8.55 (dd, J=6.0 Hz, 5.6 Hz, 1H), 7.89 (d, J=6.8 Hz, 1H), 7.49-7.41 (m, 6H), 7.23 (dd, J=7.2 Hz, 6.8 Hz, 1H), 6.89-6.85 (m, 2H), 6.19 (s, 2H), 5.15 (d, J=3.6 Hz, 1H), 4.58-4.56 (m, 1H), 4.46-4.42 (m, 1H), 4.38-4.34 (m, 2H), 4.27-4.22 (m, 1H), 4.03-3.91 (m, 3H), 3.66-3.60 (m, 5H), 3.17-3.10 (m, 5H), 2.67-2.63 (m, 3H), 2.43 (s, 3H), 2.09-2.03 (m, 1H), 1.93-1.88 (m, 1H), 0.93 (s, 9H); LC/MS: 786.4 (M+1)$^+$.

Example-IX: Synthesis of (2S,4R)-4-hydroxy-1-((S)-2-(2-(4-(3-hydroxy-6-(2-hydroxy phenyl)pyridazin-4-yl)piperazin-1-yl)acetamido)-3,3-dimethylbutanoyl)-N—((S)-1-(4-(4-methylthiazol-5-yl)phenyl)ethyl)pyrrolidine-2-carboxamide (Compound-54)

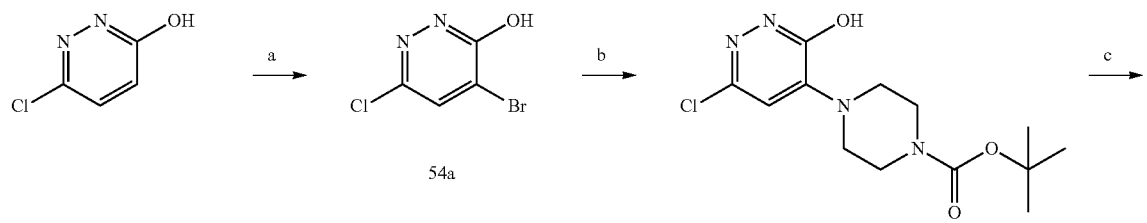

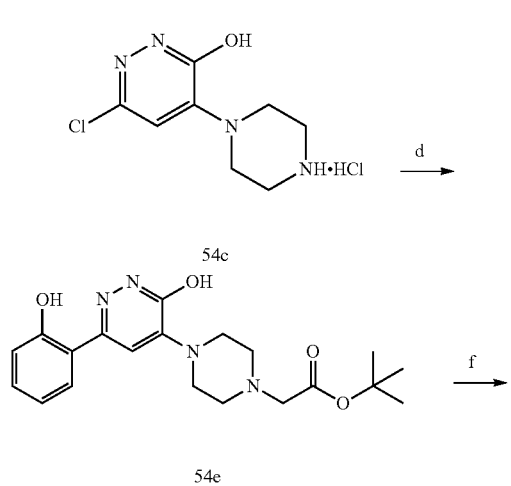
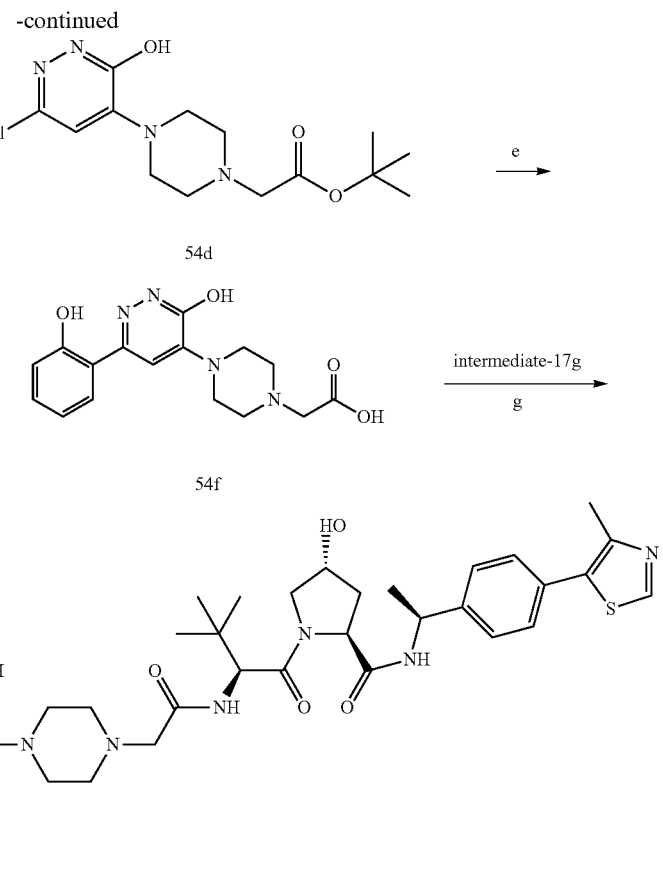

Compound-54

Conditions: a) KBr, KOAc, Br₂, H₂O, 100° C., 2 h; b) tert-butyl piperazine-1-carboxylate, K₂CO₃, DMF, 90° C.,16 h;
c) 4M HCl in 1,4-dioxane, DCM, 0° C. - RT, 16 h; d) tert-butyl 2-bromoacetate, DIPEA, DMF, 60° C., 16 h;
e) (2-hydroxyphenyl)boronic acid, Pd(dppf)Cl₂DCM, K₂CO₃, Dioxane:water (5:2), sealed tube, 120° C., 1 h;
f) 4 M HCl in Dioxane, DCM, 0° C. - RT, 16 h; g) HATU, DIPEA, DMF, 0° C. - RT, 16 h.

Step-a: Synthesis of
4-bromo-6-chloropyridazin-3-ol (54a)

To a stirred solution of 6-chloropyridazin-3-ol (4.00 g, 31.00 mmol) in H$_2$O (10 mL) was added KBr (11.06 g, 93.02 mmol), KOAc (4.50 g, 46.5 mmol) in H$_2$O (40 mL) followed by dropwise addition of bromine (4.74 mL, 93.02 mmol). Stirring was continued for 2 h at 100° C. Progress of the reaction was monitored by TLC. The reaction mixture was cooled to RT, the obtained solid was filtered and washed with water (50 mL) and dried under vacuum to afford the title compound (4.0 g, 62.2%). $^1$H NMR (400 MHz, DMSO-d$_6$): δ 13.52 (s, 1H), 8.19 (s, 1H); LC-MS: m/z 210.9 (M+1)$^+$.

Step-b: Synthesis of tert-butyl 4-(6-chloro-3-hydroxypyridazin-4-yl)piperazine-1-carboxylate (54b)

The title compound was synthesized using the same procedure which was followed for Intermediate-1b using 4-bromo-6-chloropyridazin-3-ol as starting material (Yield: 66%). LC-MS: m/z 315.1 (M+1)$^+$.

Step-c: Synthesis of 6-chloro-4-(piperazin-1-yl) pyridazin-3-ol hydrochloride (54c)

The title compound was synthesized using the same procedure which was followed for Intermediate-1c using tert-butyl 4-(6-chloro-3-hydroxypyridazin-4-yl)piperazine-1-carboxylate as starting material (Yield: 94%) LC-MS: m/z 215.1 (M+1)$^+$.

Step-d: Synthesis of terttert-butyl 2-(4-(6-chloro-3-hydroxypyridazin-4-yl)piperazin-1-yl)acetate (54d)

The title compound was synthesized using the same procedure which was followed for Intermediate-1d using 6-chloro-4-(piperazin-1-yl)pyridazin-3-ol hydrochloride as starting material (Yield: 74%). $^1$H NMR (400 MHz, DMSO-d$_6$): δ 12.68 (s, 1H), 6.47 (s, 1H), 3.53 (s, 4H), 3.06 (s, 2H), 2.60-2.58 (m, 4H), 1.41 (s, 9H); LC-MS: m/z 329.1 (M+1)$^+$.

Step-e: Synthesis of tert-butyl 2-(4-(3-hydroxy-6-(2-hydroxyphenyl)pyridazin-4-yl)piperazin-1-yl) acetate (54e)

The title compound was synthesized using the same procedure which was followed for Intermediate-1e using tert-butyl 2-(4-(6-chloro-3-hydroxypyridazin-4-yl)piperazin-1-yl)acetate as starting material (Yield: 83%). ¹H NMR (400 MHz, DMSO-d₆): δ 12.78 (s, 1H), 10.81 (s, 1H), 7.66 (dd, J₁=1.5 Hz, J₂=1.5 Hz, 1H), 7.25-7.23 (m, 1H), 6.97 (s, 1H), 6.90-6.87 (m, 2H), 3.60-3.50 (m, 4H), 3.17 (s, 2H), 2.70-2.60 (m, 4H), 1.47 (s, 9H); LC-MS: m/z 387.2 (M+1)⁺.

Step-f: Synthesis of 2-(4-(3-hydroxy-6-(2-hydroxyphenyl)pyridazin-4-yl)piperazin-1-yl) acetic acid (54f)

The title compound was synthesized using the same procedure which was followed for Intermediate-1f₁-1f₁₂ using tert-butyl 2-(4-(3-hydroxy-6-(2-hydroxyphenyl) pyridazin-4-yl)piperazin-1-yl)acetate as starting material (Yield: 95%). ¹H NMR (400 MHz, DMSO-d₆): δ 12.96 (bs, 1H), 10.81 (s, 1H), 7.67 (d, J=7.8 Hz, 1H), 7.28-7.24 (m, 1H), 7.11 (s, 1H), 6.97-68 (m, 2H), 5.26-5.18 (m, 2H), 4.54-4.38 (m, 2H), 4.20 (s, 2H), 3.49-3.42 (m, 4H); LC-MS: m/z 331.1 (M+1)⁺.

Step-g: Synthesis of (2S,4R)-4-hydroxy-1-((S)-2-(2-(4-(3-hydroxy-6-(2-hydroxy phenyl)pyridazin-4-yl) piperazin-1-yl)acetamido)-3,3-dimethylbutanoyl)- N—((S)-1-(4-(4-methylthiazol-5-yl)phenyl)ethyl) pyrrolidine-2-carboxamide (Compound-54)

The title compound was synthesized using the same procedure which was followed for compound-1 using 2-(4-(3-hydroxy-6-(2-hydroxyphenyl)pyridazin-4-yl)piperazin-1-yl)acetic acid and (2S,4R)-1-((S)-2-amino-3,3-dimethylbutanoyl)-4-hydroxy-N—((S)-1-(4-(4-methyl thiazol-5-yl)phenyl)ethyl)pyrrolidine-2-carboxamide hydrochloride as starting materials (Yield: 17%). ¹H NMR (400 MHz, DMSO-d₆): δ 12.81 (s, 1H), 10.81 (s, 1H), 8.97 (s, 1H), 8.41 (d, J=7.2 Hz, 1H), 7.77-7.60 (m, 2H), 7.43 (d, J=8.4 Hz, 2H), 7.36 (d, J=7.6 Hz, 2H), 7.27-7.24 (m, 1H), 7.01 (s, 1H), 6.92-6.89 (m, 2H), 5.11 (d, J=3.2 Hz, 1H), 4.93-4.86 (m, 1H), 4.52-4.50 (m, 1H), 4.47-4.42 (m, 1H), 4.28 (s, 1H), 3.63-3.51 (m, 6H), 3.15-2.98 (m, 2H), 2.70-2.60 (m, 4H), 2.45 (s, 3H), 2.09-2.01 (m, 1H), 1.82- 1.72 (m, 1H), 1.37 (d, J=6.8 Hz, 3H), 0.95 (s, 9H); LC/MS: 757.1 (M+1)⁺.

Example-X: Synthesis of (2S,4R)-1-((S)-2-(2-(1-(3-amino-6-(2-hydroxyphenyl)pyridazin-4-yl)-4-hydroxypiperidin-4-yl)acetamido)-3,3-dimethylbutanoyl)-4-hydroxy-N—((S)-1-(4-(4-methylthiazol-5-yl)phenyl)ethyl)pyrrolidine-2-carboxamide (Compound-55)

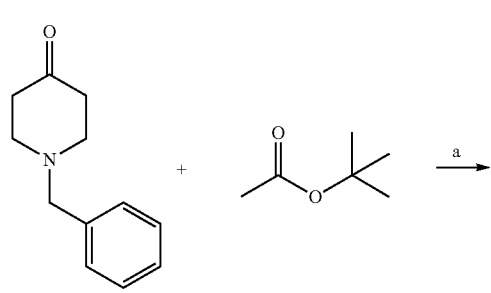

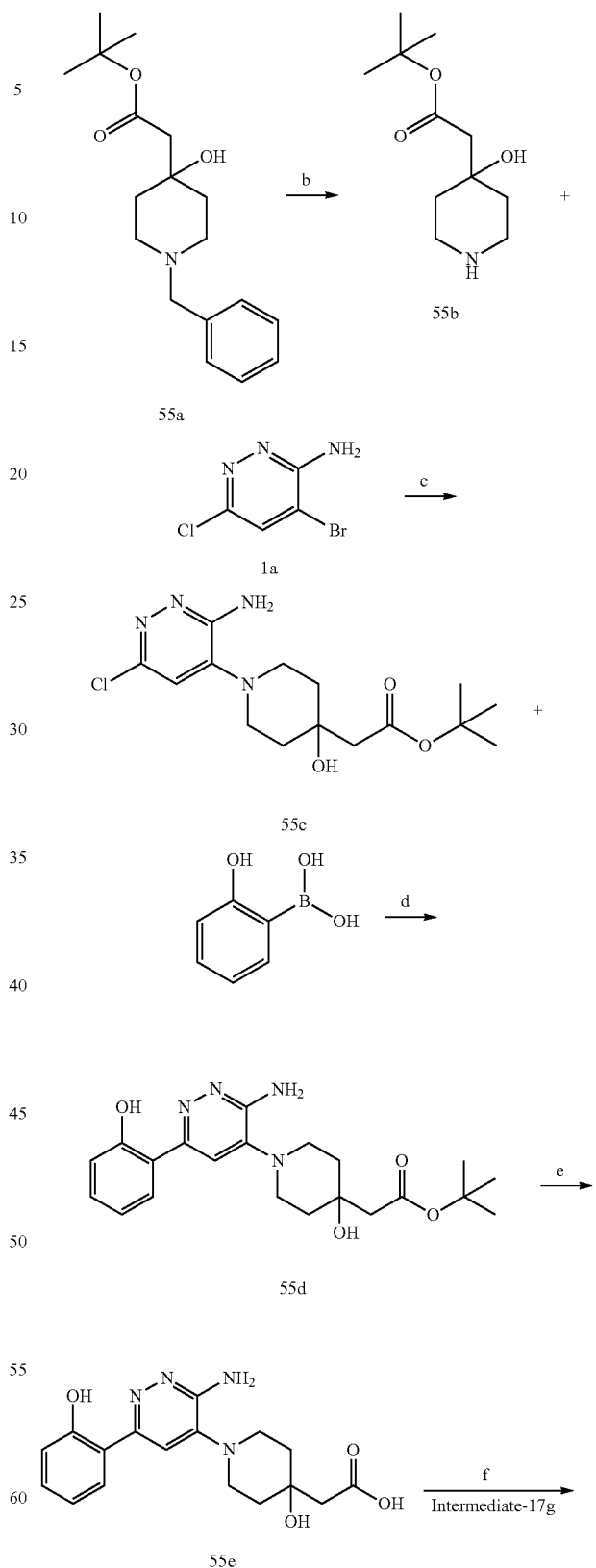

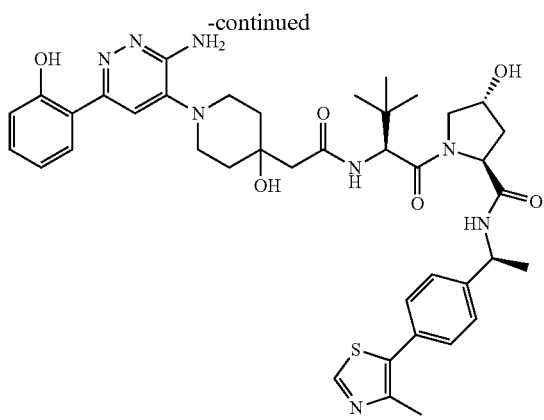

Compound-55

Conditions: a) 2M LDA, THF, 0° C. - RT, 16 h; b) 10% Pd/C, Methanol, H₂ gas, RT- 16 h; c) DIPEA, ACN, 90° C.-16 h; d) Pd(dppf)Cl₂:DCM (1:1), K₂CO₃, Dioxane: water (5:2), MW, 1 h; f) 4M HCl in Dioxane, DCM, 0° C. - RT, 16 h.

Step-a: Synthesis of tert-butyl 2-(1-benzyl-4-hydroxypiperidin-4-yl)acetate (55a)

To a stirred solution of tert-butyl acetate (10.0 g, 52.84 mmol) in THF (100 mL) in two neck RB was added 2M LDA in THF (63. 40 mmol, 31.70 mL) drop wise at −78° C. and stirred for 30 min at 0° C., then 1-benzylpiperidin-4-one (6.40 mmol, 8.60 mL) in THF was added dropwise over period of 20 mins at −78° C., stirred for 1 h at same temperature, then allowed to RT and stirred for 16 h at RT. The reaction mixture was quenched with saturated NH₄Cl solution and extracted with ethyl acetate (2×100 mL). The combined organic layer was washed with water (100 mL), brine (100 mL), dried over anhydrous sodium sulphate and concentrated under vacuum to give the residue which was purified by combi flash column chromatography using 80% ethyl acetate in hexane as eluent to afford the title compound (4.0 g, 25%). ¹H NMR (400 MHz, DMSO-d₆): δ 7.35-7.23 (m, 5H), 3.61 (d, J=7.2 Hz, 1H), 3.51 (s, 2H), 2.75 (t, J=6.0 Hz, 1H), 2.58-2.56 (m, 2H), 2.47-2.43 (m, 2H), 2.42 (s, 2H), 1.70-1.60 (m, 3H), 1.45 (s, 9H); LC-MS: m/z 306.1 (M+1)⁺.

Step-b: Synthesis of tert-butyl 2-(4-hydroxypiperidin-4-yl)acetate)(55b)

To a stirred solution of 10% Pd/C (1.25 g) in methanol (40 mL) was added tert-butyl 2-(1-benzyl-4-hydroxypiperidin-4-yl)acetate (4.0 g, 13.11 mmol) and degassed with vacuum and flushed with N₂ gas and reaction was performed under hydrogen atmosphere (60 psi) at RT for 16 h. After completion of the reaction (monitored by TLC) the reaction mixture was filtered through celite. The filtrate was concentrated to afford title compound (2.70 g, 95%) which was used in the next step without further purification. ¹H NMR (400 MHz, DMSO-d₆): δ 4.49-4.23 (m, 1H), 2.99-2.96 (m, 1H), 2.89-2.85 (m, 1H), 2.67-2.60 (m, 2H) 2.45-2.42 (m, 1H), 2.26 (s, 2H), 1.64-1.52 (m, 4H), 1.47 (s, 9H); LC-MS: m/z 216.1 (M+1)⁺.

Step-c: Synthesis of tert-butyl 2-(1-(3-amino-6-chloropyridazin-4-yl)-4-hydroxypiperidin-4-yl)acetate (55c)

To a stirred solution of 4-bromo-6-chloropyridazin-3-amine (1.0 g, 4.80 mmol) in ACN (20 mL) was added tert-butyl 2-(4-hydroxypiperidin-4-yl)acetate) (1.55 g, 7.21 mmol) and DIPEA (0.88 mL, 4.80 mmol) at RT. The reaction mixture was stirred for 16 h at 90° C. in sealed tube. Then the reaction mixture was poured into ice cold water and extracted with ethyl acetate (2×200 mL). The combined organic layer was washed with water (100 mL), brine (100 mL), dried over anhydrous sodium sulphate and concentrated under vacuum to give the residue which was purified by combi flash column chromatography using 85% ethyl acetate in hexane as eluent to afford the title compound (0.60 g, 36%) ¹H NMR (400 MHz, DMSO-d₆): δ 6.86 (s, 1H), 6.02 (s, 2H), 4.56 (s, 1H), 3.13 (d, J=12.4 Hz, 2H), 2.92 (t, J=11.6 Hz, 2H), 2.34 (s, 2H), 1.86-1.79 (m, 2H), 1.67 (d, J=12.5 Hz, 2H), 1.41 (s, 9H); LC-MS: m/z 343.0 (M+1)⁺.

Step-d: Synthesis of tert-butyl 2-(1-(3-amino-6-(2-hydroxyphenyl)pyridazin-4-yl)-4-hydroxypiperidin-4-yl)acetate (55d)

The title compound was synthesized by using the Genereal procedure of Suzuki coupling which was followed for Intermediate-1e₁-1e₁₂ using tert-butyl 2-(1-(3-amino-6-chloropyridazin-4-yl)-4-hydroxypiperidin-4-yl)acetate (Yield: 43%); ¹H NMR (400 MHz, DMSO-d₆): δ 14.29 (s, 1H), 7.93 (d, J=1.6 Hz, 1H), 7.51 (s, 1H), 7.25-7.21 (m, 1H), 6.89-6.85 (m, 2H), 6.18 (s, 2H), 4.58 (s, 1H), 3.22 (d, J=12.0 Hz, 2H), 3.04 (t, J=10.4 Hz, 2H), 2.37 (s, 2H), 1.98-1.86 (m, 2H), 1.72 (d, J=13.2 Hz, 2H), 1.42 (s, 9H); LC-MS: m/z 401.45 (M+1)⁺.

Step-e: Synthesis of 2-(1-(3-amino-6-(2-hydroxyphenyl)pyridazin-4-yl)-4-hydroxypiperidin-4-yl) acetic acid (55e)

The title compound was synthesized by using the same procedure which was followed for Intermediates-1f₁-1f₁₂ using tert-butyl 2-(1-(3-amino-6-(2-hydroxyphenyl)pyridazin-4-yl)-4-hydroxypiperidin-4-yl)acetate (Yield: 90%), ¹H NMR (400 MHz, CD₃OD): δ 7.47 (d, J=7.6 Hz, 1H), 7.45 (s, 1H), 7.32-7.31 (m, 1H), 6.96-6.92 (m, 2H), 3.55-3.52 (m, 2H), 3.28-3.21 (m, 2H), 2.45 (s, 2H), 1.92-1.89 (m, 2H), 1.82-1.79 (m, 2H); LC-MS: m/z 345.0 (M+1)⁺.

Step-e: Synthesis of (2S,4R)-1-((S)-2-(2-(1-(3-amino-6-(2-hydroxyphenyl)pyridazin-4-yl)-4-hydroxypiperidin-4-yl)acetamido)-3,3-dimethylbutanoyl)-4-hydroxy-N—((S)-1-(4-(4-methylthiazol-5-yl)phenyl)ethyl)pyrrolidine-2-carboxamide (Compound-55)

The title compound was synthesized by using the same procedure which was followed for Compound-1) using (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (Yield: 21%); ¹H NMR (400 MHz, DMSO-d₆): δ 14.20 (s, 1H), 8.96 (d, J=9.6 Hz, 1H), 8.38 (d, J=7.2 Hz, 1H), 8.03 (d, J=9.2 Hz, 1H), 7.93 (s, 1H), 7.52 (s, 1H), 7.44-7.42 (m, 2H), 7.39-7.34 (m, 2H), 7.27-7.21 (m, 1H), 6.89-6.86 (m, 2H), 6.21 (s, 2H), 5.10 (d, J=2.8 Hz, 1H), 5.03 (s, 1H), 4.95-4.90 (m, 1H), 4.56 (d, J=9.2 Hz, 1H), 4.37 (t, J=7.6 Hz, 1H), 4.29 (s, 1H), 4.01-4.00 (m, 1H), 3.61 (s, 2H), 3.30-3.20 (m, 2H), 3.08-3.07 (m, 2H), 2.50 (s, 3H), 2.05-2.00 (m, 1H), 1.85-1.66 (m, 6H), 1.46 (d, J=6.8 Hz, 3H), 0.95 (s, 9H); LC-MS: m/z 771.40 (M+1)⁺.

Example-XI: Synthesis of (2S,4R)-1-((S)-2-((R)-2-(4-(3-amino-6-(2-hydroxyphenyl)pyridazin-4-yl)piperazin-1-yl)propanamido)-3,3-dimethylbutanoyl)-4-hydroxy-N—((S)-1-(4-(4-methyl thiazol-5-yl)phenyl)ethyl)pyrrolidine-2-carboxamide (Compound 56, 57& 58)
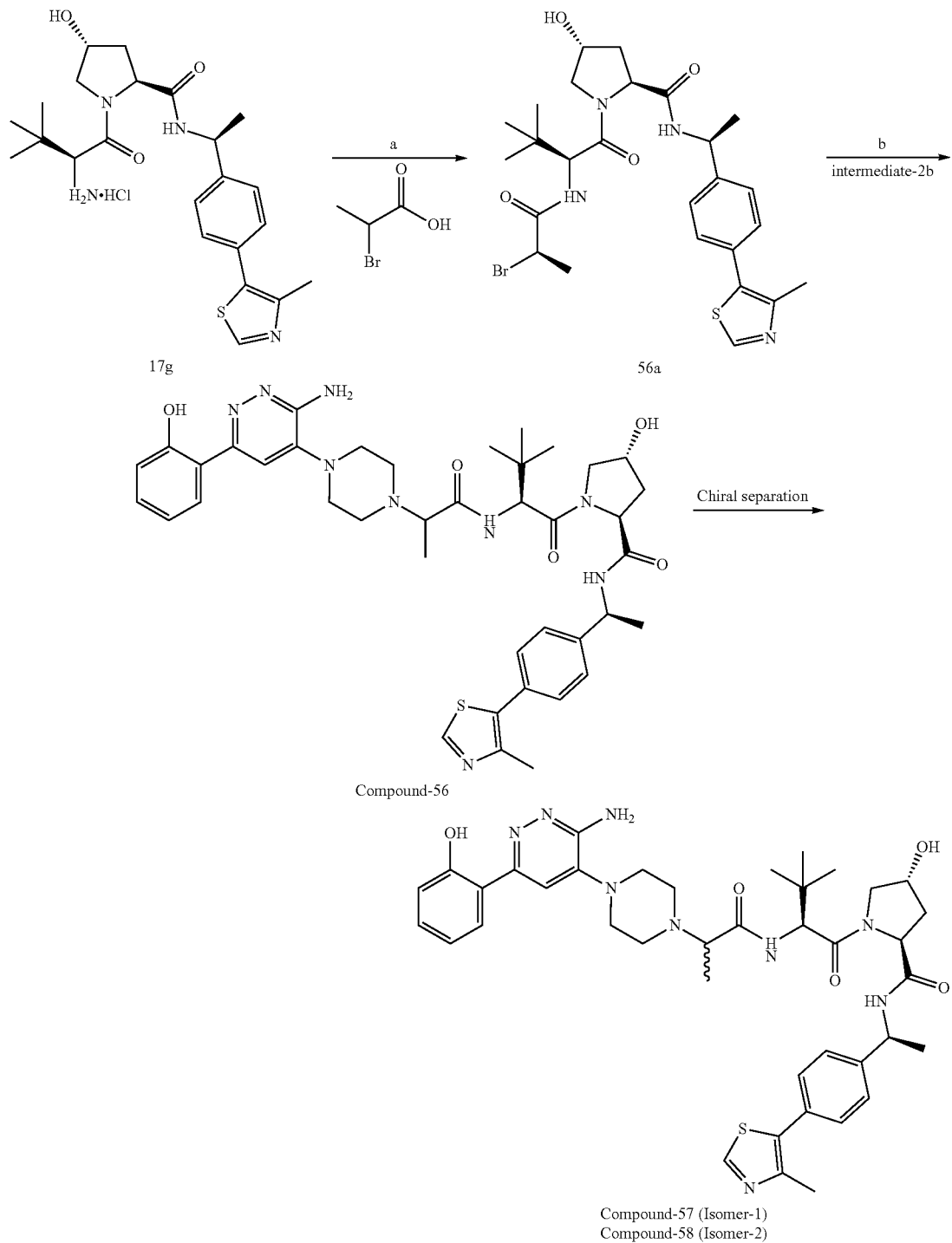
Conditions: a) HATU, DIPEA, DMF, 0° C.-RT, 16 h; b) DIPEA, DMF, RT-50° C.-8 h.

Step-a: Synthesis of (2S,4R)-1-((S)-2-((R)-2-bromopropanamido)-3,3 dimethylbutanoyl)-4-hydroxy-N—((S)-1-(4-(4-methylthiazol-5-yl)phenyl)ethyl) pyrrolidine-2-carboxamide (56a)

To a stirred solution of (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (17g) 0.7 g 1.45 mmol) and 2-bromopropanoic acid (0.15 mL, 1.74 mmol) in DMF were added DIPEA (1.06 mL, 5.80 mmol) and HATU (0.82 g, 2.17 mmol) at 0° C. The reaction mixture was stirred at RT for 16 h. After completion of the reaction (monitored by TLC) the reaction mixture was quenched with cold water (20 mL). The precipitated solid was filtered and dried under vacuum to get crude compound and which was purified by combi flash using 5% methanol in DCM as eluent to afford title compound (0.30 g, 35.62%). $^1$H NMR (400 MHz, DMSO-$d_6$): δ 8.98 (s, 1H), 8.88-8.85 (m, 1H), 8.64-8.62 (m, 1H), 7.44-7.35 (m, 2H), 5.49-5.40 (m, 1H), 5.12-5.11 (m, 1H), 370-3.55 (m, 2H), 2.50-2.41 (m, 6H), 2.10-2.0 (m, 1H), 1.64-1.62 (m, 1H), 1.54-1.52 (m, 4H), 1.38-(m, 2H), 1.06 (s, 9H), 0.85 (s, 3H), LC-MS: m/z 579.0 (M+1)$^+$.

Step-b: Synthesis of (2S,4R)-1-((2S)-2-(2-(4-(3-amino-6-(2-hydroxyphenyl)pyridazin-4-yl) piperazin-1-yl)propanamido)-3,3-dimethylbutanoyl)-4-hydroxy-N—((S)-1-(4-(4-methyl thiazol-5-yl) phenyl)ethyl)pyrrolidine-2-carboxamide (Compound-56)

To a stirred solution of 2-(6-amino-5-(piperazin-1-yl)pyridazin-3-yl)phenol hydrochloride (2b, 0.20 g, 0.65 mmol) in DMF (100 mL) in a two neck round bottomed flask were added DIPEA (0.35 g, 1.95 mmol) and (2S,4R)-1-((S)-2-((R)-2-bromopropanamido)-3,3-dimethylbutanoyl)-4-hydroxy-N—((S)-1-(4-(4-methylthiazol-5-yl)phenyl) ethyl) pyrrolidine-2-carboxamide (56a, 0.35 g, 0.56 mmol) at 0° C. The reaction mixture was stirred for 24 h at RT and then stirred additional 8 h at 50° C. After completion of the reaction (monitored by TLC) the reaction mixture was quenched with water (10 mL) and extracted with EtOAc (2×15 mL). The combined organic layer was washed with water (20 mL), brine (20 mL), dried over anhydrous sodium sulphate and concentrated under vacuum to give the residue which was purified by combi flash column chomatography using 5% methanol in DCM as eluent to afford title compound (50 mg, 10%) as a solid. $^1$H NMR (400 MHz, DMSO-$d_6$): δ 14.22 (s, 1H), 8.97 (s, 1H), 8.38 (d, J=7.9 Hz, 1H), 7.93 (d, J=6.9 Hz, 1H), 7.85 (d, J=9.2 Hz, 1H), 7.53 (d, J=6.0 Hz, 1H), 7.43-7.34 (m, 4H), 7.25 (t, J=7.3 Hz, 1H), 6.89 (d, J=7.8 Hz, 2H), 6.23 (bs, 2H), 5.10 (d, J=3.4 Hz, 1H), 4.90 (d, J=7.3 Hz, 1H), 4.49-4.44 (m, 2H), 4.29 (bs, 1H), 3.60 (bs, 2H), 3.20-3.13 (m, 5H), 2.71-2.66 (m, 4H), 2.44 (s, 3H), 2.08-2.03 (m, 1H), 1.76 (s, 2H), 1.35 (d, J=6.9 Hz, 2H), 1.15 (t, J=5.9 Hz, 3H), 0.96 (s, 9H); LC/MS: 770.4 (M+1)$^+$. Isomers of compound 56 were separated by chiral HPLC method to give compound-57 (isomer-1) and compound-58 (isomer-2)

Isomer-1: (Compound-57):
$^1$H NMR (400 MHz, DMSO-d6): δ 14.21 (s, 1H), 8.97 (s, 1H), 8.38 (d, J=7.2 Hz, 1H), 7.93 (d, J=7.6 Hz, 1H), 7.85 (d, J=9.2 Hz, 1H), 7.52 (s, 1H), 7.42 (d, J=8.4 Hz, 2H), 7.35 (d, J=8.4 Hz, 2H), 7.25-7.22 (m, 1H), 6.90-6.86 (m, 2H), 6.23 (s, 2H), 5.10 (d, J=3.6 Hz, 1H), 4.91-4.85 (m, 1H), 4.49-4.42 (m, 2H), 4.29 (s, 1H), 3.67-3.53 (m, 2H), 3.26-3.09 (m, 4H), 2.71-2.66 (m, 4H), 2.45 (s, 3H), 2.08-2.01 (m, 1H), 1.81-1.72 (m, 1H), 1.36-1.34 (m, 3H), 1.14-1.13 (m, 4H), 0.96 (s, 9H); LC/MS: 770.4 (M+1)$^+$; (Yield: 1%).

Isomer-2: (Compound-58):
$^1$H NMR (400 MHz, DMSO-$d_6$): δ 14.22 (s, 1H), 8.98 (s, 1H), 8.39 (d, J=8.0 Hz, 1H), 7.94 (d, J=7.6 Hz, 1H), 7.86 (d, J=9.2 Hz, 1H), 7.53 (s, 1H), 7.43-7.34 (m, 4H), 7.26-7.22 (m, 1H), 6.90-6.87 (m, 2H), 6.25 (s, 2H), 5.10 (d, J=3.6 Hz, 1H), 4.88 (t, J=6.8 Hz, 1H), 4.50-4.42 (m, 2H), 4.29 (s, 1H), 3.63-3.56 (m, 2H), 3.30-2.77 (m, 4H), 2.72-2.55 (m, 4H), 2.49 (s, 3H), 2.07-2.02 (m, 1H), 1.79- 1.76 (m, 1H), 1.49-1.47 (m, 1H), 1.39 (d, J=6.8 Hz, 3H), 1.36 (d, J=6.8 Hz, 3H), 0.96 (s, 9H); LC-MS: m/z 770.1 (M+1)$^+$; (Yield: 16%).

Example-XII: Synthesis of 2-(5-(4-(2-(((S)-1-((2S,4R)-4-acetoxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)piperazin-1-yl)-6-aminopyridazin-3-yl)phenyl acetate (compound-59)

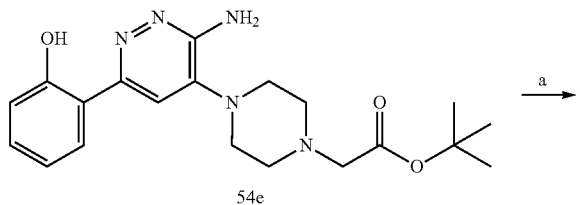

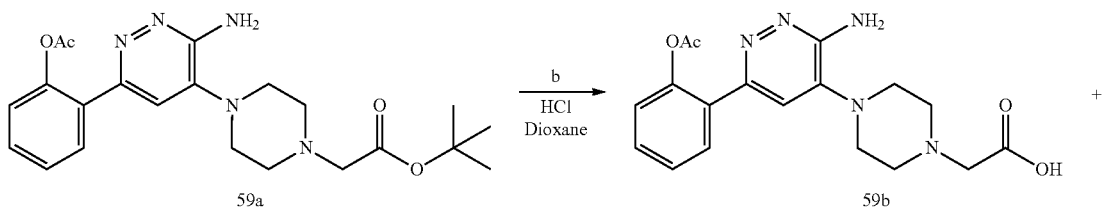

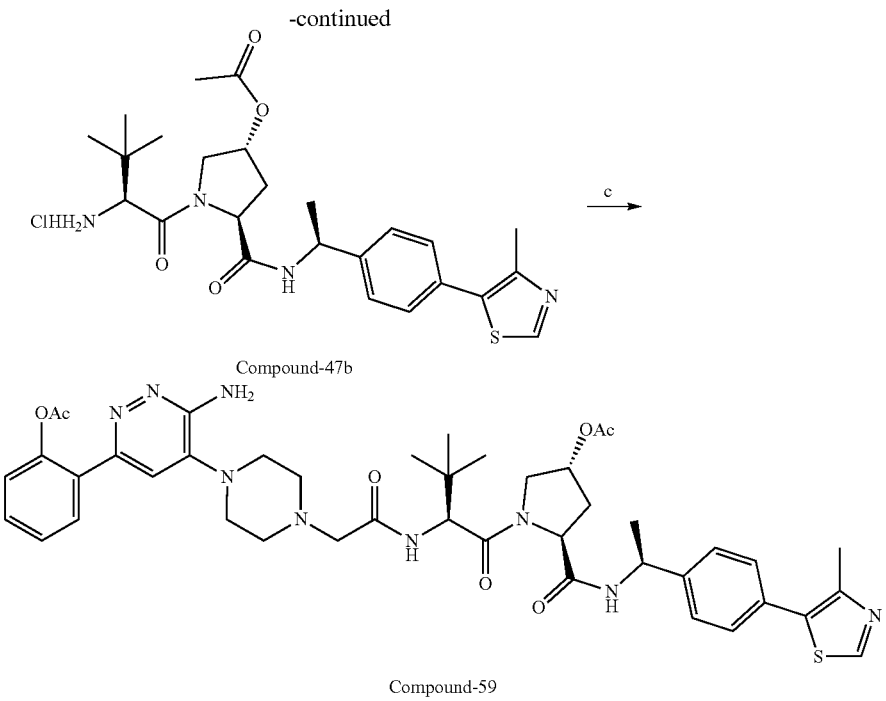

Compound-47b

Compound-59

Conditions: a) Acetic anhydride, DMAP, DMF, RT-16 h; b) 4M HCl in 1,4-dioxane, DCM, RT-16 h; c) HATU, DIPEA, DMF, 0° C.-RT, 16 h.

Step-a: Synthesis of tert-butyl 2-(4-(6-(2-acetoxyphenyl)-3-aminopyridazin-4-yl)piperazin-1-yl)acetate-Compound-59a To a stirred solution of tert-butyl 2-(4-(3-amino-6-(2-hydroxyphenyl)pyridazin-4-yl)piperazin-1-yl)acetate (0.5 g, 1.29 mmol) in DMF (5 mL) were added DMAP (0.16 g, 1.29 mmol) followed by Ac₂O (0.2 mL, 1.94 mmol) at RT continued for 16 h at RT, the reaction mixture was quenched with water (10 mL) and extracted with EtOAc (2×50 mL). The combined organic layer was washed with water (20 mL), brine (20 mL), dried over anhydrous sodium sulphate and concentrated under vacuum to give the residue which was purified by combi flash column chomatography using 5% MeOH in DCM as eluent to afford the title compound as a brown solid (0.065 g, 11%) $^1$H NMR (400 MHz, DMSO-$d_6$): δ 7.70 (dd, J=1.6 Hz, J=7.6 Hz, 1H), 7.45-7.43 (m, 1H), 7.37-7.36 (m, 1H), 7.21 (dd, J=1.2 Hz, J=8.0 Hz, 1H), 6.98 (s, 1H), 6.03 (s, 2H), 3.18 (s, 2H), 2.98 (s, 4H), 2.72-2.71 (m, 4H), 2.16 (s, 3H), 1.43 (s, 9H); LC-MS: m/z 428.6 (M+1)⁺.

Step-b: Synthesis of 2-(4-(6-(2-acetoxyphenyl)-3-aminopyridazin-4-yl)piperazin-1-yl)acetic acid-59b The title compound was synthesized using the same procedure which was followed for 1c using tert-butyl 2-(4-(6-(2-acetoxyphenyl)-3-aminopyridazin-4-yl)piperazin-1-yl)acetate as starting material. (Yield: 90%); LC-MS: m/z 372.0 (M+1)⁺.

Step-c: Synthesis of 2-(5-(4-(2-(((S)-1-((2S,4R)-4-acetoxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)piperazin-1-yl)-6-aminopyridazin-3-yl)phenyl acetate. Compound-59

The title compound was synthesized using the same procedure which was followed for Compound-1 using (3R, 5R)-1-((S)-2-amino-3,3-dimethylbutanoyl)-5-(((S)-1-(4-(4-methylthiazol-5-yl)phenyl) ethyl) carbamoyl) pyrrolidin-3-yl acetate hydrochloride as starting material. Yield: 10% $^1$H NMR (400 MHz, DMSO-$d_6$): δ 8.91 (s, 1H), 8.69 (d, J=7.2 Hz, 1H), 7.70-7.66 (m, 2H), 7.40-7.28 (m, 6H), 7.15 (d, J=7.6 Hz, 1H), 6.96 (s, 1H), 6.02 (s, 2H), 5.13 (s, 1H), 4.84-4.82 (m, 1H), 4.41-4.30 (m, 2H), 3.86-3.70 (m, 2H), 3.06-2.96 (m, 5H), 2.69 (s, 4H), 2.38 (s, 3H), 2.18-2.16 (m, 1H), 2.10 (s, 3H), 1.94-1.90 (m, 4H), 1.71-1.68 (m, 1H), 1.32-1.29 (m, 3H), 0.89 (s, 9H); LC-MS: m/z 840.4 (M+1)⁺; (Yield: 10%).

Example-XIII: Synthesis of 2-(5-(4-(2-(((S)-1-((2S,4R)-4-acetoxy-2-((4-(4-methylthiazol-5-yl)benzyl)carbamoyl)pyrrolidin-1-yl)-3,3-dimethyl-1-oxobutan-2-yl)amino)-2-oxoethyl)piperidin-1-yl)-6-aminopyridazin-3-yl)phenyl acetate (compound-60)

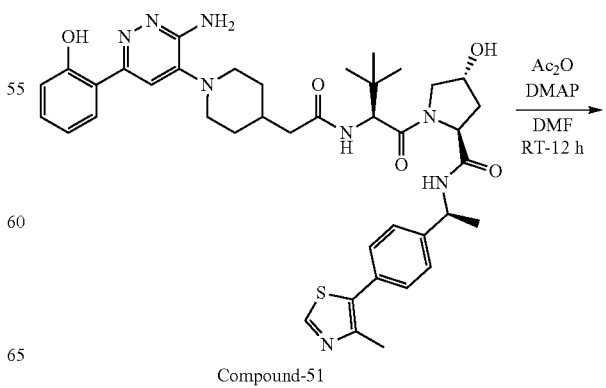

Compound-51

-continued

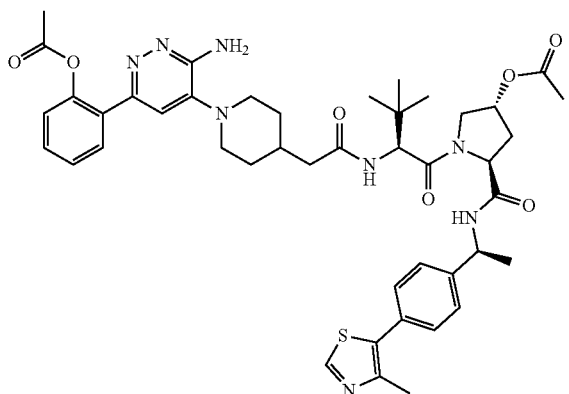

Compound-60

Conditions: a) Acetic anhydride, DIPEA, DMAP, DMF, RT-12 h.

Step-a: Synthesis of 2-(5-(4-(2-(((S)-1-((2S,4R)-4-acetoxy-2-((4-(4-methylthiazol-5-yl)benzyl) carbamoyl)pyrrolidin-1-yl)-3,3-dimethyl-1-oxobutan-2-yl) amino)-2-oxoethyl)piperidin-1-yl)-6-aminopyridazin-3-yl)phenyl acetate (compound-60)

To a stirred solution of (2S,4R)-1-((S)-2-(2-(1-(3-amino-6-(2-hydroxyphenyl)pyridazin-4-yl)piperidin-4-yl)acetamido)-3,3-dimethylbutanoyl)-4-hydroxy-N-(4-(4-methylthiazol-5-yl)benzyl)pyrrolidine-2-carboxamide (0.22 g, 0.29 mmol) in DMF (5 mL) were added DMAP (8 mg, 0.058 mmol) and DIPEA (0.16 mL, 0.87 mmol) followed by Ac$_2$O (0.29 mL, 0.87 mmol) at RT continued for 12 h, the reaction mixture was quenched with water (10 mL) and extracted with EtOAc (2×50 mL). The combined organic layer was washed with water (20 mL), brine (20 mL), dried over anhydrous sodium sulphate and concentrated under vacuum to give the residue which was purified by combi flash column chomatography using 5% MeOH in DCM as eluent to afford the title compound as a brown solid (20 mg, 9%).
$^1$H NMR (400 MHz, DMSO-d$_6$): δ 8.98 (s, 1H), 8.39 (d, J=7.6 Hz, 1H), 7.89 (d, J=8.8 Hz, 1H), 7.70 (dd, J=1.6 Hz, J=8.0 Hz, 1H), 7.46-7.44 (m, 3H), 7.40-7.34 (m, 3H), 7.21 (d, J=8.0 Hz, 1H), 6.96 (s, 1H), 5.96 (s, 2H), 5.19 (s, 1H), 4.91 (t, J=7.6 Hz, 1H), 4.46 (t, J=8.8 Hz, 1H), 4.38 (d, J=8.8 Hz, 1H), 3.98 (d, J=10.8 Hz, 1H), 3.75-3.71 (m, 1H), 2.42 (s, 3H), 2.25-2.24 (m, 4H), 2.16 (s, 3H), 1.99 (s, 3H), 1.98-1.97 (m, 2H), 1.71-1.68 (m, 4H), 1.68-1.48 (m, 3H), 1.37 (d, J=7.6 Hz, 3H), 0.96 (s, 9H); LC-MS: m/z 839.4 (M+1)$^+$.

Example-XIV: Synthesis (2S,4R)-1-((2S)-2-(2-(3-(3-amino-6-(2-hydroxyphenyl)pyridazin-4-yl)-3,8-diazabicyclo[3.2.1]octan-8-yl)acetamido)-3,3-dimethylbutanoyl)-4-hydroxy-N—((S)-1-(4-(4-methylthiazol-5-yl)phenyl)ethyl)pyrrolidine-2-carboxamide (Compound-61)

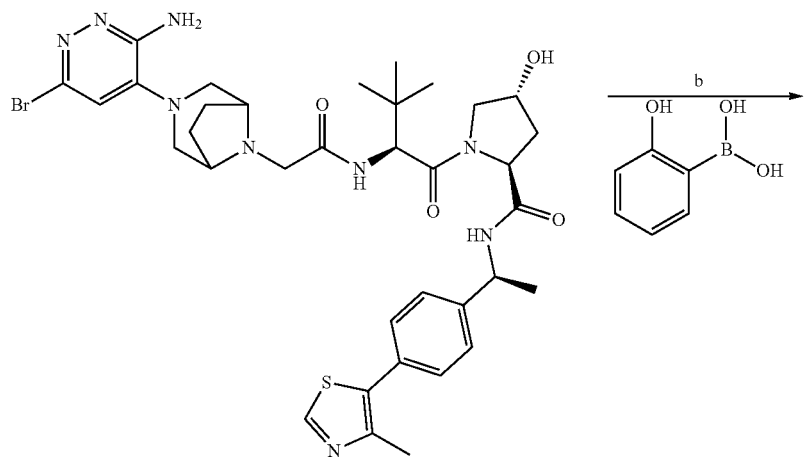

61a

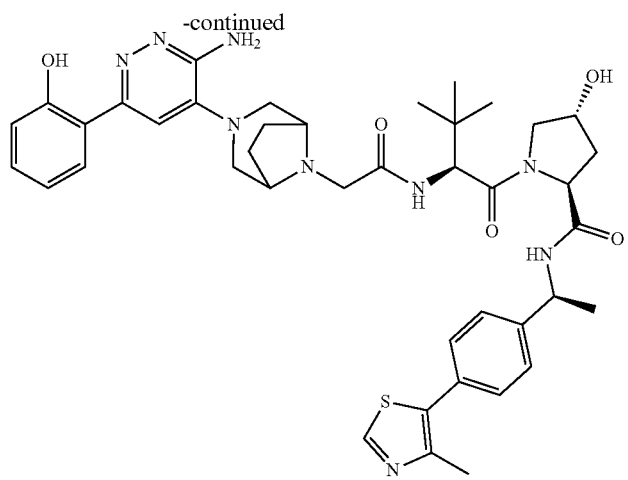

Compound-61

Conditions: a) HATU, DIPEA, DMF, 0° C-RT, 18 h; b) Pd(dppf)Cl$_2$:DCM (1:1), 2M K$_2$CO$_3$ solution, 1,4-Dioxane, MW, 120° C., 1 h.

Step-a: Synthesis (2S,4R)-1-((2S)-2-(2-(3-(3-amino-6-bromopyridazin-4-yl)-3,8-diazabicyclo [3.2.1]octan-8-yl) acetamido)-3,3-dimethylbutanoyl)-4-hydroxy-N—((S)-1-(4-(4-methylthiazol-5-yl)phenyl)ethyl)pyrrolidine-2-carboxamide (61a)

The title compound was synthesized by using the same procedure which was followed for Compound-1 using 2-(3-(3-amino-6-bromopyridazin-4-yl)-3,8-diazabicyclo[3.2.1] octan-8-yl)acetic acid (Yield: 32%) LC-MS: m/z 770.2 (M+2)$^+$.

Step-b: Synthesis (2S,4R)-1-((2S)-2-(2-(3-(3-amino-6-(2-hydroxyphenyl)pyridazin-4-yl)-3,8-diazabicyclo[3.2.1]octan-8-yl)acetamido)-3,3-dimethylbutanoyl)-4-hydroxy-N—((S)-1-(4-(4-methylthiazol-5-yl)phenyl)ethyl)pyrrolidine-2-carboxamide (Compound-61)

The title compound was synthesized by using the Genereal procedure of Suzuki coupling which was followed for Inermediates 1e$_1$-1e$_{12}$ using (2-hydroxyphenyl)boronic acid (Yield: 5%) $^1$H NMR (400 MHz, DMSO-d$_6$): δ 14.19 (s, 1H), 8.97 (s, 1H), 8.43 (d, J=7.6 Hz, 1H), 8.01 (d, J=9.2 Hz, 1H), 7.94 (dd, J=1.6 Hz, J=8.4 Hz, 1H), 7.51 (s, 1H), 7.43-7.33 (m, 4H), 7.24-7.22 (m, 1H), 6.90-6.88 (m, 2H), 5.93 (s, 2H), 5.14 (d, J=3.6 Hz, 1H), 4.90-4.82 (m, 1H), 4.53 (d, J=10.0 Hz, 1H), 4.50-4.40 (m, 1H), 4.30 (s, 1H), 3.60 (s, 2H), 307-3.01 (m, 6H), 2.54 (s, 2H), 2.44 (s, 3H merged in DMSO), 2.10-1.80 (m, 6H), 1.33 (d, J=7.2 Hz, 3H), 0.95 (s, 9H); LC-MS: m/z 782.4 (M+1)$^+$.

Example-XV: Synthesis of (2S,4R)-1-((S)-2-(2-(4-(3-amino-6-(3-fluoro-2-hydroxyphenyl)pyridazin-4-yl)-1H-pyrazol-1-yl) acetamido)-3,3-dimethylbutanoyl)-4-hydroxy-N—((S)-1-(4-(4-methylthiazol-5-yl)phenyl)ethyl)pyrrolidine-2-carboxamide (Compound-62)

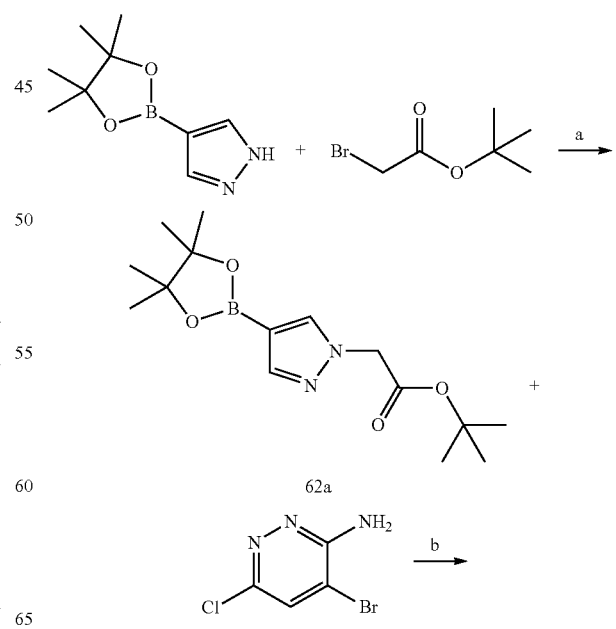

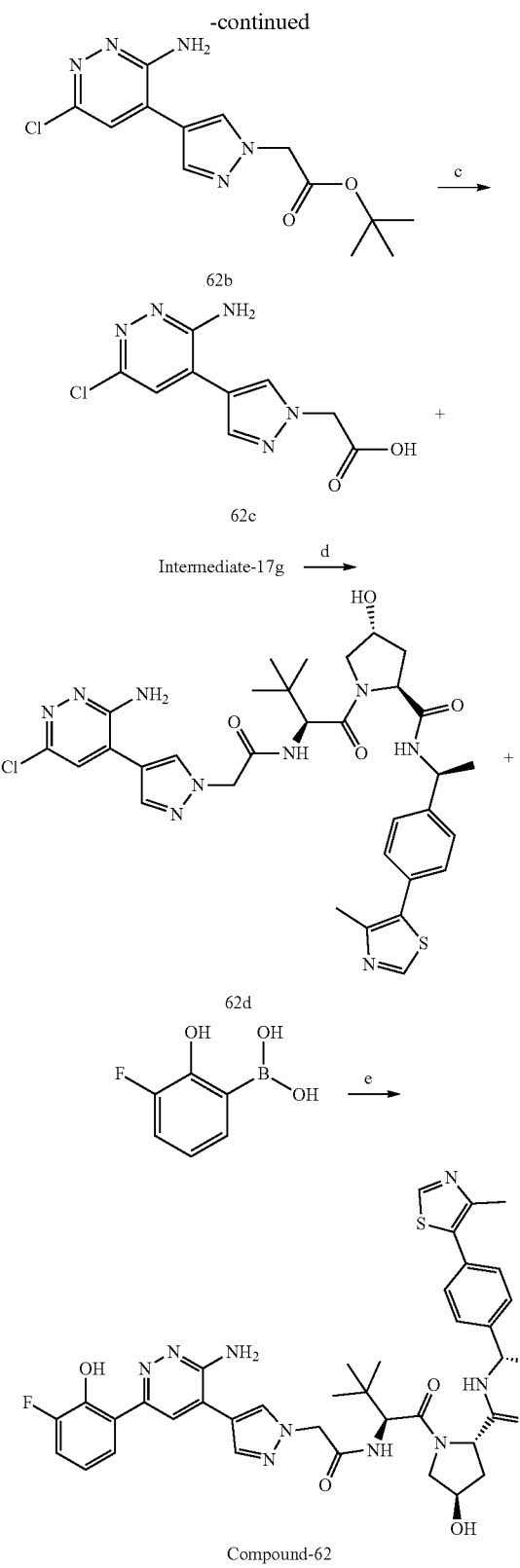

Compound-62

Conditions: a) Ethyl bromo acetate, K₂CO₃, Acetone, 65° C., 16 h; b) Pd(dppf)Cl₂: DCM(1:1), 2M K₂CO₃ solution, 1,4-Dioxane, MW, 120° C.-1 h; c) 4M HCl in 1,4-Dioxane, DCM, 0° C.- RT, 16 h; d) HATU, DIPEA, DMF, 0° C.- RT, 18 h; e) (2-hydroxyphenyl) boronic acid, Pd(dppf)Cl₂: DCM(1:1), 2M K₂CO₃ solution, 1,4-Dioxane, MW, 120° C.- 1 h.

Step-a: Synthesis of tert-butyl 2-(4-(4,4,5,5-tetramethyl-1,3,2-dioxaborolan-2-yl)-1H-pyrazol-1-yl) acetate (62a)

To a stirred solution of 4-(4,4,5,5-tetramethyl-1,3,2-dioxaborolan-2-yl)-1H-pyrazole (1.0 g, 5.15 mmol) in Acetone (10 mL) in a two neck RB were added K₂CO₃ (0.85 g, 6.18 mmol) and followed by tert-butyl bromoacetate (1.20 gm, 6.18 mmol) at RT and stirred for 16 h at 65° C. The reaction mixture was evaporated by vacuum to get residue which was quenched with water (30 mL) and extracted with EtOAc (2×50 mL). The combined organic layer was washed with water (50 mL), brine (50 mL), dried over anhydrous sodium sulphate and concentrated under reduced pressure to give the crude product which was purified by combi flash using 50% ethyl acetate in hexane as eluent to afford the title compound (0.27 g, 18%). $^1$H NMR (400 MHz, DMSO-d$_6$): δ 7.91 (s, 1H), 7.58 (s, 1H), 4.95 (s, 2H), 1.42 (s, 9H), 1.25 (s, 12H).

Step-b: Synthesis of tert-butyl 2-(4-(3-amino-6-chloropyridazin-4-yl)-1H-pyrazol-1-yl)acetate (62b)

The title compound was synthesized by using the General procedure of Suzuki coupling which was followed for Intermediates-1e$_1$-1e$_{12}$ using 62a to afford compound. $^1$H NMR (400 MHz, DMSO-d$_6$): δ8.39 (s, 1H), 8.09 (s, 1H), 7.62 (s, 1H), 6.35 (s, 2H), 5.00 (s, 2H), 1.44 (s, 9H); LC-MS: m/z 310.1 (M+1)$^+$.

Step-c: Synthesis of 2-(4-(3-amino-6-chloropyridazin-4-yl)-1H-pyrazol-1-yl)acetic acid (62c)

The title compound was synthesized by using the same procedure which was followed for Intermediate 1f$_1$-1f$_{12}$ using 62b (Yield: 90%) $^1$H NMR (400 MHz, DMSO-d$_6$): δ 8.43 (s, 1H), 8.08 (s, 1H), 7.88 (s, 1H), 5.04 (s, 2H); LC-MS: m/z 254.1 (M+1)$^+$.

Step-d: Synthesis (2S,4R)-1-((S)-2-(2-(4-(3-amino-6-chloropyridazin-4-yl)-1H-pyrazol-1-yl) acetamido)-3,3-dimethylbutanoyl)-4-hydroxy-N—((S)-1-(4-(4-methylthiazol-5-yl)phenyl)ethyl)pyrrolidine-2-carboxamide (Compound-62d)

The title compound was synthesized by using the same procedure which was followed for Compound-1 using 2-(4-(3-amino-6-chloropyridazin-4-yl)-1H-pyrazol-1-yl)acetic acid (Yield: 68%)$^1$H NMR (400 MHz, DMSO-d$_6$): δ (s, 1H), 8.41-8.38 (m, 2H), 8.26 (d, J=9.6 Hz, 1H), 7.60 (s, 1H), 7.44-7.37 (m, 4H), 6.32 (s, 2H), 5.10 (d, J=3.2 Hz, 1H), 5.10 (d, J=3.2 Hz, 1H), 4.98 (s, 2H), 4.96-4.90 (m, 1H), 4.52 (d, J=9.2 Hz, 1H), 4.43 (t, J=8.0 Hz, 1H), 4.27 (s, 1H), 3.62-3.53 (m, 2H), 2.44 (s, 3H), 2.08-1.99 (m, 1H), 1.80-1.78 (m, 1H), 1.38 (d, J=6.8 Hz, 3H), 0.96 (s, 9H); LC-MS: m/z 680.3 (M+1)$^+$.

Step-e: Synthesis of (2S,4R)-1-((S)-2-(2-(4-(3-amino-6-(3-fluoro-2-hydroxyphenyl)pyridazin-4-yl)-1H-pyrazol-1-yl)acetamido)-3,3-dimethylbutanoyl)-4-hydroxy-N—((S)-1-(4-(4-methylthiazol-5-yl)phenyl)ethyl)pyrrolidine-2-carboxamide Compound-62

The title compound was synthesized by using the General procedure of Suzuki coupling which was followed for (1e$_1$-1e$_{12}$) using (3-fluoro-2-hydroxyphenyl) boronic acid to afford compound. $^1$H NMR (400 MHz, DMSO-d$_6$): δ 14.40 (s, 1H), 8.98 (s, 1H), 8.47 (s, 1H), 8.40 (d, J=7.6 Hz, 1H), 8.29-8.22 (m, 2H), 8.18 (s, 1H), 7.85 (d, J=7.6 Hz, 1H), 7.43 (d, J=8.0 Hz, 2H), 7.38 (d, J=8.4 Hz, 2H), 7.26-7.18 (m, 1H), 6.88 (s, 1H), 6.55 (s, 2H), 5.12 (s, 1H), 5.01 (s, 2H), 4.97-4.90 (m, 1H), 4.53 (d, J=9.2 Hz, 1H), 4.46-4.42 (m, 1H), 4.27 (s, 1H), 3.63-3.54 (m, 2H), 2.40 (s, 3H), 2.05-2.00 (m, 1H), 1.82-1.76 (m, 1H), 1.34 (d, J=11.2 Hz, 3H), 0.97 (s, 9H); LC-MS: m/z 756.3 (M+1)$^+$ (Yield: 18%).

Example-XVI: Synthesis of (2S,4R)-1-((S)-2-(2-(4-(3-amino-6-(5-fluoro-2-hydroxyphenyl)pyridazin-4-yl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide (Compound-63)

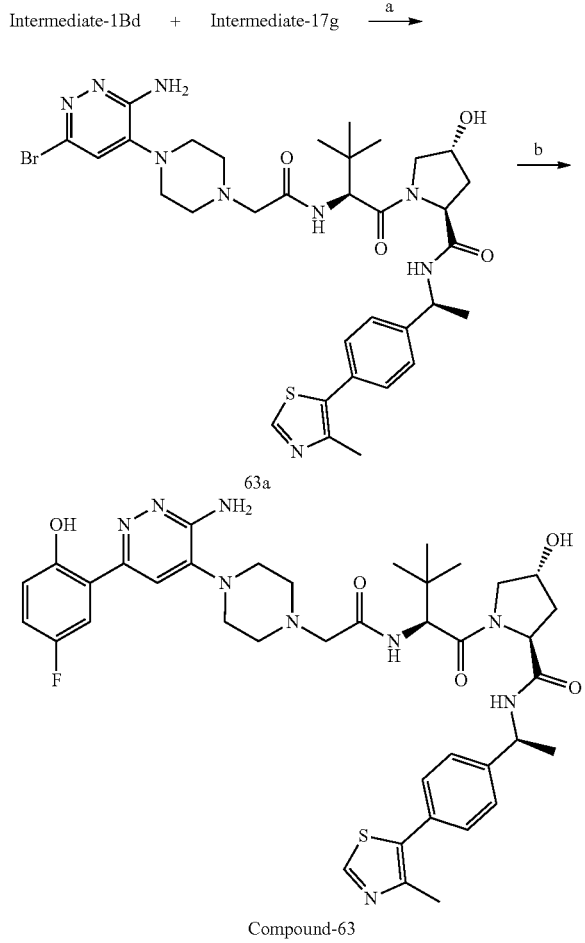

Compound-63

Conditions: a) HATU, DIPEA, DMF, 0° C.-RT, 18 h; b) Pd(dppf)Cl$_2$•DCM, 2M K$_2$CO$_3$ solution, 1,4-Dioxane, M.W, 120° C., 1 h.

Step-a Synthesis of (2S,4R)-1-((S)-2-(2-(4-(3-amino-6-bromopyridazin-4-yl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide (63a)

The title compound was synthesized by using the same procedure which was followed for Compound-1 using (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamidehydrochloride (Yield: 73%) $^1$H NMR (400 MHz, DMSO-d$_6$): δ 8.90 (s, 1H), 8.45 (d, J=7.6 Hz, 1H), 7.99 (s, 1H), 7.74 (d, J=9.6 Hz, 1H), 7.44 (d, J=8.4 Hz, 2H), 7.37 (d, J=8.4 Hz, 2H), 7.03 (s, 1H), 6.14 (bs, 2H), 5.22 (d, J=2.8 Hz, 1H), 4.99-4.89 (m, 1H), 4.67 (d, J=7.6 Hz, 1H), 4.52 (d, J=9.6 Hz, 1H), 4.24 (s, 1H), 3.74-3.58 (m, 2H), 3.19-3.08 (m, 2H), 2.73-2.69 (m, 4H), 2.42 (s, 3H), 2.18-2.08 (m, 1H), 1.87-1.76 (m, 1H), 1.38 (d, J=6.8 Hz, 3H), 1.25-1.20 (m, 3H), 0.80 (s, 9H); LC-MS: m/z 742.2 (M+1)$^+$.

Step-b: Synthesis of (2S,4R)-1-((S)-2-(2-(4-(3-amino-6-(5-fluoro-2-hydroxyphenyl)pyridazin-4-yl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide (Compound-63)

The title compounds were synthesized by using the General procedure of Suzuki coupling which was followed for Intermediates 1e$_1$-1e$_{12}$ using (2S,4R)-1-((S)-2-(2-(4-(3-amino-6-bromopyridazin-4-yl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide (Yield: 50%) $^1$H NMR (400 MHz, DMSO-d$_6$): δ 14.09 (s, 1H), 8.98 (s, 1H), 8.44 (d, J=7.2 Hz, 1H), 7.91 (d, J=8.4 Hz, 1H), 7.79 (d, J=9.2 Hz, 1H), 7.59 (s, 1H), 7.44-7.35 (m, 4H), 7.10-7.06 (m, 1H), 6.90-6.87 (m, 1H), 6.37 (s, 2H), 5.14 (s, 1H), 4.90-4.87 (m, 1H), 4.51 (d, J=9.6 Hz, 1H), 4.46-4.42 (m, 1H), 4.29 (s, 1H), 3.59-3.56 (m, 2H), 3.20-3.10 (m, 5H), 3.09-3.00 (m, 1H), 2.80-2.60 (m, 4H), 2.45 (s, 3H), 2.08-2.03 (m, 1H), 1.79-1.74 (m, 1H), 1.36 (d, J=6.8 Hz, 3H), 0.96 (s, 9H); LC-MS: m/z 774.3 (M+1)$^+$.

Example-XVII: Synthesis of (2S,4R)-1-((S)-2-(2-(4-(3-amino-6-(hydroxymethyl)pyridazin-4-yl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide-(Compound-64)

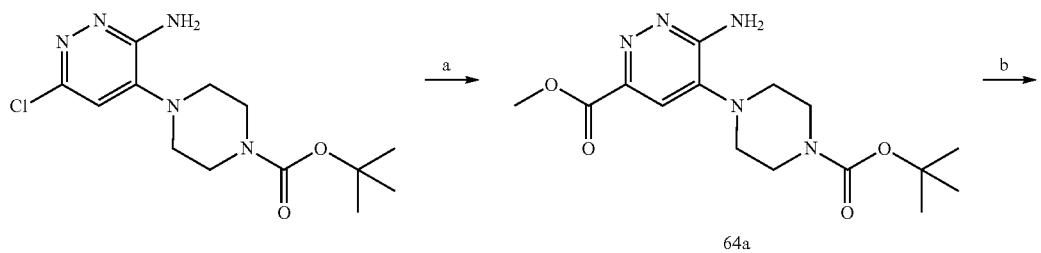

64a

-continued

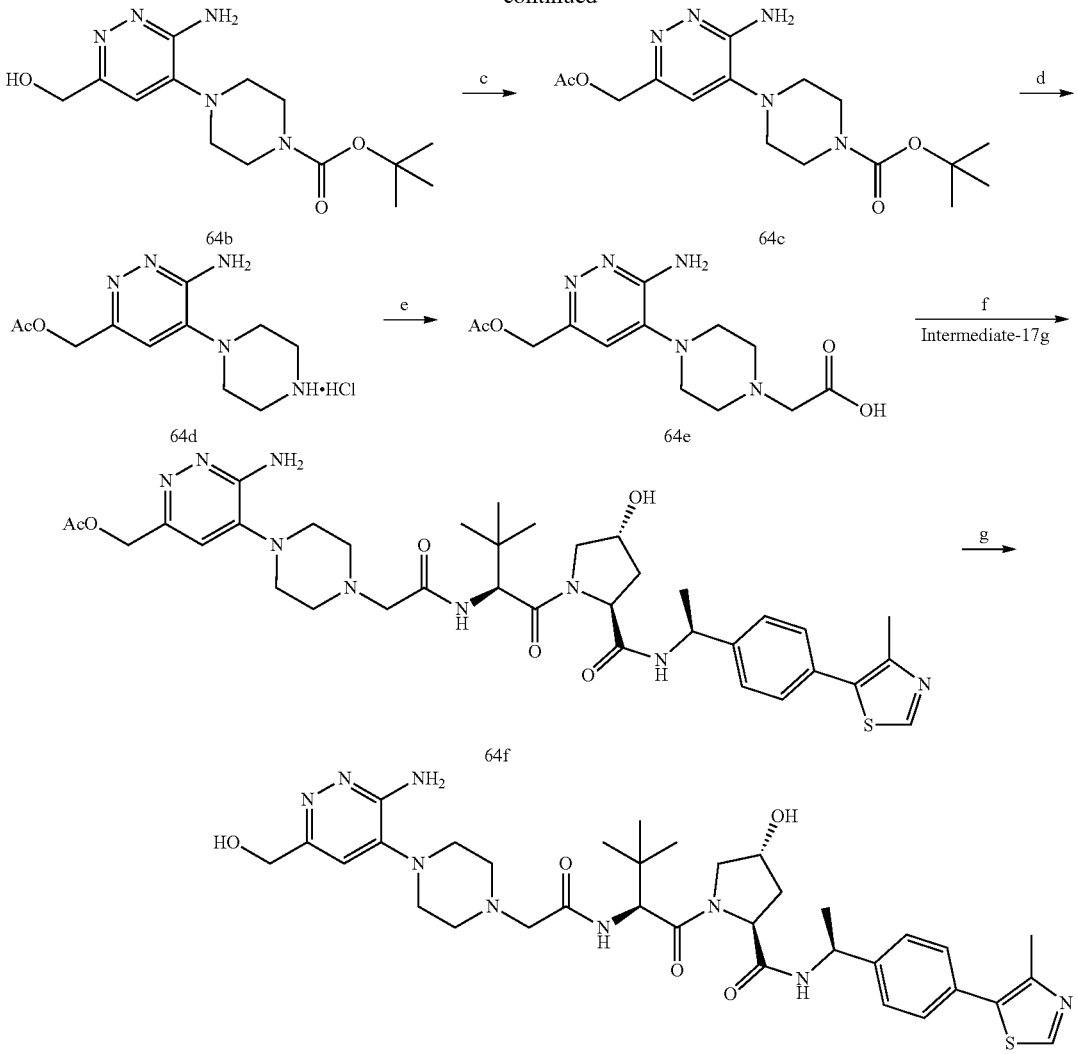

Compound-64

Conditions: a) Pd(dppf)Cl₂:DCM(1:1), Pd(OAc)₂, TEA, EtOAc:MeOH (1:1), CO gas, steel bomb vessel, 80° C.-7 days; b) LiAlH₄, THF, 0° C.-RT-1 h; c) Pyridine, Acetic anhydride, 100° C.-2 h; d) 4M HCl in 1,4-Dioxane, DCM, 0° C.-RT-16 h; e) ter.Butyl bromoacetate, DIPEA, DMF-60° C.-16, ii) 4M HCl in 1,4-Dioxane, DCM, 0° C.-RT-16 h; f) HATU, DIPEA, DMF, 0° C., RT-18 h; g) LiOH•H₂O, THF:MeOH:H₂O, RT-16 h.

Step-a: Synthesis of methyl 6-amino-5-(4-(tert-butoxycarbonyl)piperazin-1-yl)pyridazine-3-carboxylate (64a)

To a stirred solution of tert-butyl 4-(3-amino-6-chloropyridazin-4-yl)piperazine-1-carboxylate (5.0 g, 15.97 mmol) in MeOH and EtOAc (1:1) in a steel bomb vessal (100 mL) were added Pd(OAc)₂ (0.35 g, 1.59 mmol) and Pd(dppf)Cl₂:DCM (1:1) (1.30 g, 1.59 mmol) and followed by TEA (6.91 mL, 47.9 mmol) and the reaction mixture was purged with N₂ gas and recation was stirred for 7 days at 80° C. under CO gas atmosphere at 100 psi. After completion of the reaction (monitored by TLC), reaction mixture was diluted with EtOAc (100 mL) and filtered off, the filtrate was washed with water (100 ml) and brine solution (100 ml) and separated organic layer was dried over Na₂SO₄, concentrated and purified by combiflash using 5% MeOH in DCM as eluent to afford the title compound (3.0 g, 56%). ¹H NMR (400 MHz, DMSO-d₆): δ 7.29 (s, 1H), 6.82 (s, 2H), 3.84 (5, 3H), 3.51-3.50 (m, 4H), 2.91-2.88 (m, 4H), 1.42 (1, 9H); LC-MS: m/z 338.2 (M+1).

Step-b: Synthesis of tert-butyl 4-(3-amino-6-(hydroxymethyl)pyridazin-4-yl)piperazine-1-carboxylate (64b)

To a stirred solution of methyl 6-amino-5-(4-(tert-butoxycarbonyl)piperazin-1-yl)pyridazine-3-carboxylate (1.0 g, 2.96 mmol) in THF (20 mL) in two neck RB was added 1M LiAlH₄ solution in THF (9 mL, 8.90 mmol) dropwise over period of 5 mins at 0° C. and stirred for 1 h at RT then. The reaction mixture was quenched with cold saturated Na₂SO₄ solution and extracted with ethyl acetate (2×50 mL). The combined organic layer was washed with water (50 mL), brine (50 mL), dried over anhydrous sodium sulphate and concentrated under vacuum to give the residue which was purified by combi flash column chomatography using 50% ethyl acetate in hexane as eluent to afford the title compound (0.5 g, 55%). ¹H NMR (400 MHz, DMSO-d₆): δ 6.88 (s, 1H), 5.86 (s, 2H), 5.24-5.20 (m, 1H), 4.48 (d, J=5.6 Hz, 2H), 3.50-3.48 (m, 4H), 2.90-2.80 (m, 4H), 1.42 (s, 9H); LC-MS: m/z 310.0 (M+1)⁺.

Step-c: Synthesis of tert-butyl 4-(6-(acetoxymethyl)-3-aminopyridazin-4-yl)piperazine-1-carboxylate (64c)

To a stirred solution of tert-butyl 4-(3-amino-6-(hydroxymethyl)pyridazin-4-yl)piperazine-1-carboxylate (0.5 g, 1.61 mmol) in Pyridine (5 mL) in two neck RB was added Acetic anhydride (0.4 mL, 4.85 mmol) at RT and stirred for 2 h at 100° C. then The reaction mixture was quenched with cold water extracted with ethyl acetate (2×50 mL). The combined organic layer was washed with water (50 mL), brine (50 mL), dried over anhydrous sodium sulphate and concentrated under vacuum to give the residue which was purified by combi flash column chomatography using 60% ethyl acetate in hexane as eluent to afford the title compound (0.5 g, 83%). ¹H NMR (400 MHz, DMSO-d₆): δ 6.90 (s, 1H), 6.16 (s, 2H), 5.18 (s, 2H), 3.52-3.50 (m, 4H), 2.98-2.89 (m, 4H), 2.06 (s, 3H), 1.40 (s, 9H); LC-MS: m/z 352.0 (M+1)⁺.

Step-d: Synthesis of 2-(4-(6-(acetoxymethyl)-3-aminopyridazin-4-yl)piperazin-1-yl)acetic acid (64d)

The title compound was synthesized by using the same procedure which was followed for Intermediate-1c using tert-butyl 4-(6-(acetoxymethyl)-3-aminopyridazin-4-yl)piperazine-1-carboxylate (Yield: 90%) LC-MS: m/z 252.0 (M+1)⁺.

Step-e: Synthesis of 2-(4-(6-(acetoxymethyl)-3-aminopyridazin-4-yl)piperazin-1-yl)acetic acid (64e)

The title compound was synthesized by using the same procedure which was followed for Intermediate-1d and Intermediates-1f₁-11f₁₂ using (6-amino-5-(piperazin-1-yl)pyridazin-3-yl)methyl acetate hydrochloride and tert-butyl acetate to afford title compound (Yield: 90%) LC-MS: m/z 310.1 (M+1)⁺.

Step-f: Synthesis of (6-amino-5-(4-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)piperazin-1-yl)pyridazin-3-yl)methyl acetate (64f)

The title compound was synthesized by using the same procedure which was followed for compound-1 using ((2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (Yield: 90%) LC-MS: m/z 736.4 (M+1)⁺.

Step-g: Synthesis of (2S,4R)-1-((S)-2-(2-(4-(3-amino-6-(hydroxymethyl)pyridazin-4-yl) piperazin-1-yl)acetamido)-3,3-dimethylbutanoyl)-4-hydroxy-N—((S)-1-(4-(4-methylthiazol-5-yl)phenyl)ethyl) pyrrolidine-2-carboxamide (Compound-64)

The title compound was synthesized by using the same procedure which was followed for Intermediate-3d using with (6-amino-5-(4-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)piperazin-1-yl)pyridazin-3-yl)methyl acetate to afford title compound, (Yield: 10%); ¹H NMR (400 MHz, DMSO-d₆): δ 8.98 (s, 1H), 8.44 (d, J=7.6 Hz, 1H), 7.78 (d, J=9.2 Hz, 1H), 7.44-7.35 (m, 4H), 6.92 (s, 1H), 5.78 (s, 2H), 5.25 (t, J=5.6 Hz, 1H), 5.12 (s, 1H), 4.90-4.87 (m, 1H), 4.52-4.41 (m, 4H), 4.28 (s, 1H), 3.58 (s, 2H), 3.18-3.00 (m, 6H), 2.70-2.60 (m, 4H), 2.46 (s, 3H), 2.10-1.99 (m, 1H), 1.78-1.74 (m, 1H), 1.37 (d, J=6.8 Hz, 3H), 0.99 (s, 9H); LC-MS: m/z 692.2 (M−1)⁺.

Example-XVIII: Synthesis of (2S,4R)-1-((S)-2-(2-(4-(3-amino-6-(2-hydroxyphenyl)pyridazin-4-yl) piperazin-1-yl)acetamido)-3,3-dimethylbutanoyl)-4-hydroxy-N—((S)-1-(4-(4-methylthiazol-5-yl)phenyl) ethyl)pyrrolidine-2-carboxamide hydrochloride (Compound-65)

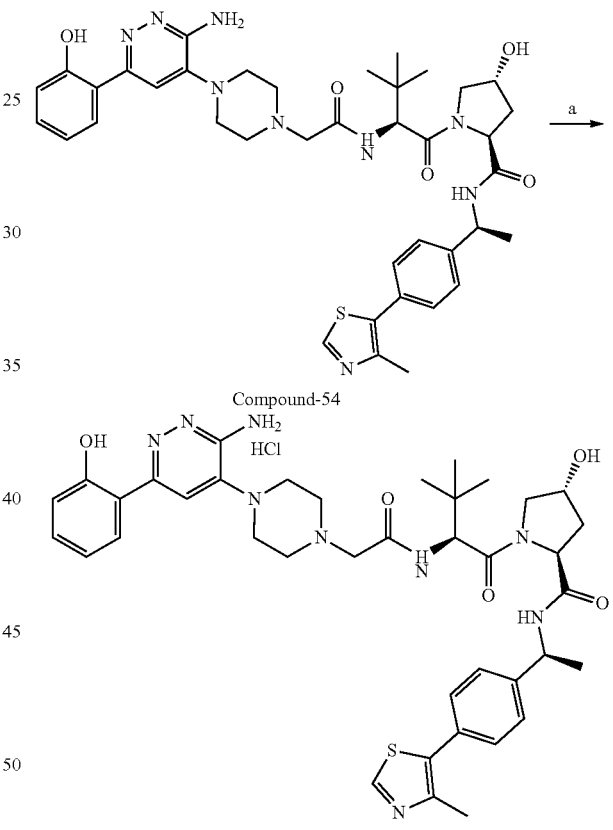

Compound-54

Compound-65

Conditions: a) 2M HCl soltuions, dry. THF, RT-16 h.

Step-a: Synthesis of tert-butyl 4-(6-(acetoxymethyl)-3-aminopyridazin-4-yl)piperazine-1-carboxylate (Compound-65)

To a stirred solution of (2S,4R)-1-((S)-2-(2-(4-(3-amino-6-(2-hydroxyphenyl)pyridazin-4-yl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide (0.30 g, 0.396 mmol) in dry THF (1.5 mL) in two neck RB was added 2M HCl (1.98 mL, 3.96 mmol) in Diethyl ether at RT and stirred for 16 h at RT. then The reaction mixture was diluted with Ether and filtered off under $N_2$ gas atmosphere. The obtained solid was dried well under vacuum to afford the title compound (0.27 g, 86%); $^1$H NMR (400 MHz, DMSO-$d_6$): δ 8.93 (s, 1H), 8.51 (bs, 1H), 8.13 (bs, 1H), 7.61 (d, J=5.2 Hz, 1H), 7.43 (s, 1H), 7.42-7.39 (m, 5H), 7.10-7.08 (m, 1H), 6.98-6.95 (m, 1H), 4.97-4.90 (m, 2H), 4.72-4.70 (m, 1H), 4.56-4.54 (m, 1H), 4.50-4.44 (m, 2H), 4.33-4.30 (m, 2H), 4.05-4.01 (m, 2H), 3.72-3.60 (m, 6H), 3.58 (bs, 3H), 2.45 (s, 3H), 2.03-2.01 (m, 1H), 1.98-1.90 (m, 1H), 1.40 (d, J=6.8 Hz, 3H), 0.98 (s, 9H); LC-MS: m/z 757.05 (M+1)$^+$.

Example-XIX-Synthesis sodium (3R,5S)-1-((S)-2-(2-(1-(3-amino-6-(2-oxidophenyl)pyridazin-4-yl)piperidin-4-yl)acetamido)-3,3-dimethylbutanoyl)-5-(((S)-1-(4-(4-methylthiazol-5-yl)phenyl)ethyl)carbamoyl)pyrrolidin-3-olate (Compound-66)

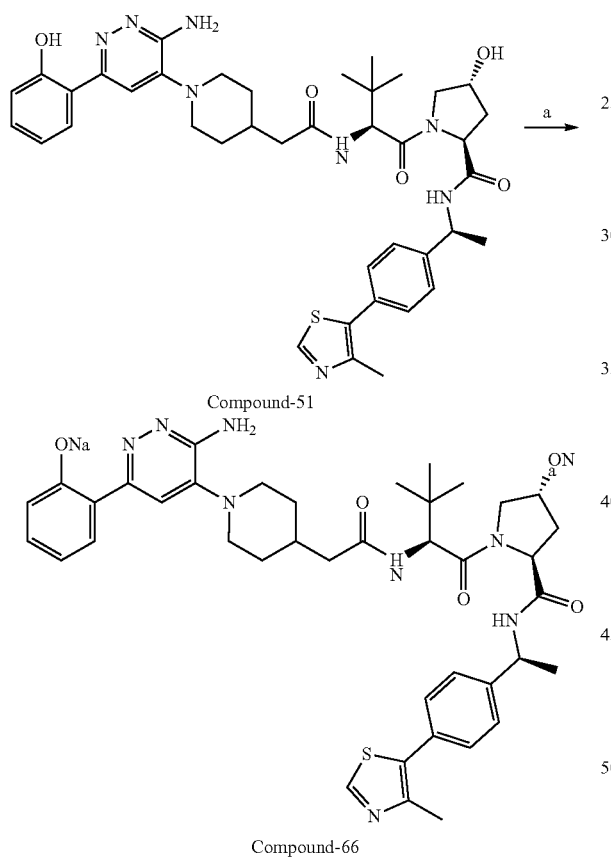

Compound-51

Compound-66

Conditions: a) 2M NaOH soltuions, MeOH, RT-16 h.

Step-a: Synthesis of sodium (3R,5S)-1-((S)-2-(2-(1-(3-amino-6-(2-oxidophenyl)pyridazin-4-yl)piperidin-4-yl)acetamido)-3,3-dimethylbutanoyl)-5-(((S)-1-(4-(4-methylthiazol-5-yl)phenyl)ethyl)carbamoyl)pyrrolidin-3-olate (Compound-66)

To a stirred solution of (2S,4R)-1-((S)-2-(2-(1-(3-amino-6-(2-hydroxyphenyl)pyridazin-4-yl)piperidin-4-yl)acetamido)-3,3-dimethylbutanoyl)-4-hydroxy-N—((S)-1-(4-(4-methylthiazol-5-yl)phenyl)ethyl)pyrrolidine-2-carboxamide (0.1g, 0.132 mmol) in MeOH (1 mL) in two neck RB was added aq. 2M NaOH solution (2.0 eq.) at RT and stirred for 16 h at RT. then The reaction mixture evaporated under vacuum to get residue which was washed with DCM and filtered off the solid, the obtained solid was dried under vacuum afford the title compound (0.080 g, 76%). $^1$H NMR (400 MHz, DMSO-$d_6$): δ 8.98 (s, 1H), 8.56 (s, 1H), 7.62-7.60 (m, 1H), 7.43-7.35 (m, 6H), 6.73-6.68 (m, 1H), 6.18-6.16 (m, 1H), 5.94-5.76 (m, 1H), 4.93-4.88 (m, 1H), 4.52 (s, 1H), 4.44 (t, J=8.0 Hz, 1H), 4.26 (d, J=3.2 Hz, 1H), 3.01 (s, 2H), 3.31-3.29 (m, 2H), 2.51-2.50 (m, 4H merged in DMSO), 2.49 (s, 3H), 2.21-2.17 (m, 2H), 2.01-2.00 (m, 1H), 1.81-1.75 (m, 2H), 1.71-1.68 (m, 2H), 1.44-1.39 (m, 2H), 1.36 (d, J=6.8 Hz, 3H), 0.95 (s, 9H); LC-MS: m/z 755.4 (M+1)$^+$.

Example-XX: (2S,4R)-1-((S)-2-(2-(4-(3-aminopyridazin-4-yl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide (Compound-67)

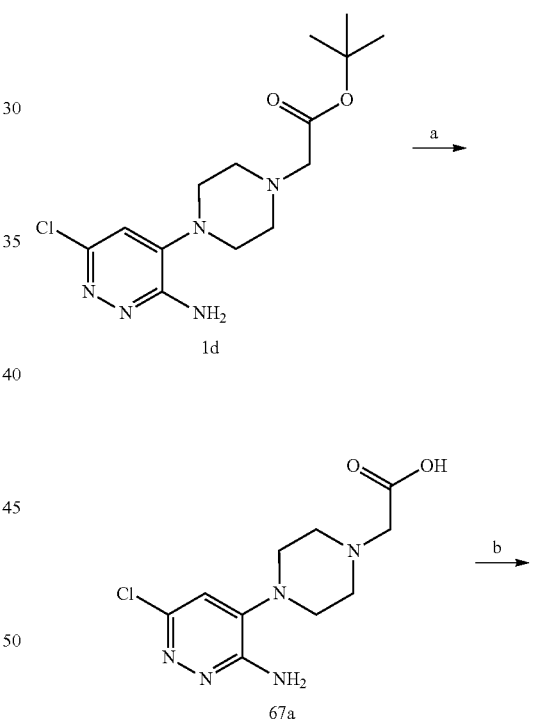

1d

67a

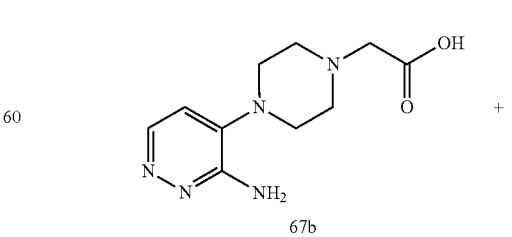

67b

-continued

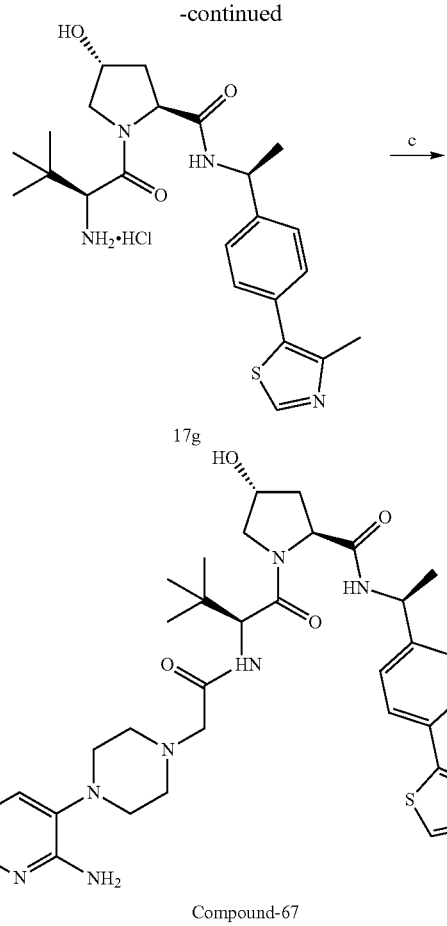

Compound-67

Conditions: a) 4M HCl in 1,4-Dioxane, DCM, 0° C.-RT-16 h; b) Pd/C, MeOH, H₂ gas, 60 psi, RT, 16 h; c) HATU, DIPEA, DMF, 0° C.-RT, 16 h.

Step-a: Synthesis of 2-(4-(3-aminopyridazin-4-yl) piperazin-1-yl)acetic acid (67a)

The title compound was synthesized by using the same procedure which was followed for Intermediate-1f₁-1f₁₂ using tert-butyl 3-(4-(3-amino-6-(2-hydroxyphenyl) pyridazin-4-yl) piperazin-1-yl) propanoate (Yield: 90%). LC-MS: m/z 272.1 (M+1)⁺.

Step-b; Synthesis of tert-butyl 2-(4-(3-amino-pyridazin-4-yl)piperazin-1-yl)acetate (67b)

To a stirred solution of tert-butyl 2-(4-(3-amino-6-chloropyridazin-4-yl)piperazin-1-yl)acetate (0.15 g, 0.45 mmol) in methanol (5 mL) was added 10% Pd/C (35 mg). The reaction was performed under hydrogen atmosphere (60 psi) at RT for 16 h. After completion of the reaction (monitored by TLC) the reaction mixture was filtered though celite. The filtrate was concentrated to afford title compound (100 mg, 75%) which was used in the next step without Further purification. LC-MS: m/z 238.1 (M+1)⁺.

Step-c: Synthesis of (2S,4R)-1-((S)-2-(2-(4-(3-aminopyridazin-4-yl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide (Compound-67)

The title compound was synthesized by using the same procedure which was followed for compound-1 using (2S, 4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (Yield: 14%). ¹H NMR (400 MHz, DMSO-d₆): δ 8.97 (s, 1H), 8.41 (d, J=7.6 Hz, 1H), 8.33 (d, J=5.6 Hz, 1H), 7.75 (d, J=9.6 Hz, 1H), 7.44-7.43 (m, 4H), 6.86 (d, J=5.2 Hz, 1H), 5.81 (s, 2H), 5.11 (d, J=3.6 Hz, 1H), 4.87 (t, J=7.6 Hz, 1H), 4.51 (d, J=9.6 Hz, 1H), 4.41 (t, J=8.0 Hz, 1H), 4.28 (s, 1H), 3.62-3.59 (m, 2H), 3.10 (s, 2H), 3.02-3.00 (m, 4H), 2.68-2.63 (m, 4H), 2.49 (s, 3H), 2.07-2.02 (m, 1H), 1.79-1.73 (m, 1H), 1.37 (d, J=7.2 Hz, 3H), 0.94 (s, 9H); LC-MS: m/z 664.3 (M+1)⁺.

Example-XXI: Synthesis of (E)-3-(4-(3-amino-6-(2-hydroxyphenyl)pyridazin-4-yl)piperazin-1-yl)-N-(2-(2,6-dioxopiperidin-3-yl)-1,3-dioxoisoindolin-4-yl) acrylamide (Compound-68)

Compound-68

Conditions: a) 29b, propiolic acid, DCM, RT, 16 h; b) Intermedaite-2b, DMF, RT, 16 h Step-a: Synthesis of N-(2-(2,6-dioxopiperidin-3-yl)-1,3-dioxoisoindolin-4-yl)propiolamide-68a To a stirred solution of 4-amino-2-(2,6-dioxopiperidin-3-yl)isoindoline-1,3-dione (1.0 eq.) in DCM (10 vol.) was added propiolic acid (1.50 eq.) at RT and stirred for 16 h at RT. After completion of the reaction (monitored by TLC) the reaction mixture was quenched with water and extracted with ethyl acetate. The combined organic layer was washed with water, brine, dried over anhydrous sodium sulphate and concentrated under vacuum to give the residue which was purified by combi flash using 1-2% MeOH in DCM as eluent to afford title compound (68a, yield: 55%). ¹H NMR (400 MHz, DMSO-d₆): δ 11.14 (s, 1H), 10.44 (s, 1H), 8.16 (d, J=8.4 Hz, 1H), 7.87 (t, J=8.0 Hz, 1H), 7.22 (d, J=7.6 Hz, 1H), 5.12-5.10 (m, 1H), 4.59 (s, 1H), 2.90-2.88 (m, 1H), 2.67-2.50 (m, 2H), 2.08-2.04 (m, 1H); LC-MS: m/z 324.0 (M−1).

Step-b: Synthesis of (E)-3-(4-(3-amino-6-(2-hydroxyphenyl)pyridazin-4-yl)piperazin-1-yl)-N-(2-(2,6-dioxopiperidin-3-yl)-1,3-dioxoisoindolin-4-yl)acrylamide (Compound-68)

To a stirred solution of 68a (0.025 g, 0.076 mmol) in DMF (10 mL) in a two neck RB was added Intermediate-2b (0.023 gm, 0.076 mmol) at RT and stirred for 16 h at RT. The reaction mixture was quenched with water (30 mL) and extracted with EtOAc (2×50 mL). The combined organic layer was washed with water (50 mL), brine (50 mL), dried over anhydrous sodium sulphate and concentrated under reduced pressure to give the crude product which was purified by combi flash using 50% ethyl acetate in hexane as eluent to afford the title compound (0.012 g, 26%) ¹H NMR (400 MHz, DMSO-d₆): δ 14.14 (s, 1H), 11.1 (s, 1H), 9.12 (s, 1H), 8.73 (d, J=8.4 Hz, 1H), 7.93 (d, J=8.4 Hz, 1H), 7.77 (t, J=7.6 Hz, 1H), 7.57-7.47 (m, 3H), 7.26-7.22 (m, 1H), 6.91-6.87 (m, 2H), 6.42 (s, 2H), 5.20 (d, J=8.8 Hz, 1H), 5.14 (dd, J=5.6 Hz, J=12.8 Hz, 10H), 3.57-3.52 (d, 4H), 3.14-3.13 (m, 4H), 2.90-2.67 (m, 1H), 2.63-2.59 (m, 2H), 2.09-2.06 (n, 1H); LC-MS: m/z 597.60 (M+1).

Example-XXII: Synthesis of Compounds: 69, 70, and 71

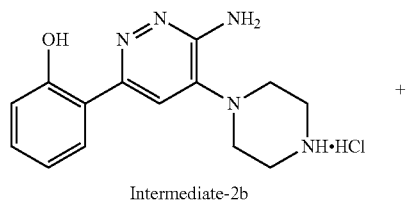

Intermediate-2b

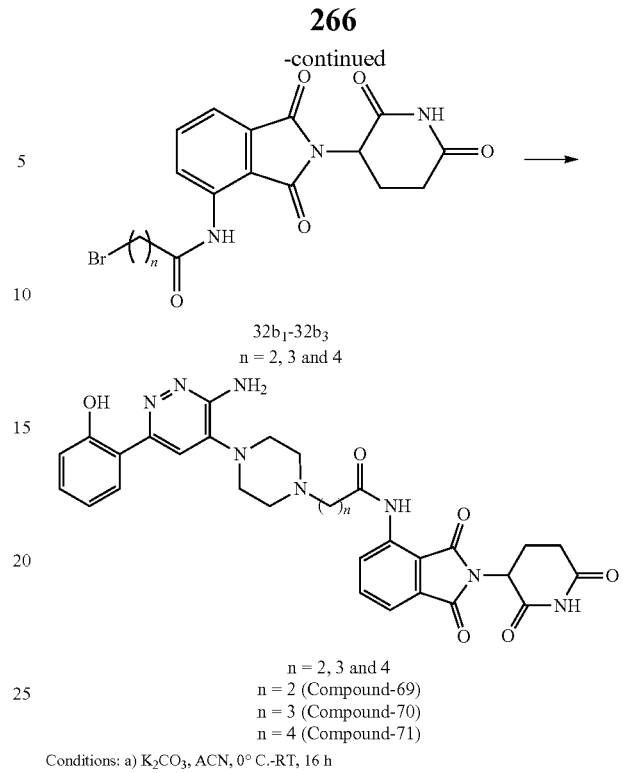

32b₁-32b₃
n = 2, 3 and 4 n = 2, 3 and 4
n = 2 (Compound-69)
n = 3 (Compound-70)
n = 4 (Compound-71)

Conditions: a) K₂CO₃, ACN, 0° C.-RT, 16 h

Step-a: General Procedure for Coupling of 2-(6-amino-5-(piperazin-1-yl)pyridazin-3-yl)phenol hydrochloride with various substitution of CRBN intermediates To a stirred solution of Intermediate-2b (1.0 eq) in ACN (10 vol.) were added K₂CO₃ (3.0 eq) followed by various substitution of CRBN (32b₁-32b₃)alkyl halides (1.50 eq) at 0° C. and the reaction mixture was stirred for 16 at RT. Then RM was quenched with water (20 mL) and extracted with EtOAc (2×50 mL). The combined organic layer was washed with water (50 mL), brine (50 mL), dried over anhydrous sodium sulphate, concentrated and purified by column chomatography to afford the title compound (69, 70 and 71) (Yield: 6.8-37%).

TABLE 27

| Structure | Characterization Data ¹H NMR (400 MHz, DMSO-d₆) |
|---|---|
| ![structure n=2] | ¹H NMR (400 MHz, DMSO-d₆): δ 14.28 (s, 1H), 11.13 (s, 1H), 10.51 (s, 1H), 8.56 (d, J = 8.8 Hz, 1H), 7.90 (d, J = 6.4 Hz, 1H), 7.83 (t, J = 7.6 Hz, 1H), 7.62 (d, J = 7.2 Hz, 1H), 7.49 (s, 1H), 7.21 (t, J = 7.2 Hz, 1H), 6.89-6.84 (m, 2H), 6.28 (s, 2H), 5.14-5.10 (m, 1H), 3.18-3.14 (m, 4H), 2.79-2.67 (m, 8H), 2.50-2.41 (m, 3H), 2.07-2.02 (m, 1H); LC-MS: m/z 599.2 (M + 1)⁺. (Yield: 6.8%). |

TABLE 27-continued

| Structure | Characterization Data<br>$^1$H NMR (400 MHz, DMSO-$d_6$) |
|---|---|
| 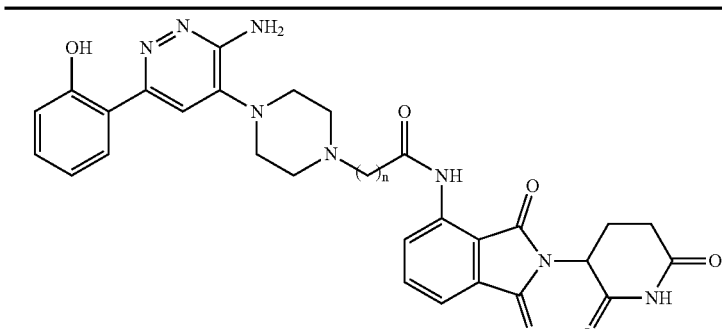<br>n = 3 | $^1$H NMR (400 MHz, DMSO-$d_6$): δ 14.20 (s, 1H), 11.13 (s, 1H), 9.70 (s, 1H), 8.51 (d, J = 8.0 Hz, 1H), 8.34 (s, 1H), 7.83 (dd, J = 14.4 Hz, J = 15.6 Hz, 2H), 7.57 (d, J = 7.2 Hz, 1H), 7.40 (s, 1H), 7.26-7.22 (m, 1H), 6.91-6.87 (m, 2H), 6.20 (s, 2H), 5.16-5.12 (m, 1H), 3.16-2.93 (m, 7H), 2.59-2.51 (m, 7H), 1.98-1.90 (m, 1H), 1.86-1.82 (m, 2H);<br>LC-MS: m/z 613.2 (M + 1)$^+$. (Yield: 19%). |
| 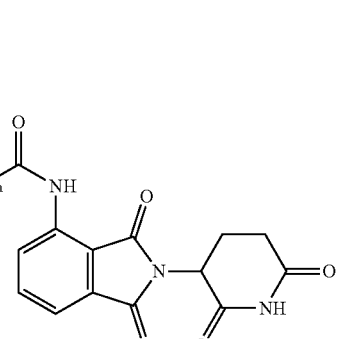<br>n = 4 | $^1$H NMR (400 MHz, DMSO-$d_6$): δ 14.22 (s, 1H), 9.70 (s, 1H), 8.48 (d, J = 8.4 Hz, 1H), 7.91-7.89 (m, 1H), 7.85-7.81 (m, 1H), 7.61 (d, J = 7.2 Hz, 1H), 7.49-7.41 (m, 2H), 7.25-7.21 (m, 1H), 6.90-6.86 (m, 2H), 6.21 (s, 2H), 5.13 (dd, J$_1$ = 6.0 Hz, J$_2$ = 12.8 Hz, 1H), 3.25-3.10 (m, 4H), 2.67-2.65 (m, 4H), 2.45-2.38 (m, 4H), 2.20-2.07 (m, 2H), 1.70-1.66 (m, 3H), 1.56-1.54 (m, 3H);<br>LC-MS: m/z 627.15 (M + 1)$^+$. (Yield: 37%). |

Example:XXIII: Synthesis of methyl 6-amino-5-(4-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)piperazin-1-yl)pyridazine-3-carboxylate (Compound-72)

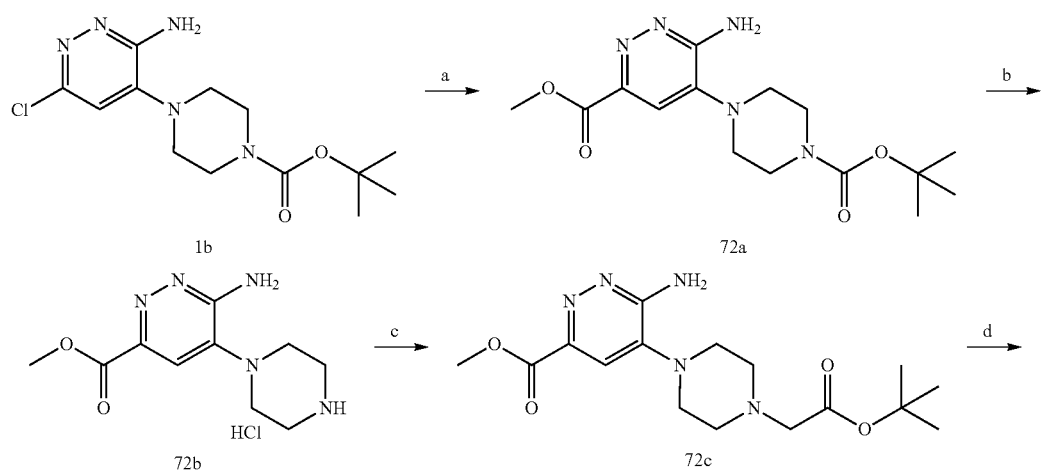

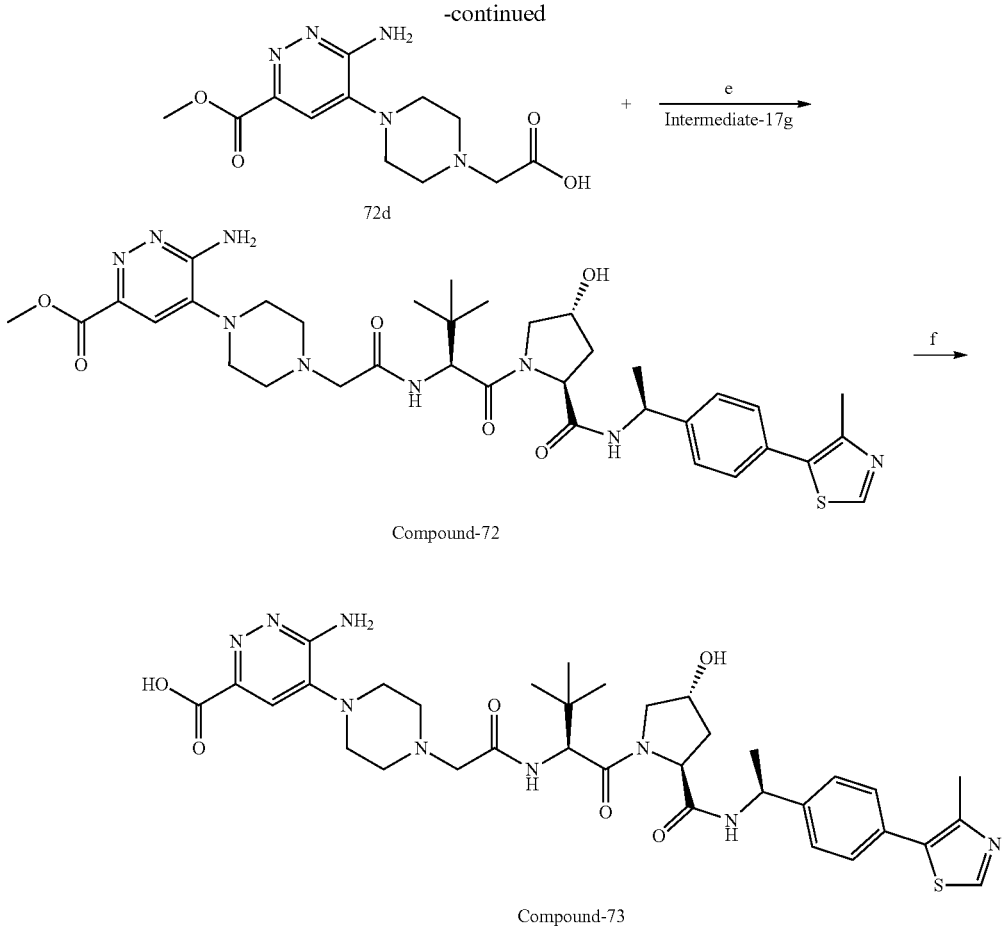

Conditions: a) Pd(dppf)Cl₂:DCM (1:1), Pd(OAc)₂, TEA, MeOH and EtOAc (1:1), CO gas, 100 psi, 80° C.-7 days; b) 4M HCl in Dioxane, DCM, 0° C.-RT-16; c) DIPEA, DMF, RT-16 h; d) 4M HCl in Dioxane, DCM, 0° C.-RT-16; e) HATU, DIPEA, DMF, RT-16 h; f) LiOH•H₂O, THF:MeOH:H₂O, RT-16 h.

Step-a: Synthesis of methyl 6-amino-5-(4-(tert-butoxycarbonyl)piperazin-1-yl)pyridazine-3-carboxylate (72a)

To a stirred solution of tert-butyl 4-(3-amino-6-chloropyridazin-4-yl)piperazine-1-carboxylate (5.0 g, 15.97 mmol) in MeOH and EtOAc (1:1) in a steel bomb vessel (100 mL) were added Pd(OAc)₂ (0.35 g, 1.59 mmol) and Pd(dppf)Cl₂:DCM (1:1) (1.30 g, 1.59 mmol) and followed by TEA (6.91 mL, 47.9 mmol) and the reaction mixture was purged with N₂ gas and reaction was stirred for 7 days at 80° C. under CO gas atmosphere at 100 psi. After completion of the reaction (monitored by TLC), reaction mixture was diluted with EtOAc (100 ml) and filtered off, the filtrate was washed with water (100 mL) and brine solution (100 ml) and separated organic layer was dried over Na₂SO₄, concentrated and purified by combiflash using 5% MeOH in DCM as eluent to afford the title compound (3.0 g, 56%) ¹H NMR (400 MHz, DMSO-d₆): δ 7.29 (s, 1H), 6.82 (s, 2H), 3.84 (s, 3H), 3.51-3.50 (m, 4H), 2.91-2.88 (m, 4H), 1.42 (s, 9H); LC-MS: m/z 338.2 (M+1)⁺.

Step-b: Synthesis of methyl 6-amino-5-(piperazin-1-yl)pyridazine-3-carboxylate (72b)

The title compound was synthesized by using the same procedure which was followed for Intermediate-1f₁-1f₁₂ using methyl 6-amino-5-(4-(tert-butoxycarbonyl)piperazin-1-yl)pyridazine-3-carboxylate (Yield: 90%); LC-MS: m/z 238.2 (M+1)⁺.

Step-c: Synthesis of methyl 6-amino-5-(4-(2-(tert-butoxy)-2-oxoethyl)piperazin-1-yl)pyridazine-3-carboxylate (72c)

The title compound was synthesized by using the same procedure which was followed for Intermediate-1d using methyl 6-amino-5-(piperazin-1-yl)pyridazine-3-carboxylate hydrochloride (Yield: 63%) ¹H NMR (400 MHz, DMSO-d₆): δ 7.27 (s, 1H), 6.65 (s, 2H), 3.84 (s, 3H), 3.16 (s, 2H), 2.96-2.90 (m, 4H), 2.71-2.70 (m, 4H), 1.42 (s, 9H); LC-MS: m/z 352.10 (M+1)⁺.

Step-d: Synthesis of 2-(4-(3-amino-6-(methoxycarbonyl)pyridazin-4-yl)piperazin-1-yl)acetic acid (72d)

The title compound was synthesized by using the same procedure which was followed for Intermediate-1f₁-1f₁₂ using methyl 6-amino-5-(4-(2-(tert-butoxy)-2-oxoethyl)piperazin-1-yl)pyridazine-3-carboxylate (Yield: 85%) ¹H NMR (400 MHz, DMSO-d₆): δ 10.6 (s, 1H), 8.05 (bs, 2H), 7.47 (s, 1H), 4.08-4.02 (m, 4H), 3.93-3.90 (m, 4H), 3.56 (s, 2H), 3.38 (s, 3H); LC-MS: m/z 296.2 (M+1)⁺.

Step-e: Synthesis of methyl 6-amino-5-(4-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)piperazin-1-yl)pyridazine-3-carboxylate (Compound-72)

The title compound was synthesized by using the same procedure which was followed for Compound-1 using with (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (Yield: 17%); $^1$H NMR (400 MHz, DMSO-$d_6$): δ 8.97 (s, 1H), 8.41 (d, J=8.0 Hz, 1H), 7.45 (d, J=9.2 Hz, 1H), 7.44-7.35 (m, 4H), 7.31 (s, 1H), 6.94 (s, 2H), 5.11 (d, J=3.6 Hz, 1H), 4.89 (t, J=7.6 Hz, 1H), 4.51 (d, J=10.0 Hz, 1H), 4.42 (t, J=8.0 Hz, 1H), 4.28 (bs, 1H), 3.85 (s, 3H), 3.58-3.56 (m, 2H), 3.14-3.01 (m, 6H), 2.88-2.82 (m, 4H), 2.49 (s, 3H), 2.09-2.00 (m, 1H), 1.76-1.72 (m, 1H), 1.37 (d, J=7.3 Hz, 3H), 0.95 (s, 9H); LC-MS: m/z 722.3 (M+1)$^+$.

Step-f: Synthesis of 6-amino-5-(4-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)piperazin-1-yl)pyridazine-3-carboxylic acid (Compound-73)

The title compound was synthesized by using the same procedure which was followed for Intermediate-3d using with (methyl 6-amino-5-(4-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)piperazin-1-yl)pyridazine-3-carboxylate (Yield: 70%); $^1$H NMR (400 MHz, DMSO-$d_6$): δ 8.97 (s, 1H), 8.43 (d, J=9.5 Hz, 1H), 7.76 (d, J=9.6 Hz, 1H), 7.45-7.42 (m, 2H), 7.37-7.33 (m, 2H), 7.32 (s, 1H), 6.27 (s, 2H), 5.11 (s, 1H), 4.47 (t, J=7.6 Hz, 1H), 4.43-4.28 (m, 2H), 4.03 (s, 1H), 3.62-3.55 (m, 2H), 3.32-3.01 (m, 7H), 2.73-2.52 (m, 3H), 2.47 (s, 3H), 2.07-2.04 (m, 1H), 1.79-1.73 (m, 1H), 1.37 (d, J=6.8 Hz, 3H), 0.95 (s, 9H); LC-MS: m/z 708.3 (M+1)$^+$.

Example:XXIV: Synthesis of 6-amino-5-(4-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)piperazin-1-yl)pyridazine-3-carboxamide (Compound-74)

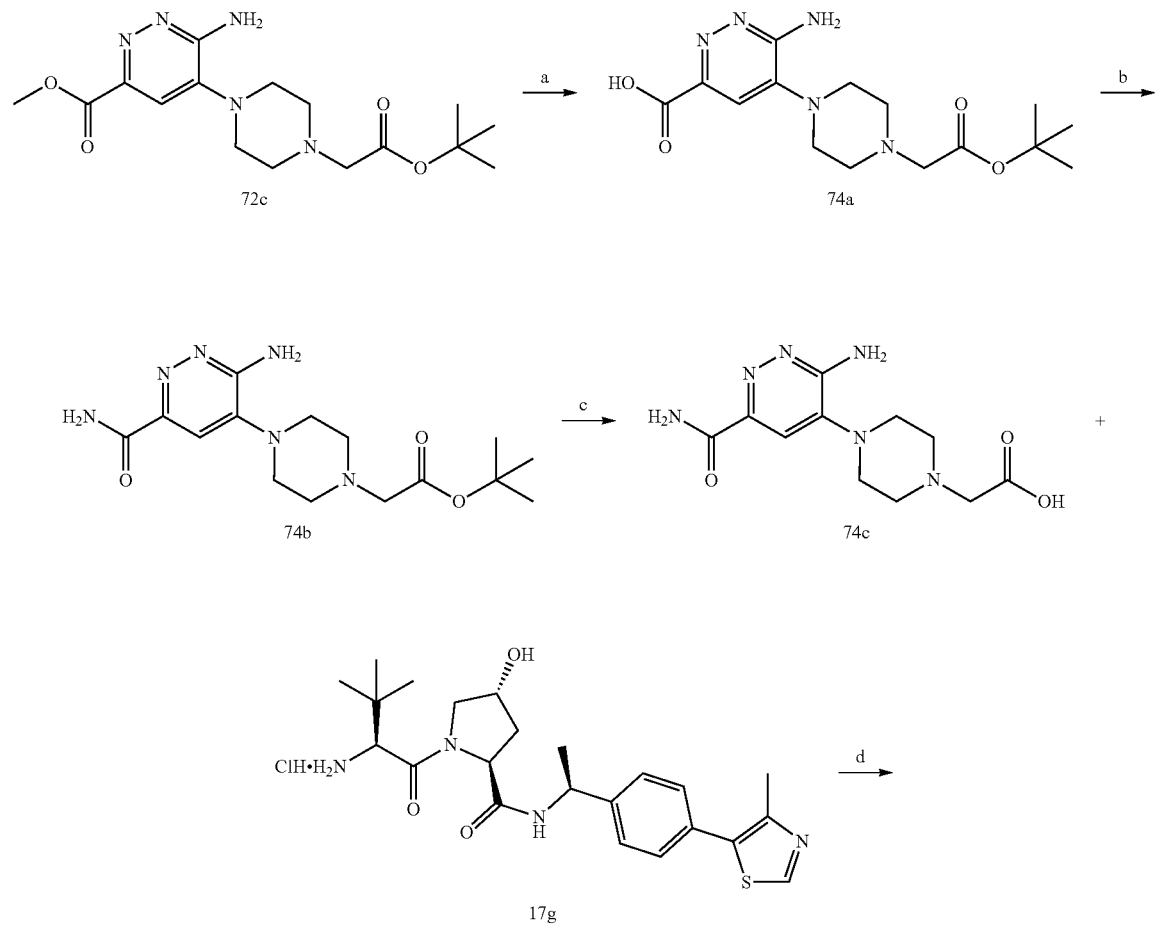

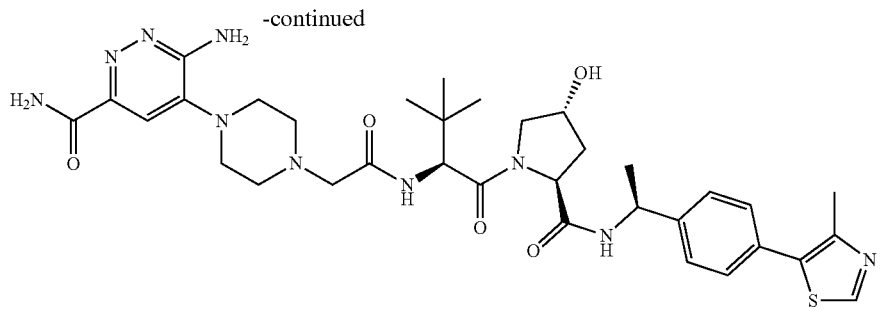

Compound-74

Conditions: a) LiOH·H₂O, THF:MeOH:H₂O, RT-16 h; b) NH₄Cl, HATU, DIPEA, DMF, RT-16 h; c) 4M HCl in Dioxane, DCM, 0° C.-RT, 16; d) HATU, DIPEA, DMF, RT-16 h.

Step-a: Synthesis of 6-amino-5-(4-(2-(tert-butoxy)-2-oxoethyl)piperazin-1-yl)pyridazine-3-carboxylic acid (74a)

The title compound was synthesized by using the general procedure of hydrolysis of methyl or ethyl esters which was followed for Intermediate-3d using with methyl 6-amino-5-(4-(2-(tert-butoxy)-2-oxoethyl)piperazin-1-yl)pyridazine-3-carboxylate (Yield: 90%) LC-MS: m/z 338.0 (M+1)⁺.

Step-b: Synthesis of tert-butyl 2-(4-(3-amino-6-carbamoylpyridazin-4-yl)piperazin-1-yl)acetate (74b)

To a stirred solution of 6-amino-5-(4-(2-(tert-butoxy)-2-oxoethyl)piperazin-1-yl)pyridazine-3-carboxylic acid (0.2 g, 0.90 mmol) and NH₄Cl (0.08 g, 0.23 mmol) in DMF (3 mL) were added HATU (0.13 g, 0.34 mmol) at 0° C. followed by DIPEA (0.157 mL, 0.92 mmol). Stirring was continued at RT for 16 h. After completion of the reaction (monitored by TLC) the reaction mixture was quenched with water (10 mL) and extracted with EtOAc (2×15 mL). The combined organic layer was washed with water (20 mL), brine (20 mL), dried over anhydrous sodium sulphate and concentrated under reduced pressure to give the crude product which was purified by combi flash using 6% MeOH in DCM as eluent to afford the title compound (0.030 g, 39%) LC-MS: m/z 337.2 (M+1)⁺.

Step-c: Synthesis of 2-(4-(3-amino-6-carbamoylpyridazin-4-yl)piperazin-1-yl)acetic acid (74c)

The title compound was synthesized by using the same procedure which was followed for 1f₁-1f₁₂ using tert-butyl 2-(4-(3-amino-6-carbamoylpyridazin-4-yl)piperazin-1-yl) acetate (Yield: 90%) LC-MS: m/z 281.00 (M+1)⁺.

Step-d: Synthesis of 6-amino-5-(4-(2-(((S)-1-((2S, 4R)-4-hydroxy-2-(((S)-1-(4-(4-methylthiazol-5-yl) phenyl)ethyl)carbamoyl)pyrrolidin-1-yl)-3,3-dimethyl-1-oxobutan-2-yl)amino)-2-oxoethyl)piperazin-1-yl)pyridazine-3-carboxamide (Compound-74)

The title compound was synthesized by using the same procedure which was followed for compound-1 by using (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (Yield: 28%); ¹H NMR (400 MHz, DMSO-d₆): δ 8.97 (s, 1H), 8.42 (d, J=7.2 Hz, 1H), 8.02 (s, 1H), 7.76 (d, J=10.0 Hz, 1H), 7.44-7.33 (m, 6H), 6.43 (s, 2H), 5.10 (d, J=3.6 Hz, 1H), 4.89 (t, J=7.2 Hz, 1H), 4.51 (d, J=9.6 Hz, 1H), 4.45 (t, J=8.4 Hz, 1H), 4.28 (s, 1H), 3.60-3.58 (m, 2H), 3.10-3.03 (m, 6H), 2.70-2.67 (m, 4H), 2.50 (s, 3H), 2.04-1.98 (m, 1H), 1.76-1.75 (m, 1H), 1.37 (d, J=7.2 Hz, 3H), 0.95 (s, 9H); LC-MS: m/z 705.25 (M−1).

Example-XXV: Synthesis of 6-amino-5-(4-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl) piperazin-1-yl)-N-methylpyridazine-3-carboxamide (Compound-75)

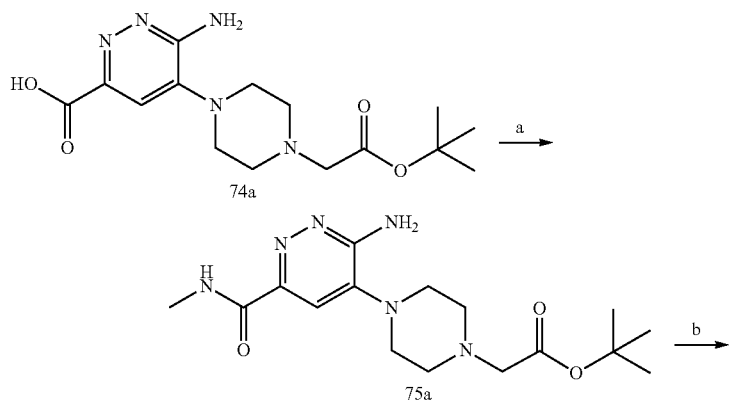

-continued

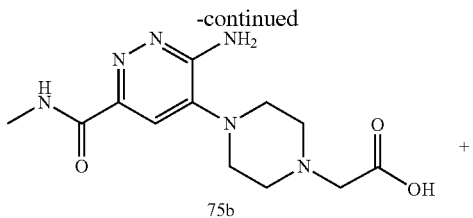

75b

+

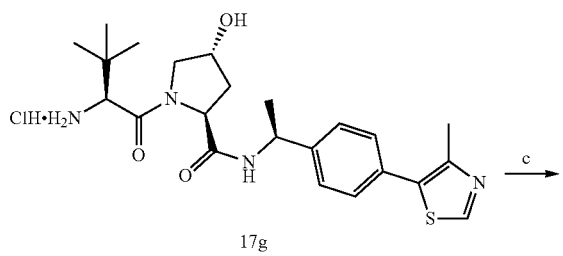

17g

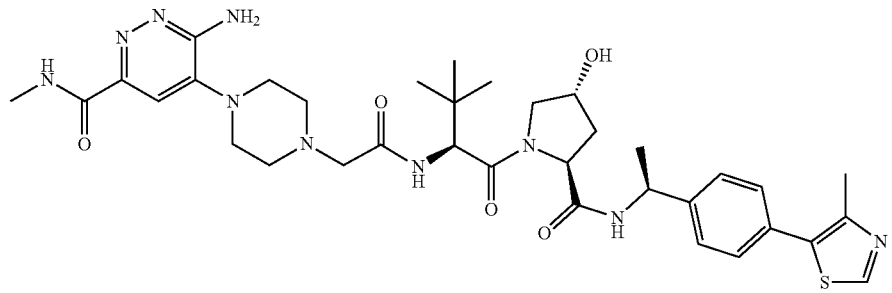

Compound-75

Conditions: a) Methyl amine HCl, HATU, DIPEA, DMF, RT- 16 h; b) 4M HCl in Dioxane, DCM, 0° C. - RT- 16; c) HATU, DIPEA, DMF, RT- 16 h.

Step-a: Synthesis of tert-butyl 2-(4-(3-amino-6-(methylcarbamoyl)pyridazin-4-yl)piperazin-1-yl) acetate (75a)

To a stirred solution of 6-amino-5-(4-(2-(tert-butoxy)-2-oxoethyl)piperazin-1-yl)pyridazine-3-carboxylic acid (74a) (0.2 g, 0.59 mmol) and Methyl amine HCl (0.060 g, 0.89 mmol) in DMF (3 mL) was added HATU (0.33 g, 0.89 mmol) at 0° C. followed by the drop wise addition of DIPEA (0.61 mL, 2.63 mmol). Stirring was continued at RT for 16 h. After completion of the reaction (monitored by TLC) the reaction mixture was quenched with water (10 mL) and extracted with EtOAc (2×15 mL). The combined organic layer was washed with water (20 mL), brine (20 mL), dried over anhydrous sodium sulphate and concentrated under reduced pressure to give the crude product which was purified by combi flash using 6% MeOH in DCM as eluent to afford the title compound (0.15 g, 75%) LC-MS: m/z 351.05 (M+1)$^+$.

Step-b: Synthesis of 2-(4-(3-amino-6-(methylcarbamoyl)pyridazin-4-yl)piperazin-1-yl)acetic acid (75b)

The title compound was synthesized by using the same procedure which was followed for 1f$_1$-1f$_{12}$ using tert-butyl 2-(4-(3-amino-6-(methylcarbamoyl)pyridazin-4-yl)piperazin-1-yl)acetate (Yield: 90%) $^1$H NMR (400 MHz, DMSO-d$_6$): δ 8.88 (d, J=3.6 Hz, 1H), 7.94 (bs, 2H), 7.58 (s, 1H), 4.23 (s, 2H), 2.88-2.80 (m, 4H), 2.79-2.72 (m, 4H), 2.68 (s, 3H); LC-MS: m/z 295.0 (M+1)$^+$.

Step-c: Synthesis of 6-amino-5-(4-(2-(((S)-1-((2S, 4R)-4-hydroxy-2-(((S)-1-(4-(4-methylthiazol-5-yl) phenyl)ethyl)carbamoyl)pyrrolidin-1-yl)-3,3-dimethyl-1-oxobutan-2-yl)amino)-2-oxoethyl)piperazin-1-yl)-N-methylpyridazine-3-carboxamide (Compound-75)

The title compound was synthesized by using the same procedure which was followed for Compound-1 by using (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride. $^1$H NMR (400 MHz, DMSO-d$_6$): δ 8.98 (s, 1H), 8.71-8.67 (m, 1H), 8.45 (d, J=7.2 Hz, 1H), 7.77 (d, J=9.2 Hz, 1H), 7.45-7.42 (m, 2H), 7.37-7.33 (m, 2H), 7.31 (s, 1H), 6.45 (s, 2H), 5.13 (d, J=3.2 Hz, 1H), 4.89 (t, J=7.2 Hz, 1H), 4.52-4.44 (m, 2H), 4.28 (s, 1H), 3.58-3.55 (m, 2H), 3.16-3.10 (m, 2H), 3.04-3.00 (m, 4H), 2.78 (d, J=4.4 Hz, 3H), 2.72-2.68 (m, 4H), 2.45 (s, 3H), 2.07-2.02 (m, 1H), 1.77-1.75 (m, 1H), 1.36 (d, J=6.8 Hz, 3H), 0.94 (s, 9H); LC-MS: m/z 721.35 (M+1)$^+$; (Yield: 20%).

Example-XXVI: Synthesis of (2S,4R)-1-((S)-2-(2-(1-(3-amino-6-(3-fluoro-2-hydroxyphenyl)pyridazin-4-yl)piperidin-4-yl)acetamido)-3,3-dimethylbutanoyl)-4-hydroxy-N-(2,2,2-trifluoro-1-(4-(4-methylthiazol-5-yl)phenyl)ethyl)pyrrolidine-2-carboxamide (Compounds-76, 77 and 78)
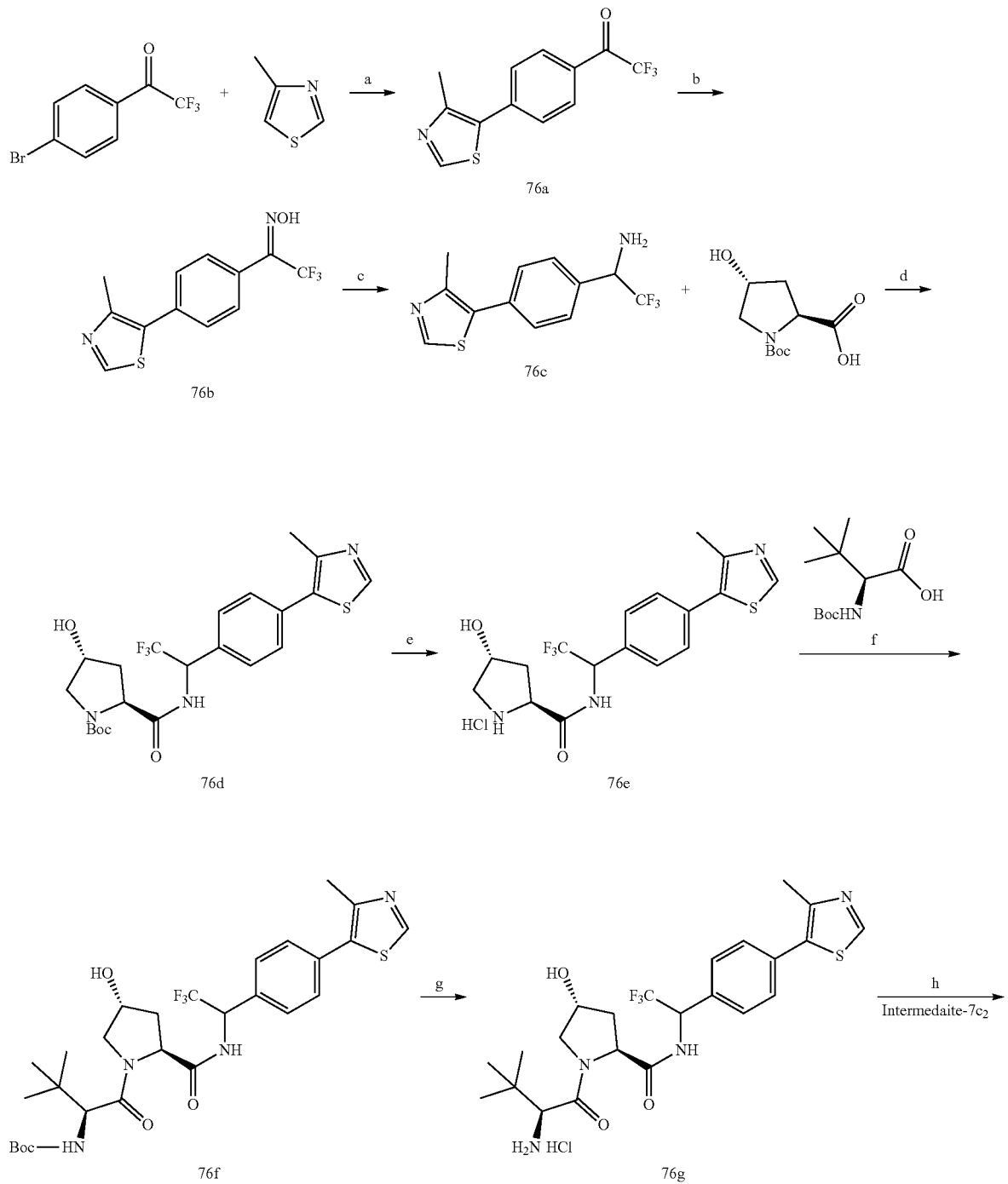

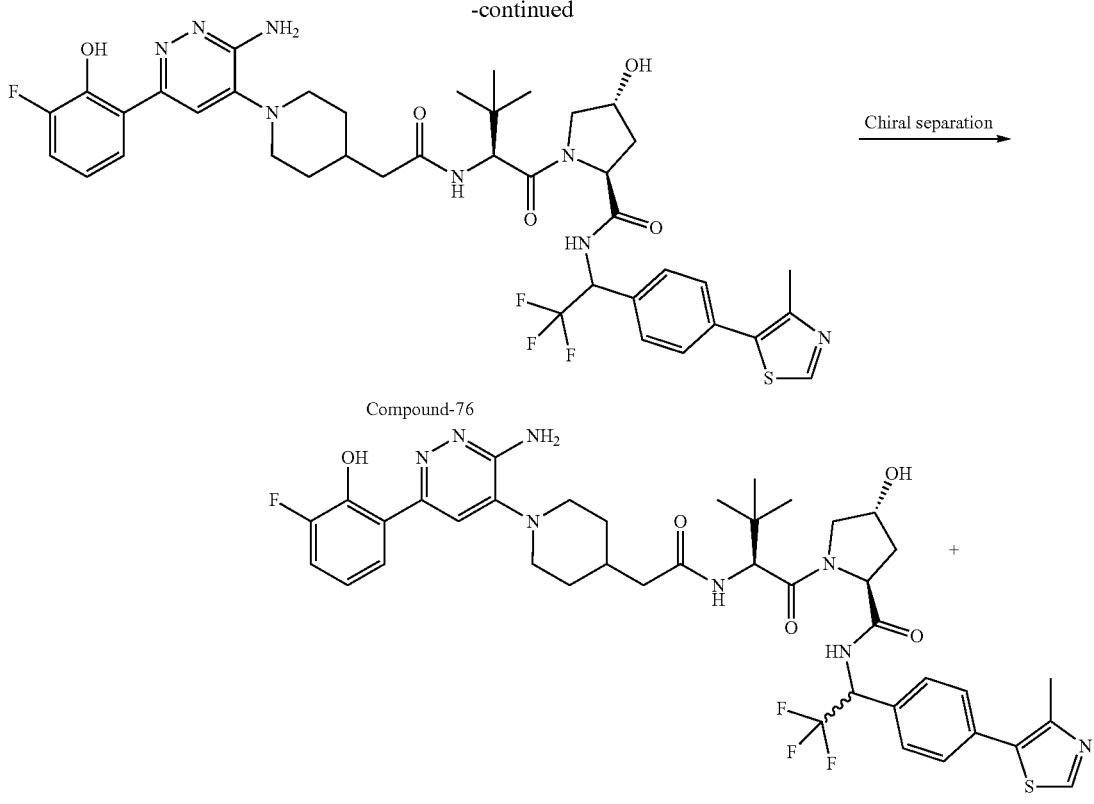

Compound-77 (Isomer-1)
Compound-78 (Isomer-2)

Conditions: a) Pd(OAc)₂, KOAc, DMF, 120° C., 16 h; b) NH₂OH•HCl, Pyridine, 100° C., 16 h; c) AcOH, Zn Dust, Ethanol, 90° C.-16 h; d) HATU, DIPEA, DMF, 0° C.-RT, 16 h; e) 4M HCl in 1,4-Dioxane, 1,4-Dioxane; f) HATU, DIPEA, DMF, 0° C.-RT, 16 h; g) 4M HCl in 1,4-Dioxane, 1,4-Dioxane, 0° C.-RT-16 h; h) HATU, DIPEA, DMF, 0° C.-RT, 16 h.

Step-a: Synthesis of 2,2,2-trifluoro-1-(4-(4-methyl-thiazol-5-yl)phenyl) ethan-1-one (76a)

The title compound was synthesized by using the same procedure which was followed for Intermediate-17b using (2S,4R)-4-hydroxy-N—((S)-1-(4-(4-methylthiazol-5-yl)phenyl) ethyl)pyrrolidine-2-carboxamide (Yield: 70%) $^1$H NMR (400 MHz, DMSO-$d_6$): δ 9.14 (s, 1H), 8.13 (d, J=8.0 Hz, 2H), 7.84-7.81 (m, 2H), 2.55 (s, 3H).

Step-b: Synthesis of (E)-2,2,2-trifluoro-1-(4-(4-methylthiazol-5-yl)phenyl)ethan-1-one oxime (76b)

To a solution of 2,2,2-trifluoro-1-(4-(4-methylthiazol-5-yl)phenyl)ethan-1-one (1.50 g, 5.5 mmol) in Pyridine (20 mL) was added NH₂OH. HCl (0.76 g, 11 mmol) at RT and stirred for 16 h at 100° C. After completion of the reaction (monitored by TLC) the reaction mixture was allowed to RT and poured into ice cold water. The resulted solid was filtered off and washed with excess water and dried under vacuum to get the title compound (1.20 g, 75.9%) $^1$H NMR (400 MHz, DMSO-$d_6$): δ 12.90 (s, 1H), 9.05 (s, 1H), 7.65 (d, J=8.8 Hz, 2H), 7.59 (d, J=8.4 Hz, 2H), 2.50 (s, 3H); LC-MS: m/z 287.1 (M+1)⁺.

Step-c: Synthesis of 2,2,2-trifluoro-1-(4-(4-methyl-thiazol-5-yl)phenyl)ethan-1-amine (76c)

To a stirred solution of (E)-2,2,2-trifluoro-1-(4-(4-methylthiazol-5-yl)phenyl)ethan-1-one oxime (1.20 g, 4.19 mmol) in Ethanol (20 mL) were added AcOH (1.2 mL) and Zn Dust (0.82 g, 12.5 mmol) at RT and The reaction mixture was stirred at 90° C. for 16 h. After completion of the reaction (monitored by TLC) The solvent was evaporated under reduced pressure to get residue which was dissolved in EtOAc (100 mL) and filter through celite pad and the filtrate was washed with aq. 3N NaOH solution, separated organic layers was washed with brine and dried over Na₂SO₄ and concentrated to afford the title compound (0.80g, 82.5%) which was used in the next step without further purification. $^1$H NMR (400 MHz, DMSO-$d_6$): δ 9.05 (s, 1H), 7.71 (d, J=5.2 Hz, 2H), 7.57-7.52 (m, 2H), 5.91-5.80 (m, 1H), 2.49 (s, 3H).

Step-d: Synthesis of tert-butyl (2S,4R)-4-hydroxy-2-((2,2,2-trifluoro-1-(4-(4-methylthiazol-5-yl)phenyl)ethyl)carbamoyl)pyrrolidine-1-carboxylate (76d)

The title compound was synthesized by using the same procedure which was used for Intermediate 21b₁-21b₇ using 2,2,2-trifluoro-1-(4-(4-methylthiazol-5-yl)phenyl)ethan-1-amine (Yield: 55.5%) LC-MS: m/z 486.2 (M+1)⁺.

Step-e: Synthesis of (2S,4R)-4-hydroxy-N-(2,2,2-trifluoro-1-(4-(4-methylthiazol-5-yl)phenyl)ethyl) pyrrolidine-2-carboxamide hydrochloride (76e)

The title compound was synthesized by using the same procedure which was followed for Intermediate-17e using tert-butyl (2S,4R)-4-hydroxy-2-((2,2,2-trifluoro-1-(4-(4- methylthiazol-5-yl)phenyl)ethyl) carbamoyl) pyrrolidine-1-carboxylate (Yield: 90%) LC-MS: m/z 386.1 (M+1)⁺.

Step-f: Synthesis tert-butyl ((2S)-1-((2S,4R)-4-hydroxy-2-((2,2,2-trifluoro-1-(4-(4-methylthiazol-5-yl)phenyl)ethyl)carbamoyl)pyrrolidin-1-yl)-3,3-dimethyl-1-oxobutan-2-yl)carbamate (76f)

The title compound was synthesized by using the same procedure which was followed for Intermediate-21 $b_1$-21 $b_7$ using (2S,4R)-4-hydroxy-N-(2,2,2-trifluoro-1-(4-(4-methylthiazol-5-yl)phenyl)ethyl) pyrrolidine-2-carboxamide hydrochloride (Yield: 51.5%.) LC-MS: m/z 597.2 (M−1).

Step-g: Synthesis of ((2S,4R)-1-((S)-2-amino-3,3-dimethylbutanoyl)-4-hydroxy-N-(2,2,2-trifluoro-1-(4-(4-methylthiazol-5-yl)phenyl)ethyl)pyrrolidine-2-carboxamide hydrochloride (76g)

The title compound was synthesized by using the same procedure which was followed for 17e using tert-butyl ((2S)-1-((2S,4R)-4-hydroxy-2-((2,2,2-trifluoro-1-(4-(4-methylthiazol-5-yl)phenyl)ethyl)carbamoyl)pyrrolidin-1-yl)-3,3-dimethyl-1-oxobutan-2-yl)carbamate (Yield: 80%) LC-MS: m/z 499.2 (M+1).

Step-h: Synthesis of (2S,4R)-1-((S)-2-(2-(1-(3-amino-6-(3-fluoro-2-hydroxyphenyl)pyridazin-4-yl)piperidin-4-yl) acetamido)-3,3-dimethylbutanoyl)-4-hydroxy-N-(2,2,2-trifluoro-1-(4-(4-methylthiazol-5-yl)phenyl)ethyl)pyrrolidine-2-carboxamide (Compound-76)

The title compound was synthesized by using the same procedure which was followed for compound-1 by using 2-(1-(3-amino-6-(3-fluoro-2-hydroxyphenyl)pyridazin-4-yl)piperidin-4-yl)acetic acid (7c₂) and 76g. ¹H NMR (400 MHz, DMSO-d₆): δ 15.05 (s, 1H), 9.29-9.20 (m, 1H), 9.02 (s, 1H), 7.96-7.88 (m, 1H), 7.77-7.70 (m, 2H), 7.66-7.64 (m, 1H), 7.56-7.50 (m, 3H), 7.19 (t, J=10.0 Hz, 1H), 6.86-6.82 (m, 1H), 6.31-6.29 (m, 2H), 5.88-5.84 (m, 1H), 5.17-5.12 (m, 1H), 4.60-4.52 (m, 2H), 4.36- 4.30 (m, 1H), 3.67-3.64 (m, 2H), 3.45-3.40 (m, 2H), 2.67-2.50 (m, 2H), 2.47 (s, 3H), 1.89-1.78 (m, 1H), 1.78-1.65 (m, 2H), 1.52-1.45 (m, 2H), 1.30-1.19 (m, 2H), 0.96-0.84 (m, 11H); LC-MS: m/z 827.3 (M+1)⁺; (Yield: 27.9%).

Example-XXVII: (Compound-77 and Compound-78)

Compound 77 and 78 were obtained from Compound 76 by chiral HPLC separation method.
Compound-77: (Isomer-1)
¹H NMR (400 MHz, DMSO-d₆): δ 15.04 (s, 1H), 9.21 (d, J=10.0 Hz, 1H), 9.02 (s, 1H), 7.83 (d, J=9.2 Hz, 1H), 7.76-7.70 (m, 3H), 7.55 (d, J=8.4 Hz, 2H), 7.50 (s, 1H), 7.18 (t, J=8.0 Hz, 1H), 6.86-6.80 (m, 1H), 6.29 (s, 2H), 5.86-5.81 (m, 1H), 5.17-5.16 (m, 1H), 4.60-4.52 (m, 2H), 4.36 (bs, 1H), 3.71-3.64 (m, 2H), 3.50-3.25 (m, 2H), 2.67-2.50 (m, 2H), 2.45-2.42 (m, 3H merged in DMSO), 2.32-2.28 (m, 1H), 2.15-2.08 (m, 2H), 1.92-1.89 (m, 2H), 1.73-1.70 (m, 2H), 1.48-1.40 (m, 2H), 0.89 (s, 9H); LC-MS: m/z 827.3 (M+1)⁺; (Yield: 20%).
Compound-78: 17276 (Isomer-2)
¹H NMR (400 MHz, DMSO-d₆): δ 15.04 (s, 1H), 9.28 (d, J=9.6 Hz, 1H), 9.02 (s, 1H), 7.94 (d, J=9.6 Hz, 1H), 7.76 (d, J=8.0 Hz, 1H), 7.64 (d, J=7.6 Hz, 2H), 7.55 (d, J=8.0 Hz, 2H), 7.51 (s, 1H), 7.19 (t, J=8.8 Hz, 1H), 6.87-6.82 (m, 1H), 6.30 (s, 1H), 5.88-5.83 (m, 1H), 5.13-5.12 (m, 1H), 4.60-4.56 (m, 2H), 4.30 (bs, 1H), 3.64 (s, 2H), 3.51-3.45 (m, 2H), 2.67-2.63 (m, 2H), 2.47-2.44 (m, 4H merged in DMSO), 2.32-2.27 (m, 1H), 2.18-2.13 (m, 1H), 2.03-1.98 (m, 1H), 1.88-1.75 (m, 1H), 1.75-1.51 (m, 3H), 1.51-1.45 (m, 2H), 0.96 (s, 9H); LC-MS: m/z 827.3 (M+1)⁺; (Yield: 35%).

Example-XXVIII: Synthesis of (2S,4R)-1-((2-(4-(3-amino-6-(2-hydroxyphenyl)pyridazin-4-yl)piperazin-1-yl)acetyl)-L-valyl)-4-hydroxy-N—((S)-1-(4-(4-methylthiazol-5-yl)phenyl)ethyl)pyrrolidine-2-carboxamide (Compound-79)

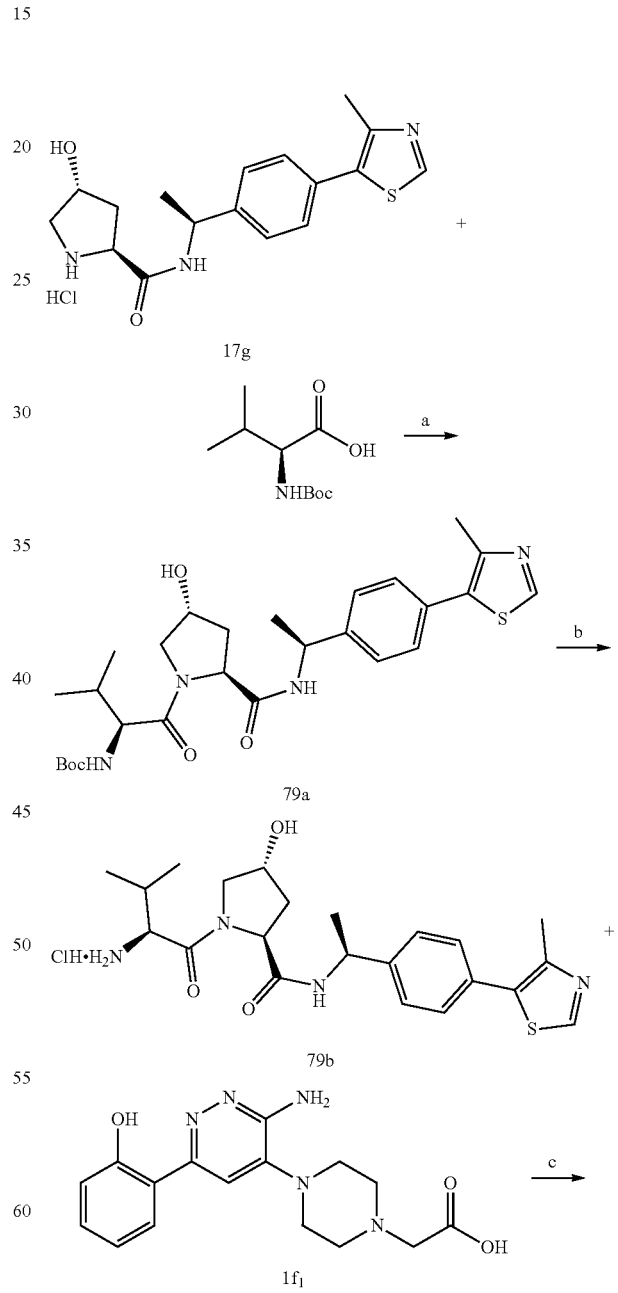

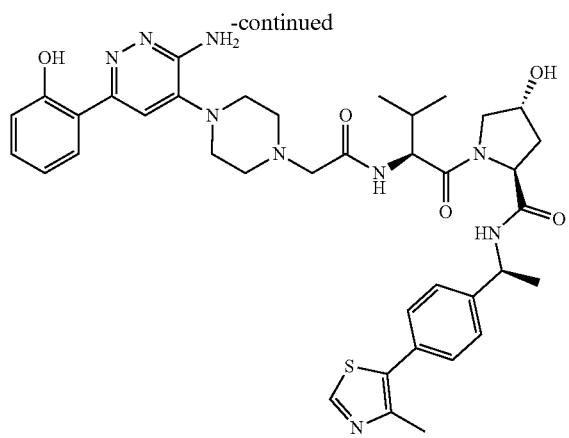

Compound-79

Conditions: a) HATU, DIPEA, DMF, RT-16 h; b) 4M HCl in Dioxane, DCM, 0° C.-RT-16; c) HATU, DIPEA, DMF, RT-16 h.

Step-a: Synthesis of tert-butyl ((S)-1-((2S,4R)-4-hydroxy-2-(((S)-1-(4-(4-methylthiazol-5-yl)phenyl)ethyl)carbamoyl)pyrrolidin-1-yl)-3-methyl-1-oxobutan-2-yl)carbamate (79a)

The title compound was synthesized by using the same procedure which was followed for Intermediate-21 $b_1$-21 $b_7$ using (2S,4R)-4-hydroxy-N—((S)-1-(4-(4-methylthiazol-5-yl)phenyl) ethyl) pyrrolidine-2-carboxamide (Yield: 52.7%) $^1$H NMR (400 MHz, DMSO-$d_6$): δ 13.80 (s, 1H), 8.98 (s, 1H), 8.35 (d, J=7.2 Hz, 1H), 7.45 (d, J=8.4 Hz, 2H), 7.36 (d, J=7.6 Hz, 2H), 6.63 (d, J=8.8 Hz, 1H), 5.08 (bs, 1H), 4.93-4.88 (m, 1H), 4.44-4.41 (m, 1H), 4.30-4.29 (m, 1H), 4.03-3.99 (m, 1H), 3.61-3.60 (m, 2H), 3.15-3.13 (m, 1H), 2.45 (s, 3H), 1.78-1.77 (m, 1H), 1.38-1.31 (m, 12H), 1.27-1.17 (m, 6H); LC-MS: m/z 531.3 (M+1)$^+$.

Step-b: Synthesis of (2S,4R)-1-(L-valyl)-4-hydroxy-N—((S)-1-(4-(4-methylthiazol-5-yl)phenyl)ethyl) pyrrolidine-2-carboxamide hydrochloride (79b)

The title compound was synthesized by using the same procedure which was followed for Intermediate-17e using tert-butyl ((S)-1-((2S,4R)-4-hydroxy-2-(((S)-1-(4-(4-methylthiazol-5-yl)phenyl)ethyl)carbamoyl)pyrrolidin-1-yl)-3-methyl-1-oxobutan-2-yl)carbamate.

(Yield: 90%) $^1$H NMR (400 MHz, CD$_3$OD): δ 9.98 (s, 1H), 7.57-7.50 (m, 4H), 5.04-4.86 (m, 1H), 4.66 (t, J=8.4 Hz, 1H), 4.47 (bs, 1H), 4.10 (d, J=4.8 Hz, 1H), 3.74-3.69 (s, 1H), 3.30 (s, 3H), 2.29-2.24 (m, 2H), 1.94-1.88 (m, 1H), 1.55 (d, J=7.2 Hz, 3H), 1.07 (d, J=7.6 Hz, 3H), 1.04 (d, J=6.8 Hz, 3H); LC-MS: m/z 431.2 (M+7)$^+$.

Step-c: Synthesis of (2S,4R)-1-((2-(4-(3-amino-6-(2-hydroxyphenyl)pyridazin-4-yl)piperazin-1-yl) acetyl)-L-valyl)-4-hydroxy-N—((S)-1-(4-(4-methylthiazol-5-yl)phenyl)ethyl)pyrrolidine-2-carboxamide (compound-79)

The title compound was synthesized by using the same procedure which was followed for compound-1 by using 2-(4-(3-amino-6-(2-hydroxyphenyl)pyridazin-4-yl)piperazin-1-yl)acetic acid (1fc) and 79b. $^1$H NMR (400 MHz, DMSO-$d_6$): δ 14.20 (s, 1H), 8.96 (s, 1H), 8.39 (d, J=7.2 Hz, H), 7.94 (d, J=7.2 Hz, 8H), 7.77 (bs, H), 7.55 (s, 1H), 7.43-7.34 (m, 4H), 7.26-7.22 (m, 1H), 6.89 (d, J=7.6 Hz, 1H), 6.28 (bs, 2H), 5.10 (s, 1H), 4.90-4.87 (m, 1H), 4.51-4.42 (m, 2H), 4.30 (bs, 1H), 3.59 (m, 2H), 3.25-3.09 (m, 8H), 2.73-2.67 (m, 3H), 2.44 (s, 3H), 2.09-2.01 (m, 2H), 1.76 (bs, H), 1.36 (d, J=6.8 Hz, 3H), 0.92 (d, J=6.0 Hz, 6H); LC-MS: m/z 742.4 (M+1)(; (Yield: 35%).

The compounds listed in below Table-28 were prepared by procedure similar to the one described in Example-I with appropriate variations in reactants, quantities of reagents, protections and deprotections, solvents and reaction conditions.

Compound 83 and 84: Compound 83 and 84 were obtained by chiral separation of there racemic mixture which was obtained by following the procedure same as that of Example-1

The characterization data of the compounds are summarized herein the below table and Compound 92 and 95 were synthesized by using the same procedure which was followed for Compound-1 and Intermediate-3d using with (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (17g).

TABLE 28

| Comp No. | Structure | Characterization Data |
|---|---|---|
| 80 | ![structure] | $^1$H NMR (400 MHz, DMSO-$d_6$): δ 14.22 (s, 1H), 8.96 (s, 1H), 8.37 (d, J = 7.6 Hz, 1H), 7.90 (d, J = 7.6 Hz, 1H), 7.50 (s, 1H), 7.42-7.34 (m, 4H), 7.22 (t, J = 7.6 Hz, 1H), 6.94 (d, J = 8.8 Hz, 1H), 6.88-6.85 (m, 2H), 6.27 (s, 2H), 5.10-5.09 (m, 1H), 4.89 (t, J = 7.2 Hz, 1H), 4.71 (bs, 1H), 4.43 (t, J = 7.6 Hz, 1H), 4.27 (bs, 1H), 4.18 (d, J = 8.8 Hz, 1H), 3.59 (s, 2H), 2.93-2.90 (m, 2H), 2.45 (s, 3H), 1.99-1.97 (m, 2H), 1.82-1.77 (m, 3H), 1.35 (d, J = 6.8 Hz, 3H), 1.25-1.22 (m, 3H), 0.94 (s, 9H); LC-MS: m/z 757.3 (M + 1)$^+$; (Yield: 19%). |

TABLE 28-continued

| Comp No. | Structure | Characterization Data |
|---|---|---|
| 81 | 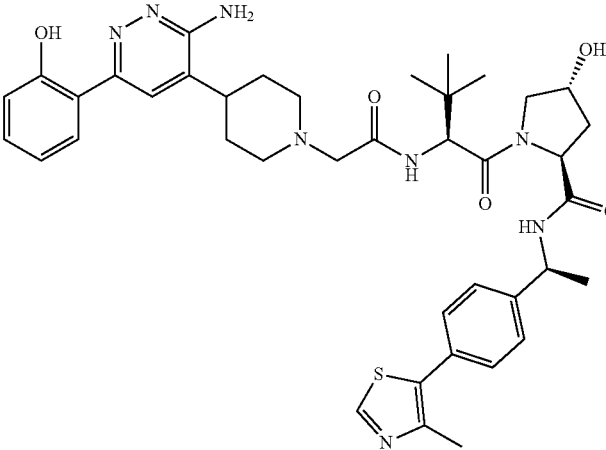 | ¹H NMR (400 MHz, DMSO-d₆): δ 13.86 (bs, 1H), 8.98 (s, 1H), 8.43 (d, J = 7.6 Hz, 1H), 8.00-7.98 (m, 1H), 7.91 (s, 1H), 7.72 (d, J = 10.4 Hz, 1H), 7.44-7.35 (m, 4H), 7.24 (t, J = 7.6 Hz, 1H), 6.91-6.87 (m, 2H), 6.69 (s, 2H), 5.13 (d, J = 3.6 Hz, 1H), 4.89 (t, J = 7.6 Hz, 1H), 4.54 (d, J = 9.6 Hz, 1H), 4.41 (t, J = 8.0 Hz, 1H), 4.29 (s, 1H), 3.63-3.55 (m, 2H), 3.29-3.21 (m, 1H), 2.97-2.89 (m, 3H), 2.50-2.49 (m, 3H), 2.45 (s, 3H), 2.07-2.00 (m, 1H), 1.90-1.76 (m, 5H), 1.36 (d, J = 6.8 Hz, 3H), 0.99 (s, 9H); LC-MS: m/z 755.25 (M + 1)⁺; (Yield: 24%). |
| 82 | 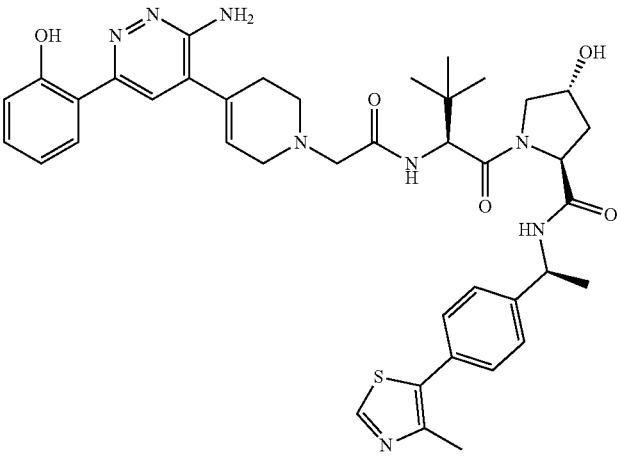 [SMILES: Cc1ncsc1-c1ccc([C@H](C)NC(=O)[C@@H]2C[C@@H](O)CN2C(=O)[C@@H](NC(=O)CN2CC=C(c3cc(-c4ccccc4O)nnc3N)CC2)C(C)(C)C)cc1] | ¹H NMR (400 MHz, DMSO-d₆): δ 13.72 (s, 1H), 8.97 (s, 1H), 8.42 (d, J = 8.0 Hz, 1H), 7.95-7.93 (m, 2H), 7.74 (d, J = 9.6 Hz, 1H), 7.44-7.35 (m, 4H), 7.24-7.22 (m, 1H), 6.91-6.86 (m, 2H), 6.50 (s, 2H), 6.06 (s, 1H), 5.12 (d, J = 3.6 Hz, 1H), 4.90 (t, J = 7.6 Hz, 1H), 4.56 (d, J = 9.6 Hz, 1H), 4.40-4.48 (m, 1H), 4.29 (bs, 1H), 3.64-3.56 (m, 2H), 3.30 (2H merged with DMSO moisture peak), 3.28-3.15 (m, 4H), 3.11-3.05 (m, 1H), 2.49 (s, 3H), 2.48-2.46 (m, 1H), 2.04-2.03 (m, 1H), 1.79-1.77 (m, 1H), 1.48 (d, J = 7.2 Hz, 3H), 0.96 (s, 9H); LC-MS: m/z 753.3 (M + 1)⁺; (Yield: 17%). |
| 83 | 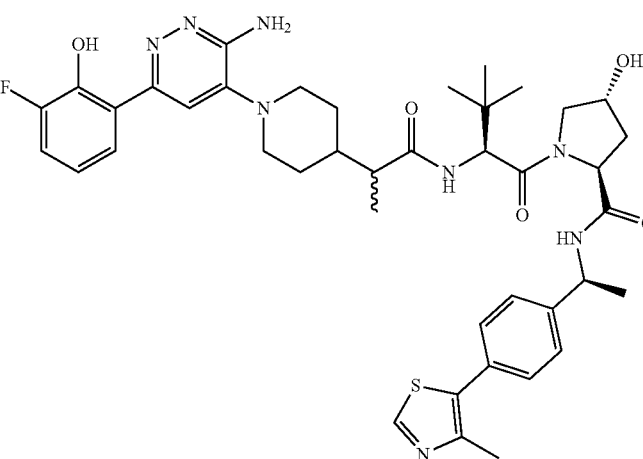<br>Isomer 1 | ¹H NMR (400 MHz, DMSO-d₆): δ 15.08 (s, 1H), 8.99 (s, 1H), 8.38 (d, J = 7.6 Hz, 1H), 7.88 (d, J = 6.0 Hz, 1H), 7.76 (d, J = 8.4 Hz, 1H), 7.50 (s, 1H), 7.44 (d, J = 8.4 Hz, 2H), 7.38 (d, J = 8.4 Hz, 2H), 7.20-7.17 (m, 1H), 6.87-6.75 (m, 1H), 6.33 (s, 2H), 5.11 (d, J = 3.2 Hz, 1H), 4.92-4.90 (m, 1H), 4.52-4.50 (m, 1H), 4.45-4.40 (m, 1H), 4.29 (bs, 1H), 3.62 (s, 2H), 3.50-3.48 (m, 1H), 2.77-2.55 (m, 2H), 2.46-2.44 (m, 3H merged in DMSO), 2.00-1.98 (m, 1H), 1.83-1.79 (m, 3H), 1.64-1.46 (m, 3H), 1.37 (d, J = 6.8 Hz, 3H), 0.99-0.81 (m, 14H); LC-MS: m/z 787.25 (M + 1)⁺; (Yield: 10%). |

TABLE 28-continued

| Comp No. | Structure | Characterization Data |
|---|---|---|
| 84 | 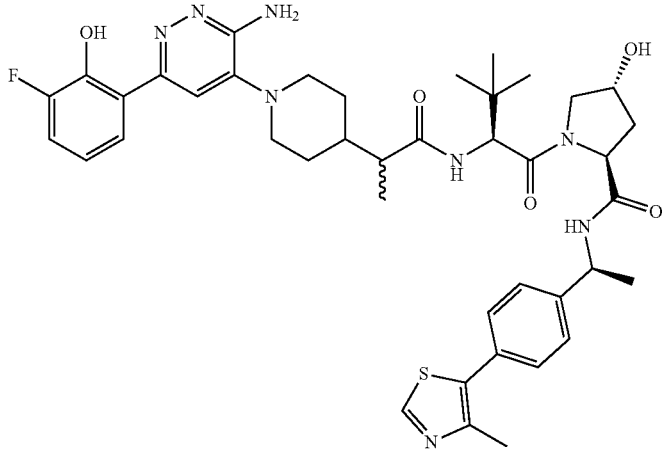<br>Isomer 2 | ¹H NMR (400 MHz, DMSO-d₆): δ 15.10 (s, 1H), 8.98 (s, 1H), 8.37 (d, J = 8.0 Hz, 1H), 7.89-7.72 (m, 2H), 7.50 (s, 1H), 7.44-7.36 (m, 4H), 7.22-7.20 (m, 1H), 6.87-6.83 (m, 1H), 6.32 (s, 2H), 5.07 (d, J = 3.2 Hz, 1H), 4.91-4.89 (m, 1H), 4.55 (d, J = 9.2 Hz, 1H), 4.43-4.42 (m, 1H), 4.20 (s, 1H), 3.68-3.60 (m, 3H), 3.40-3.29 (m, 1H), 2.67-2.66 (m, 2H), 2.66-2.46 (m, 3H), 2.46 (s, 3H), 2.09-1.98 (m, 1H), 1.79-1.78 (m, 2H), 1.58-1.57 (m, 2H), 1.36 (d, J = 6.8 Hz, 3H), 1.05 (d, J = 6.8 Hz, 3H), 0.85 (s, 9H); LC-MS: m/z 787.2 (M + 1)⁺; (Yield: 10%). |
| 85 | 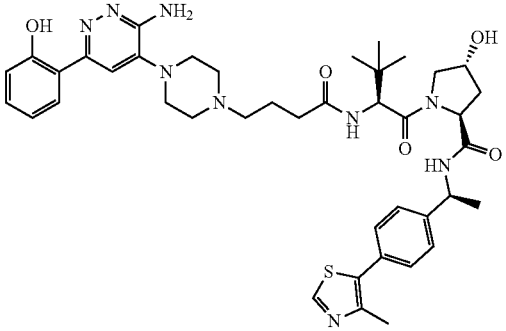 [SMILES: Cc1ncsc1-c1ccc([C@H](C)NC(=O)[C@@H]2C[C@@H](O)CN2C(=O)[C@@H](NC(=O)CCCN2CCN(c3cc(-c4ccccc4O)nnc3N)CC2)C(C)(C)C)cc1] | ¹H NMR (400 MHz, DMSO-d₆): δ 14.23 (s, 1H), 8.98 (s, 1H), 8.38 (d, J = 7.2 Hz, 1H), 7.91 (d, J = 8.4 Hz, 1H), 7.83 (d, J = 8.8 Hz, 1H), 7.49 (s, 1H), 7.44-7.36 (m, 4H), 7.25-7.22 (m, 1H), 6.90-6.87 (m, 2H), 6.24 (s, 2H), 5.11 (d, J = 3.2 Hz, 1H), 4.93-4.89 (m, 1H), 4.53 (d, J = 9.6 Hz, 1H), 4.42 (d, J = 8.0 Hz, 1H), 4.28 (s, 1H), 3.61 (s, 2H), 3.10 (s, 4H), 2.57 (s, 4H merged in DMSO), 2.35 (s, 3H), 2.29-2.27 (m, 2H), 2.21-2.15 (m, 2H), 2.09-2.00 (m, 1H), 1.82-1.60 (m, 3H), 1.37 (d, J = 8.4 Hz, 3H), 0.94 (s, 9H); LC-MS: m/z 784.4 (M + 1)⁺; (Yield: 12%). |
| 86 | 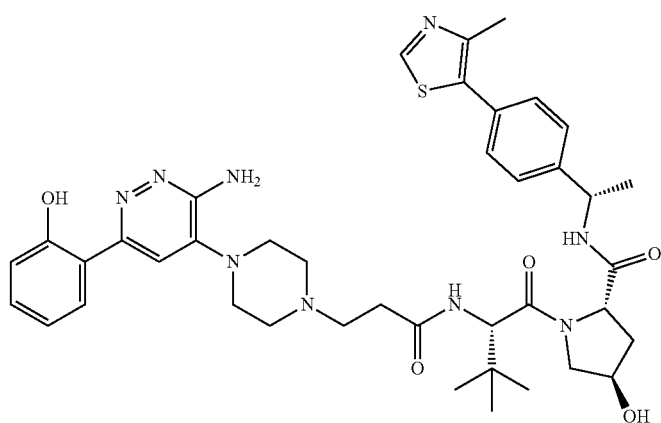 [SMILES: Cc1ncsc1-c1ccc([C@H](C)NC(=O)[C@@H]2C[C@@H](O)CN2C(=O)[C@@H](NC(=O)CCN2CCN(c3cc(-c4ccccc4O)nnc3N)CC2)C(C)(C)C)cc1] | ¹H NMR (400 MHz, DMSO-d₆): δ 14.23 (s, 1H), 8.98 (s, 1H), 8.37-8.33 (m, 2H), 7.91 (dd, J = 8.4 Hz, J = 1.2 Hz, 1H), 7.47 (s, 1H), 7.41 (d, J = 8.4 Hz, 2H), 7.34 (d, J = 8.0 Hz, 2H), 7.26-7.21 (m, 1H), 6.90-6.86 (m, 2H), 6.24 (s, 2H), 5.11 (d, J = 3.6 Hz, 1H), 4.90-4.87 (m, 1H), 4.53 (d, J = 9.2 Hz, 1H), 4.43-4.41 (m, 1H), 4.28 (s, 1H), 3.61-3.59 (m, 2H), 3.19-3.10 (m, 4H), 2.78-2.60 (m, 6H), 2.45-2.44 (m, 5H), 2.10-1.98 (m, 1H), 1.82-1.70 (m, 1H), 1.33 (d, J = 7.2 Hz, 3H), 0.96 (s, 9H); LC-MS: m/z 770.4 (M + 1)⁺; (Yield: 24%). |

TABLE 28-continued

| Comp No. | Structure | Characterization Data |
|---|---|---|
| 87 | 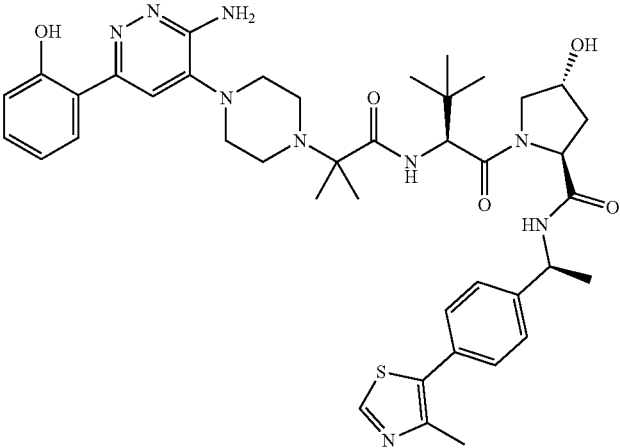 [SMILES: Cc1ncsc1-c1ccc([C@H](C)NC(=O)[C@@H]2C[C@@H](O)CN2C(=O)[C@@H](NC(=O)C(C)(C)N2CCN(c3cc(-c4ccccc4O)nnc3N)CC2)C(C)(C)C)cc1] | ¹H NMR (400 MHz, DMSO-d₆): δ 14.20 (s, 1H), 8.97 (s, 1H), 8.38 (d, J = 8.0 Hz, 1H), 7.93 (d, J = 8.4 Hz, 1H), 7.79 (d, J = 9.2 Hz, 1H), 7.52 (s, 1H), 7.40-7.32 (m, 4H), 7.24 (t, J = 7.6 Hz, 1H), 6.90-6.86 (m, 2H), 6.27 (s, 2H), 5.08 (s, 1H), 4.89 (t, J = 6.4 Hz, 1H), 4.46-4.40 (m, 2H), 4.27-4.24 (m, 1H), 3.59-3.36 (m, 2H), 3.22 (s, 2H), 3.17 (d, J = 5.6 Hz, 1H), 2.73-2.67 (m, 2H), 2.58-2.50 (m, 2H), 2.45 (s, 3H), 2.08-2.03 (m, 1H), 1.77-1.71 (m, 1H), 1.49 (d, J = 6.8 Hz, 3H), 1.21 (s, 3H), 1.11 (s, 4H), 0.95 (s, 9H); LC-MS: m/z 784.4 (M + 1)⁺; (Yield: 10%). |
| 88 | 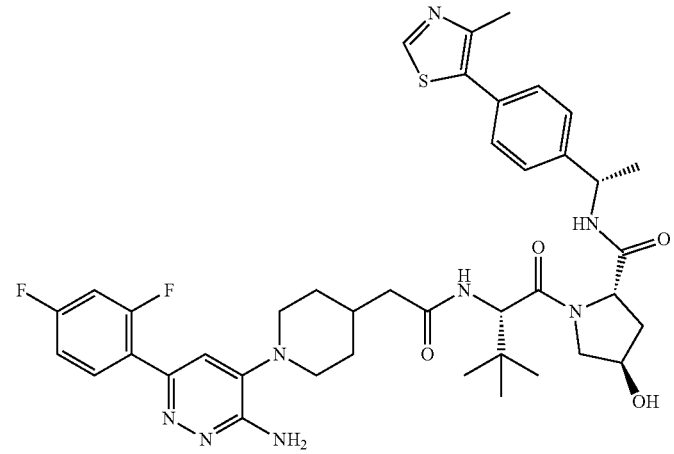 [SMILES: Cc1ncsc1-c1ccc([C@H](C)NC(=O)[C@@H]2C[C@@H](O)CN2C(=O)[C@@H](NC(=O)CC2CCN(c3cc(-c4ccc(F)cc4F)nnc3N)CC2)C(C)(C)C)cc1] | ¹H NMR (400 MHz, DMSO-d₆): δ 8.98 (s, 1H), 8.38 (d, J = 7.6 Hz, 1H), 7.91-7.82 (m, 2H), 7.44-7.31 (m, 5H), 7.24-7.19 (m, 1H), 7.12 (s, 1H), 6.27 (bs, 2H), 5.10 (d, J = 3.2 Hz, 1H), 4.93-4.90 (m, 1H), 4.54 (d, J = 9.2 Hz, 1H), 4.45-4.40 (m, 1H), 4.30-4.25 (m, 1H), 3.64 (d, J = 2.0 Hz, 2H), 3.41-3.37 (m, 4H), 2.54-2.52 (m, 2H), 2.46 (s, 3H), 2.33-2.32 (m, 1H), 2.16-2.15 (m, 1H), 2.08-1.94 (m, 1H), 1.80-1.78 (m, 1H), 1.72-1.69 (m, 1H), 1.50-1.44 (m, 2H), 1.37 (d, J = 7.2 Hz, 3H), 0.93 (s, 9H); LC-MS: m/z 775.3 (M + 1)⁺; (Yield: 54%). |
| 89 | 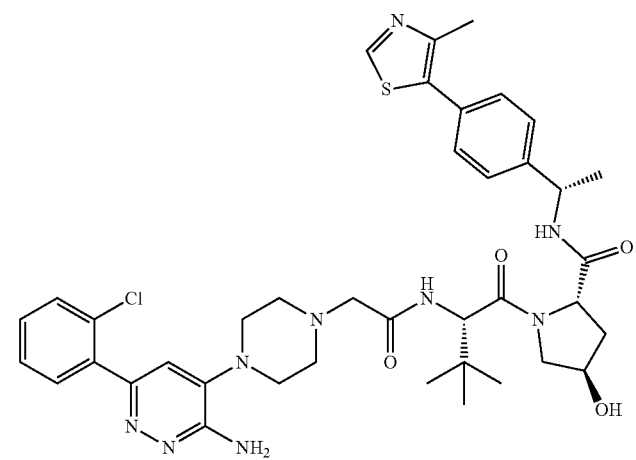 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4Cl)nnc3N)CC2)C(C)(C)C)cc1] | ¹H NMR (400 MHz, DMSO-d₆): δ 8.93 (s, 1H), 8.40 (d, J = 7.2 Hz, 1H), 7.74 (d, J = 10.0 Hz, 1H), 7.57-7.54 (m, 2H), 7.44-7.33 (m, 6H), 7.08 (s, 1H), 6.05 (s, 2H), 5.11-5.10 (m, 1H), 4.90-4.88 (m, 1H), 4.51 (d, J = 9.2 Hz, 1H), 4.45-4.41 (m, 1H), 4.28 (s, 1H), 3.59-3.58 (m, 2H), 3.17-3.11 (m, 4H), 2.70-2.66 (m, 4H), 2.45 (s, 3H), 2.10-1.98 (m, 1H), 1.80-1.76 (m, 1H), 1.36-1.33 (m, 5H), 0.95 (s, 9H); LC-MS: m/z 774.1 (M + 1)⁺; (Yield: 9%). |

TABLE 28-continued

| Comp No. | Structure | Characterization Data |
|---|---|---|
| 90 | 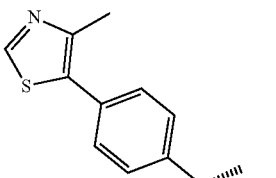 | $^1$H NMR (400 MHz, DMSO-$d_6$): δ 14.49 (bs, 1H), 8.97 (s, 1H), 8.41 (d, J = 7.2 Hz, 1H), 7.82-7.60 (m, 2H), 7.58 (s, 1H), 7.44-7.35 (m, 4H), 7.22-7.17 (m, 1H), 6.87-6.83 (m, 1H), 6.38 (bs, 2H), 5.12 (d, J = 3.2 Hz, 1H), 4.89 (t, J = 7.2 Hz, 1H), 4.53 (d, J = 9.6 Hz, 1H), 4.44 (t, J = 8.4 Hz, 1H), 4.29 (bs, 1H), 3.61-3.59 (m, 2H), 3.18-3.10 (m, 5H), 2.73-2.70 (m, 4H), 2.49 (s, 3H), 2.08-2.03 (m, 2H), 1.78-1.77 (m, 1H), 1.48 (d, J = 6.8 Hz, 3H), 0.96 (s, 9H); LC-MS: m/z 774.3 (M + 1)$^+$; (Yield: 22%). |
| 91 | 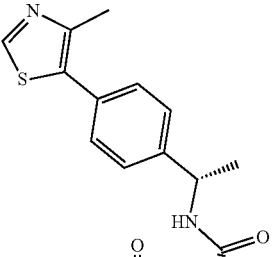 | $^1$H NMR (400 MHz, DMSO-$d_6$): δ 14.64 (S, 1H), 8.99 (s, 1H), 8.45 (d, J = 8.0 Hz, 1H), 7.81-7.77 (m, 2H), 7.55 (s, 1H), 7.43 (d, J = 8.4 Hz, 2H), 7.36 (d, J = 8.0 Hz, 2H), 7.13 (d, J = 6.8 Hz, 1H), 6.79 (t, J = 7.6 Hz, 1H), 6.29 (s, 2H), 5.15 (d, J = 3.2 Hz, 1H), 4.90-4.88 (m, 1H), 4.53 (d, J = 9.6 Hz, 1H), 4.29 (bs, 1H), 3.60-3.56 (m, 2H), 3.30-3.18 (m, 6H), 3.17-3.14 (m, 1H), 2.73-2.72 (m, 4H), 2.45 (s, 3H), 2.20 (s, 3H), 2.06-2.05 (m, 1H), 1.77-1.76 (m, 1H), 1.36 (d, J = 6.8 Hz, 3H), 0.96 (s, 9H); LC-MS: m/z 770.3 (M + 1)$^+$; (Yield: 19.8%). |
| 92 | 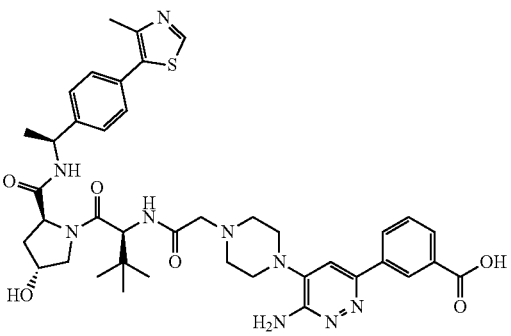 [SMILES: Cc1ncsc1-c1ccc([C@H](C)NC(=O)[C@@H]2C[C@@H](O)CN2C(=O)[C@@H](NC(=O)CN2CCN(c3cc(-c4cccc(C(=O)O)c4)nnc3N)CC2)C(C)(C)C)cc1] | $^1$H NMR (400 MHz, CD$_3$OD): δ 8.89 (s, 1H), 8.52-8.50 (m, 1H), 8.45-8.20 (m, 2H), 7.77 (s, 1H), 7.54-7.52 (m, 1H), 7.45-7.30 (m, 3H), 5.15-4.95 (m, 1H), 4.66 (s, 1H), 4.52-4.50 (m, 1H), 4.48 (bs, 1H), 3.85-3.65 (m, 2H), 3.57-3.56 (m, 1H), 3.52-3.50 (m, 4H), 3.45-3.40 (m, 4H), 2.47 (s, 3H), 2.44 (S, 1H), 2.25-2.15 (m, 1H), 2.00-1.54 (m, 1H), 1.52-1.51 (m, 1H), 1.50 (d, J = 7.2 Hz, 3H), 1.07 (s, 9H); LC-MS: m/z 782.3 (M − 1); (Yield: 20.4%). |

TABLE 28-continued

| Comp No. | Structure | Characterization Data |
|---|---|---|
| 93 | 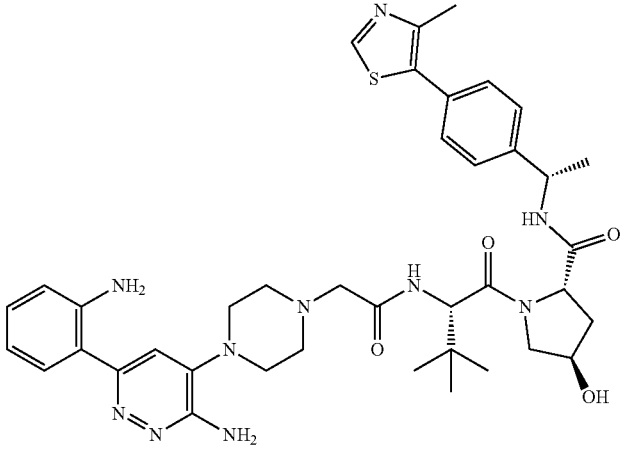 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4N)nnc3N)CC2)C(C)(C)C)cc1] | $^1$H NMR (400 MHz, DMSO-$d_6$): δ 8.98 (s, 1H), 8.73 (d, J = 7.2 Hz, 1H), 7.77 (d, J = 9.6 Hz, 1H), 7.50-7.49 (m, 1H), 7.48-7.38 (m, 4H), 7.16 (s, 1H), 7.06-7.02 (m, 1H), 6.74-6.72 (m, 1H), 6.61-6.60 (m, 1H), 6.47 (bs, 2H), 5.59 (s, 2H), 5.14 (d, J = 3.6 Hz, 1H), 4.90 (t, J = 7.2 Hz, 1H), 4.52 (d, J = 9.6 Hz, 1H), 4.43-4.40 (m, 1H), 4.28 (s, 1H), 3.59-3.58 (m, 2H), 3.29-3.00 (m, 6H), 2.71-2.51 (m, 4H), 2.44 (s, 3H), 2.07-2.04 (m, 1H), 1.77-1.75 (m, 1H), 1.47 (d, J = 6.8 Hz, 3H), 0.96 (s, 9H); LC-MS: m/z 755.4 (M + 1)$^+$; (Yield: 25%). |
| 94 | 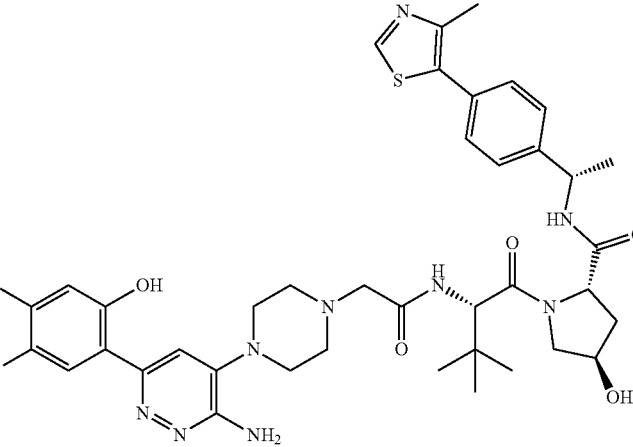 | $^1$H NMR (400 MHz, DMSO-$d_6$): δ 14.83 (s, 1H), 8.98 (s, 1H), 8.44 (d, J = 7.6 Hz, 1H), 8.21-8.15 (m, 1H), 7.78 (d, J = 9.6 Hz, 1H), 7.56 (s, 1H), 7.45-7.42 (m, 2H), 7.36-7.33 (m, 2H), 6.96-6.91 (m, 1H), 6.38 (s, 2H), 5.14 (d, J = 3.2 Hz, 1H), 4.88 (t, J = 7.2 Hz, 1H), 4.53 (d, J = 9.6 Hz, 1H), 4.41 (t, J = 11.2 Hz, 1H), 4.28 (s, 1H), 3.60-3.59 (m, 2H), 3.17-3.01 (m, 6H), 2.73-2.66 (m, 2H), 2.52-2.50 (m, 2H), 2.49 (s, 3H), 2.08-2.05 (m, 1H), 1.76-1.75 (m, 1H), 1.48 (d, J = 7.2 Hz, 3H), 0.96 (s, 9H); LC-MS: m/z 792.3 (M + 1)$^+$; (Yield: 14%). |
| 95 | 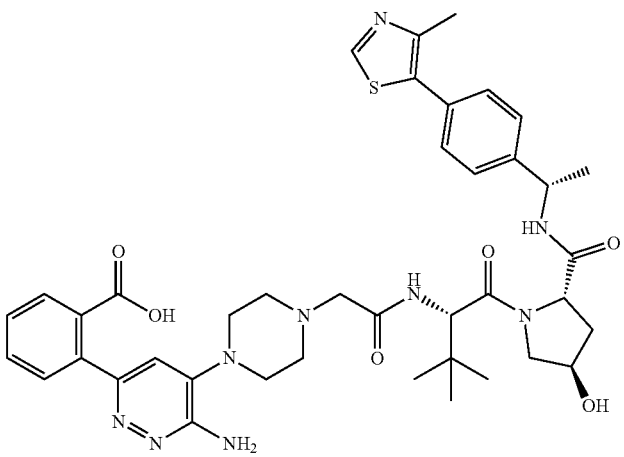 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4C(=O)O)nnc3N)CC2)C(C)(C)C)cc1] | $^1$H NMR (400 MHz, CD$_3$OD): δ 8.77-8.76 (m, 1H), 8.44-8.35 (m, 3H), 7.93 (d, J = 7.6 Hz, 1H), 7.42-7.38 (m, 1H), 7.34-7.29 (m, 5H), 4.92-4.81 (m, 2H), 4.55 (s, 1H), 4.50-4.48 (m, 2H), 4.34 (bs, 1H), 3.77-3.74 (m, 1H), 3.66-3.65 (m, 1H), 3.17-3.16 (m, 3H), 2.72-2.67 (m, 4H), 2.38 (s, 3H), 2.10-2.05 (m, 1H), 1.93-1.84 (m, 1H), 1.39 (d, J = 7.2 Hz, 3H), 0.96 (s, 9H); LC-MS: m/z 784.3 (M + 1)$^+$; (Yield: 20.4%). |

TABLE 28-continued

| Comp No. | Structure | Characterization Data |
|---|---|---|
| 96 | 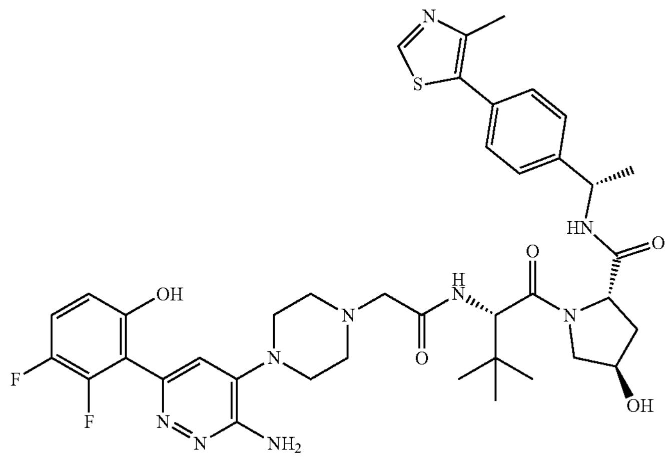 [SMILES: Cc1ncsc1-c1ccc([C@H](C)NC(=O)[C@@H]2C[C@@H](O)CN2C(=O)[C@@H](NC(=O)CN2CCN(c3cc(-c4c(O)ccc(F)c4F)nnc3N)CC2)C(C)(C)C)cc1] | $^1$H NMR (400 MHz, DMSO-$d_6$): δ 12.92 (s, 1H), 8.98 (s, 1H), 8.44 (d, J = 8.0 Hz, 1H), 7.78 (d, J = 9.6 Hz, 1H), 7.42-7.27 (m, 6H), 6.76-6.73 (m, 1H), 6.39 (s, 2H), 5.14 (d, J = 3.2 Hz, 1H), 4.88 (t, J = 7.2 Hz, 1H), 4.52 (d, J = 9.6 Hz, 1H), 4.43-4.40 (m, 1H), 4.28 (s, 1H), 3.61-3.58 (m, 2H), 3.12-3.05 (m, 6H), 2.72-2.54 (m, 2H), 2.53-2.52 (m, 2H), 2.49 (s, 3H), 2.05-2.02 (m, 1H), 1.78-1.75 (m, 1H), 1.36 (d, J = 7.2 Hz, 3H), 0.98 (s, 9H); LC-MS: m/z 792.3 (M + 1)$^+$; (Yield: 11%). |
| 97 | 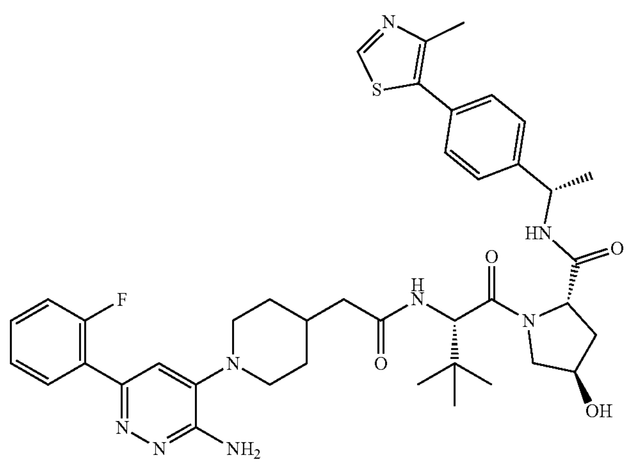 [SMILES: Cc1ncsc1-c1ccc([C@H](C)NC(=O)[C@@H]2C[C@@H](O)CN2C(=O)[C@@H](NC(=O)CC2CCN(c3cc(-c4ccccc4F)nnc3N)CC2)C(C)(C)C)cc1] | $^1$H NMR (400 MHz, DMSO-$d_6$): δ 8.98 (s, 1H), 8.35 (d, J = 8.0 Hz, 1H), 7.88-7.79 (m, 2H), 7.46-7.36 (m, 4H), 7.30 (t, J = 8.0 Hz, 2H), 7.11 (s, 1H), 6.06 (s, 2H), 5.08-5.07 (m, 1H), 4.54 (d, J = 9.2 Hz, 1H), 4.43 (t, J = 7.6 Hz, 1H), 4.28 (s, 1H), 3.60 (s, 2H), 3.39-3.31 (m, 3H), 2.67-2.61 (m, 1H), 2.45 (s, 3H), 2.28-2.24 (m, 1H), 2.17-2.12 (m, 1H), 2.00-1.98 (m, 1H), 1.86-1.70 (m, 4H), 1.47-1.36 (m, 3H), 1.37 (d, J = 7.2 Hz, 3H), 1.09 (t, J = 6.8 Hz, 1H), 0.95 (s, 9H); LC-MS: m/z 757.2 (M + 1)$^+$; (Yield: 9%). |
| 98 | 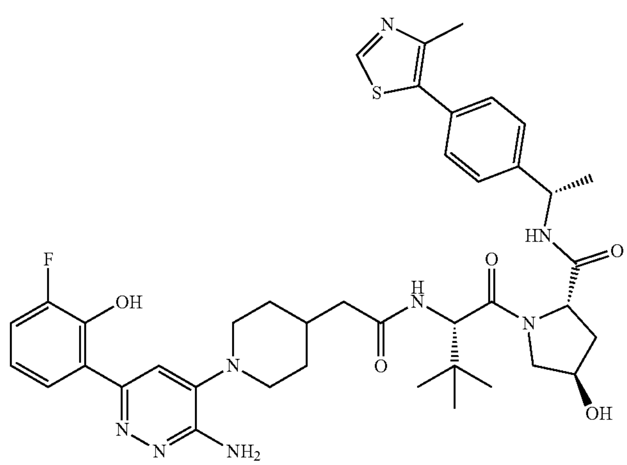 | $^1$H NMR (400 MHz, DMSO-$d_6$): δ 15.04 (bs, 1H), 8.98 (s, 1H), 8.36 (d, J = 8.4 Hz, 1H), 7.88 (d, J = 9.2 Hz, 1H), 7.76 (d, J = 8.0 Hz, 1H), 7.51 (s, 1H), 7.44-7.37 (m, 4H), 7.19 (t, J = 8.0 Hz, 1H), 6.87-6.81 (m, 1H), 6.30 (bs, 2H), 5.08 (d, J = 3.7 Hz, 1H), 4.92 (t, J = 7.2 Hz, 1H), 4.55 (d, J = 9.2 Hz, 1H), 4.41-4.29 (m, 1H), 4.30 (bs, 1H), 3.62 (bs, 2H), 3.46-3.40 (m, 2H), 2.49 (s, 3H), 2.32-2.30 (m, 2H), 2.02-1.80 (m, 6H), 1.50-1.42 (m, 3H), 1.38 (d, J = 6.8 Hz, 3H), 0.96 (s, 9H); LC-MS: m/z 773.3 (M + 1)$^+$; (Yield: 18%). |

TABLE 28-continued

| Comp No. | Structure | Characterization Data |
| --- | --- | --- |
| 99 | 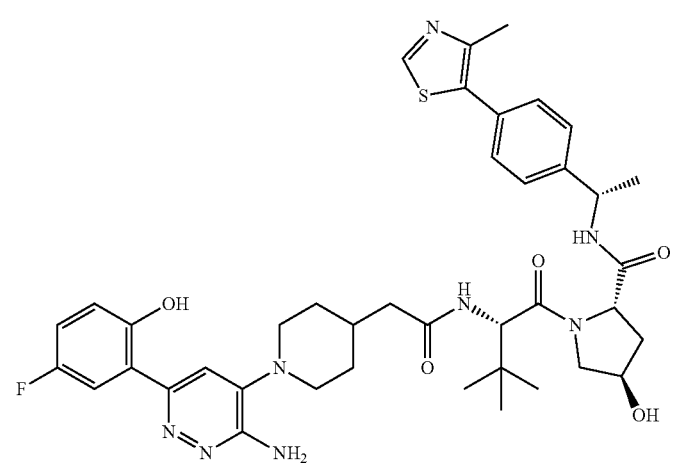 [SMILES: Cc1ncsc1-c1ccc([C@H](C)NC(=O)[C@@H]2C[C@@H](O)CN2C(=O)[C@@H](NC(=O)CC2CCN(c3cc(-c4cc(F)ccc4O)nnc3N)CC2)C(C)(C)C)cc1] | $^1$H NMR (400 MHz, DMSO-$d_6$): δ 14.12 (s, 1H), 8.98 (s, 1H), 8.37 (d, J = 7.6 Hz, 1H), 7.90 (d, J = 9.6 Hz, 1H), 7.80 (d, J = 7.6 Hz, 1H), 7.51 (s, 1H), 7.44-7.32 (m, 4H), 7.11-7.09 (m, 1H), 6.91-6.87 (m, 1H), 6.36 (s, 2H), 5.09 (s, 1H), 4.92 (t, J = 7.6 Hz, 1H), 4.55 (d, J = 5.2 Hz, 1H), 4.43 (t, J = 8.0 Hz, 1H), 4.29 (s, 1H), 3.62 (s, 2H), 3.47-3.45 (m, 2H), 2.77-2.63 (m, 4H), 2.45 (s, 3H), 2.32-2.28 (m, 1H), 2.18-2.12 (m, 1H), 2.04-2.01 (m, 1H), 1.78-1.72 (m, 4H), 1.38 (d, J = 6.8 Hz, 3H), 0.96 (s, 9H); LC-MS: m/z 773.3 (M + 1)$^+$; (Yield: 21%). |
| 100 | 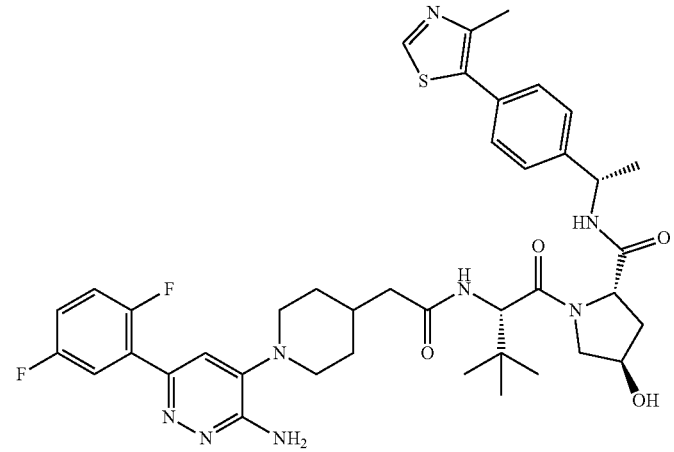 [SMILES: Cc1ncsc1-c1ccc([C@H](C)NC(=O)[C@@H]2C[C@@H](O)CN2C(=O)[C@@H](NC(=O)CC2CCN(c3cc(-c4cc(F)ccc4F)nnc3N)CC2)C(C)(C)C)cc1] | $^1$H NMR (400 MHz, DMSO-$d_6$): δ 8.98 (s, 1H), 8.35 (d, J = 8.0 Hz, 1H), 7.87 (d, J = 8.2 Hz, 1H), 7.66-7.61 (m, 1H), 7.44-7.28 (m, 6H), 7.14 (s, 1H), 6.08 (s, 2H), 5.08-5.07 (m, 1H), 4.90 (t, J = 7.2 Hz, 1H), 4.54 (d, J = 9.2 Hz, 1H), 4.42 (t, J = 8.0 Hz, 1H), 4.28 (s, 1H), 3.62-3.61 (m, 2H), 3.38-3.30 (m, 2H), 2.67-2.60 (m, 2H), 2.45 (s, 3H), 2.49-2.28 (m, 2H), 1.98-1.91 (m, 1H), 1.85-1.70 (m, 4H), 1.47-1.38 (m, 2H), 1.37 (d, J = 6.8 Hz, 3H), 0.92 (s, 9H); LC-MS: m/z 775.2 (M + 1)$^+$; (Yield: 15%). |
| 101 | 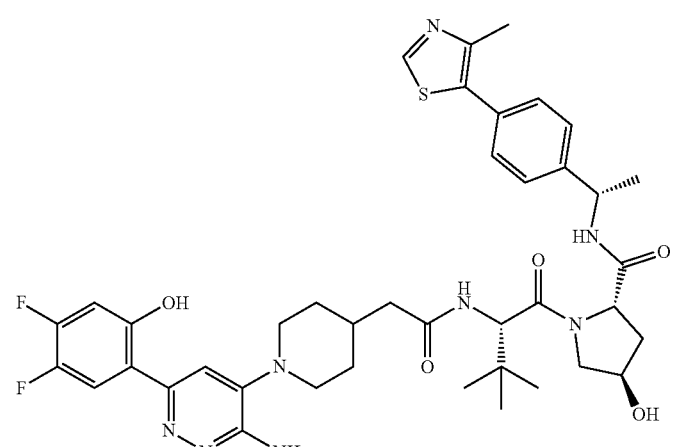 | $^1$H NMR (400 MHz, DMSO-$d_6$): δ 14.91 (s, 1H), 8.99 (s, 1H), 8.40 (d, J = 7.6 Hz, 1H), 8.17-8.13 (m, 1H), 7.93 (d, J = 9.6 Hz, 1H), 7.51 (s, 1H), 7.43-7.30 (m, 4H), 6.95-6.90 (m, 1H), 6.30 (s, 2H), 5.12-5.11 (m, 1H), 4.92 (t, J = 7.2 Hz, 1H), 4.55 (d, J = 9.6 Hz, 1H), 4.43-4.42 (m, 1H), 4.28 (s, 1H), 3.65-3.61 (m, 2H), 3.46-3.44 (m, 2H), 2.67-2.52 (m, 2H), 2.47-2.46 (m, 3H), 2.33-2.25 (m, 2H), 2.11-1.98 (m, 1H), 1.90-1.80 (m, 1H), 1.75-1.71 (m, 3H), 1.47-1.38 (m, 2H), 1.37 (d, J = 7.2 Hz, 3H), 0.92 (s, 9H); LC-MS: m/z 791.3 (M + 1)$^+$; (Yield: 20%). |

TABLE 28-continued

| Comp No. | Structure | Characterization Data |
|---|---|---|
| 102 | 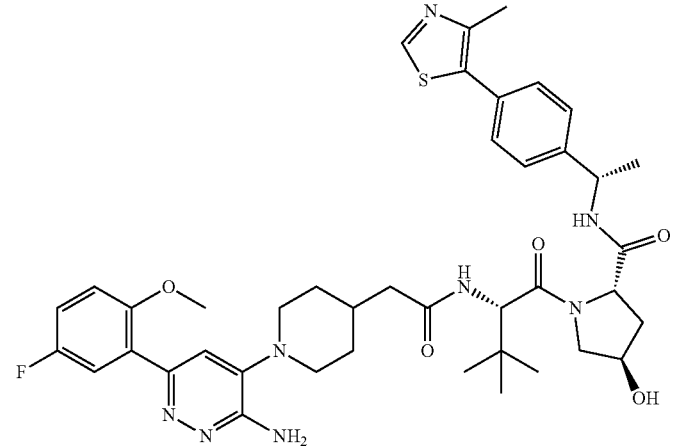 [SMILES: COc1ccc(F)cc1-c1cc(N2CCC(CC(=O)N[C@H](C(=O)N3C[C@H](O)C[C@H]3C(=O)N[C@@H](C)c3ccc(-c4scnc4C)cc3)C(C)(C)C)CC2)c(N)nn1] | $^1$H NMR (400 MHz, DMSO-d$_6$): δ 8.98 (s, 1H), 8.38 (d, J = 8.0 Hz, 1H), 7.90 (d, J = 9.6 Hz, 1H), 7.46-7.42 (m, 3H), 7.39-7.36 (m, 2H), 7.24-7.21 (m, 2H), 7.16-7.14 (m, 1H), 6.04 (s, 2H), 5.10 (d, J = 3.6 Hz, 1H), 4.93-4.90 (m, 1H), 4.54 (d, J = 9.6 Hz, 1H), 4.42-4.40 (m, 1H), 4.28-4.27 (m, 1H), 3.81 (s, 3H), 3.62-3.61 (m, 2H), 3.36-3.33 (m, 2H), 2.52-2.49 (m, 2H), 2.45 (s, 3H), 2.24-2.23 (m, 1H), 2.17-2.16 (m, 1H), 2.01-1.90 (m, 1H), 1.79-1.69 (m, 4H), 1.44-1.40 (m, 1H), 1.37 (d, J = 6.8 Hz, 3H), 1.26-1.24 (m, 1H), 0.99 (s, 9H); LC-MS: m/z 787.4 (M + 1)$^+$; (Yield: 46%). |
| 103 | 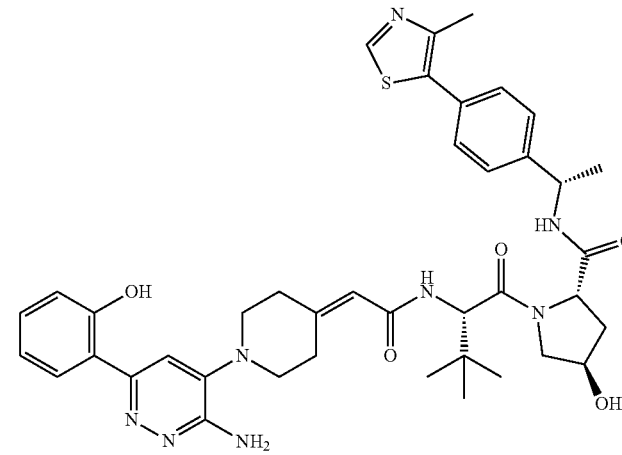 | $^1$H NMR (400 MHz, CD$_3$OD): δ 8.77 (s, 1H), 7.78-7.67 (m, 1H), 7.42-7.38 (m, 1H), 7.35-7.29 (m, 3H), 7.15-7.11 (m, 2H), 6.84-6.76 (m, 2H), 5.74 (s, 1H), 4.90-4.84 (m, 1H), 4.76-4.68 (m, 1H), 4.53-4.40 (m, 1H), 4.33-4.28 (m, 1H), 3.77 (d, J = 10.8 Hz, 1H), 3.63-3.47 (m, 3H), 3.30-3.20 (m, 1H), 2.98-2.89 (m, 2H), 2.37 (s, 2H), 2.21-2.20 (m, 4H), 2.09-2.05 (m, 1H), 1.86-1.84 (m, 1H), 1.40 (d, J = 7.2 Hz, 3H), 0.97 (s, 9H); LC-MS: m/z 753.3 (M + 1)$^+$; (Yield: 13.5%). |
| 104 | 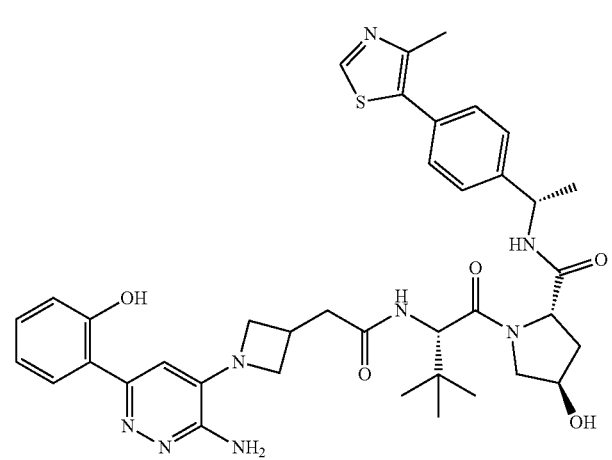 [SMILES: Cc1ncsc1-c1ccc([C@H](C)NC(=O)[C@@H]2C[C@@H](O)CN2C(=O)[C@@H](NC(=O)CC2CN(c3cc(-c4ccccc4O)nnc3N)C2)C(C)(C)C)cc1] | $^1$H NMR (400 MHz, DMSO-d$_6$): δ 14.25 (bs, 1H), 8.98 (s, 1H), 8.36 (d, J = 8.0 Hz, 1H), 7.96 (d, J = 9.2 Hz, 1H), 7.80 (bs, 1H), 7.44-7.36 (m, 4H), 7.28-7.22 (m, 1H), 6.89-6.83 (m, 3H), 5.98 (bs, 2H), 5.11 (d, J = 3.2 Hz, 1H), 4.94-4.91 (m, 1H), 4.52 (d, J = 9.2 Hz, 1H), 4.42-4.29 (m, 4H), 3.90 (bs, 2H), 3.61-3.58 (m, 2H), 2.98-2.93 (m, 1H), 2.50-2.44 (m, 5H), 2.08-2.00 (m, 1H), 1.82-1.79 (m, 1H), 1.37 (d, J = 6.8 Hz, 3H), 0.94 (s, 9H); LC-MS: m/z 727.1 (M + 1)$^+$; (Yield: 13%). |

TABLE 28-continued

| Comp No. | Structure | Characterization Data |
|---|---|---|
| 105 | 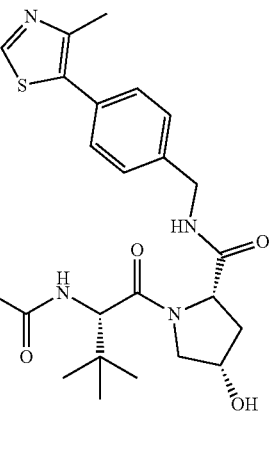 | $^1$H NMR (400 MHz, DMSO-d$_6$): δ 14.21 (s, 1H), 8.90 (s, 1H), 8.65-8.62 (m, 1H), 7.92 (d, J = 8.0 Hz, 1H), 7.75 (d, J = 7.6 Hz, 1H), 7.53 (s, 1H), 7.53-7.39 (m, 5H), 7.24 (t, J = 8.0 Hz, 1H), 6.90-6.85 (m, 2H), 6.26 (bs, 2H), 5.44 (d, J = 7.6 Hz, 1H), 4.50-4.24 (m, 5H), 3.92-3.90 (m, 1H), 3.49-3.45 (m, 1H), 3.16-3.09 (m, 5H), 2.72-2.67 (m, 5H), 2.35 (s, 3H), 1.76-1.73 (m, 1H), 0.93 (s, 9H); LC-MS: m/z 742.1 (M + 1)$^+$; (Yield: 13.5%). |
| 106 | 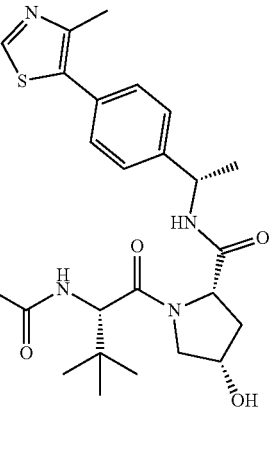 | $^1$H NMR (400 MHz, CD$_3$OD): δ 8.85 (s, 1H), 7.79 (d, J = 7.6 Hz, 1H), 7.55 (s, 1H), 7.44-7.38 (m, 4H), 7.27-7.23 (m, 1H), 6.93-6.90 (m, 2H), 5.00 (q, J = 8.0 Hz, 1H), 4.58 (s, 1H), 4.48-4.46 (m, 1H), 4.37-4.33 (m, 1H), 4.01-3.75 (m, 1H), 3.71-3.67 (m, 1H), 3.27-3.12 (m, 8H), 2.81-2.79 (m, 4H), 2.41 (s, 3H), 1.50 (d, J = 7.2 Hz, 3H), 1.06 (s, 9H); LC-MS: m/z 756.3 (M + 1)$^+$; (Yield: 25%). |
| 107 | 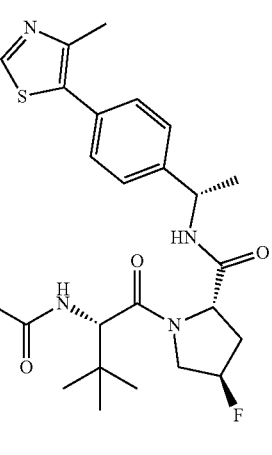 | $^1$H NMR (400 MHz, DMSO-d$_6$): δ 14.22 (s, 1H), 8.97 (s, 1H), 8.49 (d, J = 8.0 Hz, 1H), 7.95 (d, J = 7.6 Hz, 1H), 7.77 (d, J = 9.2 Hz, 1H), 7.56 (s, 1H), 7.44-7.42 (m, 2H), 7.38-7.36 (m, 2H), 7.24 (t, J = 7.2 Hz, 1H), 6.90-6.88 (m, 2H), 6.26 (bs, 2H), 5.40 (bs, 1H), 5.26 (bs, 1H), 4.92-4.89 (m, 1H), 4.51-4.46 (m, 2H), 4.15-4.05 (m, 1H), 3.80-3.62 (m, 1H), 3.17-3.04 (m, 6H), 2.73-2.67 (m, 4H), 2.45 (s, 3H), 1.98-1.80 (m, 1H), 1.38 (d, J = 7.6 Hz, 3H), 0.98 (s, 9H); LC-MS: m/z 758.4 (M + 1)$^+$; (Yield: 17%). |

TABLE 28-continued

| Comp No. | Structure | Characterization Data |
| --- | --- | --- |
| 108 | 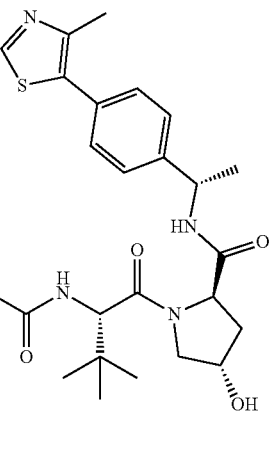 | ¹H NMR (400 MHz, DMSO-d$_6$): δ 14.23 (s, 1H), 8.84 (s, 1H), 8.16 (d, J = 8.0 Hz, 1H), 7.85-7.83 (m, 1H), 7.65 (d, J = 9.2 Hz, 1H), 7.41-7.35 (m, 3H), 7.27-7.21 (m, 3H), 6.88-6.83 (m, 2H), 6.23 (s, 2H), 5.13 (d, J = 3.6 Hz, 1H), 4.91-4.87 (m, 1H), 4.49 (d, J = 9.2 Hz, 1H), 4.40-4.33 (m, 2H), 3.75-3.71 (m, 1H), 3.70-3.62 (m, 1H), 3.15-3.11 (m, 3H), 2.96-2.92 (m, 3H), 2.72-2.60 (m, 4H), 2.34 (s, 3H), 2.20-2.10 (m, 1H), 1.98-1.87 (m, 1H), 1.31 (d, J = 6.8 Hz, 3H), 0.97 (s, 9H); LC-MS: m/z 756.4 (M + 1)⁺; (Yield: 12%). |
| 109 | 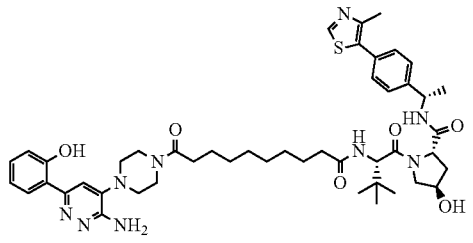 [SMILES: Cc1ncsc1-c1ccc([C@H](C)NC(=O)[C@@H]2C[C@@H](O)CN2C(=O)[C@@H](NC(=O)CCCCCCCCC(=O)N2CCN(c3cc(-c4ccccc4O)nnc3N)CC2)C(C)(C)C)cc1] | ¹H NMR (400 MHz, DMSO-d$_6$): δ 14.15 (s, 1H), 8.97 (s, 1H), 8.35 (d, J = 8.0 Hz, 1H), 7.90 (d, J = 7.2 Hz, 1H), 7.76 (d, J = 9.2 Hz, 1H), 7.53 (s, 1H), 7.43 (d, J = 8.4 Hz, 2H), 7.37 (d, J = 8.4 Hz, 2H), 7.23 (t, J = 7.0 Hz, 1H), 6.90-6.87 (m, 2H), 6.39 (bs, 2H), 5.16 (d, J = 4.0 Hz, 1H), 4.93-4.89 (m, 1H), 4.51 (d, J = 9.2 Hz, 1H), 4.41 (t, J = 8.0 Hz, 1H), 4.27 (bs, 1H), 3.68 (bs, 4H), 3.60-3.59 (m, 2H), 3.07-3.03 (m, 4H), 2.45 (s, 3H), 2.30-2.20 (m, 2H), 2.14-2.07 (m, 2H), 1.82-1.76 (m, 1H), 1.51-1.45 (m, 5H), 1.37 (d, J = 6.8 Hz, 3H), 1.26-1.23 (m, 8H), 0.93 (s, 9H); LC-MS: m/z 882.40 (M + 1)⁺; (Yield: 25%). |
| 110 | 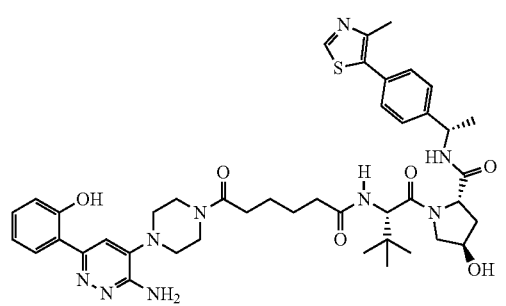 [SMILES: Cc1ncsc1-c1ccc([C@H](C)NC(=O)[C@@H]2C[C@@H](O)CN2C(=O)[C@@H](NC(=O)CCCCC(=O)N2CCN(c3cc(-c4ccccc4O)nnc3N)CC2)C(C)(C)C)cc1] | ¹H NMR (400 MHz, DMSO-d$_6$): δ 14.15 (bs, 1H), 8.98 (s, 1H), 8.36 (d, J = 5.8 Hz, 1H), 7.91 (d, J = 7.1 Hz, 1H), 7.80 (d, J = 7.0 Hz, 1H), 7.52 (s, 1H), 7.42 (d, J = 8.3 Hz, 2H), 7.38 (d, J = 8.3 Hz, 2H), 7.24-7.01 (m, 1H), 6.90-6.88 (m, 2H), 6.40 (bs, 2H), 5.09 (d, J = 3.5 Hz, 1H), 4.97 (d, J = 7.0 Hz, 1H), 4.53 (d, J = 9.2 Hz, 1H), 4.43 (t, J = 8.0 Hz, 1H), 4.29 (bs, 1H), 3.75-3.65 (m, 4H), 3.60 (s, 2H), 3.04 (d, J = 17.6 Hz, 4H), 2.50 (s, 3H), 2.49-2.45 (m, 2H), 2.44-2.36 (m, 1H), 2.08-1.99 (m, 1H), 1.54-1.52 (m, 6H), 1.37-1.36 (m, 3H), 0.93 (s, 9H); LC-MS: m/z 826.35(M + 1)⁺; (Yield: 37%). |
| 111 | 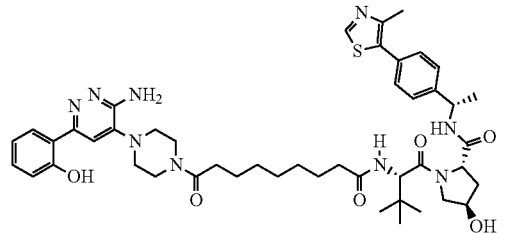 [SMILES: Cc1ncsc1-c1ccc([C@H](C)NC(=O)[C@@H]2C[C@@H](O)CN2C(=O)[C@@H](NC(=O)CCCCCCCC(=O)N2CCN(c3cc(-c4ccccc4O)nnc3N)CC2)C(C)(C)C)cc1] | H NMR (400 MHz, DMSO-d$_6$): δ 14.15 (bs, 1H), 8.36 (d, J = 5.8 Hz, 1H), 7.92-7.90 (m, 1H), 7.77 (d, J = 9.2 Hz, 1H), 7.52 (s, 1H), 7.43 (d, J = 8.3 Hz, 2H), 7.37 (d, J = 8.3 Hz, 2H), 7.53 (s, 1H), 7.44-7.36 (m, 4H), 7.25-7.21 (m, 1H), 6.90-6.86 (m, 2H), 6.39 (bs, 2H), 5.10 (d, J = 3.6 Hz, 1H), 4.93 (t, J = 7.1 Hz, 1H), 4.52 (d, J = 9.3 Hz, 1H), 4.42 (t, J = 8.0 Hz, 1H), 4.27 (s, 1H), 3.68-3.57 (m, 3H), 3.07 (d, J = 17.0 Hz, 2H), 2.50 (s, 3H), 2.36-1.98 (m, 6H), 1.82-1.76 (m, 1H), 1.47-1.45 (m, 4H), 1.38 (d, J = 6.2 Hz, 3H), 1.36-1.20 (m, 6H), 0.93 (s, 9H); LC-MS: m/z 866.35 (M − 1); (Yield: 48%). |

TABLE 28-continued

| Comp No. | Structure | Characterization Data |
|---|---|---|
| 112 | 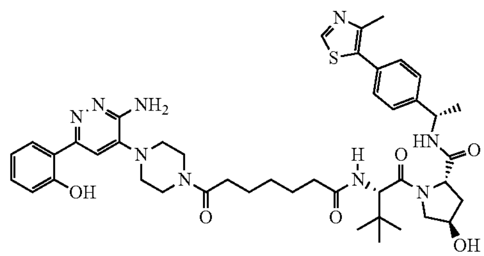 [SMILES: Cc1ncsc1-c1ccc([C@H](C)NC(=O)[C@@H]2C[C@@H](O)CN2C(=O)[C@@H](NC(=O)CCCCCC(=O)N2CCN(c3cc(-c4ccccc4O)nnc3N)CC2)C(C)(C)C)cc1] | ¹H NMR (400 MHz, DMSO-d₆): δ 14.15 (bs, 1H), 8.98 (s, 1H), 8.36 (d, J = 5.8 Hz, 1H), 7.91 (d, J = 7.1 Hz, 1H), 7.80 (d, J = 7.0 Hz, 1H), 7.52 (s, 1H), 7.42 (d, J = 8.3 Hz, 2H), 7.38 (d, J = 8.3 Hz, 2H), 7.24-7.21 (m, 1H), 6.91-6.88 (m, 2H), 6.40 (bs, 2H), 5.09 (d, J = 3.5 Hz, 1H), 4.97 (d, J = 7.4 Hz, 1H), 4.53 (d, J = 9.2 Hz, 1H), 4.43 (t, J = 8.0 Hz, 1H), 4.29 (bs, 1H), 3.68-3.60 (m, 6H), 3.17 (d, J = 4.5 Hz, 2H), 3.08 (d, J = 19.1 Hz, 2H), 2.50 (s, 3H), 2.36-2.34 (m, 2H), 2.33-2.32 (m, 1H), 2.19-2.09 (m, 1H), 2.00-1.90 (m, 1H), 1.72-1.65 (m, 1H), 1.54-1.52 (m, 6H), 1.37-1.36 (m, 3H), 0.93 (s, 9H); LC-MS: m/z 840.1 (M + 1)⁺; (Yield: 20%). |
| 113 | 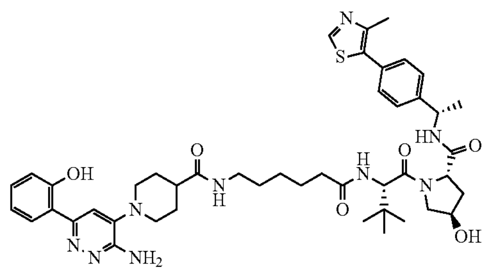 [SMILES: Cc1ncsc1-c1ccc([C@H](C)NC(=O)[C@@H]2C[C@@H](O)CN2C(=O)[C@@H](NC(=O)CCCCCNC(=O)C2CCN(c3cc(-c4ccccc4O)nnc3N)CC2)C(C)(C)C)cc1] | ¹H NMR (400 MHz, DMSO-d₆): δ 14.25 (s, 1H), 8.97 (s, 1H), 8.35 (d, J = 8.0 Hz, 1H), 7.91 (d, J = 8.0 Hz, 1H), 7.77 (d, J = 9.2 Hz, 1H), 7.49 (s, 1H), 7.43 (d, J = 8.4 Hz, 2H), 7.37 (d, J = 8.4 Hz, 2H), 7.25-7.21 (m, 1H), 6.90-6.86 (m, 2H), 6.20 (s, 2H), 5.08 (d, J = 3.6 Hz, 1H), 4.93-4.89 (m, 1H), 4.51 (d, J = 9.2 Hz, 1H), 4.42 (t, J = 8.0 Hz, 1H), 4.27 (bs, 1H), 3.61-3.60 (m, 2H), 3.51-3.48 (m, 2H), 3.06-3.01 (m, 2H), 2.45 (s, 3H), 2.30-2.23 (m, 3H), 2.14-2.12 (m, 1H), 1.90-1.87 (m, 1H), 1.81-1.79 (m, 3H), 1.77-1.76 (m, 4H), 1.51-1.46 (m, 4H), 1.44-1.38 (m, 5H), 0.93 (s, 9H); LC-MS: m/z 854.10 (M + 1)⁺; (Yield: 19%). |
| 114 | 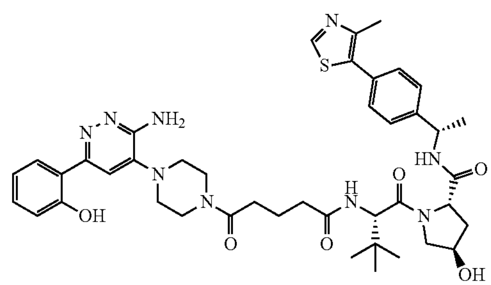 [SMILES: Cc1ncsc1-c1ccc([C@H](C)NC(=O)[C@@H]2C[C@@H](O)CN2C(=O)[C@@H](NC(=O)CCCC(=O)N2CCN(c3cc(-c4ccccc4O)nnc3N)CC2)C(C)(C)C)cc1] | ¹H NMR (400 MHz, DMSO-d₆): δ 14.16 (s, 1H), 8.97 (s, 1H), 8.33 (d, J = 7.6 Hz, 1H), 7.93 (d, J = 7.2 Hz, 1H), 7.84 (d, J = 9.2 Hz, 1H), 7.55 (s, 1H), 7.43-7.35 (m, 4H), 7.24 (t, J = 7.2 Hz, 1H), 6.89 (d, J = 8.0 Hz, 2H), 6.40 (s, 2H), 5.09 (s, 1H), 4.89 (t, J = 7.2 Hz, 1H), 4.53 (d, J = 9.6 Hz, 1H), 4.24 (t, J = 8.0 Hz, 1H), 4.28 (s, 1H), 3.69-3.62 (m, 5H), 3.08-3.03 (m, 4H), 2.45 (s, 3H), 2.36-2.28 (m, 3H), 2.27-2.20 (m, 2H), 1.82-1.73 (m, 3H), 1.34 (d, J = 7.2 Hz, 3H), 1.28-1.23 (m, 1H), 0.95 (s, 9H); LC-MS: m/z 812.1 (M + 1)⁺; (Yield: 8%). |
| 115 | 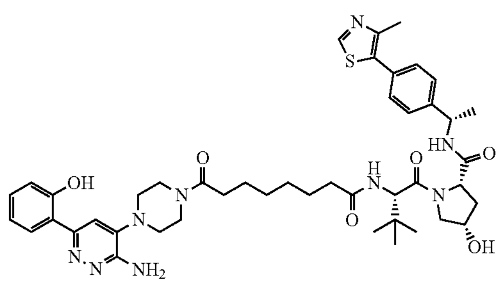 [SMILES: Cc1ncsc1-c1ccc([C@H](C)NC(=O)[C@@H]2C[C@H](O)CN2C(=O)[C@@H](NC(=O)CCCCCCC(=O)N2CCN(c3cc(-c4ccccc4O)nnc3N)CC2)C(C)(C)C)cc1] | ¹H NMR (400 MHz, DMSO-d₆): δ 14.15 (s, 1H), 8.98 (s, 1H), 8.29 (d, J = 8.0 Hz, 1H), 7.90 (dd, J = 1.6 Hz, J = 8.4 Hz, 1H), 7.79 (d, J = 7.2 Hz, 1H), 7.53 (s, 1H), 7.44-7.37 (m, 4H), 7.25-7.21 (m, 1H), 6.90-6.86 (m, 2H), 6.40 (s, 2H), 5.30 (d, J = 6.8 Hz, 1H), 4.92 (t, J = 7.2 Hz, 1H), 4.44 (d, J = 8.0 Hz, 1H), 4.32 (t, J = 2.4 Hz, 1H), 4.21-4.18 (m, 1H), 3.90-3.87 (m, 1H), 3.67-3.60 (m, 4H), 3.40-3.37 (m, 1H), 3.07-3.03 (m, 4H), 2.45 (s, 3H), 2.36-2.34 (m, 3H), 2.33-2.32 (m, 1H), 2.19-2.12 (m, 1H), 1.66-1.63 (m, 1H), 1.52-1.50 (m, 4H), 1.37 (d, J = 6.8 Hz, 3H), 1.27-1.23 (m, 4H), 0.94 (s, 9H); LC-MS: m/z 854.4 (M + 1)⁺; (Yield: 15%). |
| 116 | 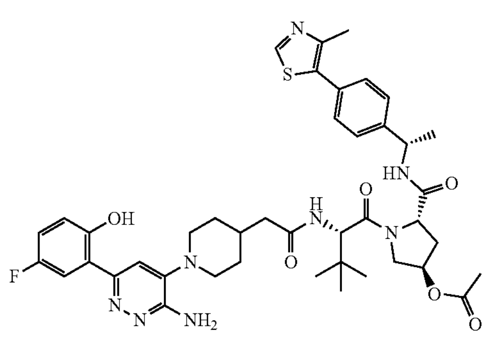 [SMILES: CC(=O)O[C@@H]1C[C@@H](C(=O)N[C@@H](C)c2ccc(-c3scnc3C)cc2)N(C(=O)[C@@H](NC(=O)CC2CCN(c3cc(-c4cc(F)ccc4O)nnc3N)CC2)C(C)(C)C)C1] | ¹H NMR (400 MHz, DMSO-d₆): δ 14.12 (s, 1H), 8.99 (s, 1H), 8.42 (d, J = 7.6 Hz, 1H), 7.93 (d, J = 8.8 Hz, 1H), 7.85 (dd, J1 = 3.2 Hz, J2 = 10.8 Hz, 1H), 7.52 (s, 1H), 7.45-7.36 (m, 4H), 7.08-7.07 (m, 1H), 6.90-6.86 (m, 1H), 6.29 (s, 2H), 5.19 (s, 1H), 4.92-4.90 (m, 1H), 4.46-4.45 (m, 1H), 4.39 (d, J = 8.8 Hz, 1H), 4.09-3.98 (m, 1H), 3.75-3.70 (m, 1H), 3.46-3.43 (m, 2H), 2.66-2.54 (m, 2H), 2.49 (s, 3H), 2.47-2.45 (m, 3H), 2.01 (s, 3H), 1.97-1.70 (m, 3H), 1.60-1.50 (m, 2H), 1.48 (d, J = 6.8 Hz, 3H), 1.38-1.37 (m, 1H), 0.97 (s, 9H); LC-MS: m/z 815.4 (M + 1)⁺; (yield: 56%). |

TABLE 28-continued

| Comp No. | Structure | Characterization Data |
|---|---|---|
| 117 | 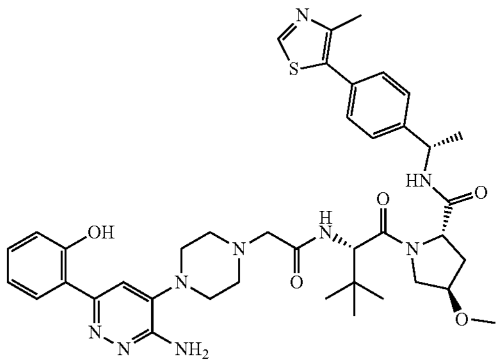 [SMILES: CO[C@@H]1C[C@@H](C(=O)N[C@@H](C)c2ccc(-c3scnc3C)cc2)N(C(=O)[C@@H](NC(=O)CN2CCN(c3cc(-c4ccccc4O)nnc3N)CC2)C(C)(C)C)C1] | $^1$H NMR (400 MHz, DMSO-d$_6$): δ 14.22 (s, 1H), 8.97 (s, 1H), 8.40 (d, J = 8.0 Hz, 1H), 7.95 (d, J = 7.2 Hz, 1H), 7.75 (d, J = 9.2 Hz, 1H), 7.56 (s, 1H), 7.44-7.42 (m, 2H), 7.38-7.35 (m, 2H), 7.26-7.22 (m, 1H), 6.90-6.88 (m, 2H), 6.25 (s, 2H), 4.91-4.89 (m, 1H), 4.53 (d, J = 9.6 Hz, 1H), 4.40-4.32 (m, 1H), 3.97 (s, 2H), 3.59-3.56 (m, 1H), 3.20-3.13 (m, 8H), 3.07-3.03 (m, 1H), 2.72-2.66 (m, 4H), 2.45 (s, 3H), 2.30-2.21 (m, 1H), 1.81-1.70 (m, 1H), 1.36 (d, J = 6.8 Hz, 3H), 0.93 (s, 9H); LC-MS: m/z 770.3 (M + 1)$^+$; (Yield: 9.5%). |
| 118 | 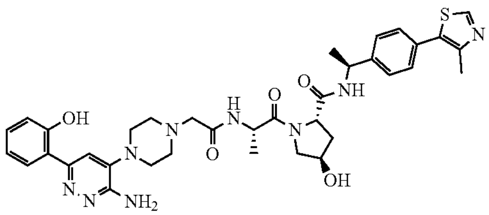 [SMILES: Cc1ncsc1-c1ccc([C@H](C)NC(=O)[C@@H]2C[C@@H](O)CN2C(=O)[C@H](C)NC(=O)CN2CCN(c3cc(-c4ccccc4O)nnc3N)CC2)cc1] | $^1$H NMR (400 MHz, DMSO-d$_6$): δ 14.19 (bs, 1H), 8.96 (s, 1H), 8.36 (d, J = 7.2 Hz, 1H), 8.20-7.80 (m, 1H), 7.54 (s, 1H), 7.43-7.36 (m, 4H), 7.30-7.20 (m, 1H), 6.90-6.88 (m, 2H), 6.27 (s, 2H), 5.10-5.05 (m, 1H), 4.89-4.80 (m, 1H), 4.58-4.50 (m, 1H), 4.49-4.43 (m, 1H), 4.31 (bs, 1H), 3.58-3.50 (m, 2H), 3.31-3.17 (m, 6H), 2.73-2.67 (m, 3H), 2.44 (s, 3H), 2.10-2.07 (m, 1H), 1.76-1.70 (m, 1H), 1.49-1.36 (m, 4H), 1.29-1.10 (m, 4H); LC-MS: m/z 714.3 (M + 1)$^+$; (Yield: 25.7%). |

Determination of Anti Proliferative Activity of Compounds in NCI-H929 and NCI-H838 Cell Lines by Cell Titer Glo® (promega) assay:

NCI-H929 (ATCC CRL-9068) or NCI-H838 (ATCC CRL-5844) cells were seeded in 96 well plate flat black clear bottom plates (Corning, Cat. No 3904) using complete RPMI-1640 media. Next day, compounds listed in the present invention were added to cells from 10 mM stocks made in DMSO (Sigma Cat no. D2650). Each concentration of compound was tested in triplicate with DMSO concentration at a final percentage not exceeding 0.3 in the cells. After the compound incubation (3 days for H929 and 8 days for H838) assay was terminated using 50 μl of CellTiter Glo® reagent (Promega, Cat. no G7572). CellTiter Glo® Luminescent reagent determines the number of viable cells based on quantitation of ATP present which is an indicator of cell number and metabolic activity. Luminescence readings were taken in Victor-3 instrument. Percent inhibition of proliferation was calculated using formula, % inhibition=100−(luminescence value of test/luminescence value of DMSO control)*100. DMSO control (0%)=Cells in complete media with DMSO; blank=Media alone containing DMSO. IC$_{50}$ was calculated using graph pad prism software.

Selected compounds of the present invention were screened in the above mentioned assay procedures for determination of IC$_{50}$ values and the results are summarized into groups A, B and C in below table 29. Herein group "A" refers to IC$_{50}$ value lower than 1 μM, "B" refers to IC$_{50}$ value between 1-10 μM (both inclusive) and "C" refers to IC$_{50}$ value higher than 10 μM or less than 50% activity at 10 μM.

TABLE 29

Anti-proliferative activity in NCI-H929 and NCI-H838cells.

| Group | (NCI-H929 cells) Compound No. | (NCI-H838 cells) Compound No. |
|---|---|---|
| A | 37, 39, 43, 47, 48, 51, 55, 56, 57, 58, 79, 81, 82, 87, 90, 98, 99, 109, 110, 111 and 112. | 43, 51, 58, 61, 63, 81, 82, 83, 90, 91, 96, 99, 103 and 55. |
| B | 23, 35, 38, 44, 49, 97, 104, 105, 106, 107, 113, 115 and 117. | — |
| C | 1, 2, 3, 4, 5, 6, 8, 9, 12, 14, 15, 16, 17, 18, 19, 20, 21, 22, 25, 26, 27, 28, 29, 30, 31, 33, 34, 42, 45, 46, 50, 53, 54, 67, 72, 73, 89, 114 and 118. | — |

Determination of SMARCA2 and SMARCA4 Degradation in H929 Cells by Western Blot:

NCI-H929 (ATCC CRL-9068) was plated in 6 well plates using complete RPMI-1640 media. Next day, compounds of present invention were added to cells from 10 mM stocks made in DMSO (Sigma Cat no. D2650). Each concentration of compound was tested with DMSO not exceeding final percentage of 0.3 in the cells. Cells were incubated with the compound for 16 hours followed by harvesting with 1× RIPA lysis buffer (Thermo Fischer, catalogue number #89900) containing protease inhibitor cocktail (Sigma catalogue number #P-8340). Equal amount of protein was loaded on SDS PAGE gel for electrophoresis. Western blot was carried out for detection of either SMARCA2 (Cell signaling technologies, catalogue number #11966) or SMARCA4 antibody (Cell signaling technologies, catalogue number #49360). Beta Actin (Santa Cruz, catalogue number #69879) was used as loading control. Percentage of SMARCA2 or SMARCA4 degradation was calculated using formula % Degradation=100−(normalized band intensity in treated sample/normalized band intensity in DMSO sample)*100.

Selected compounds of the present invention were screened in the above mentioned assay procedures for determination of % SMARCA2 and SMARCA4 degradation 100 nM and the results are summarized in below table 30.

TABLE 30

SMARCA2 and SMARCA4 degradation in H929 cells.

| Compound No. | SMARCA2 Percent degradation @ 100 nM. | SMARCA4 Percent degradation @ 100 nM. |
|---|---|---|
| 37 | 96 | NA |
| 38 | 99 | 17 |
| 39 | 97 | NA |
| 41 | 64 | 60 |
| 43 | 100 | 100 |
| 44 | 93 | 82 |
| 47 | 87 | 87 |
| 48 | 5.4 | 28 |
| 51 | NA | 99 |
| 56 | 99 | 100 |
| 57 | 79.6 | NA |
| 58 | 100 | 100 |
| 76 | 90 | 12 |
| 79 | 99 | 99 |
| 83 | 100 | NA |
| 84 | 58 | NA |
| 87 | 83 | 93 |
| 90 | 100 | 101 |
| 98 | 88 | 99 |
| 99 | 99 | 100 |
| 109 | 100 | 38 |
| 117 | 45.4 | 47 |
| 118 | 20.2 | NA |

"NA" indicates Not Available.

Determination of SMARCA2 Degradation in NCI-1H838 Cells by Western Blot:

NCI-1H838 (ATCC CRL-5844) was plated in 6 well plates using complete RPMI-1640 media. Next day, compounds of present invention were added to cells from 10 mM stocks made in DMSO (Sigma Cat no. D2650). Each concentration of compound was tested with DMSO concentration not exceeding a final percentage of 0.3 in the cells. Cells were incubated with the compound for 16 hours followed by harvesting with 1× RIPA lysis buffer (Thermo Fischer, catalogue number #89900) containing protease inhibitor cocktail (Sigma catalogue number #P-8340). Equal amount of protein was loaded on SIDS PAGE gel for electrophoresis. Western blot was carried out for detection of SMARCA2 with antibody (Cell signaling technologies, catalogue number #11966). Beta Actin (Santa Cruz, catalogue number #69879) was used as loading control. Percentage of SMARCA2 degradation was calculated using formula % degradation=100−(normalized band intensity in treated sample/normalized band intensity in DMSO sample)*100".

Selected compounds of the present invention were screened in the above mentioned assay procedures for determination of % SMARCA2 degradation at 100 nM and the results are summarized in below table 31.

TABLE 31

SMARCA2 degradation in H838 cells.

| Compound No. | SMARCA2 @ 100 nM. | Compound No. | SMARCA2 @ 100 nM. |
|---|---|---|---|
| 43 | 97 | 51 | 99 |
| 58 | 71 | 61 | 35 |
| 62 | 27 | 63 | 94 |
| 65 | 94 | 69 | 12 |
| 70 | −11 | 74 | 21 |
| 75 | 12 | 77 | 9 |
| 78 | 26 | 80 | 13 |
| 81 | 34 | 82 | 61 |
| 83 | 7 | 90 | 85 |
| 91 | 82 | 93 | 74 |
| 96 | 76 | 99 | 75 |
| 100 | 9 | 103 | 64 |

We claim:

1. A compound of formula (I):

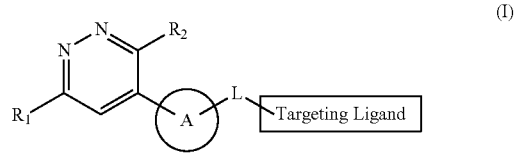

(I)

or a pharmaceutically acceptable salt thereof or a stereoisomer thereof;

wherein, $R_1$ is hydrogen, halo, alkyl, alkenyl, alkoxy, hydroxy, hydroxyalkyl, —$COOR_a$, —$CON(R_a)_2$ or aryl; wherein, the aryl is optionally substituted with one or more groups independently selected from hydroxy, alkoxy, halo, alkyl, amino, —O—Na, —$COOR_a$ and —$OCOR_a$; wherein $R_a$ at each occurance is selected from hydrogen and alkyl;

$R_2$ is —$NR_3R_4$ or —$OR_3$; wherein, $R_3$ and $R_4$ are independently selected from hydrogen and alkyl;

Ring A is heterocyclic ring optionally substituted with one or more groups independently selected from hydroxy, halo and alkyl;

L is a linker, selected from the group consisting of:

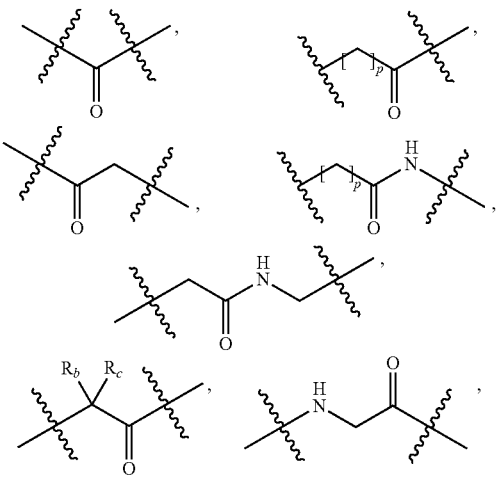

311
-continued

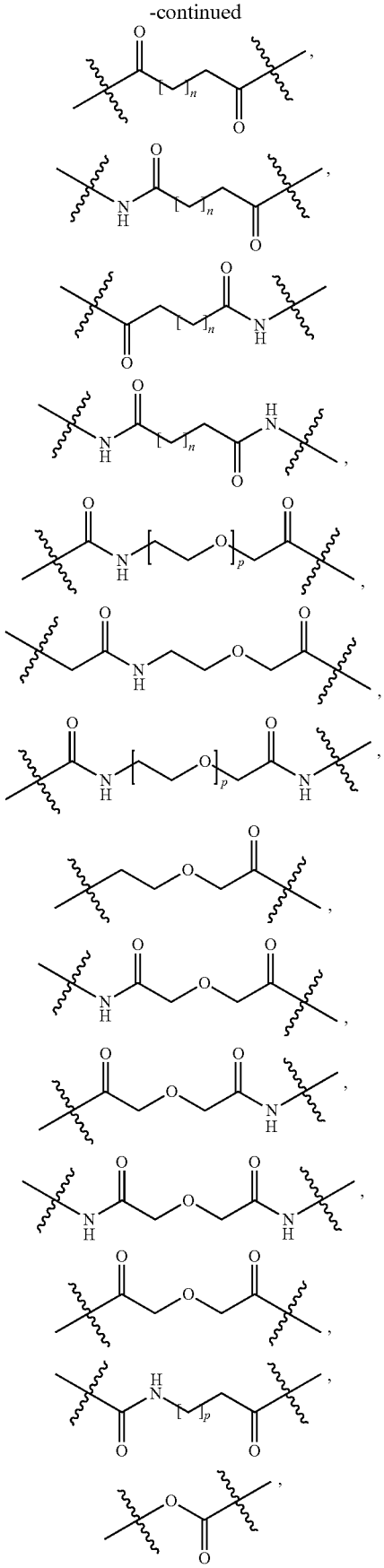

312
-continued

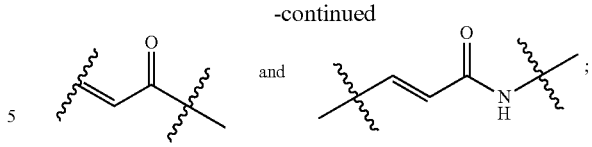

wherein,
the left side of the linker is attached with ring A and the right side of the linker is attached with Targeting Ligand (TL);
$R_b$ is hydrogen or alkyl;
$R_c$ is alkyl;
'n' is 0 to 10 and 'p' is 1 to 5;
Targeting Ligand (TL) is selected from the group consisting of:

TL-1

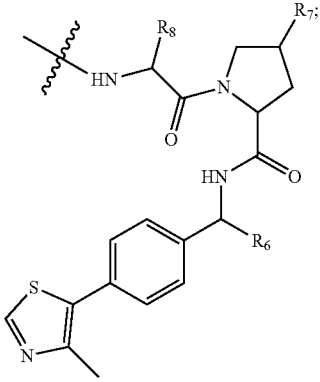

TL-2

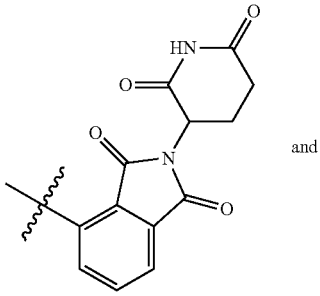

and

TL-3

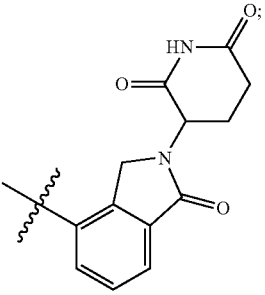

wherein,
$R_6$ is selected from hydrogen, alkyl, acyl and haloalkyl;
$R_7$ is selected from —O—$R_5$ and halo; wherein $R_5$ is selected from hydrogen, alkyl, acyl and Na; and
$R_8$ is selected from hydrogen and alkyl.

2. The compound of claim 1, having a compound of formula (IA):

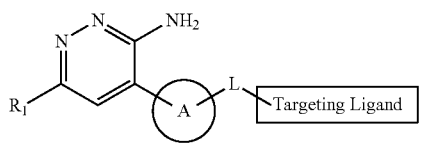

or a pharmaceutically acceptable salt thereof or a stereoisomer thereof.

3. The compound of claim 1, having a compound of formula (IB):

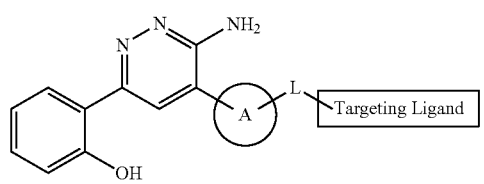

or a pharmaceutically acceptable salt thereof or a stereoisomer thereof.

4. The compound of claim 1, having a compound of formula (IC):

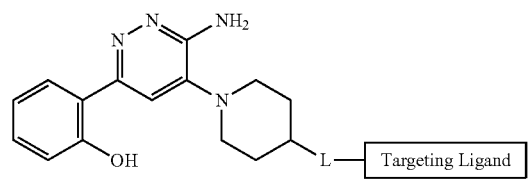

or a pharmaceutically acceptable salt thereof or a stereoisomer thereof.

5. The compound of claim 1, having a compound of formula (IE):

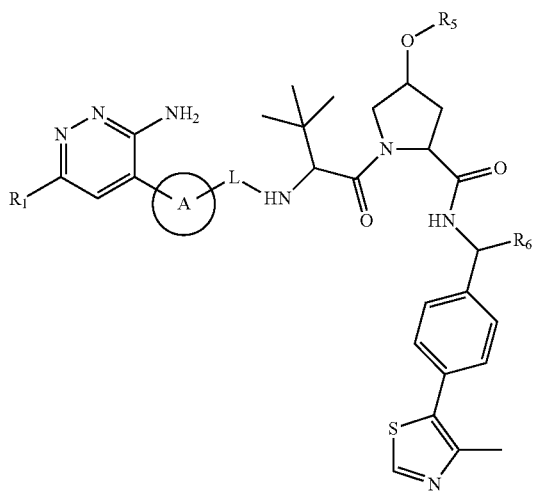

or a pharmaceutically acceptable salt thereof or a stereoisomer thereof.

6. The compound of claim 1 wherein, $R_1$ is hydrogen, halo, hydroxyalkyl, —COOR$_a$, —CON(R$_a$)$_2$ or an optionally substituted aryl.

7. The compound of claim 1 wherein, ring A is an optionally substituted 4-10 membered monocyclic or bicyclic heterocyclic ring.

8. The compound according to claim 7 wherein, ring A is

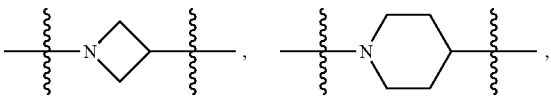

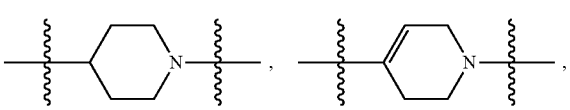

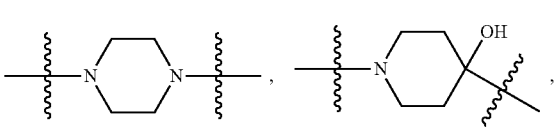

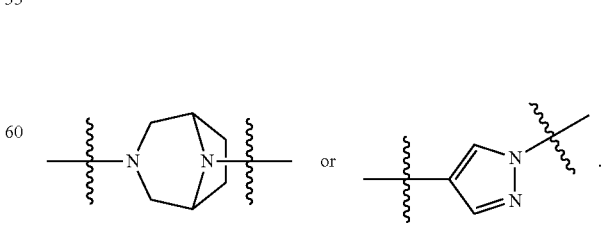

9. The compound according to claim 1, wherein TL is represented by the structure:

TL-1

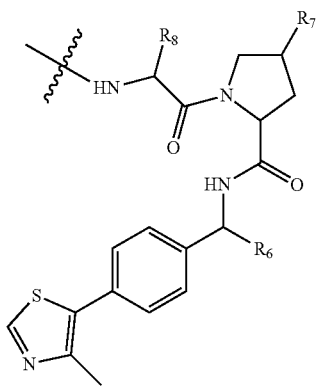

wherein,
R_6 is selected from hydrogen, alkyl and haloalkyl;
R_7 is selected from —O—R_5 and halo; wherein R_5 is selected from hydrogen, alkyl, acyl and Na; and
R_8 is selected from hydrogen and alkyl.

10. The compound according to claim 1 wherein,
R_6 is selected from hydrogen, methyl and —CF_3;
R_7 is selected from hydroxy, —OCH_3, —OCOCH_3, —ONa and fluoro; and
R_8 is selected from hydrogen, methyl, isopropyl and tert-butyl.

11. The compound according to claim 1, wherein TL-1 is represented by the structure:

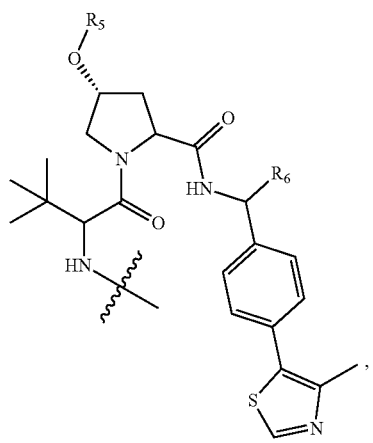

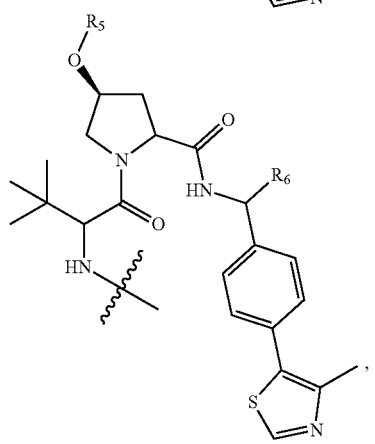

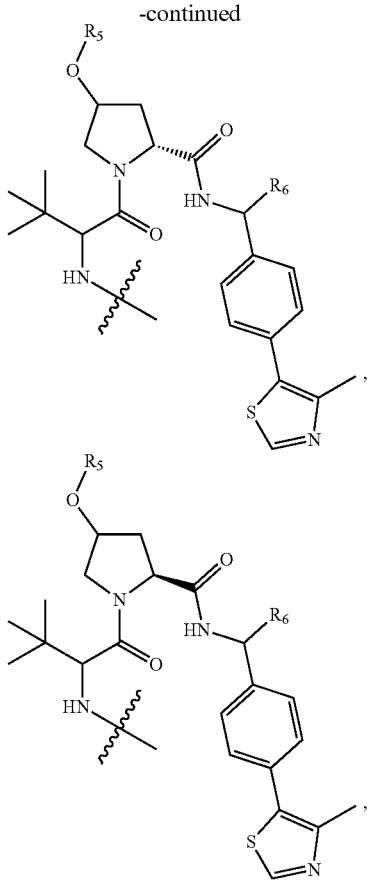

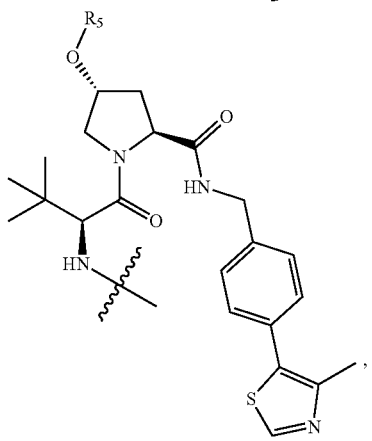

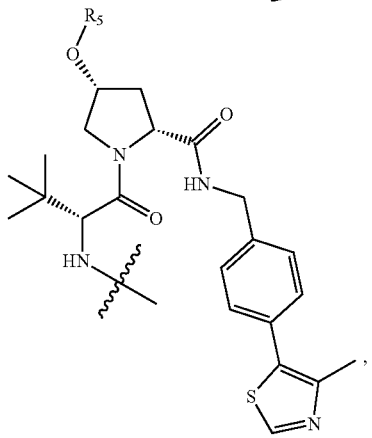

317
-continued
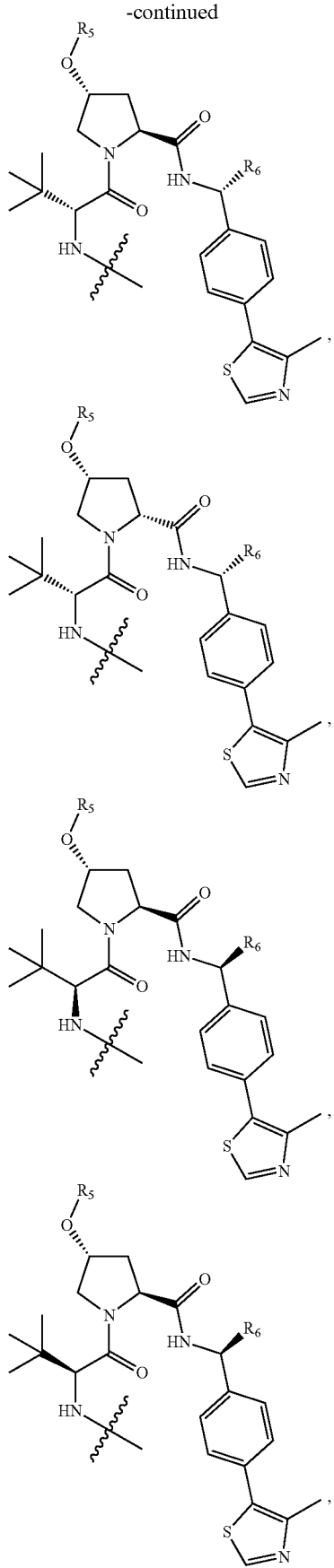
318
-continued
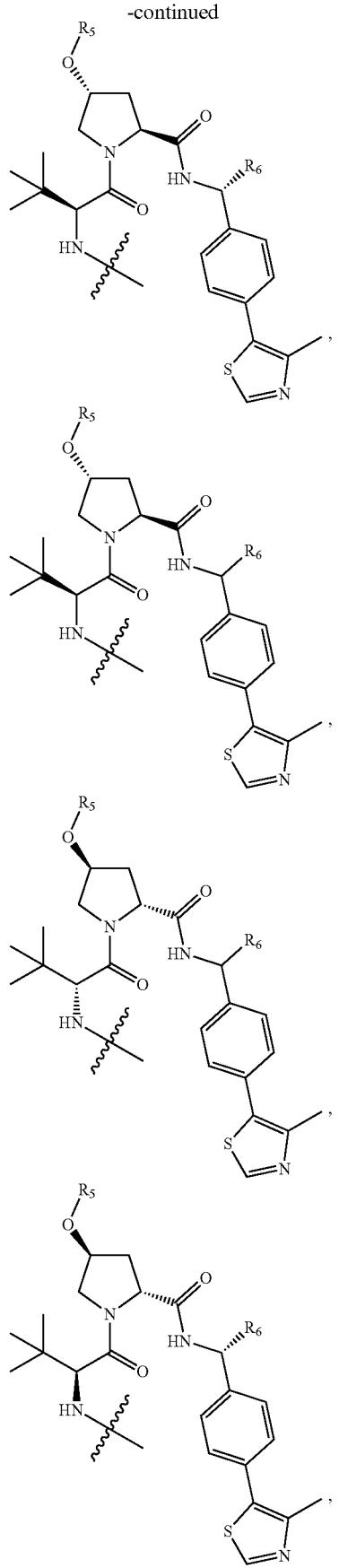

319
-continued
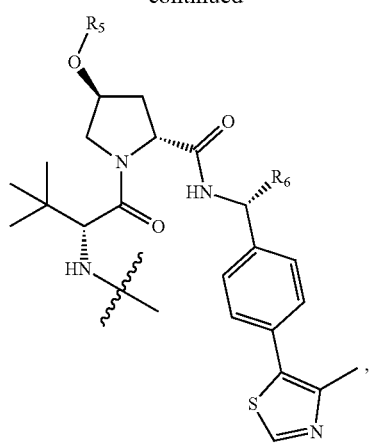
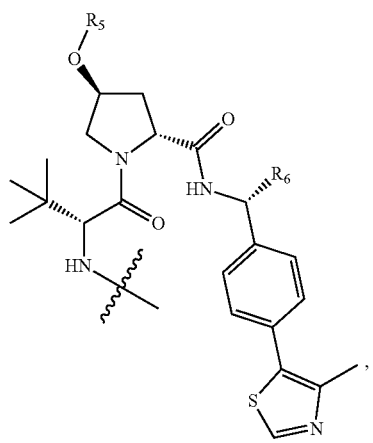
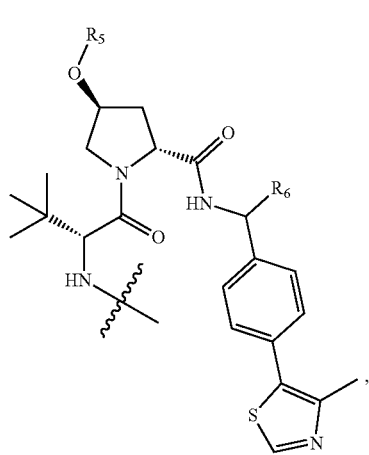
320
-continued
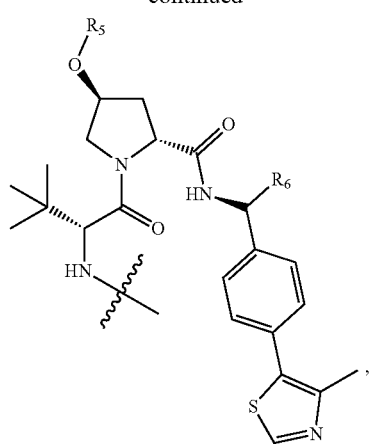
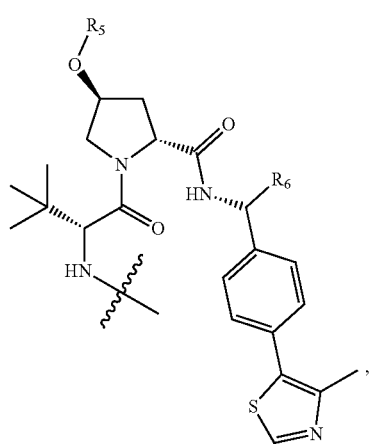
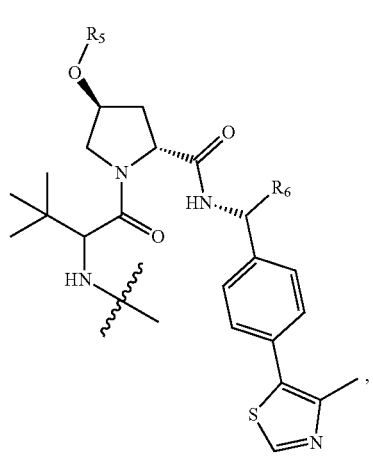

321
-continued
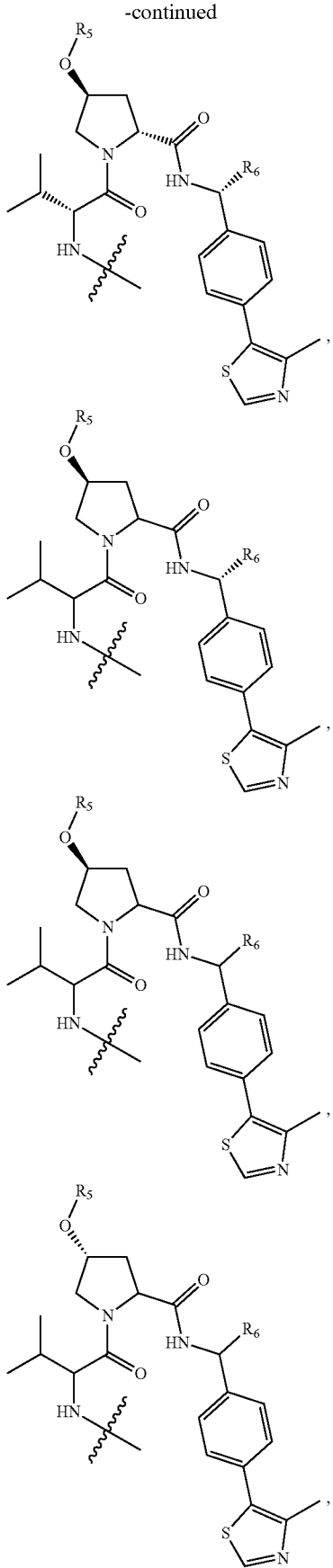
322
-continued
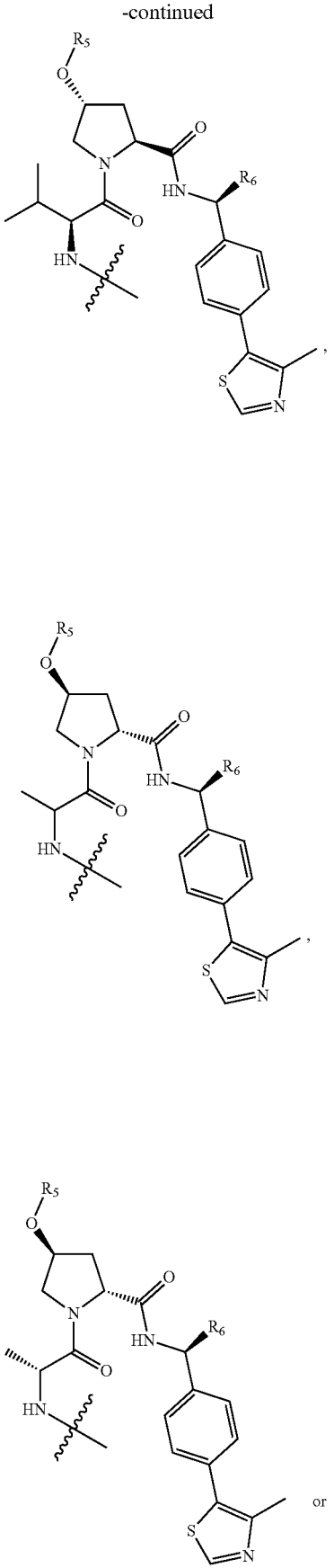

323
-continued
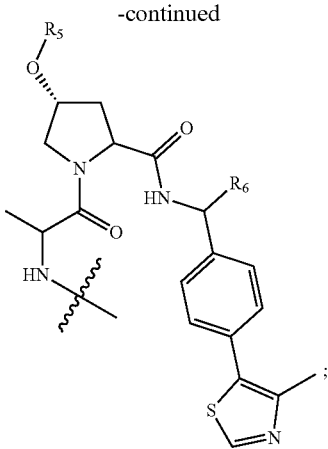
wherein,
R₅ is selected from hydrogen, alkyl, acyl and —Na; and
R₆ is selected from hydrogen, alkyl and haloalkyl.
12. The compound according to claim 1 wherein linker (L) is selected from the group consisting of:
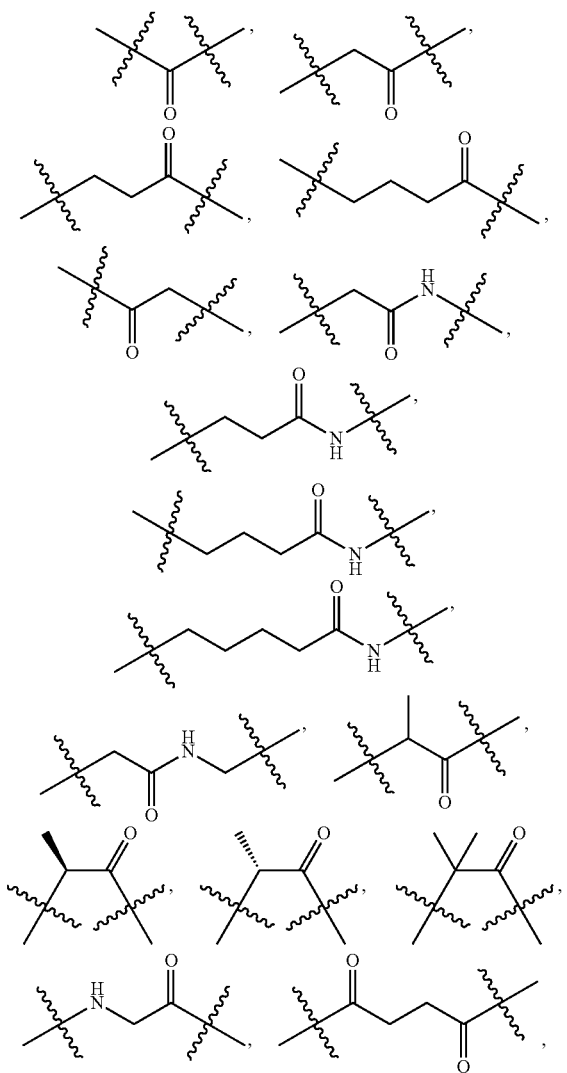
324
-continued
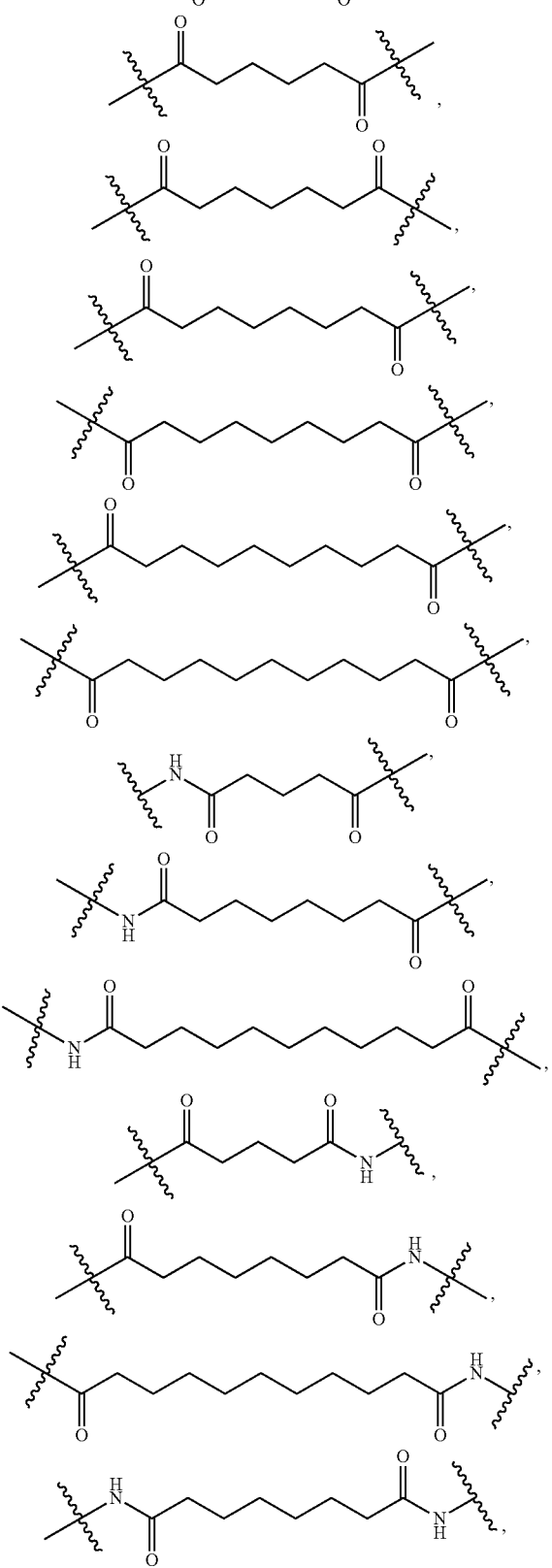

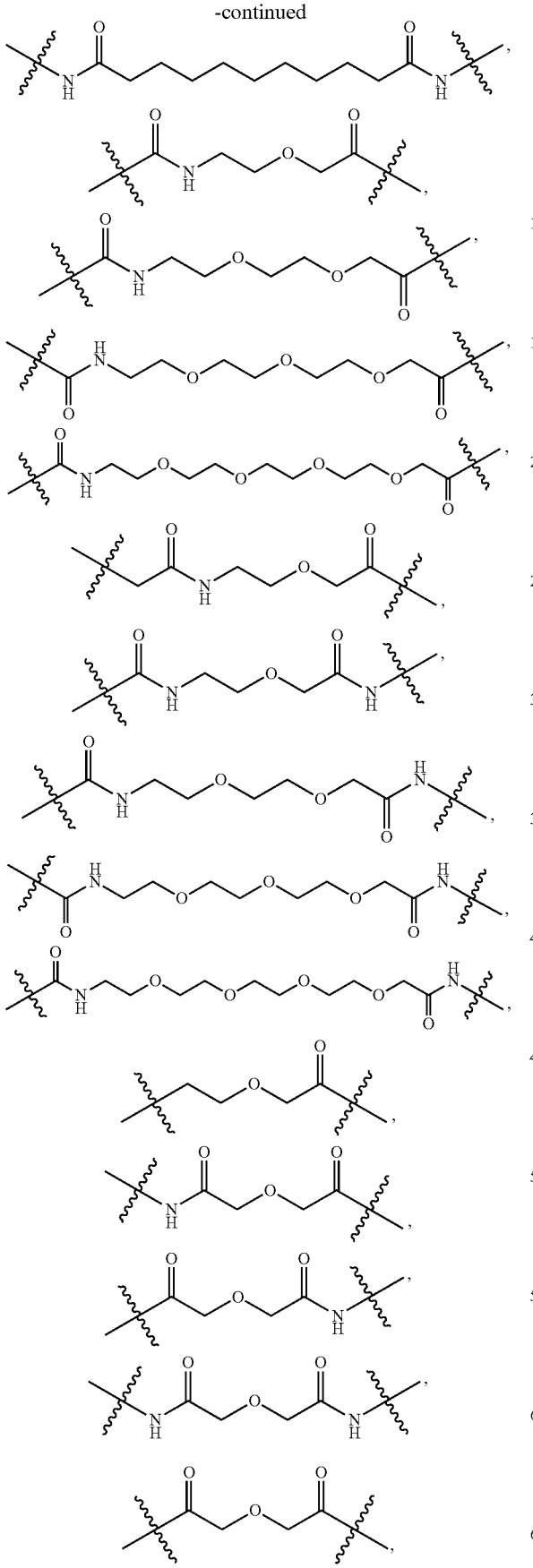
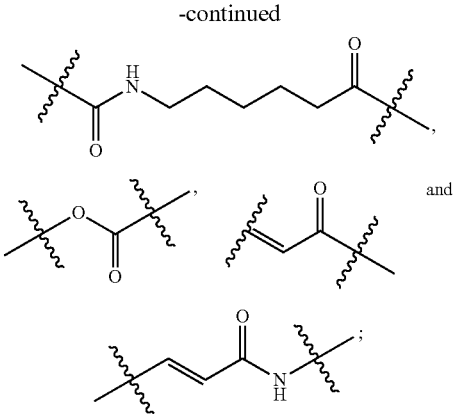
wherein, the left side of the linker is attached with ring A and the right side of the linker is attached with Targeting Ligand.
13. The compound according to claim 1 wherein,
R₁ is an optionally substituted phenyl; the said phenyl is
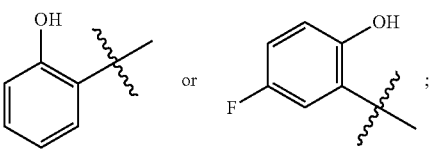 [SMILES: *c1ccccc1O ; *c1cc(F)ccc1O]
R₂ is —NH₂;
Ring A is
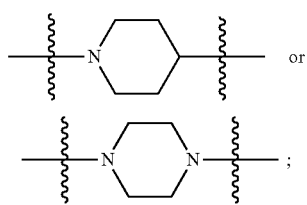
Targeting Ligand (TL) is
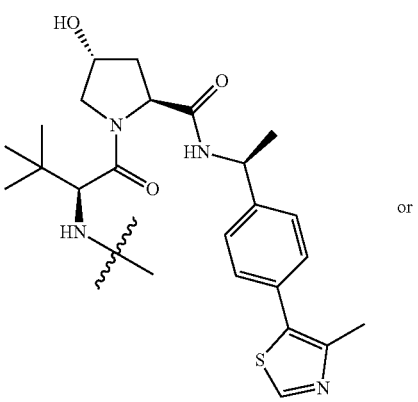

327
-continued
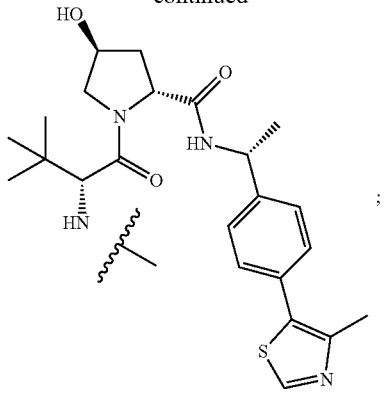
;
328
and
L is
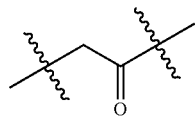
.
14. The compound of claim 1, selected from the group consisting of:
| STRUCTURE |
|---|
| 1. 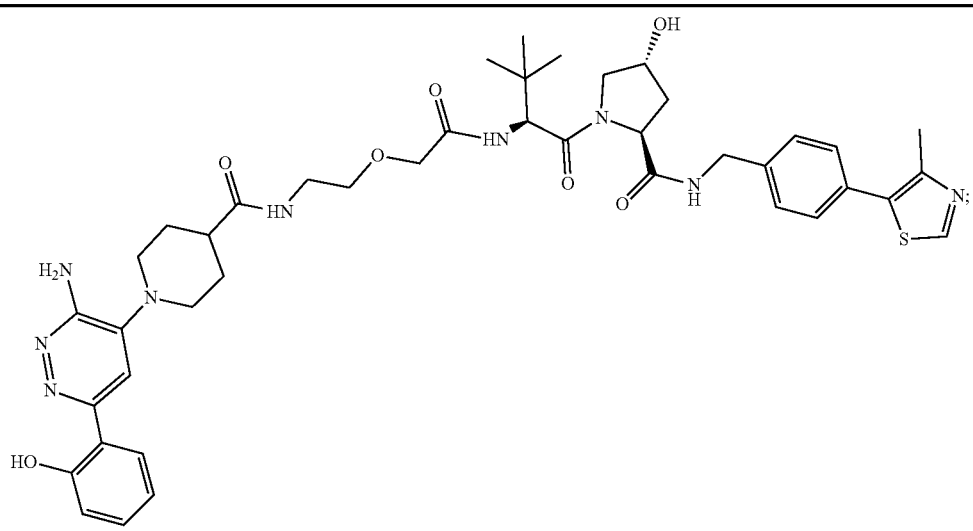 |
| 2. 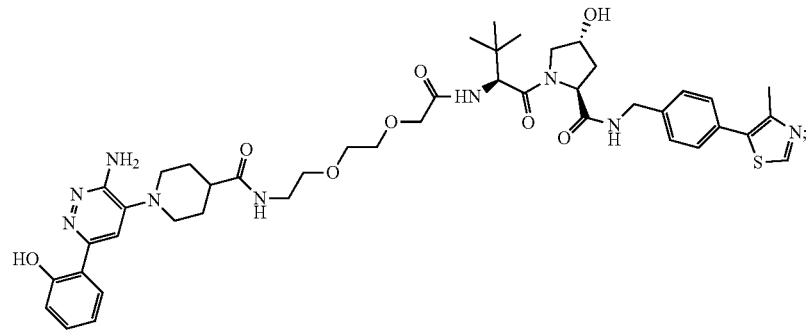 [SMILES: Cc1ncsc1-c1ccc(CNC(=O)[C@@H]2C[C@@H](O)CN2C(=O)[C@@H](NC(=O)COCCOCCNC(=O)C2CCN(c3cc(-c4ccccc4O)nnc3N)CC2)C(C)(C)C)cc1] |

| | STRUCTURE |
|---|---|
| 3. | 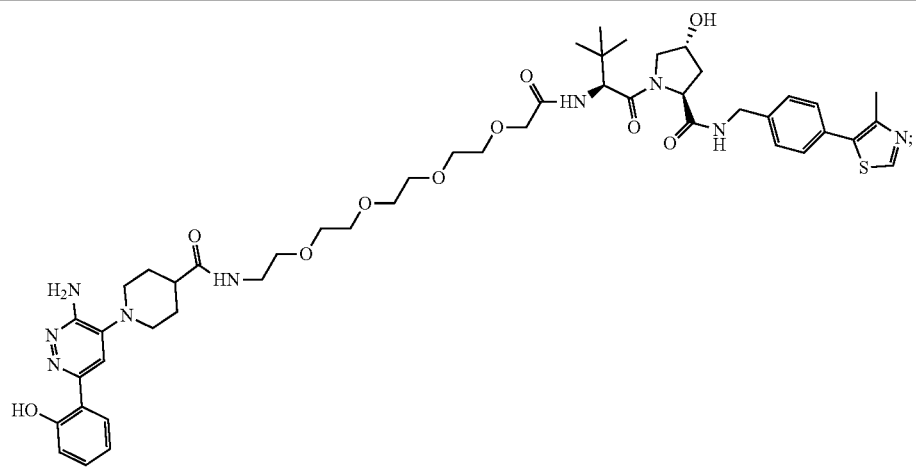 [SMILES: Cc1ncsc1-c1ccc(CNC(=O)[C@@H]2C[C@@H](O)CN2C(=O)[C@@H](NC(=O)COCCOCCOCCOCCNC(=O)C2CCN(c3cc(-c4ccccc4O)nnc3N)CC2)C(C)(C)C)cc1] |
| 4. | 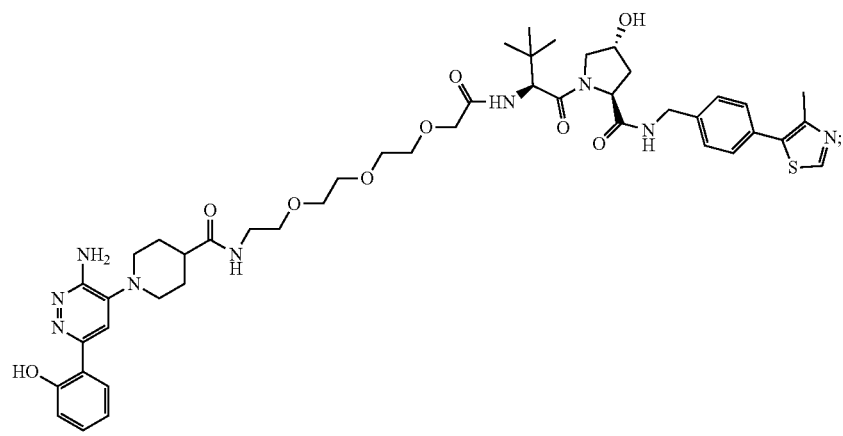 [SMILES: Cc1ncsc1-c1ccc(CNC(=O)[C@@H]2C[C@@H](O)CN2C(=O)[C@@H](NC(=O)COCCOCCOCCNC(=O)C2CCN(c3cc(-c4ccccc4O)nnc3N)CC2)C(C)(C)C)cc1] |
| 5. | 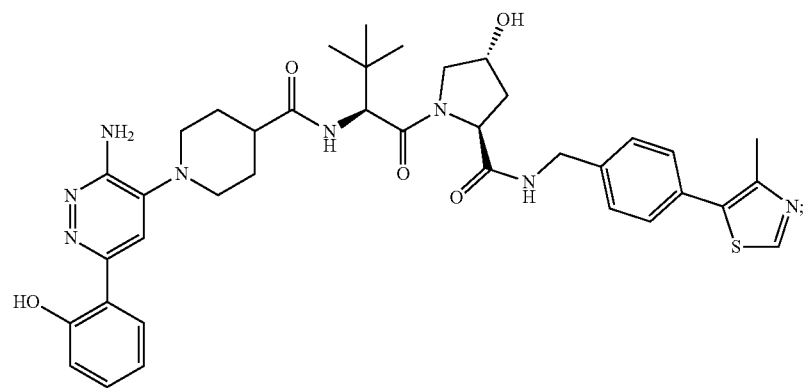 [SMILES: Cc1ncsc1-c1ccc(CNC(=O)[C@@H]2C[C@@H](O)CN2C(=O)[C@@H](NC(=O)C2CCN(c3cc(-c4ccccc4O)nnc3N)CC2)C(C)(C)C)cc1] |
| 6. | 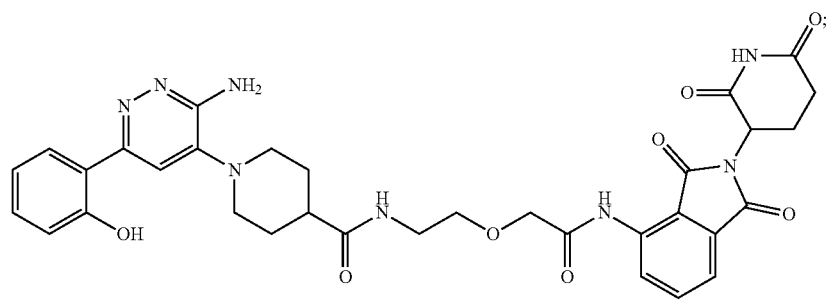 [SMILES: Nc1nnc(-c2ccccc2O)cc1N1CCC(C(=O)NCCOCC(=O)Nc2cccc3c2C(=O)N(C2CCC(=O)NC2=O)C3=O)CC1] |

| | |
|---|---|
| STRUCTURE | |
| 7. | 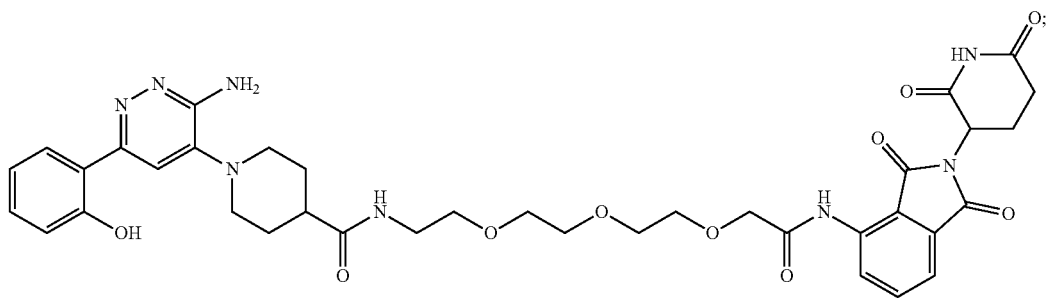 [SMILES: Nc1nnc(-c2ccccc2O)cc1N1CCC(C(=O)NCCOCCOCCOCC(=O)Nc2cccc3c2C(=O)N(C2CCC(=O)NC2=O)C3=O)CC1] |
| 8. | 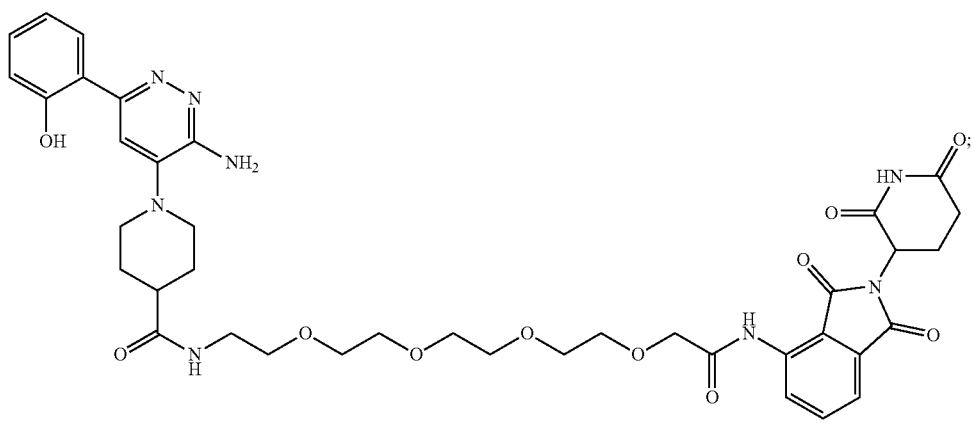 [SMILES: Nc1nnc(-c2ccccc2O)cc1N1CCC(C(=O)NCCOCCOCCOCCOCC(=O)Nc2cccc3c2C(=O)N(C2CCC(=O)NC2=O)C3=O)CC1] |
| 9. | 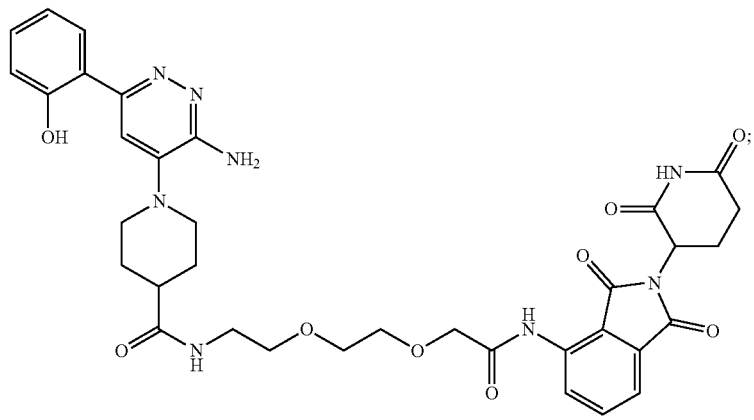 [SMILES: Nc1nnc(-c2ccccc2O)cc1N1CCC(C(=O)NCCOCCOCC(=O)Nc2cccc3c2C(=O)N(C2CCC(=O)NC2=O)C3=O)CC1] |
| 10. | 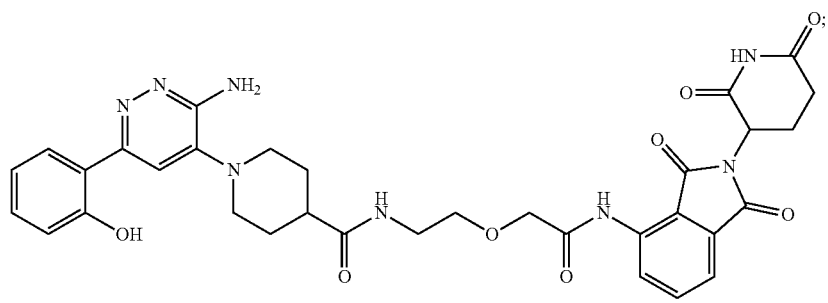 [SMILES: Nc1nnc(-c2ccccc2O)cc1N1CCC(C(=O)NCCOCC(=O)Nc2cccc3c2C(=O)N(C2CCC(=O)NC2=O)C3=O)CC1] |

| STRUCTURE |
|---|
| 11. 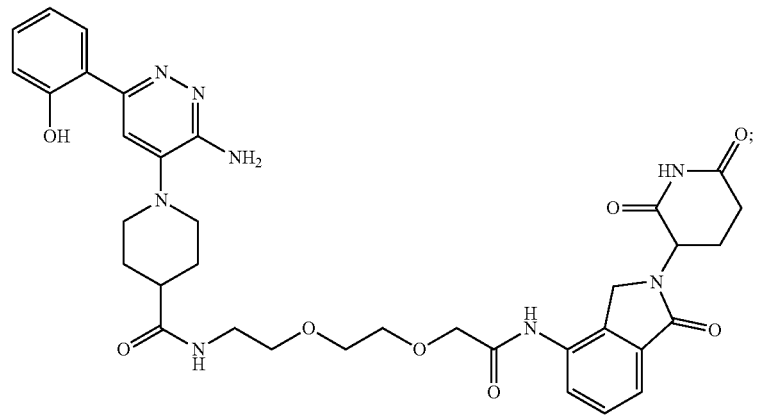 [SMILES: Nc1nnc(-c2ccccc2O)cc1N1CCC(C(=O)NCCOCCOCC(=O)Nc2cccc3c2CN(C2CCC(=O)NC2=O)C3=O)CC1] |
| 12. 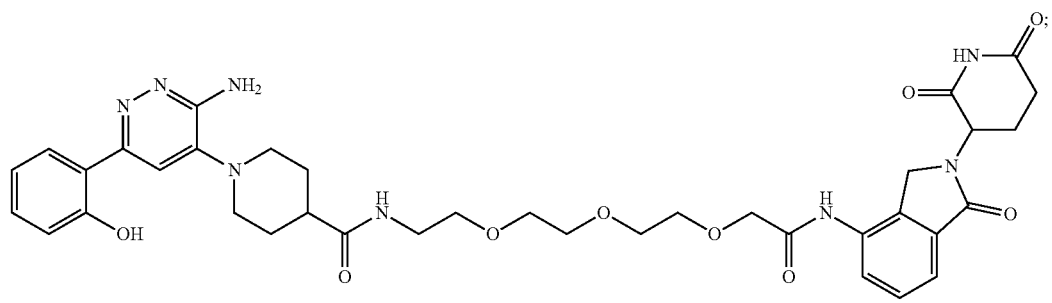 [SMILES: Nc1nnc(-c2ccccc2O)cc1N1CCC(C(=O)NCCOCCOCCOCC(=O)Nc2cccc3c2CN(C2CCC(=O)NC2=O)C3=O)CC1] |
| 13. 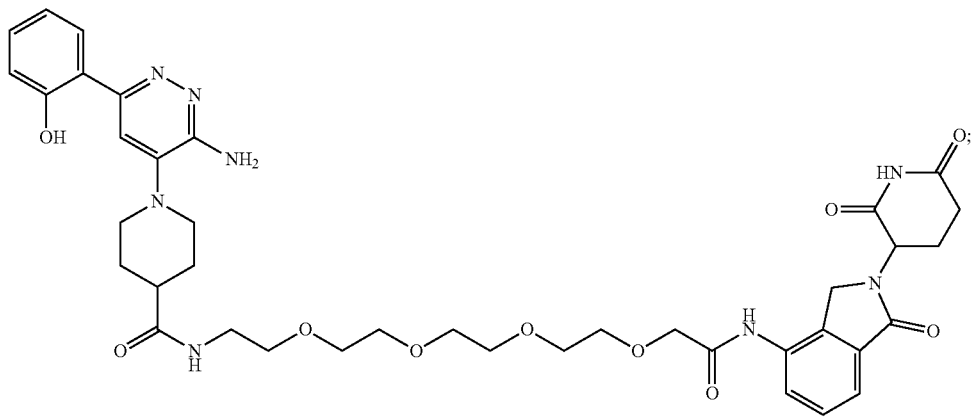 [SMILES: Nc1nnc(-c2ccccc2O)cc1N1CCC(C(=O)NCCOCCOCCOCCOCC(=O)Nc2cccc3c2CN(C2CCC(=O)NC2=O)C3=O)CC1] |
| 14. 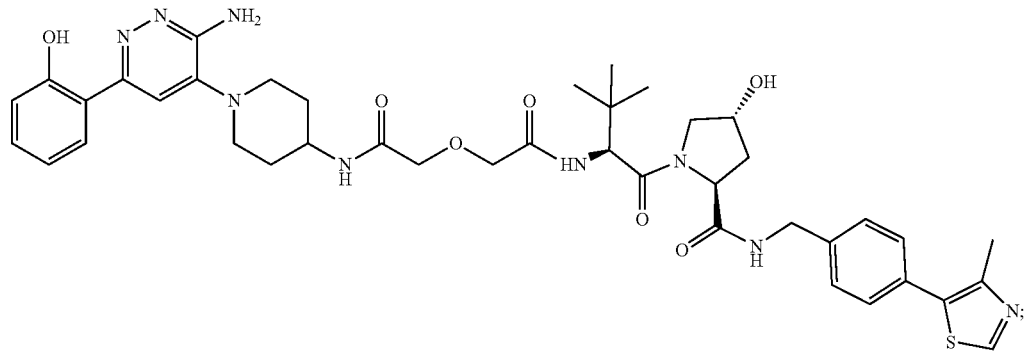 [SMILES: Cc1ncsc1-c1ccc(CNC(=O)[C@@H]2C[C@@H](O)CN2C(=O)[C@@H](NC(=O)COCC(=O)NC2CCN(c3cc(-c4ccccc4O)nnc3N)CC2)C(C)(C)C)cc1] |

-continued
| STRUCTURE |
|---|
| 15. 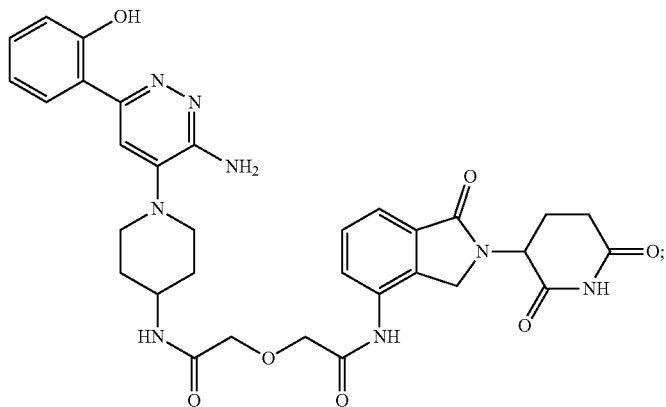 [SMILES: Nc1nnc(-c2ccccc2O)cc1N1CCC(NC(=O)COCC(=O)Nc2cccc3c2CN(C2CCC(=O)NC2=O)C3=O)CC1] |
| 16. 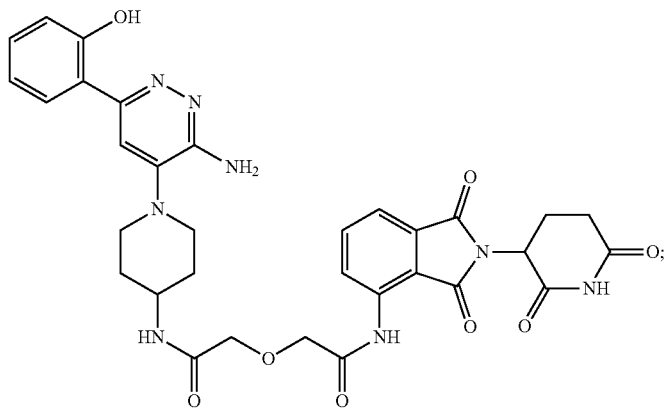 [SMILES: Nc1nnc(-c2ccccc2O)cc1N1CCC(NC(=O)COCC(=O)Nc2cccc3c2C(=O)N(C2CCC(=O)NC2=O)C3=O)CC1] |
| 17. 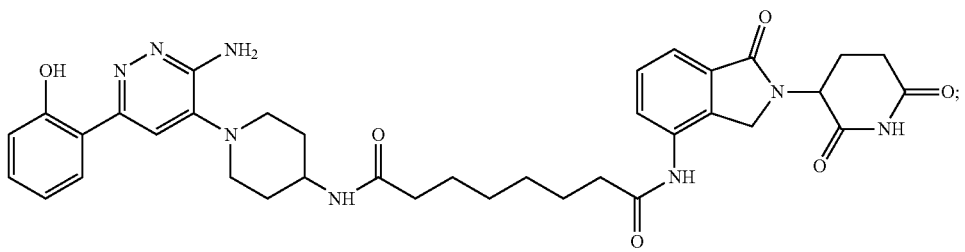 [SMILES: Nc1nnc(-c2ccccc2O)cc1N1CCC(NC(=O)CCCCCCC(=O)Nc2cccc3c2CN(C2CCC(=O)NC2=O)C3=O)CC1] |
| 18. 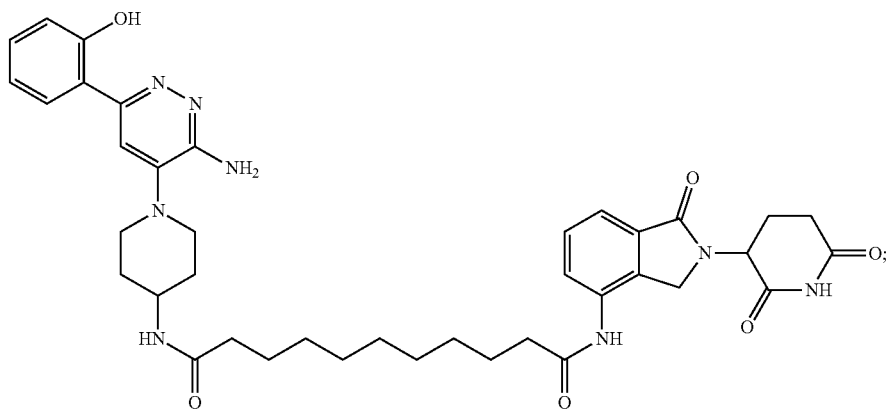 [SMILES: Nc1nnc(-c2ccccc2O)cc1N1CCC(NC(=O)CCCCCCCCCC(=O)Nc2cccc3c2CN(C2CCC(=O)NC2=O)C3=O)CC1] |

| STRUCTURE |
|---|
| 19. 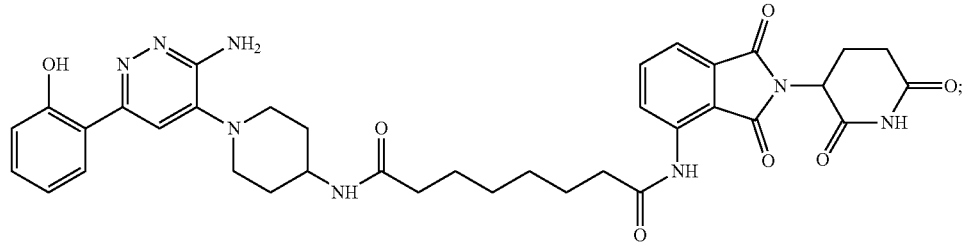 [SMILES: Nc1nnc(-c2ccccc2O)cc1N1CCC(NC(=O)CCCCCCC(=O)Nc2cccc3c2C(=O)N(C2CCC(=O)NC2=O)C3=O)CC1] |
| 20. 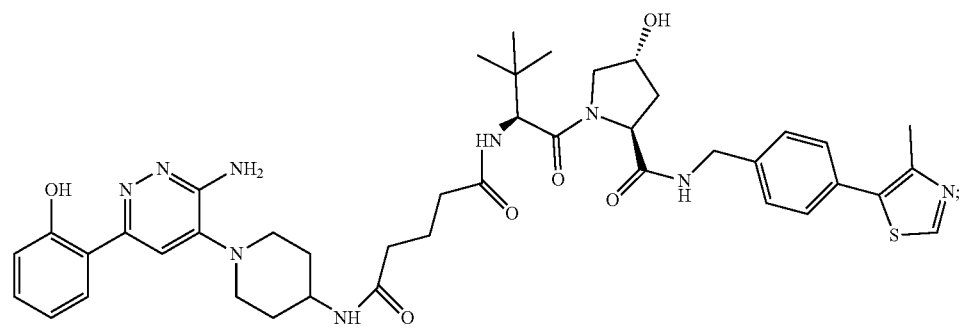 [SMILES: Cc1ncsc1-c1ccc(CNC(=O)[C@@H]2C[C@@H](O)CN2C(=O)[C@@H](NC(=O)CCCC(=O)NC2CCN(c3cc(-c4ccccc4O)nnc3N)CC2)C(C)(C)C)cc1] |
| 21. 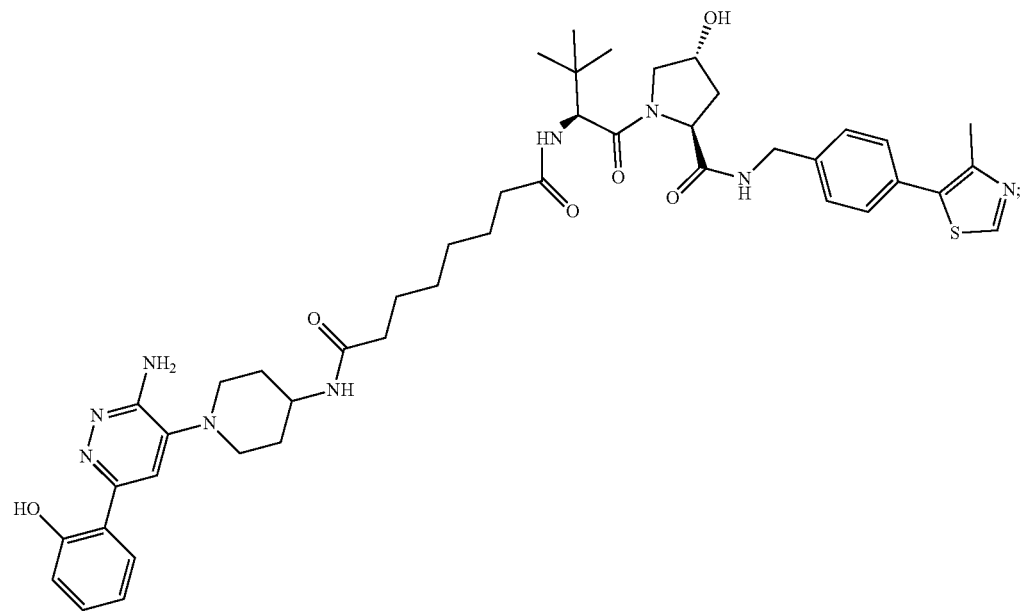 [SMILES: Cc1ncsc1-c1ccc(CNC(=O)[C@@H]2C[C@@H](O)CN2C(=O)[C@@H](NC(=O)CCCCCCC(=O)NC2CCN(c3cc(-c4ccccc4O)nnc3N)CC2)C(C)(C)C)cc1] |

| STRUCTURE |
|---|
| 22. 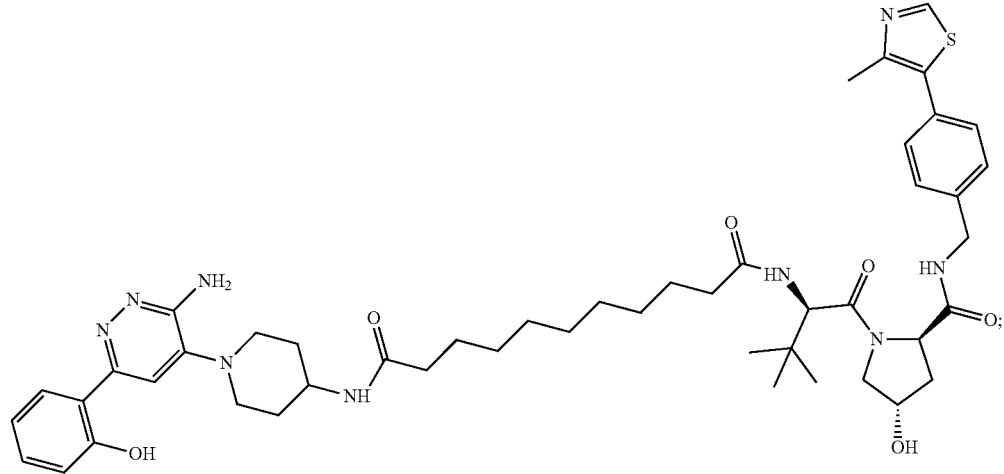 [SMILES: Cc1ncsc1-c1ccc(CNC(=O)[C@H]2C[C@H](O)CN2C(=O)[C@H](NC(=O)CCCCCCCCCC(=O)NC2CCN(c3cc(-c4ccccc4O)nnc3N)CC2)C(C)(C)C)cc1] |
| 23. 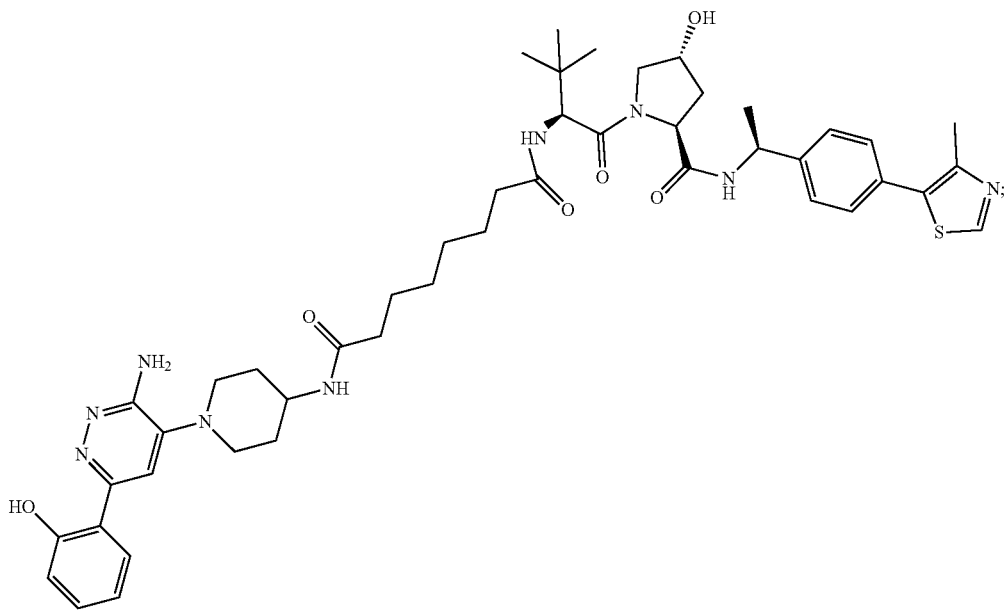 [SMILES: Cc1ncsc1-c1ccc([C@H](C)NC(=O)[C@@H]2C[C@@H](O)CN2C(=O)[C@@H](NC(=O)CCCCCCC(=O)NC2CCN(c3cc(-c4ccccc4O)nnc3N)CC2)C(C)(C)C)cc1] |
| 24. 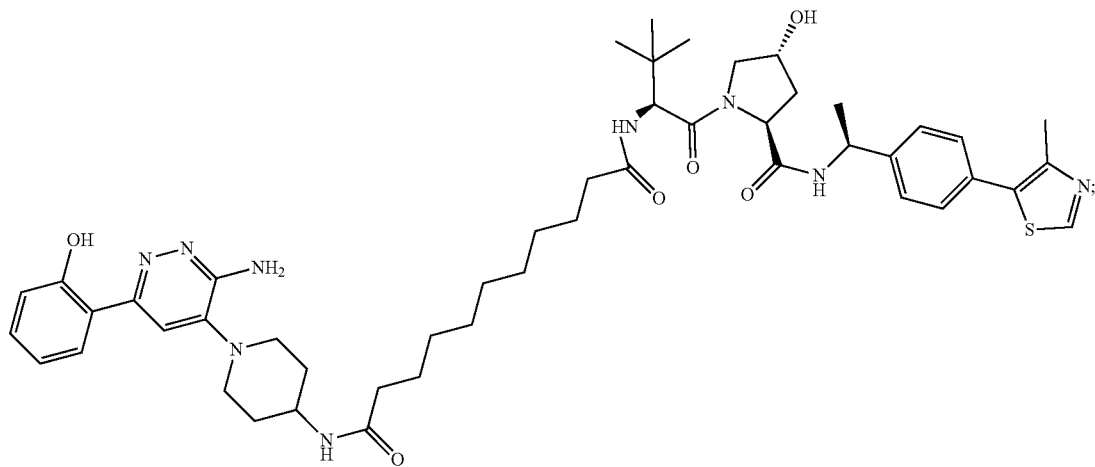 [SMILES: Cc1ncsc1-c1ccc([C@H](C)NC(=O)[C@@H]2C[C@@H](O)CN2C(=O)[C@@H](NC(=O)CCCCCCCCCC(=O)NC2CCN(c3cc(-c4ccccc4O)nnc3N)CC2)C(C)(C)C)cc1] |

| STRUCTURE |
|---|
| 25. 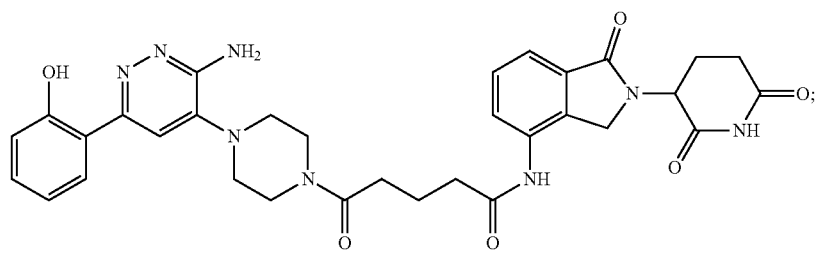 [SMILES: Nc1nnc(-c2ccccc2O)cc1N1CCN(C(=O)CCCC(=O)Nc2cccc3c2CN(C2CCC(=O)NC2=O)C3=O)CC1] |
| 26. 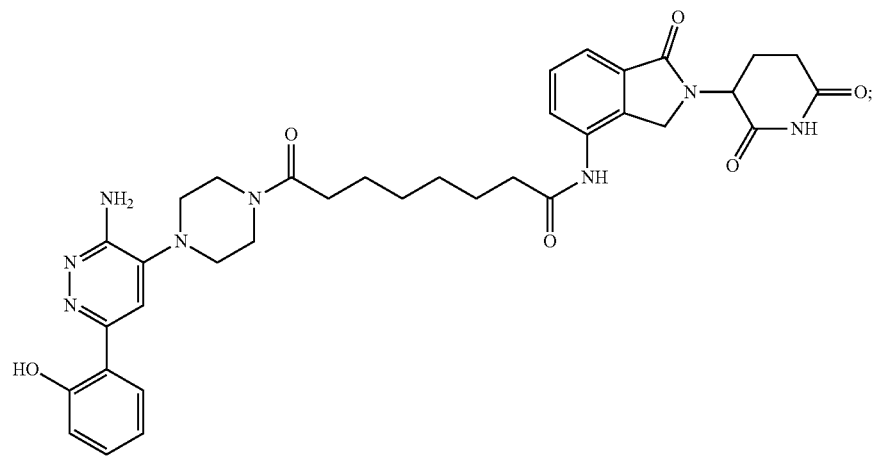 [SMILES: Nc1nnc(-c2ccccc2O)cc1N1CCN(C(=O)CCCCCCC(=O)Nc2cccc3c2CN(C2CCC(=O)NC2=O)C3=O)CC1] |
| 27. 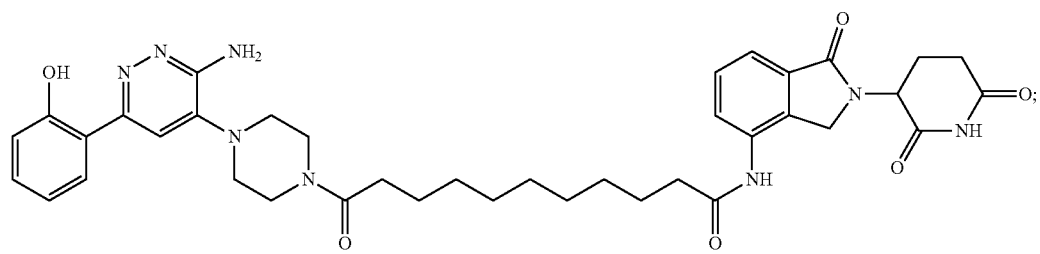 [SMILES: Nc1nnc(-c2ccccc2O)cc1N1CCN(C(=O)CCCCCCCCCC(=O)Nc2cccc3c2CN(C2CCC(=O)NC2=O)C3=O)CC1] |
| 28. 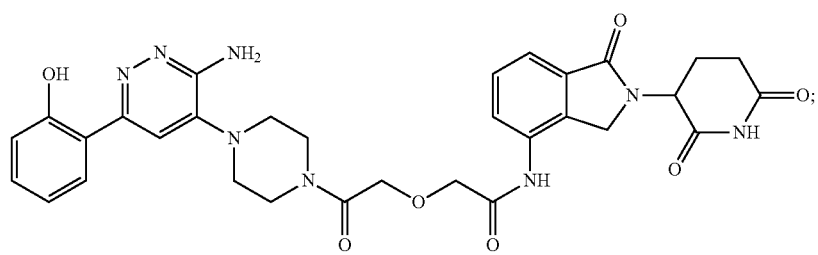 |
| 29. 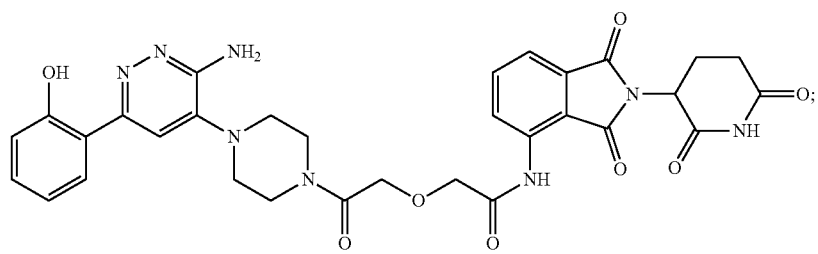 [SMILES: Nc1nnc(-c2ccccc2O)cc1N1CCN(C(=O)COCC(=O)Nc2cccc3c2C(=O)N(C2CCC(=O)NC2=O)C3=O)CC1] |

-continued
| STRUCTURE |
|---|
| 30. 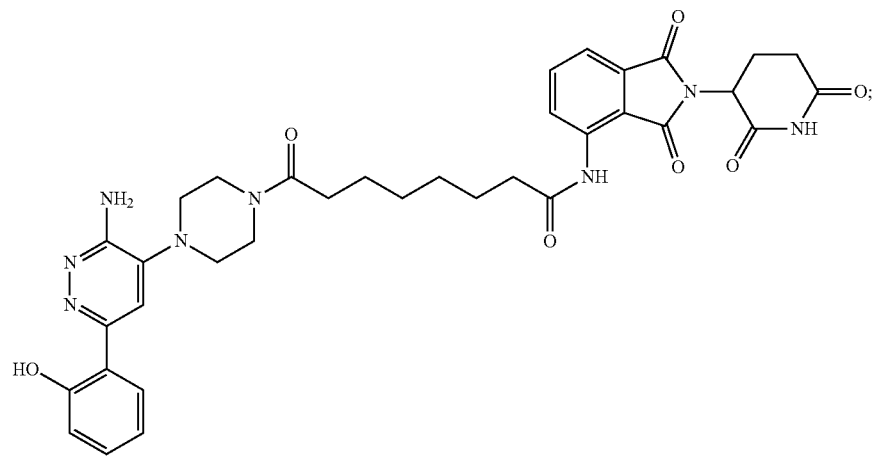 [SMILES: Nc1nnc(-c2ccccc2O)cc1N1CCN(C(=O)CCCCCCC(=O)Nc2cccc3c2C(=O)N(C2CCC(=O)NC2=O)C3=O)CC1] |
| 31. 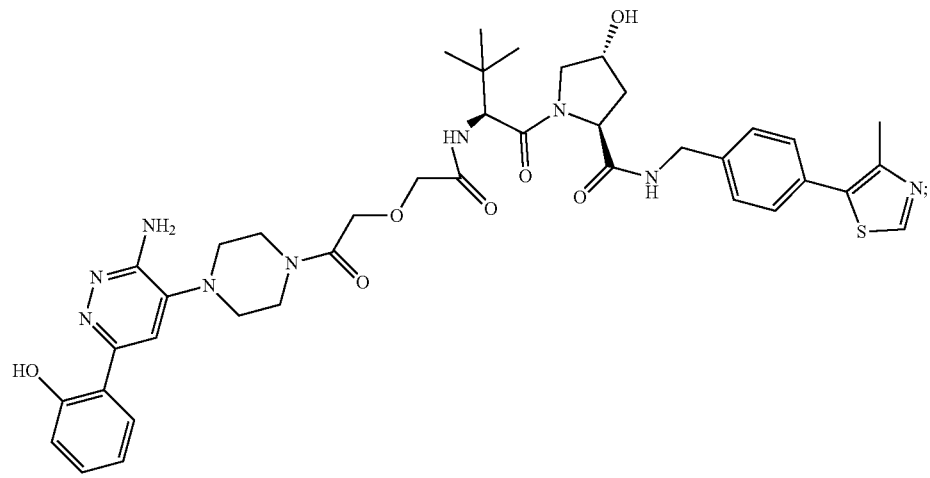 [SMILES: Cc1ncsc1-c1ccc(CNC(=O)[C@@H]2C[C@@H](O)CN2C(=O)[C@@H](NC(=O)COCC(=O)N2CCN(c3cc(-c4ccccc4O)nnc3N)CC2)C(C)(C)C)cc1] |
| 32. 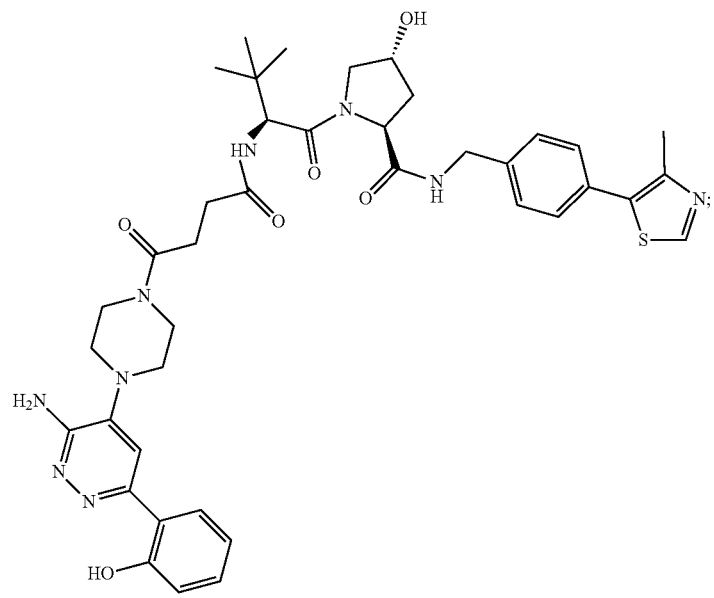 [SMILES: Cc1ncsc1-c1ccc(CNC(=O)[C@@H]2C[C@@H](O)CN2C(=O)[C@@H](NC(=O)CCC(=O)N2CCN(c3cc(-c4ccccc4O)nnc3N)CC2)C(C)(C)C)cc1] |

| | STRUCTURE |
|---|---|
| 33. | 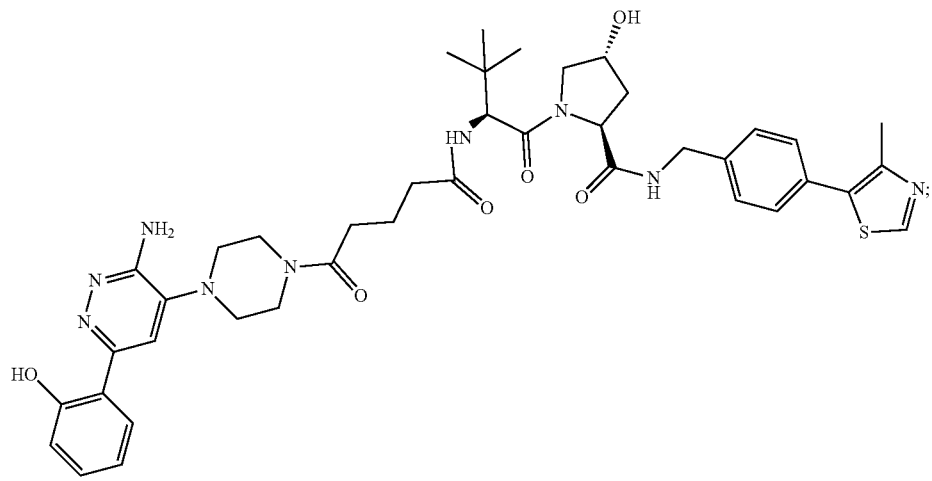 [SMILES: Cc1ncsc1-c1ccc(CNC(=O)[C@@H]2C[C@@H](O)CN2C(=O)[C@@H](NC(=O)CCCC(=O)N2CCN(c3cc(-c4ccccc4O)nnc3N)CC2)C(C)(C)C)cc1] |
| 34. | 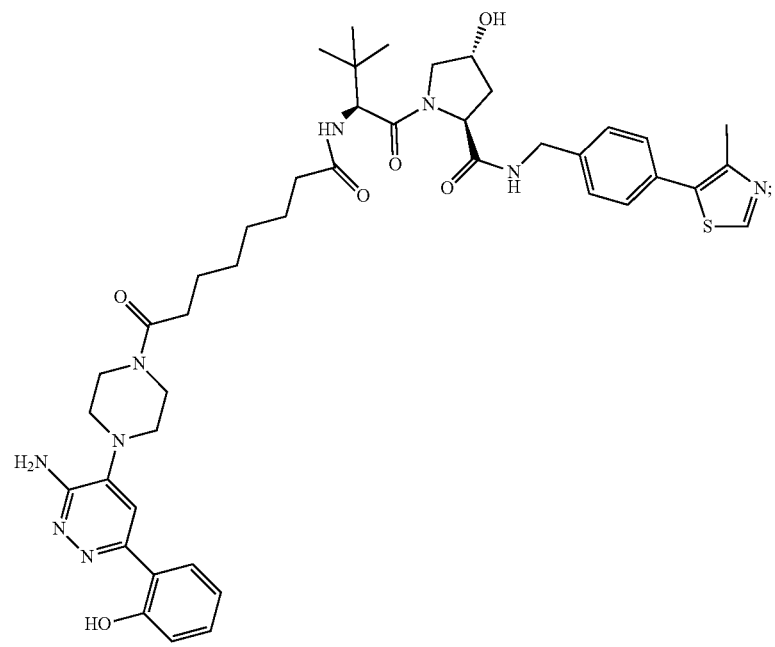 [SMILES: Cc1ncsc1-c1ccc(CNC(=O)[C@@H]2C[C@@H](O)CN2C(=O)[C@@H](NC(=O)CCCCCCC(=O)N2CCN(c3cc(-c4ccccc4O)nnc3N)CC2)C(C)(C)C)cc1] |

| STRUCTURE |
|---|
| 35. 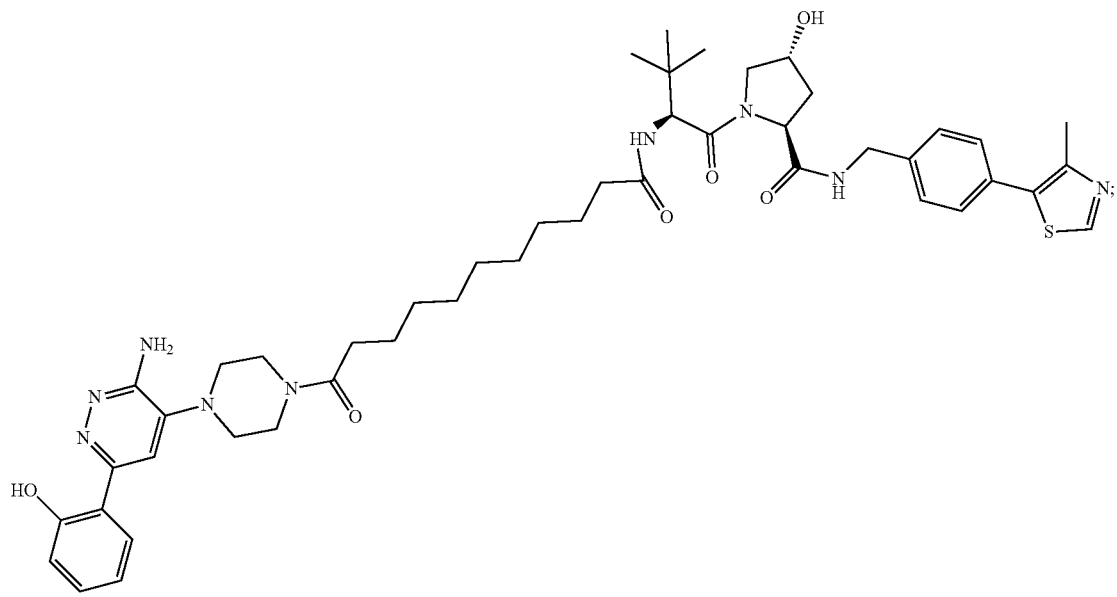 [SMILES: Cc1ncsc1-c1ccc(CNC(=O)[C@@H]2C[C@@H](O)CN2C(=O)[C@@H](NC(=O)CCCCCCCCCC(=O)N2CCN(c3cc(-c4ccccc4O)nnc3N)CC2)C(C)(C)C)cc1] |
| 36. 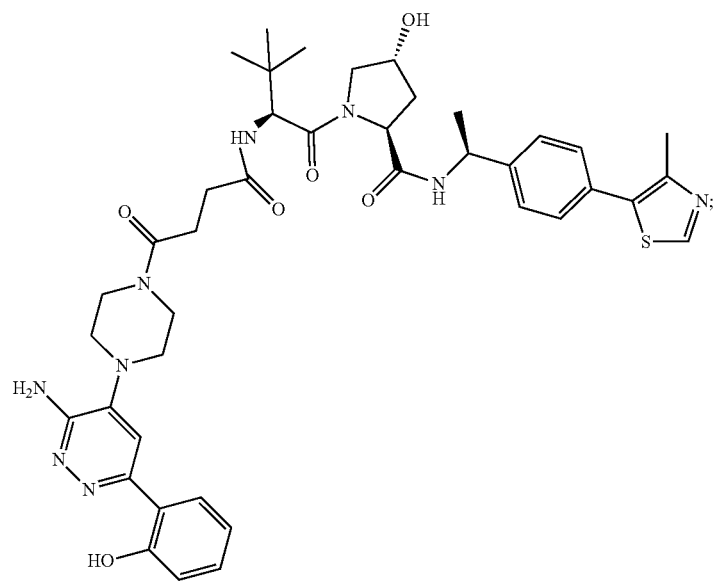 [SMILES: Cc1ncsc1-c1ccc([C@H](C)NC(=O)[C@@H]2C[C@@H](O)CN2C(=O)[C@@H](NC(=O)CCC(=O)N2CCN(c3cc(-c4ccccc4O)nnc3N)CC2)C(C)(C)C)cc1] |

| | STRUCTURE |
|---|---|
| 37. | 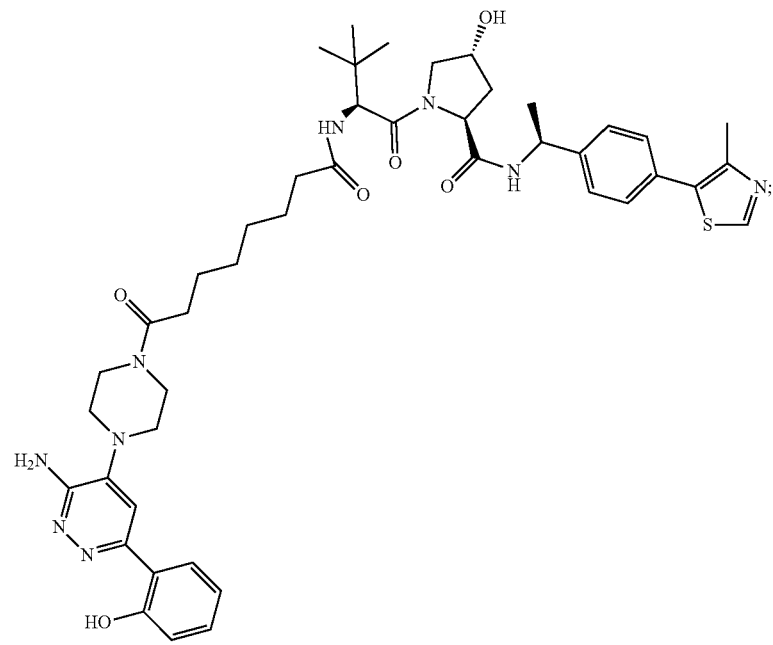 [SMILES: Cc1ncsc1-c1ccc([C@H](C)NC(=O)[C@@H]2C[C@@H](O)CN2C(=O)[C@@H](NC(=O)CCCCCCC(=O)N2CCN(c3cc(-c4ccccc4O)nnc3N)CC2)C(C)(C)C)cc1] |
| 38. | 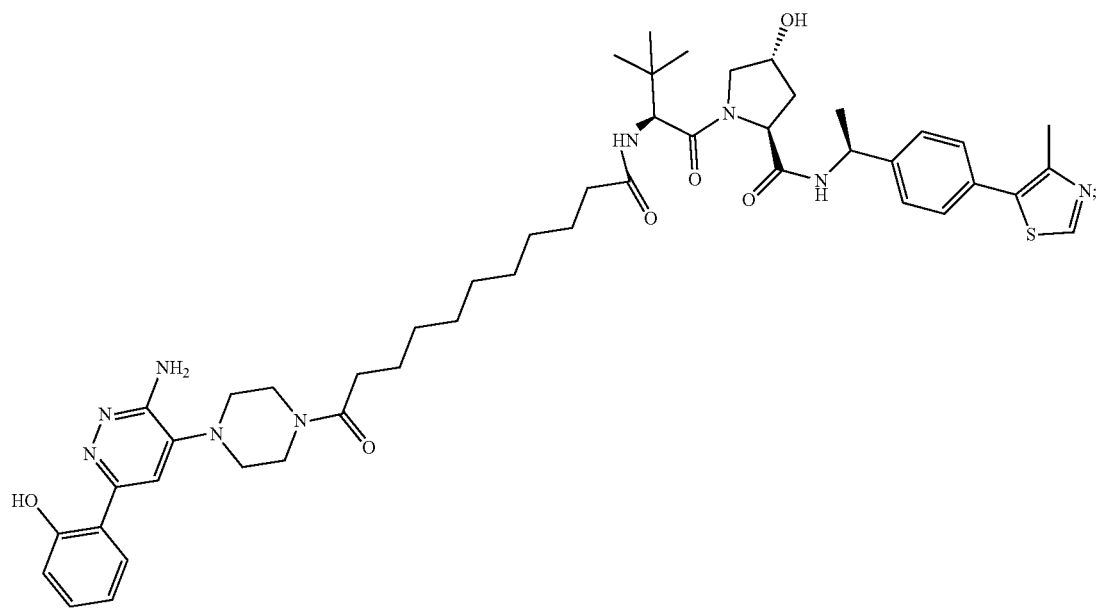 [SMILES: Cc1ncsc1-c1ccc([C@H](C)NC(=O)[C@@H]2C[C@@H](O)CN2C(=O)[C@@H](NC(=O)CCCCCCCCCC(=O)N2CCN(c3cc(-c4ccccc4O)nnc3N)CC2)C(C)(C)C)cc1] |
| 39. | 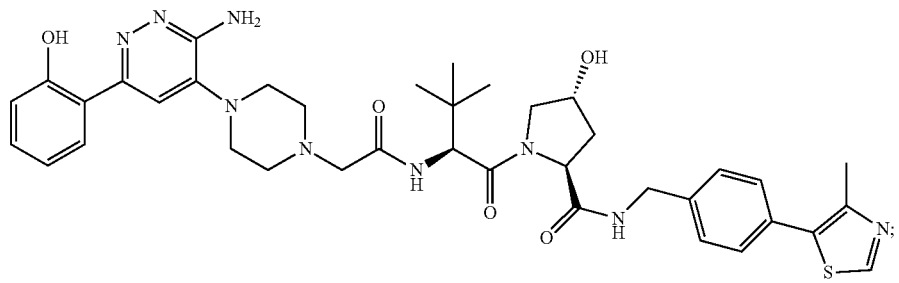 [SMILES: Cc1ncsc1-c1ccc(CNC(=O)[C@@H]2C[C@@H](O)CN2C(=O)[C@@H](NC(=O)CN2CCN(c3cc(-c4ccccc4O)nnc3N)CC2)C(C)(C)C)cc1] |

|     | STRUCTURE |
| --- | --- |
| 40. | 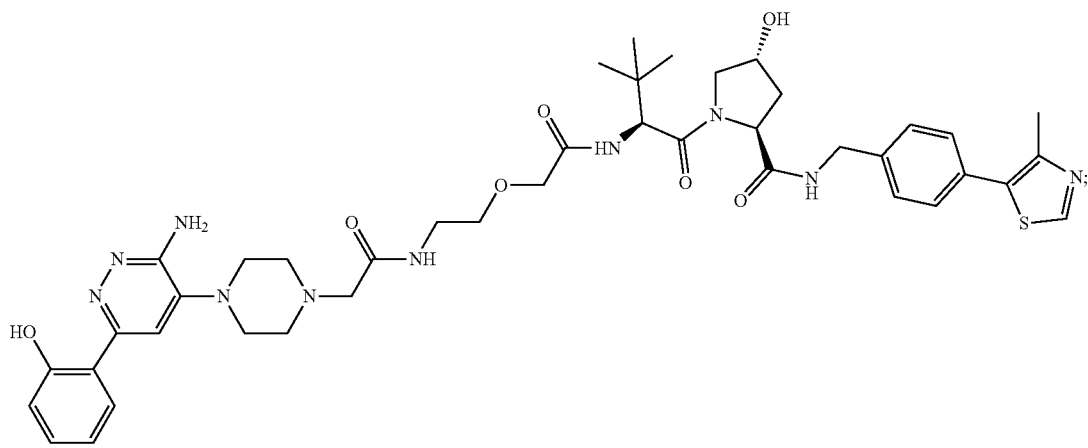 [SMILES: Cc1ncsc1-c1ccc(CNC(=O)[C@@H]2C[C@@H](O)CN2C(=O)[C@@H](NC(=O)COCCNC(=O)CN2CCN(c3cc(-c4ccccc4O)nnc3N)CC2)C(C)(C)C)cc1] |
| 41. | 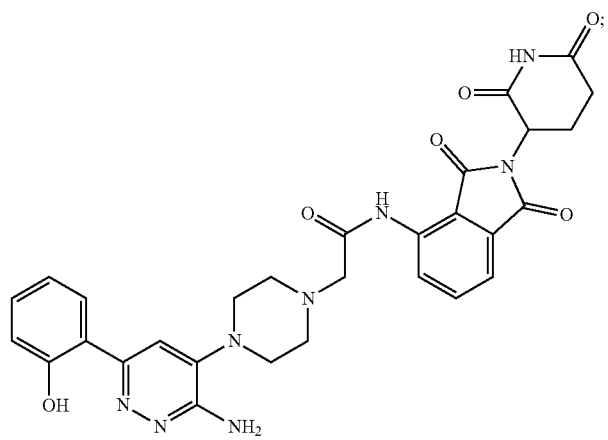 [SMILES: Nc1nnc(-c2ccccc2O)cc1N1CCN(CC(=O)Nc2cccc3c2C(=O)N(C2CCC(=O)NC2=O)C3=O)CC1] |
| 42. | 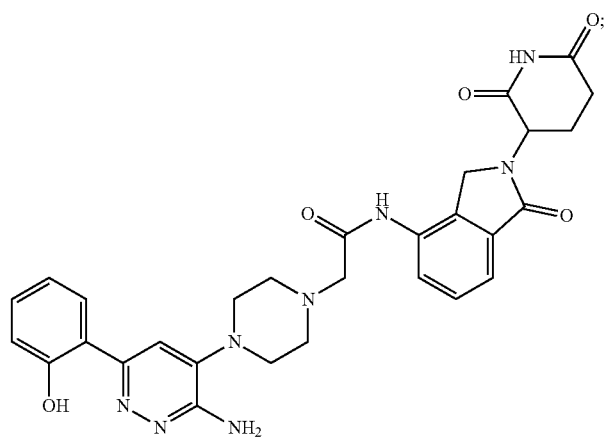 [SMILES: Nc1nnc(-c2ccccc2O)cc1N1CCN(CC(=O)Nc2cccc3c2CN(C2CCC(=O)NC2=O)C3=O)CC1] |
| 43. | 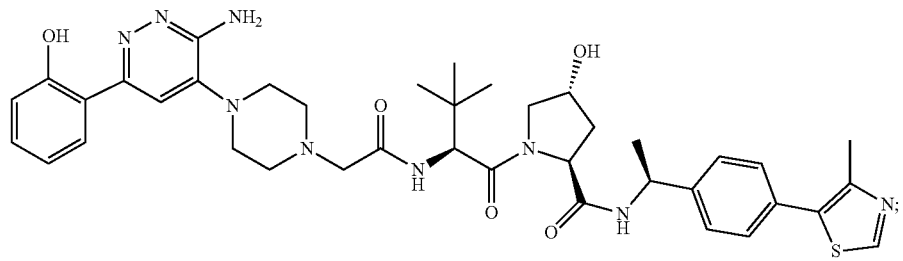 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4O)nnc3N)CC2)C(C)(C)C)cc1] |

| STRUCTURE |
|---|
| 44. 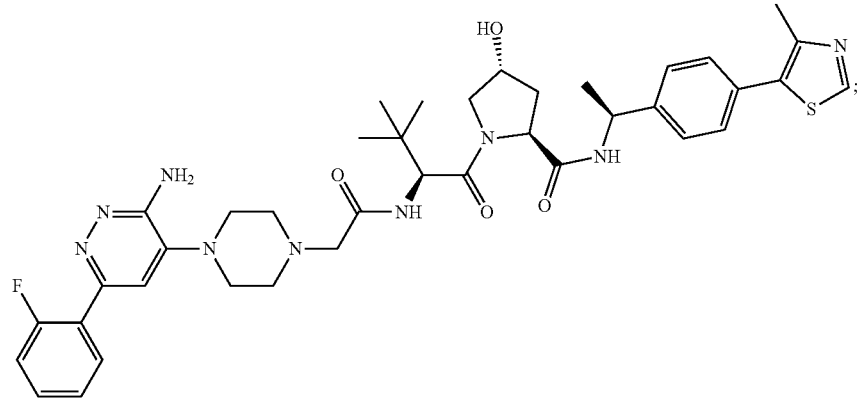 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4F)nnc3N)CC2)C(C)(C)C)cc1] |
| 45. 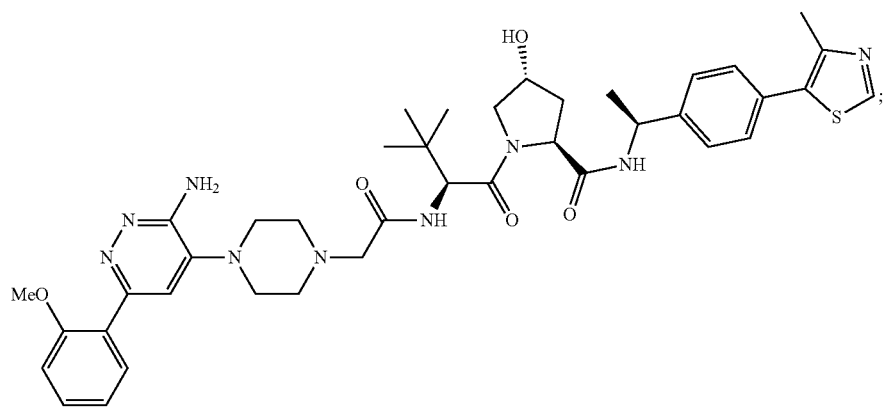 [SMILES: COc1ccccc1-c1cc(N2CCN(CC(=O)N[C@H](C(=O)N3C[C@H](O)C[C@H]3C(=O)N[C@@H](C)c3ccc(-c4scnc4C)cc3)C(C)(C)C)CC2)c(N)nn1] |
| 46. 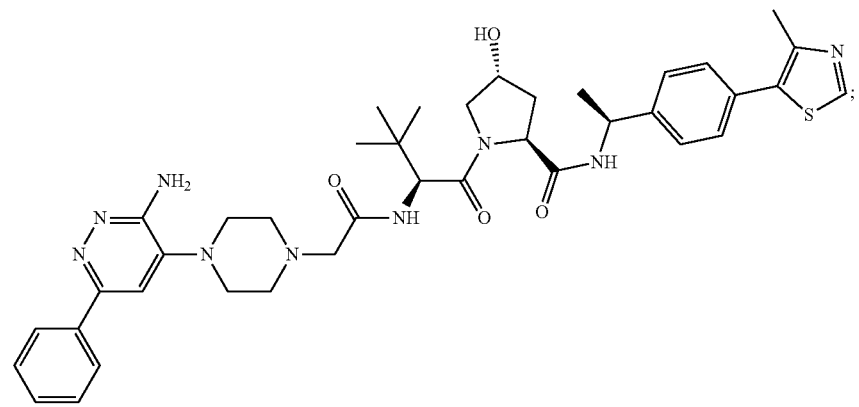 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4)nnc3N)CC2)C(C)(C)C)cc1] |
| 47. 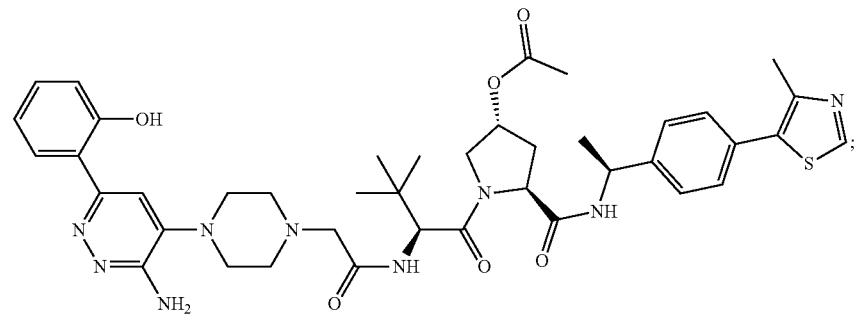 [SMILES: CC(=O)O[C@@H]1C[C@@H](C(=O)N[C@@H](C)c2ccc(-c3scnc3C)cc2)N(C(=O)[C@@H](NC(=O)CN2CCN(c3cc(-c4ccccc4O)nnc3N)CC2)C(C)(C)C)C1] |

| STRUCTURE |
|---|
| 48. 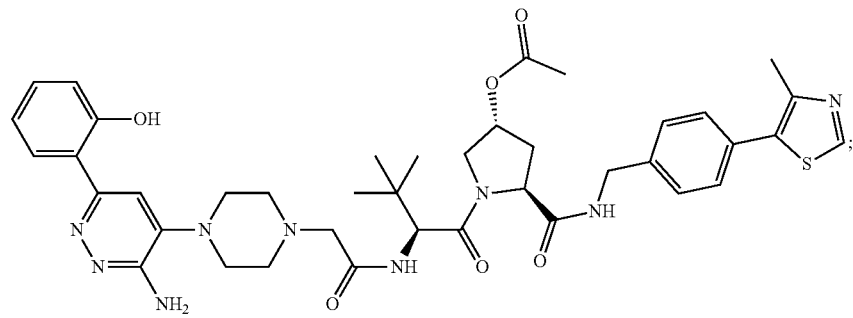 [SMILES: CC(=O)O[C@@H]1C[C@@H](C(=O)NCc2ccc(-c3scnc3C)cc2)N(C(=O)[C@@H](NC(=O)CN2CCN(c3cc(-c4ccccc4O)nnc3N)CC2)C(C)(C)C)C1] |
| 49. 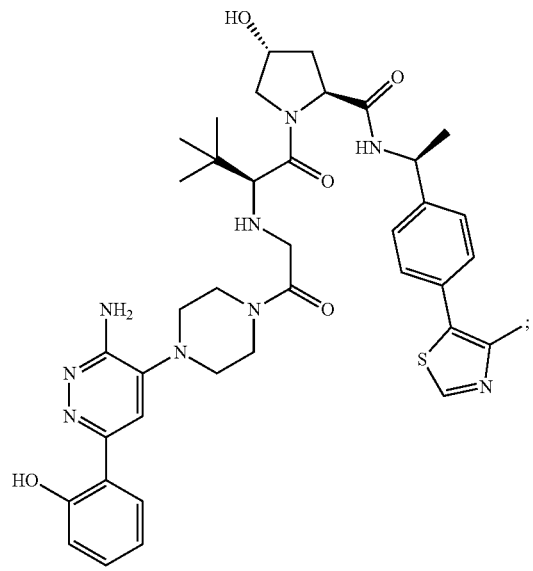 |
| 50. 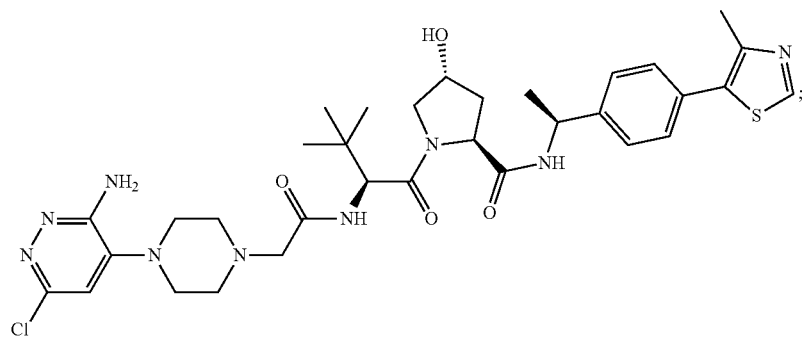 [SMILES: Cc1ncsc1-c1ccc([C@H](C)NC(=O)[C@@H]2C[C@@H](O)CN2C(=O)[C@@H](NC(=O)CN2CCN(c3cc(Cl)nnc3N)CC2)C(C)(C)C)cc1] |

| STRUCTURE |
|---|
| 51. 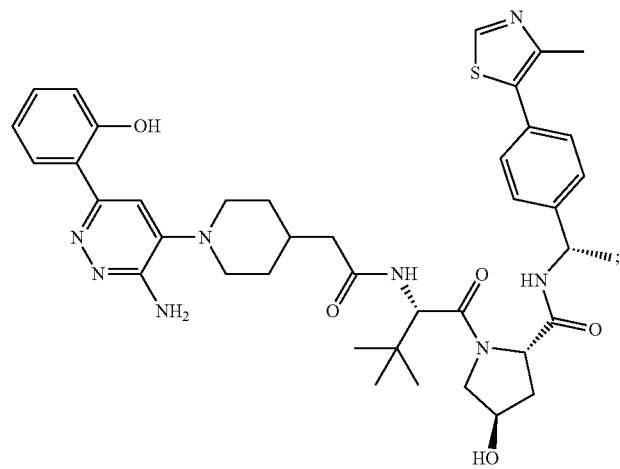 [SMILES: Cc1ncsc1-c1ccc([C@H](C)NC(=O)[C@@H]2C[C@@H](O)CN2C(=O)[C@@H](NC(=O)CC2CCN(c3cc(-c4ccccc4O)nnc3N)CC2)C(C)(C)C)cc1] |
| 52. 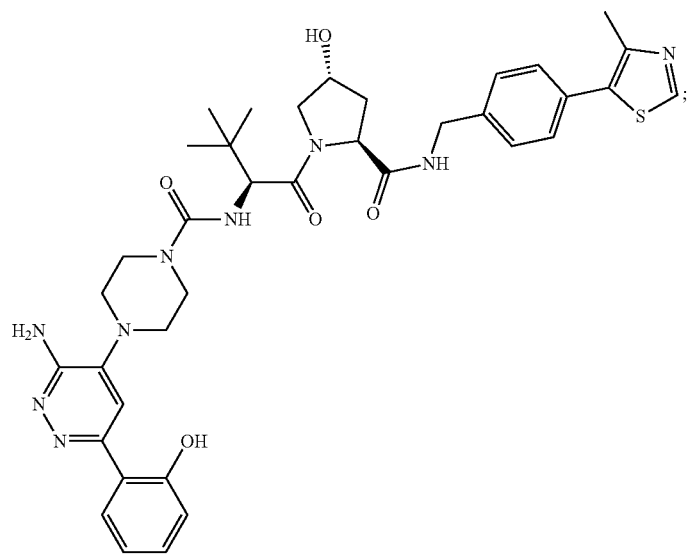 [SMILES: Cc1ncsc1-c1ccc(CNC(=O)[C@@H]2C[C@@H](O)CN2C(=O)[C@@H](NC(=O)N2CCN(c3cc(-c4ccccc4O)nnc3N)CC2)C(C)(C)C)cc1] |
| 53. 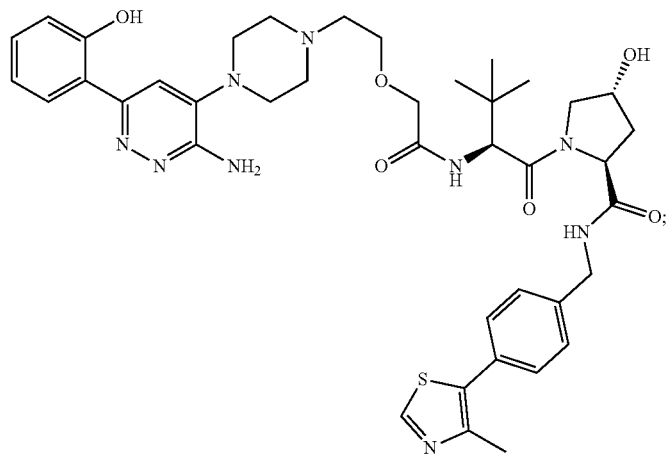 [SMILES: Cc1ncsc1-c1ccc(CNC(=O)[C@@H]2C[C@@H](O)CN2C(=O)[C@@H](NC(=O)COCCN2CCN(c3cc(-c4ccccc4O)nnc3N)CC2)C(C)(C)C)cc1] |

-continued
| | STRUCTURE |
|---|---|
| 54. | 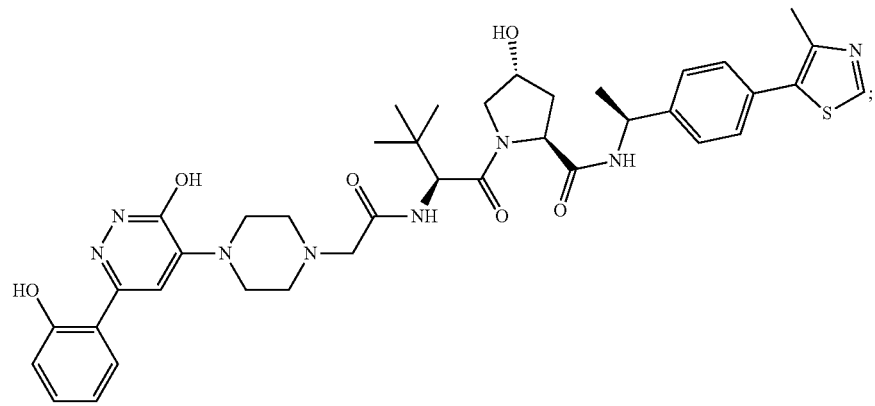 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4O)nnc3O)CC2)C(C)(C)C)cc1] |
| 55. | 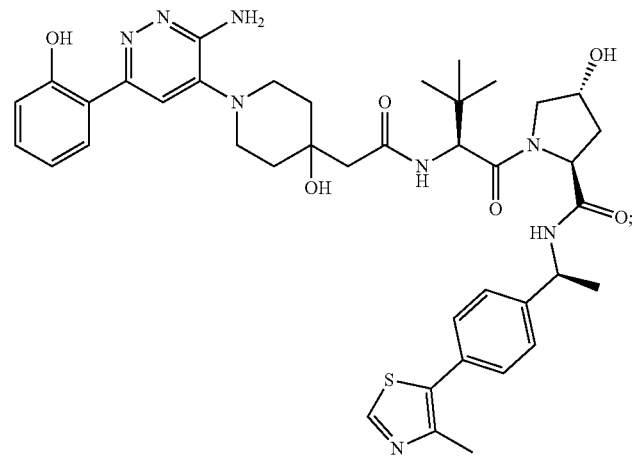 [SMILES: Cc1ncsc1-c1ccc([C@H](C)NC(=O)[C@@H]2C[C@@H](O)CN2C(=O)[C@@H](NC(=O)CC2(O)CCN(c3cc(-c4ccccc4O)nnc3N)CC2)C(C)(C)C)cc1] |
| 56. | 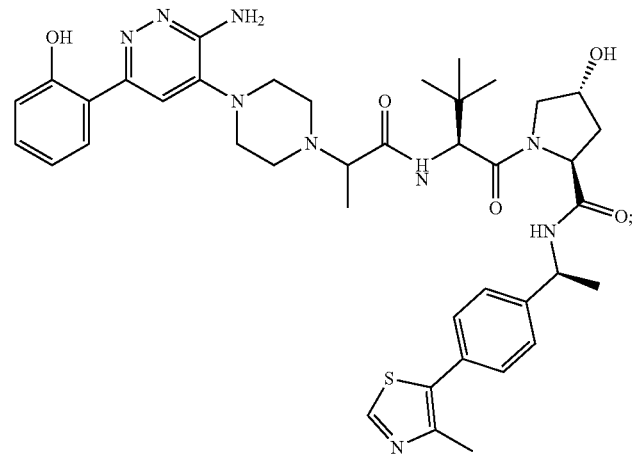 [SMILES: Cc1ncsc1-c1ccc([C@H](C)NC(=O)[C@@H]2C[C@@H](O)CN2C(=O)[C@@H](NC(=O)C(C)N2CCN(c3cc(-c4ccccc4O)nnc3N)CC2)C(C)(C)C)cc1] |

| STRUCTURE |
|---|
| 57. 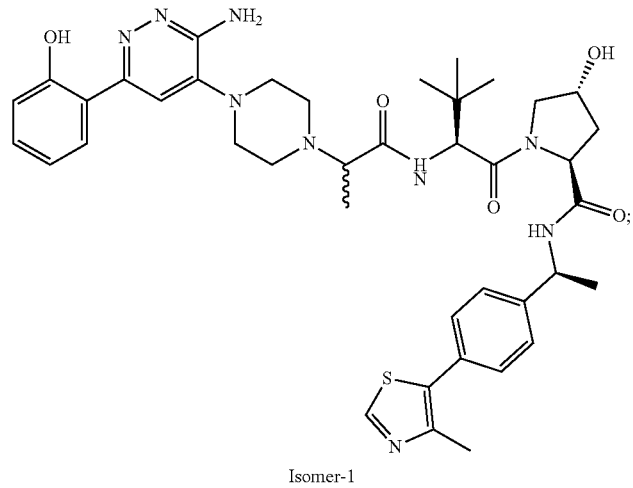 [SMILES: Cc1ncsc1-c1ccc([C@H](C)NC(=O)[C@@H]2C[C@@H](O)CN2C(=O)[C@@H](NC(=O)C(C)N2CCN(c3cc(-c4ccccc4O)nnc3N)CC2)C(C)(C)C)cc1]<br>Isomer-1 |
| 58. 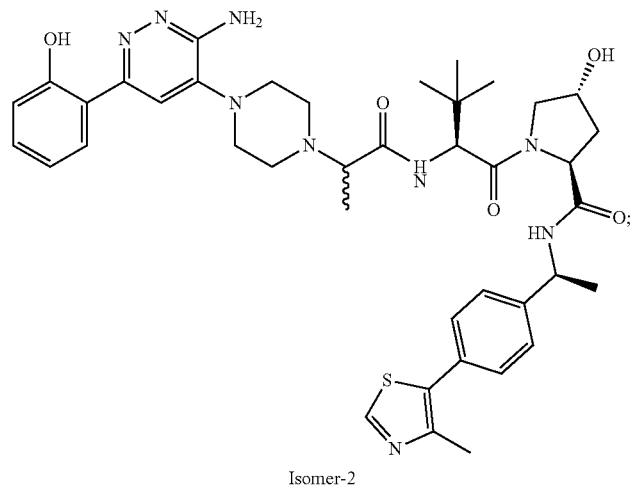 [SMILES: Cc1ncsc1-c1ccc([C@H](C)NC(=O)[C@@H]2C[C@@H](O)CN2C(=O)[C@@H](NC(=O)C(C)N2CCN(c3cc(-c4ccccc4O)nnc3N)CC2)C(C)(C)C)cc1]<br>Isomer-2 |
| 59. 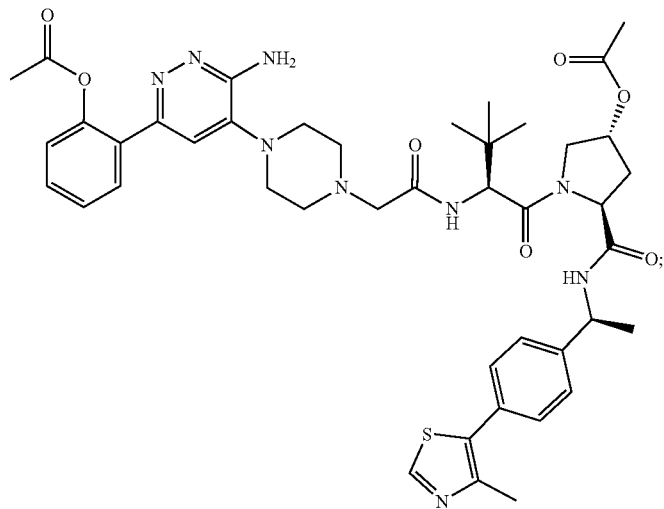 [SMILES: CC(=O)Oc1ccccc1-c1cc(N2CCN(CC(=O)N[C@H](C(=O)N3C[C@H](OC(C)=O)C[C@H]3C(=O)N[C@@H](C)c3ccc(-c4scnc4C)cc3)C(C)(C)C)CC2)c(N)nn1] |

| | STRUCTURE |
|---|---|
| 60. | 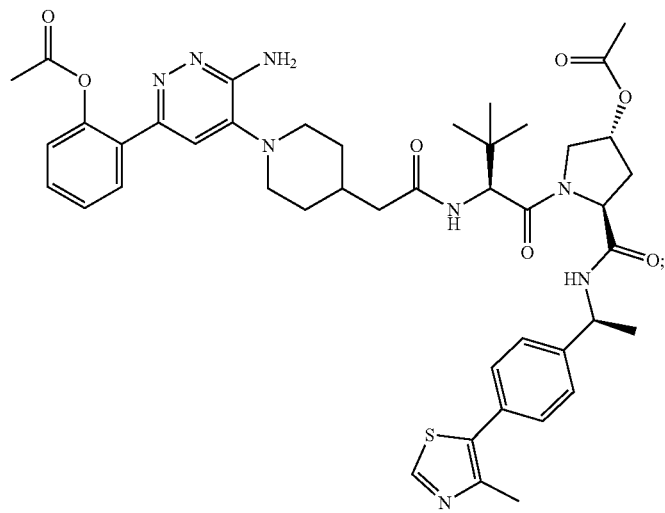 [SMILES: CC(=O)Oc1ccccc1-c1cc(N2CCC(CC(=O)N[C@H](C(=O)N3C[C@H](OC(C)=O)C[C@H]3C(=O)N[C@@H](C)c3ccc(-c4scnc4C)cc3)C(C)(C)C)CC2)c(N)nn1] |
| 61. | 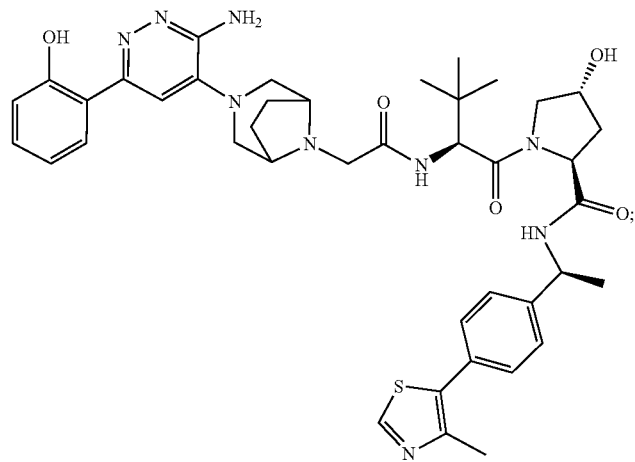 [SMILES: Cc1ncsc1-c1ccc([C@H](C)NC(=O)[C@@H]2C[C@@H](O)CN2C(=O)[C@@H](NC(=O)CN2C3CCC2CN(c2cc(-c4ccccc4O)nnc2N)C3)C(C)(C)C)cc1] |
| 62. | 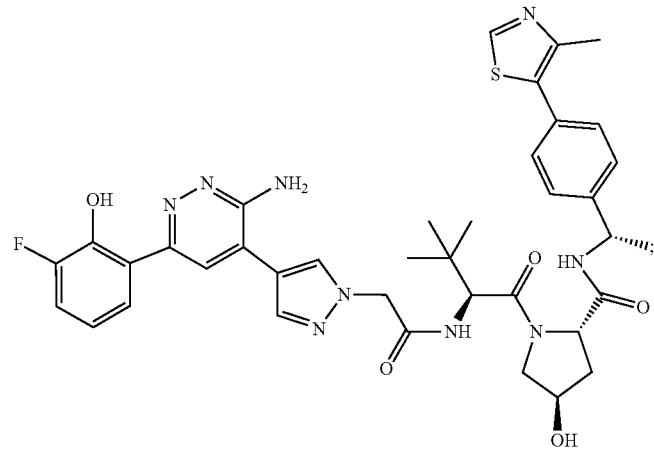 |

| | STRUCTURE |
|---|---|
| 63. | 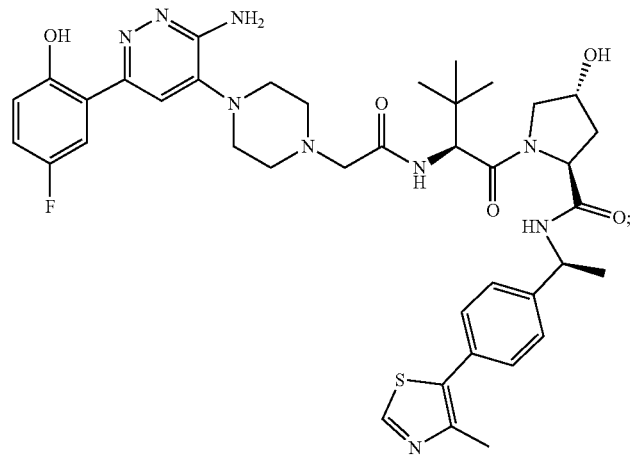 [SMILES: Cc1ncsc1-c1ccc([C@H](C)NC(=O)[C@@H]2C[C@@H](O)CN2C(=O)[C@@H](NC(=O)CN2CCN(c3cc(-c4cc(F)ccc4O)nnc3N)CC2)C(C)(C)C)cc1] |
| 64. | 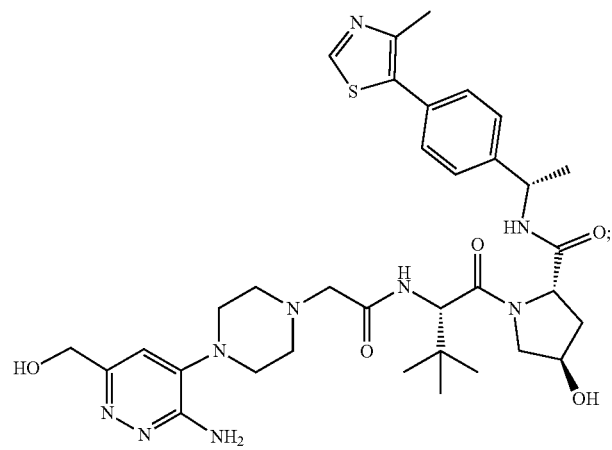 [SMILES: Cc1ncsc1-c1ccc([C@H](C)NC(=O)[C@@H]2C[C@@H](O)CN2C(=O)[C@@H](NC(=O)CN2CCN(c3cc(CO)nnc3N)CC2)C(C)(C)C)cc1] |
| 65. | 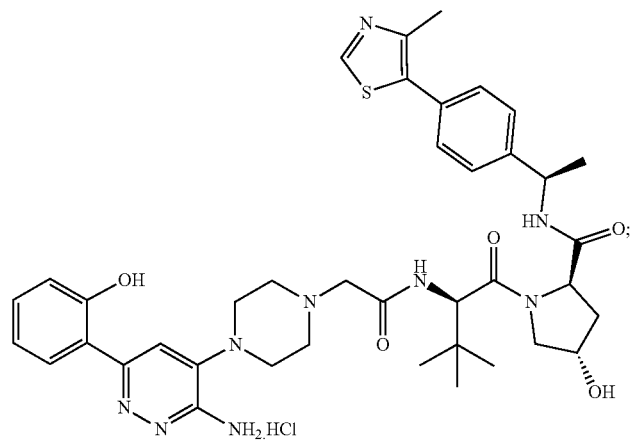 |

| STRUCTURE |
|---|
| 66. 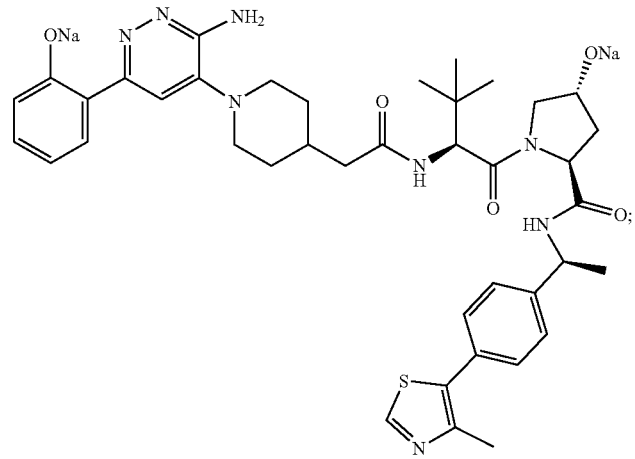 |
| 67. 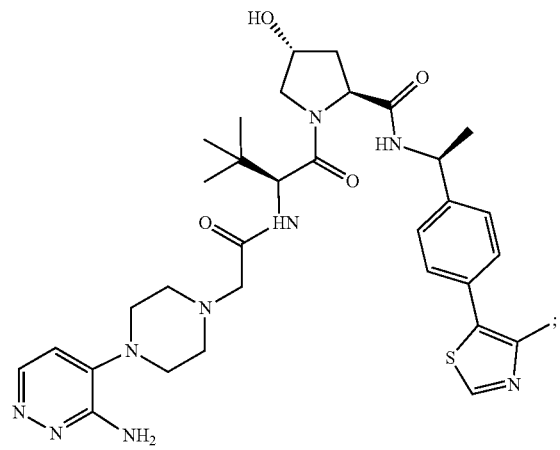 |
| 68. 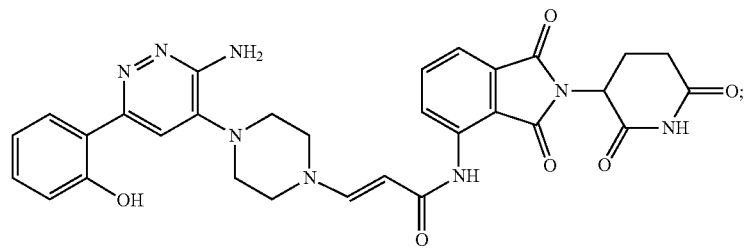 [SMILES: Nc1nnc(-c2ccccc2O)cc1N1CCN(/C=C/C(=O)Nc2cccc3c2C(=O)N(C2CCC(=O)NC2=O)C3=O)CC1] |
| 69. 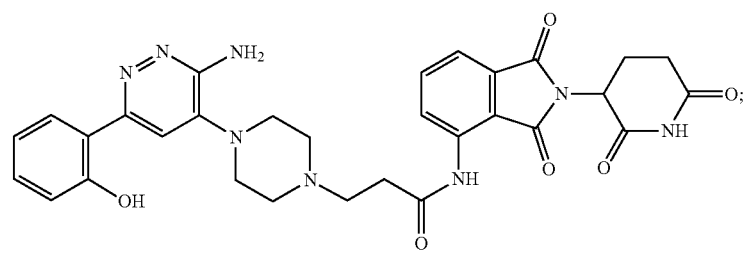 [SMILES: Nc1nnc(-c2ccccc2O)cc1N1CCN(CCC(=O)Nc2cccc3c2C(=O)N(C2CCC(=O)NC2=O)C3=O)CC1] |

| | STRUCTURE |
|---|---|
| 70. | 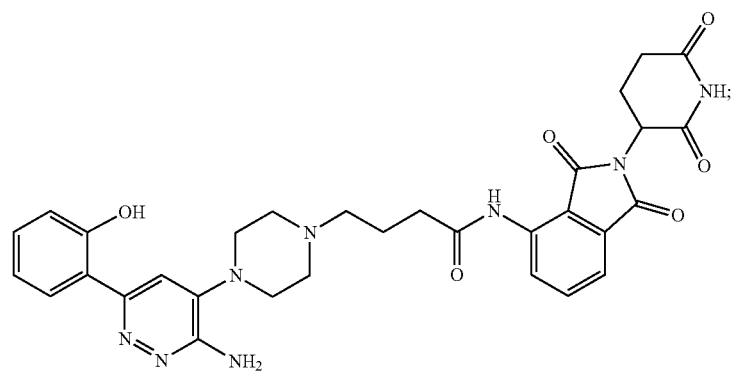 [SMILES: Nc1nnc(-c2ccccc2O)cc1N1CCN(CCCC(=O)Nc2cccc3c2C(=O)N(C2CCC(=O)NC2=O)C3=O)CC1] |
| 71. | 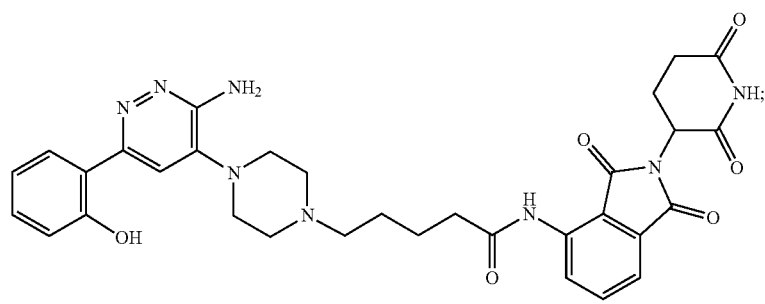 [SMILES: Nc1nnc(-c2ccccc2O)cc1N1CCN(CCCCC(=O)Nc2cccc3c2C(=O)N(C2CCC(=O)NC2=O)C3=O)CC1] |
| 72. | 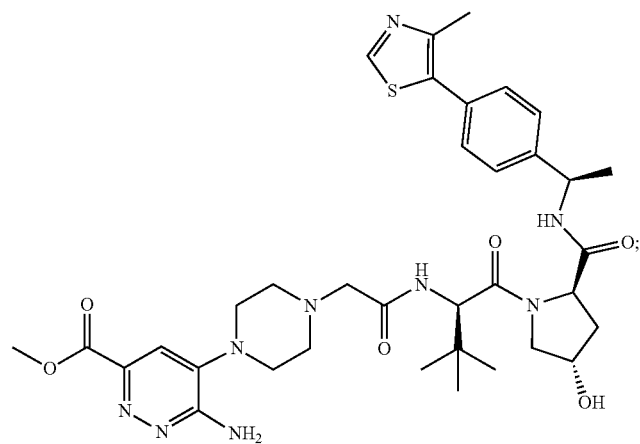 [SMILES: COC(=O)c1cc(N2CCN(CC(=O)N[C@@H](C(=O)N3C[C@@H](O)C[C@@H]3C(=O)N[C@H](C)c3ccc(-c4scnc4C)cc3)C(C)(C)C)CC2)c(N)nn1] |
| 73. | 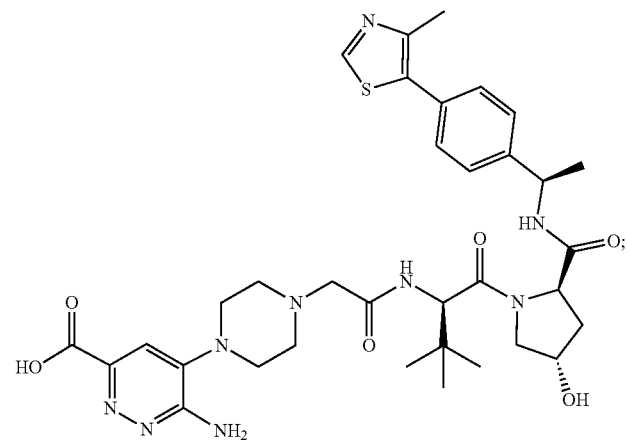 [SMILES: Cc1ncsc1-c1ccc([C@@H](C)NC(=O)[C@H]2C[C@H](O)CN2C(=O)[C@H](NC(=O)CN2CCN(c3cc(C(=O)O)nnc3N)CC2)C(C)(C)C)cc1] |

| STRUCTURE |
|---|
| 74. 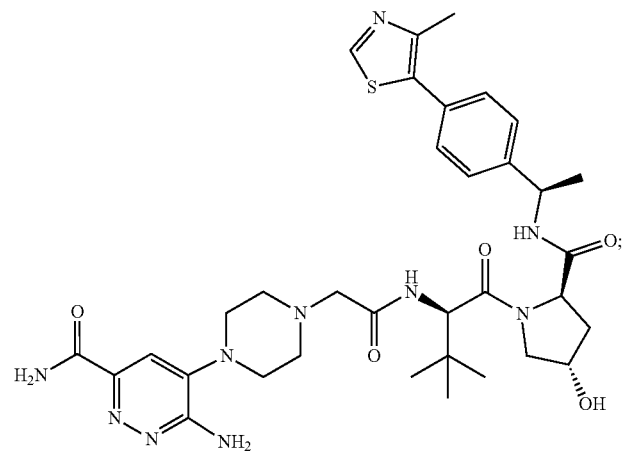 [SMILES: Cc1ncsc1-c1ccc([C@@H](C)NC(=O)[C@H]2C[C@H](O)CN2C(=O)[C@H](NC(=O)CN2CCN(c3cc(C(N)=O)nnc3N)CC2)C(C)(C)C)cc1] |
| 75. 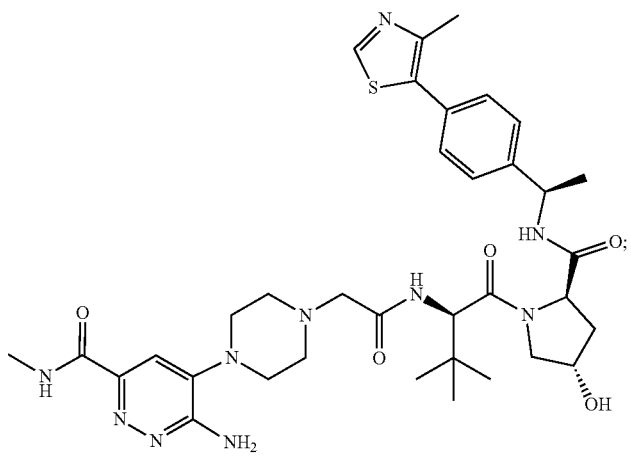 [SMILES: CNC(=O)c1cc(N2CCN(CC(=O)N[C@@H](C(=O)N3C[C@@H](O)C[C@@H]3C(=O)N[C@H](C)c3ccc(-c4scnc4C)cc3)C(C)(C)C)CC2)c(N)nn1] |
| 76. 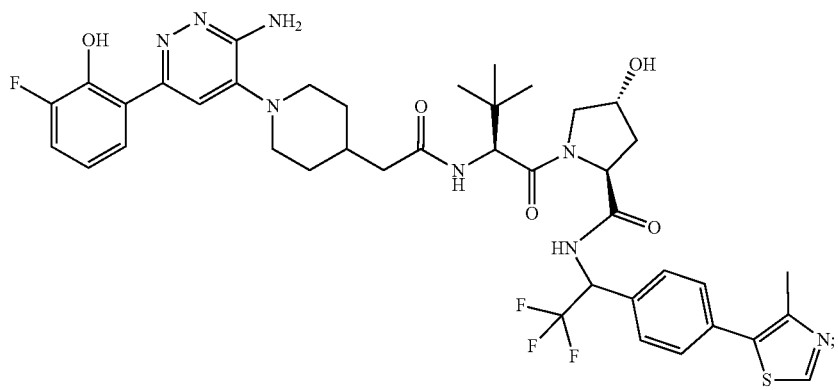 [SMILES: Cc1ncsc1-c1ccc(C(NC(=O)[C@@H]2C[C@@H](O)CN2C(=O)[C@@H](NC(=O)CC2CCN(c3cc(-c4cccc(F)c4O)nnc3N)CC2)C(C)(C)C)C(F)(F)F)cc1] |

| STRUCTURE |
|---|
| 77. 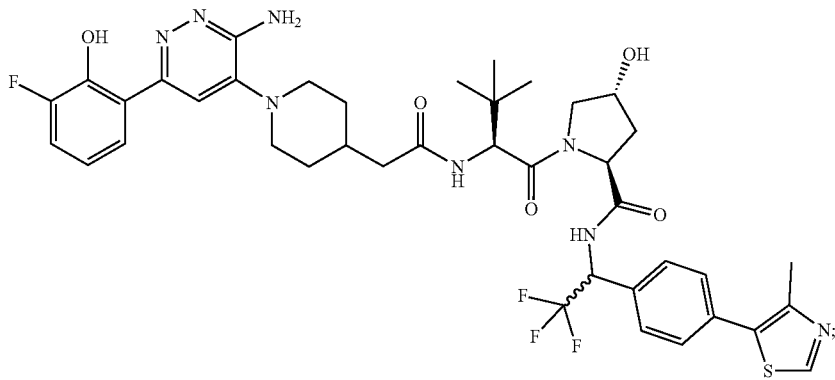
Isomer-1 |
| 78. 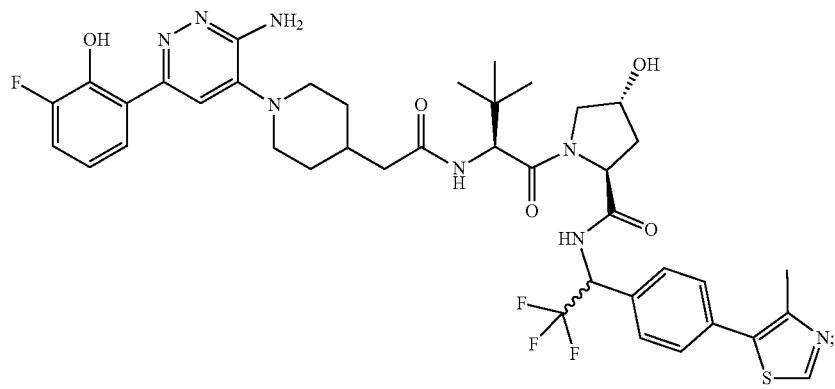
Isomer-2 |
| 79. 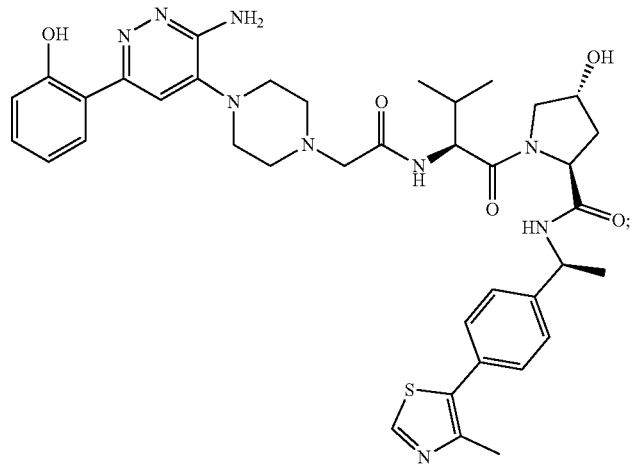 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4O)nnc3N)CC2)C(C)C)cc1] |

| STRUCTURE |
|---|
| 80. 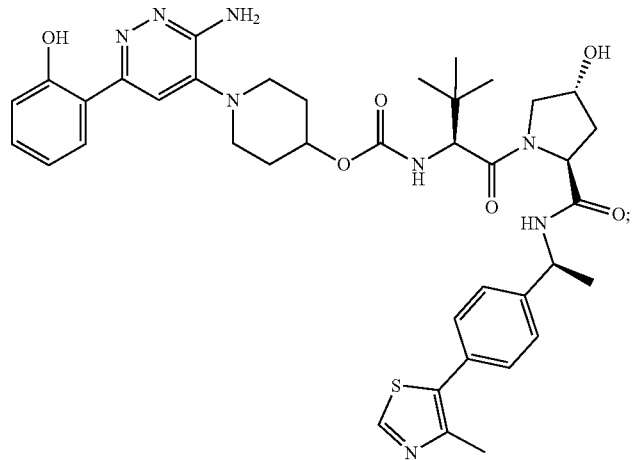 [SMILES: Cc1ncsc1-c1ccc([C@H](C)NC(=O)[C@@H]2C[C@@H](O)CN2C(=O)[C@@H](NC(=O)OC2CCN(c3cc(-c4ccccc4O)nnc3N)CC2)C(C)(C)C)cc1] |
| 81. 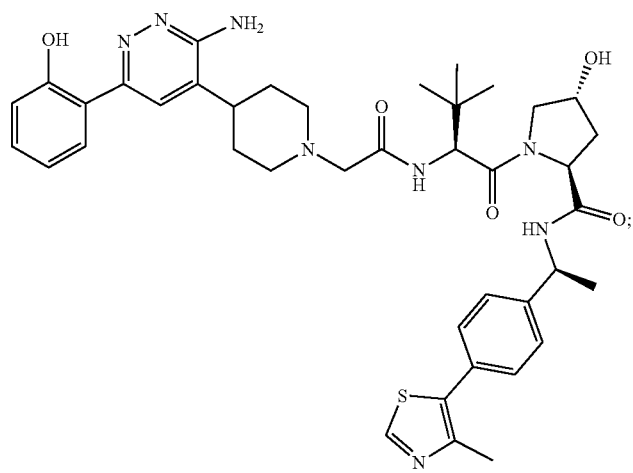 [SMILES: Cc1ncsc1-c1ccc([C@H](C)NC(=O)[C@@H]2C[C@@H](O)CN2C(=O)[C@@H](NC(=O)CN2CCC(c3cc(-c4ccccc4O)nnc3N)CC2)C(C)(C)C)cc1] |
| 82. 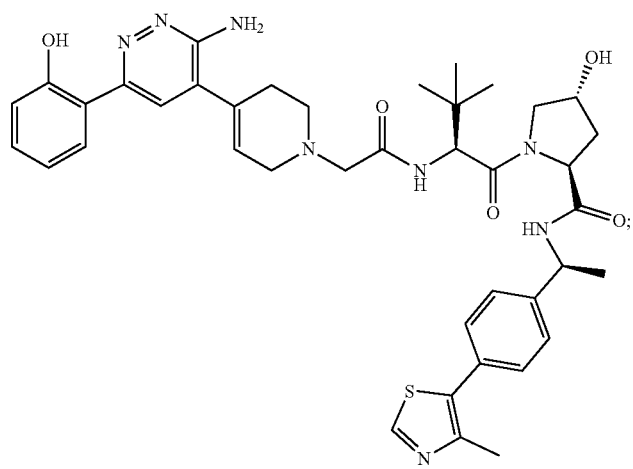 [SMILES: Cc1ncsc1-c1ccc([C@H](C)NC(=O)[C@@H]2C[C@@H](O)CN2C(=O)[C@@H](NC(=O)CN2CC=C(c3cc(-c4ccccc4O)nnc3N)CC2)C(C)(C)C)cc1] |

| STRUCTURE |
|---|
| 83. 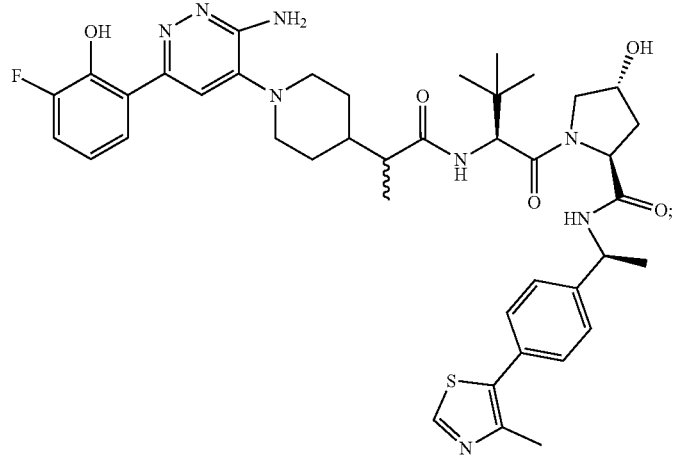<br>Isomer-1 |
| 84. 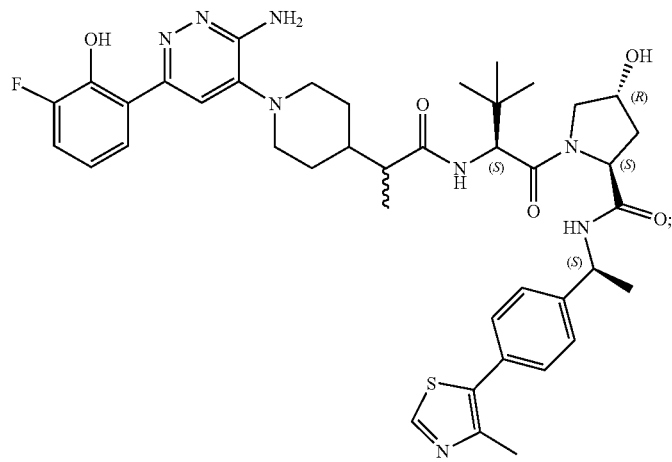<br>Isomer-2 |
| 85. 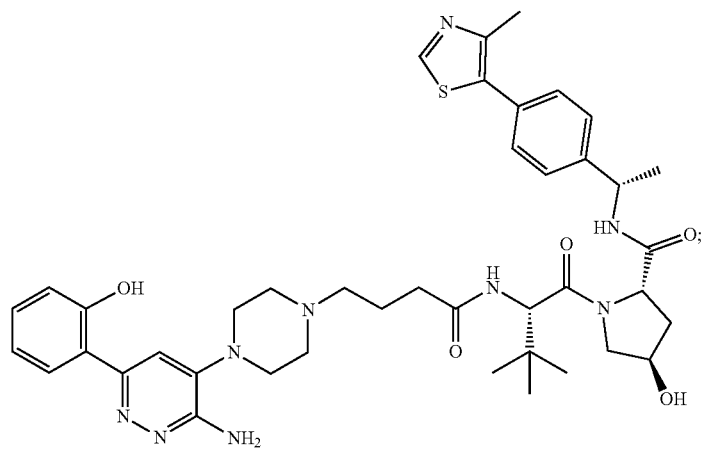 [SMILES: Cc1ncsc1-c1ccc([C@H](C)NC(=O)[C@@H]2C[C@@H](O)CN2C(=O)[C@@H](NC(=O)CCCN2CCN(c3cc(-c4ccccc4O)nnc3N)CC2)C(C)(C)C)cc1] |

| STRUCTURE |
|---|
| 86. 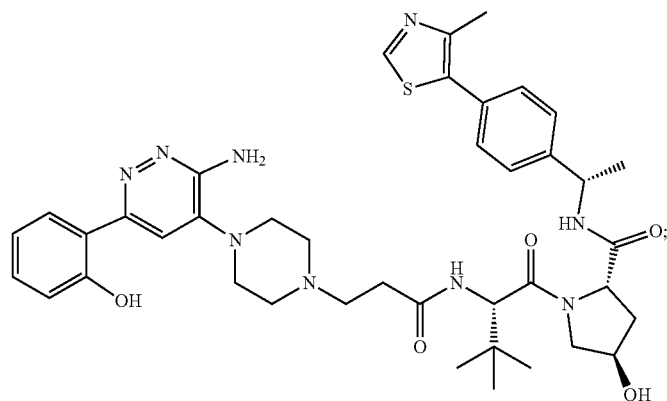 [SMILES: Cc1ncsc1-c1ccc([C@H](C)NC(=O)[C@@H]2C[C@@H](O)CN2C(=O)[C@@H](NC(=O)CCN2CCN(c3cc(-c4ccccc4O)nnc3N)CC2)C(C)(C)C)cc1] |
| 87. 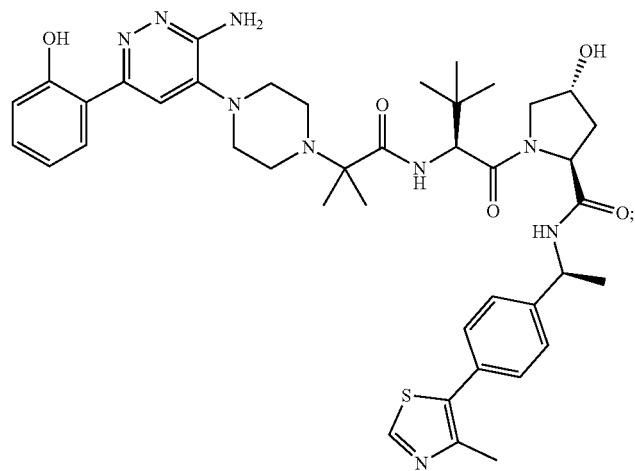 [SMILES: Cc1ncsc1-c1ccc([C@H](C)NC(=O)[C@@H]2C[C@@H](O)CN2C(=O)[C@@H](NC(=O)C(C)(C)N2CCN(c3cc(-c4ccccc4O)nnc3N)CC2)C(C)(C)C)cc1] |
| 88. 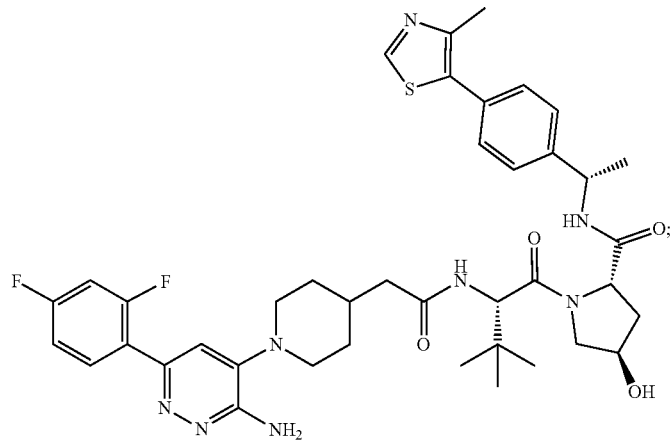 [SMILES: Cc1ncsc1-c1ccc([C@H](C)NC(=O)[C@@H]2C[C@@H](O)CN2C(=O)[C@@H](NC(=O)CC2CCN(c3cc(-c4ccc(F)cc4F)nnc3N)CC2)C(C)(C)C)cc1] |

| | STRUCTURE |
|---|---|
| 89. | 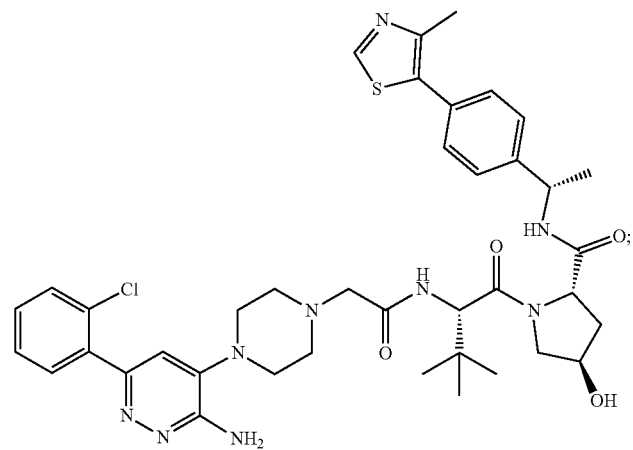 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4Cl)nnc3N)CC2)C(C)(C)C)cc1] |
| 90. | 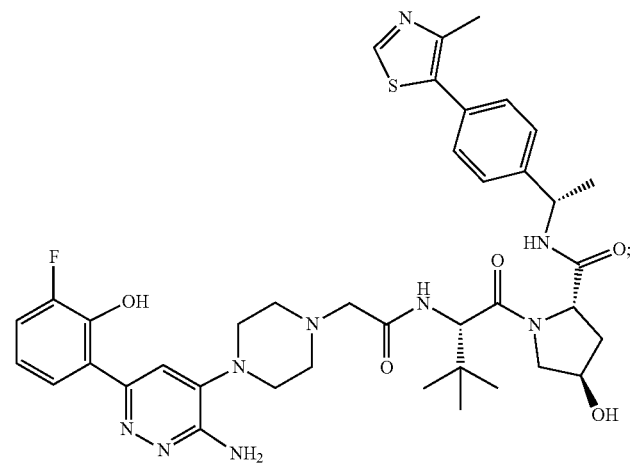 [SMILES: Cc1ncsc1-c1ccc([C@H](C)NC(=O)[C@@H]2C[C@@H](O)CN2C(=O)[C@@H](NC(=O)CN2CCN(c3cc(-c4cccc(F)c4O)nnc3N)CC2)C(C)(C)C)cc1] |
| 91. | 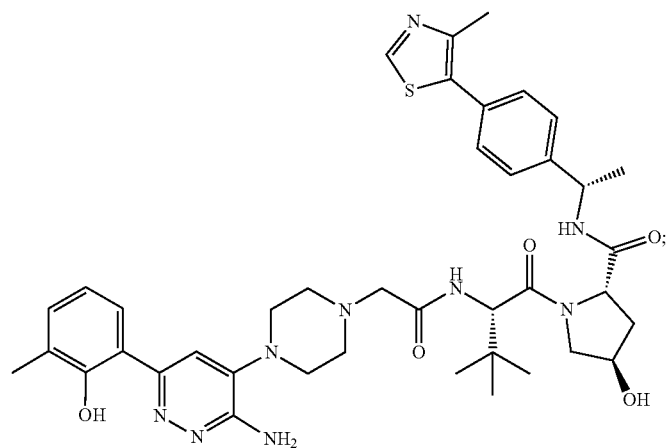 [SMILES: Cc1cccc(-c2cc(N3CCN(CC(=O)N[C@H](C(=O)N4C[C@H](O)C[C@H]4C(=O)N[C@@H](C)c4ccc(-c5scnc5C)cc4)C(C)(C)C)CC3)c(N)nn2)c1O] |

| STRUCTURE |
|---|
| 92. 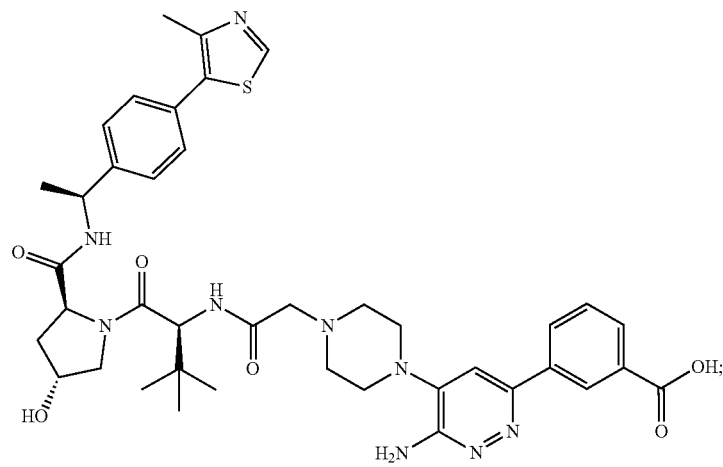 [SMILES: Cc1ncsc1-c1ccc([C@H](C)NC(=O)[C@@H]2C[C@@H](O)CN2C(=O)[C@@H](NC(=O)CN2CCN(c3cc(-c4cccc(C(=O)O)c4)nnc3N)CC2)C(C)(C)C)cc1] |
| 93. 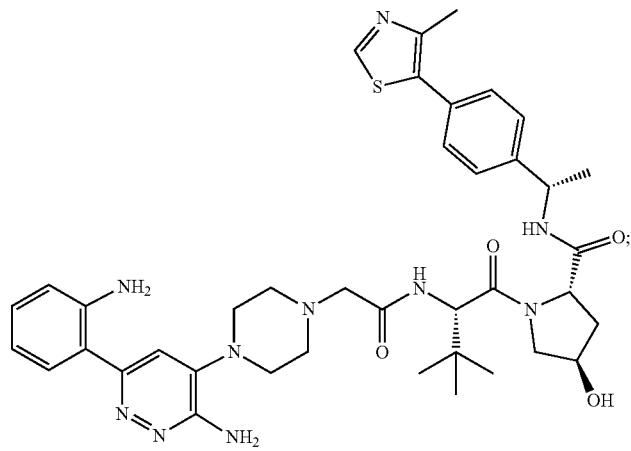 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4N)nnc3N)CC2)C(C)(C)C)cc1] |
| 94. 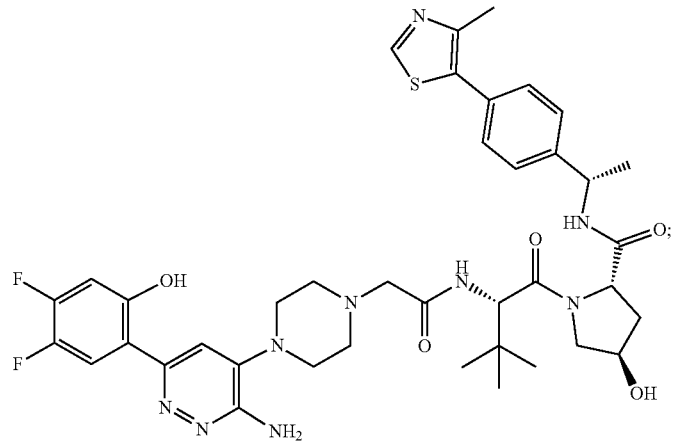 [SMILES: Cc1ncsc1-c1ccc([C@H](C)NC(=O)[C@@H]2C[C@@H](O)CN2C(=O)[C@@H](NC(=O)CN2CCN(c3cc(-c4cc(F)c(F)cc4O)nnc3N)CC2)C(C)(C)C)cc1] |

| STRUCTURE |
|---|
| 95. 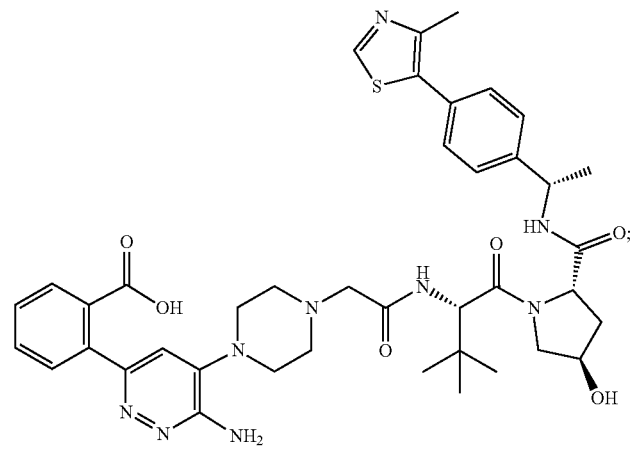 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4C(=O)O)nnc3N)CC2)C(C)(C)C)cc1] |
| 96. 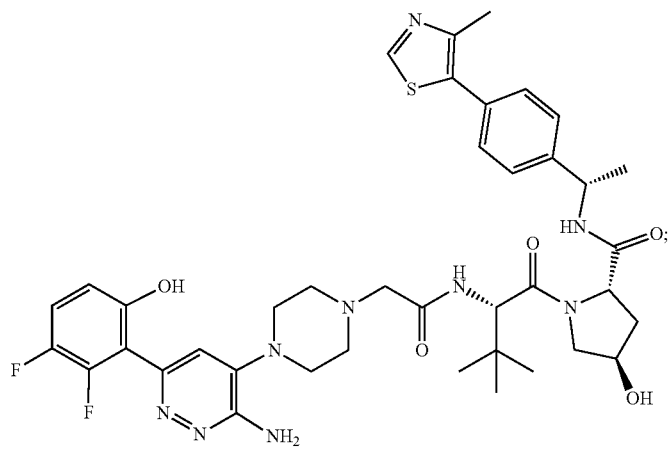 [SMILES: Cc1ncsc1-c1ccc([C@H](C)NC(=O)[C@@H]2C[C@@H](O)CN2C(=O)[C@@H](NC(=O)CN2CCN(c3cc(-c4c(O)ccc(F)c4F)nnc3N)CC2)C(C)(C)C)cc1] |
| 97. 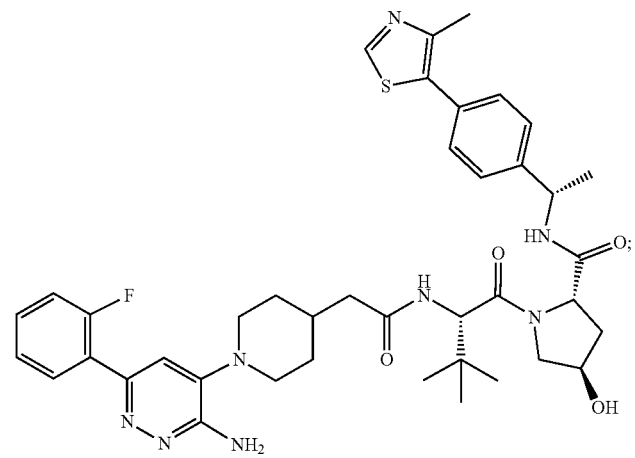 [SMILES: Cc1ncsc1-c1ccc([C@H](C)NC(=O)[C@@H]2C[C@@H](O)CN2C(=O)[C@@H](NC(=O)CC2CCN(c3cc(-c4ccccc4F)nnc3N)CC2)C(C)(C)C)cc1] |

| STRUCTURE |
|---|
| 98. 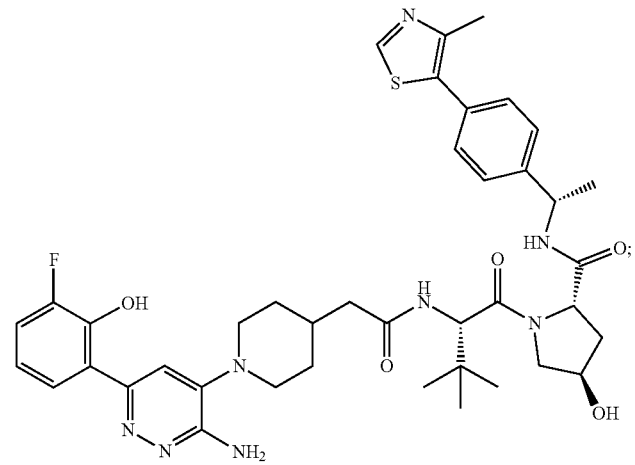 [SMILES: Cc1ncsc1-c1ccc([C@H](C)NC(=O)[C@@H]2C[C@@H](O)CN2C(=O)[C@@H](NC(=O)CC2CCN(c3cc(-c4cccc(F)c4O)nnc3N)CC2)C(C)(C)C)cc1] |
| 99. 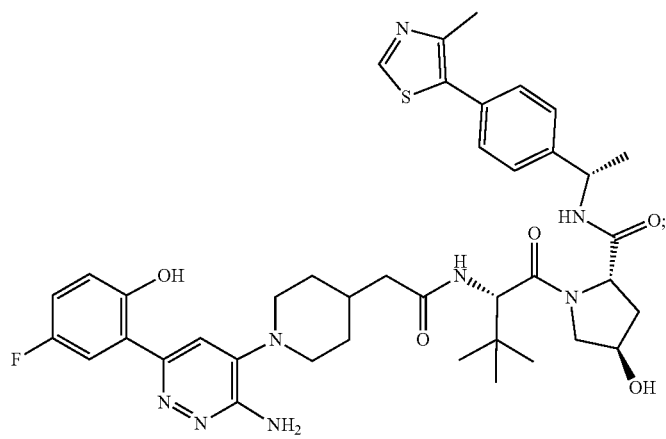 [SMILES: Cc1ncsc1-c1ccc([C@H](C)NC(=O)[C@@H]2C[C@@H](O)CN2C(=O)[C@@H](NC(=O)CC2CCN(c3cc(-c4cc(F)ccc4O)nnc3N)CC2)C(C)(C)C)cc1] |
| 100. 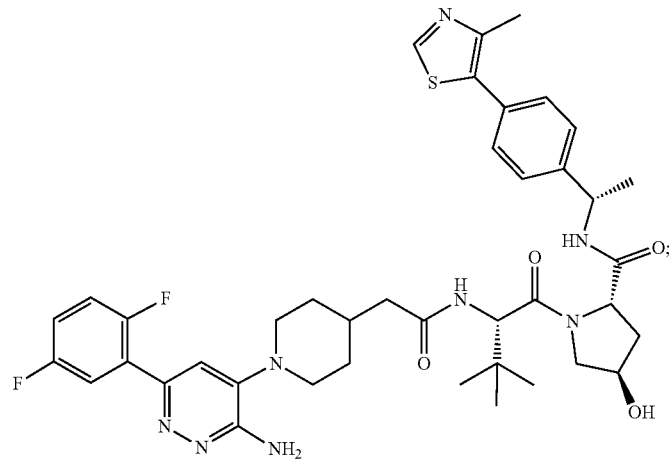 [SMILES: Cc1ncsc1-c1ccc([C@H](C)NC(=O)[C@@H]2C[C@@H](O)CN2C(=O)[C@@H](NC(=O)CC2CCN(c3cc(-c4cc(F)ccc4F)nnc3N)CC2)C(C)(C)C)cc1] |

| | STRUCTURE |
|---|---|
| 101. | 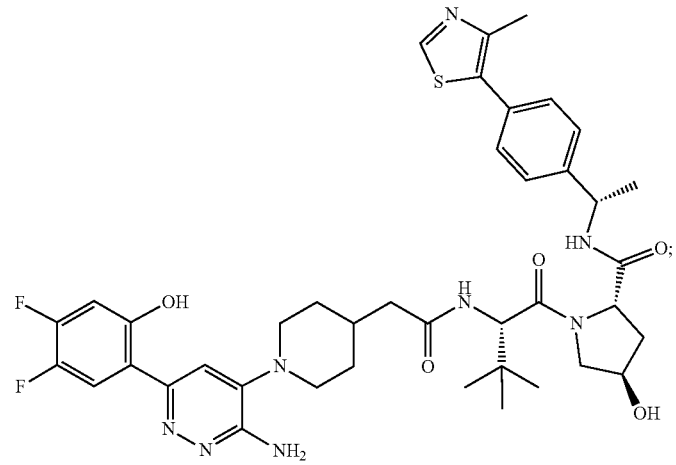 [SMILES: Cc1ncsc1-c1ccc([C@H](C)NC(=O)[C@@H]2C[C@@H](O)CN2C(=O)[C@@H](NC(=O)CC2CCN(c3cc(-c4cc(F)c(F)cc4O)nnc3N)CC2)C(C)(C)C)cc1] |
| 102. | 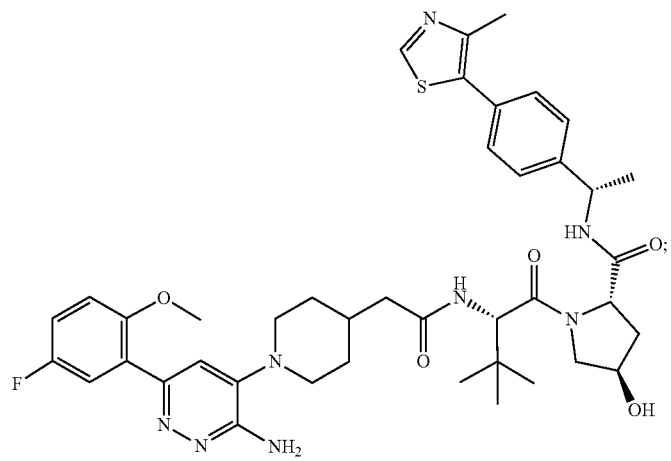 [SMILES: COc1ccc(F)cc1-c1cc(N2CCC(CC(=O)N[C@H](C(=O)N3C[C@H](O)C[C@H]3C(=O)N[C@@H](C)c3ccc(-c4scnc4C)cc3)C(C)(C)C)CC2)c(N)nn1] |
| 103. | 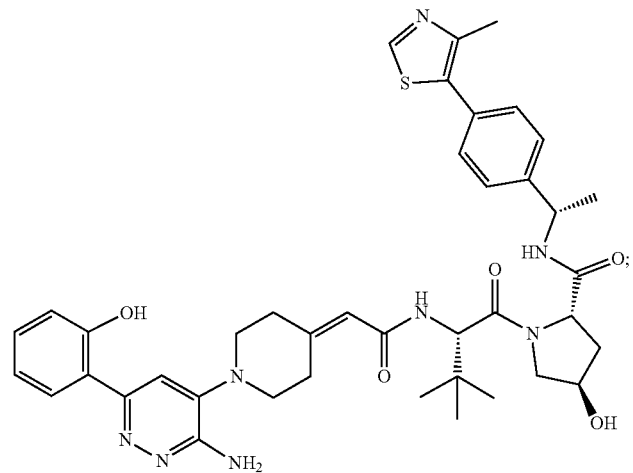 [SMILES: Cc1ncsc1-c1ccc([C@H](C)NC(=O)[C@@H]2C[C@@H](O)CN2C(=O)[C@@H](NC(=O)C=C2CCN(c3cc(-c4ccccc4O)nnc3N)CC2)C(C)(C)C)cc1] |

| STRUCTURE |
|---|
| 104. 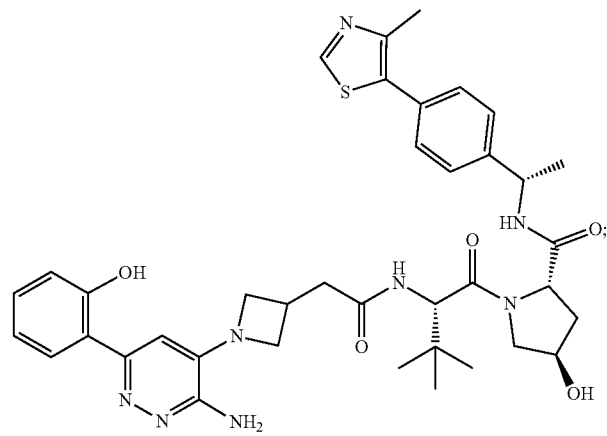 [SMILES: Cc1ncsc1-c1ccc([C@H](C)NC(=O)[C@@H]2C[C@@H](O)CN2C(=O)[C@@H](NC(=O)CC2CN(c3cc(-c4ccccc4O)nnc3N)C2)C(C)(C)C)cc1] |
| 105. 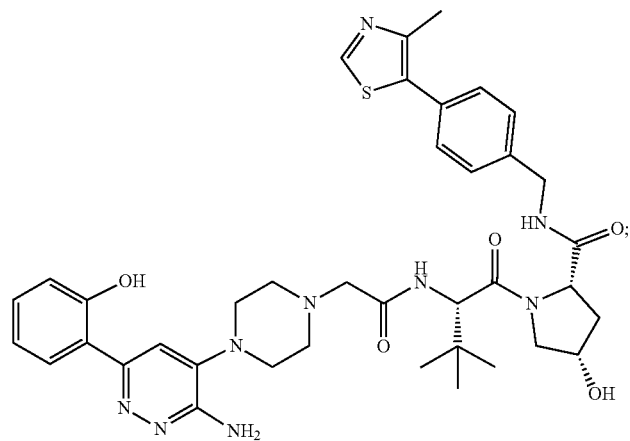 [SMILES: Cc1ncsc1-c1ccc(CNC(=O)[C@@H]2C[C@H](O)CN2C(=O)[C@@H](NC(=O)CN2CCN(c3cc(-c4ccccc4O)nnc3N)CC2)C(C)(C)C)cc1] |
| 106. 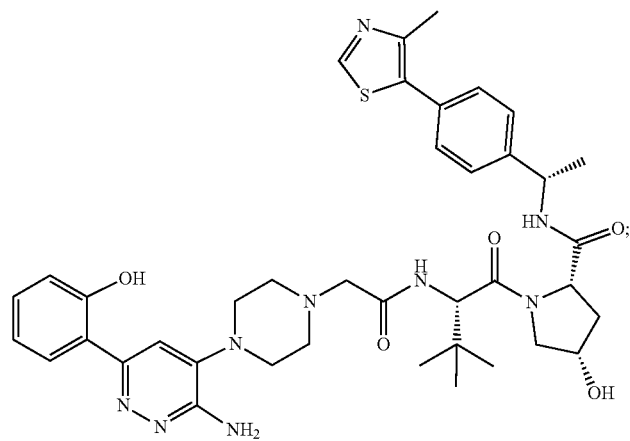 [SMILES: Cc1ncsc1-c1ccc([C@H](C)NC(=O)[C@@H]2C[C@H](O)CN2C(=O)[C@@H](NC(=O)CN2CCN(c3cc(-c4ccccc4O)nnc3N)CC2)C(C)(C)C)cc1] |

| | STRUCTURE |
|---|---|
| 107. | 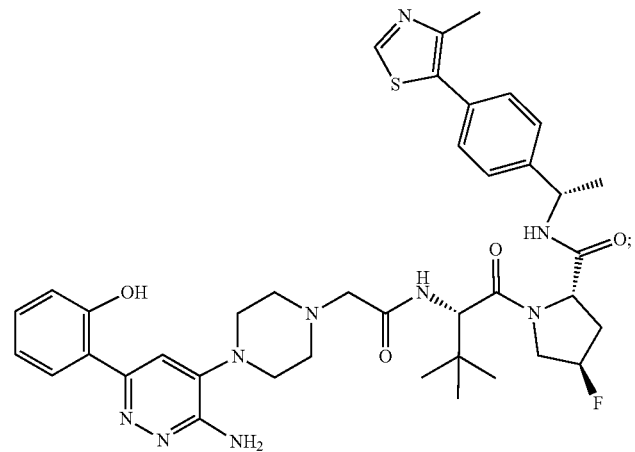 [SMILES: Cc1ncsc1-c1ccc([C@H](C)NC(=O)[C@@H]2C[C@@H](F)CN2C(=O)[C@@H](NC(=O)CN2CCN(c3cc(-c4ccccc4O)nnc3N)CC2)C(C)(C)C)cc1] |
| 108. | 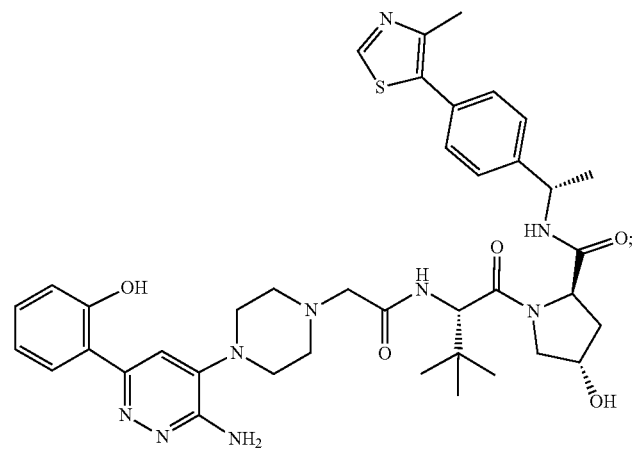 [SMILES: Cc1ncsc1-c1ccc([C@H](C)NC(=O)[C@H]2C[C@H](O)CN2C(=O)[C@@H](NC(=O)CN2CCN(c3cc(-c4ccccc4O)nnc3N)CC2)C(C)(C)C)cc1] |
| 109. | 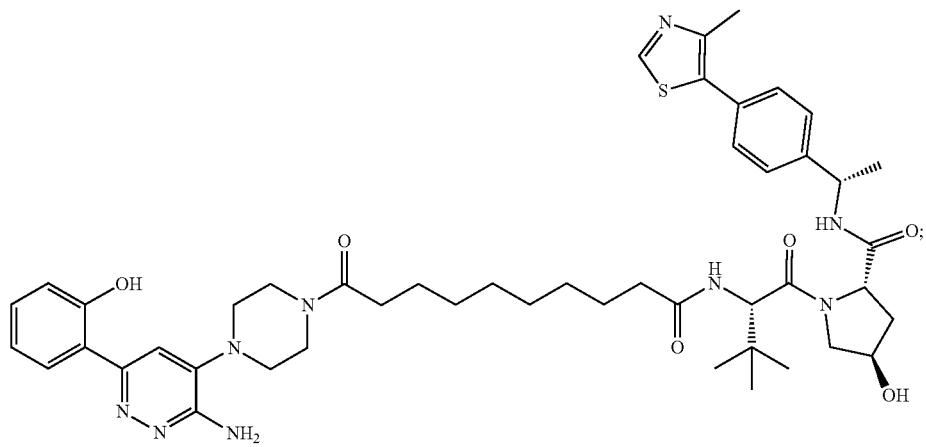 [SMILES: Cc1ncsc1-c1ccc([C@H](C)NC(=O)[C@@H]2C[C@@H](O)CN2C(=O)[C@@H](NC(=O)CCCCCCCCC(=O)N2CCN(c3cc(-c4ccccc4O)nnc3N)CC2)C(C)(C)C)cc1] |

| STRUCTURE |
|---|
| 110. 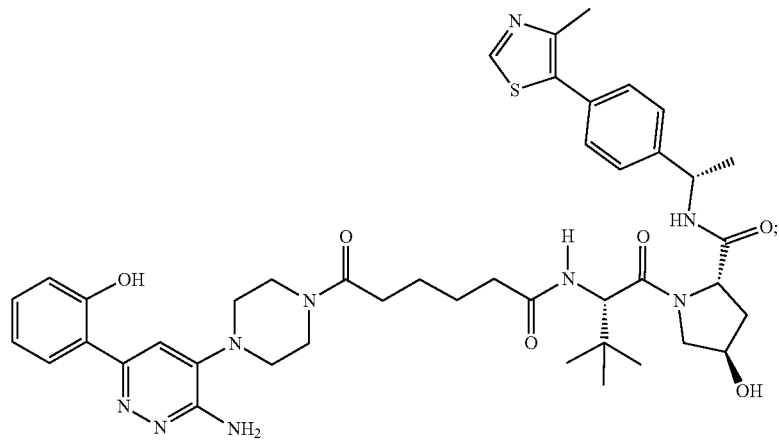 [SMILES: Cc1ncsc1-c1ccc([C@H](C)NC(=O)[C@@H]2C[C@@H](O)CN2C(=O)[C@@H](NC(=O)CCCCC(=O)N2CCN(c3cc(-c4ccccc4O)nnc3N)CC2)C(C)(C)C)cc1] |
| 111. 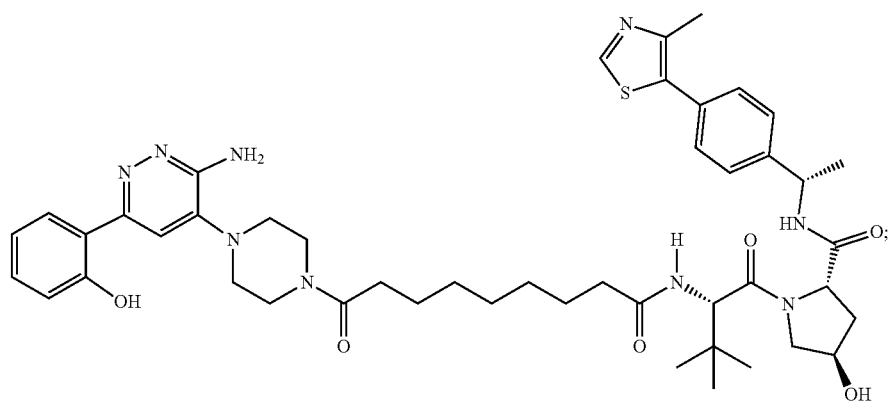 [SMILES: Cc1ncsc1-c1ccc([C@H](C)NC(=O)[C@@H]2C[C@@H](O)CN2C(=O)[C@@H](NC(=O)CCCCCCCC(=O)N2CCN(c3cc(-c4ccccc4O)nnc3N)CC2)C(C)(C)C)cc1] |
| 112. 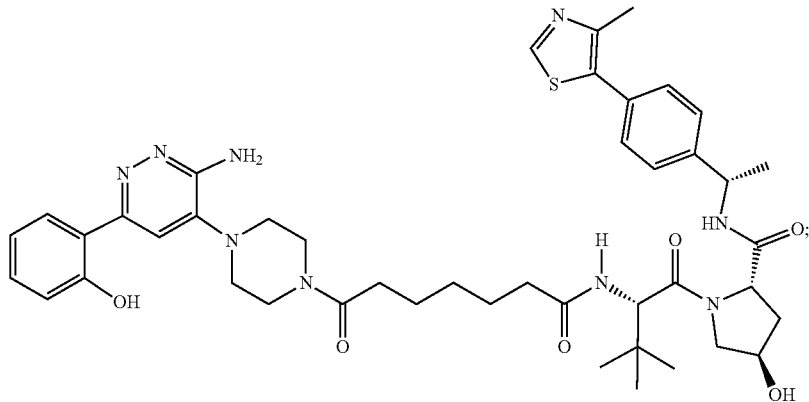 [SMILES: Cc1ncsc1-c1ccc([C@H](C)NC(=O)[C@@H]2C[C@@H](O)CN2C(=O)[C@@H](NC(=O)CCCCCC(=O)N2CCN(c3cc(-c4ccccc4O)nnc3N)CC2)C(C)(C)C)cc1] |

| STRUCTURE |
|---|
| 113. 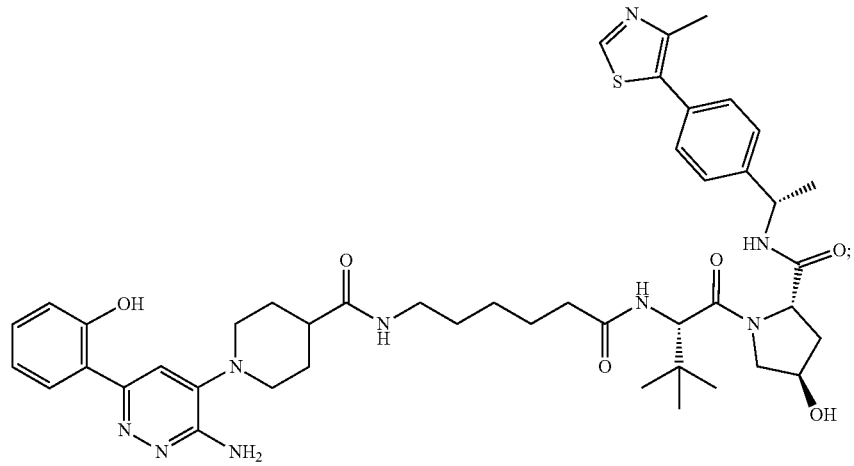 [SMILES: Cc1ncsc1-c1ccc([C@H](C)NC(=O)[C@@H]2C[C@@H](O)CN2C(=O)[C@@H](NC(=O)CCCCCNC(=O)C2CCN(c3cc(-c4ccccc4O)nnc3N)CC2)C(C)(C)C)cc1] |
| 114. 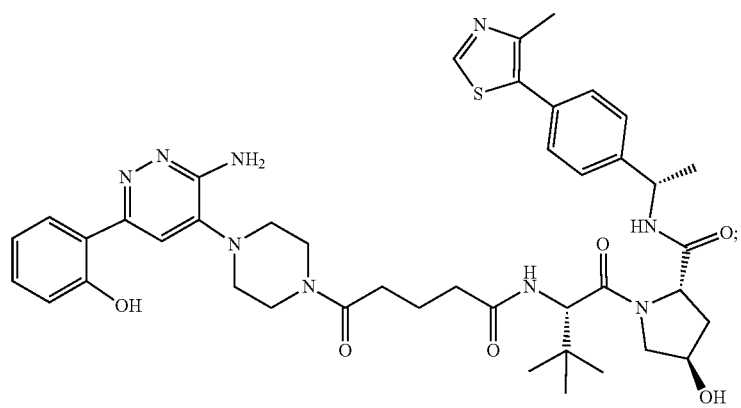 [SMILES: Cc1ncsc1-c1ccc([C@H](C)NC(=O)[C@@H]2C[C@@H](O)CN2C(=O)[C@@H](NC(=O)CCCC(=O)N2CCN(c3cc(-c4ccccc4O)nnc3N)CC2)C(C)(C)C)cc1] |
| 115. 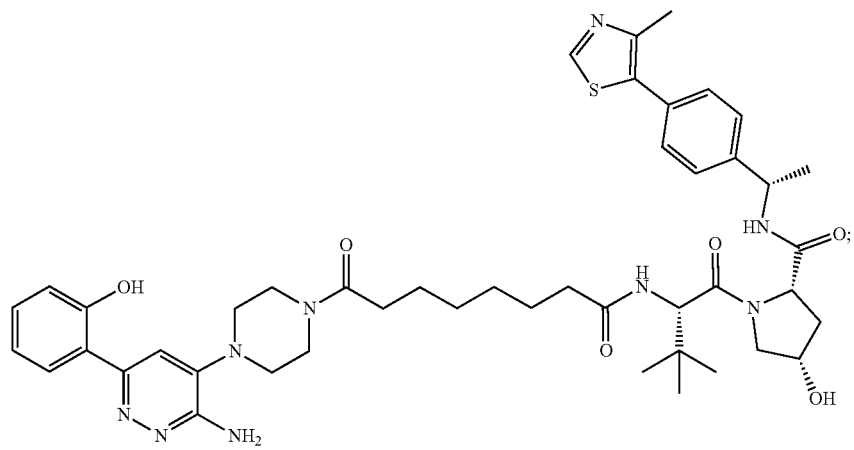 [SMILES: Cc1ncsc1-c1ccc([C@H](C)NC(=O)[C@@H]2C[C@H](O)CN2C(=O)[C@@H](NC(=O)CCCCCCC(=O)N2CCN(c3cc(-c4ccccc4O)nnc3N)CC2)C(C)(C)C)cc1] |

| | STRUCTURE |
|---|---|
| 116. | 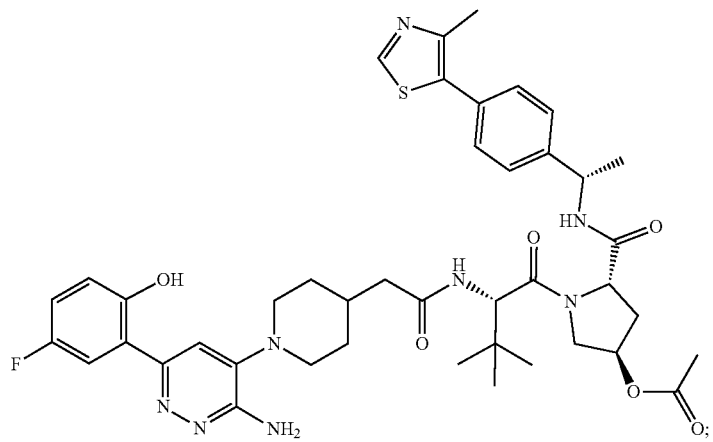 [SMILES: CC(=O)O[C@@H]1C[C@@H](C(=O)N[C@@H](C)c2ccc(-c3scnc3C)cc2)N(C(=O)[C@@H](NC(=O)CC2CCN(c3cc(-c4cc(F)ccc4O)nnc3N)CC2)C(C)(C)C)C1] |
| 117. | 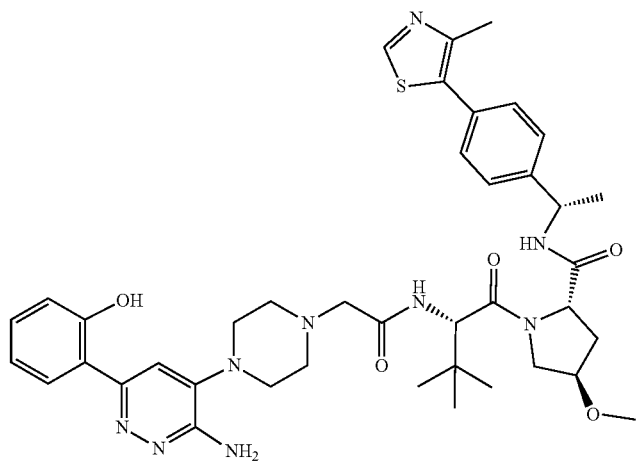 [SMILES: CO[C@@H]1C[C@@H](C(=O)N[C@@H](C)c2ccc(-c3scnc3C)cc2)N(C(=O)[C@@H](NC(=O)CN2CCN(c3cc(-c4ccccc4O)nnc3N)CC2)C(C)(C)C)C1]
and |
| 118. | 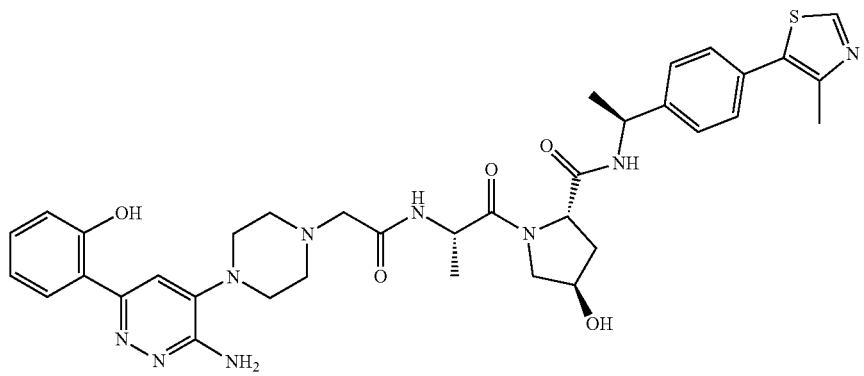 [SMILES: Cc1ncsc1-c1ccc([C@H](C)NC(=O)[C@@H]2C[C@@H](O)CN2C(=O)[C@H](C)NC(=O)CN2CCN(c3cc(-c4ccccc4O)nnc3N)CC2)cc1] |
or a pharmaceutically acceptable salt, or a stereoisomer thereof.
15. A pharmaceutical composition comprising the compound of claim 1 or a pharmaceutically acceptable salt or stereoisomer thereof, and a pharmaceutically acceptable carrier or excipient.
* * * * *